US011180768B2

(12) United States Patent
Flasinski et al.

(10) Patent No.: US 11,180,768 B2
(45) Date of Patent: Nov. 23, 2021

(54) PLANT REGULATORY ELEMENTS AND USES THEREOF

(71) Applicant: Monsanto Technology LLC, St. Louis, MO (US)

(72) Inventors: Stanislaw Flasinski, Ballwin, MO (US); Barrett C. Foat, St. Louis, MO (US); Mohammed Oufattole, Wildwood, MO (US); Randall W. Shultz, St. Louis, MO (US); Xiaoping Wei, St. Louis, MO (US); Wei Wu, Chesterfield, MO (US); Shiaw-Pyng Yang, St. Louis, MO (US)

(73) Assignee: Monsanto Technology LLC, St. Louis, MO (US)

( * ) Notice: Subject to any disclaimer, the term of this patent is extended or adjusted under 35 U.S.C. 154(b) by 0 days.

(21) Appl. No.: 16/722,287

(22) Filed: Dec. 20, 2019

(65) Prior Publication Data

US 2020/0199606 A1 Jun. 25, 2020

Related U.S. Application Data

(62) Division of application No. 16/549,573, filed on Aug. 23, 2019, now Pat. No. 11,046,966, which is a division of application No. 15/802,843, filed on Nov. 3, 2017, now Pat. No. 10,550,401, which is a division of application No. 14/117,342, filed as application No. PCT/US2012/037561 on May 11, 2012, now Pat. No. 9,845,477.

(60) Provisional application No. 61/485,876, filed on May 13, 2011.

(51) Int. Cl.
*C12N 15/82* (2006.01)

(52) U.S. Cl.
CPC .............................. *C12N 15/8216* (2013.01)

(58) Field of Classification Search
None
See application file for complete search history.

(56) References Cited

U.S. PATENT DOCUMENTS

| | | | | |
|---|---|---|---|---|
| 5,489,520 | A * | 2/1996 | Adams et al. | A01H 4/00 536/23.7 |
| 5,500,365 | A * | 3/1996 | Fischhoff et al. | C12N 15/8216 435/418 |
| 6,462,258 | B1 * | 10/2002 | Fincher et al. | C12N 9/1092 800/300 |
| 6,660,911 | B2 | 12/2003 | Fincher et al. | |
| 9,845,477 | B2 | 12/2017 | Flasinski et al. | |
| 10,550,401 | B2 | 2/2020 | Flasinski et al. | |
| 11,046,966 | B2 | 6/2021 | Flasinski et al. | |
| 2004/0055039 | A1 | 3/2004 | Hiroshi et al. | |
| 2007/0204367 | A1 * | 8/2007 | Flasinski et al. | C12N 15/8231 800/278 |
| 2010/0058495 | A1 | 3/2010 | Abbitt | |
| 2012/0084885 | A1 | 4/2012 | Alexandrov et al. | |
| 2020/0056195 | A1 | 2/2020 | Flasinski et al. | |

FOREIGN PATENT DOCUMENTS

| | | | |
|---|---|---|---|
| CN | 101880657 | A | 11/2010 |
| CN | 101952435 | A | 1/2011 |
| CN | 102016049 | A | 4/2011 |
| JP | 2001-346580 | A | 12/2001 |
| WO | WO 01/44457 | | 6/2001 |
| WO | WO 2005/098007 | | 10/2005 |
| WO | WO 2006/039449 | | 4/2006 |

OTHER PUBLICATIONS

Donald & Cashmore (1990) EMBO J 9:1717-26.*
Kim et al. (1994) Plant Mol Biol 24:105-17.*
Dolferus et al. (1994) Plant Physiol 105:1075-87.*
Cho & Cosgrove (2002) Plant Cell 14:3237-53.*
Potenza et al. (2004) In Vitro Cell Dev Biol Plant 40:1-22.*
Saha et al. (2007) In Silica Biol 7(1 ):7-19.*
Rose (2008) Curr Top Microbial Immunol 326:277-90.*
NCBI (2014) XM_008459007.*
Odell et al. (1985) Nature 313:810-12.*
China Office Action and Search Report regarding China Application No. 201710186179.8, dated Nov. 7, 2019, 13 pages.
Australia Office Action regarding Australia Application No. 2019246918, dated Jan. 15, 2020, 7 pages.
GenBank Accession No. AM740200, Sep. 27, 2007.
GenBank Accession No. HN296636, Nov. 23, 2010.
Gonzalez-Ibeas et al., "Melogen: an EST database for melon functional genomics", BMC Genomics (2007), 8:306.
Gonzalez et al., "Genome-wide BAC-end sequencing of Cucumis melo using two BAC libraries", BMC Genomics (2010), 11:618.
Clepet et al., "Analysis of expressed sequence tags generated from full-length enriched cDNA libraries of melon" BMC Genomics (2011), 12:252.
Honored et al., "Use of Ubiquitin Fusions to Augment Protein Expression in Transgenic Plants," Plant Physiology 119:713-723, 1999.
Yuebing et al., "UBI1 intron-mediated enhancement of the expression of Bt cry1ah gene in transgenic maize (*Zea mays* L.)," Chinese Science Bulletin 53(20):3185-3180, 2008.
Callis et al., "Introns increase gene expression in cultured maize cells," *Genes Dev.* 1:1183-1200, 1987.

(Continued)

*Primary Examiner* — Russell T Boggs
(74) *Attorney, Agent, or Firm* — Dentons US LLP; Amanda Carmany-Rampey

(57) ABSTRACT

The invention provides DNA molecules and constructs, including their nucleotide sequences, useful for modulating gene expression in plants and plant cells. Transgenic plants, plant cells, plant parts, seeds, and commodity products comprising the DNA molecules operably linked to heterologous transcribable polynucleotides are also provided, as are methods of their use.

19 Claims, 6 Drawing Sheets

Specification includes a Sequence Listing.

(56) References Cited

OTHER PUBLICATIONS

Chee et al., "Expression of a bean storage protein 'phaseolin minigene' in foreign plant tissues," *Gene* 41:47-57, 1986.
Cho et al., *Plant Cell* 14:3237-53 (2002).
Christiansen et al., "Maize polyubiquitin genes: structure, thermal perturbation of expression and transcript splicing, and promoter activity following transfer to protoplasts by electroporation," *Plant Mol. Biol.* 18:675-689, 1992.
Clancy et al., "Splicing of the maize Sh1 first intron is essential for enhancement of gene expression, and a T-rich motif increases expression without affecting splicing," *Plant Physiol.* 130(2):918-929, 2002.
Dean et al., "Sequences downstream of translation start regulate quantitative expression of two petunia rbcS genes," *Plant Cell* 1 (2):201-208, 1989.
Dolferus et al., *Plant Physiol.* 105:1075-87 (1994).
Donald & Cashmore, EMBO J. 9:1717-26 (1990).
International Preliminary Report on Patentability regarding PCT Application No. PCT/US2012/037561, dated Nov. 19, 2013.
International Search Report regarding PCT Application No. PCT/US2012/037561, dated Sep. 12, 2012.
Jeon et al., "Tissue-preferential expression of a rice alpha-tubulin gene, OsTubA1, mediated by the first intron," *Plant Physiol.* 123(3):1005-1014, 2000.
Kim et al., Plant Mol. Biol. 24:105-17 (1994).
Kuhlemeier et al., "Upstream sequences determine the difference in transcript abundance of pea rbcS genes," *Mol. Gen. Genet.* 212:405-411, 1988.
Lasserre et al., "Differential activation of two ACC oxidase gene promoters from melon during plant development and in response to pathogen attack," *Mol. Gen. Genet.* 256(3):211-222, 1997.
Leon et al., "Transient gene expression in protoplasts of Phaseolus vulgaris isolated from a cell suspension culture," Plant Physiol. 95(3):968-972, 1991.
Li et al., Advanced genetic tools for plant biotechnology, *Nat Rev Genet* 14:781-93 (2013).
Loganantharaj, *Int. J. Bioinf. Res. Appl.* 2:36-51 (2006).
Mascarenhas et al., "Intron-mediated enhancement of heterologous gene expression in maize," *Plant Mol. Biol.* 15(6):913-920, 1990.
McElroy et al., "Isolation of an efficient actin promoter for use in rice transformation," *Plant Cell* 2(2):163-171, 1990.
Norris et al., "The intron of *Arabidopsis thaliana* polyubiquitin genes is conserved in location and is a quantitative determinant of chimeric gene expression," *Plant Mol. Biol.* 21(5):895-906, 1993.
Piechulla et al., Plant Mol. Biol. 38:655-62 (1998).
Potenza et al., *In Vitro Cell Dev. Biol. Plant* 40:1-22 (2004).
Rose et al., "Introns act post-transcriptionally to increase expression of the *Arabidopsis thaliana* tryptophan pathway gene PAT1," *Plant J.* 11(3):455-464, 1997.
Rose et al., "Intron-mediated enhancement of gene expression independent of unique intron sequences and splicing," *Plant Physiol.* 122(2):535-542, 2000.
Saha et al., *In Silico. Biol.* 7(1):7-19 (2007).
Sherf et al., "Dual-luciferase reporter assay: an advanced co-reporter technology integrating firefly and Renilla luciferase assays," *Promega Notes Magazine* No. 57, p. 2, 1996.
Sinibaldi et al., "Intron splicing and intron-mediated enhanced expression in monocots," *Prog. Nucleic Acid Res. Mol. Biol.* (42):229-257, 1992.
Vancanneyt et al., "Construction of an intron-containing marker gene: splicing of the intron in transgenic plants and its use in monitoring early events in Agrobacterium-mediated plant transformation," *Mol. Gen. Genet.* 220(2):245-250, 1990.
Vasil et al., "Increased gene expression by the first intron of maize shrunken-1 locus in grass species," *Plant Physiol.* 91(4):1575-1579, 1989.
Welsch et al., Planta 216:523-34 (2003).
Xu et al., "Rice triosephosphate isomerase gene 5' sequence directs β-glucuronidase activity in transgenic tobacco but requires an intron for expression in rice," *Plant Physiol.* 106(2):459-467, 1994.
Yamagata et al., "TGTCACA motif is a novel cis-regulatory enhancer element involved in fruit-specific expression of the cucumisin gene," *J. Biol. Chem.* 227(13):11582-11590, 2002.
GenBank Accession No. HN314561, dated Nov. 24, 2010.
GenBank Accession No. JG468661, dated Mar. 16, 2011.
GenBank Accession No. HN298588, dated Nov. 24, 2010.
GenBank Accession No. JG469358, dated Mar. 16, 2011.
GenBank Accession No. HN327993, dated Nov. 24, 2010.
GenBank Accession No. JG467489, dated Mar. 16, 2011.
GenBank Accession No. HN319913, dated Nov. 24, 2010.
GenBank Accession No. JG480182, dated Mar. 16, 2011.
Office Action regarding Chilean Application No. 201601540, dated Jun. 14, 2017.
GenBank Accession No. LN713263, dated Mar. 5, 2015.
Office Action regarding Eurasian Application No. 201690416, dated Jul. 28, 2017.
GenBank Accession No. HN320890, dated Nov. 23, 2010.
USPTO Written Description Guidelines. (2008).
Wang and Oard, Rice ubiquitin promoters: deletion analysis and potential usefulness in plant transformation systems, Plant Cell Reports 22:129-134, 2003.
Joung and Kamo, Expression of polyubiquitin promoter isolated from Gladiolus, Plant Cell Reports 25:1081-1088, 2006.
U.S. Appl. No. 17/229,604, filed Apr. 13, 2021, Flasinski et al.

* cited by examiner

```
P-CUCme.Ubq1-1:1:15 (SEQ ID NO: 2)    ATCTGAAAGGAACACCTAGCAAGGGGCTACTCTACAAGCATACTAAGTCTACAAAGCTAG
P-CUCme.Ubq1-1:1:16 (SEQ ID NO: 6)    ------------------------------------------------------------
P-CUCme.Ubq1-1:1:17 (SEQ ID NO: 8)    ------------------------------------------------------------
P-CUCme.Ubq1-1:1:18 (SEQ ID NO: 10)   ------------------------------------------------------------
P-CUCme.Ubq1-1:1:19 (SEQ ID NO: 12)   ------------------------------------------------------------

P-CUCme.Ubq1-1:1:15 (SEQ ID NO: 2)    AGTTGTATGGTTATGCAGAAGACCTGGACAAAAGAAGATCACTCGCTGCTTTTACTTTTA
P-CUCme.Ubq1-1:1:16 (SEQ ID NO: 6)    ------------------------------------------------------------
P-CUCme.Ubq1-1:1:17 (SEQ ID NO: 8)    ------------------------------------------------------------
P-CUCme.Ubq1-1:1:18 (SEQ ID NO: 10)   ------------------------------------------------------------
P-CUCme.Ubq1-1:1:19 (SEQ ID NO: 12)   ------------------------------------------------------------

P-CUCme.Ubq1-1:1:15 (SEQ ID NO: 2)    TCCTAAGAGGAAATGTGATTTTATGGAAGTTTAACCTATAGCCTGTAGTGGCACTATTCA
P-CUCme.Ubq1-1:1:16 (SEQ ID NO: 6)    ------------------------------------------------------------
P-CUCme.Ubq1-1:1:17 (SEQ ID NO: 8)    ------------------------------------------------------------
P-CUCme.Ubq1-1:1:18 (SEQ ID NO: 10)    ------------------------------------------------------------
P-CUCme.Ubq1-1:1:19 (SEQ ID NO: 12)    ------------------------------------------------------------

P-CUCme.Ubq1-1:1:15 (SEQ ID NO: 2)    CAACAAAAGTAAAGTTTATAGCCATGACTGAAGTTGTTAAAGAAGTCGTCTGGCTAAAAG
P-CUCme.Ubq1-1:1:16 (SEQ ID NO: 6)    ------------------------------------------------------------
P-CUCme.Ubq1-1:1:17 (SEQ ID NO: 8)    ------------------------------------------------------------
P-CUCme.Ubq1-1:1:18 (SEQ ID NO: 10)   ------------------------------------------------------------
P-CUCme.Ubq1-1:1:19 (SEQ ID NO: 12)   ------------------------------------------------------------

P-CUCme.Ubq1-1:1:15 (SEQ ID NO: 2)    GACTACTTGAAGAACTTGGCTTCTTTTAACAGTCAGTAAACATCATGTGTGATAGTTAAA
P-CUCme.Ubq1-1:1:16 (SEQ ID NO: 6)    ------------------------------------------------------------
P-CUCme.Ubq1-1:1:17 (SEQ ID NO: 8)    ------------------------------------------------------------
P-CUCme.Ubq1-1:1:18 (SEQ ID NO: 10)   ------------------------------------------------------------
P-CUCme.Ubq1-1:1:19 (SEQ ID NO: 12)   ------------------------------------------------------------

P-CUCme.Ubq1-1:1:15 (SEQ ID NO: 2)    GTGCAATACACTTGTCTAAAAATCTGCAATATCACGAAAGAACTAAGCATATTGATGTGA
P-CUCme.Ubq1-1:1:16 (SEQ ID NO: 6)    ------------------------------------------------------------
P-CUCme.Ubq1-1:1:17 (SEQ ID NO: 8)    ------------------------------------------------------------
P-CUCme.Ubq1-1:1:18 (SEQ ID NO: 10)   ------------------------------------------------------------
P-CUCme.Ubq1-1:1:19 (SEQ ID NO: 12)   ------------------------------------------------------------
```

FIG. 1a

```
P-CUCme.Ubq1-1:1:15 (SEQ ID NO: 2)      AGCTATATGTCATTAGAGAAGTCATAGCAAAGAGAAAAGTAACAGTATCAAAGGTTCAGA
P-CUCme.Ubq1-1:1:16 (SEQ ID NO: 6)      ------------------------------------------------------------
P-CUCme.Ubq1-1:1:17 (SEQ ID NO: 8)      ------------------------------------------------------------
P-CUCme.Ubq1-1:1:18 (SEQ ID NO: 10)     ------------------------------------------------------------
P-CUCme.Ubq1-1:1:19 (SEQ ID NO: 12)     ------------------------------------------------------------

P-CUCme.Ubq1-1:1:15 (SEQ ID NO: 2)      CAAAAGAAAATGCAGCAGATATGTTGACTAAAATAGTTACTAATGCTAAACTCGAGCACT
P-CUCme.Ubq1-1:1:16 (SEQ ID NO: 6)      ------------------------------------------------------------
P-CUCme.Ubq1-1:1:17 (SEQ ID NO: 8)      ------------------------------------------------------------
P-CUCme.Ubq1-1:1:18 (SEQ ID NO: 10)     ------------------------------------------------------------
P-CUCme.Ubq1-1:1:19 (SEQ ID NO: 12)     ------------------------------------------------------------

P-CUCme.Ubq1-1:1:15 (SEQ ID NO: 2)      GCCTACAGTTGCTCAAGGTAATAGACTACTTAAAAGAATAGAATCAGAAGAAATAGTCAT
P-CUCme.Ubq1-1:1:16 (SEQ ID NO: 6)      ------------------------------------------------------------
P-CUCme.Ubq1-1:1:17 (SEQ ID NO: 8)      ------------------------------------------------------------
P-CUCme.Ubq1-1:1:18 (SEQ ID NO: 10)     ------------------------------------------------------------
P-CUCme.Ubq1-1:1:19 (SEQ ID NO: 12)     ------------------------------------------------------------

P-CUCme.Ubq1-1:1:15 (SEQ ID NO: 2)      TGGTAGCAATAAAATTCAAGGTGGAGGATTGTTAAAAAGAAGAGTGAATTTTATTACTTA
P-CUCme.Ubq1-1:1:16 (SEQ ID NO: 6)      ------------------------------------------------------------
P-CUCme.Ubq1-1:1:17 (SEQ ID NO: 8)      ------------------------------------------------------------
P-CUCme.Ubq1-1:1:18 (SEQ ID NO: 10)     ------------------------------------------------------------
P-CUCme.Ubq1-1:1:19 (SEQ ID NO: 12)     ------------------------------------------------------------

P-CUCme.Ubq1-1:1:15 (SEQ ID NO: 2)      AAGAAAATCTCGGTGAAACTCGAAAGATCTCGATTCGAAACTCTATTGCTTAAGAACCTG
P-CUCme.Ubq1-1:1:16 (SEQ ID NO: 6)      ---------TCGGTGAAACTCGAAAGATCTCGATTCGAAACTCTATTGCTTAAGAACCTG
P-CUCme.Ubq1-1:1:17 (SEQ ID NO: 8)      ------------------------------------------------------------
P-CUCme.Ubq1-1:1:18 (SEQ ID NO: 10)     ------------------------------------------------------------
P-CUCme.Ubq1-1:1:19 (SEQ ID NO: 12)     ------------------------------------------------------------

P-CUCme.Ubq1-1:1:15 (SEQ ID NO: 2)      GTGAAGCTCGAGAGATCTTGATACAATCCCAGTGCCCTAACTCTTCAACAAGCTAAGCAA
P-CUCme.Ubq1-1:1:16 (SEQ ID NO: 6)      GTGAAGCTCGAGAGATCTTGATACAATCCCAGTGCCCTAACTCTTCAACAAGCTAAGCAA
P-CUCme.Ubq1-1:1:17 (SEQ ID NO: 8)      ------------------------------------------------------------
P-CUCme.Ubq1-1:1:18 (SEQ ID NO: 10)     ------------------------------------------------------------
P-CUCme.Ubq1-1:1:19 (SEQ ID NO: 12)     ------------------------------------------------------------
```

FIG. 1b

```
P-CUCme.Ubq1-1:1:15 (SEQ ID NO: 2)     GTTGTACTGTGGGGCTCAATCTCGGTTCAATCTCGACGCACCTGATGCTTTGTTCCCTGT
P-CUCme.Ubq1-1:1:16 (SEQ ID NO: 6)     GTTGTACTGTGGGGCTCAATCTCGGTTCAATCTCGACGCACCTGATGCTTTGTTCCCTGT
P-CUCme.Ubq1-1:1:17 (SEQ ID NO: 8)     ------------------------------------------------------------
P-CUCme.Ubq1-1:1:18 (SEQ ID NO: 10)    ------------------------------------------------------------
P-CUCme.Ubq1-1:1:19 (SEQ ID NO: 12)    ------------------------------------------------------------

P-CUCme.Ubq1-1:1:15 (SEQ ID NO: 2)     CTACTCGATGAAGAAGCAATTACTTCTCAGGACAACTCGGTACCCCTAAATACAGATTTT
P-CUCme.Ubq1-1:1:16 (SEQ ID NO: 6)     CTACTCGATGAAGAAGCAATTACTTCTCAGGACAACTCGGTACCCCTAAATACAGATTTT
P-CUCme.Ubq1-1:1:17 (SEQ ID NO: 8)     ------------------------------------------------------------
P-CUCme.Ubq1-1:1:18 (SEQ ID NO: 10)    ------------------------------------------------------------
P-CUCme.Ubq1-1:1:19 (SEQ ID NO: 12)    ------------------------------------------------------------

P-CUCme.Ubq1-1:1:15 (SEQ ID NO: 2)     GAGCTTCGTGATCCTACAACTGAAATCAAATAGAAAAACTAATAAGTTAGTTAGAGTTTG
P-CUCme.Ubq1-1:1:16 (SEQ ID NO: 6)     GAGCTTCGTGATCCTACAACTGAAATCAAATAGAAAAACTAATAAGTTAGTTAGAGTTTG
P-CUCme.Ubq1-1:1:17 (SEQ ID NO: 8)     ------------------------------------------------------------
P-CUCme.Ubq1-1:1:18 (SEQ ID NO: 10)    ------------------------------------------------------------
P-CUCme.Ubq1-1:1:19 (SEQ ID NO: 12)    ------------------------------------------------------------

P-CUCme.Ubq1-1:1:15 (SEQ ID NO: 2)     TTATATTTACTGCCATTAAATAACTCTGTAATGTAAATAATAAACCATTTAACTCAATAT
P-CUCme.Ubq1-1:1:16 (SEQ ID NO: 6)     TTATATTTACTGCCATTAAATAACTCTGTAATGTAAATAATAAACCATTTAACTCAATAT
P-CUCme.Ubq1-1:1:17 (SEQ ID NO: 8)     ------------------------------------------------------------
P-CUCme.Ubq1-1:1:18 (SEQ ID NO: 10)    ------------------------------------------------------------
P-CUCme.Ubq1-1:1:19 (SEQ ID NO: 12)    ------------------------------------------------------------

P-CUCme.Ubq1-1:1:15 (SEQ ID NO: 2)     GAAATATAGAATGAGAAAAAGAAAAAGAAAAAGTTAAAGAGAGAGAGGAAGAAAACTCAT
P-CUCme.Ubq1-1:1:16 (SEQ ID NO: 6)     GAAATATAGAATGAGAAAAAGAAAAAGAAAAAGTTAAAGAGAGAGAGGAAGAAAACTCAT
P-CUCme.Ubq1-1:1:17 (SEQ ID NO: 8)     ------------------------------------------------------------
P-CUCme.Ubq1-1:1:18 (SEQ ID NO: 10)    ------------------------------------------------------------
P-CUCme.Ubq1-1:1:19 (SEQ ID NO: 12)    ------------------------------------------------------------

P-CUCme.Ubq1-1:1:15 (SEQ ID NO: 2)     TTTCAAATTCTCTATACTTGTTTGATCCTTGAATAAGTTGAATAAAAGCTCTATGGCGGC
P-CUCme.Ubq1-1:1:16 (SEQ ID NO: 6)     TTTCAAATTCTCTATACTTGTTTGATCCTTGAATAAGTTGAATAAAAGCTCTATGGCGGC
P-CUCme.Ubq1-1:1:17 (SEQ ID NO: 8)     ------------------------------------------------------------
P-CUCme.Ubq1-1:1:18 (SEQ ID NO: 10)    ------------------------------------------------------------
P-CUCme.Ubq1-1:1:19 (SEQ ID NO: 12)    ------------------------------------------------------------
```

FIG. 1c

```
P-CUCme.Ubq1-1:1:15 (SEQ ID NO: 2)    TTCAAAGTGGATGTAGGCACTATTAGTCGAACCACAATAAATTTGTTATGTTCTTTTGCT
P-CUCme.Ubq1-1:1:16 (SEQ ID NO: 6)    TTCAAAGTGGATGTAGGCACTATTAGTCGAACCACAATAAATTTGTTATGTTCTTTTGCT
P-CUCme.Ubq1-1:1:17 (SEQ ID NO: 8)    ------------------------AGTCGAACCACAATAAATTTGTTATGTTCTTTTGCT
P-CUCme.Ubq1-1:1:18 (SEQ ID NO: 10)   ------------------------------------------------------------
P-CUCme.Ubq1-1:1:19 (SEQ ID NO: 12)   ------------------------------------------------------------

P-CUCme.Ubq1-1:1:15 (SEQ ID NO: 2)    ATTCCTTGTAATCTCCATAAATATTTTCTTACTAAGCTCTAGAAATCTGCTTGTCAAGAG
P-CUCme.Ubq1-1:1:16 (SEQ ID NO: 6)    ATTCCTTGTAATCTCCATAAATATTTTCTTACTAAGCTCTAGAAATCTGCTTGTCAAGAG
P-CUCme.Ubq1-1:1:17 (SEQ ID NO: 8)    ATTCCTTGTAATCTCCATAAATATTTTCTTACTAAGCTCTAGAAATCTGCTTGTCAAGAG
P-CUCme.Ubq1-1:1:18 (SEQ ID NO: 10)   ------------------------------------------------------------
P-CUCme.Ubq1-1:1:19 (SEQ ID NO: 12)   ------------------------------------------------------------

P-CUCme.Ubq1-1:1:15 (SEQ ID NO: 2)    ATTAGGTATCATTTATGCCTTTTATATTTCCTTTCGGTTGCATATCTTGAGCTAGTTAAG
P-CUCme.Ubq1-1:1:16 (SEQ ID NO: 6)    ATTAGGTATCATTTATGCCTTTTATATTTCCTTTCGGTTGCATATCTTGAGCTAGTTAAG
P-CUCme.Ubq1-1:1:17 (SEQ ID NO: 8)    ATTAGGTATCATTTATGCCTTTTATATTTCCTTTCGGTTGCATATCTTGAGCTAGTTAAG
P-CUCme.Ubq1-1:1:18 (SEQ ID NO: 10)   ------------------------------------------------------------
P-CUCme.Ubq1-1:1:19 (SEQ ID NO: 12)   ------------------------------------------------------------

P-CUCme.Ubq1-1:1:15 (SEQ ID NO: 2)    ATCGAGAGGTTACTGTTGTTGAAACCGAGATTAGTATCTTTGGATTAACACGTGCCTACC
P-CUCme.Ubq1-1:1:16 (SEQ ID NO: 6)    ATCGAGAGGTTACTGTTGTTGAAACCGAGATTAGTATCTTTGGATTAACACGTGCCTACC
P-CUCme.Ubq1-1:1:17 (SEQ ID NO: 8)    ATCGAGAGGTTACTGTTGTTGAAACCGAGATTAGTATCTTTGGATTAACACGTGCCTACC
P-CUCme.Ubq1-1:1:18 (SEQ ID NO: 10)   ------------------------------------------------------------
P-CUCme.Ubq1-1:1:19 (SEQ ID NO: 12)   ------------------------------------------------------------

P-CUCme.Ubq1-1:1:15 (SEQ ID NO: 2)    AAAATTTGAAATTTTGTATTTACCCCATTCATTGGATAATAAGCAATTCTTATAGTGTTA
P-CUCme.Ubq1-1:1:16 (SEQ ID NO: 6)    AAAATTTGAAATTTTGTATTTACCCCATTCATTGGATAATAAGCAATTCTTATAGTGTTA
P-CUCme.Ubq1-1:1:17 (SEQ ID NO: 8)    AAAATTTGAAATTTTGTATTTACCCCATTCATTGGATAATAAGCAATTCTTATAGTGTTA
P-CUCme.Ubq1-1:1:18 (SEQ ID NO: 10)   ------------------------------------------------------------
P-CUCme.Ubq1-1:1:19 (SEQ ID NO: 12)   ------------------------------------------------------------

P-CUCme.Ubq1-1:1:15 (SEQ ID NO: 2)    TCAATTAAACTCCTATAAAGTGTAATAATTGAATCCATGAACTATTTTCATATGTAATCT
P-CUCme.Ubq1-1:1:16 (SEQ ID NO: 6)    TCAATTAAACTCCTATAAAGTGTAATAATTGAATCCATGAACTATTTTCATATGTAATCT
P-CUCme.Ubq1-1:1:17 (SEQ ID NO: 8)    TCAATTAAACTCCTATAAAGTGTAATAATTGAATCCATGAACTATTTTCATATGTAATCT
P-CUCme.Ubq1-1:1:18 (SEQ ID NO: 10)   ------------------------------------------------------------
P-CUCme.Ubq1-1:1:19 (SEQ ID NO: 12)   ------------------------------------------------------------
```

FIG. 1d

```
P-CUCme.Ubq1-1:1:15 (SEQ ID NO: 2)    TAATAAAATGAATTTAGAAGTTTAATTAAAATAATATATTTTGTATGCTATTTTTCAAAG
P-CUCme.Ubq1-1:1:16 (SEQ ID NO: 6)    TAATAAAATGAATTTAGAAGTTTAATTAAAATAATATATTTTGTATGCTATTTTTCAAAG
P-CUCme.Ubq1-1:1:17 (SEQ ID NO: 8)    TAATAAAATGAATTTAGAAGTTTAATTAAAATAATATATTTTGTATGCTATTTTTCAAAG
P-CUCme.Ubq1-1:1:18 (SEQ ID NO: 10)   ------------------------------------------------------------
P-CUCme.Ubq1-1:1:19 (SEQ ID NO: 12)   ------------------------------------------------------------

P-CUCme.Ubq1-1:1:15 (SEQ ID NO: 2)    TTTGAAGAATGTGTTAATTGATACACATACAAAAAATCTAGGTTTTACATGAAAAACTAT
P-CUCme.Ubq1-1:1:16 (SEQ ID NO: 6)    TTTGAAGAATGTGTTAATTGATACACATACAAAAAATCTAGGTTTTACATGAAAAACTAT
P-CUCme.Ubq1-1:1:17 (SEQ ID NO: 8)    TTTGAAGAATGTGTTAATTGATACACATACAAAAAATCTAGGTTTTACATGAAAAACTAT
P-CUCme.Ubq1-1:1:18 (SEQ ID NO: 10)   ------------------------------------------------------------
P-CUCme.Ubq1-1:1:19 (SEQ ID NO: 12)   ------------------------------------------------------------

P-CUCme.Ubq1-1:1:15 (SEQ ID NO: 2)    GGAAGTGAAAGATAGCATCTAATATTTTATGACACAAAATGCAAACTAATATATAAAGGA
P-CUCme.Ubq1-1:1:16 (SEQ ID NO: 6)    GGAAGTGAAAGATAGCATCTAATATTTTATGACACAAAATGCAAACTAATATATAAAGGA
P-CUCme.Ubq1-1:1:17 (SEQ ID NO: 8)    GGAAGTGAAAGATAGCATCTAATATTTTATGACACAAAATGCAAACTAATATATAAAGGA
P-CUCme.Ubq1-1:1:18 (SEQ ID NO: 10)   -----------------------------TGACACAAAATGCAAACTAATATATAAAGGA
P-CUCme.Ubq1-1:1:19 (SEQ ID NO: 12)   ------------------------------------------------------------

P-CUCme.Ubq1-1:1:15 (SEQ ID NO: 2)    TTTAATTAATTTTTATAGGTTTCAAATTTGTTAGACTTGTCAAATACAAAATTTTATTGA
P-CUCme.Ubq1-1:1:16 (SEQ ID NO: 6)    TTTAATTAATTTTTATAGGTTTCAAATTTGTTAGACTTGTCAAATACAAAATTTTATTGA
P-CUCme.Ubq1-1:1:17 (SEQ ID NO: 8)    TTTAATTAATTTTTATAGGTTTCAAATTTGTTAGACTTGTCAAATACAAAATTTTATTGA
P-CUCme.Ubq1-1:1:18 (SEQ ID NO: 10)   TTTAATTAATTTTTATAGGTTTCAAATTTGTTAGACTTGTCAAATACAAAATTTTATTGA
P-CUCme.Ubq1-1:1:19 (SEQ ID NO: 12)   ------------------------------------------------------------

P-CUCme.Ubq1-1:1:15 (SEQ ID NO: 2)    ACCAAATACATACAAACATCAAAATTAAGAACAGAAAATCTAAATTCAAATGAAATTTAT
P-CUCme.Ubq1-1:1:16 (SEQ ID NO: 6)    ACCAAATACATACAAACATCAAAATTAAGAACAGAAAATCTAAATTCAAATGAAATTTAT
P-CUCme.Ubq1-1:1:17 (SEQ ID NO: 8)    ACCAAATACATACAAACATCAAAATTAAGAACAGAAAATCTAAATTCAAATGAAATTTAT
P-CUCme.Ubq1-1:1:18 (SEQ ID NO: 10)   ACCAAATACATACAAACATCAAAATTAAGAACAGAAAATCTAAATTCAAATGAAATTTAT
P-CUCme.Ubq1-1:1:19 (SEQ ID NO: 12)   ------------------------------------------------------------

P-CUCme.Ubq1-1:1:15 (SEQ ID NO: 2)    TAATAGAAAAATTAGAAAAAAGAAAAAGAAAATAAAAGGAATCGTATTGTTTTTTCCTTC
P-CUCme.Ubq1-1:1:16 (SEQ ID NO: 6)    TAATAGAAAAATTAGAAAAAAGAAAAAGAAAATAAAAGGAATCGTATTGTTTTTTCCTTC
P-CUCme.Ubq1-1:1:17 (SEQ ID NO: 8)    TAATAGAAAAATTAGAAAAAAGAAAAAGAAAATAAAAGGAATCGTATTGTTTTTTCCTTC
P-CUCme.Ubq1-1:1:18 (SEQ ID NO: 10)   TAATAGAAAAATTAGAAAAAAGAAAAAGAAAATAAAAGGAATCGTATTGTTTTTTCCTTC
P-CUCme.Ubq1-1:1:19 (SEQ ID NO: 12)   ------------------------------------------------------------
```

FIG. 1e

```
P-CUCme.Ubq1-1:1:15 (SEQ ID NO: 2)   CTTTTTCCCATTTGAGAGGTGAATAAAGCTAATTGAGCTGCTCTAACTTCCTAATCTTTA
P-CUCme.Ubq1-1:1:16 (SEQ ID NO: 6)   CTTTTTCCCATTTGAGAGGTGAATAAAGCTAATTGAGCTGCTCTAACTTCCTAATCTTTA
P-CUCme.Ubq1-1:1:17 (SEQ ID NO: 8)   CTTTTTCCCATTTGAGAGGTGAATAAAGCTAATTGAGCTGCTCTAACTTCCTAATCTTTA
P-CUCme.Ubq1-1:1:18 (SEQ ID NO: 10)  CTTTTTCCCATTTGAGAGGTGAATAAAGCTAATTGAGCTGCTCTAACTTCCTAATCTTTA
P-CUCme.Ubq1-1:1:19 (SEQ ID NO: 12)  ------------------------------------------------------------

P-CUCme.Ubq1-1:1:15 (SEQ ID NO: 2)   TGCTTTCCCCATAAAGCTTTCCCAACTGCGCGTAATCGTATAAATGGAAAATTGACCTTT
P-CUCme.Ubq1-1:1:16 (SEQ ID NO: 6)   TGCTTTCCCCATAAAGCTTTCCCAACTGCGCGTAATCGTATAAATGGAAAATTGACCTTT
P-CUCme.Ubq1-1:1:17 (SEQ ID NO: 8)   TGCTTTCCCCATAAAGCTTTCCCAACTGCGCGTAATCGTATAAATGGAAAATTGACCTTT
P-CUCme.Ubq1-1:1:18 (SEQ ID NO: 10)  TGCTTTCCCCATAAAGCTTTCCCAACTGCGCGTAATCGTATAAATGGAAAATTGACCTTT
P-CUCme.Ubq1-1:1:19 (SEQ ID NO: 12)  -----------------------------------TCGTATAAATGGAAAATTGACCTTT

P-CUCme.Ubq1-1:1:15 (SEQ ID NO: 2)   CCAACTAGATTCTTCCAGAACTAAACAATACGTAACACGCAAGTAATCAAAGACACGTTT
P-CUCme.Ubq1-1:1:16 (SEQ ID NO: 6)   CCAACTAGATTCTTCCAGAACTAAACAATACGTAACACGCAAGTAATCAAAGACACGTTT
P-CUCme.Ubq1-1:1:17 (SEQ ID NO: 8)   CCAACTAGATTCTTCCAGAACTAAACAATACGTAACACGCAAGTAATCAAAGACACGTTT
P-CUCme.Ubq1-1:1:18 (SEQ ID NO: 10)  CCAACTAGATTCTTCCAGAACTAAACAATACGTAACACGCAAGTAATCAAAGACACGTTT
P-CUCme.Ubq1-1:1:19 (SEQ ID NO: 12)  CCAACTAGATTCTTCCAGAACTAAACAATACGTAACACGCAAGTAATCAAAGACACGTTT

P-CUCme.Ubq1-1:1:15 (SEQ ID NO: 2)   CATTTTCCTATAGAATATTATAGTTATTCGTGATTAACGGAAGTCGGCAATTTTAGGTAT
P-CUCme.Ubq1-1:1:16 (SEQ ID NO: 6)   CATTTTCCTATAGAATATTATAGTTATTCGTGATTAACGGAAGTCGGCAATTTTAGGTAT
P-CUCme.Ubq1-1:1:17 (SEQ ID NO: 8)   CATTTTCCTATAGAATATTATAGTTATTCGTGATTAACGGAAGTCGGCAATTTTAGGTAT
P-CUCme.Ubq1-1:1:18 (SEQ ID NO: 10)  CATTTTCCTATAGAATATTATAGTTATTCGTGATTAACGGAAGTCGGCAATTTTAGGTAT
P-CUCme.Ubq1-1:1:19 (SEQ ID NO: 12)  CATTTTCCTATAGAATATTATAGTTATTCGTGATTAACGGAAGTCGGCAATTTTAGGTAT

P-CUCme.Ubq1-1:1:15 (SEQ ID NO: 2)   AAATACGTGAATTCTCGAGCGCTAATTT
P-CUCme.Ubq1-1:1:16 (SEQ ID NO: 6)   AAATACGTGAATTCTCGAGCGCTAATTT
P-CUCme.Ubq1-1:1:17 (SEQ ID NO: 8)   AAATACGTGAATTCTCGAGCGCTAATTT
P-CUCme.Ubq1-1:1:18 (SEQ ID NO: 10)  AAATACGTGAATTCTCGAGCGCTAATTT
P-CUCme.Ubq1-1:1:19 (SEQ ID NO: 12)  AAATACGTGAATTCTCGAGCGCTAATTT
```

FIG. 1f

SEQUENCE LISTING

```
<160> NUMBER OF SEQ ID NOS: 212

<210> SEQ ID NO 1
<211> LENGTH: 2611
<212> TYPE: DNA
<213> ORGANISM: Cucumis melo

<400> SEQUENCE: 1

atctgaaagg aacacctagc aaggggctac tctacaagca tactaagtct acaaagctag     60

agttgtatgg ttatgcagaa gacctggaca aaagaagatc actcgctgct tttactttta    120

tcctaagagg aaatgtgatt ttatggaagt ttaacctata gcctgtagtg gcactattca    180

caacaaaagt aaagtttata gccatgactg aagttgttaa agaagtcgtc tggctaaaag    240

gactacttga agaacttggc ttcttttaac agtcagtaaa catcatgtgt gatagttaaa    300

gtgcaataca cttgtctaaa aatctgcaat atcacgaaag aactaagcat attgatgtga    360

agctatatgt cattagagaa gtcatagcaa agagaaaagt aacagtatca aaggttcaga    420

caaaagaaaa tgcagcagat atgttgacta aaatagttac taatgctaaa ctcgagcact    480

gcctacagtt gctcaaggta atagactact taaaagaata gaatcagaag aaatagtcat    540

tggtagcaat aaaattcaag gtggaggatt gttaaaaaga agagtgaatt ttattactta    600

aagaaaatct cggtgaaact cgaaagatct cgattcgaaa ctctattgct taagaacctg    660

gtgaagctcg agagatcttg atacaatccc agtgccctaa ctcttcaaca agctaagcaa    720

gttgtactgt ggggctcaat ctcggttcaa tctcgacgca cctgatgctt tgttccctgt    780

ctactcgatg aagaagcaat tacttctcag gacaactcgg taccccctaaa tacagatttt    840

gagcttcgtg atcctacaac tgaaatcaaa tagaaaaact aataagttag ttagagtttg    900

ttatatttac tgccattaaa taactctgta atgtaaataa taaaccattt aactcaatat    960

gaaatataga atgagaaaaa gaaaaagaaa aagttaaaga gagagaggaa gaaaactcat   1020

tttcaaattc tctatacttg tttgatcctt gaataagttg aataaaagct ctatggcggc   1080

ttcaaagtgg atgtaggcac tattagtcga accacaataa atttgttatg ttcttttgct   1140

attccttgta atctccataa atattttctt actaagctct agaaatctgc ttgtcaagag   1200

attaggtatc atttatgcct tttatatttc ctttcggttg catatcttga gctagttaag   1260

atcgagaggt tactgttgtt gaaaccgaga ttagtatctt tggattaaca cgtgcctacc   1320

aaaatttgaa attttgtatt taccccattc attggataat aagcaattct tatagtgtta   1380

tcaattaaac tcctataaag tgtaataatt gaatccatga actattttca tatgtaatct   1440

taataaaatg aatttagaag tttaattaaa ataatatatt ttgtatgcta tttttcaaag   1500

tttgaagaat gtgttaattg atacacatac aaaaaatcta ggttttacat gaaaaactat   1560

ggaagtgaaa gatagcatct aatattttat gacacaaaat gcaaactaat atataaagga   1620

tttaattaat ttttataggt ttcaaatttg ttagacttgt caaatacaaa attttattga   1680

accaaataca tacaaacatc aaaattaaga acagaaaatc taaattcaaa tgaaatttat   1740
```

-continued

```
taatagaaaa attagaaaaa agaaaaagaa aataaaagga atcgtattgt tttttccttc   1800
cttttcccca tttgagaggt gaataaagct aattgagctg ctctaacttc ctaatcttta   1860
tgctttcccc ataaagcttt cccaactgcg cgtaatcgta taaatggaaa attgaccttt   1920
ccaactagat tcttccagaa ctaaacaata cgtaacacgc aagtaatcaa agacacgttt   1980
cattttccta tagaatatta tagttattcg tgattaacgg aagtcggcaa ttttaggtat   2040
aaatacgtga attctcgagc gctaattttc catacagact cgaaatactc taaactttct   2100
catcgcgctt tattcctatt tcgtaattcg ctcttcttca acctctcaag gttttcatct   2160
tttctctatc ttctgttttc agattgcatc ttttccccct cctgttcgat taattgatgt   2220
ttgaattttc gagaaacgat ttgaagtctt tgttgtattt ttcatttctg ttcgttaggt   2280
aggtcgattt ttaatcgtga tgtccgacgt tgttcggatg attcacattt ggtttttgtc   2340
atcttctttc tatgttgtga ttatcatgat ttttatcttt ttttcttctc aagatttgta   2400
atttatcgat tccccatggt tcttggtttt ttatacatgt attgaatctg gttactagaa   2460
ttatgttctt cgacggacgt ctttcagatt taaattgcat tgtaggaaat atgatttgct   2520
atctgagtaa cgtttttcca gagtattctt gattgcgcga tctatcttca attgttaaat   2580
tgtttttgtt taattggggt catgacaggt g                                  2611
```

<210> SEQ ID NO 2
<211> LENGTH: 2068
<212> TYPE: DNA
<213> ORGANISM: Cucumis melo

<400> SEQUENCE: 2

```
atctgaaagg aacacctagc aaggggctac tctacaagca tactaagtct acaaagctag     60
agttgtatgg ttatgcagaa gacctggaca aaagaagatc actcgctgct tttactttta    120
tcctaagagg aaatgtgatt ttatggaagt ttaacctata gcctgtagtg gcactattca    180
caacaaaagt aaagtttata gccatgactg aagttgttaa agaagtcgtc tggctaaaag    240
gactacttga agaacttggc ttcttttaac agtcagtaaa catcatgtgt gatagttaaa    300
gtgcaataca cttgtctaaa aatctgcaat atcacgaaag aactaagcat attgatgtga    360
agctatatgt cattagagaa gtcatagcaa agagaaaagt aacagtatca aaggttcaga    420
caaaagaaaa tgcagcagat atgttgacta aaatagttac taatgctaaa ctcgagcact    480
gcctacagtt gctcaaggta atagactact taaaagaata gaatcagaag aaatagtcat    540
tggtagcaat aaaattcaag gtggaggatt gttaaaaaga agagtgaatt ttattactta    600
aagaaaatct cggtgaaact cgaaagatct cgattcgaaa ctctattgct taagaacctg    660
gtgaagctcg agagatcttg atacaatccc agtgccctaa ctcttcaaca agctaagcaa    720
gttgtactgt ggggctcaat ctcggttcaa tctcgacgca cctgatgctt tgttccctgt    780
ctactcgatg aagaagcaat tacttctcag gacaactcgg taccccctaaa tacagatttt    840
gagcttcgtg atcctacaac tgaaatcaaa tagaaaaact aataagttag ttagagtttg    900
ttatatttac tgccattaaa taactctgta atgtaaataa taaaccattt aactcaatat    960
gaaatataga atgagaaaaa gaaaaagaaa aagttaaaga gagagaggaa gaaaactcat   1020
tttcaaattc tctatacttg tttgatcctt gaataagttg aataaaagct ctatggcggc   1080
ttcaaagtgg atgtaggcac tattagtcga accacaataa atttgttatg ttcttttgct   1140
attccttgta atctccataa atattttctt actaagctct agaaatctgc ttgtcaagag   1200
```

-continued

```
attaggtatc atttatgcct tttatatttc ctttcggttg catatcttga gctagttaag   1260

atcgagaggt tactgttgtt gaaaccgaga ttagtatctt tggattaaca cgtgcctacc   1320

aaaatttgaa attttgtatt taccccattc attggataat aagcaattct tatagtgtta   1380

tcaattaaac tcctataaag tgtaataatt gaatccatga actattttca tatgtaatct   1440

taataaaatg aatttagaag tttaattaaa ataatatatt ttgtatgcta tttttcaaag   1500

tttgaagaat gtgttaattg atacacatac aaaaaatcta ggttttacat gaaaaactat   1560

ggaagtgaaa gatagcatct aatattttat gacacaaaat gcaaactaat atataaagga   1620

tttaattaat ttttataggt ttcaaatttg ttagacttgt caaatacaaa attttattga   1680

accaaataca tacaaacatc aaaattaaga acagaaaatc taaattcaaa tgaaatttat   1740

taatagaaaa attagaaaaa agaaaaagaa aataaaagga atcgtattgt tttttccttc   1800

ctttttccca tttgagaggt gaataaagct aattgagctg ctctaacttc ctaatcttta   1860

tgctttcccc ataaagcttt cccaactgcg cgtaatcgta taaatggaaa attgaccttt   1920

ccaactagat tcttccagaa ctaaacaata cgtaacacgc aagtaatcaa agacacgttt   1980

cattttccta tagaatatta tagttattcg tgattaacgg aagtcggcaa ttttaggtat   2040

aaatacgtga attctcgagc gctaattt                                      2068
```

<210> SEQ ID NO 3
<211> LENGTH: 82
<212> TYPE: DNA
<213> ORGANISM: Cucumis melo

<400> SEQUENCE: 3

```
tccatacaga ctcgaaatac tctaaacttt ctcatcgcgc tttattccta tttcgtaatt     60

cgctcttctt caacctctca ag                                              82
```

<210> SEQ ID NO 4
<211> LENGTH: 461
<212> TYPE: DNA
<213> ORGANISM: Cucumis melo

<400> SEQUENCE: 4

```
gttttcatct tttctctatc ttctgttttc agattgcatc ttttcccccct cctgttcgat     60

taattgatgt ttgaattttc gagaaacgat ttgaagtctt tgttgtattt ttcatttctg    120

ttcgttaggt aggtcgattt ttaatcgtga tgtccgacgt tgttcggatg attcacattt    180

ggtttttgtc atcttctttc tatgttgtga ttatcatgat ttttatcttt ttttcttctc    240

aagatttgta atttatcgat tccccatggt tcttggtttt ttatacatgt attgaatctg    300

gttactagaa ttatgttctt cgacggacgt ctttcagatt taaattgcat tgtaggaaat    360

atgatttgct atctgagtaa cgtttttcca gagtattctt gattgcgcga tctatcttca    420

attgttaaat tgtttttgtt taattggggt catgacaggt g                        461
```

<210> SEQ ID NO 5
<211> LENGTH: 2002
<212> TYPE: DNA
<213> ORGANISM: Cucumis melo

<400> SEQUENCE: 5

```
tcggtgaaac tcgaaagatc tcgattcgaa actctattgc ttaagaacct ggtgaagctc     60

gagagatctt gatacaatcc cagtgcccta actcttcaac aagctaagca agttgtactg    120

tggggctcaa tctcggttca atctcgacgc acctgatgct ttgttccctg tctactcgat    180
```

-continued

```
gaagaagcaa ttacttctca ggacaactcg gtacccctaa atacagattt tgagcttcgt    240

gatcctacaa ctgaaatcaa atagaaaaac taataagtta gttagagttt gttatattta    300

ctgccattaa ataactctgt aatgtaaata ataaaccatt taactcaata tgaaatatag    360

aatgagaaaa agaaaaagaa aaagttaaag agagagagga agaaaactca ttttcaaatt    420

ctctatactt gtttgatcct tgaataagtt gaataaaagc tctatggcgg cttcaaagtg    480

gatgtaggca ctattagtcg aaccacaata aatttgttat gttcttttgc tattccttgt    540

aatctccata aatattttct tactaagctc tagaaatctg cttgtcaaga gattaggtat    600

catttatgcc ttttatattt cctttcggtt gcatatcttg agctagttaa gatcgagagg    660

ttactgttgt tgaaaccgag attagtatct ttggattaac acgtgcctac caaaatttga    720

aattttgtat ttaccccatt cattggataa taagcaattc ttatagtgtt atcaattaaa    780

ctcctataaa gtgtaataat tgaatccatg aactattttc atatgtaatc ttaataaaat    840

gaatttagaa gtttaattaa aataatatat tttgtatgct atttttcaaa gtttgaagaa    900

tgtgttaatt gatacacata caaaaaatct aggttttaca tgaaaaacta tggaagtgaa    960

agatagcatc taatatttta tgacacaaaa tgcaaactaa tatataaagg atttaattaa   1020

tttttatagg tttcaaattt gttagacttg tcaaatacaa aattttattg aaccaaatac   1080

atacaaacat caaaattaag aacagaaaat ctaaattcaa atgaaattta ttaatagaaa   1140

aattagaaaa aagaaaaaga aaataaaagg aatcgtattg ttttttcctt ccttttttccc  1200

atttgagagg tgaataaagc taattgagct gctctaactt cctaatcttt atgctttccc   1260

cataaagctt tcccaactgc gcgtaatcgt ataaatggaa aattgacctt tccaactaga   1320

ttcttccaga actaaacaat acgtaacacg caagtaatca aagacacgtt tcattttcct   1380

atagaatatt atagttattc gtgattaacg gaagtcggca attttaggta taaatacgtg   1440

aattctcgag cgctaatttt ccatacagac tcgaaatact ctaaactttc tcatcgcgct   1500

ttattcctat ttcgtaattc gctcttcttc aacctctcaa ggttttcatc ttttctctat   1560

cttctgtttt cagattgcat cttttccccc tcctgttcga ttaattgatg tttgaatttt   1620

cgagaaacga tttgaagtct ttgttgtatt tttcatttct gttcgttagg taggtcgatt   1680

tttaatcgtg atgtccgacg ttgttcggat gattcacatt tggtttttgt catcttcttt   1740

ctatgttgtg attatcatga tttttatctt tttttcttct caagatttgt aatttatcga   1800

ttccccatgg ttcttggttt tttatacatg tattgaatct ggttactaga attatgttct   1860

tcgacggacg tctttcagat ttaaattgca ttgtaggaaa tatgatttgc tatctgagta   1920

acgtttttcc agagtattct tgattgcgcg atctatcttc aattgttaaa ttgtttttgt   1980

ttaattgggg tcatgacagg tg                                             2002
```

<210> SEQ ID NO 6
<211> LENGTH: 1459
<212> TYPE: DNA
<213> ORGANISM: Cucumis melo

<400> SEQUENCE: 6

```
tcggtgaaac tcgaaagatc tcgattcgaa actctattgc ttaagaacct ggtgaagctc     60

gagagatctt gatacaatcc cagtgcccta actcttcaac aagctaagca agttgtactg    120

tggggctcaa tctcggttca atctcgacgc acctgatgct ttgttccctg tctactcgat    180

gaagaagcaa ttacttctca ggacaactcg gtacccctaa atacagattt tgagcttcgt    240
```

gatcctacaa ctgaaatcaa atagaaaaac taataagtta gttagagttt gttatattta 300
ctgccattaa ataactctgt aatgtaaata ataaaccatt taactcaata tgaaatatag 360
aatgagaaaa agaaaaagaa aaagttaaag agagagagga agaaaactca ttttcaaatt 420
ctctatactt gtttgatcct tgaataagtt gaataaaagc tctatggcgg cttcaaagtg 480
gatgtaggca ctattagtcg aaccacaata aatttgttat gttcttttgc tattccttgt 540
aatctccata aatattttct tactaagctc tagaaatctg cttgtcaaga gattaggtat 600
catttatgcc ttttatattt cctttcggtt gcatatcttg agctagttaa gatcgagagg 660
ttactgttgt tgaaaccgag attagtatct ttggattaac acgtgcctac caaaatttga 720
aattttgtat ttaccccatt cattggataa taagcaattc ttatagtgtt atcaattaaa 780
ctcctataaa gtgtaataat tgaatccatg aactattttc atatgtaatc ttaataaaat 840
gaatttagaa gtttaattaa aataatatat tttgtatgct atttttcaaa gtttgaagaa 900
tgtgttaatt gatacacata caaaaaatct aggttttaca tgaaaaacta tggaagtgaa 960
agatagcatc taatatttta tgacacaaaa tgcaaactaa tatataaagg atttaattaa 1020
tttttatagg tttcaaattt gttagacttg tcaaatacaa aattttattg aaccaaatac 1080
atacaaacat caaaattaag aacagaaaat ctaaattcaa atgaaattta ttaatagaaa 1140
aattagaaaa aagaaaaaga aaataaaagg aatcgtattg ttttttcctt ccttttttccc 1200 atttgagagg tgaataaagc taattgagct gctctaactt cctaatcttt atgctttccc 1260
cataaagctt tcccaactgc gcgtaatcgt ataaatggaa aattgacctt tccaactaga 1320
ttcttccaga actaaacaat acgtaacacg caagtaatca aagacacgtt tcattttcct 1380
atagaatatt atagttattc gtgattaacg gaagtcggca attttaggta taaatacgtg 1440
aattctcgag cgctaattt 1459

<210> SEQ ID NO 7
<211> LENGTH: 1507
<212> TYPE: DNA
<213> ORGANISM: Cucumis melo

<400> SEQUENCE: 7
agtcgaacca caataaattt gttatgttct tttgctattc cttgtaatct ccataaatat 60
tttcttacta agctctagaa atctgcttgt caagagatta ggtatcattt atgcctttta 120
tatttccttt cggttgcata tcttgagcta gttaagatcg agaggttact gttgttgaaa 180
ccgagattag tatctttgga ttaacacgtg cctaccaaaa tttgaaattt tgtatttacc 240
ccattcattg gataataagc aattcttata gtgttatcaa ttaaactcct ataaagtgta 300
ataattgaat ccatgaacta ttttcatatg taatcttaat aaaatgaatt tagaagttta 360
attaaaataa tatattttgt atgctatttt tcaaagtttg aagaatgtgt taattgatac 420
acatacaaaa aatctaggtt ttacatgaaa aactatggaa gtgaaagata gcatctaata 480
ttttatgaca caaaatgcaa actaatatat aaaggattta attaattttt ataggtttca 540
aatttgttag acttgtcaaa tacaaaattt tattgaacca aatacataca aacatcaaaa 600
ttaagaacag aaaatctaaa ttcaaatgaa atttattaat agaaaaatta gaaaaaagaa 660
aaagaaaata aaaggaatcg tattgttttt tccttccttt ttcccatttg agaggtgaat 720
aaagctaatt gagctgctct aacttcctaa tctttatgct ttccccataa agctttccca 780
actgcgcgta atcgtataaa tggaaaattg acctttccaa ctagattctt ccagaactaa 840
acaatacgta acacgcaagt aatcaaagac acgtttcatt ttcctataga atattatagt 900

```
tattcgtgat taacggaagt cggcaatttt aggtataaat acgtgaattc tcgagcgcta    960

attttccata cagactcgaa atactctaaa ctttctcatc gcgctttatt cctatttcgt   1020

aattcgctct tcttcaacct ctcaaggttt tcatcttttc tctatcttct gttttcagat   1080

tgcatctttt ccccctcctg ttcgattaat tgatgtttga attttcgaga aacgatttga   1140

agtctttgtt gtatttttca tttctgttcg ttaggtaggt cgatttttaa tcgtgatgtc   1200

cgacgttgtt cggatgattc acatttggtt tttgtcatct tctttctatg ttgtgattat   1260

catgattttt atcttttttt cttctcaaga tttgtaattt atcgattccc catggttctt   1320

ggtttttat acatgtattg aatctggtta ctagaattat gttcttcgac ggacgtcttt   1380

cagatttaaa ttgcattgta ggaaatatga tttgctatct gagtaacgtt tttccagagt   1440

attcttgatt gcgcgatcta tcttcaattg ttaaattgtt tttgtttaat tggggtcatg   1500

acaggtg                                                             1507
```

<210> SEQ ID NO 8
<211> LENGTH: 964
<212> TYPE: DNA
<213> ORGANISM: Cucumis melo

<400> SEQUENCE: 8

```
agtcgaacca caataaattt gttatgttct tttgctattc cttgtaatct ccataaatat     60

tttcttacta agctctagaa atctgcttgt caagagatta ggtatcattt atgcctttta    120

tatttccttt cggttgcata tcttgagcta gttaagatcg agaggttact gttgttgaaa    180

ccgagattag tatctttgga ttaacacgtg cctaccaaaa tttgaaattt tgtatttacc    240

ccattcattg gataataagc aattcttata gtgttatcaa ttaaactcct ataaagtgta    300

ataattgaat ccatgaacta ttttcatatg taatcttaat aaaatgaatt tagaagttta    360

attaaaataa tatattttgt atgctatttt tcaaagtttg aagaatgtgt taattgatac    420

acatacaaaa aatctaggtt ttacatgaaa aactatggaa gtgaaagata gcatctaata    480

ttttatgaca caaaatgcaa actaatatat aaaggattta attaattttt ataggtttca    540

aatttgttag acttgtcaaa tacaaaattt tattgaacca aatacataca aacatcaaaa    600

ttaagaacag aaaatctaaa ttcaaatgaa atttattaat agaaaaatta gaaaaaagaa    660

aaagaaaata aaaggaatcg tattgttttt tccttccttt ttcccatttg agaggtgaat    720

aaagctaatt gagctgctct aacttcctaa tctttatgct ttccccataa agctttccca    780

actgcgcgta atcgtataaa tggaaaattg acctttccaa ctagattctt ccagaactaa    840

acaatacgta acacgcaagt aatcaaagac acgtttcatt ttcctataga atattatagt    900

tattcgtgat taacggaagt cggcaatttt aggtataaat acgtgaattc tcgagcgcta    960

attt                                                                 964
```

<210> SEQ ID NO 9
<211> LENGTH: 1022
<212> TYPE: DNA
<213> ORGANISM: Cucumis melo

<400> SEQUENCE: 9

```
tgacacaaaa tgcaaactaa tatataaagg atttaattaa tttttatagg tttcaaattt     60

gttagacttg tcaaatacaa aattttattg aaccaaatac atacaaacat caaaattaag    120

aacagaaaat ctaaattcaa atgaaattta ttaatagaaa aattagaaaa aagaaaaaga    180
```

-continued

```
aaataaaagg aatcgtattg ttttttcctt cctttttccc atttgagagg tgaataaagc    240

taattgagct gctctaactt cctaatcttt atgctttccc cataaagctt tcccaactgc    300

gcgtaatcgt ataaatggaa aattgacctt tccaactaga ttcttccaga actaaacaat    360

acgtaacacg caagtaatca aagacacgtt tcattttcct atagaatatt atagttattc    420

gtgattaacg gaagtcggca attttaggta taaatacgtg aattctcgag cgctaatttt    480

ccatacagac tcgaaatact ctaaactttc tcatcgcgct ttattcctat ttcgtaattc    540

gctcttcttc aacctctcaa ggttttcatc ttttctctat cttctgtttt cagattgcat    600

cttttccccc tcctgttcga ttaattgatg tttgaatttt cgagaaacga tttgaagtct    660

ttgttgtatt tttcatttct gttcgttagg taggtcgatt tttaatcgtg atgtccgacg    720

ttgttcggat gattcacatt tggtttttgt catcttcttt ctatgttgtg attatcatga    780

tttttatctt tttttcttct caagatttgt aatttatcga ttccccatgg ttcttggttt    840

tttatacatg tattgaatct ggttactaga attatgttct tcgacggacg tctttcagat    900

ttaaattgca ttgtaggaaa tatgatttgc tatctgagta acgtttttcc agagtattct    960

tgattgcgcg atctatcttc aattgttaaa ttgtttttgt ttaattgggg tcatgacagg   1020

tg                                                                  1022
```

<210> SEQ ID NO 10
<211> LENGTH: 479
<212> TYPE: DNA
<213> ORGANISM: Cucumis melo

<400> SEQUENCE: 10

```
tgacacaaaa tgcaaactaa tatataaagg atttaattaa tttttatagg tttcaaattt     60

gttagacttg tcaaatacaa aattttattg aaccaaatac atacaaacat caaaattaag    120

aacagaaaat ctaaattcaa atgaaattta ttaatagaaa aattagaaaa aagaaaaaga    180

aaataaaagg aatcgtattg ttttttcctt cctttttccc atttgagagg tgaataaagc    240

taattgagct gctctaactt cctaatcttt atgctttccc cataaagctt tcccaactgc    300

gcgtaatcgt ataaatggaa aattgacctt tccaactaga ttcttccaga actaaacaat    360

acgtaacacg caagtaatca aagacacgtt tcattttcct atagaatatt atagttattc    420

gtgattaacg gaagtcggca attttaggta taaatacgtg aattctcgag cgctaattt     479
```

<210> SEQ ID NO 11
<211> LENGTH: 716
<212> TYPE: DNA
<213> ORGANISM: Cucumis melo

<400> SEQUENCE: 11

```
tcgtataaat ggaaaattga cctttccaac tagattcttc cagaactaaa caatacgtaa     60

cacgcaagta atcaaagaca cgtttcattt tcctatagaa tattatagtt attcgtgatt    120

aacggaagtc ggcaatttta ggtataaata cgtgaattct cgagcgctaa ttttccatac    180

agactcgaaa tactctaaac tttctcatcg cgctttattc ctatttcgta attcgctctt    240

cttcaacctc tcaaggtttt catcttttct ctatcttctg ttttcagatt gcatcttttc    300

cccctcctgt tcgattaatt gatgtttgaa ttttcgagaa acgatttgaa gtctttgttg    360

tatttttcat ttctgttcgt taggtaggtc gatttttaat cgtgatgtcc gacgttgttc    420

ggatgattca catttggttt ttgtcatctt ctttctatgt tgtgattatc atgattttta    480

tctttttttc ttctcaagat ttgtaattta tcgattcccc atggttcttg gtttttttata    540
```

catgtattga atctggttac tagaattatg ttcttcgacg gacgtctttc agatttaaat 600
tgcattgtag gaaatatgat ttgctatctg agtaacgttt ttccagagta ttcttgattg 660
cgcgatctat cttcaattgt taaattgttt ttgtttaatt ggggtcatga caggtg 716

<210> SEQ ID NO 12
<211> LENGTH: 173
<212> TYPE: DNA
<213> ORGANISM: Cucumis melo

<400> SEQUENCE: 12
tcgtataaat ggaaaattga cctttccaac tagattcttc cagaactaaa caatacgtaa 60
cacgcaagta atcaaagaca cgtttcattt tcctatagaa tattatagtt attcgtgatt 120
aacggaagtc ggcaatttta ggtataaata cgtgaattct cgagcgctaa ttt 173

<210> SEQ ID NO 13
<211> LENGTH: 2000
<212> TYPE: DNA
<213> ORGANISM: Cucumis melo

<400> SEQUENCE: 13
cttattcagc gctttcctgt aaaattaaag acttgatgag ggagaaaaag aaaaccggtt 60
cgcagcttca agaagacggc ttccgaataa gaatcagata ctcgatgatg gggaaacaat 120
aacaaagata tcaaaagaaa tcatgaaaca tagcataaga acgaaaaccc agaggtgaag 180
aacagtgccc aaacgcaact ttacccaaag aacatgtata aaacgtcttc cagacgttca 240
aaataagaaa gtggacaaaa tcaaagctac aaacgatctc caataactag atggaaaaca 300
ctaattgcac tagagatttt gaatgctttg ttgttgattt ataatcctcg acttccaaga 360
aaaagtaaca agtagaaatg aacgaatcag atccgcaatc gaagatctga aggcaagata 420
aggtaaggct aaagaaccat aggaaaacgg taaaaacgtc caaaacagtg tgagaaatat 480
cgcagattca aaggtccgaa ccctaagaac ggtgttatgc agctataaag gtgagaatca 540
aaaccctcta tccataacgt ggacggcgcg gttgaatcat tgtcttgttc cttgaaactg 600
aaggtatgcg agacatagaa ttcgatctca ctattatctt ctaatcaacg acgaagtaaa 660
gaagtgaaat ccagaacaaa gaatggagaa ttggaaatga caagaaaaac ggcagaggaa 720
agtggaaaag tgaaagcgga ctcacctaga tcaatgccct tggctggtcg agcttcagga 780
acctgtcgtc ggagagaaag agaaagagaa aagagcaaga gagagagaga gagagcacaa 840
ggagaagaga acgaggacaa tggaggcttt tgtttcgata ctccctgatc tggaattcta 900
taataacata actataaact tctctgggtt ggcccatcat cacgtatatt gggcttttag 960
cccaattatt tgttcactgc tcatgggccg gtgattttgg gctttcttct gggccttggt 1020
acataacaac ccagtatatg acgtattttc ggtgatagct attttcaaga acaccaactt 1080
ttttgttcaa caatgtggag atcaaataac agtatgtata tatacacaaa catatgctca 1140
tttatgaaaa atagaaagaa aaagaatgtt ggtaatttgt tacaaaatta taatttctct 1200
ctctttgttt gatttcatga acggtgtgtt ctatataaaa caatgaaata acataattat 1260
taaaatgatt cttaaaacat gatgatttca atattcatgg tttacatttg gtgggatgat 1320
tcgtttaatt attattgata atgtatagtt attgtgtgtc ccgttttctt tttctttggt 1380
ggaagaaaag aaaaaagtag gaaggcatgt aatattgcga tccttcacgg gacagatcca 1440
ttttccaatg tgatcgagta ctagttaggt ggagagtgga agaatcttcg tgcatgcata 1500

-continued

```
aatcaagtca caacttgcca atttggaaag aatcatgtta tattctacct ttactttcaa   1560

gtagggttaa gtgaattaga ccacaacgaa gcaatcaagt ccaaccaaac tcacttaggt   1620

caagcagttt agtgatatag acaggtcagt ggtcgttttt ttaatactaa gaaatgtcaa   1680

ttctatctag ttgactatta ttcatataga aggagaaaaa tgataactat gattgtccca   1740

caaacaacaa ctaccgatcg atctaaacca acaagtcgat gattggtgcc actttaaatt   1800

taaatctgac gccactcaat tgatgatcac ccctattcaa gcacacaaga acgcatgctc   1860

ttaaaacatt tggtaatatg attggaatta gtacaaaatg tttattcgat ctatacaaac   1920

aactcctttt taacacaaat gttttattgt actttcccgt gaaatggggt tagtaaaact   1980

atggagttaa taaaacataa                                               2000


<210> SEQ ID NO 14
<211> LENGTH: 2000
<212> TYPE: DNA
<213> ORGANISM: Cucumis melo

<400> SEQUENCE: 14

tataacaaaa tatgtgaaat tagccattat gtttgtcctt tcgttcttct tattcacttc     60

gttgcgattt ctttctatcg tctatcgtct ttcttctttt ttctgttgaa atttattttc    120

atcgtttttc ttctttttcc atcgtgaaaa aaatagtcaa atctaaatga tcgtgtataa    180

agaataaacg atcgtgtaga caaatctaaa tggtcgaata ttaagaaaat tgataggaaa    240

atttattcat tagaaaaatt ttagtaagaa aaattagaaa tgaaagggtt gaaccagaaa    300

gaaataaaag taatagacaa atgaaaattt taaataaaaa gaaatttggg atgggtgcat    360

ttactattta gtcttgagtt ttaattcttt tattacttta cataagatgt attaaattaa    420

agaggtaaga tagaattttt ttttaaaaaa aactatcatt agtaaattta acaaaagtga    480

catagcacca ttttcgttaa aagaataatt gttttatgta gtaaaattgg tagaaatatt    540

ttttaagtat agcaaaatat ctttgtcttt ttatatcttt cactgacaga taataataat    600

ttattaatat atcatttata tagtcccatt ttcggtaaat tttaatattt gaacataaaa    660

cactatttaa aataatgaaa aaaaacttta caaacttttt tatttttatt atatttgtaa    720

atatttctaa aaaattttac atttaaaata atattttcaa ggttaataca gaagaaaaaa    780

aacaaaaaaa gaggaaaagg caatttaaga agaatgacaa gaaaatcggg aggtggtgtg    840

gctaagagga agaagggacc ggttcttcaa gatccaacgc tccacattca atctcacttc    900

cttcttcaat tccgtcttct ccgtttcctc ctttatatgc ttctctcttt ccctcccttt    960

ctttctctcc ttcaatcaat caatcaatca atcaatcaat cctcccattc ccattacatt   1020

gccaaaaggt tctattctca ttctctacat ccatttccct ttctttcctt cttcttcctc   1080

tgtttcttct tcgtttcctt gattcatttc tctttgtacg ttccttcctt ccttctgcat   1140

tttgattatt ttcttttgtt ttacgtccgg aattgcaatg tggtttatct ttatttctgt   1200

ttttggacgt caagatgcct gttgttttta acattttgat ttgattcatc gttcatggcg   1260

taatcatgtc ttttggaatt gtttgaaatc caaggatcac attgatttca ctattgtttc   1320

atttgttctt ttttgttaat tttgtataat gaatcgtata ggggatcatt tttccattgg   1380

ttctcttgaa aatctttaag agttgcatta tgtatactaa gtctctctta tggcgtctgt   1440

ttgagtgaga attgataaaa gatccatggg aggaagaagt tttctttcat gaggcttggt   1500

tttattcagc tgtttcttct cgttgcaatt tgttgaagaa gggacatggg tatcttttac   1560

atcaaagtat aactaactat ataattcaat ttggttgata aagtagatac atgtaggagt   1620
```

caaccgattt gagtgtataa taatgttgtt atgtcccttg caacttaatg tagtgcatat 1680
ttgggagtga ttataaaatt gtataaatca ttttatgttt agaatcatct tgaaacacgt 1740
tttttagtat ttaaaaacta atttaatatt tagttttgca cttttaaatg aaatttttgt 1800
ttcactaata ttagttttga ttcattaaat gcatgctcca tcgtaatatt aaaagtaact 1860
agtgatttta accattttat aatcacatgt ctgtgatata gtgaagtgta cggctgcctt 1920
gttgagaatt gttacccttt agaagaaaca caggatgtat ttgatgttta acttgcattt 1980
tcttctggca ggcttagaaa 2000

<210> SEQ ID NO 15
<211> LENGTH: 1990
<212> TYPE: DNA
<213> ORGANISM: Cucumis melo

<400> SEQUENCE: 15
tatttgtaca atgaaaatat ttatttcttt tctcgattct ttaacaaaag ttcaaaatct 60
tttatcataa atacaaatat ttagtaattt aagtttagac taggtgtatc agatgtgcac 120
caagtgtata ttacgtgcat caagtatata tcaaatgtgt accaaacgta tatcacgtgt 180
atcaagtgtg tatcaagtgt ctatttgaag tcaagtgcat taagaatata tcacatgtgt 240
accaaatata tcaaaataaa tactgattga gcatcaagta tgtctattag tagtgtatca 300
agtgtattaa ttaagtttgt agcaaaggtg tatcatgatg tataacgtgt attatgtggg 360
ttggtttttt tttttttttg tcatttttgc aaaagtaatt aagtttgtgt tatgaaccta 420 atttttttaaa tttcttttttg tcacgtataa gagacttgaa aataggttta aaaggtctta 480
agggtatttt agtttgactt ttttaaaaag tatttatatg atatttaaaa attagaattt 540
tttagaaaga ataggagttt tataaattat tcttttaaga aaaattgcat cagatgacaa 600
aaaaaattta gaaataagca gcccataata actctttaaa tttgctatca gacgactatc 660
cgagggttat catcttttaa atttgctact tttacaattt agaaaatgta gtgacatgga 720
ccctattatc ataagatttt tttttgctat ttttgcaaac acatgttctt ttaaaatgac 780
ataattattt aaaataaaaa tataaagtta tttgatggat cttttgaacc tatttttaaa 840
agctaaagta ctaaaaagat acatattgaa aacttgaggt caaatgggct attattataa 900
atatgtggac taaaaatgta catttctaaa acttagagac taaatgcaca tatttaaaaa 960
agcatgtgaa ctaaaaaagt cgtttttcct aatatttttt tacaacaatg actaaattga 1020
acctcaaatt tgaagggtgg aaaaccatac taattattca ctaatgaact aaactcattt 1080
gatgatttca agacatatga ggttcattga gtagttgggt ttgaggggat gaaatgagtg 1140
gtggaagaaa gtttatgtaa cgacccaacg aaataggaag gtcatcccaa ggaagtcgca 1200
catccaatga gtaattacca caaaacaacc tctccttttt tctcaaattc ccttttaata 1260
aataatttga ttccccattc cttcctttct cccttggcag ccttctcctt ttttcaaagg 1320
tttttgtttt ttcttttctt ttttaaattt cattcctttg tttctctctt tctttcttca 1380
ttaacattct tcttatttcc tcattactga tcatctcctt ttcttggtat tattcttctt 1440
tcttttctca aagttttgtt tttcattgat gtagatgttt ttgtatcaat caatggaaat 1500
ttgagttttt cttatctcat tgtatcatca ttgagtgtgt gtttatgtta gggatccatt 1560
attaggatgg atgagaatca taatttcatt gctaatctat gaaccatgaa taaagaaatc 1620
taaatccaac atagaagata gaacatttgc attgtgttat gagtaaccag ctctgtcact 1680

-continued tcaattggtt cttctacaca tttgatggca atggctttgt ttgatattcg tgatggcatc 1740
taagcattgg ttcttcctat gtttttcgtt ggctcttggt ttgatttgca attagtgaag 1800
agcatgtttg gaatgaatga gttgaaatca cctttaacat ttttaaaatc actttaaata 1860
ttaaattaat tttgagtgat aaaagtaatt ttaacaatga taaaattact ttcaaatgtg 1920
ggccgaatca aattgtctag aatgtttagg gttctccaac taatagcaat ttatccaaac 1980
agggtaaaaa 1990

<210> SEQ ID NO 16
<211> LENGTH: 2005
<212> TYPE: DNA
<213> ORGANISM: Cucumis melo

<400> SEQUENCE: 16
ttgttagagg agttagcttt tcagggagtc ggttacaact tacaagacag acaaccatac 60
tgtacaatca atcactactg cctcaaagtc gaaaccattt aataccagtt gagcctcatt 120
gtgactgcat aattttgacc cctaccacga ggtaatttca gttcaaatca attgtatctc 180
tcttctggat atcagtcaag aatctcatgt tctcaagtta tagtacattg ataattactg 240
tgcattttta ttaatttatg agttaaaatc ctgctgatta attcaactaa aggaataaaa 300
tagttattgg catttggatg agaatagaat gtgaatccca tcattcatcg ctagattgga 360
ccgtaattat aagtgagagg gagaaacttc tgttgctatt cccttttat ttcttaattc 420 atttataaat tgtttttagg ccttttatat atatatattt ctaccatttt tacatttaaa 480
attcttttaa ctttattatg tatggactca aactaacaag ctttatttga taaaattgtt 540
caaactatta tattagtttt atatttgtaa accataaaac aaatccataa aattccacct 600
gcatcactca ctcatgttgt tgaatggtac gaaataaaca atacatgtga aagatgaaaa 660
taagaattgt tctcttatta aatctaaaat ctagattttc tttttagtac atttaacact 720
tcaatgaaag gtctaaaaca ttattgaatg acgtcacgaa ctattacaaa agattattcc 780
gatttatctc aaaaggggtc tatttcacta attttggtgt cccacatctg taaagagaat 840
tttcgtgata tgtgtagata tttaaatata attgaattcg atgaaagcaa agcaagaatc 900
gatatccgta gttattttga tatagatcgg tgataaataa aagacaatat gcataaagtt 960
tgtgggtaca gagtcggcta gttgcaatga ggggtatggc cccaagactt ttccccaacc 1020
ccaacggtca attaatcacc ccaatggggc atcgaatctt ccccaccatt ttccttttct 1080
tcgccgactc ttctacccat ctcttttgcc gactctttct cacaggtttg attaaatccc 1140
attcatattc agatacacta tttcaaaata actcgcaaat taatttgttt tttaaatatt 1200
ggtataataa taaaattaat tataaattgt gacctaaaaa gtactttgtg gaagagggga 1260
tatagtctgt ctaatatatt attgattaaa tatataatag aaccataaat gcaaaccact 1320
agaattgtta ataaaaatca acgctctttt aagtctttcc atagaaagaa aggcaaagac 1380
gcgcaacgtc tagaattttc tttataacgg aagctaactc tgttataacg gccgtccaca 1440
taatatggta gatttaaaat gacgtcagca tgtcgcttct aaatttgggt ccaaaggggg 1500
gattcattta tagggaaggg aaacggcaaa tgcaagcata gtgagtaaat acgtggcggc 1560
aaagtaatgg ataattctgc ctctgccgtg acgacattgc ccttccattt cactataaat 1620
acacctcctc tatccctcga tttcttcgca attgaatttc tcttctcatc tctgtcgtag 1680
caaaccaaat cgatttcttc aaaggtattt cttcctttcc ttttttttt ttttttttt 1740 tttttaaatc atgttgttca aactttgaga gatgaaatga ttaggggctt tcaaagtggt 1800
tttcgtttga tatgtttctt agatcgatag ggtttagaat cgagcatcct tgtaggtatc 1860
ctgaggtttg gtggttggat ctgcttaatt tttatgtggt tgcatggaaa attgggattt 1920
tttttttcta attacgtgat tctggaaata ttgatctgtg gttcagatgg aattgaatct 1980
gatctttctg ttttgttctg tatag 2005

<210> SEQ ID NO 17
<211> LENGTH: 2004
<212> TYPE: DNA
<213> ORGANISM: Cucumis melo

<400> SEQUENCE: 17
tagaaaaaaa ttgaagatct tcttaatgct aataataaaa gcatatataa aaaggcttca 60
tattacacaa gcatcttaaa accaaaccga acttgatttg aaattatccc actaattctg 120
tagatttcac caaagtcctt aacctttata ctaacatctg catttgactc tttcatttga 180
cctccaacat attctttctc attttccttc cattcaccac aaaaaccaac aaatacaaaa 240
aaccacaaat acatagaaaa ttaataaaaa aatcaaaatt tcgagatgaa atcattataa 300
actcatccga taactttgag atttgaaacc ttacactata taaagaaact catccgataa 360
ctttgaattc gcatcgaaat tacgtaagtg aagacgaaaa tgtaaatgat tagatgcgaa 420
taacaaaaaa aacataattt ctaaacgtaa aacactatat tcaccttatt atacttgatt 480
attttggaaa agtatgaaat ttgagtgtgg gagaggagcc aaagaattgg aaacttgtta 540
ttaggagtcg ttatgaaaca ttttcaacaa gccaatattc tttcacatac tataatgata 600
tacatagaaa taatacaata atatttttga aattgaggca tttttgtcgt aatttatcta 660
aaaatgtcag ggtagattca tcatgtatac aaatctctcg ctatcaaaac tatataaaaa 720
tcttgtgaat gatttcaatc gaaatggacc gagaaaaaac atcgtaacca cctctaaaat 780
cgataaattt gtttcaattt caaatcccta aaactaaagg tgctactttg tacaatttcc 840
cctgattagg gtgctaaagt taaaccctaa ataaaggtgt gtacgtttcc ggaagtttct 900
agaatcccca gcgaagttct ccaaatcgtg gcttgcagac caaggacccc cattaaaatt 960
cgtttcttcc tctaaacctc ctcccttaat tttggcattt tggtattttg gctcctataa 1020
attcaccccc tccttatccc taatcctttg tcttccaaat tttccttcaa agcctgcttt 1080
tcccatttcg tcgtgctttt tcttcatcta aaggtatatt tcagttctag ttttctttct 1140
ctgttgatct cttggatttg agggacgttt gaagttggct ttgtttaatt ctttgttatt 1200
caatctcttt ttttgttaga gttgttgttt aatcgtttcc cttgttgttt ttctcccttc 1260
tagttcgatt ttagaacgct ttttgtgggt tgattttaat ttctccgttt tcttacatct 1320
ttcacaaaga aacgattgaa atcgtgtttg ttttttttcc cacggcatac gttattagat 1380
cttgtagata atgatctcaa tctattgttt agtttttgca aataagaagt tggtttttta 1440
tctccaactt ttatatattc gattcgatga gatgttctac accgttagga tggaaccaag 1500
aagtgaggta agggtgtttg attgaaaaat tgaactgaga agttaaagtt ccttcctaac 1560
tttttaatgg attgtataat tcgttcaatt ccttgtcgtt ccatttttat ttctgtttcg 1620
tttttcgtgt tgctgcgtat cgcttccctt gttgttttcc tcccctattg attttgcgtt 1680
tcttggagtt tctctgtttt ctctcttcat ttttctacaa aaatcaattc tatttttatt 1740
cgttttcaat tcccgagctc cttggaatgt tatccttttc tcctgtgtaa ataagaaccc 1800
gtattcaatc ccagttcata gtttggcttt cccaaataag agcaaaaaga ttgtactgag 1860

-continued

```
aagttgaaga tttcaaaatt ttgtacatga tttcttctaa tttatcaatt tgattggact   1920

ttttgtatat agatttggtt cttgagctat ttatgttatg acgttttcat attgaggcca   1980

tgcgttgaat tggtttctta acag                                          2004
```

```
<210> SEQ ID NO 18
<211> LENGTH: 1935
<212> TYPE: DNA
<213> ORGANISM: Cucumis melo

<400> SEQUENCE: 18

tatacaaatg acaaaatatc gttgaagtcc aaaaaagatt tattgttggt aaatatcgtt     60

aaagttagta aatagatttt agagaaagga gatatagccc ttgtagtaga aacacacaca    120

caaattgaat tagatgtgtt taatgtttaa ttaaattaga tatgagtcaa cttatatcta    180

atataggaca ttattaaaca aataagaaat aagaaacatg aaacaagaaa aacaagaaat    240

agaaacaata tcaaacacat tcctatttct tgttctaaaa aaagaaaaaa catggtacaa    300

gaaataggaa acggaaaaga ggaaacaagg aacaaatgct accaaacggg cctaagtttc    360

taacaaaatg agctaggtgt agtttattgg tatagatagt gactttcaat tattttaaat    420

ttttttatcc atacctccac gtctttagaa tctttcttat ttatatgtga tcttaattca    480

ttcatgtctc aatcttaaaa ttagaacatt acatgttcat catttttttcc ttttgttact    540

gtgtttaatc tttcctaaca agacaaatag tttaacctta atccacacat tattataacc    600

aaattaaaat aatctacctt caaagaaaac attattataa tcttatatta accacaaatt    660

ataataccaa actctaacgc tccaacccaa cctaggaaga atgacaaggc tgtcataatt    720

tagttggttt ggcacgttgt tggaagttct caaaattatg gaaatattta tttccttctt    780

ctttatccat catcctcctt gggagggtga atttgtgtta aaaaagaata gaaactaaag    840

tctaagtggc aggacttaca ttatgtgtgt atgtggaagt aaaattgcag taacagttta    900

caaaaacaac tcatccatga ttcataacca acttaaatga atataatttt ttgcctaaag    960

attttaaatt aatatataag cggaagaatt aacctataac ttcaagttta acaacacaaa   1020

tattatatca tactgattaa ttattggaat gatgtttagg ctttaaacat aaagtattga   1080

gaggctaatt tgagtttaac tcactaaact atcattaccc tttcaaaata gatccaatca   1140

tccatttatt ataatactca atgaaataaa gcaaaagatg agtaaaataa ttcaccatga   1200

acattgataa ttaattttcc cactaagata aactactact cctcaaatct tcatatgtgt   1260

ttttcctttt tgagttgcac tcaaattttc atagttgaaa tttacccatc aaaacaacca   1320

acaatctttc aaattcaaca aacatttgac cttacaccct ttgatgccaa atccttaccc   1380

tctccctctt ccataaaaat tcttatataa accaccatca ctctcacttc tcaattcact   1440

ctcttctcta ctcccaatca cctgacttgc ctcttactcc accgccaggt tccgccccaa   1500

cttccccggt aagttccagt tcttcagatc tggttaccac atttgatttc ttgcttgtat   1560

ttgacgtggg aattttcata tcggcgtttt ttcgaactgg gttttgcttt atgatcatat   1620

tcttgtagta aaatgccatg aatctgttat ttgattccgt ttttttgga gatcggtcta   1680

gctttatggc catattctgg catttaaatg ccatgaatcc gtgatttggt tgaatttcac   1740

ttccgatcca atgtttatgc tgatattgac atctttgcat tcaatgcaga ggagttttgt   1800

ttcgatttat tactgatctc atcacactga tcttgaattt tttatacttt tatgtgtgtg   1860

tgtgtatttt ctttaatatc tatgccaatt gaactatgtg gttaacttca gagtgttctt   1920

gtgggcagtg agaag                                                    1935
```

<210> SEQ ID NO 19
<211> LENGTH: 1606
<212> TYPE: DNA
<213> ORGANISM: Cucumis melo

<400> SEQUENCE: 19
atatattgta tcgattcttt agttgctcta tgtttttgtt tgcttcattt gtcgattaaa 60
ctgtaaaatt aatttctttg acaaggaaaa agatataatt taattctata atttattaca 120
atctaatcca tatggtttaa taaaacactg aaaattgttt atgaaaattt tatcgaacta 180
caagaactat taataaagtt tttttaaacc gtaaattgaa tgaattttct ccacggtgta 240
aatttgaaaa cattaattaa ttaattaatt aattttaatt tcaaggtttt ttctgaccca 300
tgaacctatt ttatgatata agttgttcag ggttgcaat agtaaccaaa taaagttgat 360
cagaaaaggt taacaactca tgaaaacttc caaatgcatt tgtgtttcaa ttattttctt 420
aaccctcttt ttttggtaat tttagtttaa aaagtgagtc ggttgatcat tattgttctt 480
taatttcttg ggagaaaaat attaatgttg attatggtga tgagttaagt ccaattcttc 540
atcaaatcat accaaattag gaacaaaaaa aacatcaatt ttaaggtgca aatccatttc 600
taatggctaa aatgtcaagc atcccaccaa accaacaatc tctaaaccca tttttactcc 660
actaatctaa tgtttaataa taatcaacaa ggttttgctc attccttttt tagttaataa 720
tcatttaaca ccaaagctca aaagtaccca cccaatggat caaaatcgag aatatatagc 780
atttaaggat ataaagacta gagataataa taacctagct tagagcttaa agggatacac 840
tagccatcaa gtcaatttgg tagacaatct aaaaacaaat aattcgatga aaataaagtt 900
gtatttttgt gttttcaaac atgttttaag acgaaggttt ttgataaatt tgatctcaat 960
aggtaaacaa tggtaattac tcgattataa ttactcacta aataccaaat cgaatataaa 1020
ttattactaa ttaattatga acatgtttta cattttaaaa aatgaataat ttttttttta 1080
gaatttgtgt tattgaaaat aattttcaaa acaatattga atgaatctta agtgaaatca 1140
atgtattaaa agaacataaa acataatcta gatggtctat cgaacaagct agaaaatatc 1200
ttccataaat ccaatgatta agacaggcag gcaggcatga agataagagg attggattaa 1260
ttggtgattt taagttatga ataaagacac aagaactagc agctctcctc ttcttgtcac 1320
cttcctttgt catccagctc acacaactcc aacttggaat ttgacaggtc tctcttcact 1380
catacattcc cacatgaaat tattaattga atcttcaaca ttgtctttga ttcttcagct 1440
gcactgtcct tttccaccat ttttttcttc aagataaaga ctaataaact ccttatatat 1500
tcctctcttc ccattcacct gtgcatactc acaaagcaac tgccatttcc ttcttgttta 1560
tctctgtttt tttcttacac atttgttgaa ctttccctct gaaaaa 1606

<210> SEQ ID NO 20
<211> LENGTH: 1487
<212> TYPE: DNA
<213> ORGANISM: Cucumis melo

<400> SEQUENCE: 20
taatgaattt gtatttgtta gtggattgag tttatatgat attaattttg acccaaacag 60
ttgagtacgt aattaatgtg gcttgcattg aaagtgatat gggcatatag tatgtgtaga 120
atgtagctga cacaacacat taacaaaacc caattttaac tttttctttt tctttttctt 180
ttaattttat atggatcaga tcacatgtca ttttccatta caactcactc tctaccaatc 240

```
atcccatccc ataggccata ccccataaca tccctttcta aatatctaaa tcatctccct    300
aaattattac atttttttc tctcaaatat aactattcaa ttcataaata ttattctttt    360
tttagctctt attatttcaa ttatgatttt aaatattcct tttcaattta cgacctttta    420
tttaccatat caacatttta attctactca attaaagatc attataatga aatttcaggt    480
ataacaaaat aaataggtgt gatataatga tggactacta atttcactaa tttcgtcatc    540
tgaaataagg acaagttcca actatcacta ttgtgaaaac ctcataactc ctaaaagtgt    600
taaaattgga ccctcaagtt tataataatt ttgcaaattg aatcccaaaa ttaaataatc    660
agtataattt atacgttttg agagtcaaat ttaatatttg aataagcttg aatacttaac    720
ttctaatttt gaaaatttaa aaatgcaact gcgagagtaa cttttgcaat tagccgtcga    780
aacaattaat tatattggtt aatttatgtc tcattctctt ttgatgacca taaagataaa    840
cccatttata atataaatat caagcaaagc taaaacaaaa tctttttttt ttcaaattag    900
atctaaatat gaataaaagc agaactttct agaagtacaa atttgattat ttttcttgag    960
ataaaatttt cgctatgaac ctttttataa taggaaaaag agaaaaagga tggttttata   1020
taaatgtatg ataaaaaggt aataatatcc attgtaatag taaaaaagaa aaaaagaaaa   1080
aaagaaaaag caattttctt tttcatgatt aggaaatata aaaacaaaaa ttggctccca   1140
attgacatct ttaatcttct ttttcttttt cttagaaaat aaaattagtg agagaaggaa   1200
aaaaacgaag ggttgagaga tagagagaga aaaaattgat ttttaattta gtttattttc   1260
ctttttggga gcacaaaata aatagataaa taaaatatta gtttgcaaaa aagcccctcg   1320
agtttatctt atttgctcaa aaaagcaagg ataaatacct cccgacatcc ctgtttatcc   1380
ctctcagttt cataattcca ttggttcgat aagaaaacaa ttctcccaat attcccgctg   1440
tagatctcgt cgattttccg tttgtttccc gggaagatca atcaaag                 1487
```

<210> SEQ ID NO 21
<211> LENGTH: 1448
<212> TYPE: DNA
<213> ORGANISM: Cucumis melo

<400> SEQUENCE: 21

```
ggtgtcttgt tgtaaggaaa tggaaagaaa agagaaaggc tcttgttgtt gtccttgttc     60
tgtgtatcga tgaaaatgga tcgacgcgaa gaagatgaag gacgagagtg gggattataa    120
gacagagaaa ctccgaaatt tgagggctaa tatggtaata acaaatggcg ggatactttc    180
aatggacgtg gacccattgc ttctttaact caccgtctga tctttatttt acggtcatga    240
tttccctctt tccccaatat ttttgggagg gaaaaccaac tttgtttttg taattttaat    300
catttttcct caaatcgtaa aaaaaaaatt atagattttt tcaaaaatag aaaaaattca    360
tataagaaaa ccaagataaa atattttgaa aaatatccta ttttttactt cttaaaaata    420
attcataaaa gaattattat aaatattaaa aaatatcagt accactatag acaactattt    480
atatagcaca tatagatata tttgttggtt tttctattta gtatttgaaa acaactccaa    540
aaacaataca tttcaatata cctacgaagc atacaaatat aattattaat tttaataagt    600
tcaaaaatat ctaatggcat ccttatttaa tcaatttttt catcgacgtt atacacggta    660
aggatgtcct aatccttgac cattgaaaga cgtttgtttt gataattata tcttttgata    720
tatacaaaca tttatctcat gattagaata gtcacctttt tatttgattt aacgattata    780
cataatattt gaaaattttt aaatccatca acacaatcaa accaaaaatt tcctaactac    840
ataatctaca agagatttac catcttcttt aaacaattgg tcattacgtt tgttaatgtt    900
```

taaaattaaa tgcaaccata ttgggtgtaa aagccaaaca ttgatttgat tattaaagtt 960
ttttctatat agacttgatg tgtaaaccta ataaccaact tgagctaaat aactttaatt 1020
tctaaaattc attaaactgt cctcatccaa attataatat caaagatttt tgaaatattt 1080
aaaaattccg aacatgggaa ctactggaac ttggcaataa attcaagcaa gaaagaggaa 1140
aacgatataa tcaaacaatt aaaaaacaac agaaatttat ttaatcaaag gaataatctc 1200
atcttttatt tattgggttt tacttttaat actgtgagtg atgattggaa cattaattaa 1260
catttaagac attaatttgc aacaatcaat caaaattgta taaatccact tgttttgatt 1320
tatttgaacc atcacttttt tttttatata tatatataat atgggagtga aagatcaaac 1380
gtataatcat gaaatgaaag atgggatatc attgaactta attaaatatc attgaactgc 1440
aatttttt 1448

<210> SEQ ID NO 22
<211> LENGTH: 1235
<212> TYPE: DNA
<213> ORGANISM: Cucumis melo

<400> SEQUENCE: 22
aaattttaat aattaaaatg aacaattttt caagagtaat agagtttgag agatgtcaga 60
gaagtttgag gaagaagata acaagtggga gaagagaata agtttgttgt gtgaaagaga 120
aggggaaatt tcattcaagg gtatattgaa ctttttactc aaattttgta agtctatttt 180
ttccgatcaa tcctaaaatc acacacaccc ttaaaaaatg gattatattt ggcaattttc 240
catgataaac tcatttttaa tttagagtta ttttttcaac gagatattaa cagttttagt 300
tcatatacta attgtaagaa tagtttcttt taagttgaat agaatttttg aaacttttaa 360
tagttcaaaa ggtatttttg aaacaaaata agaatgtttt tgaacttttt ataaaaagaa 420
ttgagatttt tttgaaattt ttgataaaga gaaaagaaaa gaagaaagaa aaaagaaaaa 480
caagtttgta gaactccgtg ggaaaatcgt cgagggccct gtgaaggaat tttgaaatta 540
taatgagggt attttcgtca acaagggaat ttagacatcg tatataagca tcctcaaacc 600
ctataattaa gcccttcaat ccaattgcca ttctccatct ctcgccgcaa gggtttaaga 660
gcagcttctc tcctcaggtt ggggtttccc cctatcttct tcattcttcc tcttctcgat 720
ttctttcttc tatttgctcg atagtctctt atttcttgag cttttgctgt ttttctcctg 780
tacatcctaa catgaattat aacttggttt tgattttgtc ttttacttct gtattaaaca 840
acttttctta cccttttatt cttctcttct tcttcgtgtc cctgcccttt tgtttttatg 900
ctaattttat gtttctgttt atcaatctat cgaggcgtga cctgtcgttc ttccaatagc 960
gtagatctgc acttaatcta ttctagctga ttggattggt cgtttttcgt ttttttaatt 1020
tattttctct gttctagttc cgataaattt ttttatatat aattaacaag ttctccagcc 1080
aaaagggtta atattgcgtt ggatatttta atttttacgt tatttagatg tgtgaatcta 1140
ataaaattag ggttattcat aaatttcagt aatgatattt tggttatctg ttcttgctgt 1200
tcctgtttcg cagttctttt acctaatatt caagc 1235

<210> SEQ ID NO 23
<211> LENGTH: 2003
<212> TYPE: DNA
<213> ORGANISM: Cucumis melo

<400> SEQUENCE: 23

```
ctagacattt ttgtctaacc tttcaaatgt tttgttttaa tcttccctct cccaaatagt      60

gaaggacatc cagtgtcaac cgtgaacgca tactgtgtca ttcatgaaac aaatcttttt     120

tgtagtgggc attgtcagca tacatagcat gtagaagcta tagacagatg ttgctttgag     180

ttgtatttag ttctctttaa aggaactttg tacaaagtac tgaatgtact ctgttatttg     240

aaatatcaat gaagtcctct taattctttt gagttcccat tccacgttta agttgttagt     300

tgtattcatt ttcgcttact aggtgttctg catgtatctc acagagagac tcacgtgaaa     360

tgtttaggcg gtcacatccc taatgacttt tgaaggggtg tgacacgatc atttgaatat     420

atcacttatc taatagtgac agtggtctat atctttgtct atctgtatag atcattggtt     480

gtttagatat tggtacacta ttgtgtagtg aaaaaagaag aagaagaaga aaaatataat     540

acttgataat gagaaaagaa taagaaaaaa tattgtcttt atgaaagatg aaaaaatgat     600

gctgaagacg agaaatgacg gaaaaggaat aaattctaga tgaagagatg aagaaattct     660

agaagaacaa atctagaatt tataaatggg ataacaataa agataaatgg gataacaaag     720

aaaaaaaatc aagaaattac ctaaatgttt caatcttgct acgccttaat tagaaaaaga     780

aaagaaacaa aaaagaaaat gcacaaaaat atctatatat atatacacac acaagcacaa     840

gaaaaaaatg aatattggaa aaagacgaaa atgcattatt ttttatttgc gttagcgagt     900

tgttgtgatt ttgtgagcaa gaaaaggata tgcaggagaa ttaagataaa taaggaagat     960

tgaatagaga ttaaaagaga aatatgggaa tagagtgggg atgaaaggtt taaagatagg    1020

gagggaggga gcgagagaga ggagaaacaa acataccttg agaaagggag aatgagagag    1080

ataataaata aatacggtga tttggaactc ataaaaagat taaaaaaaaa aaccttagag    1140

taaagacttt tccatgcatt tcgagaaaat ggaaaagaat attctattct atttgcttgg    1200

acaccaagtt ccttttttgtc gcatgcatac gtctatttat ttctgcttgc ttgcataggc    1260

agtttttgtc caaggaaatt cagcaaaggc ggtatcaatt tcgtcaactt agaatccact    1320

cagtactatt tgaagttcct cactaccaat ttgcaccatc caatctcttc tctctccaac    1380

ttcctgccag ggcttaacct ctcttaattc cttatcctta cttgttacct tacctggttc    1440

cactcttcac gtctctctat tctatattgt tttttttca ttcataattt tgttactctc     1500

ttctctgtcc cctttgtctt ggattttatc tctccatata ttcattggaa taatttaagt    1560

tctttgtaga ttttatgaaa ttaccaattt aatttttcaa acagtttttg gatttgttta    1620

atttctcctt ctctaaatcg cgttgacttt atgttatttc gcccttgctc tgttttctct    1680

gatcataaag tatgtacttg attttatggt gaatgctttc ttgatttaac aaccctggtg    1740

ctgaaatctt ttttaaatcc tacttttgtt gttttacata tgttcttact ctaaaatgag    1800

cgacttattt ccttttattc ttccttcttg attaaggatt taatcgttga agtatgctta    1860

tattgtggaa atttggtttt aattgatcat acgagctagt attactagct tctcggtttc    1920

tttggatgag ttatatgcat atgatgattt caattccaat ttttattttg caacagattg    1980

tttttgtgg ctgaaattca agt                                               2003
```

<210> SEQ ID NO 24
<211> LENGTH: 2015
<212> TYPE: DNA
<213> ORGANISM: Cucumis melo

<400> SEQUENCE: 24

```
gatcagagta gcagttgagc aaacccaaac caaacccttt atctatacaa tcctctcaaa      60

ataaaattat tgtttaatta ttcccatatc tattatcatt tttccataat tgcattgaga     120
```

-continued

```
gaaaaaaaaa aaattctagg agacctaaat acaacaacaa ctatttaata atagccccat    180
gtcacattaa ataaaactaa caaaaagttt aatacgtcaa gaaacgatac ttgtggatat    240
tgaggcatgg gtccctcctt ctttgtatat tcaaatctgt ggtctgccat cagataaggc    300
ctttaccata taataagttt tcaaaaaagt aagcaccact tgctgctttt ttaatttaat    360
tatatttaat ctaattattg aaacttatag ttgttttcta tccttattct tttcttctct    420
tcaaacaccc tcctattaat ttaaaataac caaacaacct ttttctttac atagacaaac    480
ttaattagat taaatataac ttgtaattag attaataata tagtttaaaa agaattttat    540
tttaagtaga attattagta aaaatgaatt ttgtggatag atacttggaa tttaagagaa    600
agttaaaaga gagaaaaata tgaaaaggaa ttaaatgatt aaagttgaat gtaagaaatc    660
aataaacata aattccatgt attaaatttt tgtcggtgtg tgaataaata aatatctatt    720
actattagat tacccagctt tgtttataaa aagaaaaaga aaaagttttt aaaatattgg    780
aaaattttgt ataattattg aagaaattgc gtggtctttg caatttgggc atcgttctta    840
tcgcttccaa tgaaggggcc gtttacctcc accactattt ccaacttgtt tttgtaccat    900
tctctatatt tctttgacac ctatattaca cgtgtcttta atccattgga ccttcgtcct    960
actatatttt tacccgaaat gacgaatctg tccttctcat ccacctataa attcacctct   1020
ccggctcctt ccctttcatt cagttttcct ctattcttct ctctatacgt catattcatt   1080
tcttccaagg ttcgtcctcc ttttatcttt cttctttctt tcactttttt tcgctttttt   1140
cttttctttc ggtttttgtt cttttaattt cattcgtttc tttttgttat atggtatgtg   1200
gtatttgttg aattgagatg ttttagggtt tcgatttagg ttttatttct tatcctactt   1260
aagggctatt gtgattttgg agaaaggagt tcttatttgt ttttttttt ttccttttc   1320
ttatctggca gatgcaaatc ttcgttaaaa ccctaaccgg taagacaatc acccttgagg   1380
ttgagtcgtc tgatacgatc gacaacgtca aggccaagat ccaggacaag gaagggattc   1440
ccccggatca gcaacgtctc atcttcgccg gtaaacaact cgaggatggc cgtaccttgg   1500
ccgactacaa catccagaag gagtccaccc tccaccttgt cctccgtctt cgtggtggca   1560
tgcagatttt cgtgaagacc ctgaccggaa agaccatcac ccttgaggtt gagtcgtctg   1620
acaccattga caacgtgaag gccaagatcc aggacaaaga aggcattccc ccagaccaac   1680
agcgtcttat cttcgctgga aagcaactcg aggatggccg cactttggcc gactacaaca   1740
tccagaagga gtctaccctc cacttggtcc tccgtcttcg tggtggtatg caaattttcg   1800
ttaagaccct gacgggtaaa accatcaccc tcgaggtcga atcctctgat accatcgata   1860
acgtcaaggc aaagatccag gacaaggagg gaattccccc agaccaacaa agactcatct   1920
ttgctggtaa gcaattagag gacggccgta cccttgccga ttacaacatc cagaaggagt   1980
ccaccctcca ccttgtgttg cgtcttcgtg gtggt                              2015
```

<210> SEQ ID NO 25
<211> LENGTH: 2006
<212> TYPE: DNA
<213> ORGANISM: Cucumis melo

<400> SEQUENCE: 25

```
accaccacga agacgcaaca caaggtggag ggtggactcc ttctggatgt tgtaatcggc     60
aagggtacgg ccgtcctcta attgcttacc agcaaagatg agtctttgtt ggtctggggg    120
aattccctcc ttgtcctgga tctttgcctt gacgttatcg atggtatcag aggattcgac    180
```

-continued

```
ctcgagggtg atggttttac ccgtcagggt cttaacgaaa atttgcatac caccacgaag    240
acggaggacc aagtggaggg tagactcctt ctggatgttg tagtcggcca aagtgcggcc    300
atcctcgagt tgctttccag cgaagataag acgctgttgg tctgggggaa tgccttcttt    360
gtcctggatc ttggccttca cgttgtcaat ggtgtcagac gactcaacct caagggtgat    420
ggtctttccg gtcagggtct tcacgaaaat ctgcatgcca ccacgaagac gcaacacaag    480
gtggagggtg gactccttct ggatgttgta atcggcaagg gtacggccgt cctctaattg    540
cttaccagca aagatgagtc tttgttggtc tgggggaatt ccctccttgt cctggatctt    600
tgccttgacg ttatcgatgg tatcagagga ttcgacctcg agggtgatgg ttttacccgt    660
cagggtctta acgaaatttg cataccacca cgaagacgga ggaccaagtg gagggtagac    720
tccttctgga tgttgtagtc ggccaaagtg cggccatcct cgagttgctt ttccagcgaa    780
gataagacgc tgtttggtct gggggaatgc ctttctttgt cctgggatct tggccttaaa    840
agaacaaaaa ccgaaagaaa agaaaaaagc gaaaaaaagt gaaagaaaga agaaagataa    900
aaggaggacg aaccttggaa gaaatgaata tgacgtatag agagaagaat agaggaaaac    960
tgaatgaaag ggaaggagcc ggagaggtga atttataggt ggatgagaag gacagattcg   1020
tcatttcggg taaaaatata gtaggacgaa ggtccaatgg attaaagaca cgtgtaatat   1080
aggtgtcaaa gaaatataga gaatggtaca aaaacaagtt ggaaatagtg gtggaggtaa   1140
acggcccctt caattggaaa gcgataagaa cgatgcccaa aattgcaaaa gacccacgca   1200
atttcttcaa taattataca aaattttccc aatattaaaa acttttcttt ttctttttat   1260
aaacaaagct gggtaatcta atagtaatag atatttattt attcacacac cgacaaaaat   1320
ttaatacatg gaatttatgt ttattgattt cttacattca actttaatca tttaattcct   1380
tttcatattt ttctctcttt taactttctc ttaaattcca agtatctatc cacaaaattc   1440
atttttacta ataattctac ttaaaataaa attcttttta aactatatta ttaatctaat   1500
tacaagttat atttaatcta attaagtttg tctatgtaaa gaaaaaggtt gtttggttat   1560
tttaaattaa taggagggtg tttgaagaga agaaaagaat aaggatagaa aacaactata   1620
agtttcaata attagattaa atataattaa attaaaaaag cagcaagtgg tgcttacttt   1680
tttgaaaact tattatatgg taaaggcctt atctgatggc agaccacaga tttgaatata   1740
caaagaagga gggacccatg cctcaatatc cacaagtatc ggtttcttga cgtattaaac   1800
tttttgttag ttttatttaa tgtgacatgg ggctattatt aaatagttgt tgttgtattt   1860
aggtctccta gaattttttt tttttctctc aatgcaatta tggaaaaatg ataatagata   1920
tgggaataat taaacaataa ttttattttg agaggattgt atagataaag ggtttggttt   1980
gggtttgctc aactgctact ctgatc                                        2006
```

<210> SEQ ID NO 26
<211> LENGTH: 2017
<212> TYPE: DNA
<213> ORGANISM: Cucumis melo

<400> SEQUENCE: 26

```
atggataagg cagagcttac cactaacctt ctaagatatt ttcgtcgctc ggcatttatt     60
cttggaggga accacaccaa ctccaaaata cccatgaaac ataggaaaaa atggttcata    120
gtctaagttt ccatttcgat tcggtttggt tcggtctttt attttaaaaa caataaatat    180
aaacctacta atttgatgat gacaagttta ctaatgttaa gtaagaattc atcaatacct    240
aagaatttgc aagtttttct taagtttgat ggtaaggatt tcgtaatcct tgaaatacaa    300
```

```
caattgtata gaaatgaagc gttgcatttt taacgtctat ataggaacac tattttactc    360
caatcaagtt gtaatttgat agataatagt ttgtataact taatgatgaa gagctttttt    420
ttttatatat aatttttatt aatacgtata gttcaaaatt ggaattagct atcactaaca    480
cgtgcttgcg atagaaacaa caataaattc aattagtgtc gcatgtattt catatggtat    540
tgatgacata agagtagttt gatacgatgg gttacatgga gtgacatgat aattgtatta    600
aatttcaata gttatgatct caagtttggg ttgtgtctca ctttgagctt tttgagaaat    660
tggcctcaag actcgcctaa tttaatgttg cttcaagcta tagatgctta catcgtgtgt    720
atgaaacata ttgcactttg atgcttaaag ttaatatagt gagtaactaa ccagatatta    780
cacgctactc ttttaaaatg gtcaaataag aacatttatt agtatgtgat ataacacgta    840
ccctccaatt acatacaata attgatcaac ccaaatcttg aggtatttaa taataacaaa    900
tacaaaatag atggattata tatctgaata gctaaagaat aaagaatatg tgttatgttg    960
tagttacata gtacaataag tcctctcaaa attagaatgg tataataaaa aataagaggt   1020
acattcttaa agaaaatgtt atcaaaactg ttgcatcata ggcattttgg caggaagaat   1080
agtggaagaa aattcttaaa cctaaattct atcgatatta aatagatttt ataagggata   1140
attgcaaatg tagcaattat atttaaaata attaagtata tagcaacatt ttaaaaaaat   1200
ggcaaatata gcaaaatttg tcaaaatcta tcgatgaccg atagatcatg taagtctatc   1260
actgataaac cataggagtt tatcaacgat agaagtctat caccgataaa ttttgttata   1320
tttataattt ttttaaaata ttgctacata gttaataatt attctaaaaa ttgctattac   1380
caccggtttt taaataggac ctaaatttaa ggtatttgac ataaattttg atgaaccaaa   1440
ctagcccaaa tcaaagaagt ttgggcccaa agcccaacga atccacaaca aacaaagccc   1500
acacaacact tcatgaaaat gatttttttca aattttagaa aaaggttata aaatataaaa   1560
aaaataatca aactatccct ggtagctaag tagttattat tatttttatg gatacgaatt   1620
gagtagtatt tattttaaaa taggataatt gatcttagtt tcacttgtga tgaactattt   1680
cactttatta tttgtttgta attcaataaa attagggttt gattgtcaat gataattatt   1740
acaacctcaa tattatactc agtaaagaaa aataaaaatt taaaattgag aaattaatac   1800
caattttttt tgtgaaataa aaggaaaagt aagtaaatat tataaaattt tggacttgga   1860
aattaaaatg cattaataat aatatttagt attattgaat taaaatggac accggaaacc   1920
ctaaaagagg gagtggccac ctataaaagg gaagcactca tctcacccaa acccttgtta   1980
ttcccaattg gccgtgcggc aaagaagcct ctcaacc                            2017
```

<210> SEQ ID NO 27
<211> LENGTH: 1353
<212> TYPE: DNA
<213> ORGANISM: Cucumis melo

<400> SEQUENCE: 27

```
tgagggtcaa aggaggagga agaacaagaa gtaaatgaag tggagtcatg ggaaaaggaa     60
aacaaatgtg agaaaagaaa gaaagccaga gagggaacat aaaattatta gtcagaatta    120
caacagaaaa tttctgaaga attgagtttg tatgcagcaa taatatattg aacaaataag    180
gagagaagga ggaggggaaa ttcaataaac agcagaggaa gaagaatggc gaaaacccaa    240
tatctaaaac tagttaattc aacaagaagc aacacaatca tttcattaaa aaaagaaaag    300
gtaaagagaa attcccagat tcgttactct agattggtcc aatggagtgg aaagggatgc    360
```

```
aatgaaatca gtaatagaaa agaaaagagt taaagtagta ttggtaggta ccgattaaaa    420

atggaaggcg tcggaaggaa acggagagtt caataaaagg aagattcttt gcttcctccg    480

gccatttgat gagaaacaaa aactccgcac ctccaagttc cttccggggg aaggagaaga    540

ctcttctatt ctggggtaca caccctccct tcctgctaca gaatcaaatc taaattattt    600

tggattggaa tggcatggga ttggtctaac ttccaatttc tcgacacaca accccaatct    660

acccgccacc tgtacccagt tttcccaaaa cgcaactcac attgcaattg caattcttgt    720

ctttaataaa tacaaattga tttttctttt tctttttttt tttttttaat aacgattaac    780

cctaaaaaaa ataaagaaaa gaaagccgat cctaaaagta gaattacttt ttttttgttt    840

ttcaaggttc acgtctgtgt ttgcatagac gtgttgtagt cggtgggtgt gtaaattaga    900

gtttgttttt ctcatctctt gttcttttta acgaaatttc aaagatacaa aagcataatg    960

aagaaaagta tacaaagcaa cgtaaactta gcattttgca catgatacaa atttagtcaa   1020

actcaaaccc tggacaacct agcactctct tgggcacgtg gtagatttat gtgaatttcc   1080

ctatttttct tttgaactca caaatgggca aataataata ataaaattta ttgttgattt   1140

ttcttatatt tcaatttatt acctctagtt ttaacctaaa gtttagatgt atataattat   1200

aaatgagcgg tgaaacgggc actgattgat gaatatattg ggccttgggt tggcccaaca   1260

aacctaatgc ccaaatataa aactttggca accatagtta accctaatct gtcaatctac   1320

tctcctcgac tcggtaaacc tgcgactccc aca                                1353


<210> SEQ ID NO 28
<211> LENGTH: 2005
<212> TYPE: DNA
<213> ORGANISM: Cucumis melo

<400> SEQUENCE: 28

cagtgtgctg gaattcgccc ttatccaagg agattaatgt cgagagatta ttatcgaggt     60

ttgaatttat tttgtccaat catatgattc caagagctga ccatcaattc aacagaacat    120

gaaccggaac ctcataccta ttgtaatggt tcacagcatc ctaatacaga acatgaaccg    180

aaacctctta cccattgtaa tggttcacag catctttata cgtattatag gtagtaccat    240

tgaagatgca tttaaatgct gtccatgctc tgttctctaa aaagttggac ttggacttgg    300

acgtcagctg aaagtatgaa atgcactgta gccaacgaag ctatgttttc aggcttcaac    360

atggttttag gaaagtggag gctctttggt tgaagggttg aatgaatgct tttctaattc    420

cagcatgatc ttcaaatttc gacacaaaaa gcttaagtat tttgttccgt tattctttta    480

atccttgtat tgttatatat tcttttctct gaactgaatg tacgatgatt gcaggggtcg    540

agagcaagtc cgatataatg aaacacgtaa ggacgtgatt gaatgaaaaa ctatgagcag    600

agatacaaag tctaacttac gggatgaacg atgagaggtt tgaccaagag ctgtgacgcc    660

tgtatatttc aacaaaagtt gatgactaac atcacatgtc agagtaatca aagaaatgca    720

gccgcacata tatatatcta tatatatatc gtttagtttt tttttttttt tttttatttt    780

ttttttatc taattatatt ttaattctat tttcctctgc cctcctcccc ctcctcttcc    840

cccacccttc ttctgcacat agtagccaag gattgatcgg tttcttttga ttcgggggga    900

aaatgttgta caatttttgc ttccatagaa gcttgaaagt tttgcagatt atgttgtaaa    960

attacccttg tgtactcaca ctagttcttc tcgtggaaac ttatattaca atggttgagt   1020

tttaaggggc atattcacac tggtaactac cattttctaa tttatgaatg ccgagtttct   1080

ctccatgaaa gacctttcaa atgccctttc ctccgcggtg cgtttgttgt tgtaaatgtg   1140
```

```
cagtgtcgtt ggatacacga ttgtgtgaaa gggaaaaggg aatacgatta actcttaaat   1200

tcaaccccta tctccatcag tatcaatcac atttcagcaa ctagctcttg aataacattg   1260

agattcttgt ttaatccacg tactactact actattacta ctatttgaca gccgatatct   1320

caaataacat ccatatttat caaattggta ttttaaggac ttttaatttc ttcgtacata   1380

tttcattata atttaactac tctgaccatc attgaaaatt tcacaaagaa gacattttaa   1440

attgaattga gttgaattaa gttgatataa tggttgaacg ttggatttaa tttataattt   1500

agtggtgtat gggtccattg taataattct taaaaaaaat atcatattct gaattctaaa   1560

gaaccatcta agaccaaaac taaggggtca ccaatgagta tggtaaagtc aacaaagttt   1620

gtctactttt cttatcctta tcatcaagag tgcaatatga tatcaaagat aaattgtacg   1680

tgggcgtcat ccattgggta agaccaagaa gcaaaatatc atagagaagt tgttttagta   1740

gccataggaa ggaaggaagc aaaataataa tatagatttg aaattgtgga tgataaactg   1800

ccaaatggga attcaaaata aactaaataa ataaaataaa aagagaaatc ttgggagttt   1860

ccattttagc caatgaggaa acagatagag atctcatcaa gataaggacc ctattctctt   1920

cttcatctat aaaacaaaaa caaatcaaac cctcatttca ctcattcaaa acaaaaagta   1980

ctccaaagtc aaactaacaa atacg                                         2005
```

<210> SEQ ID NO 29
<211> LENGTH: 1445
<212> TYPE: DNA
<213> ORGANISM: Cucumis melo

<400> SEQUENCE: 29

```
tcccttcagc cacttaacac ttaaaaatct taggaaactc cattggctcc tctttctcca     60

atgaaatttt gacatctgtg ttgttgatag ctcctatatc ctttgagaat ttgatataca    120

cctgtcattt gctgatttgt ggataactgt tagccttttg atattgatac gttccttttt    180

tatgaatttt tgtaaatcca ttcaatttta atgctgtcgt aaatgaaaag ccctttcatt    240

aatgttgttt atatacatat tttaaaatta attcaataac aagtttagtt ctgttagctt    300

ctaggtttgt atctatttta tctattaaag gtatgtttgg gcttcaggtt ggaatggagt    360

agaattgaat gggttgggga gtaaattttc cattcaacaa gttcaatttc aaaatggcta    420

ataagttttg aactcaattt tattttcaat aaattcctta attttttgtt ccttgtttgt    480

aaactattga cttattcgat atattttaaa attgaggtat tttaaaaaaa taatacaata    540

ttaaaattat ttataaaata taacaaaatt tatgtatagt ttatttgaaa attttactat    600

agtttcattt ttatattatt cctaaccatt tccatttaaa attatttcaa ttatttcttt    660

tattaatata attgaaattt catggattta ttagacacat gatttgaaat tttatgggtt    720

tattaagtat tttctaacac aaaatcgctt ccgcatcgtt ttcaattcat tcagtaatag    780

aagtaatttt ttaaaagaac caaatttgcc aaattttgag ttccataagg actctgaaaa    840

ctcattatgt ctattactct tcactaattg tagagactta aattcaagat aagagacact    900

aattgatgat aattgcccaa aaaataaaaa taaaaatgtt tcttccccat cctcaacctc    960

catgaattca cagagcccaa agattaatta ttgggcccca attcctactc atatatacct   1020

tacagtccct caaagaaatc ttaggaagta atcaatttct gtttattcaa gatgtagcct   1080

cccaaaagaa aaatacatca catcaaattc aaacaaaaat atctacagct agcaaaacct   1140

caaaccgtta aaatttcaag ccacataaat gaaattttca tctgaaaaaa ggacaatcta   1200
```

```
tctagacgtt agatttcagc cctaatatga atctgaagca tttggtggac gagaaagagc   1260

catgtaggaa tgcatcaaac aaaggaaaaa tctttgaact ccaatgggat tgaagataca   1320

gataccaatg gataagaatc tgttctcttt gcccactatt taaactcacc aaacccacca   1380

gtatcttcct caccacaaaa tacattccac cgttgatcac aagccttatt ccaccacctc   1440

caaca                                                               1445
```

<210> SEQ ID NO 30
<211> LENGTH: 1282
<212> TYPE: DNA
<213> ORGANISM: Cucumis melo

<400> SEQUENCE: 30

```
tgcaattaag aataagctaa tcttaatgaa gaaaagaaaa tgttctttgt atttgataaa     60

tggtggcgtt ttgggggact ttatatgctt tttttttccc atgagattgg ttatcttcat    120

ttccgtcatg atgtcgccaa gtggcgcttc attgatgata tcttaaaatc tataatgatc    180

atcctctttg ccaatggtgt ggtgacacgt ggaaggactc tccatcttct aaaagattct    240

tcaaataaaa ataaataaat aaagaaaaaa cttgtaagaa gatacatatg tacattttta    300

tatgaaatta atatgagaaa taatcgactt tacagtgact tgatcaaact ttcttatttg    360

tttcatatgt taggttaaat tactaatcaa ttcacgtact ttactagatg agatttcacg    420

tactttactc attgagtcca acggttgatt aacttatttc aagaaaattg attcattcaa    480

ggatgtttcc aactctcata taatttccat gttgttccac ttctatcaag tacaatccta    540

tcgaacacaa gtttgtttaa ctgaagttca ataatcgaga tcaagatagg ccttattatt    600

tcttctagag gttcaagtga tcaatcaaaa aaggtttatc acatgattca ttccaattca    660

actaagctaa taagtggtgt tgcatgatag agtatcggac tagctcgaac ccctatcaat    720

atgataaatg tctatgtata taaataggta cttaacccaa cgaacaatgt gtcttacgtg    780

agaaagcttt tttctaatat acataaaaag cttgcatgac tttttgatga attgtgtttt    840

gataaaacat atttgtgagt atattatctt tataaattta agttataaca acaatgtata    900

ggtgtgagta tgcttttaaa cttaataaaa aaattagaaa aaattacctt tttagtatga    960

aagttttaat gatatatcaa tttgtgtctt tatgatcaaa atgtatactt ttagtctcaa   1020

atgtttataa gaattaactc cttaataatt atcctaaaca atcatgttca aacttggatt   1080

cttattgaca catatttcat tttaatctaa gtttagaaat gaagataatt aggataagga   1140

tctttagctt atgatatctt atccaatatc ttaaataaat cttcaacacc aagaaatttc   1200

cctattgcgg atatttcaat atcgaatgcc ttggagtatc aaaggcattg gataacaagt   1260

gggacataat tgcgataaaa aa                                            1282
```

<210> SEQ ID NO 31
<211> LENGTH: 2002
<212> TYPE: DNA
<213> ORGANISM: Cucumis melo

<400> SEQUENCE: 31

```
ccgtagattg aacttatggc ttcggtcagt tattgagatt ttaattctct ttaacattag     60

gctaatccat gagtttacgt gtgctaacat gttaatatga aaagtatagt agaaaagtaa    120

aataatataa ataaataaat tggattgttt tgaaaagttg aaagattaga atatacataa    180

gattctgaaa tatctcaaat ttttgaccca gcaaactgaa attagccaaa gtaggttgtg    240

ttgtaaataa ttatacttta tattgttctt tttgtataag cttttatgtg tcaatgacaa    300
```

```
ttttaacagc taaataattt aaacagaata ttgccaagat gggtggctac aaaaataatt    360

gtaaatagaa cccaataata attagtttaa tcaattatgt ttttattaac ttgtaaatta    420

aatttacact gaaaagttga aagagtttgg aaaatatttt atttgaataa atcaaacaat    480

tgaatactaa tttgcgtaaa atacgtagtt taaaatatat atatatgtat atatatatat    540

atagtgtaat tttcaagtaa taaataaaat gaaaattaaa ggtttaaaaa taagctaatg    600

ggtgcttaaa gtatctacgg aaacgagatt gcattcgact cacgtacgac atgaaaaaga    660

tataaatgaa ttttacatta aaactattaa attgcacata tgattgtcca acaagtaaga    720

agaatcacaa tcaaagtaaa aagaatcaca atcaaaagag aatgtatcta atggatgatg    780

acaatttact taagatttaa gaattaatct aaaaatttag agagaggggt aaagatatca    840

acttttattt accagaacta aaaattatcc ttaggcctca attgctttag taatggatat    900

atatatatat atatacacat ctacctaaca aagctttaat aatagtaata ataaaaattt    960

aaataataaa taaaagaaat cgaccaatat aaaaacatat aaaaaatgta tagttaaaaa   1020

gaaagagaga aagagagaaa gagagaagag tacatgcaag agatttgatt tggaaggagc   1080

acataatagg acaagagaag ggtaattttg gaatttgggt caattattct tagtccaagg   1140

gttacactac aaaaacctaa cagccttcac aaatttttcc ctctttcgct cgcttcgctt   1200

tgcccaaaca ctcgcctcca actccacgga tcagatccga agagtttggc aaaccctagc   1260

ttcctctctt caatctccat ctttttcttc tctaacaatc cacaggtttg tttttcattc   1320

ctttctcttt cgattttgcc ttcctcttct acttattcga ctgcacgaat atggttgtat   1380

gtatgtttcc gccctctttt catatccctt tttgttcctt tagccttgaa ctactctggg   1440

ttttcttttc tttttttact tttttctatt attgtatatc tcaagatttg acgctaatct   1500

ggtctgtggt tgtgggttga gttcgttttt attcgtttgt ttgtttgttt gtttatggcc   1560

atggcttgta attgcttctg taatctacgt gaatctgttt ttgctttgga acgtttttgt   1620

tgttcaactc atacgagaat cgtcgtctat agttgggttg ggtttttttt ttcagtagca   1680

tcttgctttg ggaaaaggtt aatgcggtgt cttttttttt tttttggaga aaaaaagtta   1740

ttagacatcc ctcaactcct tttcctacat tgagacagaa gtttaatgct tgttttcctc   1800

tttatctgga ttgcaagttt ggcttttctg ttacagattt cctttctcag gatagctttg   1860

aacagatttg taatgttgtt ctgtttattc cttggtgggg ttgataaaat ggttatgatt   1920

ttttgtttgt tggcggcata attctggata tttttatctg tttggtctgt gttcatattt   1980

gcattgtttt ccacttacag ct                                            2002
```

<210> SEQ ID NO 32
<211> LENGTH: 2003
<212> TYPE: DNA
<213> ORGANISM: Cucumis melo

<400> SEQUENCE: 32

```
tggatcgacc atgacattca aaaaccttta agatatggat cttataaaat aaatgtaaag     60

ggtaaacaat tcttccttgc ttaacccaag ctatatattt tatgcactaa tttaggtatt    120

agagtatatt cagctgaaca ccacctacca atgctagtac tttaatcagt caattctaac    180

ttcgataata tatctcaacc aaattagtga aaaagagtcg taaatgaaaa actatgtacc    240

aagatattct atttgttttt tttatgttta aatatctcaa agataatacc taaaacgttt    300

tctcctcgta caaagattcc tcatttactt tttattgtcg taaactctaa tacaataaac    360
```

```
taaaacaagt acaaatacac tagctttaga aatctacttt ttattgaaac caaaaccaat    420
aattcaacat ttcattttca ccgacaaacc tttgtaaaca attgaagtaa tttttgttgg    480
tactatgaat agtaacatca agtcttcaag tgcatcatat caaccaagac atgttcttaa    540
aagcgacact aaaagattta aaaccaaaag catttatgaa atccgaactt aatcaaatcc    600
taaatatttt tcacttaaaa aaaaaaaaat aggaagaaaa attgacataa atgggatatt    660
ttcgttttca aactggcaag ccagcatgca ccacgttgtt gacgtgtcct tccacgtcgg    720
aaaaaaaaat attaccacag taaaaagaga ataaaatgaa agtcgttgac tctcccttag    780
tcggaggaag cgcgtgaagc tgaagccgga ttagaaatcg gcaataaccc cgacacgtca    840
tcgaaatgct agtatcaaat attgtccgtt ggatcttcct tcaccaactc tatttgaacg    900
gccacgatct tccaggtcca acggttcgga agaatctttt cgaaattcca tggctagtcc    960
ctacactcct ccctattggc tccctagggc atcccgaccg gttattccgg ttgccgggaa   1020
ggtggctgga cgctataaat acccgctttg ttcatctcgt agtccttgta ccgttgagct   1080
tcgccttcta atagagctct ggttcggttg gcgtattagc tcgaattctt tctctcttcc   1140
agatctacgc tgccgatttc atcaggtttg cgagctctgt tccaccattt ttcttttcct   1200
gaagctttga gcatgcttgt gattcttcat ttcctcattt ctttgatggt ttatgaaaga   1260
atttagggga attttctctt tttgtattct agtggtactg gtagatttgt ttgaagtttg   1320
tttctcttct tctgagaagt gaattcttcc agatctgaca gttgcttttg attttttctt   1380
tgggaattag tgaatgatac ttcgatactg ttttttgctc tctgagattc tggatctcgg   1440
gccttggggt tttctattgt cttttggtag ctatgtttcg tttgtcagct tgtatttgtc   1500
attgttgaat ggttcgatcc ggtttgtaaa taaaataaat tttgtaggcg cacttgtttt   1560
ccacggtttt cgtgttacgg tttcatgatt ccctagatct ctggttagaa ctaagttttt   1620
tgtcggtaat tggatttggt aagggactgt tactgtggtt gaattgtaga tccagtcatc   1680
ttctacatga gtgtagggtt ccttagggca gatcttgtgt tttataattt taattttgtt   1740
gtttccctga ttttgaacct gtttggttgt tcagattcgt cgagtcattt ccattcatta   1800
aaagtttcta taattttatt tgaatcttct gaatctgtgc ttgtattacc cagatttcta   1860
taaacctatc ttgatttcaa gtgtgctatg tggtaactgt tgatattttc aagcttaagc   1920
aatactgatg tgactaaaac ttaactaatg aactgaatgt tttttgtaca cgaactaata   1980
tggtgttttg ttatgtttca gag                                           2003
```

<210> SEQ ID NO 33
<211> LENGTH: 1372
<212> TYPE: DNA
<213> ORGANISM: Cucumis melo

<400> SEQUENCE: 33

```
aaataaaacg cggagacaaa cttggacttc cattcccttc ttcttccttt ttcttgtagg     60
aattcttctt tcttccttat aaaattctcg gacccttttt ttttcctttt taattttatt    120
tttccttctg tagttcgttt cttgatttag attttcgaca aaggtacctt ttacaggttt    180
gttccttctc ttcatcgttt actccgattg atgcatttcc tctattttca cttttggatt    240
ggaattatta cgatctatgt tcaatatcgt ttgatccatt ccctagatgg aaattatgtc    300
tctgtaatta tacatagtgt ttgatttgtt tgggaaattt tgtttctttg tgataatgtc    360
ttcatcgatt tgatgatgta tttgtttttt tttttttggt ggaatcgata tgatttatga    420
tttgggtgtt tttttgcttt tgagaattat gatttgatca gagtttttct tattatttct    480
```

-continued

```
gttgttttgt ttcatttcct gccgttttta aagatgtgtt tagattctgg ttgtttttgt     540

ccttttgatt atgtttttat ttttcatgta gttggaaatc aataggattt cagataattc     600

atttggttgc atagggattt gaggattgga agttcggcac tctataactt tgcagtgaat     660

gatttgggtg aagtttttcc tcttgtttgt gctttcatgc ttcagttgcc tcaaccaata     720

tcgctttttg gaagtcttga aaatctgtag ctttgagctt gtgtttagtt cgcaactgaa     780

gcttcaagga aaaagtaatt tctttcgatt ttcgtaaaag gggggaaaaa ggaagtaatt     840

ctactaaaat tttctcctat gaactcgtag gtcacatagt tgttatttgg tcagttgaca     900

ctctagacta tcttgttacc attccacata actcaaaggt tttaagaata aactcaatat     960

gggaatggtt tcattaggat tgcagagtca ggaacaagag aggttgcttt gcacaagtta    1020

catactttct attcttaggg agaaaagcca gttgtcattg ttcagggaga agattaattt    1080

ggttggaaag atttattgtc cttctgtctt taggttgtca ttggtttgtt ataattaaag    1140

tttcttgttt cctagaaaat agaagttttt ccctatgagt aatgttatac ttcattgtct    1200

tttattttgt gacaagcaaa cagtgattta ttggatgaac tacagttaaa ttctgaatcc    1260

attaattttt ctgaaatcca ttgtgattag aatcatgcaa tgccaactga agaaattttc    1320

accaattatt aaatgaatat gtttatttgc agggtgtttt aaatagatca ag            1372
```

```
<210> SEQ ID NO 34
<211> LENGTH: 1122
<212> TYPE: DNA
<213> ORGANISM: Cucumis melo

<400> SEQUENCE: 34

atatatttat tgctagggtt ttccggttcc tgtttgctcc actatttcag ccgcctaggg      60

ttgaaacaac tcattcctcc gatttcagga ttactatctt cctcctcgac cttctccggt     120

aatactttct cttcacaccc cttttgttgt ttgtgatttt taacttcctt tggattgaaa     180

tgcgagatct gtgtgtttct accactcttc tttcttaact tttcgatagt attgcatgtt     240

ccttacttat ggagaggata atgtgtactt agggatatca attttcgttc acagtattca     300

atattcatga cttactgagg tgtgaggagt tttcatttca tagaccgact gatgctatga     360

tctcaagccg agtttgaccc ctgtttttct ttttatattc tttttcttat ttttgtgtca     420

atatattagg tgatcaatga catcctaatc tattattagt gaattgagta ataagaagta     480

aagtcttgtt tatccaattt tttggtttgg atttattact attttgttgg aatgcttgaa     540

tgaattctaa tggagtccgt agaaatttgt ttcaggcgtg cgccttttct tctcactaaa     600

tttttcatta ggaatgggtg tatttatttt caggagaatt tgtcgattgg cgatagttgt     660

cttgttcttt ttcatttcct ttataaattc tttatggaaa aaatgtattt gctgcaacct     720

ctgtcttatt acccctattt gaatcaatag agttcctgat ccttcctacg atgtggtttc     780

tggggatttc tctctgggtt cgtgtgatag atgggtgacc gagggaacac cctttattgg     840

aaatgctcct attcttcaga gtcggtttct cattttctca cctttacgct ttgctgctgc     900

tctcattgac agtcgaaccg ttttggaatt cgtgatattg tgtgtatttt ggggatgaaa     960

gttttcttta ataagactag tgacagttca ttattgattg tggagaaatt tatgaccatc    1020

taattttaat ttgaacaagg gaggatgaaa atgattgggc gcattgcatg ttttatccaa    1080

ctagtactca ttttttcttt gttctgatat tcttcaggaa ca                       1122

<210> SEQ ID NO 35
```

<211> LENGTH: 2017
<212> TYPE: DNA
<213> ORGANISM: Cucumis melo

<400> SEQUENCE: 35
actattggag acgacgaagg aaaactctaa tgtgagctta gaattgaaga tggtgaacaa 60
ttgggagtct tttttaaaaa tctttcgtcg gtatattgaa atttcctttt acactcaaat 120
aacccccctt ttcacgcgtt caacgtcttc aaaccttcct ttttcaatta ttttttcgtt 180
tacattaatg acatttaggt aataagataa attagtggat tcttttgtga aaaatgttag 240
cccatttaag acttttatga aatatattag aaaaaaatca tatagcaatt tatattattc 300
tagttaaaag cccataatag aaactaaccc aacctaaagt aacgtaaaca ttcaataaga 360
gagacaaatt ttaaaataat ttctaattaa aaaaaaaatt gtcaagaccg tccgggtcgg 420
atccaaaata taacccgaac cggccggttt agcatctata taaatacacc tttagggttt 480
ttattctctc aagacttcac cgcatttcca cttctctgag gccacggtca gccattggag 540
cagctcaata atcctttgac tccctactac ggtaagtcga ccttactgct ttcggcttct 600
agttttttca atcctgtcat tagtcctttg gagttcttct gtacatttat gacgttttcg 660
gctcgtgttt tgtttcgcct gtatgtagtg ggtttttcga gttttgtttt tacttttttt 720
tatacttgca ggaattagtt gaaatctatg tacttcatgc cttggataat actcttgatc 780
tgttgtgtta ttcaaaaatg aattgtttta agatggtatt tgagaatggt catgtgagtt 840
ttgcctactt ggttattaaa atgaattgtt ttaggatggt atttgagaat ggtcttctgg 900
gtatttggtt ggaacctttg tgctctgcta tgaattaggg tgttctcccc gttttttttt 960
tttttttctt tttggttatt aatatatctt ttatgactac ttattcatat atgatatctt 1020
ttactcgtaa attttgactc atttgaaagt tttatcctta gtcctttctc attcagggtg 1080
taaaggtatg ttgttagggt taaaatagcc tatgcaggaa agttctgtat ttgttctaat 1140
tattgcattt gtgtgcattt gtatctagtt tatttcttgc tgagagtatg cttcattttt 1200
tagtacacat cacttgtgcc actttattat agttgcacat ttttgtttat ggagaggatg 1260
aatagcattt agggatgtca atttttttatt gagaaaaccc tctctcctac ttaagcttgg 1320
ggaatttttg ttctaaatgt ggtaaacata atacttcttc ttattttaat ttgaatggaa 1380
ggggaagacg aatactaata ttttcaacga accttcacaa cttttttttc ttatttagga 1440
agccatgttt ttcaaaattg tactgtgtga tccacatatt tatcgattat tagtgaatcg 1500
aataataatt agagttttat tggtataatt ttgaagttca gacttattac atttgtggaa 1560
agtttggtta caattttcaa ttttattgga atcctaagaa ctttgtgtta acatatattg 1620
agttttcttc tctttttttt tactcattaa gttctctatt aggaatgttt ggttcaatgt 1680
cacatagtcg atagctaaga ccagtgaccc acaaagctat gattgaacga aaaacaagcc 1740
tttcacatct tggtaggaat ttgttatttc tcaatagatt tacagagctg tttcatgtga 1800
tcacaatttt tttctatttt tctgaagttc tctattagga atgggctatc tggttagttg 1860
cttttgagag aacatgtgga ttggtgttgc tcggtttcct tgcctttgta attttgtcct 1920
tggaaaaagc aaaatgatta ggtatcctga tatgcataac atgtttaagc caactagttc 1980
tcactttttt agtgcaaata attgatcttc aggaatc 2017

<210> SEQ ID NO 36
<211> LENGTH: 2000
<212> TYPE: DNA
<213> ORGANISM: Cucumis melo

<400> SEQUENCE: 36
aagttgttga ggctttcaat ccaaccaaat aattgtttcg ttttccacta caatttccta 60
gtactaaggt agcaatggat cgatccatag agaaccattt gatttttcac taaaatcaat 120
ggttgctaag taaccaaggg aggattggtt gaattgattc ctaatttcac ttcaataatt 180
aaagcaatgg caataaaaca aaaattggaa gattgttgaa ttaaatttag caatgagata 240
aatacctagg ccaagactta cgtaggttac tttagattca caactcaatt attgattcat 300
aatgatatta gattccttgc aacatatgaa caaaatctta gttgaccacg tctagagaag 360
ctaatgtgat gttctataaa tcaaatcaat ccttatgtct agattaaaag catcctagag 420
atgaaaatca attggcatta aggtttgagg ctaaagctaa gtcgatcaaa caatttggag 480
ttgtctaatt gattgttcga tgtgatacaa ttctaaacta gttagataaa cgtaattaga 540
atggaattgt caattcaata aatgattcta acttagctta tgttatcttg cagtctaaaa 600
ataacaatta catattagat ctagatctat aacaattaat taaacatgct tggaaaatcg 660
ccaatatttc cgaacacact caatcaaaga aataagtcca aggaaagaat tcattaaatc 720
ttaagattca caggatgaaa atgttcataa catcacacaa gtgtgtgaat caaaagataa 780
gactagaatc tcgagataat agtaccttag ctatgataca tcctcgaaaa catccaacaa 840
aatcaatgaa agtcttgagt caattcgtct agtaaaatac gaagagttca agagaaaatg 900
cctaaaattt agtgccaaaa attgtgtaaa aagtgttggc ggctagggta ataatgcaaa 960
attaagtcac agcaccgcaa caacgtgcaa aacacatgtg ctatactctc gaaaaactct 1020
atagcatcgc agtcaacacg ataccgctac acaacacgtt gtagggctga ggtgtttgca 1080
tgaaattaga ccattctacc ttacagcatc gtgccttctt cgttccattt caattttctt 1140
gccccagttg acacactaaa cctccaatta atctcgttta atataaaaga taattatgat 1200
tttctttatc tacgaacaac attattgtga aaagatataa ggatgatata tcacaatttt 1260
tagggaaaaa aggaaaatat attggcattt attatctcta tcaaatagat gattttacaa 1320
ttatatgtta agatgtttta atccttgcta atgtgaatat ttattttatt tttgttcaca 1380
tgaaacaatg gtattttgta cactccaagt acaatagttt ctttaaaaaa atttaaaatg 1440
atacgtaaat tatctaaatt gacatcttaa ctaagcaaac aaaaatagtt gtttgaaaac 1500
tagacttatt tagtttacaa aaacatgcac cagatatcct cacttaatca ctagctctac 1560
acccaaaata tagactaaat aacttcacat ataatataca aatttaccaa actcaattcg 1620
gcatctcaat tggcgaaaga tctttttaac ccaaaagaag acgttggggc attaactttt 1680
caaaatgaac tttggcttca tagtaggaaa ttgggagtga aacatgaggc tgaaaaaggg 1740
ctaacaaaga gagcgatcgt ccacgtggtt ggcagtcaag aggtctttat agaagaggat 1800
gaagaacttg tttcccattg gtccgaaatc tatccaacac cctcctatta gatttccctt 1860
ccagattctc atcttcatga ttcctacttg gctccattta aacccacaat tcaattcaca 1920
atatctccca cacatcctct tcttcatcat atcataaaac acagtccgtt acatacctga 1980
aatcttccat ctcaaaaacc 2000

<210> SEQ ID NO 37
<211> LENGTH: 1760
<212> TYPE: DNA
<213> ORGANISM: Cucumis melo
<220> FEATURE:
<221> NAME/KEY: misc_feature
<222> LOCATION: (1)..(1760)

<223> OTHER INFORMATION: n=g, a, t or c.
<220> FEATURE:
<221> NAME/KEY: unsure
<222> LOCATION: (1)..(1760)
<223> OTHER INFORMATION: unsure at all n locations

<400> SEQUENCE: 37

```
ataatgaata gcaaactacg taagttaagt tttggttact caaatttaaa cgacgtaaaa     60

aaaagaagaa gaaaagaaaa aatacgatgg aaagaaatca cagagaaaaa aagaaaggaa    120

aaaaagaaag acgatggaaa gattaaacga cgtatagaaa gaagaagaaa agaagaaann    180

nnnnnnnnnn nnnnngcagc gaaaaaaaaa gaggaaaaca ataaagatga caaaagaaat    240

cggagcgaag agaagaaaaa gatggaagaa taaacttgaa ttggacaaat tttatggact    300

ttttacatag acactaattt ggttttttg ttagcttcct acaaattttc ctcttttatt    360

ttatttttgt aaaagtaaat aaatatgtgt cattagtcta attttttgaa cttattttgg    420

gagagataga ggaagacttt aaaaaattat tattactctc cattttaatt ttgagaagag    480

attgtgttgt accattcctc ttattgcttc caatttcttt gagggcagcc ctagcctttg    540

tacaacgcaa gcttcctgta gtatctctat ctctctctct ccctcttccg acggtgatct    600

cttttctctc tctcacattc atcacccgcc gccgccggta gcttctcttt ctctgacgcc    660

accgccgccg gtaatctctc actcgtcgct ctcaacacag agaaatttct gattgagcat    720

caccaggtcc ggcaactaac attccttgct tctgcatctc tttttcttca atttctggta    780

tagttttgat ggatggattg tgtgtattca atcatttatt gtgttttgat ggatgaaccc    840

gtttattatt ctttttatg acttcaagta attgcaactg ggtacttcta tctgcaactt    900

cttggctgaa gtaattttta gttaagtgca aacggacggg ctgggaccga gccaatctaa    960

cgcttatttt atcgaatttt gaggagttgg ttttgtttgg gtttatagct taggaagggt   1020

ttttggtttc gaagaaccta ccatttgaag ggttgggtct aaaatgtcgc ttaattcgac   1080

ccaatatgac tctgaatgtt aaatattgaa tagaaaagaa atgaaatact atccctaacc   1140

tgtctgccaa tttcgtgcaa aaaagcctaa tagccagttt tttctcgccg gcagtacatt   1200

cgccttcccc ttccaagcgc tacggactgt tgctcaatct ccagaatctc tcaattcgca   1260

gggggcaagt tctttccatc aatcatttta tgtatttttg cttctgccct agatcgttca   1320

tctaaagttc tttacctttt tcttctgttt tgttttttgg tgtataactt atttgatggt   1380

gatggattat gattcagtat cattttctta ttttatatca gcaacaaatt tggatttgaa   1440

atcatttttt aaatacottt tgatgttaag ggtttaggct tattattatg attcagagtc   1500

attttctacg tgttaaatta gtttactttc caagtatgca gttatgttca agcagttatg   1560

cagtcatttt ctgatgtggg agatagtgct gttttcctta aatgttttct atttaaacca   1620

ttgtgcgctt ggttggtggc cgtgcagata attgcatttc tttttttgga ttggggcagg   1680

ttggttactc tctggtttaa ctttcacaaa gaaccaagac agacatccgt aacttgtttg   1740

cataaagaca ttcaaccaag                                               1760
```

<210> SEQ ID NO 38
<211> LENGTH: 1767
<212> TYPE: DNA
<213> ORGANISM: Cucumis melo
<220> FEATURE:
<221> NAME/KEY: misc_feature
<222> LOCATION: (1)..(1767)
<223> OTHER INFORMATION: n=g, a, t or c.
<220> FEATURE:
<221> NAME/KEY: unsure
<222> LOCATION: (1)..(1767)
<223> OTHER INFORMATION: unsure at all n locations

<400> SEQUENCE: 38
aatataaata aatctcatta ctctttatga gctagaaagg atgcctaatg gacctacaga 60
ctagaagcta caacgatatg agattaattg gctaaactca ttaaccacat tatgatatat 120
ttgttaactg tgtgtacact ccactaaaga ctcgcagctg aactcttctc actgtagata 180
tatttatgtg tccacggata tagaccaata ccaataagtt agtccttcac aagtgttcat 240
aacactagct gggtcaaatt actgttttcc ccttgggtta cttctagtcc ttaaatacca 300
atgctcctct aatgaacaac ctgtttaatg tccaaccact aaacagaatc ctttctcatg 360
ccatagagag ggtaagacct tcaagtcctg gatacaccat ttaaaggagc gcttatctat 420
ttaccataaa gtcaagaagg agtgaattcc atcttnnnng attatgttcc cagctcccca 480
cccggttttg tcctcaaaat gataaatata ttgagttgac aatctgacca ctctcacccg 540
tacaaatcaa aagacaatcc ctcgcgaata ggagttcata atatactcat aattaagact 600
aagttatcca tgtcattcta atgaaataga aacccaacta gttaatggag ttacatcttg 660
tggttactat ttcgtggtcg ggtcttatgc aaactcatta catacgatac cctcactcgc 720
atgtcgctta cttgaacatg ttgaataaat gcatttatat tagatacaaa gtaagtcgta 780
tccatagtgt taccaggata agttacctag ccttaaccct atactataga cnnnttaagc 840
tgatcttgaa cattgtttcc tgtatgtctc tacatactgt tcaagactca tcaaacaact 900
caagatgtta atttattgga tttaggttat taagataaaa cgaataatat aattaataac 960
acttcttgaa attataataa tataacactt tattaataac taccaatgaa ttatatttac 1020
tatatacgag ttttaagaca taaaatccaa tataagggtg tatgaactgt taaagatgat 1080
gtgctattct tgttggatat tataggaggt atttagtgga ttatttgtga aagaataagg 1140
aggtacttat gggaagactg ctggaggtta gggaggatct ttgaaaatta ggaagtaggg 1200
atcaacaaaa aaaacgaaag ggaaagctta aagcttaaaa aagaaacgaa ataaagaaaa 1260
atgatttaga ccagcatact aaaatggcaa tgtaatctga ggctaatgta tcaattgaga 1320
actttgtagt cataatgatt aatcccaaac aaattagttt tcaagaaatc aaccccaaat 1380
aaaatgactt aaatattgaa gagtttaaat ggtctaaaat tattgttact gttttttatt 1440
tttggaaaag agacgaaaaa ggaaaaataa gaaacgccca ccgtggggct cgaacccacg 1500
accacaaggt taagagcctt gcgctctacc gactgagcta gacgggcttg gtgtccaaaa 1560
atccaataat attgaaaata ccatatagtt taatgaactg ggcaattgga ataggcccaa 1620
tatattagat atagcgaccc aattgttagg cgtgtcttct tccaaaaatt ggaggcaaaa 1680
cacaaaccct agcatccgct tctgctcctt tatcgtttct ctcggcgatc aattttcacg 1740
gagctaggtt taatcaagct tcaagca 1767

<210> SEQ ID NO 39
<211> LENGTH: 2000
<212> TYPE: DNA
<213> ORGANISM: Cucumis melo

<400> SEQUENCE: 39
tttaaataaa aataaaaacc atctctttat tttaagtagt taaatgattg tcgtttacta 60
aattaactct agcctatttt aagacggtct ggtcaaaaaa tcgattacga ccgaccaata 120
ttcatctaac ggtcttatta tttttaaaag atatagaaat gtatctcgtt aataaagcca 180

```
cgacggtctt tttctaataa aaattcaact aaaccatata acaaaattat tgtaccatga    240
aaaacacttt catacataat gcaaaacaac aatagcaaaa aaccaaagag gaaggggaca    300
atttggggaa aagtaatctc aaatttccct ttttgacttt gttctaaatt agtttattga    360
aataaaatct actaatttcc catttccaaa ttaaaatgct taatctttgt ctcattagca    420
ttgctagaac aaattgtctt ctcaaaataa aaataaaaat acaatatcaa ctatttatac    480
ttaattatct aacatttctc caacataaaa agagttatat atatatccta ttttgttctc    540
taatttttcc tcttttttttg gtaattaatt ataatattgt cctaacatat tatattagat    600
agcttcgaca aaccgttgct taaaaaaaga aaagagaaat ccaacctaac tcaatccgaa    660
aatatacaaa gtacaaaata attataataa ggtagatggt atatgcatca atgaaataat    720
attgtcaact ttcctcgatg atgatggtaa taataataat aattttatat ttattaggcg    780
taatattttc ctcaatttta gtgtttgtat atactttcat atgtttaatt taagttttaa    840
aatttagtcc ctcaattaac ttgaaattaa ttaaagaatg tgaaaatgtt aatgggtgaa    900
ataaataatt tagagaaaaa ccaaaataaa ttagaggtag ggagtaattt tagaagttca    960
aaaaaaaaaa aaaaataaat tagatgtttg aaagtacaga tttgtttaaa tatgaaccaa   1020
cttcgaatag tctttccatt ttttcttata aaaagtcttt ctgatgtgga tactagttag   1080
agtatcctat caactcatcg atccaaagaa catactttca atcgtaagtc gtccattcta   1140
cttcgatcta aaatgatgct aggtttgctt caccttcacc cttcacaaag acaagtgcag   1200
gtgtgcttcg ctctatcaca tgattttgat tatgtcttca agaacttcac agcggtttta   1260
aaaaaacaag aaagaaaaga gtgagagtgt ttttatgtca gaaacatatg cccaagctta   1320
tgaaacttgt tgatcttgta gcgattgaat aacaaatgga aagtatctca tacaatttct   1380
ctatttttca cttttatcga agaactttgt ctcactaact cgtaatctaa aatacaaact   1440
cttcgactct aatatattaa ctccaaactt catttttcac atctatggaa cagataaagg   1500
tctaattttt taaaaatatg atgggaatta aagtatagta aagagattag cttcatcaat   1560
gggcttggat tggagtccaa agggttagcc caaacccaaa acatagtaaa tccaagccct   1620
ggaacaatga atagcacgga aagtttgtgc tgccggagga gcgtattgga aatgaagggt   1680
ttaggatagt tatggagcag aaaacgacac cgcatcatta aggacggatt tgggatttta   1740
agaatatatt agggacagaa taggaatttg aaaagtagcc ctagccactc aatttggtaa   1800
cagtagcaca aaaattggag gatacctaag gtaagcgaca tggggtaata cacagaattg   1860
tggctatggc agaattggat agaactccca tttgaggctc tcttttctct taccatttct   1920
acaagataac actactcttc ttcactctcc aaaaccccat cttcttcttc ttctcttagg   1980
ttcctctctc ccttcctcca                                               2000
```

<210> SEQ ID NO 40
<211> LENGTH: 2000
<212> TYPE: DNA
<213> ORGANISM: Cucumis melo

<400> SEQUENCE: 40

```
aattggaacc tgctgatatg aaatgcataa gagaactgaa cctatcagta tcatgcgaaa     60
cctgcagcat agacatacta ccgtgatgtt tcaatttttc aagcaaacaa aatatccaaa    120
aacacacaaa atagaggaaa ataaggcgaa attacaaacc tctctaggat tttcaagatc    180
ttccatattc ctctcagatc cgggtgtaaa gacaaccagt tcgaagttcc aaagctgttg    240
caatactact tgtctaaacg tcatagcaag tatatttttg gacgaggtac ttgaatggaa    300
```

```
atcttgagcg agagactttc tgagcttcgt ggccttttcc ttgacttctc tggcaggtaa    360
aaactgttaa cacagtcaac ttaggaatga caaatacaat cggatagcta aattttatct    420
aacgacaata ttccagagag gggagagaga cacattgttt tataacaaga ctcccaattt    480
catgagatga caacatcgca cgacagtcaa acaaaattct aagagaacat caaataatac    540
tagaaacgga catattagtg aaggagctct taaaggtagc cttgaaccag agatgggaac    600
gccatcaaat caatctcatt catcaatcat ggagttaatt gttccgatgg tggaattcaa    660
aatcggtcat agatttttat tttaagaata aaaattaaaa tggaggctcc tgaagctaac    720
atgccaggtg caaaagtttg ggagaacgcg ttcacgtcaa cattcgaatt cagtctcata    780
aatggaaatt gtagcaatga cgaaaaatat tcatagttgt tagtcacgga aatcggttcc    840
ataatacacc accgtcgaat gcgagctaaa acgagcacca aattacgcag tcaggttaaa    900
aaataactaa ccagccgggt cgagacagtg ctgtgttcat cagaaattcc cggaaataca    960
gtctccacaa ccattgcagg catcccagaa tcaaggtgct cagtggcggt ttcaccgcca   1020
tcagccgcag ccgcagtaac agactgccgg aaatcgacgc ctccgaccag agaaagccga   1080
gacaagtcat tctcgtacgt ccggacacag ggaagaatct tctcatcgga ctccagcaca   1140
gcttgaagaa cctcttcctc ggtcgtcgga attggcctcc cagcagagca agagaaggta   1200
gaaaagcaat gccttgagtt tttcagaaca attttgggag tataaattaa gggtatagca   1260
aacagttggc gagctggtat agcctgtata ggagaataat ggataaaaga caaactcaac   1320
gccattggag aaatggccat aaacctctga gcgagtgcta gggttttcgt tttatagtgc   1380
tactagctgt gcgtcgccgg agaagcgatg tctcgtgccc acatcttttt ccctccattt   1440
cttttcgggg ttatttctct atataccctc ccaaaatatt acaattaaaa cagttccatt   1500
ttgttttaaa aaaataataa aaatttattt ctcaataatt ttttttgaaa attgaccgtc   1560
aatttcgtac aatctacttt taaagaaatg attacttcat ggatggtttc taaagggaat   1620
ccaaaattta aaagtttaat taatttagat tatgttttat ataacattga ttaaatgaaa   1680
tatgaaataa ggtgtaagtt gatattagcc ctaatatcaa agatgagggt aaaagtaaaa   1740
taatagtgaa aagatatcca actgattctt gggtaccggt tcgggtaggg tttgggggaa   1800
tccggttggc gttttttgag cacagagaga tgtaaacggg acgggaagaa ataaaggcca   1860
acacaactat aaattctcct ctcggcggaa aggcggagca gcgtccaact tcgcctttca   1920
caaaatttac taagaggggg cttccattct acgtcgattc tgctcctctt ctactttttc   1980
ccttctgctt tttgtcgacg                                                2000
```

```
<210> SEQ ID NO 41
<211> LENGTH: 2000
<212> TYPE: DNA
<213> ORGANISM: Cucumis melo

<400> SEQUENCE: 41
```

```
ggtctcagac ccataggaat agatcattta ttgccttatg aattagttta tgagtacata     60
ataattgtca accgtataca aatcaacatg aaagaatata atgttgtaca tagtcattcc    120
aagtttacta atattatatt ttaggagtgt tctacaccga acctgtcaca tgtacactgg    180
gtatgctacc cctgaattca atatcataaa gcaactttaa ttgtcaagca ttctcttgac    240
catttgtgac ccatttgctc ctactttttc aatcaataac tatcacaaaa agctagatac    300
cacatgtgat aaactcactg aaatcaggta tatggttacc tgtgcttggt cagcactcaa    360
```

-continued

```
tcagattcga aggcctagtc tttgtatttc ccccctctg cacactacaa atagtcctcc    420
acgtaaagac ccataacaaa acgcaaacca agtacagaaa atctagccga aatccagacc    480
actcaaacat aacaaatctt ctggtaagtt tgaataaaat ataaaactaa cctaatttaa    540
tcaaataata caataaaatg gaagcaacta acataacata tctaaatatg atcacgtagt    600
aggaaaaaaa aaaacattcc aaaactatta acaatcattc ttaatggtat gggtcaatcc    660
ccattattta ggactataac aagaattcct catacctaat gccacatcct atgtccaacc    720
ctcgagatta cctcgtgagt aatcaatctt attcatcctt atttcaaatt atgtgaaatt    780
tctcatcagg ttgatcatat tgactttcaa tacaacttat gattaatctt tcccttgata    840
taatttcgta tgaaaaggaa gttgacatta tgtgattttc tcataaggta aaccaagtaa    900
acttgacatg acgtcttaac aagtcttggt ttctaagtgt aatttactgc agaaaaaatc    960
ctaaattcta tgacttttcc tatgagattg accaaatcaa ctttacgaga aatcttggga   1020
agccatacct acaaagtctt cccccaagaa attacaattt ctagtaaaga ttgttgaaat   1080
ttaccctcca atttttccgt gaaatttgac aaacttgtaa gaatatcaaa tttgggttgg   1140
atattgacat tccaaaataa gtagttttaa aaaggattta tccaacaata atagaagaaa   1200
aaagatagga aataacatac ccacgtaaat ggaatgtaaa tatttatata ttaggtgtct   1260
tgaacgaccg tcaaacgaaa ataaattgtt catccgaagt tgaaactctt taagtgtaca   1320
tttatctttt cgtaagaata aaatgtaaaa ttaacgtgtg aaaggttggg ttaaataagt   1380
tatgtagaga taatattgaa gatgatagaa taatcacgat cgatgaatta gtatagtccc   1440
agagcggatt taaacctctc tcactttcat gctttctata tatatcaaaa taatttcaag   1500
tagttggttt agtcgtaaaa aagtcaacca atctctttta gataaacctt gagttattaa   1560
aaaattagat caaagataat cgttgaaatt gaaattttaa gagtataatt ataacaaatt   1620
ggaaagttct aaagtagttt ttgcaatatt ctccatcaaa atagagtaga aaaatatttt   1680
agtaattttc ttatcttaat tttagttttg taatagttat taggatggtc ctaagttctc   1740
aatccgcttt tagtccataa aaagaaagaa gagagagaaa aaaagtcccc gatccgcgac   1800
acataccaat ccaaccaatt atgcacaatc catgtgatat cgaacggtca caagaataaa   1860
tgctttctac acacggatca ccatccaacg gcttttcctt ccatctcatc ctctatataa   1920
tctaccaact ctgtcatctt cgacacactt caattatctc agcttttatt tcatcggatt   1980
ttccatcaaa caaggcaaca                                               2000
```

<210> SEQ ID NO 42
<211> LENGTH: 2000
<212> TYPE: DNA
<213> ORGANISM: Cucumis melo

<400> SEQUENCE: 42

```
actccattat ttggtttgat taaagcttcc atctgattaa taaataataa taattataaa     60
ataaaaaaaa gcgagagttc cattaagtaa tattatctac cgaaagagag caactatcac    120
ctcaaacttc aaaaagataa aatagagacg aaacttgacc aagtcaaaca caaaccacaa    180
acaaccgatc tgacagaaag tttgccagaa tcttcaatgt acacgcgaag ataaacaaat    240
aattaaatct cgttcgtctg gataacataa cacagcaaat gaattttttt aatacatatt    300
ttaaaaaaga aatttaaaat tggtagattt tataaatcat ttccaaaggg tttttcttgt    360
tttaaaatgt ttttttgttt aaaataggca gttcatcacc acttgagaag atccaaactg    420
ggcggcaccg gttctgcgac gcttgagggc cgtctccgac tcttcgccgt aggaggccga    480
```

-continued

```
tttacgcaaa gaataaccgg acaatgttgg acagttttga cgagaagtta aaccgagtaa    540

gggcttatgc ttcttctcaa tgcgctcgtc gtcgtcgtcg gcgacggcgg cagcggtgat    600

ggggacttgc tctgttgcgg ggtgaacatt gggattccga caagaaggtg ggttcttagg    660

gttggaggga aagtggaaag cgttatgggg ttcttgatgc tgttcctgca acttttgctg    720

tttgaggaag cgcttttgga gatctaaaag agaagggcga cccttttttct tcttcttctt    780

catggtggat ttagaaacct cgcccattgt tcttcttccc tttctcgcag gaacgaagcg    840

cagggaggtt aattgatttc agttttcacg gcggagggtg caggatttct aggcacgtgc    900

gaatcgcatg accctatcac gtgcgaatca gtgacggtat aacgtgcatg caaaggaata    960

gaaacacaaa ccgctcttac aattataaaa ctctaaacta aactacgaac gcatctcata   1020

atgggcccac tccatcatcc tatgggcctt ttgaatttta tgtatactat tttttttttt   1080

tttttttttt tctttaatca caatcaattt ttctggtatt tttttaaata ttcaacaaac   1140

tttttgtttt aatgttgtgt atatctaatt aatttagttt tattggatgt cattttttct   1200

atttttgaaa aaactcttaa aaaaaatata aacaaaaaaa gaatggaaaa agaatatcaa   1260

acaaagagag gagagagcaa ccatacctaa aaagtttgaa agtaaaattg aaaaaaagaa   1320

tatacattga gggcagtgtt gaaaatgaaa ttaatgaaaa aggaaagggt acgtaacaat   1380

aaattacatt ttcttgcagg cttaaacgaa ggcccatata tgaaaaggga agcttcgatt   1440

tgggttcagt tatgcgggcc tggggttggt attgggctta attttataaa gaaggcccaa   1500

atgttggaaa gacgggcttt gagagagggt gttcggcttt tgcccgaggg gggtggggga   1560

gtggcaccgc caagcgaaga caacgaatat taggagagaa aacacaaaga ggcggagaga   1620

tggaagagaa tgaggtggac caatgagata agagtgcgca gattattgag gtggcaataa   1680

atttagaatc ccgcctaaat cccagctttc atttcatgcg caattgaatt tcaatttgcc   1740

attcccctcc atagggactt aattatcccc tttttttttac tctcataact ccctctcttc   1800

ccaccacgtt cgcttcttcc tccccccttcc tcttcaaacc ctaaacctaa cctaacctaa   1860

cctccttccc caacttcttc cgtcggtacg tttcatccat ctcctcccac ttttcatctt   1920

tttttccttc taatttcatc tcttttcttt gtttttcctt ccaattgttg ctgatcccat   1980

actatactgc aggattcgaa                                               2000


<210> SEQ ID NO 43
<211> LENGTH: 1115
<212> TYPE: DNA
<213> ORGANISM: Cucumis melo
<220> FEATURE:
<221> NAME/KEY: misc_feature
<222> LOCATION: (1)..(1115)
<223> OTHER INFORMATION: n=g, a, t or c.
<220> FEATURE:
<221> NAME/KEY: unsure
<222> LOCATION: (1)..(1115)
<223> OTHER INFORMATION: unsure at all n locations

<400> SEQUENCE: 43

aaagaaatca aagcgaaaaa acgaggagga aaagaagaaa aacgannnnn nnnnnnnnnn     60

acataaataa agaatagaaa aataaggaag atgaggaaag aaatcgcaga aaagaaaaag    120

agaaaagaat aaagacaaaa ttgcagggaa agatggagaa gatgaaataa taggaagaag    180

acgaatcgcg agaagaaaat aaagatgaga gggcaaacct gaaatattta aaaaattgct    240

aactttatgg gttttgttac acgggccgta aatagttttg ttacatttat gtaaatttac    300
```

-continued

```
aatcaattaa ttatacaatt aatcaaattt ccacaaatac aataattgga tattttccca    360

aaatatctaa taagtttcaa tttctaccca tcaaatattt caaccattat taacaccaaa    420

aaattcaaag attaaactta agataattac aaanaaatta ccttaaattt ggggcattac    480

acatttacat tgaactatac aattgtttac cataatcaaa acgatcgttt ttttatgatc    540

gacatgataa tttcctatga tcaacacgat tttttatcat atcaacacct tcatttaaat    600

ttgaagtttt tttcccatcg ttaaaaagaa gtacacgatc ttttagaaga agattacttg    660

cgcgggctga ttaatcgtct gttgactgtg acattttttta tatttttcat catgagcctg    720

tatgtctttt ttgtttttat aattgtttta catcgtgtaa atagtttgcc gattagttat    780

atttgttaga aaacactttt tcaaatgtcg aaaatttgat tttgatttat taaaacttta    840

gtaaaggata gtgtttatta cgtatagaat cccaaatttt cacaataatt tttcaaaagt    900

aatccaaaag aaaaaagcaa caataataaa aggctcaaag cgacgtcgtt tagggcaaca    960

gctggggaga agaggacgat ctgaaaaatc atttcttgag cgaagggaaa aggagctcta   1020

ctaaagcagt cgaaaaaaga aaactcaaac ctcgctgcga ctctcgacat tgattctgtt   1080

ttcaattcat tttgccaaag ttaatcgatc cgaac                              1115
```

<210> SEQ ID NO 44
<211> LENGTH: 2000
<212> TYPE: DNA
<213> ORGANISM: Cucumis melo

<400> SEQUENCE: 44

```
tatagtttgt aacaatctac tctatgttct ttcaattttg atacatttga atcttaaact     60

ttattgagtt acacaatata gtccttgtat tttaaaattt ataatgactc tatttatatt    120

aatattatag aaatttttgt taaggtttaa taaaaatttt tctgtataaa taaatcgaac    180

acgaagtcta tatttagact gcaatatagt aaaacctgac atctaagttt ggtgaatttt    240

gttttgcttt aaaaactaaa ctattacaat tttaaaaata ttttaattta gttaatgcac    300

attaacttta cggagtaaat ttttacaaga ttgaatatac atagattaaa tagttataaa    360

accaaagatt agagtaaaaa catttaaata gaaagaacta agattttttt aaaacgaaaa    420

tgatactaga tacatatata tgtatctata ttataattac tcattttaac atatagtttt    480

gaaagaacaa agattagttg catgtgttga ttgtttttaa gaaggaaata atttttgaat    540

ggaaaatttt caaaagtttt aaatttgaca ataaactcat atttaaagtg tactacaaat    600

tttaactttt ggttaaactc cttgtttagt tcaatcatgt aataaattct cattccaaga    660

atcgttttag aaaattttat tgtgcattta ataaaatata gaacatatat ggcatataaa    720

aattgattac ttttttcttt ttttgggacg aaaaacacat tagatataat ctttttttgaa    780

agtttatgaa ctttaaaaat gggttatttt atacggtggt caactttatt ttattgaaat    840

tattgagttt ataaagattg ttatatcatt ttcttcttct ctttcactag aatacaatca    900

aacctatcaa actctctatg acttatttag aattcttttt gttatatttt tgaaattaat    960

aaatgaaaag cttagagtct aaattataac aattaaaatt gaaaattttg caataatttt   1020

atttttagca aaatgacgtt tggtttttgg ggattgggaa tggatcgata ctatcccgat   1080

tccggacaaa gaaaccgacc cgagattcga atttttttcca ttcccaaaca gagcacttaa   1140

aatttaagca acgttataac ggcgtcaccg aactaaacgg aaaaatatga agaaaattag   1200

aaaaagaaaa acggaacagt caaacgttac ttcacgtcaa tggcaatatt catttttttt   1260

tttgtttaaa taattgaatt taattaattt ggtttataaa aatagagtcc tcatatatcg   1320
```

```
cgaatgcgca tttgatcgtg aaggacagct tctcccttgt gttcaagaga gagagatcta   1380

tcattcttat ttggggccga tctctctatt ctcctctctt ctattccgta agtttttctc   1440

attcattctc ctctctcatt tctctccgag atctgtttac aatccttttg attttcattt   1500

ttcctgcttc gatctgtgct cctggtgatt ccccttttcct gttttatctt ttgttgatct   1560

tggaattgat tgttcttttg tgggttttca ttgatttgta ttttctgatc tgggtttctg   1620

ttttctcgcc ttgatgtttt gtatttggat ctgatctgac gtaccctttt ttttttttt   1680

tatttgaatt gcttttccaa tgtttatacc tggattttta ttgatgcatg ggtttaaccg   1740

attggttgga tgcgttttct ttgtgctgga tctaggtgtc cttgttttta atttgaattg   1800

tgggtaaaaa tggcattatt gtaatgtgtt tggagtttga ttttgaatct tggctagttg   1860

atttttgaat tacaaagatc ggatcctctt cttttttggg ttgtcttaag atttttggct   1920

ggtttaagta tttgatgtcg ttgtatttta aggggtaact gatgccggct tgttgtgttt   1980

gtattcagtt tacttgaaaa                                               2000
```

```
<210> SEQ ID NO 45
<211> LENGTH: 2000
<212> TYPE: DNA
<213> ORGANISM: Cucumis melo
<220> FEATURE:
<221> NAME/KEY: misc_feature
<222> LOCATION: (1)..(1115)
<223> OTHER INFORMATION: n=g, a, t or c.
<220> FEATURE:
<221> NAME/KEY: unsure
<222> LOCATION: (1)..(2000)
<223> OTHER INFORMATION: unsure at all n locations

<400> SEQUENCE: 45

attatctaaa cattaactgc aactaataca gattacagta aatttgaatt atgatgttat     60

ctagagtcat ttgtcttcaa tgatattgac tcagattcaa actttatgaa aatgttaccc    120

tggaaaatat tctaccgcaa aatttcaatc caaagttaaa ggttgaataa tttagaagtt    180

ttctgcgact tccacccact tattatttag aagacctgaa atcaaaatga tagaagatga    240

atataaatat attttttgc tttaaaattt ataaatcaaa catttgacct agtaattgat    300

aatacataat attatgtgac tcgtaagtaa aaaagaaatt gaaataatat atatatacgg    360

agatcgcaaa aaataaaaat gaaagtaata taaagtaaac gcaaagtaag aaagcaagca    420

ttttcaagta agattgaaac ccccgtccct gggggctcca agataacacg ggtgcccaat    480

tacccggtac acgacttttg ttgaacaaca ttgaataatt agcccaaatg aaaatatttg    540

tcgacatatc tttcttataa tatgtaaatt agataccaac acaaacactt gtaacaatat    600

cctaactaac ttggttttaa atatatatat atatattatt ttttttcta tttatttatt    660

tnnnnnnnnn nnnnnnnnnn nnnnnnnnta gataccaata tttagtggcg ggtccataaa    720

ttttatatag ggttattata taataaacac taaaaattta gatattatta ttttcaaagt    780

taggccacaa gtaaaagtgg ggatataatt attatactat aaccatattt tggtaaaatt    840

aagtattaaa tatactttaa aattaatatt aaaatataaa aatcgataat gtgtgggata    900

aatttatgga tgtaaatatc aatgttttaa tgttcaaata aataaatagt aaatagaaac    960

aaaacaagaa gtcagtcttt actactaatc gggactaaaa tttgaatttg atttaaaatt   1020

taaaacttaa ataggactaa aaatgttagg acaaaatagt aacaaacacg aaatttaggc   1080

aaagaaatat aattttattt atttattatc atttttttta tatatataat tgaaaattga   1140
```

ttactaaaaa aaacaaagaa cggtaaaacc ctagattaaa atcaaaatag aaannnnnaa 1200
cccgaaagga gaattttgat ttccagagct aaacataaca cgatccaaac ccataaatcc 1260
cgcatcgagt ggaaccgata tcttctcccc ttcgaagttc caactctccg tttccgtctt 1320
tcttttcgat tctccttcaa accctctttt cttcgtcttc ttcaaatctc tacatttcaa 1380
aatcttcgct aatctcttct tccccttctc ttccgatctg accgtgaccc cattcgaagc 1440
ttcttctttc accaagcttt ctctccgcta tcaactttaa ctttcgtcct gtattcctta 1500
gccttccctt gcttttgcag tctccgccac cgaacaattc ctatcccgag ataatcccac 1560
ttttgggtcg tgtttctcac ttattcaaat cgctggttct ttgattttgg gcttatttca 1620
ctctgcatct gctgcgactt ggaggttata acatctctct ctcggtcttg ttaggtatga 1680
aggatttgag atattttcta atctatctga actgggtttt ctttcgcttc cgtttatgag 1740
atgtaatttg ttgttctggg aagttttcag atcctttcta atgggcttct ttaatttaat 1800
ttaaagcttc tttgtttgta cgagatgtca agtcttaatt tctagcaata tcagtatctg 1860
ggttggtggt atttaggatg atcaagtctt ttgttattta atggatgaga acaattattg 1920
tcattgttat tattattttt tggaaaaaaa atcaatgggt tttcactggt tttgttgatc 1980
tttttagata attgaagttc 2000

<210> SEQ ID NO 46
<211> LENGTH: 2000
<212> TYPE: DNA
<213> ORGANISM: Cucumis melo

<400> SEQUENCE: 46
cttctcgatc gcagcaattc aacttcataa acaagtccaa gaacgaagag tttgattccc 60
ctaatttaac ttaattttct ggtgaaaatg gaccatactt ttaattacat attattttgg 120
ttattgcctt ttaaatggtc tattttaatc tctaattttt tttattaaac aatgatggtg 180
aatcttttct aaaagaaaga aaaaacttct ttacaaacta tccaactcta ataacaacac 240
taattataaa ctagtctact acctttatta taacagcaat taaaagaaaa aatcgtattc 300
actgacaaaa attcgttctt ttgaatgctt atcgaatgtt ttaatttttt taaaaaaata 360
tataaatatt tgtaagggaa ggatcagaat taaaactctc tcccctcaat gaaattgaat 420
tatttgtttt tcttgttttt ctttttttaa aataaaccta tggatttagt tggtcggtcg 480
aattaaaatc gtgaggtcgc acacgcggtg tcttgtggat tcaaaattat gattatttcc 540
atcacccctt ggctttttcg ctccattcgg ccatgcctta caaatttcgc tccactccca 600
ttcttctctt cctctcctct ttcaactgca ttgaggccga tcctttaggt aaatggttct 660
ctcccatttc atctctaatt cctctgtttc tttttatttt acttgttctt tttccagccg 720
gatcctccat ttctgtggtg aaactgaatt gttcttatcg atttcttgtt tgaattctgt 780
ttttctctgt ttgtgtctgt gtgtgttttt aatttgtttt ggcatgttga agtttaaaga 840
taccaaaagt tgcgcttcac tactttccag tttcgatggt agctgctagt tgtaacgctt 900
acgttcttgg ttttttagtt aaaatttttt tgcttcttgt tgtttactgt ttagcaaaaa 960
gcatggggaa tactaccaaa gtcccgaact taatagatag atgatcatgt gctaagaagt 1020
gcgatacttt ccgtagctga tacgtgacac agtgtctgac atttgtttga cacatattag 1080
aaacttgtta gtataacata tgtgttaaac aggcatagaa cacctgttgt actaaaaaaa 1140
atatttgtat gataataata ataactttga agtgtaaaat atatccagct aagttttttc 1200
aagtatacaa gtgcattaac tcatttcctc ttgattttct tttggtataa aaattatata 1260
tattttgaaa accgtatact ttaataaatg tatccttgtg cattatgtcc tagattttta 1320
gaatatggtg tgttgttgtg tctatatcgt gtcgtatcaa tatctcgtat tcgtatctgt 1380
gtttgttaga tcatatgtat aagcgaggac agctatttct gatgttacaa gaccttcttc 1440
aaattttaca ggaaatcatt caatttgaaa attcaagatt acaaatgcaa tctaaaccaa 1500
acttcaagaa caaaaagtgt tatttgttaa tatccttgcg acctcaccca aagtatctat 1560
tacaaacttc agaaaaaact tcataataag ggttgggttg aaaaaaaaca tgaagaagtc 1620
ccaccccaac ctaactctaa aaagcataaa aaattcaacc caacccaaac cttacaattt 1680
gggttgggta gtccgtgttg ttcgggttgt cgggttattt gaactcctag ttttagctaa 1740
gtgtaaactt atttaaggat gttgaaggtt agcattgatc tttctctctc aaatttggtc 1800
aagaggaatt attttttgag tcattcatat agttccattt tgcttttgag catttgaatt 1860
gtttgttaac tacttctttg attaatatat tcgaaagtga aatttccttg gtttacttta 1920
ttgatcagtg tcccatttta ccagttattt cagttctcct aataaccttc attggacttg 1980
agttcggtta acacaaaaca 2000

<210> SEQ ID NO 47
<211> LENGTH: 2000
<212> TYPE: DNA
<213> ORGANISM: Cucumis melo

<400> SEQUENCE: 47
aatgtatcgt gggcatttat tatgacaata gtgtaaaaat gttgttaaca tatctgtgta 60
ttgtcgatga tgtagatcta ctacgccaat agttatagtt tccatcggta tatctatgaa 120
atgtcaacgc cttaaaatag ttgcatgggc atagacttgt ttttttagaa aaatatgttt 180
tatatttgta tttttttcac taacatcctt ttggttttgt atctaaacac aactcaaaat 240
atatcaaata ctgaaattca tttcctaaaa aagttacaat tgtttcaaat ataagtcacc 300
tgaatgaagt tcttaaaaca caaagaattg ttccttacaa aattaacata agcaaaatag 360
taagatcgtc caaaataaca aacattacat aaactttaga ccaacttcta atttgtttgc 420
caggaagtga tctccattga aagtttgtct taaaaaacaa ataaaaagaa aataatagaa 480
acatattcaa taaactagta cattttgcac cttacatata tatacaaaaa ctttacctac 540
tttaatttct tgaaaatcta aattttgaat taagaacttt tcttacaacg ccaaaacaat 600
aataacttat aaatcttagt gatggaataa taagttataa ttcattggtt gattgtatca 660
ttaaccattt ctttctttg gtgtgagaaa cttatccaac taaaaatatt cacaatagta 720
gggcgggttt gtcgtggctt tgtctgaatt tctacaacat gtgtaaatat tttcaactgt 780
tttatcctct aagacaattt tcctaaaaac aatcatgttg ttcacacgag atttccaagg 840
aaatttaatt caaggagttg aacttgtatt tatgttgatt tgatgcctat gcttaatttt 900
aagatttgag aaagcacgtt atatttgtaa agttggagta ttggaagaaa agtttgtatt 960
ttcaaaagaa cctcaatatt cgagatcgac ggttggcttc aaaagttagg aagtctttga 1020
ctcataggag aatcctatct agactttatg caatataaag agagttctgt tttatggact 1080
tagttggata aataattaat ttgattcaac ggtcataatg aaaacatgtg acatcattat 1140
aattaaccaa tttatatctt taatacacat atcaactttt aaatagttct aaattcaatt 1200
atttgtattt atcatcatta attaaataaa taatgtgaca atttgtgatt gatccaaaaa 1260
tttcatattc aatctatact atattagtta agcttaaaat tttactaaat gcttaaagtt 1320

```
ttggattatc gagcttccta ccaaacaaaa gcctctattg cacatttaaa atatagaata   1380

gtaggtttat ataatatgaa agattgactc ttaagaccat actctatgac ctaatgaaat   1440

cgacatttat gtaattgata attaataatt aataaaaaaa gtgtgacaaa aaagtggaca   1500

taataaaaga aaggaaattg tgaagcatta gcatccgaat ttcgaagaaa acaaagggcg   1560

ccctcagatc aaagaggaca tactataaag tctccacgct atttcaagaa ttggcgtgat   1620

tctcaagcga catttccgta attcaccaca aaaattaaaa acaaaaaaga actcacagat   1680

tctgatttga cttttgaaac cccaaccccc atcatctccc aatttaattt tccctcgata   1740

tttatccaaa ttcagaaaca taatcttgac aattttatgc tccattcttc caatctcagc   1800

cgtacgtttc attcaaactc caattctccc ccactgcgcc ttccactacc tttttccttt   1860

ctattaaagt gtcctcacaa actcacctcc tctctctgtt tctgtctgcg gtaggatcgc   1920

cgactccgga tttacatttc aggggtcgaa gatttgttct ggggtttctt taatttcttt   1980

atatatatac acacacaatc                                                2000
```

<210> SEQ ID NO 48
<211> LENGTH: 2000
<212> TYPE: DNA
<213> ORGANISM: Cucumis melo

<400> SEQUENCE: 48

```
gccaaggaaa atgaattgtc taagaagaag aaagaaaaga aagaacattt tttgcaaggc     60

tacaaatcaa aacttaaatt atccacgtga cacaacaagt tcagagagga aagaaccctc    120

taaaactccc atataccttg gcaataacca tgacaatagc aataaataaa caagtccatg    180

acataaaata aatattgttt tcattaaatc tcaataattc atatgtagtc cgctccgatt    240

atgccacagt catatatcaa gttcagtatt ttaacaattc aagtagacat acataaagct    300

actatggaaa acataaacaa gaatggaaga aggagggtta aggaaacctt tatccctgat    360

ggagtttcag taaaactgag cttgtaggta ttagtacgaa agctgtgaaa tgaacaacct    420

tggccaggta attgaggcac cccaagattt cctttatcaa cactatcaaa gaaagtaaag    480

aaagttatca cttcaaaacc caactcccaa aagcagctca tcattttcca gtaagttaat    540

actttgaaag atcaaaatca aatctacaat caaattagac ttcttaatag ttattgccac    600

gaaccatgca tttgtcacgt tattaagact atggtttgca ataatctcct atctggttgg    660

atcactactt atactaggca cagcataaac taaagtagtt tcccagagaa ggaagaaaca    720

tgaacctggt tgggtccatc ttggcagtaa aggatttaag ggagaagagc aaaccaaaca    780

taagtttatg gtcttgctgg ggattcaatg tccggagagg ccgattccac tccctgtaga    840

acaagcaaac tccattccta ttgaaaatat acatcatatg cacattgttt ccagtcgctg    900

tcggtaccgg aggcgaggga ctaatttctg acccaccaaa gaactgcatg gtttctggaa    960

taaactaaac taaatcaaat caattgtcat ataaaatgat ctacgaatct aagattctaa   1020

caaacccaac atttcactca actctacaat cagtaaccta gcaaagcaac taataattca   1080

atcattccta ataattcatt gaggttaaaa ataaaatagc gaattgtcaa caggtaaaat   1140

ctaacccgac ccaaatcagg aatcactaaa gcaagaagct gtatgactcg atcaaaaata   1200

acccagatgc atttcccttt ggcctctcta cagaaccact caatatagtt agaaacaaat   1260

ctagtgtaaa attgggagtc ctattcatac ataattccaa ggaaaatgga ttttacttat   1320

gcatcgtata agagactgtg agcaggggaa aatggagaga taatcaccaa tgagctggat   1380

ggtgacagat tcaagaagaa gcatcaaaat caaacaacgg agagcagaaa gatacctcaa   1440
```

agagcagaga ctgcaaagta aaggaagcga tcaattcaac gacgaagctc ttgattcgtc 1500
aggcaatgat tgccggcgac aacaacgtca gcagatcgga gccttacggc accggagacc 1560
cctccgacaa ggacagagtg aacgaacgtc gtttgtgaac ggtgtaagca aatcgatctc 1620
tcggagtcca actccaaagt actgtttcga tatgcattaa tacatttgat ttttgttata 1680
tcaaaaataa atattatatt aaaatttata aacattaaca aaaaaaaatt aatttcacat 1740
aatttaaagg accatttggt aatatataca aaattgcaaa aatcaaattg ggcctatttt 1800
gttgttattg gaggcccaag atgggtggtg ataaatatgg gcctccaaaa gaataagcaa 1860
aaaaccctaa tttcctctct tcctctcttt cccaatacta taaatcttca ccatttcct 1920 gattagggtt tttgttcgtt cttggccgtc cccttcatcg ttcccagaga gagggagaga 1980
gtaagttgca atagtaaaac 2000

<210> SEQ ID NO 49
<211> LENGTH: 2000
<212> TYPE: DNA
<213> ORGANISM: Cucumis melo

<400> SEQUENCE: 49
aattagcaaa ttgtatgtaa caacgtcatg aagaggcatt tcatcgaaca atttaatagc 60
agagtcaaga tggcccagtt ttataagttt attgatttct cgattcttaa ggtaaatgag 120
atcgcgagca tggaaatgca gacccaaacg agaatatggg tgtggtaaat ggaccggtga 180
tgttgtggct acaaattcgg attttacagc agtaatagtt ctgacgaagg aagcgaattt 240
agtgaccttt cgcatcacag tttaagctta tcagagacct gaacaagggc tctagctcta 300
caacttagaa aggtttgata tggtccgtga tcgggaggga ccgaataaca ggcgcttaaa 360
ttgttgttca taaagaagag gattgtcgtt gatgtatttt aaccaagaga tgattagtta 420
tccacatcca cagagagaac agaagacggc tttctaaatc tacaccgata aaaataaccc 480
taccactttg tttctttaga aaagggtcac attctttaaa aacattagcg tcgaggatta 540
atagggtata ttgactaatg ctctgtttgg atttcgagaa ataccaattt acaattgatt 600
tcaaattaat tatgttttgt tgttgcacga aagataaaaa gaatttaaaa ttcaaaagga 660
tctcaaatct tatttttaac ttaaaaactt ttatgaccca aacggtttat gtatgattta 720
aaagtagaat acctctgtga attcttaatt tttttttctt tccaattacc acataaatat 780
gaaattttaa atacatttat tttaaatttt atatccgaaa caaaataata atttaaaact 840
atttctcata tatgaagtgt gattcgatct aaattataaa ataataaaaa tttacatcta 900
gttttgatta tttttttcg ttagatacta aattgttaag aaaataacat ttttaatcca 960
aagttttgaa gaatatatga cttttaaaat ggtatttatc tttttagtgt ctgattttta 1020
aaaaatggat ttcaaaagtt catcaaatag cattgtattt ttattttaaa taattttgac 1080
atttaaaatt agagtaatgg tttataaaag acacttgatc tctaaaacta ttttcttaga 1140
tataaatacg tatgattatt tttaaaaatc aatcaaaata ggtaaattgt aaaaaaaaaa 1200
aaaaatcaca tgaatagtag ttgtaattat gctctcaaac tttcggttat gaaaaataaa 1260
cattttaact tttagacgtg tcaaagttga gtcaagttgg accttcaaag ttatgtagtt 1320
atataaattg taatatatgt ataagcttgt ggattcaatt ttatcattta tgggtccaat 1380
ctctacaatt atcgtaagtc tatgggtcaa ttgtaacaca tgtggagttt aagagctcaa 1440
ttttggacgt ggatgtgttt tgcaaccaac tccacacctt aaaaaggtgt ttttttttaa 1500
tttatcaaaa aacaagaatt tagaatcttt aagtttatct ttaaaaatca acggacattt 1560
tgaaaaccaa ttgaaactac tgttataaac ctaacaacta aaagtatatt ttttaagacc 1620
gaaagcataa atccataaaa aaaaaatcca gaactgaaaa tgtaactttt atagttgaaa 1680
atttagctaa attatacata ttaaaattca aggaccatat aaaattaaag tacctgatta 1740
aataataacg aattaatgtt tggtattttt aacctacatt agaaaaaaaa aacaaaagaa 1800
aaacggcata ctatttgtca agcgtccgat gggaagaaaa tccaacggtg agtgttagta 1860
ttgaaatacg cagttctcgt gaatgagcct ggcttagatt tgggaacaag agccaacccc 1920
tttcgaccga gaagccgtcg tcttcaccat attcgcctca accattcgat agccacgttt 1980
gaagaagaat taggattgcc 2000

<210> SEQ ID NO 50
<211> LENGTH: 2000
<212> TYPE: DNA
<213> ORGANISM: Cucumis melo

<400> SEQUENCE: 50
agccaatggt tcaattaaca gctctagttc tagcatggct accgctggta acctttctat 60
gactagagac gtcttggagg tggagggtag ggcacgagga ttgaaaggtg agggtttggt 120
gaaaactcaa gcctttcaaa ttcaagaaag catgcttgac ctagtagcat ctggtgatct 180
tggggaattt gcaatggata ctcataccct tagtcggcat tcgtctcttg gttctgctgg 240
tatatatttt tttctcttgt tttctagtga tatttttcttt tatcaatttc cattatgaag 300
atggaatctt atgttctatt ttttcatttg gaatgtaggc tttcacaatg aaaaaattgc 360
taatacgttt ccagaagagg ttgctaaaga cccgtaagtt cttatttctt aacaatttcc 420
tcagtttaac aagttttatt tactaacata tccttagttg tataaatatg aatctattat 480
attaactatt tcatttatct atcttttaac agggtgacca ttcacaacaa agataatact 540
tcattgaaac gccctcctgt ctcacgcact tcggcatccc aggatggatt gtctgtcctg 600
attcctgatc cggttgttag aggaaagaac tcagatggta aataataagt gatccattct 660
gttatcttct ttattcattt tcaattttgt attttgtata tatttatata atattttaga 720
aagataaaag atccatcctg aaactttgtt tcaggtggaa gaccggaccc aactagtatc 780
ttggtgaacc aagaaaacat ggcagccatg aagaaagaga tgcgtttccg gcgctcttct 840
tcttgtagtg acagcgacgt gtcagagact tcttttattg atatgctgaa gaagacagct 900
ccacaagaat cccatttgac aacggcggga gttccagagc catctgatgg aatgcaggga 960
gggaaaggtg ggaaaaagaa agggaagaag gggagacaga tagatcccgc actactcgga 1020
ttcaaagtca ccagcaaccg aattatgatg ggtgaaatcc aacgcttaga cgattgatcc 1080
attaggcaag atatagaaca gaaattgatt tttttttttt tttttccaat catttttgta 1140
gattgtgcag ttatttgttt tcgtgtttgt ttaaccctct tgtaagttgt tgtatatagg 1200
tttcttagag ttgtcagctg cgttgaaaca tgtggccggt atatgtattc caattctttt 1260 ctttttttccc gcagttgtaa atgatcaaat ttgagttggt caaattacca aacctttgta 1320
caggaacttc gaagagagtt gaaattttat tctttttctt ttttgttctt ttatagagtt 1380
cgagattatt tgtatgaata taatcaaaag caaagcatgt aaaaataaaa tgatttgaaa 1440
gggaggtttt ctatcccatt caatgtgacg aatccaacac ttaaagtaaa tttgaaaact 1500
gtctaattta tatgtatgga atgtaatgct cttcaagaaa ttatcttatc ttctaatatt 1560
taatgggatt cacataaata tgaaatttca acgtttttct tttcctttttt gttgtgagat 1620 taaggatact agataataac cgacctcaac cttttaggcc aagaggtctg gagtctttat 1680
acttgaaaaa agtttacaca tattctaaaa gattaaaagg ttaattgttt ggtaaaacat 1740
taatgatgac gatacttaag gtttcattaa aaaaatattt ggaacaattt gtttataatt 1800
taataaaatt gtaactttga acattttgaa ttacattttg tttttccatt tttacggtcc 1860
tcgaactcat cgatactcac aatggagaaa aatatcacaa tgccgaaaat acccttcttg 1920
ttcccttctt atacaaaagc aacactattg gccttatcaa cggagcagca gctactctcc 1980
tttagcacaa atctccatcc 2000

<210> SEQ ID NO 51
<211> LENGTH: 2000
<212> TYPE: DNA
<213> ORGANISM: Cucumis melo

<400> SEQUENCE: 51
tggtgtaccc acttggtttt ttctcttttt ttcttttagc tttttgctcc taaatttctt 60
gccttagttt tcaaaagctt gtttttattt ttgaaattta accaagtgaa tagaaaaaaa 120
aaagagaaaa caaaagcttt taaaagcttg tttttatttt tgaaatttaa ctaagtgaat 180
aggaaaaaaa gaaaaaagct tataaaattt gacgaaattt gctgtatttt gtacatttta 240
ctatttttct attttaaaaa atgtgtctga acgaaaaact tatattatga gatttaattt 300
tcaaaataaa attataccaa acagacttta gaattgtcaa tcaaatttga caatgattag 360
gtgcattttt taaagttatc ctaaagtttt tttttttttc gtagtcttgc ccttgctttt 420
atcgttaaca aataaaattt tccttatata tatatacaca tttaactact caaggtctgt 480
attttttcca cctgatttat ttaatatttt tttttttgc agaaaatcta tttgtatttt 540
aggggaaaca aatgagtgaa gagatcatca agcaacggtt gcgatgttgc agcggaaaaa 600
tctttggttt gtcatttctt gtgatggggg tttatagggt agtatggtta ttgtatttta 660
ggatgttgat ttttatttta atgagccaag agagagatgt ggattctaaa attgatgatt 720
gatattattg atgtgatata aatatataat tttgtgcgaa aattgctatt ttattttctg 780
tatgctcatt cagatcacac aataatattt gatgtagctt tacttattga caaaatatag 840
gttttaatct tgtgctcata caaacaacag ctatgggtga aattattttc tgattttatt 900
tggcaaagat gatgtcagca ttgtgtaaat ttaatgtgaa ttacacttct gatttcttcc 960
caatgtgccc tctcaaatat tggcaccaag ccatttaatt gtaaatacgg aaaggtcata 1020
aatttccatg caagatttat ttcatgttta aaatgattgt gtgaaacaaa atgaaaaaca 1080
agaaattctt acctccaacc tcaaagtagt cgatatgtca aggttcaata tcaattttaa 1140
atatccatga atagctttga tatcttttat aaatgcttgt aatatatata tactaatagc 1200
aatgtctata agttagtttt gagagtaata cttgttatag ataacaatgt tactctattt 1260
accactctac tattgaaagc ttctttttct tccatttatg aattaataac ggtcaagatc 1320
caattgcatg agttactttt aattaattac aatctaaaat gttaatataa gtctaaaatt 1380
gtccaatata tgtgattttt tttttctctc tcaaaccttc ccttcttttc attgaacttg 1440
tggttcaaat ttgatggagg acactgggaa acagcacaat tcaaagagcc aaagattgag 1500
taattttttg atttcagagt tttcatctct tcttcattct acacctttca cttctcatcc 1560
acaactatcc aatcaaccat tgccacgtgg catcaaaaat atccaaaact gaatgagatc 1620
caccacaaag ttcctctcat cactgtttgt catcaactca tcaagaactt catcatcaat 1680

```
cagaaatcca acatttcaac ttctcttagg aaatgacatt tttaccagtc tccaatgtca   1740

aaaactcaca caaaatccct ctttccaatc taaattttac aaagataaca ggggtaattg   1800

aagaaactta gcagtaagtt aacatattat agctttcatc aacccaagtt tttttggttc   1860

ctttctaaac tgtagtttgt tttcttgatc cattctaaat atttcctctg catgaaaaga   1920

agaaaggaaa agtgaaggcg aaacctgttt tatgcttcag aaaaccaatt cagagtaacc   1980

aaagatctga acttcagacc                                               2000


<210> SEQ ID NO 52
<211> LENGTH: 2000
<212> TYPE: DNA
<213> ORGANISM: Cucumis melo

<400> SEQUENCE: 52

cgctcaaatt actaacatcc ttctctttct tgttcccatt cgactagaga gacactatct     60

tatccacctc agttggctgg gtgaaatcat tgaaactaac ggttgattgt ccagattgtt    120

aaactaccct atgttttatc atcttggtta catttatagg attgtcagaa taataattcc    180

ttttgaaatc atattctaat tggcacagga ctaaaataat gcctttctta agctgtaata    240

attagaatct aaacagtgaa gttagtaact gattgatgac atttccacga ttttcattta    300

tatcctgtgc agctattctg acatcacaaa acatttcttg attttcattt ttacttgtca    360

tccatcagtc aggacgatat cggcgcgctt gttgacgacc ttgtcctaaa tacaaagagg    420

cttatccgag ctacttcaag ggagattgac aagtggaaaa gatgaaatta ctcatttgtt    480

attacattgt acaagtgatc tattaggaag aaccacaatc aaaactgaag aaaaaagaaa    540

cgtgctggct gtctacgtgg cttttagagg tagaatttat gtacaattgt ttagaaagat    600

gtatttaatt gctctaaatc tcatatgcat tggattttga gcaatcttaa aatgccgaat    660

acttaatgta ttatcgtagg ggtccctaga tggcagattt atcatgtcca ttctccagaa    720

agaaagaaaa aaaccctttt tattatactt gttcatttta agctttttct ggttgattat    780

aatgtcagta atttaaaaaa aaaaaaaaat tactgtgtat tggcatcggt tatatgttat    840

atacaaccct agttaaaagg taaagttttg ttcattcggt cattagtcat tcctatacga    900

acgtcacatt gtgctttata atttcaatag gttaaaagta ttcaatatag ttttttaagt    960

tacctagtag aggtgatcat tggttgatcg gaatcggttt tttgacaaaa ccgccactga   1020

accgatcata gtcggtttag taaatgttca aatcgacctt gacatcgatg agtaaagatc   1080

ggtcggtcgg tttttgtcgg atgggccggt ttaacacttg gaaatactat tttgaaattt   1140

ttcgaaatta atccctcttg ttttcctacc gaccgatttt gggtttggtc ggtcagttcg   1200

attttttcgg cctatcttac tcactcttat tacctaggga ttgaatttca ttttatcctt   1260

agttttaggg ttcttttttt atacttttga aatatttatg tcgatgtcta gagtttaaaa   1320

ataacacttg aaattataat ataatttttt ataattgtta gctataattt tacgtccaaa   1380

tatcaactca ctcgcaactt gtttaatcaa ccaataatat gtgtctggaa tagtaagtat   1440

ataacttgtg gaaaatgact ttaaaagact tttttaaagt atttatttaa tgccaaaata   1500

tctatattta tgtttataca ttaacataca tatccaaagt tacatattag atttgttaaa   1560

taattcaaaa tgagctaaag aaaaaaagaa gttccatata ccaaaataaa atataaaaag   1620

ttgaagacta aaatagagat tttgaaacaa ggtaagttag atttacaaat tgcaatatgg   1680

gagaccaaac caccacataa caaaaatccc aatgtccaaa tggcgcaatt ttgtttagga   1740

tagctcacgt tatccaaatc actcaatcgg agagaccaac ttaaaggcca catctgccac   1800
```

-continued

```
gtcaccatac tccaccaatc acaacacagc attggatttc tcagcttatg agaccaatca   1860
caaacctgaa tccgacgtgg catgtccaca tccaccagta ccaaccatat agcttctacg   1920
ttctccacat ctaatcttca ccatttacac aatattcttc attcttcttt cctcccttca   1980
atccttcatc ctctccgccc                                               2000
```

<210> SEQ ID NO 53
<211> LENGTH: 2000
<212> TYPE: DNA
<213> ORGANISM: Cucumis melo

<400> SEQUENCE: 53

```
aattctaaca actccggaac caaataattt agcatggatt gaaatataaa tcttcttgac     60
ttgcaaaaaa atcattgtaa tggtcttatg ttggttatag ttagggtatc gaaacgccat    120
acaggaatat gggattaaag ttaacttttg ttcatcaatt tcagcttatg aacttctaaa    180
atatcaattt tacctttgaa cttatatgtt attacccctt tcgattgtgg tatgttaatt    240
aatatctgaa tctcagtcct tatgaaactt ttttatactg tcacaaacat atgaagtttt    300
attgtaagtt cttagaaatc atctaaaaag agtagtttgt tggactattt attttatttt    360
ttcttattaa gttgttttca cgccatttca gtaaaataac tatagtgaat agagaatcaa    420
acttctaatc ttaagttaag gtagtagggt atatgctaat tcaataagat aatccgtgat    480
gcttgacatc tgacttaatt gttataagtt ttaaattttt tattgtaata tttaaaatac    540
tagtttttgg tttctaataa agaaataatt gaacaattac aaatatttat acaaaattaa    600
actagaatat atgatcattt tccttcgtgt tagaaaaagg gaaatatatg tgtgtattta    660
tacatattag atattgtttt actatattcc attttcctca cgggaaatgg aggattgagt    720
gggagataaa cattgtcccc aagagaattg ggaatggaaa tgcaaatgac atggccctcc    780
acaaaattgt tcgcctaaaa atgggctttc tcacttctca ctccgcaaga aaaatatcgt    840
ttcccttcga attattcggg cggcaagatc tcaaaaccac atgtttttct ttctttattt    900
ttcaagccta cattatttat aaaaatataa cttaagcaga gaattatgta aattcaagtc    960
catttttcgc ttcacttagc taaatcatta acaaatctgt aattttgttc ataaattagc   1020
tcaccaatta tgttttagcc cactaaggcc cattagacat ttttattaga aaaacatgaa   1080
ccgttggatc aagatgtgtg ttttcttttc tttttctttt tatttttttt gggttttggt   1140
ggggttttgg tggatcatgg tggatcaatt cgtagcttta gcaacctatt attatatgga   1200
gggaaagggc gtattaatct gttagcgccg tccgggagtt tagctttctt ccccgagcct   1260
cggtcttatc ccctaactcc aaaaccctag cccaaaggta atccactcct tccccctccg   1320
ctcttcatct ttttctattc atcatcttta atctgttctc ccttttggtt cttagattct   1380
tcttttgttg gattctttta atctttactc atggttggcc ttgtaagttt agacgacgtt   1440
tttatacatt ggttaatcct gcttctctat ctattcgcac gctagggttt tcctattgtt   1500
ttctattctg ctctacttct gcaaggttgt gttcttcttc gttcaggtcc ctttttttaa   1560
ccgaaattaa attaatgcaa attcgtttgt gcttctaatt aggaagcctt ttggaacatc   1620
tcgacatttt gattgctgca tttcatttcg ggtatatttc tatgattgaa ggatgtgggt   1680
ctgttcactg catggtcatt acttatgcag ctatgcttat cgagtccatt atgtttgtgc   1740
aatctgtttc cggattcata attttttagt aattgatcag tagatgaaaa aagatattgt   1800
aatattcctt gagtgttgca ccagtcttgg tgggtatctg ctcctgctct ttgcttgtgg   1860
```

```
attttacttt tattatatct gtattattcg aaatgttctg ttcttgttat aacttatacc   1920

cgaagatgtg ttcctccccg cgtctagcgt tgtgggttac ttatgatgga catggttttg   1980

attctgtttg gtttgtgcag                                               2000


<210> SEQ ID NO 54
<211> LENGTH: 1547
<212> TYPE: DNA
<213> ORGANISM: Cucumis melo
<220> FEATURE:
<221> NAME/KEY: misc_feature
<222> LOCATION: (1)..(1547)
<223> OTHER INFORMATION: n=g, a, t or c.
<220> FEATURE:
<221> NAME/KEY: unsure
<222> LOCATION: (1)..(1547)
<223> OTHER INFORMATION: unsure at all n locations

<400> SEQUENCE: 54

ataatgtgtt gatgttgatg atcatgcatg gtatattaat ctcatgatta aagacgttaa     60

gattaatatt cattccatgt ttatgatggg tgttcttagg gttgtaccca tatgggtgtc    120

cctcgggatc accacctttt ttatgactgt atggttctac gagaccacca gtctgtcatg    180

atatgtttat gaatggtacg acggggtcac ttacagccca attgcttaag tgttccttcg    240

ggttcactga agacctattt ttcctaggtt ttcctttgac ttcagcaaaa atcagttttg    300

tcctaggtgt tcctcgagtt cactgaagac tagttttgtc ctaagtgttc ctttaggttt    360

atcgaagatc agatgtgttc ctacagaatc attagattgc aagtgttcgg gaacacatcg    420

gtttaggggt acttctttac atgaacccta atggaaaatt aacagacatc tagcggaatt    480

agtagttggt cccttactga gtatatattt atactcactc tttttatgtt taatatttca    540

ggcaaaggtt aaggtagagg aaagttgacg agtgatagaa aaggatctgt gacatgtcat    600

atggggactc agtttcgttt ctgcttctat gtatcagtgt ttcagtattt tgtttnntaa    660

tgaaaattta gtcttcctct attcaagaaa gtgtctcttg ttattgttta tttttagtaa    720

tgatttcaac ttagtataaa tagttggatc attacaaata atatattggt gatatacttt    780

gtaatgatac attgagttat attattcata tgtttaatat acaaaactgc aatattaaaa    840

aatgaaaatc acgtaataag tatatcaaca aaataataca tatattacaa gcacgtcaca    900

acactaatat acaaaactaa tataaagtaa gatcaaagca aaaccaacgt aaaaaataaa    960

acaaaatcat ttgaaattaa atttaactca aaatacacat cgaagaaagt ggagaaaaat   1020

cacaatagag ttaaattact ttgattaata accattatat ttcatattga aaataatatg   1080

tcattagtat tttaaaatca agattaagat aggaagaatg aattgctctt ttcgtataaa   1140

aagggatgat tggggcctta cgaaaggaga aaaatacata tgttatcgaa aaaacaaatt   1200

atttttcttg taagagagaa tgattatatc cttaaaaaaa tgaaagaaag aaacaatcat   1260

ggcattaaaa aggaaaataa ataaattatt aaagggcagt tcgataataa taacaaattc   1320

aacgagagta ttaaaagaaa atgagaattt gcaaaattta aacaaatgtg tatattaagt   1380

acagccaatg caattttcaa attttaattt atttggttta cccaaaattc aatttctaaa   1440

ttgagaggag gatatagtaa attcacacgc attatcccct tcgagtttca tcatctcacc   1500

cattcttgca tacagtgcag ttacaattcc ttcattctgg atagaca                 1547


<210> SEQ ID NO 55
<211> LENGTH: 2000
<212> TYPE: DNA
<213> ORGANISM: Cucumis melo
```

<400> SEQUENCE: 55
aaacacttat catgttatgt atcccacatc gaaaagataa aagagacttc atgatcttta 60
catgatatat gagttactcc ttcgactacc attggttttg gagatggatt caacccaata 120
atatgaatct gacccaacaa tggtcaactc aaagagacac catcttgaga tacatgttgt 180
gtacccatat tagatgaatg actatacctc gcaatattta taacatacat gaattacttc 240
tcttactgta atttggtttt gacgtggagc ccatgattat ctaattaacc ataactggta 300
tatgatatat tagtaggtaa cccgaagagg ttctaagata aacacagaat tcaatagaat 360
cagagccttt ccaatgatat ggctttagat gggaatgatt tgaagtataa tcattctacc 420
acacccttta tatttgtctg tcaccagaaa tctcatcttt tcttgaggta ttattcactc 480
gaaaagaggg aggcattttt gggttaccca tctaatgcac gatgaactaa gggaggtcaa 540
gttctgggaa tacagctagg caaccttcac agtggataca ttcgaacaaa tgataaatgt 600
gaaaatgaat catttcatga gtgtgactaa cccaatcatt cctccttcta tatctttgaa 660
tcccacagtg agtcagagta aaagttccag caacaagtcc tacaacccaa attctttagc 720
tatttcttcc accagaacaa aaccaagcaa aaaatcagcc acaaacacag ctcaacaatc 780
tataaaggcc aaaatactaa gacagtcacc attaccacat tgaaagccgt attttccaac 840
agactttgcc tgcaaaatag atcacaaaga cacgatttca cattggacag acgccacagc 900
tccacaatct caatttcaat caaataaaag taaatcaaag ctaaatagca agtgtatggt 960
accacgaaag cagcatggct gacgccactg aggcctgtaa gagagaaaac aaaataagtg 1020
tagaagataa agtgaaatag aaaaatcaat cgataagata gattttcaga ttaccatttt 1080
tacgggaatt gtacggaccc aaacacaaac cccatagagc gccggcctga agatgaacag 1140
gggcaggaaa ttcagaggaa gaaattaaag aaaatgaatc atagtttgag aaattattcg 1200
taaagtttac cgttccgacg cgaatgctgg attcgacggc gagggaagaa caaggaacga 1260
cgccgttgag ttcgtcttcc atcttccaat tctcaatttc cttcggaggt ccgtatgctg 1320
agagctctgt gtctaccaag ttccaaccat actacgtcgt tttggatttt tatttttatt 1380
ttctttcctc tcttttgcca aaaaagaaaa aaatagtatt ccaacctaaa acctcaaaat 1440
aacatatttg ttgtacaaat tataattagt aaacatttgt cattgtgagc ttggtatgta 1500
atattaacac gaactttatc gctaataatt tagacgttaa tgaataattt gagcattgcc 1560
ttcttatatt gttattgtgt ttataatagg attgcttaca atgtaaccta gtatgttgtt 1620
gagctcgtta actttttgt ttttcttgaa tattcaaagt taaaaaattg tacaagtttt 1680
tggtgacgtt ttcttactac attatcggga tgaagatcaa atatagctta gattagagaa 1740
gataatcatg ttgatttatc gttaaacttt gactacaaaa tccgtttaat tttttttttgg 1800
atgaattagt tatacaattt aaacttaaaa ggggtgaatg aagaaagagg atagttttac 1860
aaattcgaag tgaaatgagt tatttctgct taaagaaaac aaatctcctt cgtgctttaa 1920
aacacaaact caaaacccta aattcagcgc cgattcttca atacatctct gcaggaagtt 1980
agggcaaagc agaagcaaaa 2000

<210> SEQ ID NO 56
<211> LENGTH: 2000
<212> TYPE: DNA
<213> ORGANISM: Cucumis melo

<400> SEQUENCE: 56

```
acttccaaaa atcagcctca tgggatattt aaagaaaacg taaattaaaa ttagcatcat      60
ttcatattga acaaactaca aaaattaact ctaaaagatg atggtaacta caactaaacc     120
ttcaattttt cattgtaaaa atcgaactct taaacttgtt caaatattaa aatttgaccc     180
tcaaacttaa aagagctaaa aaaagacctt caaatagtaa aagtagaact ctcaagctta     240
tagaattatt acggttatga ttatagccat agatgattca atcgattttc ctccaagatg     300
atggagtata attcttcaaa tctagctgct tagatgttat cacgataatg aaatcatatg     360
ggaactcaac aaaaagaaag cacttaatgt tgaaagacat tattctttgg gtgttgagtt     420
gggcgaactt gatttttatt attaatccgc aaaggacctt ttgagtaagt tgtggcaatc     480
tttattggag tgctaagatt tgttattcga aatttcttgt tttgatattt ttccaactaa     540
aactaatttt tttaagaaat gcaccttcaa ctgatttcat gcgtgtcctt ttgcaagact     600
cgcatgggac ataacacatc atcttatatg gcaaggccta tgtgtcagtg gagatttgac     660
gtcaatttct ttccactgag agtcgtcctc tttgtgatgg cagaactttg gagagtcatc     720
aaaattggtt ctttgaaaat gtttcttatt ttgatttttt tttttgaaag aaatgagagg     780
aataagatat ttttacgagg actctactag tgggtcaatt tgcccgcata tggatatgca     840
taagagtcct tttggagaga aagggtatga tggaaagaca ttgcaaaggc ccgtccacta     900
actttctatt atacaattag gtggaagcca cccatagcaa tgtcttggtt gaacactgat     960
attacttgaa accatgcatt taagatgtga aatctcgact agatgcttta ggaatttgga    1020
ttgtgtctgt tttgttgaat tcaagttcat tcctaaatac catgaagtta agatccttga    1080
agcaatgaag accatttatt tagatcctta attcaaatct ctttactaaa gatgattgtt    1140
tataaatgat caatttgttg aatgatgttc tacttgatat ctctaaagca tctcttttcg    1200
gtgagaagcc cacaacttga atagtattcc ataaatcatc tatttttagt ttctatcatg    1260
ttctttaaca tcaaaacatt ttagcgcact ctcttataac taagacttag aaaaacacga    1320
atcttccttt cttacgatat atatcctaaa tggttttcta tatttgtgcc ttacaatata    1380
atcaattctt tttctatttg atattgtcat aaaataatac tgataacata gtttttatgt    1440
tttattaaca cctaacaaga aatatggaag acgttaatat atcttcaatg tcgatattga    1500
atcattttat ttatgaatat atccacgcgt caaaaaaatat tttaatcatt aacttctagg    1560
actaaattca aacattcttg gaaccataga caaaagaaca aaatttgcaa cctcaacaaa    1620
caaaatttta tctttacatt tgcggctaca attcacaaat tcccaaacca tgatagaaag    1680
gccccaatct cccacgtgat aaacacacat atggcacgtg accaaatcaa aatcatccac    1740
atgatgaaaa cttaatggac agctcggatc ccaacaccca ataaaaagca gccatgaagc    1800
tgacgtggca gatttccccg aaaacctttt aaataataaa caataaaaaa atatatacat    1860
aaccgttggc aacgtttttc cctccacaca ttttcccatt gccttatctt tctttccctc    1920
caaacagcga gggaagaaga atccaatcat cttcttccaa taatttctaa aacgaaattc    1980
tgctcgattt tccctctcca                                                2000
```

<210> SEQ ID NO 57
<211> LENGTH: 2000
<212> TYPE: DNA
<213> ORGANISM: Cucumis melo

<400> SEQUENCE: 57

```
tgggtaacat tatgagtttt attataattt aaatgaagat caaactttaa gttgtagggt      60
caccatagga ataaaatata atcaataagt tagggcccct tagtcccacc tcgtaaagga     120
```

-continued

```
gttctgtcat acatatacat tatgatatta attctatctc catgagtcat acatgtgatt    180
ttagtacttg taattttcat tctttttcct attataattc attcaagtac tgtcaatatg    240
gttaggtatt gaaattaatt atagactcag atatcatctt cattaatgga aatggaatgt    300
tatattctac ctctcatttt tacacgttga tgataaatta gaagaaaaaa aattattatt    360
tatattgttt taattgtgag atattagttc aaaatgtaat taataaaatg atacgtgtct    420
tataataaaa ttaaacaagt ataattaaat ataaaacaac atacacactc tttaactaaa    480
agacacaact cacctaatgc tcgacttaaa atcactttgt gtcgtaactt aaccatcaaa    540
gcatgttagg gtaaacacaa taaagatgat ttttgagtta tgcatgtcat ataatgtcac    600
ttccaatttg acttatcttg cttgcttgat tcatgtatat aaacaaaaac atgaaaagta    660
gtgtaaggat accaattacc tactgatttt ttttaaaagt agtttgtcta agacgtgtta    720
aattactaac ttagtcacat ttgagtttta gttctaactt attaaacata aagtaggtat    780
ctcccttact catgtgtgtt tcgataatgt caaattccaa tgtttgatta accaaattgg    840
gtaatttaac ataaatattc ataatataat atttttatg gaataccgac atctaaaaag    900
aaatcaaaat gaatattatt aggaggtgag tttttaagag agaggaaaat aataaaatat    960
ggcatcaaca agaacaataa taataagaat agaaatccga caaaggaaga agtggatgcg   1020
tgttagtact attgacattg gcatatgaac ggttgggttg ggcctcaaat aatttgcatt   1080
tctaacttcc aaacacctaa ttcctttttt tttatccata cttgcaaata tatatttata   1140
tatattcaac aagtagttta atttatttga tataccactt taagttttaa attgatggta   1200
gtgtataaat aaataattta ggattaagca tgtctatgaa ccttttgaaa tttgatggag   1260
tatatataaa acagaatact catgggttca ttataaaaat ctaatagtaa atgtattttt   1320
tatttcattt aaacattttc aaacttttaa aaattaaaat tatcttaaaa aacacgtgtg   1380
gtttcgaacc atatggttaa aaatattgag gttctctatt ttgcaaaaaa tttggaaacc   1440
ttcatggaag ttgatataaa ttgttgtaat tagttagtat tttttcttta tttgtggctt   1500
aatcatgcta tgattgatca ttttatcatc atttctataa tgtaaaacaa tatatttgat   1560
gtgtattgta aatttttatg caagagtaga aaattaataa aaaaaaaaga gagaaaaata   1620
attataaagt aatataaagc tattaacatt ttaagaaaaa taatagtgaa aatgaaagtt   1680
tcggacaata attcaataaa gaaatttgta gatttcgatt aaaatttcca aaattaagat   1740
tttcattaac acgtgtgcct cgcaaccgtc tcctacgtta tcccgtaagt agcccaatct   1800
atcccattct tacacaagcc gtcggcccaa attgattgta ggccatcggc ccactcaaca   1860
cccacaaacc ctagcccctt gctcctcctc ctcctctttt cacggctgct cactccctct   1920
ctttttacac cttctccttc tccttctccg tccctcttcc cttttctgct actatcttca   1980
gcacttgctg agcttcaacc                                               2000
```

<210> SEQ ID NO 58
<211> LENGTH: 1591
<212> TYPE: DNA
<213> ORGANISM: Cucumis melo
<220> FEATURE:
<221> NAME/KEY: misc_feature
<222> LOCATION: (1)..(1591)
<223> OTHER INFORMATION: n=g, a, t or c.
<220> FEATURE:
<221> NAME/KEY: unsure
<222> LOCATION: (1)..(1591)
<223> OTHER INFORMATION: unsure at all n locations

<400> SEQUENCE: 58
aatgttgatt tacccttgct ttgtttgaat ttcgtcctcg tggacttgac ctttggtctg 60
cttcgtatag gactatttac ggctgccctc atagtccaag tccttgtccg ccttacccta 120
tactctctat ctctagacaa tgtgaagcgg gcccttctat aatattgggc cttgaagttt 180
tgggctttgg atctgccgaa ttgtgttggg tttctctccc aatttatttc atttctttat 240
tcaaataatt ataaatatgg aattttattt tatttaaaat ataaaagtta aaattgaacg 300
aatccaaaaa taatggaatc aaatcgacgt tttaacatat ttttcaatta tgtttttaca 360
ttcattttcg tcctacaaaa atattcccac ctttatttcc tcgatatcgg aggtcacttt 420
gtatgtttca ttcgggtgat gtgatataga tcgagtttct atgcttgatt gactatggaa 480
atatatttta agaagatgtt ataaaagtaa aataaatgtt ttgattgtgg atataattat 540
attttaaaca agatgaggaa taattagatc cgaaccaata atcttgagtc aagagtgtac 600
attgaaagtc gtatattaaa taatggttga gtttataata atattgatag attgcagtta 660
accatatttt ctcaagttgt tgaccaaagt acttatttta taaacagttt agggaatgtt 720
tatgaagttt tgccaagtgt tttgaaccta tatgagtatt gacttaattg gtatataagt 780
gcattaacaa tcaagaggta tttaatttga atcgtcctac ccctatcatg ccaacaaaac 840
aattatatgt ttgtcatatt ttattgaaag tgttttcagc gcaatttagt ttgatttgcg 900
tacaaaacat gtctacacgt atcgagttag tagtaatggt tgctagttaa gactgtgaac 960
taaaacttta aatttacatt aaaaanaaaa acattatggt cgtttggtcc tcatatgtga 1020
ttgatagata ttgattaatg agtatttgtg gttgttgcca acaataaaga tgtagacaag 1080
tgaactatgt tggttgtcaa atcttgtttg tatttgttat gtgtggtttt caccaccaat 1140
gttgtagagt gtcagatcca gaatagcttg atcatttttc atatatatct acagactcaa 1200
ttagtagata aaaactataa gactttgact tatttctctt aaaatgtctc ctcgttctgt 1260
acaatcctca acaacgtttg gtgactttaa aacatcacaa gaatctaaga agaatgatga 1320
attagatgca atgcaaagat ttggacctta attttgttac tttaaacttt atatccgaac 1380
attggaagag gcaagcaaaa agcgcgcttt agaatcgcgg tttctttggg ccgagtgggt 1440
tgctcataac agcggaggtt tgcttttctg ccaagaaaac ccctcaaaga aaaagggctt 1500
aataagcagc tgctccattt ctaagtgggt ttagccttta gcacggaagc gccaattcga 1560
ttcaactctg atacactgca aaaattccgc c 1591

<210> SEQ ID NO 59
<211> LENGTH: 2000
<212> TYPE: DNA
<213> ORGANISM: Cucumis melo

<400> SEQUENCE: 59
aaagaatgga gcaagctgat attgctaagc aaaagcttct gcatgattgt gaagttcttc 60
accaccgcct tcaagattct actgtcgact ttttcattga gcaggaaaat aaactaattt 120
tggaaactgc ttcgacagct gacgacgcaa tagatctgtt ggcaacatct gataatcaca 180
ttaaccttct tttagcagag gtacttgcgt ttgtttccat tgaaatgcat ttgcatattg 240
aacttcttca tcctgaatgg cacaagtttt tgtccataca aacaggcaaa gcttctggct 300
catgatgcta acaacagcga tgacactgct ggatcagccc gtccaaatgg aactgataaa 360
ggggcagctg accaagtatt aagtaacata ctagcaaata tgcttgtcga aaatgcccga 420
ttaaggatgc agatgaacgc cgtcatccgc tgtgttctaa atgcaaatgg gacaagtgag 480

```
aaagatgaag atgaatctct caaggaagaa ctgttctaag caagtttttta gaggaagaga    540
ttcctgaatg cacatataca atgaccttat actgtcgtgg caagaaatgg gagagctgta    600
gattttgaat aaatgcaaca gatgttgccc attaatttgc aagtcctgac aaatttggtt    660
gtcggaggtg tagaaatgat gtatcaatta aatatttaac aaagtgcctt ttggcttggc    720
taatcatggg catttgaaga ctttgcactt ggtaagagct caaacaaaat ctgggtggct    780
aaatttagtg ttgattaaat ggaatttcac tgatattcat gatctgtctc ttcttccttc    840
attgatatat tatcttctca gtaaactcct gggcctgatg cagaattgct tttaaccatc    900
tgcatacaga gaagaagtaa aaactagctc acgtggataa agggaaattt ctactgacat    960
gttggcatta gaagaaaatt ttgaaagagt tctattacca taacatcatc tacttccgtg   1020
tattattgaa actattattt ctcttacccg gagatattaa attaataaat ttctatttac   1080
attttgaaga tgctcgtgat tattgataaa aatgatgaat cattattttg attacgttac   1140
aaaaaagtca aagagagtaa caaagctatc aacaaaatat tagtaatata tacaaaaaaa   1200
gtgtaaattt aatattaaca ctgagaaata tacacttaag ctaatgggtt aaaatattta   1260
tccattgaat taaatatggt ttttctgtat ttgtgatatt ccaataaata tgaagctgtt   1320
atactgtcaa attcatattc tgcctataca atcaatttca agtcactcaa ttttgcaaaa   1380
ccatatcata ttgagttcaa ataaaatttc atatctatat acataacgaa aatgttatgt   1440
ttttgctttt aatgttttgg gtatctttct aagctacaag aaaatgtaaa aatgataata   1500
agaaatagat tatattaaaa ttattttaca aatcaaattg cggggatagc tcagttggga   1560
gagcgtcaga ctgaagatct gaaggtcgcg tgttcgatcc acgctcaccg caaatttttt   1620
tcttcttttt tttcccttgt gtatcatttt aaatgggctg ttcttacttt gaactgcgga   1680
agcccatgaa agctaggccc aatttagaaa ccgaccatct caagggtcgg ttcgtcattt   1740
atcaagatcc gataacccga ttcgctccat tttagtctct gctctttcat ctccctcacc   1800
cattctcgct tccactgagc gggcaaggga gcttaacccc tcaaagccct agaaaccgcc   1860
attggagaag ctccactagc ttcttcttct atcagcgaac gtattttcgt cttgtataga   1920
cctttcatct ctggaaccga tcggaagttt ggagtttctt ggtctcagtt tgtagattag   1980
ttttatcttg gcgtctcaat                                                2000
```

<210> SEQ ID NO 60
<211> LENGTH: 2000
<212> TYPE: DNA
<213> ORGANISM: Cucumis melo

<400> SEQUENCE: 60

```
gtgcatttaa aataatctag ttgcatgttc taggttcgat ttattatttg gggatttagt     60
tgtgtctgta tgattgaaaa aattaatgtt gatcttgtaa cacaattgtt tttccctcga    120
tgatttgaga ttatttcaac aatttagatc caatgtttaa aaagccacct tggcatcttg    180
ccttcctcat tcgcaacctg cctccagttg aagcctcgag gctcaaagcc cagtgcccta    240
ggacttcttt attaatttta cttaaaaata aagtttgtat ccctaaatgc ataaaatacc    300
cttgtgttta aggctttctg tttcttcgcg tttcacgtca ggtcagacca tgctcagcta    360
tttttccacc attcttcttc ttctctccca aagtctatca agtattttat ttccacacat    420
atattcacct acgccaattt ctttttaaaa ttttatagat atatacagtg cacctcacga    480
aaacaaagtt tgcacttctt cagttttttg tttcgcctca cacttaagct acaaaaggtt    540
```

```
attacgtttt agtaacccac tactcagctt taaaaacact atttgtatca tatgacgtcg    600

cccttatgga ataatttcac ttgattatcg ggttgtttca taaacaatct tactctgttg    660

tacctttgac aggcctggag agcatgcaac tcctctcttg cttgagtttg agtaacaata    720

aaatcggaaa ttttactgca ttggagcctc tgagactgat aaaattctta aaagttttgg    780

atatatcgta caacgagata ggttcgcatt cgatcgacac aaccagatat ctcttctcat    840

ctccactgtc gcattccgaa gaaattgatt tgagcagtga tgaaatggca acaaatttta    900

ctgatatggc aagttactgg gaagcatatt ttctattcaa agatataagc ttgatgcaat    960

tggatataga aggaaacaca atatctagtg aaagtttcaa agcatttctg gtaaagattc   1020

ttcccaaact ccactggctt gatgggaaac gggtacaata gatatggctt aatttatcta   1080

catccaatcc tctgtccatt gtggttgttc atcccctgaa tgtaaaaagg tacgctacga   1140

actagcattg atcctaaatt gaagacattg gttttgattt cttcccaatg caaggttaag   1200

aactaaggat ttgatattgc atccaataag cataggttat ttaagatttt ggtgatagtg   1260

aaaattaggt gacatgtctc gaaagcttaa agggatacat gaggtatgga gatggagatg   1320

gatgtggtta caacatggaa atgaatacgg tgcccagttt tttggactgc tctaaatcaa   1380

attttatcat atacattatg atactgtgtg ccaattgtat ttaaaaaggt actgaacttt   1440

acatttttgt tgtcccaaat tttgaaggat tgtagtttta ataattctta taataactat   1500

caatgttaat taaaaacttc agtatattta caatttttct aaaaatgttt gctatacgtt   1560

tagttattat cttgatcaat tgccccaaga gaaaaattac cctggactat ttcccaaaaa   1620

catcttctag tcgtccatca gctatagttt caaatctgtg tgggcccagt cggcccagtt   1680

cattgggcct gagaatagag atcatgaacc ggacggccca aaccttttc aggccccagc    1740

caagcctggc ctacaaactt ctaacctaaa accttatccg ttgaagcaat ccaataaaac   1800

aaagccacgt aagcacccag gatctaaaaa tgtatccaaa tccaccaatc tgaggccaca   1860

aatttagcct ctgtggctga atggatgtcg aattacaaga atctctcgat ttcttcctct   1920

taaatccatt tacccttcaa acaaataaac acaaaataaa gaaaaggaga agaaacaatt   1980

gtcgtaatta gcagcaagaa                                               2000
```

<210> SEQ ID NO 61
<211> LENGTH: 2000
<212> TYPE: DNA
<213> ORGANISM: Cucumis melo

<400> SEQUENCE: 61

```
acctagaact tctaaacgat aatctcggaa aaaaaattgg aacaaatcat aataatgaca     60

attaagaagc aagaaccgtt gacaaaagca agatttagag ggagtaaatt tgcatggttt    120

ggtgatgatt atttagttga atttagccta ctcttaggaa gtatccaata atcatacgca    180

aatttcacgt agcatatgaa gcaagtgcat cataataccg cataacctgc ggggttttgt    240

catctcgatt aaacacaatg tgaacatgat gatgtctatg tgtttccagc ttttgttcta    300

atgatgatag acgatagtgt ggtatagttc atatccttga tttaattgtt tccatgtata    360

ctatcgaatt tttaatatat aattaatgta tgaaatcaaa tatcaaataa tgattgtgat    420

ttaatggaat aagatcatgt ctaaaattgg taatagtaat aacgaagaag gaagagaata    480

ataaactacg atttcttgtg aatctcctag ataaattagg ataaaaacta cgagtaagaa    540

tagaataatt atactatata aaataggagt tacaaatttt gtttcttaaa ataccaagct    600

ctgttacaag aaaaaacttt aggtattata tcttcaacat tttgttaatt tgttagagat    660
```

```
tttaggatag tttgtcaact atgggtcttc taagaaactt ggtcatcaag caaatctaat    720
gactcgaatt gtccttgatc gatgtgaaag atccaatgac ttcgaattat ctttatgcaa    780
tgtgtaagat ctaattgtca taaattgatc tcatgtgcaa agtgtaagat ccaatgatcc    840
aaaattgtct ccaacaactt cttgaacaat aagataactc tttgaagaat cttgaatatt    900
aattttgaca tagatagatt gatcttgaat attaggaaat aaggaaattt tcttatgtac    960
atgcctgaac tccttcaaca tagcattttg aatcatatct cttctctagt aacttgtata   1020
gttgcaatat attttgcttc tgttgttgat atatcaacac tgattgaagt tttgaaaccc   1080
aacatatagc tctagtggca agagttaaga catatatgtg gtgaatttac ttctatcaag   1140
atcacaatct aagcagatat actttgaaaa taaagttaga ttatccatta tacaatgtaa   1200
tatttacgga ccatttaact cgcttagaaa ttagagttat tttgcaaact ttattgacaa   1260
atatcttcaa aaatttcata caccgtatag acactatcat aagatgttaa agaaaaaaaa   1320
aaggtgaatt ttccatacaa ttaaaaaaaa tcttaaacta taaaggtggt ttcgatacct   1380
ttaaactttg aaaagtttca ttttaattct cgcacttatt gttttaaaac aaacttagta   1440
aaattttcgt ataaatttag aaagaaattt tatatttaca ggtggggaaa attctaaaca   1500
catagatgaa gataaataaa aacacgatca actataaact atacctatta ttaccttcat   1560
ccttaacacc atgcactcaa atattcatta attctctata ttttttctta tcttagcctc   1620
aaaatttact ttcatcctaa acttcgagcc ctcaaatttg cgttatttca ttcacgatat   1680
tcctttttta cgttctttca tttatggtat tcttctttac gttcttctat ttacgatatt   1740
cttcttgctt ttatagtgtt ttagatttgt tcataaacaa cgtataaatt gaaaacttta   1800
taaatttagg gcattaaggt ataattgaaa ttaaaaccat atttatagtc attaaccaca   1860
gtattattta tcctttattt attaaaaaaa aaatctactt ttagttttaa atttaggcat   1920
tttacgcaaa gctaattacg acataaaaca ccaaaaggag accccgttcg atcttcacat   1980
cttctcggcc agaaacgacc                                               2000
```

<210> SEQ ID NO 62
<211> LENGTH: 2000
<212> TYPE: DNA
<213> ORGANISM: Cucumis melo

<400> SEQUENCE: 62

```
gcaatggcgg aaataacgta gcagagggca caaacaacga agaggagctt cgttcttcgg     60
tgcgccatct gggaaagtga gaaatggtgg acgaaacaca aacgggggaa tcggattgga    120
tctctcagaa aagaaatggt tggattcgat cacagatcaa tgaagcacat tactcggttt    180
ttcaagaaga ttacaagaac ttgcttcttg aaacctctct tcttctgttt gaaatttttg    240
ggcgtagaat tgaggaccgg agcagtcgcc tgaatttggt cgtcgaatcg attccacgga    300
aacaaaaata tgaagaaacc aaatgaatga cttagcccac tcactacgct tggcgacgtg    360
ttcttcttac gaacggacca atcaaatgcg agcctgatga atatgggcca atcatattat    420
gccacgtaag actttacttt tgcccctgac ctatgggaag aaaattgtgg tcttttctta    480
tgtcaataga agaaaaataa aattatatga aagtcttaaa aggaaaaaaa caaaccatgt    540
taatattact gtttaaaacc ataacacaaa atcaattatt gtttatgttt tgagactccc    600
ttatggtgtt tgctagatag tgtggatttt gtttttgaaa attgtttttg aattttgtta    660
ttcttaagtt tttttatccg aaaatttcat tctagaaaac aaaattatat aaaaccattt    720
```

-continued

```
taaaacataa tatatcgtgt tatagttttt taatgtaacg ggattacacg gcctattatc    780
aattatataa taagatagat taaataaaca aaaatgattt atatggcttt tttaaaaata    840
aaatttaatc tctaccgctt ataactataa ttaagtcatt ttggtttaat aaaatcatat    900
tatatagtct cactcgtatg tattatttac aaaagatgtc gactttttat caaattatag    960
actaaactat aatttttcttc gaggctaaaa ttataattta accaaattta taaatgtaaa  1020
atgtatttat aaataaacga ataatagctt gtcgtcaact atattttagt ggataagtaa   1080
gattagtttt atgatttata aatatatagt ataaaacaca tttaaacatg ttttgttcat   1140
tgcgtttggt tgatatttaa acctagtaac gaaaaagtat taggtattac attaaattag   1200
catccaccta caatgttaaa tttttaagtc agttaataat ttaagagact ctcttcaaca   1260
ttgacttcat gcaacataaa atggtagaaa ttttcacacc attgtttatc gacattacta   1320
cgtaggagaa tggcaaaact ttcttatatg tatgtgtgct tttagatgtg tctttacatc   1380
ccttatcaaa acgaaaacct aattctaacc aaatcaaacc aacccgggtt gttgggttat   1440
tcttacaagc catttgttgg attaaaaaac caaaatagag gatgttcggt tcaagcattt   1500
taaagttttg ggctatttag ttcgaccact ggtttgttca aagtcgggtc ggaccaaacc   1560
gtgagcgatg taaacaacaa aggtctaaat tgggccggga tcagatgggc tgaagatcca   1620
cgattctggt ttccaaccca aggcccaatg aattacaaca aaaaagcgta ctcaggaaat   1680
ccgaatctgg atctcaacgt actctaacct ctcacagttc gccacgtcaa gaaaacacgt   1740
caatacttta ggcgaaaatc aagtgaagaa ttccccacaa taaggaatcg tatatccacg   1800
aaactatcca atcagcttac gccatcggaa gattcggaac aaagcaacag ttcaatggta   1860
tatcataggg tgagaataag tcggttccgc agactagtat ttcttagtca aactttacct   1920
gcttcaatcg gccgccgatt tcccgatatt tacaacattt agttccgatt tttccctcga   1980
agctctgaag tatcgtaaaa                                                 2000
```

<210> SEQ ID NO 63
<211> LENGTH: 2000
<212> TYPE: DNA
<213> ORGANISM: Cucumis melo

<400> SEQUENCE: 63

```
gatcaacctt gaaattttcc cacatactgt gttgtaaagt tgtccccaat ttcattcaca     60
aattacctac ttgaggaatc ggcagtaaga agagatcata atgtattttt gctactacac    120
tcgcaagtct aatcagagga tttgattaca atatcttgct gctgtaatag attcgttcat    180
aaattaatcc agattgaaaa gtcaagcttt acttcatttt catcgacaat gtagaaattt    240
tgtttataac tttgtactat tgaatctatt gctcctcgat ttgcccccctt ggtacgatat    300
caagccatta tttttccaac tcttactcgc aacttcaacg catgaacttg accagcttca    360
acctataatc ttatgcatgt ttttaatgat taaagctgaa atagattgtg aaacgtacct    420
tattctcact accgctgcca aagccaacca agcttccacg ggtacccata aggtccacaa    480
tcatggcact cttggatgac atgtattggt tcctactgtc tcttccgggt tctcttatta    540
atggccccga aagcaacctc tcccggcatt ctcgaaattc ggctcactaa tattctttag    600
ctactaaaac acatgtcctc aaatttctca tttaaatgtg atctgagaaa gtcattcgac    660
ccattttagt ttaaataagc atcaagtcaa aaaccattta acgtgggctt aaaaatttac    720
agcagcgcag cgtacactaa agtttatgaa cgatgaaagt gggtggcaga agaaagcaag    780
aagtccgaga gacatgccaa aaagagtaaa agtcatttgt tggggccttg acagcaaggt    840
```

tccatatgca tcggtccatt gcagcatggc ggctcaaaat taaattttca cccttgcttt 900
tgcttctcta acctaccctt ctacgcatcg tgtctatctt ccttcacact cattttgtgg 960
taagctttaa cgcaacattt tcttaatgta atttaagctt ggcccaccaa tccctttgaa 1020
aagtttcctc tagatggtgc gtgtcaattt caaattaaca atttgaactt atagttctaa 1080
cccccatatt gtctgccctt tttctcttct tcttcttctt cttctagttt tgttctggtt 1140
taatcttttt cggttttctc tgtgcagggt agtagctttt aagcttagtg attttctctt 1200
gttaacaact ctaagcagtg aattgttaga gacctattat ttcatataaa tactagatga 1260
cttcgactca ttgattaggc tggaagctgt caaaattaaa gagtttgaca aatacccact 1320
aatttggtaa ccaagagcca gcaggaacat ttgtatttat tgagacaagt gaaagtttgt 1380
tattttcttt actcaaaatc tctctttaat tttatagata tagacattac ttggataaga 1440
aagggagttc accggccgga ggttttcctt caaatttaac agtgactgag gtctctttca 1500
gctttgtttt tttggtgtta ttactgtttg ctcaatcctt tgaacgagtg gtgtaacttg 1560
ttaaatgccc acaaattcat gggacgcaat cctttaggag aaaggttggc cactagttat 1620
tggtggttac cgtggctctt agcaacttag catcagaatt tgtcttgaac ttctagtcgt 1680
tgaaaattct cttcatacaa agctaagtct gcttatttgt aggatccata aacatgagat 1740
gataagggtg atgggcctaa gaatgcttga tggaaacatg gtcattggac ttgcttatta 1800
attgaaaaaa ccagccccgt ctctggttag aaccctcatt aggattgtat tgtttcaatt 1860
ctttcagctt gttctggatt ttaaaggctc caatggtttg agatgatagt catggaggtg 1920
ggaaggaatg gacaatacag ttttgaagaa ctgggttatc tcaaatggga aggtgaaatg 1980
tttatgtcag tatttgcttg 2000

<210> SEQ ID NO 64
<211> LENGTH: 2000
<212> TYPE: DNA
<213> ORGANISM: Cucumis melo

<400> SEQUENCE: 64
atcttcaccg ttaaatcgcc gtggttgtta gcggcggcga ggagagagag tgctctttct 60
ctgagaactc ctgccatagt agacctaaag gaagaaagtg gtagtgaaac aaggaatggt 120
gaggagggtg agaattgagg aagtggttag ggctttgaag gaacggggaa ttttatttcc 180
gggaagggaa acaacagggg agaacacagc cggagcggtg tggttgtgag aaaatttaag 240
caagcagatg agacgacggc ctggcgccga ggacaggcat atgaatatca cgtggctatg 300
gctatgggaa attgaacgta ggccctttct cattcttata ccaatcttca tttttctatt 360
ttctagggtt tcttttcttt cttttttctt tttcctttt cacattttta tatgtcattg 420
aatttcgaag tttggagtta atatgttgga gtcgtgtatc tatttagctt catgggttat 480
aacattattt tggatgatgt atgatattta atctcaattt aagaaggaaa cgagtaacca 540
aaaaatctta taatgaggtt tgtccatctt ttatgtatta ttctccactt atcacatttg 600
tttgaaataa ataaataaat aaatgttgtg tcacctcaaa cacaaccata tggttcaaat 660
tgaaatttaa cacttgatgg tccctatgtt ccatacgacc taacaaggtc atcttttgat 720
tgtgaggttc atccaacata aagttgttat aaactaagaa tatttcactt atgagtgttt 780
atgtgcacgt tgttggtata ggccataatt ttcaatcatt taaaactttt attaaccatg 840
atttcacatt atcttgatct ctcccattcg aatatgattt tggttcatct atattcccct 900

```
tataaactca acgttacgtg cctaccagtt ttcgcttggc tcatccccaa cccatatctt    960
actgtggaat gttttttctc tgataccatt tgtattgttt cacaccttcg aatcatattt   1020
tagaatgttg atacagtacc taatgcatgt gatattcccc tccatttgtt gtgacatggc   1080
agcatttgtt cttacttgtg tttgaattgt tttctaagag aaaaaaatga tatctccaca   1140
aaccaacgca catcatttta gcatatcatg tgtctcattc acgtggttct taaaaaaaaa   1200
tcaggacatt atccaataag acgtggtcaa gggatgaacc aaatgaaaat taaaagggca   1260
tgtaatggcc gagttcatga atgcgtcata aatgaatcaa tatcacacta aaataagacc   1320
gatcacaagg gtgtgaaagc atagttaaca ataatataaa aaaaactaaa agctcatatc   1380
tatgccaaca acatacacat tattttcgat tgcttaatcg tatgaacttt aaagttaaac   1440
gtgtttattt taaagttaaa cgtgcttatc ttaaaacaat cttatgttgg acgacctcca   1500
caattttttc cattacgcat gtgagaaaca cattgaaagg actcgaatta gcatgtagag   1560
aatggtgtag cccccattct ataaaagcaa ctcaagatct gaacatgcat tgaaatttca   1620
ctcttcattc ctgacacata cataaagaga agcaagtacg agaatcatcc tctacttttt   1680
attcacaagt tttaagtcaa atttcaactt gatttgtatg tttcaaaacg acacacctac   1740
tcatttaatc ttgagcgtta cttcaattgt ttttatgttt caaaatgtta aaaaagaaaa   1800
aaaaaaaaag ttcaatagtt ttgtaaattg caaaaaaaga gaattacgag tatgcccctg   1860
tacatttaga agaagcgtaa ggtccatatg ggaatcagaa caatcaatcg acggccacat   1920
ctcacgagac ataaacaggg ggagttggag gaatcgacgg agatcggaat ctggtttagg   1980
gttttagcaa aagaagaaca                                               2000
```

```
<210> SEQ ID NO 65
<211> LENGTH: 2000
<212> TYPE: DNA
<213> ORGANISM: Cucumis melo

<400> SEQUENCE: 65
```

```
aactcagtga atacgataag aaatttaatt gaagttaaca aactcaaact taaatatttt     60
ttaacacgga caatttaaaa ccaaattcat agtctccttg tatagtgttt agagtgtgtc    120
gcttcattaa acctttctat cgtggaacaa atctcttcta atattttgtc aaaaacctat    180
catcacccaa aatatcatga taattatttg atgaggatca aggcttagag aggaacaagg    240
gaacttttca caagggtgga gagatttagc tattaggttt aactcgttgc ttctaatggt    300
ggatgaataa cgacaaattt taaacaatga acgttatcac gttgaaacta tctacttctc    360
tcaacctact actttatcat aaggtttgaa aagttctatc gaaaatttta aatacataaa    420
acataaaaag gaaaattttc attggagaat tttccatata tgtttaccca caaaactaag    480
gctaattaaa aagctaacct taagactaag gctaaaatgg tatcttatgc tacatttttc    540
agttgctatg ttttgaagca aaagctaatt atttgctaat aatgagatag gcatgtgggt    600
gagtgatgag cttagcctgg cctgcctttg tgtttcttct tattctctta aatatcattg    660
ttcaatcaaa atagttttgt taaatttagc ccatcctcac ttcaacctct tatatttgga    720
ttggccttct ttgtttttg ggcttttgat atttgatgta atggacttca atcatttata    780
gaagccttac cctacagaaa caaacaaaca aaaagaggaa aaaaaaaatg gtgagttggt    840
taataacaac tttctaactc aaccaatata tggtgtgtgt atatatatat atatatcgaa    900
tacaaaatat gaatatgata tgaccacata aaattgttga aagggttgaa aattagtgaa    960
ttggactttt aaattttgta gtgtagtggt ttacctatga tgctcgtaat gttatttaat   1020
```

-continued

```
tttaaatgtg ttttttttt ttacaaaaaa aagtctcgcg gtgcaagttc aataagttga   1080
tttaaaaaca aatccatcaa aataatgttc gcttgatatg atcgagtata gagccgaatg   1140
tgtatcaaac ataaattcaa actttaatag agtgaaaaat aaatgctacg caaacaaagt   1200
ttttgtatta gcttcttaaa tgtacatata tacttttccg attcaaacac ctccaaaata   1260
aaactcaaaa gttaaaattt agactcagaa aatgagagaa aaagaaaact aaaaacgaat   1320
tctaaagata agcattttca aatataggaa aatgaacaat aaatatttac aaaatagaag   1380
aattgtaaaa aacgacaaat tgacataata cttacaaaac ataacaaaat ttcagattct   1440
atcaatgaca tacactgata tatctttatt agtcatagaa agtctatcat ttataaaatc   1500
caaattttg ttatatattg taaatattta aatttgtttt accatattta aaaattttag   1560
atttatcacc aacaaataac catagatttc aaattttgct ataaatattt ttaaccgttt   1620
atttaccata atttttctat tataaaaaca aaaaaaacaa aaaacagata aaagcgaaga   1680
aaaagtaaga gagcagaaat attttttgat ttaggtttca tttggtaaaa aattgttatt   1740
aaaaaataca aactaatggg aaacaataat aataatttaa ttttttaaa atctaaaaag   1800
aaaatagttg acaacaataa tttaataatt taatacacaa gccagtgtta ttaatctctt   1860
tttttctaac aacgcctttc acgagacatc ctctcaatcc tcgacatcca gtggaaaaac   1920
agtatccctc aaccctcagc tttccccaac cgccctccgt cgttcttctg atcgtcgcca   1980
ccctactccg tcatcggaaa                                              2000
```

<210> SEQ ID NO 66
<211> LENGTH: 2000
<212> TYPE: DNA
<213> ORGANISM: Cucumis melo

<400> SEQUENCE: 66

```
catatattta ttatgttcca cttgataacc attttgtttt tgaaaattaa gtttaaagac     60
gacactaatt ccatcttcaa ctttcttctt ttgttatcaa cattcgacca atagtccaga    120
aaaccaatta agttgttgaa aactaaaaaa aaaaaaaatt cttataaagt tgttttttt    180
ttaaatttgg ttaaaaattt taatcattat acttaaaaaa tatatacacg aatcatagta    240
gaaaattgaa aacaaataaa cttaattcca aatctacttt aaaggctcac tatctgtcaa    300
gaggctttgg tatagttgtc tgtactgatt aagtgtgaga gttcttttaa tatttgtagc    360
tgaccaataa attctttcct ttcttttctaa ttttgcttta actccctatc ctattcatac    420
acaataaata tacaccatat tctaattgac aatattgttt ggatttgttt gttttcttta    480
cggtaggcaa gaagttgcct agttgttgtc tgacctcaaa accctttgtt gataagagca    540
aacaaagtct agttttccaa aaaaaaaatc accaactcaa ccaaatcttg agccttttac    600
taatttccat cccaaactaa tatctaatca gtgcttacat gtttgagcct tcaactcaat    660
ttaacatcaa aacatcttgc aaccacacct tgacatgagt atgaaaacaa tataggagag    720
aactttagta ttacattgag ttccattatc attgtacatt ctcaaccaac gaaaccaacc    780
caaaacaaaa tagttttttg taacatatga gattaggtat cgtcctagtt aatgatttta    840
caaagttata tgagtattca tttgttgata tagtttgacc ggatcggaca gttggctaca    900
atggtatatt tctataaact aaggtataca atttttcatg tatgttgttt gatattgttt    960
tattattggc acatgtcttt tgtgtccaat agtaataaca aggttgtttc ttatctaaat   1020
aaaataaact cttgccagat aattgaagtt agacttttaa tcaaaacgta atattaaatg   1080
```

gggatgagaa ataattgatt attaggtaaa cctaacaata aaatctttaa attgtgttag 1140
aatcatttag ttagtcgagt tctacactaa aaaaaattaa aaacactaaa atcatttata 1200
aataaaatat tcaatatctt caaaatgtac taaaacattg aagctcataa aactaatcat 1260
ttttcttttg attaaatttc tctctcatat taccaagaaa cctaagataa cattaccaac 1320
gattcatacc aaaaaaattt attatcattg aacatatctc aaactagtgt attcaataat 1380
ggttagagta gtagttatat taaggtgcca tgagtttgat atttttcttt tttgcctaaa 1440
ttaggttaag ccgtagctag cttgaacaat gctaaagatc ttcttaagag tttcgtagtt 1500
taacgtttat atgataaatt ttattacatc cgaacttgat atttaatttt tgtggctctt 1560
atctgtgttt agtttttctt attctctttt aacttgtagt aatcaaatga aagccatttg 1620
caaatgagga caaatgcatc tgcaagatat atattagcca atctcttgat atttttatgc 1680
tctatgagac aatatattct gccatttgcc catcaaatgg ccataatttc tcaagatttt 1740
tccatttcga gtttgtttca atcttctact ccttttgttt ttcctttgtt caatttttg 1800 gacctttgat gaaatatctt cataactcct atgacgtggg caccatccat tggttgtcat 1860
ttgataagaa atatgtgtca atggcacaat tcccattcca tttatatatt atatagttcc 1920
taaagccata tccccatgat ttatatcctt cttcaagctc acaattgaac tttaacatta 1980
cttcttccct acacaaagat 2000

<210> SEQ ID NO 67
<211> LENGTH: 2000
<212> TYPE: DNA
<213> ORGANISM: Cucumis melo

<400> SEQUENCE: 67
aaataatttg tggattttat catattatgt accttagact ttgtaaggtt tataacacaa 60
gatgtggaga aatcccatga tgaacatgga cgttattata tcctttgaaa ctaaaaacaa 120
aggaaaaaaa gacaaatggc tgagtataag aaaaagagaa gaaacaacca aaaagctaaa 180
atgtcatgct ctcatatgta acatatttga attgggattg atttcaagat gtattttaaa 240
ataatttaac acacgataaa ataattctaa caaactcaaa attactctta aacatttact 300
tgatatcttc gacataatga cttttgtttt aatacaactc aaaacataat taaggttggt 360
tttaaatgac aacaaacgaa aaactcgatt ctaatttcaa tactagtctt tgaaagccct 420
aaggagcgtg gttttgaatt gtatagcaag gtttcgaaaa ttttaatcat caaacaatag 480
gtatatttac ctgttcctca agtacagtta attcatagct acttgtcgtg cttcctacga 540
caacattgta agacttgcca cacactaatt gaagccgttg ttgaaggtag ttttccatgt 600
atagcttgaa tcgacggatg accaaagagg ttgaagaagg tttgaaaaat aggggaaggg 660
atatacaaag tttgagagtg agagagggag agaaatagaa atagaagaga ctgaaaaatg 720
taaaagaaag gatgaaaaaa tgtggggtaa acgcaaattg gatttttata gtagtatttt 780
gaaaatgcta tagaaaggct atgtatagta gtgcttccaa agttctatat gaatgagaca 840
aatcaaaata tatttttttt gattaattaa ccccaaaaag actcataaaa aaatcttata 900
aatcccacta agatattgca tgttatatgt agtaaaattt atcgttcaaa taaaccttaa 960
acataattca aacgaagaaa gtaaaaattt gaatttctta tcttacatca ttcaaccaaa 1020
caatttccat ataagagatt aaacttctaa ctttaagaga gagatatcca gcatatgcaa 1080
cctaaaccaa cagtgacttt gctatatatt tgcacaaaat gtgggggaca aagttgtaat 1140
ttcggaatat caatgattaa agaaaaggta aaatttaaaa ttcggaagct tgacgtggca 1200
acacggaatg gtgatgatat ttccaactcc tcgcgacttt tagaagttgg cctcaccaac 1260
cgcatatccg ccccttttgcc acgtgtcaga ctacaacaac ttccaacaat ttcctttaag 1320
aacaccaaat tatatcaata aatatttaac ttaaattaag aatatatttg ttacaatttt 1380
cctactgagt tagatagata gacagacttg tcaattaact aataagtcca aagtcaattt 1440
actcaacata gatacaattc taatttgagt gtgaaataca tattcaaatc aaaattatta 1500
ttaagaggaa aaactgattt gctttctcaa tttaaaatat aatattttga aaaagaaaca 1560
cacatgtatt atggttttca atatatttac tttcttagtc acctaatctc aaactaattt 1620
ttgaagaaat taaatatata tattatcatt tttattttct tggttatgat attggtatag 1680
aatcaacaaa actacaagtg tcctctcctc tgctatcgat ggggattaga ctctaaactt 1740
gtttagcgat tagtaattat atattagaaa aagtttatgt taatgtggac ccgacaatct 1800
caccaatagg ctcttcactt caccaacccc cgacccattc cctctaataa ttcgacacgg 1860
ctcatccccg gttcgaaccg ggccgacgtc ttcctattta acacacctcc atttcctctt 1920
ccctccgcaa cacaaacaga gacctcaccg gaaaatcaag ttaaagcaaa accaaagaga 1980
agcttcatca ctctccggaa 2000

<210> SEQ ID NO 68
<211> LENGTH: 2000
<212> TYPE: DNA
<213> ORGANISM: Cucumis melo

<400> SEQUENCE: 68
taatagttgc aggtcttgtt taaaatacta atctaggtgt gtaaaacata gaaagtttaa 60
tgtggaattt cttatgagaa cgattaaggc tggtgaatct cgcttggtta aatttgaagt 120
agtttcactt cgatggagac tagacgttta ggcattcgta atttcagaga caacataacg 180
aggctacgtt gggaaaatag ttatgtcatt ttatcataac tgcatacttt gtggtaagga 240
tcatactgat tagtaagtac ggtttccact ctatagtgtt tgagtcaact tctgtgcccc 300
tttactaatc tcacgagaga atccgcctgg tcctgtaaca tttgggtgtc aaagaaactt 360
gtaggaaaga ttccgaccac catggattga atcataagtc aagggccatt agtaaaaacc 420
tctaacttgc tcttgcttta aattttcctc tattctcctt attcgttaag cattgggtgt 480
gggtgctata ctaacttttg tgggttgtta atggcctttg tttctgtaga tagtaaggac 540
ttctactgta aacttgcttt ttgtttgcac tttctcactc tttcattttg ttaaaaaata 600
taagacaaca taacagagcg acagagagaa agagagacta accatagcaa ctggagctcc 660
ttgtgaaatt tatccaattc ctcagaagta gacaatatag gcttctttac agcaactttt 720
ctaccatcca accttccttc atacacagta ctctcggccc ctgcatcacc attcgataaa 780
aatccaatat gtcaacagaa cctctcaggc aattgaaccg gaataaatta gtgcagcgtt 840
gagtgcttac ctcgggcaat tggagagagc agcgtgaatg cggaaggttg aagatgaaga 900
ggaatcgaat tgctggagca gcagccctga tgcaggtgtt cggatccata attcccaaat 960
ccatatccgt tttcgtgaag aaatgttgag gaaaaattca ttatgcgttc agtttatacc 1020
attggagagt gggaaagttc gtattgtttt gctaatttcg tcgattctca ggtcttggag 1080
taaaaacgtt gtacccgcca cttcccattg ggccattgtc caatattgtt tgggttgggc 1140
gggtggatga cccaaatttt ggggaagata tgagatttgt ccaactctgt tatcaaatat 1200
gaccaaatga acaaaatatt gacttttttt tttctatatt tttttgaatg aagtataagt 1260
agttgtttta ttttgtttat tttaactcaa aattaccaaa tttggatttc acaaacataa 1320
aatagatttt atacttttta taattcaatc gaaagttgat cgtatatgaa aagaacaatg 1380
aataaagaaa gaaatgtaaa atttatatca acttaattaa aacctcgcaa tacaaaaatc 1440
gagtgaaata gagggtggag gatgagagga agagggagaa gacatccata ccctccatgg 1500
acatgggtag atgtatgggt tgggttgggt tgggttgaat tgggtcaacc catccactcg 1560
gttcatatag acagcattcg ttttataatt tatccaaaat aaaatataat taaaagaaga 1620
aaataaaaga aaaacgaaat ctccaattcg cgtaggaaat taaaaaggaa gagttaattc 1680
aattcgattc tctcccatct tcatcataat tttgcgaaag gatcgtaagt tgtatacttc 1740
tctccttgct gcttttcgaa tcgggataag aatattttct ttttgtcttc cccattccta 1800
ctcttcaaaa ttctctgcat tttctaccca tcacttttac ttcaaccatt tttgttgttg 1860
ggagttccat attttgattt cctctacaac gcctaaactc ttcttcttct tcttcttctt 1920
cttcttcttg gagtgatttt tcagttcaat tttggggatt tcatctattt ctttgatctg 1980
cagcgttgct ggaagttgcg 2000

<210> SEQ ID NO 69
<211> LENGTH: 2000
<212> TYPE: DNA
<213> ORGANISM: Cucumis melo

<400> SEQUENCE: 69
agtttattct gttgtagcaa ttcaaagcag tgtgatccag atgagtacat atttggtagt 60
agactcaatt atcattttat ggttgaaaac cacatcctct tctgtcattg ttcatattat 120
tacgaggaaa aaagccacgt cctctttcaa aatttcttcc acaaactctt tcttaaaagg 180
aggaattaga gtttgaaaga ctaattagat cgagaattat tcatattcag attggtacct 240
aattgagtag caaccatcgc agtaggttga agagaaaggt cctcttgttt acgatgtttt 300
gcaagagcaa attcttcaaa tttcaagaga gtatgaagtt cttcaaagat tactgattgt 360
gaacgagtgc gcatagagat gtgaaaatat tgtattcatc tagaaatcaa atgagagtat 420
agatcaacaa atcttcatcg tttactattg aaacacacat ttgcaagttt atctttgatt 480
tttttgcccc tcctcatgta tgaattaata gattcatcaa cttctttgaa atcgattgaa 540
gattagtttt gagattaaca atatttgatc gtaaatttga gtagtgattt tcaagtgcga 600
cccagacttc ctttgatgaa gtacaaccaa caattagggt ttttacagac atagtagcac 660
tgatcaaggt cataaaagct tgatctttag caatttaatc tttatatata aaagattcaa 720
cattgtcgtc gattgatttt gtattgtaga tgaactagtg gtcgaagaaa tcaaaatcga 780
ttttgaaatc aaaatcgatt ttgctagagc tgtacttatg tcatcaacaa atccatataa 840
atccatatag cttgtgtgct ctcaaaatag tggagaattg gaatttctaa gaaacataat 900
ttgttgattc gagtctgata aatatgaggt acatatattt gtgaggaaga tcaaaaaatt 960
gatttctttt gttcaagaag actcagcgga agccattgat ggagagaaca aaaatcggag 1020
gggatggtta atcatgggtc tttgatctgc tctaatacca tgtgatcttt accaagttgt 1080
gaaaaaataa tctctcattt tctcattaat ttacaataat agaatatggg tatctattac 1140
aacccaattt acagaggaaa tactagctga ttacaacaga atcagtgcca aatcaattat 1200
taaaactaat actcaacact aattaccaaa gaattagtgg tttttttacc acgaatttat 1260
ggggtaaaaa aagtgaactt ttaccaaatt agtaaaataa aaaaagaaag aaaaaaaaac 1320
gtaatattca aatggatggt gaggcatgaa gaagagtagc ctaaagtaca tgaagagcta 1380

```
aaagacttat tatcttccat tggtcccatt gaagaccaca aagaaaatat cagtcctttt   1440
tctctttaga gacacaaacc caaagtagaa agaatctttc acaagaatta ggaatttaat   1500
gcaatttttc tttttaaaaa aaatctccaa ttttctatct cattatccac cctttccact   1560
ctaaacttca ctacaatttg atgaaatctg tttccaccaa tcagattgca ccaaattcca   1620
tcaaaaacgc cccatcagat aattatggat gtcttcttct tcctctcttc tttcgtggct   1680
gaaattgaag ctcaactcaa aaatacattt cattttcaaa attccctgat gacccaattc   1740
gccacgtgtc ccttccactc accactaccc acacaaaaca actgcttctc ttcctcttcc   1800
tcttcttctc cattaaattc ccagacccat ccctctgcaa cttcgaatgc aacagaaaga   1860
aaacggacca aaaatccctt gaggaatttc tcatttttga agcataattc aaagattaaa   1920
cccgtattaa ccctcttcat cttaccagag gtttgattta ttgatcgaat tgttttattg   1980
gtttttttc aaggtcacca                                                 2000
```

<210> SEQ ID NO 70
<211> LENGTH: 2000
<212> TYPE: DNA
<213> ORGANISM: Cucumis melo

<400> SEQUENCE: 70

```
gcatcttatg gatgtagtca caacatattt atatggattt tctgataatg atatttatat     60
gaaagtccca aaaggattta agatacctaa aacatataaa tcaaattccc ataaactatg    120
ttcaataaag ttacagagat cattgtatgg attgaaaaaa tcatgacgaa tgtgatacaa    180
tcgcctgagt gaatatttag ttaaaaaaat aatatcaata taattcaata tgtccatgcg    240
tttttataaa gaaatcaccg tcaggatttg ctattataac tgtatatgtt gatgatttaa    300
atataattga aattttgaag agttttcaaa ggcaatagaa tattaagaaa gaatttgaga    360
tgaaagatct cagaaaaata aaattttgtc ttgattttca aatcgagcat ctagtaaaag    420
ggatatttgt tcatcaatta acttatacag agaaaatttt aaaaagattt tatatagata    480
aaacacattc attgaacatt ctaatgcaag ttcattcatt aaatgtgaag aaagatattt    540
ttcgacgtcg agatgataat gaagaactcc ttagtccaga agtaccatac cttaatacaa    600
ttggtgcact tattttgtca ataatcaaga ccagatattg cattttctat aaatttatta    660
gctagattca gttctccaac aaaacaacat tggaatgaag ttaaacatat acttcgttat    720
tttcgaggaa caattaatat aagattattt tattcaaata aatcaaattt taacctagtt    780
agttttgcat attcttgatt tttatctgat ccacataaat ctagatctca aacaggttat    840
ctattcacat gtggaggaac tgctatatct taacgatcag tgaaacaaat taccataaca    900
gtcaactctt caaaccgtgc tgaaattctt acaattcttg aggcattcat gaggctagcg    960
gagaatgaat atggttaagg tcgatgactc aacacattcg aaaattatgt ggtttgtctt   1020
ctagtaaact ccttccaaca acattatacg aagacaacac aacttgtata gctcaaataa   1080
aatgaggtta tattaaaagt gatagaacaa aacacatctc accgaagttt ttctatactc   1140
atgatcttga agaaaatggt gacatcacag tacaaaaaat ttgttcaaaa gataatttgg   1200
tagatttatt tacaaaatta ttacctactg caacctttga aaaattggtg cacaacattg   1260
gaacgcgacg acttagatat ctcaagtaat gttacatctt acttgccaag ttaactatac   1320
atagtgacat ttggtggagt tgtaagaaac actaatattg gagaaaaatc gaaagaaatt   1380
ggaaaatatg gagaattgaa ttttttttag atttttctta ttttctaatt ttaggtttcc   1440
```

gtattctgat tatgcctcat tttcacaaca ttaataactt taataagatg atttcttggg 1500
ttaagggaaa aaatcatttt tttagagttg cacgtacaaa aatattatca taacatatcg 1560
attataataa accaattcac cgtcaaccta acctaggtag agtttgagtt aaatgttaaa 1620
agaatatcca cccctcaaca ttgtaatccc aactaataaa tcagcaacct aaagtttttt 1680
ttaaaaaact aaaaagaaga gcaatatatt tttttacta ttattttttt aaagagtgga 1740
tttatttatt aaattaaaaa atgaaaagaa gaaaatttgt tagtttgggt aatccgaaaa 1800
cccgattatt tgggcccgag aaaccgacgt tttgtttatt gttcctcacg gcaataagta 1860
atggcgtgaa tcgaccgcgt gcgcttcaag ctatctagac atttttatat cctccgatta 1920
gaaaccctaa ttcagattct ccgtattacc caccctggaa catctttgaa acgcgaaaag 1980
gtgacccgaa gaaacttgaa 2000

<210> SEQ ID NO 71
<211> LENGTH: 2000
<212> TYPE: DNA
<213> ORGANISM: Cucumis melo

<400> SEQUENCE: 71
taataaagtc gatgatatga attaattaga cggatgggtt atactatagt tattttattg 60
tcttttatag agaatttaac attggtagcg gggaaaatcc gatagatatt ggtgaagagg 120
aattcgttgg tggatgtaaa ggaaagttag tttcgccttg gcacaacgaa gggtttgaat 180
ggaaaatcat gataagttcg actgcctgtt caactaaacg aaagatacca agtcaaacct 240
tagttttctt taaggattta tgatcttagt agtgtatcta tttaaagatt caaaggtatc 300
aatagactat ttatttcaat cgttgtgttg aaatctagga gtatatttaa cgattaactt 360
aaaagatttt gctatcttgt tttgtgtttt tcattttttt gggaaaacct agtgtctttt 420
tattttattt gatacaataa gtattataaa aatgactaga atgactatat acttgatcat 480
tattttgaca tatttgcaat atattaaaaa tgactactta ttttaattac cttcatggtc 540
ttttttttaat ttatgaaggg gtgggctcgt gtggcagatg aggcctgtca taattagcct 600
taccttaaat aattgggccg gttctttggg aaatatcggc ccaacctaac ttttcatggg 660
ctcaaatgat gctttatcta atacccatac tttccattac ctttgtatat tgaattagaa 720
tgatagaaaa acatactaca cagttgagtt aggatataaa taaatgcatt gaactatgta 780
ttacatagtt gagaaaaatg agaatgaagt tttgtctttt gaatatatat tctgtgaaag 840
ttagatgtat atagaaatga tgatacttcg gcgtttgttg aagattgagt ggggtgtcaa 900
cctaatcata gttggtttaa gaaaagtttt aattataaga taaccgtttt aagtgactta 960
tgccatattt tgattgcagg ttcacaatga aatgttttaa tttggtgatt agactttgac 1020
aatgtggtaa tttatgttaa gtgagttgtt gtctcgttta ccttgatcat ttgtctctac 1080
tcatttctca ttttgtttca tcccttgtta tatggcatcc attgttgttg tatttgtcat 1140
tgttcacatt cgatgcttaa ctaggtaaga acaacatttt cattttagaa ttggaacgat 1200
agaaattcat aagttttatt tttgaggcac ttggttcatt ttaatcatag aacattagtc 1260
cacaatcgtt tggaataaat ttacactcta tctagatatg gaactcttga caacctctac 1320
caaggaagga tgaaaagcaa aaaaagagta gaaaaacgaa agtagacact ataacaagcc 1380
aattagccca ttgacaaata ttaccacgtt attaaagttc attttaatca tcgtgtcaat 1440
tatcaacctt ataggtcaaa taccatttat aattattttc aaattcaatt aatgaaacaa 1500
gactcaaaaa accaaacaaa tatccaaacc caatatttga gtttagaata taataatttc 1560

```
atagttagac ttggagacag atttgtacgt atatgttaaa ttaaaaattt aatcaaagta   1620

taaataaatg atttggagtg gcaagaaaat attggccaaa atttcataag aaaaaggaag   1680

aaaataaaaa ggtgtattgg ctaacaaaaa cccaattcca tggggaggag aaaatttgag   1740

tcctcaaaaa aggatttcag atagggaacc aaccaatcaa aacgaaggac gtctccacgt   1800

gtcgctacaa gaggccatct ttccaaaatg agatcgcgga taaacaagcc ttttctgagc   1860

atagaaaaat ggcgaatttt aacaaaaaga aaaatctcag taaagtcatc agctacagct   1920

gctctttgac ggccacttga ttcactattt ccctctcttt ccggcgctga ttctagtgtg   1980

gttgaacttt ctgcaaagaa                                                2000
```

<210> SEQ ID NO 72
<211> LENGTH: 2000
<212> TYPE: DNA
<213> ORGANISM: Cucumis melo

<400> SEQUENCE: 72

```
attacttgaa cttaatccac atttatgtct ttatataaag ttcgaatact cataatatag     60

ccaagaaacc ttgtttattg gattttgagt tttatcataa gcaaatctct tatccaataa    120

caaattatta aacaacactt caacaataac tttattcaac aatatattag tttaacattc    180

acaaatcacg agtattagaa cataaaacgc aacaaagaat ggactaaggt actatattct    240

aacttaggtt gtttaggatt tccatatgtc aatgcttttg tgatttttga actagatttt    300

cttgttagat taattcaatt ctatttttaa atggcttaat atcttatttt cggatgcttg    360

gggattgcta gactaccgct ttgttgaagc aataagttaa atttgtttgt tacaggtatt    420

gatcaatcta acatagaatt gaatttgtat gaatatttag ttagacgctt gaaaactaat    480

tattctacca atgagccgta gatcttaatg caattgttat taatttgaac tttgtatgct    540

tctcatcgat taaatttata tcaagtagtt aattaggaca aatctattgg ctttttcatt    600

taattttgtt aagtaaaagc aacttagaat tttgaaaatg atgaacccat gatccaatac    660

attgaaagag aattttgttt aactcaaact aggattcttc tcacattgat ttcgtataat    720

ttaacttttt caatttatat caatcccccc agggtgaaaa aaatttgttt gaagaattca    780

tgtgctttct aaatctgatc tagacttgcc actaaaatta acttttgata tgtaatttgg    840

ttaaatattt gattcggatt tcgacgacaa acaattgatc aatgtggtat taaattctga    900

tctccatgta agaaatttac acattttcat aagttcaatg ttgacacaaa gagagtaaga    960

gcattttaaa aaaaaagata cttttaatct tttctaaaaa aacaccaaaa tgccattatg   1020

taaatgtaac ctaaataata aacatttaaa cttagaattc atgcaattag gctttgtatg   1080

ggacattgaa ttgattatta aaatcagtag ttatagaccg tgagttataa tggtttgtat   1140

tagaagcata aattatttta attttgatcg taatagcatg tatttgagat ataaattaat   1200

ttagtttggg tggcaaatag taaacagtaa agcaaaatat aaaaaaatga atttaaaata   1260

gtaagatttg taacaaatga ttaatactat aacaaacgtg gttttaaaat aacgttgatc   1320

gtagctaatt gaacattatt tattgtaaaa ttgagtgttt ttaatatttg gagcctcaaa   1380

cttcgggtgg atcaccacaa tataatcata ttcaaattta aaattttatt tttttattta   1440

attataaata ttgattgtta atagatgctc attatgggcc atctgtcact ccctccgtgc   1500

atatcctacc tgaaacatca tatatcttaa acaatgtcca ttgccatgtg tcactatttt   1560

tacatcccat ccacttgaca aatatgttga agatgcctac ttttttaggg atcatgtaat   1620
```

```
ctatctcatg cttgtcaaat tgttcgataa tagtgttaca aaaaatttag taattattat   1680

tattatattt cttcgatatt tatgcttcat atgccattgt gctctccatt tttaccatac   1740

ttaaaaaaat ttcttattat aaattttttc aaaaaaaaat ttactatata gtcatcatct   1800

ttattaaaat taaaattgag aacctgatat ttttgatatt aataatttaa aatttgaatt   1860

aatccacttt aaaattatta ataatttatt cgaatttggg ccttaaggaa gagatacgga   1920

aacaaaccct agatcccatc tatatataaa tcgccacaaa accctacctt tctctcagtt   1980

tctcgtttta gccggcaaaa                                               2000


<210> SEQ ID NO 73
<211> LENGTH: 2000
<212> TYPE: DNA
<213> ORGANISM: Cucumis melo

<400> SEQUENCE: 73

tgaaaaacta aattaaattg tccttacatg tgtataaaag aaaccttcgg acatttgatc     60

tgagaactat gttaaataat aagatccaaa aaactgaacc ccaacatctt cgaaatcgat    120

ttgatttcaa ttcttaagat aagctacatt caagttacct agatgatcta agaaactaat    180

gattggacaa agttagaaac tcccaataaa ccaatgatct tcaaagcact ctacgatcaa    240

gacagattaa tttttagttt gaatgctttg aacactcgtg cattctatca caagaacaaa    300

aattatacgt tttagaattt tcaaatatca ttcatcccaa tttttatttt aaacgtgaaa    360

attacaactc tatttatact aattaaaata ttaattaaca tgttacaata tttaatttta    420

tgtcatttca actaatgtaa taaataaaaa caaataagac aacgtaaata cacaatttca    480

taaacattta atttcacgac ttttaagttt tctaaataaa ttttcaactt tttcatttga    540

tttaattatg atttctcgga tcatatctat atatatatat atatatgaag ctgagtttta    600

gaaattgtaa attcaaattt ctttaaatgg tacaaattca attagtaaga ggaaaaacag    660

ctaattaaat aatgtgtgat gccccactcc ctaaaacagt gggtttggat cgattaatca    720

actaaaactg accacaaaac aatattcttc tacaacccca ttgatttttt taatcattaa    780

gtgccgattc aaagaaacaa taaacaaaag aagttgaaaa gattgagact tttaaattaa    840

atctgcaaga ttctctccaa actcatgttg tattcaagtg tttaaagctt aaaatatcag    900

taattatgtg ttatttaacg gtgaaaccaa tcaaatcaag caagattctt caatattcaa    960

ttccaaatcc tcaagtttcc atgaaaactt cataacgcct ttatccctcg aaagccaaaa   1020

ttcaatttcc tccattcatc ttgcagccct atctactttc caaaagccaa caaataccct   1080

tttaagcagt agccttttgt ttggttgtag taggatcttt gtttctcttc cattttaaca   1140

caagccacag gagaatctct atctctatcc tgcaaccttc atccccacat tgttcttcct   1200

ccattatcgg aaaaacccag tacagggttt gctttccggc cactatccgg ttgttctttg   1260

taagtttttt gggttttcat tatctgggtt tgtggctgct tgtggattca gggtaatgtg   1320

gccatgtttt atagtccaca gccttttttt cttcttttga catgggatta tttctgattc   1380

tatttgtcta ttgttacttt gtgctttttc tggtttgttc ttgtggtcat catttcttat   1440

gcttggaagt tcgaacatga atcaattcaa caactaagtt gagagtgttc gactctctca   1500

tctcattgac cctgatggta tatcttggct tggaagttag aacatgaatc aattgaacag   1560

cttacttgag actcgagagt gttcaactct ttcatctcat tgaccctgat gatatatctt   1620

ggctttggag ttatgaacta tgagagcttg gaggatgaac taaaaagaag ggactatttt   1680

ttgagatgga tatttagttt tagtaattta gcttttttttt tttagtacat agtacattaa   1740
```

```
ctttgttcgc gaggaaatag tggtcttgtt gacgagcatt tcttaaacaa tgtagttttt   1800
gtctcatctc tttaaaagtt tatggagggg caaacaagtg agatcaatag ttatagtatt   1860
tcaatctata actttggaac agctgatttt taacttttcc tttgtctttt ttttattata   1920
gaacacatta gagtgcgtta gattcttcag ttctgagatt ttgatctttg agtgctctct   1980
tttagcagta gaggcaaaca                                               2000
```

<210> SEQ ID NO 74
<211> LENGTH: 2000
<212> TYPE: DNA
<213> ORGANISM: Cucumis melo

<400> SEQUENCE: 74

```
actttcagta gattttatct cataaaagag tcataaagat aattagtaat gaataaagct     60
ttgtttgaag aaatgtttca ttgcaactga tatttgtcat tgatgtacaa atggctttgt    120
aactctccac tttttctaat ctaaccattt acatacaaaa tatctacgat acactaaaat    180
gaataaagaa attttttttg tcaaaaactg tggggagaat tgctccttgt tctcaaatca    240
ttcatgaact ttgcaattta gaagtaacat caatgaaggc ttcttccttg cagggaattc    300
tcaaacctcc agttgggtgg ctgaatccaa actcttcttc agccttgttg agcaagtcta    360
tgaatgaagg ctgactcaag tacgatattg gaacgaaaaa ccgctttctg tcggtttctc    420
ccacgtacac tggaatgtgg cctttgggaa caatggactg acatcttgct gagacagact    480
gcatcttgag aacttgcttg gcagcggaaa gaagaaccga aggcaaacga attcccatgg    540
ctaaattgga ttgaatcttt ttggaagtgg taaacttcaa tgcttgaatg agaatatgtg    600
aaagatttga agttggagat tagttgtttg tttagagtct atatatagaa tgagaaaaga    660
gaaggtattg tgacatatga atagaagatg ggaaaccaag aaagttgggt tcatcaatgg    720
ctcacatggg ttgctccatt ggttaaggta cattcatttt ctcattggca ccaatttctg    780
gtaagatggc cccatatgtc ataatacgtg aagtcatatt gatctaaaca aaatgggaca    840
caaaaattgt aactatttca attagcatta aaatcatgtc aagaaaacta cattaaatat    900
agatatatta gttaatgatg taataatagt ttcatgtgag atcaaactac gatttttttt    960
tataaataat gttactttta aaaaaatgtc aaaaatatgg tagaagaaaa gctattacaa   1020
aaagttaagt catctactcg gttcataatg cgttatcgtg gatcgggtac acgacaaggc   1080
aatgaagaca tagacccagt ctatgacttc gatgtaaaat gtgggttttt cctaattact   1140
cgtaaaaaaa tatttttgaa aacttttctt tttaacaaac ttaaattttg gttaattata   1200
tatataaata ccatctttac tttcttatta tccaaaacaa tttaccatat ataattatat   1260
ttattcaata aataataata taaaatattt agataaacaa aatcaattat ttcaatctta   1320
tatattttaa atatacacta agctaattta aatttacatt ctgaaaattt taattatatt   1380
tctatctaat ttaagatttt aattatattt ctatttaatt taaaatttta atggaaaatt   1440
aaattgtaaa taagaataag agtacaaact tactattttt atttcatttt taatttataa   1500
acttcatctc ttttttcata tatttttaag aaatccaacc ttatatttcg aaatttattt   1560
aaaaaaatta taaaattttt taaactatat ataaataaaa attgtaattt ttgaaataat   1620
ttattaattc ttacaacaaa cttataataa taacaataat aataataata atgagggtac   1680
tcgattctca aaaaaaccga accgatcaaa caacgttaga tcaccaacac agaagtaggg   1740
tttttcatcg gcacataaaa accctcactt cttcttcata aaaaccctca cttcttcttg   1800
```

acctaattcg cgccgttgat ctccggttcg atcggtttct acgctgtaat ctcaagctat 1860
ctcctacctt atccttccct ctctttttct tcttcttctt cgtatatgca tatcttcaaa 1920
tttgctgctt tttttgtctg attattcatc tgggtttgtt tgcaacagga aggaggaaga 1980
atttcaaatc aagaagaaaa 2000

<210> SEQ ID NO 75
<211> LENGTH: 2000
<212> TYPE: DNA
<213> ORGANISM: Cucumis melo

<400> SEQUENCE: 75
tttattaatc tgaatcattc tgtttcttct gagagtttta ttccttttaa gattctaatt 60
ttattttgga tagttgaatt ttggtgtgct ctctttgccc cttctttatt atacattcct 120
ttatcttaaa aaagccaaaa agttaaaaaa caaaaactaa tcaaaattgt aacatttaca 180
attttatgag catgacattt aaaatatcga ttttgaagtt aagacgttgt attctcacca 240
tcggttttta tctcttccca ttccattaga gtgataggct ttatctttca tcactgtcaa 300
aattcatcca acgtccaaga tctcttctgc aaagagttac ccacaattct ctcagactca 360
ttggcccacc ggataccgag tggatggata gaacctccaa gattgcgaga gcaaaagctc 420
agccaaaact tgcacaaact cacccatggc ttccctctct tgtactacct ccattaatct 480
caccccaaga tccttcaatt ctcgccccca ttcaaattag cttcccattt tcttggtctt 540
cagtccaacc ttcgatggct ctcacccctc tccattggac cctccaatgg gtctagagca 600
acttgctggt tcaatttaag gcaaaatgcc gagggtgcag gcatttatgg cagccagtcc 660
cgagatgatt tcaacagaga tgatgttgag caggttcttt tactaatttc tctcttcttt 720
ctttgtattt tgttttgtga ctttgattgt tgaagagtgg tgtcttttgt ttaattgctg 780
gtttgggctg attcttatgg gtttggagtt gaaattgttc ttaccctctg gctgttctgt 840
tttcttttaa gtattgtgaa ttttcaatgg ctcctttagt gaagatagat gaagaaattt 900
aaattagtaa tttttcgtac cgatgactct cttccagtgg tgttaatgtc aaactaacct 960
tttctttacg tcataaagca cttaatcggt tggaactcag tagacgtctc actcatgttt 1020
gtagccctaa cctaatgcca tggcaatcga aatttatatc gtatccctat tgcgattatt 1080
aaacatcacc ataggtgaga cattcctaac gtgatatact gagttctaga tggttaagtg 1140
ctctgacatt tcacattaac gcctcatccg cactggttag tcgaaagaag aaggtgtttc 1200
tgttatgaga ttgtgagaaa ggacctcctt aaacattata accaacctca taacttgtgc 1260
atttgtgtat caaactctgc tttcacataa agaaactaaa acaaggtatc acattgccgt 1320
tatgaaaagt gcatagaact tcctgcttcc ctcaaacaaa acttgcaaat attactgatt 1380
ggccttagcc tttaggtaag ggaagaatca aaagtattcc ttcatccttc tgctttaaaa 1440
atgtgctaaa tgacgttgtc catagtttaa aaactcgacc aaatcgcatt tgtcttacag 1500
tctctcaacc ctttttaagc actctcagag tcaatccaaa tagattccta gttcctaata 1560
tgtaacaaga agagtgatac tatgaaaacc cacaaaaaac ccacaaacat gtgacttgag 1620
ttaagatgac tcccaatccc actgtatcaa gcttttcaaa tagaggaatc acgatgagat 1680
gaacaataat atcccaacgt gctgctatcc caaattagat acagaagtct acttgtggtg 1740
ttcttaatcc aataattcat tatgaaattc ttatataatt tcttaatgag tatcttagaa 1800
ttaatgttac aacttatctc ttattctata tgatagaatc ttaacataag tattcatatt 1860
aagagcaaga ttatgttgat acttctcgaa tcataccaaa aacttggaac catgacatta 1920
acttcattcg tggaaacaag ttttgaagga aaaagaagga ttgacaaatg aacgttatgg 1980
ttgtgcagta ttttaactac 2000

<210> SEQ ID NO 76
<211> LENGTH: 2000
<212> TYPE: DNA
<213> ORGANISM: Cucumis melo

<400> SEQUENCE: 76
atctaaaact gcatttttta ctacatacag attcaccttt aggtgctggg gcttccccta 60
tttcatttta tcaatgaaat gtttcttatc tagaaataaa aagaactaca tacagattca 120
caccactgca gaaaggtcaa ataaaacatt catcataatt caaggtaagt aagcataatt 180
ttgtgaaact tatgtgatgc acttaatata tgaacgattg ccccttgttc tctcaaagtc 240
agatcttctt tttcctaaca attgaagaaa gtggaaataa gttaattacc acggccacgc 300
aataatctcc tgatggcctc caatgaaccc cccaaacata atgctgtagg gaatgtcttc 360
ttgcaatcct tcaagacgca caatgtgaga catgcaaaat attaaaaagt gacatcttca 420
aatatagcaa aagaaatcaa aatatttaca aaaaatatag caaagtttca tattttatca 480
attatacaca ctgatcgaca tattttgtaa atattttcaa tagttttgac atctacaata 540
attagttgag attttgtagt caacaggatc cagatttgtg tgttgaaagt tgaaacccat 600
gataagataa aatcccggtt aaatatttca ttttcattct taagtttttg aaaaaggaat 660
agcttggtaa gctacattcc gcatggtaaa caagcataca acttttgttt caaagaacca 720
acaagtacta caaacaaaag agtaattgat ttaatccaag ttaacaatga caaattggta 780
atatttatag gatattagtg agataataca atcaagttcc aaaagatgtt atatttacaa 840
ctatgagcat tcatcttgtt actaccacca agaaaaagta gcggttttcc aatctctgtc 900
aagtatccat ttgagttatg atttcatatt caagactgtc acaaaaattt cattaaaagg 960
tgcaagtgca acatttcctt aagaaaagga taactgagag atcaatgact ggaattcaca 1020
agttaaaatg aacacaactt cagaacatca caagctaata cctccaaacg gtccaataag 1080
ttttctgcaa cactgtcaac aagcgaatcc tttgggcgca tcaaccaagc agctcggtcc 1140
cgctgttacc aagaaacagc aatttcagca agaacaaaat atagaaatcc tccaagaaaa 1200
ataaacaaac aaataagttc gaaggcacca catatcagaa agcttatgga ggagtacatg 1260
tagtacaaac gctcttgcca tttagtttta cttgttaaaa gtgatttgct cagaataaac 1320
ataaccaaag cagaatccga acatatgaac caatgaatta ataaacccca tcacagaaag 1380
acaagtaata ctcccagaat tgtactctat acagacgacc actacaattt agccacacaa 1440
tatcaccatg ttctctccaa atatatttaa aaaaaaaaaa aaaaaccctc ctattgttgc 1500
ggttaacaca aatagatcaa aaagaagaaa gaaaaaacta aaaggagaca aaggtgttaa 1560
atttggttta cctgtttacg cttaagatca cgatcaaaaa ccttaacctt tgagctgtgc 1620
attccatcac cgattcttcc gtcataatta tcatcaccag tagagaaaga acaacaagga 1680
attgaatttg gaaaatctcg ccatcttgca cttctcaaca ctgagaacga tcttatgatc 1740
gtagacggcg acagccctct catttcacag tcaccgattg aacctcgccg gagagacgga 1800
gggaaatttt gtaaattttt aatgggcctg ggccgtaaag tcgtgtccaa acactcctta 1860
aacggaccaa aaccggcgta gaaatgaaac tatccagata agggacgtgc tatacattta 1920
tccaaacgag gtctcttatc gtatcttgta caagttcgtt gcttttcacg gctgtctcta 1980
gaattttggg ttgggcgaaa 2000

<210> SEQ ID NO 77
<211> LENGTH: 2000
<212> TYPE: DNA
<213> ORGANISM: Cucumis melo
<220> FEATURE:
<221> NAME/KEY: misc_feature
<222> LOCATION: (1)..(2000)
<223> OTHER INFORMATION: n=g, a, t or c.
<220> FEATURE:
<221> NAME/KEY: unsure
<222> LOCATION: (1)..(2000)
<223> OTHER INFORMATION: unsure at all n locations

<400> SEQUENCE: 77
aaacctactc tgtaaatgaa ggtttacatc tcttaaggca gtaccatttc tgccattact 60
tctaccattc ccacgaaacc acctcttttc tctttcattc tccccgtcag gtatgcattt 120
ctcatctcta agtccgccca ctgttttccg actgattttt cgatttttaa ttagtgagtc 180
ggttttattg tttcttattc taagctttct tttactcttt atatttttag atatttaatt 240
tcggatccat tcttcccatc atgcccaatc caaagactgt cgaaagtttt gattgttggt 300
aatgggacat taggtctggg gtttctgttt ttcttatcct ataaattggt tatccttcgt 360
ttcctctatt ttgactttat tccgtagtta ggttagaaga agaaactact gaataatgtt 420
tactatacaa acacctcaaa atagccaagc ctgtcgaaac acatttagct gataagctag 480
ggatgaagag atcaagagat ggttagctca gctgtattgc atctcatggg ggacgggtga 540
aacgaaccag agaagtaata tacacgtttt ttttttaaaa aaaaaaccga ataatttacc 600
tgttcttgct acaattacac cgataagttt tcaacttgag caattacacc gtctaatttg 660
cattgctgaa gaaattggtc tgttccatta ccactgttga ttaaaaagtt ctacttgtca 720
gcacagcatg tccatgtgcc cagatagttc ttgatctttg gaaaaagtgc tatgtttgca 780
tgcttcggta agatgtgagg ttaaaatgag gaggacataa tgttggcata gggaggtcaa 840
aatgtgttaa ttgagagaaa aaatgtggtg gatattggag aggagacatg gaagtagaga 900
gaaagagatg aggagggagg ggtgaaggta aagggaaata gacatacaga aataaagaac 960
tgtgcgagta atgtgttgcg ataagtgaaa gagagaaagc aagagaaaca gtggtagaaa 1020
attgaagtat agagagagat gtagagaggg aaaatatgga gaactacaag ataaaatatc 1080
tttattcttt ctctatctaa gtatttatct ctttagaagt tatctctctt tgtttctgag 1140
tttaccccta gtattttctt ttttctttct caagcccttc ctctctaaca caatttctct 1200
ctctctcttc tccctctctc tctgtatctg gctgtggcac ttttttttgac ctcttccttt 1260 ctgtctttat ctcctttgaa gacattttga ttttcctaca cccctcaatt ggtcttctac 1320
tcaaactcat ctacttgtta ttatattaaa tgcatgaaat cctaatattt taggaagctg 1380
gagactcatt gtgcgtgcat ctgcttgctt gtagaaagtt ttaaattgaa aggcaagccg 1440
aaggggccta attattcagg ccaggacaat gatgttggtt ttagtttttt gtttttgaaa 1500
nnnnnnnnnn nnnnnnnnnn nnnnnnnnnn nnnnnnnnnn nnnnttttga aactaatttt 1560
tttcttagtt ttcaagactt ggcttggcat ttaaaaacat tggtagaaaa tggataacaa 1620
aaccaagaaa cttacatgtg gaagtagtat tttataaagct tacttatgtg tggaagtagt 1680
gtttagaagc ttaattttta aaagtctata accatatggt catcagtaga gtctcatgca 1740
acttatgttg tgacagtggt gtaattgttc taattaaaaa ttttcgggta caaatgtaaa 1800
aaacattatc gaacagtggt ggtttgtgaa atatgcatta actttttgaa aatttgatgt 1860

```
gtcatcatat tcattccatg ccgtgccttg tttccctccc agctccttat ccatgctaat   1920

tagattcaga ccattatccc tttggaacag ctatgcttaa ctctgttctt ttctccctct   1980

gtacaacagt atatcaaaaa                                               2000
```

<210> SEQ ID NO 78
<211> LENGTH: 2000
<212> TYPE: DNA
<213> ORGANISM: Cucumis melo

<400> SEQUENCE: 78

```
tagcttgtta attcttgtgt tgaagacgtg tttcaacaaa tctgatgggg tattcatctt     60

aagtgtccac tgaagaatgg gggttctgtg gcagatctgt atgttatgta gtgaaaacaa    120

atctgtaaag ttttttttta cttcgaattt aacgttgctt aagcttctgt gtacagtttt    180

atcactgcct cgaggttatg attattattg gattaaatta caatttagtt tacgtttacc    240

ttggaactgt gtatttcttt tgattgctca acttttctcg gggatttttc aagaattgta    300

tttttaaaat tttaatttat ttggaacatt aagaagttgg ttatttacag atgagatata    360

acactgtgat tggggtggaa aataaacaca gcttcaaaca cggagtgaga tatagttaat    420

tacattacat agtactagag attatataaa tcactccact cacatgagtt ttcatcttaa    480

aagattggaa tttacatctt aacagatgca atcttttaat gtagagttct taacgtgttc    540

tcttacggtt gtatcttttc gttttcatta ttctttggtc aaatcaaaat tagactttat    600

agtttttaat gaaatattgg acacactacg attcatcaaa gtaacccatg atcttataaa    660

gttgtgaaat gtatgtatat tgtctttgat caaactttac gtttaattat atcttgaatt    720

tataattttg tatttaagag atgaatgaat tttagaaaat tctaaagttc ctaggccaaa    780

gttgttatag aagggtaaag aatgctttaa atcatttatt ccataatcat tagttttata    840

atttttattc ttcgtaacta ttttttaaca aaaaaaaaaa aagttatgca tctcttaaat    900

actatctttt aaaagggaaa ttttcataaa taaataaaaa aagacgatag tatacacata    960

aaaaaaactc aaatgattta tagagagttt gatgaatttt gctggattta taaatagttt   1020

agaaaaataa gtattaacct aaaattttgc ctatatctca atggccttct atgtctatgt   1080

tatttcttaa ctaaaatcga aaggatatag gcttatggat tggcttaagc taaaaaatgt   1140

cggtccaaat agttgagatg tcaaacctta aaagtactac gattatgtga ttttcacatg   1200

acatagtgtt ctatggtcaa attttatagc gtacttattc caatccatca ctttttatag   1260

aactaaaatt catagttcct attttaatat atatatatat attaaaaaca cacattaaat   1320

gatgatttta tctcttctag gttgattgaa aattactaac taaaaaacac ggtgcctcaa   1380

acctccaacg taaatacgat ttctaagaac tgtgtttttt gtaaacgcca agtgactgat   1440

taaatctctc cattctctgt ttacttctat ttggggttat ttatgctaaa ggatattatt   1500

cattcaatag aataaatgtg agatagtcga gttatattca tagatgttac aatgaggtga   1560

ttcattcctt tgtcaaacaa tgctttctcg actcgtattt tactgtattg gatcgaaatc   1620

cttcttactc gcatggtttg ccttcgttga ttagttttgg tatgaattga tgctttgttt   1680

aagggggaaa atgaaaatgg ttcaattgga ggacaattgt ccaaatttcg ggacattatg   1740

ggttaaacac aaagaagaag tccaacagtg taattttgtt aaagattgcg ttacatttcc   1800

gaaatataaa tgagggtatt ttggggaaag gaaatcaata taggccttgg ccgggtgaga   1860

tgcgaaaaag tctcaaaact gagtgagaag cgtttgagct gggctcgcag ctattgaaaa   1920
```

| agagagaaca aaccctttcg tcgctcttat tttcttcctt tgatctgaaa tttcctgttc | 1980 |
| cgatctcgct ttaggacgca | 2000 |

<210> SEQ ID NO 79
<211> LENGTH: 2000
<212> TYPE: DNA
<213> ORGANISM: Cucumis melo

<400> SEQUENCE: 79

| aattcattcg ggattgttat gaggtaataa aaaatatctg agtgcgaaca tgataattgg | 60 |
| taaagtgaaa aaatgttcag ctattctgtt ctagatacag ggatggaagt gggaacaatg | 120 |
| ccaccttgct tattgacaat aaaatgagga gtggcaatat tttgtttctg aataaatatt | 180 |
| cactagcata acatattagt gatgattcaa actaaagtgc actaggtcac tagtttcttg | 240 |
| attcatcgtg tttggtagta atggtaggta ttgtatctta tagtattgga caaagcttta | 300 |
| ccgaccataa attgtggata atgtgcagag aagaattggc agttgaacgt tcctggatat | 360 |
| tcaagtgatg agtggaagaa tcacaacaaa aatgtaagaa aattatatta ccctctctaa | 420 |
| aacatcattc tattctcctc cctaaaaaat cattctgttt caatttaact ttcaaaattt | 480 |
| tgttttagtt taaccatatt gagtttttt tcttttttaa ttatcgtagt tatcatcaag | 540 |
| tgatgtccac aagaaacgtt tggacatggt aagttggact tatctcttca agtgtttgct | 600 |
| ccatttcttc ttttatcatt tgtctcaaat tttctcttct ggggtttcat cagatacgcc | 660 |
| tattgaagga agcctcctgt gtcgaaacaa atgtaaacag ccctaaagag atggtacgac | 720 |
| aaggggttgg aatgtcaatt ggtcccaaca ctctaacaag gccttcaccg agttcagaac | 780 |
| aactattatc acaaacgtct ggttcacagt tgctgcagca aatgatgagg ttttagtgta | 840 |
| ttaactacgt ttgaaactaa tgcttggtag agatcccaac tacttggtga ataaccaacc | 900 |
| ccagtgtcag ttcagggata caacaaataa aatgagattt agaggatgcc atatcagagg | 960 |
| gaacctggac tggacatctg tgtggagtgg agtgtgatga tttttagtga tacgtctttc | 1020 |
| ggaatcaatt ttttttaggct gtataatatg aagttgcatt atctggaaca cgggcgtaat | 1080 |
| gttaattgta caaaatattt ggcaggtcat attagtatag gccttaagta ttgttgttgt | 1140 |
| ctaccatgaa ggacattttc caatttatga ttgataatct ttacttacaa tctcgagtca | 1200 |
| tatgaagttt gttgatcagg atcatagcac aattattaca aaaatgaaat agaagatatg | 1260 |
| atttttcacc cccccccac cccccccccc cccccccctc ccattcccat cccccctttt | 1320 |
| aaactgttac attacaactt gttaactgtt gattttccag atgagagaaa gggcctactt | 1380 |
| gtcttgtaca gaaaattcat ccatgacgat aaatgcagat gacctgaacc aaacgtgaca | 1440 |
| gtaggggttt cttctatgcc acaaagctcc aagccattca tggtgcgcat gtggtacaga | 1500 |
| gaggcttgat ggagcctctt caccttggtc cttagctatc taaaaattgg cttcttatgc | 1560 |
| tgatatatct cttcccatgt gcatttggtc cactccactt tcttcgtcga atatccttgg | 1620 |
| gttaatcctg aatggtaagc acaacattct tgctaattaa tccctctttt tatcctactt | 1680 |
| gccaactgta caagatgagc agaagaagaa ttgcccaatc atgaggtcat taactgcaaa | 1740 |
| aaagagaatt tatttctttc tttgagaatc tgatcttctt gagagttcat tgacagccac | 1800 |
| atgcatcaca aaatgaaatg ctgtgtggcc ctcattcatt cattcatcaa tcttcctatc | 1860 |
| ctgccatttg agtgaatgtt actccaactt gcaggaagct aaattagtac tttttttatat | 1920 |
| aaaccctatg aaactcatca agaaaccaca ccatcccaaa aaggaaacga gtgaacaact | 1980 |
| agacaactca ccccgaaaaa | 2000 |

<210> SEQ ID NO 80
<211> LENGTH: 2000
<212> TYPE: DNA
<213> ORGANISM: Cucumis melo

<400> SEQUENCE: 80
cagcgatctt cgtagaaact aattcaatgc tagctcatta tttgactttt ctcaggcaag 60
gctccgcgag gaagagaaaa ggtccaattt caggaaccaa gggcatggac aggttccggt 120
cagaagaagc tttttacgta aaccctttgc cagattgttt atgtcaagga gaattaccaa 180
atggaagtac gacttccatt ttcagatagt tcagtagaac atcaaagata aaatgctctt 240
agagagctca atgtatatgc aggcgaccac tcaacgtgtc accagctttg tacatccaat 300
aagccagcta cgatggaacg acggagtgtt tataacctga gttttggtag ttggcggagg 360
cggtgatggt ggtatagaag gaaggtcgag ggatggcaaa ccctttacgc caagtagtgg 420
aagggagtag ttggagatga acacattttg agaagtttcc aagatcactc catttggggg 480
agaggggatg ttggttattt agcacaattg ttttcatgtt ttagtaattt tatccaataa 540
tgagcgaggc attgaagcaa ttaaatttat ttttaatgat tttttcaccc ttccataggc 600
tttttctttt ttcttttcct tttagtttgc aaactttagc tccttttatc ggctgtcgaa 660
ctcatttttg aagttattga atgaaacaca gtttgggctg tgtcagatgg gtggtgaaat 720
tttatacatt ataattacta cataaaatga aatcatattg taattttcta tctatgccac 780 aattttttt tattgcatca tgaggattaa attgtacgag tccaaatttg tacagtcatg 840
tttttaaagc tttcgagcat tgttactaat gcatggaaag gatcgattat caagtatcct 900
cccaacttca tgaaagttat tatttgtctt ctaaatttgt tttagaaaat gtttaattaa 960
ttatttgaga agaaagttta actaaatcct attggtttcc tctaaggttg tcatacttat 1020
ccaataacaa ttacgtttaa aatcaaaatt attctaatgg tataagacta atgttttaaa 1080
agcataaaat tgatgaggaa ggattggaag taatactatt tattttgaag gtaaacattc 1140
ttgaatgtct gtcctaaaat cactaatgtt ttcttagttt gagactttga gtcgttgaac 1200
ctctccatct ttataaaata taatacgagt ccttcacaat aacttaaaat atatactaaa 1260
tcctaattaa tgaaaaataa ataaataaaa ggtacaaaat cattaaagcc taaaaatcta 1320
ttactccttt aaaacttttc aagggtccct acaaccaatg agaaactacc acgtcatttt 1380
cacaatccgt tcagtgttta gaaaagtcaa atcgcaccgt ccatttatcc actcgtacca 1440
agtacggtag gaatctatct accgtccgat taagcacaaa gaagcacagt aaatgtcaat 1500
cgtgtccatc cgccgccata ccgcacatcc ttcgtccgac cggaaggccc tatataaagt 1560
cctttggttt tccgaatttc tacttcattc gcttttgaaa gatttcccaa tctcttcgtc 1620
ggccaaaatt ctctctcgct tctcaaccct tcttcggctt tttcatccag gtttgtttct 1680
cttctctttt ttcttccttt gttgttcttg gaatatgttt aatttcattt gtttttccat 1740
tcaatttcat gctagatttt acgattaggt tgattttctg ttcgtagatt gtaattgatg 1800
gttagggtta gctttttctc ccattccttc tggaatctgt ttcttgacct tcgaacttcg 1860
ttgataaatc tttagaaaca tttacataac caaacaataa ttgaacaact cgtgttgtta 1920
tgcctatata atagcggtta ggaaactgga aacgccctta taattgaaat cgccttagaa 1980
atttgttttg attcatacag 2000

<210> SEQ ID NO 81

<211> LENGTH: 2000
<212> TYPE: DNA
<213> ORGANISM: Cucumis melo

<400> SEQUENCE: 81

```
tgtaatgact aaacatacta tagcctattt ggaccgggtc gaaaatccaa attaaccaat      60
ctcccctcag cctcacacca aggataaatc atgtcaacct tctccatttg acatgctagc     120
tggacaaaga gaaatactaa ctcaaattcc atataaatat atctttacga ctccttatca     180
ggtaatttag actcaacaat tagtaataaa tttagtataa tgaatgatag tttccataga     240
tcaattatat catttattga tttgctagat ctagagtgaa cttattgact aatataccaa     300
atataaaata tatcaatgaa cttacccacc aaacataaaa atgtaatatt tatatctaca     360
tgaattttac aataaaaagt gtatcatata aaatacttat atacataaac cctattatat     420
atatatatat ataaaaggaa ggtaagatgg aaaaaattgg aagagaataa tttgacctaa     480
aaaaatcgaa agagaaaaga gtatttaata tataaataaa aagaaaaaga gagaaagaaa     540
aaaatcttgt tcgtcgactc ctcaaaaacc ccagcgtgta gcggttgtga gagaaggaga     600
gctcgtttcc atcacgataa aaccttatct ttctccattc ttctatcttc tcttccggag     660
ctctctccat ttctcagccg ctccccacaa tttcctctaa acacacacat acacgactat     720
ttttccattc aaattccttc acttcgtttt ccattttcct tttctttacc ccacccactc     780
acccacctct cgtcgatgga ctccatggac ttggcccaac aaccgtcgca acagaattca     840
gtctcctcag gttcttcttc cacttcctcc tcctctttta cgtcttctac cgttgattcc     900
catgtcgata ctccctctct cgatgaacct gagatggggg ttgctgaaat taaaactagt     960
gtagttgccg atgggggtgg tagtgatggt gctggttccg aaactgaagg gtttttgagt    1020
ggggaggagg aatttgagtc tgcttcagat agaccaattg tgggttatcc agaggaagag    1080
tccatcggga agtccgccca aggggctgat actggtactt cttttgtggg ttattctcaa    1140
ctttctgctc cggttagtgt taggccaatt gcgaaggttt ctgttgatag tgacgttgag    1200
gaggaggatg aggaggagga ggaggaggag gatgaccttc aggtggatga gaacttgagg    1260
ggaaaggagg aaattgagga taaagtgggt ggagaagatg tttttgttga gagtaagaag    1320
gggaaggaag ttgaggttcc agtggaaaag gaggagacta ttgttgtatc tgatggaaac    1380
aagaatttgg atgatgtggt gaatgatgat gatgatgcca gtcaagtgca ggaaagaaca    1440
attgagttgt cggggaactc aaaagagggc aatgtgcctg aaagcttagt agctgaagat    1500
gttggctctg tgcccgagga atctgttgat ggtgggaagc aggtgtcaga aggggatgaa    1560
ttgaatgatg tgacagttaa acagtcacaa aatgaggctt cagatggaaa aaagaagcag    1620
agttggataa agaaactctg gcgtctggga agcaggctgg taaagggatt gacttgagtg    1680
agaaggtggt tgctgaggat gtagagcaat tgaaagaaca ggaaacacct ggttcttctt    1740
ctgacgagaa agctgttttg ggagaccaag caagctctaa gcttgtgaaa ctagcagatg    1800
aaaaacaaga agaggagacc tctgcggctg agaagcaggt agatgtggag gtcaaattga    1860
atgacacggt ggctgctgct gaagatggag agcagttaaa aaatttagaa actgattctc    1920
ctgttgacga caaaattgtt ctagctgatg acgaaaactc taaggtttta gaaccagcag    1980
atggaggaca agaagcagaa                                                2000
```

<210> SEQ ID NO 82
<211> LENGTH: 1072
<212> TYPE: DNA
<213> ORGANISM: Cucumis melo

<400> SEQUENCE: 82

```
tttaatatgg tatcagagca aatggtccag agaggtcttg tgttcaagcc cctgcattta      60
cgtttccttc ccaattaaaa ttgtttccac ttgttgggct tttcaaatat ttcaagccca     120
caagtgaggg ggagtgttag tgtatataat taaatttgcc ttcttcaacc actagctgaa     180
gtttgtgggt gaattggtgg tttaatagta actatatcat gcaattagct tttttgagtt     240
caacaatatc tgtggtggag atttgaaatc gagattatga tgccttaacc atgtgaacta     300
tgcttaggtt gacaactata tcatgcaact atcgaaaaca tcatctctaa tttataggtc     360
ttttttaaca tagttgaagt ttcaatattc tatatgaaca cagctggcta tttaaattac     420
catattgaaa agcagcactt gaaatgcttc taaaaattaa tgccaattag aagtgtttat     480
gattctaatt ggttaacatt actgaacaca gattagttat agttattgaa agaataaaaa     540
ttgtaaaatg ccgaactaat accaaatgga tgggtagtct gcaaatttta ccaaatggta     600
ctacagctgg tgatgaactt agaaggggta aaggtatagt gtaactgtct aagttaatgc     660
cataaaggta tagtgtaact gtctaagtta atgccattag cagatcaagt ccgttgtatt     720
atgtactgaa cacatttttt aatcgtatag ttctaaatcc tataatctgt cgaccaagtt     780
ttaggtttgt taggctgaaa gttcatgcaa atctaggtgc ttttttgtac taattgtttg     840
agattcagaa attgtatctc aatgttctcc atgattatgt gcgtgtattt gcaaacagct     900
ctttggtttt ttcttcttct tctgacaagg atagtcaaat caattacagg acataatttc     960
aagatttaag gagagaaagc aagggaaaga ttcacgggag tggactgagt ttccaagcag    1020
agttgcagtg caattaaatg atactcatcc aacccttgca attcctgaac tg            1072
```

<210> SEQ ID NO 83
<211> LENGTH: 1730
<212> TYPE: DNA
<213> ORGANISM: Cucumis melo

<400> SEQUENCE: 83

```
gttcaactcc acaagtcaaa tttttttgga aatctcgtgt gaacacttgt gaaacacttt      60
atttttatat taaaagaaac aagaagattt aagatgagaa tcccgtattt gtttggttga     120
aggacaatga aattggtaaa tatatcccat cgaaaaataa tcaaatctag acacaaaaat     180
ttaaagttaa aacttactta ataatcagct ggagcatagt ttaatttgaa tgaaaataaa     240
aatcctaaac tagagaagtt tcttatggta ttgaaaggcc agtttagaaa gcccaatagc     300
gtgggttttt cttggaccca tgtgtatgtc tcactcatga aattaaatta attggcctcc     360
acattcacct ctctcctccc aattcccata actcaatttt agacctctta aatgaaacat     420
atcatatttt cataaacttc ttttttacgt tacttatgag attaaaagac tttaaataaa     480
gtgtcaattt atattatagt agatgagatg gagtgtgtgt ctttgtgccc tccttggggc     540
ccaaggacta agtaaggatg aaagggcaaa gaaatacaaa atagaagaga gtagaaagaa     600
aatgaaatgg aatatatagt aagggttatc gtttatggtt attatgaggg aagggctgaa     660
attgataatg aacctatcct tatcttccct tcttcacctc tcattttgct tgaaattaca     720
aatgactttt ttttcaatta ttttgtgtgt acatccaaat gtggtatgca catatgggcc     780
tcccattaac ttgtgatcca aattaattct tttgcaacct aagttgaaat taaacacttt     840
tacctctctt tttttcccta acaattttac tttcattgtt agatggttga ttatcttgac     900
atgtaacaaa aagttctctc atgtcaagat agaaaaatcg aatatttgat tttgagattg     960
```

-continued

```
ataatattat aatatcagtt gagctatact cattttaact atcagtaaag cttcattaac   1020

atatttttta tttagtaaac taagattaat ataaatagaa tcttactttc attatatact   1080

ttgacgagac ttaaaaccta tttagcgcat gatttttaaa agttggtagg attttaaccc   1140

ttgaaaaatt ggtcattcgg gaatcaaaac attagtttcc ctttgagcat ttattttaa   1200

agcacttcaa aagctaaatt agtagcatta aaaaaaaaag tcaaatagta tatatatata   1260

ccaaaacttt gtttttcaaa actatatttt aaaccaacat tcttttttt ttattattta   1320

ttactaatta agtgcagatt atagtggttc tcttttgtag ttggatcaaa tatttcattc   1380

tttttgaca ataacaaaag ttaaaatact cattaaatgc taaaaacttc catactaaca   1440

ttattgaacc attaaatata tgagcaacga aagtataggt aagaatttat attgttgttg   1500

tttagtttgg aaatagaaaa tggaccaatg ggtgagcttg gtttaagtta gggttcttgt   1560

ggttggatga taatgaaata aaatggccaa aattttaatg gagaagaaga tccctttaag   1620

ttcaaccact aatggagtct tttaggatca attcacaacc cctttctcct tctgccacgt   1680

gtcatctcag ctaatctcaa ctgtgtggtt gttgagaaat tttgaaactc              1730
```

```
<210> SEQ ID NO 84
<211> LENGTH: 2000
<212> TYPE: DNA
<213> ORGANISM: Cucumis melo

<400> SEQUENCE: 84

aactagacta gcgagtgcac aaccaaatta caaaatcctt aacagagaca accatctatc     60

tcctttaaag caacaataac atcaaccgaa ttagaatcca caatcagtaa agacgatgcc    120

gacaccaatg accaaaaccg atcaaatata gcttattacg gaccattact tcaacagtta    180

catcaacaaa aaaaaaaaat taaacattgc taataaaatc tgaaaatgag gaaaaagaga    240

ttaaaagttt tgaagataga aagaataaat ctgaaatgtt ctaatttgat atataagaaa    300

tatgaggtaa tatgacgaaa gcattttgat agttttcacc aactcccttt gtgaaaggat    360

acatccaacc aattttacaa tttctgttca aattttgtcc acctaccctt ctcttctgcc    420

ccccaaggct gctttctttc ttttattatt tgctaaatta ccaaaaacta ttttcgaatt    480

aaaccatcta tttcaattat atacgtcatt cgaattttaa cttaattaac attagtatat    540

gtttcggatc aaggatagtg gtataaatca tcctaatttc aatttgtatt tagaaaagtt    600

caattatact taaaacttct aaaaatttta tattttaaat ttggatataa attaaattta    660

agatttatgg aaggtaaata attagagcaa aacaaacttc aaactatatg gaaaatagaa    720

aaggaatatt ttagccaaac aaaaacactt attatattta ttttgttttt tgtttttttt    780

aatttaacaa tttttttttt tattggttga atgtgtttct ccactggtga gtctccaact    840

ttgacctgca aagggtctat atagcgagtt tcacgagcac ctaaccaata tctgtgtaat    900

aattcccatt tttctttcat acccacttca tttgatcatc tttttcacaa ccccggatct    960

ctaattcttg ggaatttgcc tctttctcga tccatttcca ccgtaattga aaaatattca   1020

ggtttgattt cttctgggtt ttcattcaac tgtctaactt cattatgccc tttatgtgtt   1080

tgttgaaagc cccccaccca ccatcgttca atgcggtttc tttacctttt gttcggtttc   1140

aacgatgatt tagaagttat agatggatgc taattgtttc gttgttggtt tgatccactg   1200

atctgccttt gattggcata aaaggagatt ctagatcttg ttttgatgtt gtgatttatg   1260

gatattattg ttatagtcgt ggaagttttt cttgtcgttc tgcggtatat ggttgtttta   1320

tttttgagt ggtaaattga gcagattgtg aacttttggg ttttatggtg aaagcatgaa   1380
```

ttagtaaatg tagagctgct gaaacaaaat ggaggtttgc tagacctctt tgtgaattct 1440
taatggtcag cctccatctt aagaggctaa gtccaaaaat ttaaggcagt cttttgttat 1500
tgttacaaag gacaagaaat aacagaggag ttattttaat tgaatcaagt tggaaagaag 1560
tactacttca tgcttctttc aaaagcaggt caaagtgctt taaagtcttc ttatttattt 1620
attttttcct gaatcaattt aaactaatga tagaaagaag tgttttttaa tgggttatta 1680
taagtaacat caatttttaa ccattccaaa agttacatca aattcatcat agtgtgagtt 1740
tacgaatttt ggaagttgta attttaagtt aatacttctt ttaaggaaat gtacactttg 1800
catgttgtgt tcataagggg tatttctttg acaaacgcag caaccacccc ttaatgaaaa 1860
ctacaccacg gtggttggtt ttttcttgtt attttttttac ttggaattta caataagttg 1920
ttatattcgg atatatggca aagcagatat ctgtttttat ccgaaacctc ataaatcttg 1980
aatgtgcagc aggtaaaaac 2000

<210> SEQ ID NO 85
<211> LENGTH: 1020
<212> TYPE: DNA
<213> ORGANISM: Cucumis melo

<400> SEQUENCE: 85
tcattgatga agaaggaaac tttaagccaa ttcgacaact tatccattca acaactttcc 60
accttcagac attcagattc aactataata taacataaat tgatagtcaa gtctttttg 120 agacaaccat aaatcatctt agcttcgaga actgtcactt ccttaaattg gtgaatatat 180
cacattccat ccattcaaaa ctttgttttc gaacttttac tgtagttatg aatcaataaa 240
ttgggagaga tattgtttaa aaagagagag catatttgtt tctattattt actctctcct 300
aagagagggt taattagtct ataaatgatc tattcttctc gtccattgaa attttgttat 360
cctaaattta tgaatacttc tacccaaaat aaagactttt ttttttgaaa agtgtcaaaa 420
aaacataaag aaattgacaa aacattcatt tttagtggat ttttacggac gtaaatagtt 480
tgttttgttt cttttaataa tacaattttt ttactttaaa aaatattttt gttataaaac 540
caccgtattt ttattcaatt ttaataaata aataaatgaa agaatataaa aaagaggaag 600
gaaaaagaag ccaacgaacc aacggttgcc acgtatcaaa ggtctaaagt gcgcaaaacg 660
aggccttcgg aaaccaaaat gcgtggcttc aattggagca agtaaacatg gaaaccacgt 720
ccattgtaac gcttcctgat ctcttcttta caaccgttgg attcgagtac tttttctcaa 780
cgattaacga ctgagtggac ctccacttgc ttctgttcca cgcgcgtggg attgacgtgt 840
ggtccacgca actcttctcg ataggatcat tcgagaacat cctttactta aaccgcctct 900
ctctgcctca atttctcgtc acttccttct ccttctttac cctttccact gcggctgatt 960
cttcttcgcc ttttattctc tcgtacgccg ccatattctt cacttctttt tccggcgaca 1020

<210> SEQ ID NO 86
<211> LENGTH: 2000
<212> TYPE: DNA
<213> ORGANISM: Cucumis melo

<400> SEQUENCE: 86
aaatcatctt ctcccatttg catgtgttaa cgcctaatgt agtacattta ccatgattcc 60
tagaataaga ccgattttac caacgagaag ttgctttcaa cttgctacaa tatacataac 120
atttctttgg tacgttattg atgagaagag gtataaagca tttcacagta ttctctcagc 180
aactcattag tttaaaaaaa aattaaagga atatttgaat atcgggggat gaattaagta 240
tagcctcaca atttgccagc tccttctcct tagcggctgc caacctccga agctttgcag 300
cctgtgcaaa tgtagacggt ctacaagaac ataaaagcaa atgaatacga tccccatgac 360
agccataaca gttgcaaaca atcatataga atgaatgatt tgagcctttt ttttttgtaa 420
gatgatttga gccgaattaa cagtgtctaa tgctgaatcg agctggaaaa tactacttac 480
tgagataagg tgctagcctc cctcagaagt tgctttattg atttgcgcaa ctccaattcc 540
acctggctgt tggaacctcc ctgaaaagta cacgcatgat ggaaacatga ttgtttcaaa 600
acaaacaagt tgacaagatt gaacggataa caattataac atagcaaatt cccagacatt 660
aaaactgaaa atgtcaatag atctccacat taaatgcatc acgtccctaa actaatcaaa 720
tcaaatgtct tcaatccaat atcgtaaact taacgaagca cagttaggca tattgcattc 780
tcaagtctgt caacgaaata ctgaaacgcg ctacagccca aacctcaaaa ttttcaacta 840
taaataacaa gctttgaatt gaaaaacaaa cggaatgata gaaaatacaa acacgaaaaa 900
attccgacgg gaaaaagaaa atcaaacgaa aaggcgaacc ttcttcaggt gctccagcca 960
tctagcgaga aactgaaaac cgataacgat aaagaaaata aatggagcgg caatggagct 1020
tccatgctct acgattcctt ccgcttccat ttccatttcc agaggacttt tctgccacaa 1080
cggtgaatta atcaaacaaa gaaactccgt tcatcgtcgc aattcgacgg aggttattct 1140
ggaagaagtt gagatcgtaa ttgggctacg aatatcatca aaggggcttc aataaaaggt 1200
ctctcaaaac ccaaggccca aaaaaacgaa aagcccagcc caattagtgg agaatcaaaa 1260
cgctgcgttg tagatacaaa tatcttagga aagggaacca agttacgaaa ataccccctga 1320
gtagtgagat caatgattac ctcaacgacg cgttaatcgt tttatcacgt ttattgtgat 1380
aagttccgca ctaaggaagg gacgagttgt aggaagggag gggtaaactg gtgatttcgc 1440
attcaaacaa cgggctttaa ctcacgtgtc cggatctgtt gagagggaac aattcacagc 1500
gaggaaattg caaataacac acaaaggaaa cacaaaagag cggaaagcaa atgtgaagag 1560
acgaagagta gccaatgaga aaaaaggacg aggatcgatg acatggcaaa agatttttga 1620
aatcccgcct aaacccggag tttcaattga tatcgcgatt tatctctccc tctctttaac 1680
gaaaccgact cccttcatat ccctctctct cgctccctct tcacttcaaa gggcttttcc 1740
ttctttccac ataaacacac gcactcgaag ccaatctcaa aaccgcatca cacgaaccaa 1800
actaagccta acccaatttt ttctcctcat atttcactct cacactcttt ccttatcttc 1860
ttcttccccc aaaccctaga gttttacagg taaactccca atctctccgc cgctccctcg 1920
ctcgattctc cttcgtttct ccgccttttt tcttataatc attacctgtt ttctccttcc 1980
ctctatctgc aggattcatc 2000

<210> SEQ ID NO 87
<211> LENGTH: 2000
<212> TYPE: DNA
<213> ORGANISM: Cucumis melo

<400> SEQUENCE: 87
gtgtagagtg agtgacggtg gccgacagtt cgtaacattt agttgttagt gagagacggt 60
gagacgtttg gtaacaaact ttgtttttag ttcaatcatt gctttgtttt ctctttcttt 120
tccttaatgt ctaatgtttt catcttcctt tctttatttc ttacccaatt tccgaatcaa 180
attttaattt ctaaaaaagt atttaaaaaa aaaaaaaaaa ttagtcgctt tattcgagaa 240
tttcataatc aacctaattt tcaaaattaa tcatcaatct ggaaactttt ttattttttt 300
tctcctttgg attatcctgt atgaaagtca acatactttg cactccttga gaatattttt 360
agtggtgttt tttttttctc ttaataaata aaaaagttta catctataat aatcaagatt 420
ccttggcagg tgtcactgtc aaaataattc ctatttgttg aagttgaaaa taatttaact 480
ataaacttta tttgaacgtc aaaaaaagaa aaaaaaaaga tatatgaatt cacccattcc 540
ataatttaac tatataactt tatttgaatg ttgaaaaaga aaaaaatgaa gacaaagcaa 600
attcacctgt tgccattacg acaaaatttc aaatgcgttt tattttgttt ttatgtccac 660
aagattctct atttgtattc tgcgaaatta aagtcacggg cttcgcacgt gtgtgattaa 720
tagtatttgt aaaagggcat gtagtcgaac aggatgggaa ttaaaggaga ttatgaatgg 780
gttgggtcgg gaaggcccat ttctataatg aattgatggg ccgtcaagga catttgtcta 840
cataaagggc atggaccatg aagttaagcc cacttcctaa acgagttcct tagtgtgtct 900
acattcatat ttaaatcatc tttaattcag aattttcacc atcatcaaat aatgtcttat 960
aaacctccca ttttatagtt taattatgga ttctaataaa aaatctctaa cttcaaagtg 1020
gataattttt tttttttttt aagttgaacc atgttcattc atttaattac atggaataaa 1080
aataacgtaa tttaggttaa aagttgagag gataagatga agttgaaaaa ttacaacaag 1140
ttaagaaggg aatatgaaga agaagaattc aaaattgaga acataataaa ggaattaggt 1200
ccaaagctgt aaagactagg agaaacgagt agagaaggga aggactcgtt tttcaaagaa 1260
aagaaaagtg tggaaaagga aaaaggttca ttaggggtgg tgaggaaatg gatggatatg 1320
gaatgatgat gatgagaaag aacagcacgg gaagtttccg agtagttgcc ttttgcatat 1380
accaacaagt tatctaataa aatgttttga ttaattacat taatttattc aattgattta 1440
tcggaaattt ccatactctt cacgtgatat gcacgtggtc ttcccatgtt ctaatatttt 1500
ttgtttttga aaatttgaat tcctactctg ttttgttatt ctgctcattt aactactcaa 1560
atattttagt ttgtagatat aactttgtaa atttttatta taacattttg taaatatttt 1620
aaattgtgcc catagattat gagtagataa atttacgaat taaaaaaagt ttaattctca 1680
cttcaattta attttttttt attattatcc aaatctattt gtcgcagtgg ggaaaacggg 1740
gacgtacggc cgattggagt ccaattagtg gatgtgaaac gtggacggta gagatgcaat 1800
atgaagctgg acatcaactt tgcgaaggaa ttgttccttc tttccctctg acgcttgtcc 1860
cgttattgct cgttttaaag caattcgagc tccgcgttgt ctcttccctc acgttttcct 1920
ttcaatccca ctgctcctcc tttcaccaat aaaacaaaaa cgcctcaaag aagaagaagc 1980
aacgaccaga aacctcaaaa 2000

<210> SEQ ID NO 88
<211> LENGTH: 2000
<212> TYPE: DNA
<213> ORGANISM: Cucumis melo

<400> SEQUENCE: 88
gttcgagcat gtgaatgtct tctgttgttt gatgttagaa ggaaagagat gggttaggga 60
gttcctgttg atgtctagta ggttcttttt tttttctctt gtgcaatgta acatagtaac 120
ttcgctgcaa agcagctctt atccttagaa tacgaaaatc ttctgttttt tgttatgttt 180
ctaactttat cccttcttga ttttaacttt tgagttaaat tccatctctc tgactttgct 240
ttgtggtatt ctgtttctgt tgtatgataa ttcttatgga actcctatgc tctctctcat 300
tgccttcttt ttcggctgtt acttaattac tttcttcact tgaaatttat agcttctctc 360

-continued

```
acaaatttga gctcattcaa gtatcaaaat tacacccatc tcataccata tttctatctc    420

tgaaggagga tttttcccct tttaaggagg gtagattgac aaagctgata gggtgagaca    480

atttaataac tcaggtcaga tgaattatac attgaagaac tctcatccag ggccagtgct    540

ttgtttataa caagatgatt aatgtgttgc tatcaaaact ttgctggttc actaaaaaaa    600

actcttggtc cttgaaagta ggcttttact agttttagct ttaatgcaca tctgtatgtc    660

aaccacgaac tccatttttc ttacttgatg catgtgcaac tttagcagct ttctaagttc    720

atatcaaagc aaatgtacct ttattcctat tgtaattcct tttctgcttt cctcttttat    780

gaattgtcaa aaatatggac aggaaagtaa gctgagcacc aacaggttgt accccttttt    840

catgtcttga aaatgaacta ccaggacaca aatcagatga tgattgttgg gagaaggaat    900

gtaagattat tcgttctgtt tgatataaga gatgtaagtt cacatgtctt acaacttttt    960

gaaatttgtg tgtcgcttat gtgcagattc ctgtatgtca ttagtggcat ttgtaagcta   1020

caattgttga atttttgtat tattatctta aaaggaaatg acaaaaggta taatcaaatc   1080

aagctgaacc taaaagaagg tacaggtttt tagtattatg catgaagaag gtttttcatg   1140

tctcttctgc catttggatt ttgtctgtga caagggacta agacactaca catgatgctg   1200

gaaactgcaa gagtgttttt accctaataa gattaaaacg tgaaaagcaa ttagattttc   1260

gtgcatatct atctttttgt gcattccacc aaactgttcg atcataactt gtcaagatct   1320

tgctttttcc tttttttat aaatatttta atatccttct aatgtgaatg gtgaaaagag    1380

atgcacaaag ataagtgata ctatagatgt atctaagtat taccccttata cctttgccac  1440

gtaagattag atacgagaag agaaaaaaat ctatgagtta gtaatagggc aacaataaac   1500

cacagaaaaa ccaattaata cctttcctca ttgtctaata atatctaaaa gaaacttctt   1560

ttcatgttaa tgaaccaaac tatgttgtgc tatagcatga gcacattatt tctacccttt   1620

agacaagtga tgagaatgga caatatttcg actgagttca ccagaatgta accaacggtt   1680

ttgcatttgt aatatgaatt tgaaagtttg agattcctta tacgaggacc ttttttcatg   1740

tatctaacaa cacgagaacc accaaaatga gaagggagtt ggtccaagcc aaaagaattt   1800

tgacctccat gaaaatccag atagtggggc atccttatct aaacaatcag aacctgaagt   1860

ccgacgtagc cttatccaca tttcaacttc aaaaacactc cctctaagat cctttcgaac   1920

caccaaaatc taagaaaatt tctcttcctc atcctcctcc gacacaaaat ctagcttcaa   1980

tttcattcct ctgtaaaaac                                                2000


<210> SEQ ID NO 89
<211> LENGTH: 2000
<212> TYPE: DNA
<213> ORGANISM: Cucumis melo

<400> SEQUENCE: 89

attcgtcttc gcattatcag taaatttatc attttaagag tttgttcttt tttaaaaaaa     60

attaatcatt tcgataaagt tggagaattc aaaaatttct ccaaataatt tataaaaact    120

ttcggttata tatcgaaaaa attaacatgg tattaaaacg atcataactc aattaacata    180

aacactccct ctcaacttta ataccaaatt tctttattaa cgcaaaattt aaaatttgtt    240

tttaaaattt tcacataaca taatagaaat acttttcttt atggcaaaaa tacaataatc    300

aaaattgatt gatggtgaca ggacaccaca caatattttt aaattttgaa tatacgaact    360

atataataag atatttatga gattcccatc ctaaagattc ctagagattt ccttgtgtac    420

aatattacac aagtatcttg gaagtccaaa gtcctgagaa aaaagctatg tataaagtaa    480
```

```
tgtgtttgtc gtaggaaatt tacttcattc gtgtcattag ctttttattg aaaaaaaaaa    540
ttaggtatat cttagtgaat ctcacttaat cgttgtcgat agttattctt ttaatatcat    600
tatatactaa aatataacaa tattgaaaag ctaaaactgt atataaaaaa aatgttacct    660
ctaaactttt atcgtttatt taaaagataa atatattctt tcaaaactta caatcaacat    720
cctacgacta tcattatagg tacaaatctt ttcatgttta cacaaaaatt agatttttaa    780
atggtgtaat gatgatatat aacgaaattt tgaatgatta ctatttgagg ttaccattgt    840
aattggtcgt gttgtttgaa atttaatttt attagaaaat ttgtcaaaag tagcaaaaat    900
gaataaacta tttaaacttt aggataaaat caagtgttat gagtttttgt ctagtttata    960
tatttttatt tttattgaaa accctttcc tatcttttca ttacttcaaa atagttttaa   1020
aatgtctatt aaggctaaag ttagtataaa taaaatttcg gaaatttttt ttcgaaaaaa   1080
attgataaat tatttatatt ttatattaaa gtcaaaattt attacgcgta gatgtttatc   1140
aaattttctt tctttttgtt gataattttc caaaatttgg ataatttttt aaaatagtaa   1200
aattattaaa aaatgaaaac aaactattta taccttaagc aagaaatact aaaaaggcaa   1260
aaattcattt acttcatgaa gcgtaaaaat taaatatttt accacttttt gttatttttt   1320
accatctcta tcaattattt gtaaaaagaa aactacaaaa ttagatgttt tttctttttt   1380
aaggtttaat caatattaaa atttcttaaa ttggcagaca agttggtgtt ggtaattacg   1440
aataaatccc gaattgacta aaaataaatt cttctccaag taaaatagac acgtggatga   1500
agaaataagt gaatcaaagg catccacagt tcaataaatg gaaaaaacta ctttctgctg   1560
actcattcat aagttttcat aaaatttcat aagaaaggcc aaagggctta tgaaagtgaa   1620
tgtcatagca gtaaatgaag cacagcgcca ttgaaagaca actcaaattg catgcaaacc   1680
cacataatta ttcaacaaac ccacatcaaa tttcccataa agatcaattc tttagggggt   1740
tcaattaccc aaaagtgagg tagttgaaaa ccattaaaca acaagaaatc aacaattttg   1800
taatttgttt gtacagaagt aagagataaa atcatcgtta accattcctt tatttcgtaa   1860
tacaacccat caaccatctc tctctctctc tctctctctc tctcggcctt tatctttctc   1920
ttcctcaatt aatttaagta ctacccaagt gagctaaaag caagttcagt ggacagtgtt   1980
gtaagaacca ctacagaaaa                                                2000
```

<210> SEQ ID NO 90
<211> LENGTH: 2000
<212> TYPE: DNA
<213> ORGANISM: Cucumis melo

<400> SEQUENCE: 90

```
aatcatcagg tctccttcca atgaaaccga cgacaacgac agtgtcggaa aagcgaggaa     60
gggatggcga aggcgaggaa ggagaaaacg aagtagaggg ttccggtaaa gcagaatgag    120
gagggagagg agttggggaa ggtgaagagg aagaggaagt gggagttgat aatggtggcg    180
gccggataag tactcggaca gaggaggaat tgggtacgtc catggatgag agaaaatttt    240
gagctttcag atgcaactga aaactgcttc actgctttca cttccgatga ccgccgaggg    300
gaaacttatt ttttccttgc cctttttgcc tcctcaatat tttcctttta ccatttcctt    360
tccaaattta tttttctatg ttttgatttt atgttttgtt atatttttga tttactttta    420
cgttattttt aaatattttt gatttaattt tgttatattt gaaaacaaga tattcattat    480
atactgtaaa tcttacttta ttattgttta aatgtcgttt tggtaattca aaattaagtt    540
```

```
gaataaacac aatattttaa atattatttt agtaaaataa tttttaggtt ggagaatggc    600

aaaagaaaca aaggattgaa agactgaacc catatttgag gatagaagtc aaagccaatg    660

tcaataagtg aaactcactt ggaccaaaat accaatttta gttttatatt tttaattgtt    720

caatcttagt ttccatactt tcaatgcata ttaaacttat agttcattat tctttttcaa    780

taaatcttaa cattttacta caaattttta aaatgtttca catactttat tttttttacat    840

gaaaatgatt gttattgttt aatccatttc aataaaatta aaatttgaaa agctaaaaat    900

tcaagaatta tcgatagaca attacaattt tgtcccatta aaattatcaa attgaagtgg    960

ctacacaatg gaatggtaaa tcctttattc ttgtattggt gtgatttgga ttgagatatg   1020

aaacattata atctaaagga acatgtttaa accgaacatc acgtattttg tctttcaaaa   1080

tttcgtaagt ttgtaggttg tttttttttt gtcattttat atagttacaa ttatttaagt   1140

cagatcggat aaattttgtt atacaccaat aggaaactaa aaattccaca aggagtatga   1200

atgacctcct acgggagcat taatgaaaat gaccaagggt taaaaaatgg taagaaaaat   1260

gttcttcact aatgacaatt cctcgtgaaa gtactaacat gttcttaaaa tgcttgcaag   1320

catatatgtc accaagaatt ctcattcatt cctctggctt ctttctctca tttctcatca   1380

acattaatat gacacacttt ttccttcttc tttttgtatg tgtttataat cttactcatt   1440

ccttattctc attgtcactc aacgattcca acaagcaata tgggaacaaa cgaaggaaga   1500

agagaaaaat acactaagaa gaagagatga acaaagttgc attagaacaa ggcgtagaat   1560

atcaaagaat tcaaaataaa aaggaaaaaa agattactag acgagagaga acgagacttg   1620

aaaagaatta gaataatttc ggtaatttta cattggacga cgaaagcaaa tgacaaaaac   1680

aatttttttt tcaaaaacat agctcaaatt tcatttagat ctttcatccc aaatggcata   1740

atttctctaa tttcacatac accacaaata taatgatgac tgattaaacg aagtaaatta   1800

caataggact aaatatataa ttaaacttct taaattgagt ttgagataaa acctttgaag   1860

ccacgagggg tcgggtcggg ggcgaaagag acatgccata taagcagttg gttgctgtaa   1920

agtggcacac gcatatctac tggaagcctc catttccaat ctcccattat cccattatca   1980

tcggcagttc cccatagcta                                               2000
```

<210> SEQ ID NO 91
<211> LENGTH: 2000
<212> TYPE: DNA
<213> ORGANISM: Cucumis melo

<400> SEQUENCE: 91

```
ctttcctgac ccaataagag atcaaatcac tgtctcctgt agcctttccc ttgccgctct     60

attattgaca tttgggccta ccttcccccc ccccccttct cccgattcat cacccttggg    120

ccttggccca ttaaaacatt acccagctcc ttactacttt ttaataacta tcacgtctat    180

tccttcgcaa gtgggtggaa gcgaatattt ataccaatta tcttttggtt gatcatgtag    240

ccaaaatttg gctcaccaaa ctcgtacaaa gacatttact tgttttccac tgtagatttt    300

aattttggaa gaagagatca gttgccaata gattgaatta atgcatttat gtacactttc    360

atacttaact tttggcaaag agttgaaagc aaggttttaa agaataaaat gaacttactt    420

tttttacaaa tctcatgatt tacgctagct caaacttagg atttctttcg tttgaaaaat    480

tggaccaaat atatatacaa tagattgaat aggagtcttt taaaatactg gcctcaaaga    540

aatagacaag ttagctaggt cgggataatt gcctcactca ttcttcacct cagagatgcc    600

tctcctccta ggcatgtttt ctaccctcat aatttaattc actcattttt gcttccttat    660
```

tgattagtaa aagtaccgat ttgccttctt ttctatgttg acaagttccc actagaaaac 720
aaattagatt atgagtttat aggaaagaat taaacacaaa tacataagtc aaattgtgaa 780
gtatcaagat aggctgttag gacagaaagt tcaaatttgg aaaacaaata tatatgttat 840
tgagttgtca tcttcttaga taatgataaa atgtgaactt ttgacacata taataaatag 900
catgttcttg ataaatagtt ttccattaaa acaataagct attattggat gatagaaact 960
cccctgggac tacaagaaaa agctaaaata gaatcagcat taaaacttcc tttaatagga 1020
tcgttatccc aaataacaac tccatctcaa aacacttcta aagaagtagt taaagaataa 1080
caatgtatat tagttatgga tgttgatgat agagaacttg gattttagct aaatttagaa 1140
tcttaaaaag ggaaggaaga aaaaaggaac aaaataaaaa gataacagta tgattactcc 1200
aacttgtgat gaacagtacc actcatggta tgtcaaacat atacatagaa tgagaacaat 1260
ttagatcaat taatttactc atttatcctt cttgctacag attgttgaga aaatagaaaa 1320
acaaattaaa gtaggaaaaa aaagaataaa tggggaatta tggaaccaaa atatcaagaa 1380
aaaggagggg caataaatta aagaggaata gtgtaggcct tctcacagtg gaagtattag 1440
cgtttaagtc agtaccttac ctttatttgt tttcatacta agttctttct ctttcatgtt 1500
aataaatttt caatcgatcc atctattcaa aatggtgtgt tttattagga agaaaggtaa 1560
tttcatacaa gaaggctaaa aaatagttga cagctgtggg atttgaaccc acgccctttc 1620
ggaccagagc ctaaatctgg cgccttagac cactcggcca aactgtcgga attgtgagtt 1680
gaataactaa gatgatcgga aatgtgacga aataaattgg gctaaagaaa agaaaagccc 1740
aaacaatgaa gaacaattcg gcccacttaa tttcacgcgc atggcacgtg taaagaaatc 1800
ccaatctgtt ctactaggtg gtggtggtgg cgaggcgaag caaagcaaag caagatcagc 1860
cttatcaaat tgtgtggtga agaatgaaga ttgtataatg tagatagaaa aagatccccc 1920
cattcccatt cccattccct tttctgaatc cgccattgtt atctctctca gacctccata 1980
acctccattt ctacccagcc 2000

<210> SEQ ID NO 92
<211> LENGTH: 2000
<212> TYPE: DNA
<213> ORGANISM: Cucumis melo

<400> SEQUENCE: 92
cttctaaaca tcctcaatgt tcgattttga tcaaggtcgt ttgcttctaa acatcctcaa 60
tgttcgattt tgatcaagag gtcgtttctc tatagtaaac atctgttaca ccttccattt 120
ctgttattca atttttccaa ttttattgag cagtttattt atttccgtaa ctactttgca 180
tcggaggcga tcatcagttt ttaaggtaca aaactagatt atatataatt atgaagcaca 240
gcaaagtata aaattttgaa gatgaaattg attggacctt gtgaacagaa ctctaaagag 300
aaaatgcatc agatagtctg gatcgttaga atttgaaatt taaatttcta tcttccacta 360
aagatatctc tgttttgcaa actaatgttc ctcattctaa acagagaatg ccagtggtat 420
tttgttcgtt ttttgcgaat atgattaaat tacccatttt atttgcatat tttatttatt 480
ctcatatcag ctccaaaaga atatgatccc tttttcctcg ataagaaaaa atatttaata 540
ctttcaactt catgcattgt gagactgccc atttgttttg tttaaagtag caccaacttc 600
tcaattgtat aagtttgtga tttttttct atctaaattg acttgaatta tttttagata 660
taattaaatt aattgctttt aagagcaagt taaattaagg tttcgtaagg atatggatta 720

-continued

```
aatttaatta agaattggct tcttgctcta aatacaaatt agagtgagat ttgaaatagg    780

aggaaaaaga gagtatggtt acaaaggata tgaaagatca aatttcaaac ctttgccaac    840

tgaggctttt cagaactctt aaaccatcac agttttttct ttgcccaaat gaaatcaaac    900

attaagaaac agtgataacg aaaacgaatt atccctatgc caaccgtgac agatgatagg    960

caagaaaccc acgattagtc tctcatccgg attgttccaa caaatgaaaa agcgttttct   1020

gagactacac aaacaacaaa cacagagtta gatagttcaa gcaaatgatt ctagcagatt   1080

agaggataag gtttcttatt aaatgtttga atacattcta accaaaaacc aaaaacccta   1140

tttgcaaatc agcttatgta aaccaaaaac atatttacta agaattcaga atttcgctgc   1200

ttgaaatttg aaggatacca tataaaacaa taatagattc ccccaatcgt gttcagtagc   1260

tcaatatagg caccgtgcaa aaggttgttt gttgtaagat taatgaacaa acacccgtgt   1320

ctgattttaa tgccaattca aactctaatt caaaaaccct acaaagacct aattgcagat   1380

aatgggatta gaaattttaa aaaatgtcga ccgggcattg tatcttaaaa ctattaagtt   1440

tcaaggatct tcctccggta acaaaatatc ggctccatgc ggcagacgga tcgccattaa   1500

aacggcgcct gctgctgact cgatgataga gccaattcag aataaccaac ccatttcatc   1560

gaaattttta aagagagaga aaataaacga ttcaagatat caaacgcatt tcgcttctat   1620

tgaaggagaa gacaatgaaa atcaaaacaa atcggaaatt aaagttaaag aagaaggaga   1680

taatctcagg acggacggaa gataattcta aaggtgcgat tcggttgaaa tttatagagg   1740

atttgtgaag gaaccctaaa ttctgattgt gaattttatc ggaaagaccg gagaggaagc   1800

ccattgtgtg aggcccaaag taactgatct gggccttttt tagtttcagc ccaaacggaa   1860

gcgacacgtc gtttctatgt agagccaaga gcgtgccacg tcaacagacg acgtcggtta   1920

gtaggaataa taccgatttg tggatttaag aattgttcat ttcggtttgt atcggaagtt   1980

ctgaatcttg atccgtggca                                               2000


<210> SEQ ID NO 93
<211> LENGTH: 2000
<212> TYPE: DNA
<213> ORGANISM: Cucumis melo
<220> FEATURE:
<221> NAME/KEY: misc_feature
<222> LOCATION: (1)..(2000)
<223> OTHER INFORMATION: n=g, a, t or c.
<220> FEATURE:
<221> NAME/KEY: unsure
<222> LOCATION: (1)..(2000)
<223> OTHER INFORMATION: unsure at all n locations

<400> SEQUENCE: 93

aagtagaaat tcagcgaaaa atgcagatgg tttcatagac aataaaaagc aggaacaagc     60

gcagagaatg gttaatcctc cagaaaatgt gataaaaggc gccaccaaga ccagtaatcc    120

ctttaccaat cacagaatac tcaacaagaa aagcgattcc agcaaaaacg aagatgaaac    180

tctcacttac aagaagaggg tcgacatttt cccgcaaaac gatgagaatg gcgagtgccc    240

agaagaagaa aatggccagt gattgctggg agaatgcgaa tctgtaagtg gggtttccgg    300

aaaaagcgag aaaaaggaaa atttcagaga aggcgacgat ggggaggagg aggatgaggg    360

aatataaatc gaaatttttc catttcggtt ctgataaata ccaggttttt gatcggtaaa    420

gagatgggtt gttgaggtaa atggaggaag aacagaggag gcgacgaagg ccaatgggga    480

tgaggaaaag ggaggcggag agatgcgttg ctagtgatgc cattgaaagg gcttttgaat    540

ttgttgaagc attcagattc ttctctgtct atggttccgt agattgttct ccaattcttc    600
```

```
cattgggaag acggagttcg gtggctgaac gttgacccta acaagtttga tcacgttgat    660
ccgttcaatg ttaaacagct cgatgatttt cgtctaaaaa agaagtgatt ttttttttaa    720
ccttttattt attgaacaaa aaaaagatct gtttatacca tagtttacgt tcttccacat    780
gagaagtttt ataatagttt atagaatcta tccaaattgt gttttattgg gtttcgattt    840
tatagaaatg tcatatcaaa aaaaaattta aaaatgataa aaatcattat aattatttta    900
tgaaattttt actgtgactt aattagatta taaaccgacc attctttaat cattattttg    960
gatgtctatc gtatgtgtat ttatagatgt caaacatgag agcatagatt taaaaaacaa   1020
atagcttaaa caaacaacaa taacttttta tctttcagaa aagnnnnnnn nnnnnnnnnn   1080
nnnnnnnnnn nnnnaagaaa agaaaagaaa agaagtcttg aaaaaagtat taaatttcac   1140
aataaatttt ttaaaataaa atacattaaa tggggatgag gaagaaacaa ctaagagtcc   1200
aagaagagaa ataaaaaatg agaggtggtg ttttttttgg tatgttaatc aaattatggt   1260
ctccacatac aagaaatgaa gccacgttaa tgacccaaca acactaacac atcaattctt   1320
aaaattcaat tccttctttt cttcccttcc aaaattatgg gtcctccaac ttacaaatta   1380
acaattgact ttagctaact atgtttttta aatataaaaa acgaatacaa gtcagtttaa   1440
taggacttga agattgtata aaccaatatt agacaatcaa aacaatcaat tttaggttca   1500
ttcccaacga tacatcaatt tggattagat taatttttca ttatggtttg atagagtgga   1560
tttagtttta gtggaatgca gggagggaaa agtaatttga aagaaaagga atgaggttgg   1620
tcaattccga agcctaggta tccaaataca agaatccata tcaaatttat gaacacctag   1680
aaaataatag taattttaat aataaaatgg agaaatgggg tccggtcgtc ctcttcctcg   1740
cggcggagat gaagccaccg cgataagaga aagagaccct tttcaataca attcaacaat   1800
cacatgaatt attccaattc acatctctgc ttttgaaact aaactaaacg ccaaaaaccc   1860
ttctgtggct cataagtttc ctctctcaaa tctccgattt ccctcaccca catcccacat   1920
ttcgcatcca aataaaaaag ggacacggac aacaagaagg agtttttaat tcagtagtgc   1980
ctctggaaga agctgtttca                                               2000
```

<210> SEQ ID NO 94
<211> LENGTH: 2000
<212> TYPE: DNA
<213> ORGANISM: Cucumis melo

<400> SEQUENCE: 94

```
ttagtgaaag ttcaagatgt aattcactct ctttaacaag gttgtttctt tgcttcacta     60
cgcatcaatt caaatattta gatattgatg tttaagctta atctcctatc ttagctcaga    120
acaaaattgt caaaatctca ttcttatttg tctacctggt aactttgctg ctatagttat    180
ttgtgggaga ttgtagcaaa tgactgtaga tcgaaaccat ttcagcatca atttcgaccc    240
actcttctcg tcaacaactt gatcggcagc ttcgacattc ttcaagcgcc agcttctatt    300
ggatctttag ctcaaccaca tcttcgtctt tgaattgcat gtgagctgtt gggctccttt    360
cttttgtgct tatcagttgg gagattatta ctataaatac aaagcctcac gggtatttta    420
agacacaaca aaaaattaaa agtctctcct ctgaatcacc acttccattt tctataaatt    480
ttgttctgag caacttttgt ttgtttctat ttcttattct gaagagtgca tgtttgagta    540
tggggagtaa tgttaacctt gaggaacaat tggcaacacg attggcacct cggtcaatca    600
tagttgcttt taggacagtg gttcgtcaca acacaacaat ttattttaag ttcaacattc    660
```

```
tcattctttt cttctacagt attcaaagtt atagtgttta tttctcttat tgttccttta    720

gttaacaatc taccctttaa ctaaagtaac aacttaaaag taaaatggat tattctactt    780

tttcttaatt gttactttta aaggtttaag aactgaattg ttactccgat gaaagtctaa    840

agaccaatag tggtttctat ccttaaaaaa ctattcaatg aaatttatgc taaaaaaata    900

atcactaatt catcgtgagc ttccaaacca cttgaaatta gctcaatgag attgtaactt    960

ggtcgggatc tcatcaaagg gatggtcttg gctagattct taaagatcat tttagaaagt   1020

agatcatgaa aggttgcaaa gatgctagaa acaactgggt tgtcgacgtt ttggaagcta   1080

aagcggtgat gattgacgta atagatatca ctaaacattg gcacaatcat acttggaaat   1140

agcttctata gatatattcc attttgtaag gtcttaaaga caagaacaaa gctacctata   1200

agcttgtatc ttagtttcct cttgcgatct tcttgtcgag agatgacttt ccggttttgg   1260

gttgtgtctt tgtttgtttt tctttataaa aaagtcaaaa caaaataaat ttggattaat   1320

tatcctcgta ctgaaatcaa ttggtttgga actaagtaac aataggatac atgcggcgca   1380

ccggatcatg ccattctccc tctttaaata tcaaagcaga tccctaaacc ctaacaaaga   1440

tccaaatatc aaacctcccc tcttactaca cgctccggca cctccaaaac tccatctcga   1500

ggtttgtcac ttttatgttc ttgtttttct ttatttagaa tatgatgatg attagaccga   1560

tggctatttt ctttaaatgc ctttactcct ctgactagag tggtctgtac tctgaatcag   1620

agggttcatt tcgaatcttc gaacgttgta tttcgcttca aaagctagac ttttcccaat   1680

ttacttgaac ttattgtaat tttagtgcta gcccattgat cttggtctcc aatgccactc   1740

tctgttccga ataactgccg attattgagg ggtttttttt ggacttcatg atttcgagtt   1800

gttgtaaaat gattggggat tcatttaaat atgaaatata tccatcgttt atctcaaaag   1860

tatatatctt aagataaacc atgaacaaga agtttccgat ctaattccca tgggttgtct   1920

aacgagttat tctcaacaga ttacgaactg ataactagac gtttgaattt tggcacagag   1980

agaaatcgca tcactttgaa                                               2000


<210> SEQ ID NO 95
<211> LENGTH: 2000
<212> TYPE: DNA
<213> ORGANISM: Cucumis melo

<400> SEQUENCE: 95

taaatgggaa attggaaact aacttgaaac gaccacaaac catggggact taaaaaagtg     60

ataatctaac aaaggcttta cactcctttt tcataataaa gaacaaaaag aaagctcaag    120

agcaatcaag tttatcataa ctaattaaag tcaaacacta catttctcaa aagaatgata    180

taaaatgacc aaacatctag ctgctttaca gtgtaatgaa cacccaccat taaaggaacc    240

aaggcaactg aataaattgg taacttaatt gccctccaaa tcagagtccc cataccaaca    300

tcctcttccc cattctcttg gggcatcgaa tcaacctcca tcgctttaca ttccgataac    360

aaacctctaa aacggacatt tctgcacaac cccaattgcg ttctacgact cccgcaggca    420

aatttatgag catcagtcga caaactcgat gaatttaaac gacccagatg aaagctgtga    480

tagtagaaga gtcaagaaga taaatggggc taaacgataa ggttttgaaa gaagatgtag    540

ttgccattgt gaagtggtac ttgccttgga gtaatggtgg tgaaggagag gtggtcgttg    600

agtttgttct ttagggcgcc gagttgggtg ggtatgcaga ctatggaggc cattggcatc    660

acatagctga agatgaaact gcagagtgaa gctgcttgtt gaagcagagg atggattaat    720

taaagtggga cgattttagt tgtgtcttat cttcttcaac tttatgtttc ctcttggttt    780
```

```
gacacggttt taccattatc gctaccattt taagtaacaa tagtagtgat gaatgggtaa    840
aatataaatc ttattccatt gttagaacct tcgacaagtt ttccattatg tgtggctgtg    900
tttgacccac caactcgagt agagttgaat ttgtttggtc tactatattt acaaactaat    960
attaaataac aaaactctat taatttcatc ggtgttcact gttgaaatat atacatttag   1020
tatgaatctt tatctatttc tctcttaccc ttcctctaac atttctagtg cctccatcat   1080
caattgtcat caacgacgaa atgtgacgat aactatagtc aacgagtatt tccaccttac   1140
tttgacaata ttcattgcca caatatgctc ttgacgacct ctagcactcc acgtatgata   1200
aagactacat ttgatgacca attaaggaaa tcgtatttga caccacattc caatggctat   1260
ctctagtgat caatttcgac tatcacttgt ggttatcgac tttcaaccat ttctaacgac   1320
taacttgacg accatcttaa tcaatcatat actagaaaaa caaaaaaaaa aataactcat   1380
caaatggaaa catttttaaa tgcaattttg aaactaccac ttctctgtat ttaatagtaa   1440
tttgacatta acaaaaacac ttttaagtac ataaaaaacc aaacaaactt gtatataaaa   1500
cacttttgaa aaaaacggat gtaaccaaac acacaagtat ttttctttta gattatgttt   1560
taaaagatag aaataaaaat attaaaagaa aagcaccttt ttacaaacat gtaaatccaa   1620
atcaaacatg ctatttttta atactaaaag aaatagaaaa aacatgttaa acatatccat   1680
tagcaaaata aagtgaaatt ccaagaatta gaaagatggt ttgaaaattg attttataaa   1740
gcgaagaaaa accttttccc ccaaaagaat aatattctta ttttggaaaa aacagaaaac   1800
aaaaaatgtg acaaaaagtt acattcctgc ggatttgacc ctctggtggc tgcattcgaa   1860
tctttgattt cgaataactg aagtaaacat taaccaaagt ccgtcgaaat cttccttttt   1920
ttcatttggg attccctcaa tcttcatcac caccatcacc atcctccact ttcactctgt   1980
ttccctccaa acatcaaaaa                                               2000
```

<210> SEQ ID NO 96
<211> LENGTH: 1373
<212> TYPE: DNA
<213> ORGANISM: Cucumis melo

<400> SEQUENCE: 96

```
tttaaatgtt actttgatat gatctatgtt tagatttgaa gtatttttct catcattaaa     60
aagaactaca cgatcgtatt catttagaag aagaattgta cgtacgcgtg tagccgatta    120
atcacgtgtt gagtgaaaca ttttttatat ttttgctaat agacctatat attgttttca    180
tttttaaaat tgatatgtaa atattttggt ttgttatata tatatatttt ttttggaaaa    240
aaaactcctt tatttatttg tcgttaagta ttaatttctt tttttagtac ttttattacc    300
attgtggcct tgttttgctc ctcaatttag atatttatta tttgtggttt atttatttct    360
tttgttttcg ggacaagtga tgtttgggat attaaagtaa aggaaaaaaa agagagatat    420
tttgattgtc aaaatgtcag aaatatctaa acccggagct tctgccacgt aggcatcact    480
ttcattacct tttataaaaa gtacgaattg aaccttcatg acactgctcc cctgctccct    540
tatataaaac ccaatcctct tccatgctca gtattatctt cactctttgc tcgaaccgcg    600
tgtttaacag ataagattca actcacaagc attcatcgct aggttcttcc aaacaaaaac    660
cctacatctt ttccatttcg cctccttaat tctctcatat ttctgtatct taatccattc    720
taaaactaca ttttaatgca ctgccttgtg ttctgtattc cactatctgt tatcgtttta    780
ttgcgttttc tttgatcaga tcgctttgtt gttgcatgaa ctgctgagtt cgtttgatga    840
```

```
ttttgtttgc gcttcagttt tcatcgtttg ccgtccagat tgtttgattg gcgagagtga    900

agtgaaaatt ctgtatgata ttggagcgtt tcgtgtaaaa tctgtcttgt ttttctatta    960

tctgtatttt agtgatttgt ttttcgttga cgattttgta tgacgtaaag atattgtcca   1020

ttttaaagga ttttcttcca ctggttacta gagatcttag attgagcttt cattcggctg   1080

tattttgatg atgcttttg tgttttttt tcctttcttt ctttagcttt tgcggactca   1140

tggagtcttt ttctgaacga catcttaaga tgtttaagat gcttatttgc tttttctat   1200

ttttggtatg acggggtcga gtctgatttt gaacgacatg ttaatattta tgatattttt   1260

gaagctagtt gtgcttgatt ctgaaaattg cttttgatac acgagaaact tttttgtttt   1320

cttcaatggt aggattttga ccattattat tattattttt taaaagatca aat          1373
```

<210> SEQ ID NO 97
<211> LENGTH: 2000
<212> TYPE: DNA
<213> ORGANISM: Cucumis melo

<400> SEQUENCE: 97

```
ccgaattcgc tattgggctg cataacttta tcacttgctg ggagactgca atttgtttgt     60

ttagtgctat gtagttttca agtttactag gctagtatgt ttgtattgcc tgagagtgtg    120

catcatgagg tggataaaat tcttaggtct tatttttgga ggggtaagga ggatggtaga    180

gggggtgtta aggtggcatg agcggaggtg tgtcttcctt ttgaggaggg caggcttgcc    240

atccatgatg ggccttcttg gaaatattgc tatgtctatg aagattcttt ggtcgctatt    300

ggcgaattct ggttctcttt ggtggcttag gtggaggctt acattcttaa ggggaggtcg    360

ttatggacga ttgatagtga ggttggttga tattgtgtct tcgggctatc ttgtgtaagt    420

gggatagttt gaaagcactt gttcctatgg aggtggggga tgggagaagg tgtagagttt    480

ggcttgatac gtagttgcat ggcggtccta tccttgatta ggttggggag agggtgcttt    540

atgacgcgac gagtcggagt gaggcttgac tttctaattt tcttggtcat gatgaggagt    600

ggaggtggcc acgagtttct ttggagttgg ttaacttatg ggatacggtt cagactgttt    660

gttcgtgtct tagtgttagt gataggtgag tatgaattcc tgacagtcat ggtggttttt    720

cgaccgcgaa tgtgtgggat actctctgtc ctcgaagtag tcaggttcct tggactggtt    780

tattgtgggg tagggggaa ttgttttcca aaacatttct ttttgagttt gacttgccat    840

caaagatagg ttgttctttt tgtagttctt tcttttggtg ctttttgttt ctatggatcc    900

tgtgagggtt ttctgctctc gtgccttaaa ctcaggctgt gaggtcctcc ttgttatggt    960

ataataatat taccttttca aacaaaaaaa aaacaaattg attcagaatg atttttttt   1020

ctttcttttg tatttattct atgtttcctt attcaggcta ctagatttga atatgttatt   1080

tgttacttcc ttttctaaca aaattagtta taattaattt tatttggttt ctttaaaaag   1140

tgtggggttg aagcttcttg cagaatatag gatcacaaat gcctaataca cttctttcta   1200

cttctttgtt ttgcagcagg gtatgaaaaa acaaattaat atgtattttt tatacttctt   1260

tctcgtatgc attattcttc ttttgtttct gttggctttg cattgtagcc gttttcttgt   1320

tcttgtctca ttttttctct accttttgtt tcttctctaa attcctttta tgttcatttt   1380

tcataatgcg gatttttttca aaaaagaaaa ttatagttgt tagttgtgtt tgatgagaaa  1440

caagaaaaga gagtgaaaag agaaaagagg tagaagagaa aagaaaagaa gaatctgagt   1500

agaggaaaaa aattgaacaa aaaagttgga attgtgttgg atgaagtgag agcaagaact   1560

aaattttgtt tgagcgtcaa gcccccaccc cacacgtttc taagaacaag atggtaattt   1620
```

taaatacaac taatataagc aaaatacaat ttctcgagga aataggaaac ttcattccag 1680
gcttcaaagg aaaaaagaaa aaaaaagaaa aagaaagtaa aacgattaga acgtgaattg 1740
cacgtcacta gacaaaacca tcttttggta gagaaaaaca cgtgattaca aaaaacaaac 1800
gaaacccaaa taaatatata tagaaaaaaa ataaataaaa gaaatagaaa aatctaaaaa 1860
aattgggtta gcgggcaaac aagaaaccct tgtttcgatc ccccaaaacc cccccaccct 1920
ttctcccatc ttctttcttc ttcttccctt ccccattttt gaagaaccaa ccagcacctc 1980
tgaccaacat ttgcttaccc 2000

<210> SEQ ID NO 98
<211> LENGTH: 2000
<212> TYPE: DNA
<213> ORGANISM: Cucumis melo

<400> SEQUENCE: 98
tagtttggtt cataggttat agtttccaaa tttgttaggc tatcattaat caaacacaat 60
acttctcttg taggatggct gccccctata gtactttttt aacttaggag aaggatataa 120
taattatatt ccttttagaa aatataataa taattgtgta gtgctttgat ataccttaaa 180
ttagctactc acgtttttag gaggaagctt ccgttgcttt tcatggtgtt atgatctttt 240
ttattttata aaggactgaa ctttaaaatt tctctttcat ctattttgga ttggattcca 300
tctattttat acgggaagtg aactctaaga tttctcttca cctattgtga atcggactcc 360
gtcatgtagg tcaagactac gacagataag aatagacttc cacgaaagaa agtggtcaat 420
cgagatggct atatttggct ctttcagctc aatttcttct tttttccttg catgttcttc 480
cgttggtaca tttcttgcac tttttttgtt ctcacatgac taatgtattc caagtttatc 540
attggcattg tgcctctttt aggcttgtaa actctcgatc caaaattatc taggacatat 600
gtttcctagt gaagaaatac tagtatattc cttatgtcaa tatgtcaaaa ttttcaattt 660
cttaaccttt gagtaaatca atattatatt tttatggagg ttatttataa ttggaaaaaa 720
gttacaccca tctcaaccct aattaacacc aaatgaaatt gtaccatgcg gcacaatatt 780
tttttgtgag ttttttgcaa agagaaacaa agtagcagac aaagaacaaa cattccccca 840
aaaacagcag agaataccta agagagaatg ctctctcgta aaaaataata cccaagaatc 900
ttcccaaaaa gagggagtaa aagagtccaa aacaaacgaa ccgaagattg acaagaaggg 960
cactctcgcc ctccactgcg ccgctaaatt gtaagaagca tattttcttg agttaacata 1020
ggaataggtg taactcaaga gaaatgtaat tcgtagaatt gaactttgta tattaattta 1080
tatggtgttg tagatacaat ctttagtatt tactcatttg gtgctttctc tcaaatacaa 1140
tttaaactta gaacttttttg atcttcgatt ttcaggaagt tggagttgca aatcaattcg 1200
agtttcaatc tctggaattt aataaaagtt tgatcttcca agttttcaat ctttcagaag 1260
acgatgatct tgatatggat aaaaaattgc acatcatgag agctttttga agtttaaatc 1320
ttcaattctc tagagcttaa attcttcctt aaaccaaaga tcaccaaatg aatgacaaat 1380
gtctctattt atcgaaaaat ttcatagact tttagatggg cttaggcaca ttacttgttg 1440
ggcttggact tgggcttatt tgcttggcgg gctcatgctc gagcccatta tttctttggc 1500
ctatttttca tgaggggctt gaacttggtt gtatacgaaa aaacttgact acctaaatct 1560
aatcaaatta taatcatcac aattttgacg tgttacgatt taattggcca aaaattcttg 1620
ttcaacactt gtctctaatc attttcctat ataatttaac taaaatattt aactttaagt 1680
aacttaaaag atatagttta attcgaatca aaatacaaat acaatttcgt ctatctattc 1740
ccatcataaa tgttgattga gattcatatt ataaacttct ttcaggaaaa gaaagaggaa 1800
aattcaccta aaccacgttt tcctattttg gtaagaatcc ccaaaccata aatcattcca 1860
aaattatttt ttttagaaaa aagaaattca catggcgtaa aatttcagcc ccgtgagata 1920
ttttcgaacc cccagataca atctacaccg tgaaaacaaa atcggacggt ggagattgct 1980
ataatgtccg tttagaggca 2000

<210> SEQ ID NO 99
<211> LENGTH: 2000
<212> TYPE: DNA
<213> ORGANISM: Cucumis melo

<400> SEQUENCE: 99
acactttgaa agtccatttg agagattagg gtaaatttga gtgaggatgg cgtgatgaca 60
acgataaaag tgaaaaatgt cagatccaag agagactcaa aagtgaatga cgtgaagaca 120
atcggaatcg aaattgaaaa atcagatttt aaattatctt aaaccacata ttaattaaat 180
ttcgattcca gtttcaattt ggtttgctgt gataaaacta aattcttaat tgtacctaat 240
tttctattaa ataaataggt aaaaaaagta tagtaaaaat attggcgtcg cccggactcg 300
aaccggagac cttcagtgtg ttagactgac gtgataacca actacaccac gacaccgttt 360
tgttacatga gtaaaatgtt tcctatttgt ctaatattat tattactact actacttctt 420
cttcttcttc gagaaaaacc aatttctatg ggtttaaatt tccaaattga tgttgagtgt 480
atcaataata tagcactcac atgctactta acaaaaatca attctttctt tttagttaaa 540
accttttctt ttatatttag tgaaaggatt aagctatgtt ctacgttaaa ttgttataaa 600
caaaatttga ttgttactta tcgagattaa tttatttaag tggatatgtt ggaatatgtt 660
actaaaatga taattgatag tgatacgtcg agtttatgct aaacacattt tgatatggtt 720
ttctttttca atataataat ttgacattaa ttacattttt ttttcatata ctctcaagaa 780
tgtttatttt tattatgtac ttttaaaaat taagattttt tatggtttta tccataaatt 840
tgtttcattt tttaatcgaa attttagtat tagactttag ttgttaaaga tcctaaaata 900
tagtcattat attttattaa agagtctccg tcacgtgtat aaattaaaat agtcttaacc 960
gttaaaagta tagtgaacaa aatttctaac aagaattgga tcggagtaga agggtgattg 1020
attcaacatg atccttgtgc cattattgtt gttactcaag ggacgttcat caatagataa 1080
cttgaaatca aaatggcata aactattgct cagttgaaag gttgtttgtt gattgaagag 1140
ttaggtttgg atatttgggt ggaagccaat ggccttgtcg tggttaataa ggtgctttca 1200
tttaattttg cactctctcc tcatggggtt tattacacta aagtggttca tttaattgag 1260
agcatattgg acgaaaataa acaattaaga ctaaggacga aagtaatatt taaacattat 1320
tttaagaaaa agtcatttta attcctaagt tctttttag tataattttc atttgtttgc 1380
tatattttaa aaggttacgc ttttatcaat aattctttag tttagttttc atttgaccta 1440
taaattttaa aatatcacct ttttcctttt atattttggg tttaattttc cttccttgca 1500
ttttcatatt ttacactaat acctttaaac aactaaggct tactcctagt ctttgaaggt 1560
taaacgttga gtttcaacta attgatttaa tcatctaaaa ttttgagatt tttttaaaag 1620
caatgattag gtgcagtctt ctgcttccca tttatttatc acgtaaaaaa attataaaaa 1680
aatcattttt taaaattgtt acctgacaat tttttgagtg caactcgaac tgcctatcgt 1740
tgtaacccga ctgtacctaa atattttcaa tattttaaaa cctttgatta aatgataaac 1800

-continued

```
aaattaaaac taagggggaa attacatttt ccttaattta aaaacaattt tgttgataag   1860

atggggcctg gcccatgagg ttttgggctg ggccttttcg aatcgtctat ttataatgag   1920

caaacgagtc tgagcttcga agaaatcccc ttttttcac ttgcgaaaga gacgaacaaa   1980

cgcaaaacag tcgaaggaag                                                2000
```

<210> SEQ ID NO 100
<211> LENGTH: 2000
<212> TYPE: DNA
<213> ORGANISM: Cucumis melo

<400> SEQUENCE: 100

```
tgttggcaat gatttctttc agaaactttt gccaccttaa tgcttgcgta gtttcaaact     60

aaatgctgat tgctgtcagt aactgattaa attttgattt aagtatagta gctgccttat    120

tgtgttaaca agtttctcca tcatttttg cattgacttg atgatttgac ttcttttggg    180

tcatatcttt gattctttcc atgtttgaaa gttctaattt agatgttggt ttgtatagcc    240

attgagaagt ttaattggca aaacatttta tagcgacctt gacatagaag aagatgatat    300

cttcgtttct gatggtgcaa aatgtgacat aacacgactt caggtatgat ttgttttagt    360

ttggaacatc tttcatccat gtaatatttt tattttcctc attttttttg aactttaatg    420

ttggttacta accttagtta aatatgtaag atagcctggt aatcgtatct ttcatcttgt    480

tactatttaa cttctcttcc caattttggc agcttgtttt tggatccaac gtgtcgatgg    540

cagtgcagga cccatcatac ccggtgattt tctcttctca ttaatgaaaa ctttcgatga    600

ttaattggta cactaataat attttgcctg tccacctata tatcagacat ttacttaaat    660

gatcatttga aaaatatcaa gctcttgggc aatcattttg tgtgtctcat ctttactgtt    720

gtgcttgaat gagtgaccac gatggataga ctttttgaga aagatccctt tgttaatggg    780

tcttttttgt tgtattcttt gtcggaaagc ggaggaaacc cagatcatct tatttaggag    840

tcttagtttg tgaggtctat gtggaatttt ctttcaaaag ttttgatgtt gtacttgctt    900

gctagaggga tgttcatttg atgattagag agtttctcct ctagttgcct ttcaaagaga    960

aatgacaact attgtgggtt ggcctagtac taaaatagga gacatagtct caataactaa   1020

ctaagaagtc atgggttcta tccatggtgg ccacctacct aggaattaat tttctatgag   1080

tttctttgac atccaaatgt agtagggtta gacgggttgt cccgtgagat tagtttaggt   1140

gagtgtaagt tggtttggac actcatggat ataataaaag agaaatgttg ttttctattt   1200

tgtggtttgt gggtgtgtca tgtgtgcttt gttgtggaat ctttaaggaa agaggaacca   1260

caaaccctat tgaggtttgg ttcttggtga agagtgtgag gtttcatgtt ctgggcttcg   1320

gtttcaaaga ctatttgtaa ttattcactc tcacttagtt gcaaacactt tcttttgagg   1380

gtttccgtgg gcttggtttt ctgtatgctg ttgtgttttt ttcacttttt ccctcaatgg   1440

atgcaattct ttattcaaaa gaaaatcttt actcttgaat ttgcatatgc accctttgat   1500

aacttttggt aggttagtca cttcagatca aaccacaaat aataatatat tttgttttcg   1560

caaaacttag aaaatatatt tttgatatca gtctgttggt ccattctccc acttattggt   1620

ttatgttttt ttggtagtta tgaagtaaca tccaaaggcc tgtattgttt aggctgtaga   1680

actttataca aacctctgct aagtcaattc ctaatcaaga atttgtggaa ctgtaggctt   1740

atgtggactc gagtgtcatc ttggggcaga ctggacagta ccagaaggat gttgagaaat   1800

atggcaatat tgaatacatg aggtgtacac cagaaaatgg attttttccc gatctatcta   1860
```

aggttcctcg aacagatatc atatttttct gttcaccaaa caatcctact ggctcatctg 1920
caactaggga acagttgacc caacttgtgc agtttgacta aaagaatgga tcaattatag 1980
tctatgattc agcatatgca 2000

<210> SEQ ID NO 101
<211> LENGTH: 1078
<212> TYPE: DNA
<213> ORGANISM: Cucumis melo
<220> FEATURE:
<221> NAME/KEY: unsure
<222> LOCATION: (1)..(1078)
<223> OTHER INFORMATION: unsure at all n locations

<400> SEQUENCE: 101
ataatattaa tttcatttaa aaataacttg aattttttcc tcctatattt atcatgcatt 60
tttacaaatc cacgttcgaa aatcccatta atcataggag ttaaattgtc atcacttgat 120
ttgaatattt attttttttt aaaattaata aataaataat gtcacgaaaa tgataaaaat 180
gcaaagtatc gaatttaaaa attaaacaga acaaaattta aaaattaaat gataaaaata 240
aatataaaat ataggtggat gttaaagata ataatttaaa tctttatcta tcatcaaatg 300
acgatcctcc aatggaaaaa gaaaaaaaaa actttattct ttacctcaaa ctcctcgcta 360
aaaagtaaca atggtaagat aaaactttat tttaaattat tcttccactt gcaagcaaag 420
taaatagtta tttgattctt acacaaaaga gaatttttac tttttacttt tcattagtta 480
tatataactt tataatacat ttccctctca tggaatttaa aactaccatt tgagcaaaat 540
attttaaact aaagaaaaat atgaaactta aaactatgtg acagggatga taatgacgtt 600
tactccaaat tttcatttta aattaacgta cgttatttta taagtatatg tcaaaatttt 660
aaggatctat tttattagac aattcaaatt atatgttgtg ctttcatatt ttgttaaatt 720
caataaatat gcctttggtt gattatacta tttttctaat taactctgga gacatttcaa 780
aagatttttt atttatttat ttaagaaaat atattaatat ggtcaataga tatgtattat 840
gcacatgata taaaaannnn nnnnnnngta ataatattat tacataatta aattctttca 900
tcttcctaac agagagagag gatcgtcctc tcagcgacgc tgatcccaac tgttccagta 960
ccaaatctct gtgtcccaat ccaacagatc cttcttttaa gctaaaccca ccattttttt 1020
ttttttctga aacccatttc ttatctctcg ccggaccttc agattttacc tcaaaacc 1078

<210> SEQ ID NO 102
<211> LENGTH: 2000
<212> TYPE: DNA
<213> ORGANISM: Cucumis melo
<220> FEATURE:
<221> NAME/KEY: misc_feature
<222> LOCATION: (1)..(2000)
<223> OTHER INFORMATION: n=g, a, t or c.
<220> FEATURE:
<221> NAME/KEY: unsure
<222> LOCATION: (1)..(2000)
<223> OTHER INFORMATION: unsure at all n locations

<400> SEQUENCE: 102
cactatctat catagataaa taagtgatag atctaaacga tcatttacca aagtctcaaa 60
gatcatgtac caatatctaa acgagtttgg tacaagattg tataccaaaa tcatttgatt 120
tgatacaaga tcgtgtacca aaattgttta gatttgatac aatatcatgt acaagatagt 180
gtatcaatat ttaaacaatt aatcgtctat cctagataaa caaagataaa ccactaggaa 240
atcgcacgaa gagaaataga ggaagtgaag aaaaaaatta ctcatataaa ttgatgaaaa 300

```
atgttatcct tctctaatat ggttttaatt tttgcactag gaaatcacac attaatgatt    360

ataatacaaa gtcctacaaa gagatctgaa ttgattcatt tgtgaaactt tacaatttta    420

atcgatacaa ttattaactt aagagtgtaa ttgatttaag ctacaaggtt taagcaaaaa    480

actaaaacat aaacagaagt caaacttttc ttaatttttg agtttagtga gctacttatt    540

tattgggtag ctttagaaaa gtcaaacttg aattgtcatt tttaagtatg atcaaactta    600

atttaaccca aacttctgtt gtaggtgaat tagcagctag tttgtatata ttgactgatt    660

tacaaattct tattttaatt aattttaacc atccattaaa atggagagtt atagttattc    720

aaggatttta actactctca aaatcatcaa gatcacttgc atatttagta taagttcaag    780

gacttaagtc cttattgata ttttcatcat catctggaaa actaatcaaa taatcatgtt    840

gatgcaactt agatgattaa gattaaagct aagacttttg aaatgataaa gaatataaat    900

aaaaaaggaa gtttttttaaa aatataacaa ataggtaaaa tatttacatt atataaaaca    960

attctagaaa cgaaaaaaac ccacggtctc acaatgaaaa atacaaaaaa taccctagtc   1020

aatagcaatt aatcagccag cttgcgcgaa gaatattctt ttaaacgact gtgtactaca   1080

atttcaacga ataatccagt attgtttagg tcatgacacg atcatgtagt tctattttaa   1140

cgatgggaaa aaaggttttg aatttaaatg atcgtattga tcatgaaaaa caactatgtt   1200

gattacgata agcgatcatg tagtccaatg taaatgaatt tcaagtctaa cgatcatgtt   1260

gaccatgcta aacgattgtg ttagctatgg taagcaattg tgtagatcat gtcaacacga   1320

tcgtttagat cattttaaac gatgtgaaaa agactnnnnn nnnnnnnnnn nnnnnnnnnn   1380

nnnnnccatg ataaacgatt gtgttgacaa tggtaaaaga ttgtgttgac gatgataaac   1440

gattgtgttg ataatggtaa agatcgtgtt gacgatggta aacgatcggc taaatcatgt   1500

caaaatgata tttagacgat gtagatattt ttgaatatga gaaagatgaa gtgactttaa   1560

agatgaagta gcttttaggt caaaagcaaa taaaaacata taaaaacata cgaggaaaag   1620

ttaacatatt tttagtctat tcagactcat ccaaatttta attgtgtcat caaatctcaa   1680

tccacagctc tcaccttgat taaatacata acatatctaa gatcttataa ttaagttcat   1740

gaacgtatct aactttttaa ttcattgatc tgccttgctt agttcaagtt acataccctc   1800

ttgcttaaaa aaaaaagtta cataccctct tgcttaaaaa aaaaaagtta tataccctct   1860

ttgacaaata tcaaaggaga aaaagacaaa aactgacatt ggcttcccat catccagaga   1920

aaagaaagaa aagccgcgcg ggttgtttat ccacttgttt cccttattat cctcatcgat   1980

tccaagtttt gaactcaaca                                               2000
```

<210> SEQ ID NO 103
<211> LENGTH: 2000
<212> TYPE: DNA
<213> ORGANISM: Cucumis melo

<400> SEQUENCE: 103

```
ttcctattta aattaactgg ttttcttaga aaataacaga attcctgtgt ggaatcccgg     60

ctctaatcca aatttcatag ggatgaaaaa tgaaatgggg agtagacatg gagatgggga    120

gtggcattcc tgacctcacc ccgtccccgt ggacatcttt ggtgacagaa tcatcccatc    180

caaatcaatc tgtgggcaaa tttcaacact cacaacaagt tgaaagactt tgttttgtaa    240

tgtatttcga gttcaactca catgtggttg tatagtctac catttcaaac ccactccaaa    300

taagaaaaaa atataaaaaa acatatttta gaaccccaca acattttttt tatttgaaac    360
```

-continued

```
aaacaaatat ctccacgtgt ttctgtttga tctcaaattg tacaaaaggg agacaaacaa    420
gagcaactta atcgtgtggt cgaaagttca taaaaaacgt tgtttttcat tactattatt    480
acatcaacca atgcgatctc aatcttgtga agatttttct tccatgtgtg agtcatttct    540
tctcgatctt aattatcttc tcacaatcca tttattatag cataatctaa gttaatttag    600
attcaaaact atacaataat aataattaag aaaattacaa atttaaatag caaaagaacc    660
atttgttctt tatagtttct acactaactt ttgaaaaggt taaggttatt ggaaatcttt    720
ttctggggca tttttctcca attctacaat agacaatttt ttttaattaa ttaattaatt    780
aaatttaaag tttaccttgg agtagtcaat aattaatttt tatgcacatt tgtcttttat    840
atgattgaat gtaacaaaca ataacttatt cttcttcttt tattctattg ttttgatgca    900
aacccacaat atttaatgag ctcatagtta tgtgtttgct ttactaatta attattttct    960
tttcataaaa taaaaaaact tgtacaatat aaactctatt atcattgaat ttttagtact   1020
taatttaaac gtactaaaat aaaatacatc attctgactg acgatccatg taaataaaat   1080
ctaaaaataa aagaaaaatg tcagaaatag caaattgaca aaatatttac aagccatagc   1140
aaaatttcat attctaccga taacaaacat ttgatagaca ttgatattct tctgtcagtg   1200
gtattggtag acagtgatag aagtctatca atttctatca tcgatagaat tcaaaatttt   1260
gttatagatc gtaaatattt taatttattt gttactttta aaaatgtctc aatataaaaa   1320
ttattaaata aacattaatt ttttattttt caattttaat atctaagctc ataaatatta   1380
actttaccca ttatttattt ggtttcttac cgcttaaatg ttgcaaaaat attttaaatt   1440
ttatttttga aatttggtta aattcgtttt tacttaaaaa tttccgtgat aaaaatattc   1500
gaatttttta ggtttttata agatttaaaa gtaaactaca taaatgaaat cgttattttc   1560
taattctcaa tttaactttt ttatactttt taattaccaa atggaaacat gaaattttaa   1620
atatatttat tttaaatctt actcgttaca aacaaaacaa taaatttaaa attatttttc   1680
cgagttttaa attacaagat ttaaaattaa tttttcaaca agaccaaaag aattgtaagt   1740
ttcgaataaa aaggtttctt tttgggctat aaagtccaat ttcctataaa agaatttgat   1800
caattggagc ccaaagtcag atccattaac ttttgggccc aaatagaaca atgaaaagaa   1860
agcccaaaag ctgacccacc aattaacctt attattaggg ttttgctctc tcttttaaca   1920
tccgaaaatc aggactctct tgccgctttt ctcttcgccg tcgccttctt cgagcttcaa   1980
gtctcccatc ctcttcagcc                                                2000
```

<210> SEQ ID NO 104
<211> LENGTH: 1974
<212> TYPE: DNA
<213> ORGANISM: Cucumis melo

<400> SEQUENCE: 104

```
tttgctattt tcgtttcatg tgggaaaaat agtatagtat gtttacgtct taaattattt     60
caaattccta gctaggaatt aaaactttaa tatatccaaa acgtttctta tttattataa    120
agatctgcaa tagcacaatg ccaatttctc ttctttgaaa tccaggttca aatcccggtt    180
gcggaataat gttttgctat tttcgtttca tgtggaaaaa atagtatagt atgtttacgt    240
cttaaattat tacaaattcc tagctaggaa ttaaaacttt aatatatcca aaacgttcct    300
tgtttattac aaagatctac actagcacaa cggtaggtag tttctcttct ttgaaatcca    360
aaatctttgc tattttcatt tcattttcaa attgaatgca tagctttaga ttgtagtaaa    420
cattgtatat atatgtttag gttgtgctaa ctttaaatgt acaaaattca aaatgtaata    480
```

gaattagatg tacatgataa agagttgcaa tatttagatt aaaatataag aatttaaatg 540
taagacttgc atatatcaaa aaaagatttc tttataaaca atattttttt atacaatttg 600
aaggcaactt attgttactc atgggcttga tccaaacttt tgttgtcttc actaaaattc 660
ctctaaatag ttcaacataa agttgttcat gagaaaactc attaagatat attccaacat 720
tatgaattgt ttgtccttgt attttgttaa ttgtcattgc aaagtataaa tgaatggaga 780
tttgttttct tttgaacttg aatagatatc cattatcatt tggtgggttt aatggtattc 840
atggaagaaa aatttatttt tctgcataat cacccattat tatttcagca tgtataaatat 900 ttttgctaaa taattgacat actaatcttg tctcgttaca caatccatta gatgaatcca 960
aatttttcaa taacaacgtt ggtaaaaaaa atcaagacag ccttttatat agtaaaaaaa 1020
atgttacaac aacttttcaa cgttcaagtc tttaaatttg tattgttgat tagaattaat 1080
aagatatttg atttgcaaca aatttctaaa atgtaaataa aaaaccattt gcattcaaac 1140
tctttacatc caatacttta attccttcgc atcctatact ttaattccac tcacttaaat 1200
ataattaatt aaaaatatag tggataaatg aaaaccaatt tgcatttaat ttttatatat 1260
gcatacttta attccactaa acttcgttag aattaattca aaaagttgtg ggagagaatg 1320
tgcattttat catattacaa gaaaaataaa attaaaaaag aatttaccat aaagtcatta 1380
aacaaaattc aaaggttgaa tggagagaat aaaatttctg cacgctttga tatatacaag 1440
atatttaaaa ttaaaaaaat agttttaaag agaatgtttc taaattatta ttctaacttt 1500
aaatataatt actcataatt atacttattt ttttttaaat ttagaaacta aaatgataca 1560
ttctcgaaaa ctataatcaa acgagttaat gttataaact ttgaaaacta ttttttgttt 1620
ttaaactctg catagcaaat agcatataga ggttttttaa aaaataataa taattaaaaa 1680
aacattaaag gcaaaatcta ttattccttg atttgtgtat agggtgtaaa tattttgtta 1740
ctgtgttatt tttaaccatt tgcgcactga tacggactaa aaggtaaaaa cataattttc 1800
tcgaattgtt attagaaaac tggggaagaa aaaggaaatc aaatcgcgcg aggtgggatt 1860
tgacccggga acctaagact agctcggtgt ggtgttgaaa tccacgcgtt gttcaccgat 1920
tttcttcata acaaacgcac ccaggctacg gcagtcttcg aagctctctc aatc 1974

<210> SEQ ID NO 105
<211> LENGTH: 2000
<212> TYPE: DNA
<213> ORGANISM: Cucumis melo

<400> SEQUENCE: 105
gtcgtcgagc agagctctgg cagttaccct acaacccgga gcacgataac tgcagtgatc 60
cctatcctca gcatcagtta aatgggccga ttcaaaactt ttatgggcct cagcccactt 120
ccacttacaa ctattacaaa catggatacg atagtcacga tcaggcccat catcttaatt 180
actccacaca ttccaatatc ttcggccgcc aaactgcctc cgtttttagc gacgaaaatg 240
tccataattg ctctattatg taataaggct aaacactaat catctatccc tttaaatctt 300
gaatttttgt aataaaacca atctatactt tttgccatag tttatttcta gaaaagttta 360
gaatacattg aagatttgag aaacttgtct acaaggcatc aacaaaacta cgtgaaaatg 420
acaaattgga aacaaataaa aatatcttat gtttgagtat atggaatgaa gggattgatg 480
taataaaact taacgtcaag tgttaatatt acgctatagt tattttcttg ttgtagtaat 540
tttctcttag ttaatttttt tattattgaa ataagtgata aattttctaa taagaacgta 600

-continued

```
aagatttaaa cctctaatta agttaaaaaa aaaaacttga attattgttt gagttatgag    660

gtaacgtaaa agacaactta aattttaaag tcaaaccgaa aggaaaagag ttaaataccc    720

acaaatggat caaagaagtt aataacacac acgcacgttg ggaagcttaa aaattagcaa    780

caaacaagca atcattggtg tgggacagta ttgaaattcc acaaaactac aagggtatat    840

tggaaaatcc aatttattta tttatttttt aataggaatt aaatttactg taaaaaaatg    900

taagaccgtc gattgacaat tggtggactg tgaaacgtgg caaaagttaa ttggcgaaaa    960

ggagaggaaa gattttctct tttcattata atgaaaaaaa ttaatgatag tacacgtggc   1020

aaaaaagtat tggagagaaa tttccgggaa ttatctctaa tacgcggcta atttggatgt   1080

caattttgca aagaccagaa tctttttgaa cagcgaagaa gaacaaatat atagacatac   1140

aataataaat aaaaataaaa atatattaag cataagagaa aaagaagatt tgaaggttat   1200

attgaagtga tattgttggt ttctccattt ctgtgggtct gactctgcct ctctcttttc   1260

gagccagaac caccaaaacg aaaaaaccca cacactgtat agcaaaccct aattctttgg   1320

tctcagatcg cccatggctt ccactaaaga acgcgacaac ttcgtttaca tcgctaagct   1380

cgccgagcag gccgagcggt ttattgtatt ggttttccta ccttcctttc cacttttttt   1440

ttttgggttt gcttctcatt tctattttat gcttttctta atttgtgttt tacttttcac   1500

tctctctttg ctcagatcgt atttcttctg gttgtttaat tttgtgttta tgtttttttga   1560

cttcggattt aagccacgat cgcttgcctt tttgtgtact attttcagaa gtgttgttat   1620

gtttatccgt ttacacgatc tgtttgaaat ttatggaaat ttagtttgct tataattttg   1680

ctacatttct attgtttagc ttctcgagca gttttttttt tttttggccg atccattgat   1740

ttatactgtt tttctgtctg atctgtttta tttaatggag aatactcttt ttttgcgaag   1800

cttggtagct catttttcac tcatacttac acagactact tggtcattgt ttttatctgt   1860

aagcacaaag caaattcaag tttctgcctg ttctttcttt gcttgtcaaa cgacaaaact   1920

atgtttgtag ttgcttttgg atgatagatg gtgattctga ttttaattta cgttttcctg   1980

ctgttttttt tttaaaagaa                                               2000
```

```
<210> SEQ ID NO 106
<211> LENGTH: 1643
<212> TYPE: DNA
<213> ORGANISM: Cucumis melo

<400> SEQUENCE: 106

tccattggcc ctctcaaacc tttatgtgca tatcactaat atggttgaat atgtatatct     60

tctttctcga atagatgatt cttggtggtt tcaataatca tttagcaaat ccagaaattg    120

ggacctcaag ttcggttgcc gtggaaatag ctaaattaac tctgaaatcc tcaaactgaa    180

atgtgagaat aatcacgatg aatctgaacc gtcaacggcg gaacatagca acagtaatca    240

gaattaccaa atttcaattg ggggaattcc tttgtatgat ccttccttgg gcctaacagg    300

gattcttgat ttgaacctct cttcttcgta aaaattacac aaaatattta gctgctagag    360

ctagacaaaa caagatttag attggaaaaa caacaatgca gctcccaaat tgcaatccta    420

attccactat ttcttttttc tttttctttt ttttaatctt aggattcaat tcatcattca    480

tcaattttat tgttactgct cattgatgac caatgttttg gattttgtgt gtcaaatatt    540

ttagtttata tatggtgaaa agataaaatg aatagtttca aattttgtgt tttatgaatt    600

cctcactacc tctttctttc actaatacgt atgaaatgtg tatggttgtt tataaataag    660

atggatggat gttttgattt tgatttgaat gttaatgtta cttaaattat agattttaac    720
```

catttgaatg aaatatggag agaacagttt ttatatgtaa aaacaaatta atgtgagaaa 780
gaaataaata gcaatgcctt tcttcactaa taaatgtatt tatatttttt attaacaaaa 840
taaaatttat attaattatt agtgtatgag gtgtgttctt gtacaaagga aagtattgca 900
aaattacaaa aatggaaagt tgaaattact gcactcattt gctaaaatca aattagttaa 960
ttatagaacg aaaaataaat aaataagttg tatttgatga tcctagataa ataacttttg 1020
aagaataaag atcaactatt taaaaaaaat atgtgtatca caaaaaagaa tagagaaaaa 1080
aatcacaaaa atcacatccc aaattataat aattcatatt ataataattt atataccaaa 1140
cataaactat aataatcacg tattattata actcatagac tataataact cactccacgt 1200
cccgtagtta ttaaataaaa gaaagtaacg gtaacattaa cattataact tcgccctcat 1260
ttatggcaag gaaaaattgg ggggattggc aagtattata tttgtttatg gaaaactttt 1320
gtgaaggtgg aaaatagaga gagccaaatt aacaaaaata ataacaaaat caaagggtgt 1380
agaattcatc cagtttgaga gcggaagatt agatgggtga agaaaggatt attctagaac 1440
cctagcccac gtgtcataat ccaaccctca ccttttcttc aaaaaccctt tctttcttct 1500
ccctccccta tatctccttc ttcgaccacc aaactctttt ctctcaattt cccagcatct 1560
tcttcatttt tcattcttaa ttcaacccat ttcttctctc ttttcgtttc tattttcatc 1620
gtttctctat aatttctccc tta 1643

<210> SEQ ID NO 107
<211> LENGTH: 2000
<212> TYPE: DNA
<213> ORGANISM: Cucumis melo

<400> SEQUENCE: 107
ggatgggcaa tcgtgcgaca cttgttctac tcgattaaca aattagccgt gtaaaatcca 60
aaaattgtgg acaatttacg gtatgatgta gcccctcttc acgttcttaa gaaatttttt 120
ataaaatgag aaagggaaag gaaatcattg aaaagatcat aaaagaaagc attgaagact 180
gttaattgca aagaaagctt agcttaaaaa gagtgcaaca aggcttagtt ggggatttaa 240
ctactatgtc tcccttattg tacattttga atatttttat ccttggcaga cttgcatatg 300
aaaatgtcga aacgtcacac actaggtcga caacataaaa atgaaagcaa tagagcaata 360
gattaaacta agtagaaaac ataaagacaa ggtgatttga aggtatttgg atatgtggcc 420
ataggcaaat aacgcgctgg acaagcatgt tcatgacata tgacactttg cacgcatgct 480
caatgtggat atatcagcat ggcgcacgtg cctcactcgg acacataaac atggtatgcg 540
cggcatcatg tgcgcacgcc ttacacgacc aacgagctag gtgtagtcca agcacacacg 600
cgatgggcaa acgtgcctat ggctgcccct ggcgcagaca gtctcgaaag atgcatgtcc 660
atcctaggcc catctagaca cgtccaaaag ttccaatgac ggtccaaaag gatacaatac 720
ctttagaagt gtcatggtag gtctagaatg ttctagagtc atttgtaaat tgttaaactg 780
ccttatatct tctagatata caggtcctcg gccgaccttc aaagcaccta ggtcggttag 840
gaaagctata aatagatgta aggtggctta tttgtaatca ccctaaaatc ttggcataac 900
ctagccaagt aagacaacct tgcctcatca tttgtacaca aggtaccttt acaaatggta 960
ataccctggc aaaggactac actcatttgt atacaacttg tacacaagca atcttggaac 1020
gcaaagtact cttccaagaa gtgtcaagct aagctccatc attctcacaa aatgatctct 1080
cttgcctttc aactatctta aatcttctac tgccatattc tttctcatag tgcttagtgc 1140

```
actaacctct caaaggctta cttggctacg tgggcgttaa tattagtcaa gtgttgtacg   1200

tttggttagt tgaaaaatct aaccacgtga caatagacaa acatcaattt tattttattt   1260

tagagtctca ccaagttctt aaataaaatg tttattgtaa gacaaacaaa aatgaaaata   1320

tgttattata gtgatataga attttcacta ttagtacaag atataaaagc gaaaggaaga   1380

atgaatgaac actcaacatt tagaaagtgt tttgagtaaa gaagtaaata gtgagaaata   1440

acgagtacaa atgtgtggaa agttataaac ttctaagatc tacagaacaa aagattgata   1500

agatataaaa ttgatgttag gataggagct acaaactcct ttgaccaaat atcgagcagg   1560

attcacaagt catactctct tactctacca aattcattag aagtacataa tgggcatgca   1620

tgtgaacgaa ttaaaaaatt ggtattttta tttttatatt ttaaaaaaat tggatgaatt   1680

ggcaatggcc atgaatgaac cagttgttaa agtttagagg acaaaaccca aaagagagaa   1740

gtgtacctca taaaaaacaa atccaccaat tgagaatcac ataaattata ggaagacgtg   1800

tcactctatc ggccgatcct caaactcttc caccaaatcc acatgcacaa tctccttctc   1860

ttcccttcca ccatacactc aaaatcccac tgatcttctt cttcataaaa acccatataa   1920

tcataaatta atttcctcaa gtttttcttt tccaattaaa caaacaactc tgcaaaagag   1980

gcctttcttc caccatttcc                                                2000
```

<210> SEQ ID NO 108
<211> LENGTH: 2000
<212> TYPE: DNA
<213> ORGANISM: Cucumis melo

<400> SEQUENCE: 108

```
agacgaagaa gaagacaggg tgtgatcatt taagaatatg cgttttaact ctgccctttt     60

tagggctttt ttcttttatt tatttgcctt ttttctcgct cctagggttt ttccctccat    120

tgaattagaa ggatgactgg gccacagact tatgatgggc ttcacggtca ttatttgaaa    180

gtgtgatatt ctaaaaaaaa taaaaactca tttgaattaa aatagggttt ccctccatgg    240

gagtatgaaa gacttttaat tgaattgggg tttttaaacc ctaaattgaa ctaaatatat    300

ttttatgatt tttacaaaaa ttaatactac aaaacaaatt atgattaata aaatttgttg    360

atatttttca aaaaacaatt atataataaa acaaactaaa tattcaattt ggtattttta    420

accatgctat aggaaaagat tcatatgggc atcaaaatga agcaagaaca tggcaaagca    480

agttgggtga agataagtat tgtcctaaat cgaaggacga ggcaataaac tcgatatctc    540

gaagagtctc caggtcaaca tcacaacgcc tgcacaaacc aaatattatt atatatatag    600

ccatcgttta ctataagact atgtatttac gaaaaattct atattgtttt cgacgattac    660

atttatatta tataggaata aaatacaaac ttttcgaaaa gtcatatatc ccaccatata    720

aagatcaaac gtggtagatt gaaaacatta tacagtatat tctctatttt tttctcataa    780

aacttattac gctttgtcaa gttataaaga ttaatggttt tggtatattg tgctaacttc    840

gtccatttgt tgtgaaatta cattttcact actttttttcc acattgcacc atttttcata    900

tgttttattt ccattatctc gtagaatatg agcaaagaaa aagattaaag atgaaatttt    960

tcaacgtgtg agagaaacat cattaaaggt tacttaataa ggaattagaa aaaagagcat   1020

gaacctagaa caacaagata caaaatatca aagacaaaag agttcgatgg agagctagaa   1080

agataaatca agattttgta aaagaaaagt gctcggtggg gaactagaaa aatgttatag   1140

aagctagaaa gataagccga taatttgtaa actataagag gccgtttaga ggaagagttg   1200

ggttgtgaaa tgttagtgtt atgataaaac tattgttatg tttggggaaa gagtttaaaa   1260
```

```
aggtactttt atgataaaat atgtctggga taagagttga aaaacgtagt tttatgggag   1320

agttgaagat atagggttat gaagagttaa aaaaggtata agaaaaggag agagagagag   1380

ggaatagggg ttatgatcat agtcttaaaa cagaattatc ataacccaat ccaagtgata   1440

acccttggac caaacgacct aaaatatcaa agagaaaact gtttggtgag gaactataaa   1500

aatgttatag aagctaaaaa tacgaactag aaagataagc ggagccaatt ataagggttg   1560

gttaagtgta gggtttattt atttgagggg aatgataatt taagatataa attaatagaa   1620

tggcaagttt tgtaagaaaa attaataaca actcgataaa cttttgtttg tgttggtaga   1680

gaaaacatgg gccacaaaca tgagcccaaa tgtggagaag cccagctgat aatttaattt   1740

taaaaataat aaagattaga ttatttttgt tcgcccaaaa ttcggcgcgg ctaggaggtt   1800

gcttataaat ggaaataaat ggaaagggtg ttaggtctcg aacaagtgtg cgacggtatt   1860

ttaaaggtcg gccacgttga ggcggccctt ttcactcctt tttcctcgct cgtattcaat   1920

ctagggtttt aggtttccaa cttctcttcc tccccttccc cttccccttc cccttccttc   1980

tctactcatc actattctca                                                2000
```

<210> SEQ ID NO 109
<211> LENGTH: 2000
<212> TYPE: DNA
<213> ORGANISM: Cucumis melo

<400> SEQUENCE: 109

```
atgggtagtt ttcaaattaa tccgaccttt gaagtacttt ggtttttaaa ataatttttt     60

atcatctgaa atcactccat agacttatgt taccgtaaat cattattctt tacaaatgat    120

ttgattttac ttaaaagtat attatttcaa acacgttata ggtattatga agttttaccg    180

tcaacaatta tagttagtaa gccaactatt tataaaaatt taaaaaggaa tatttgaagc    240

atggtgcatg atgtatgttc ttctctctct taagttgact atcaaaactt aatcatgctc    300

agaataacat acctcacata gcatgtgcaa tttaatctaa gcaattcaaa attcattaac    360

aataattcat acacactaca aagtcatacc acctatgtca cccaagaact actattattg    420

taacaagtca aataagaagt ccctatccta tccatcctaa gatggagtaa tttttctttt    480

ccttaaattt ttggaaagaa gaatattgaa attcaggaca ttaaatcaaa gctgttcgga    540

gataaatgaa ccattcttca agtaaaattc atatttgtca tcatgcaaac aaatattgaa    600

aacatgatat caagaaaaag aacaaattat ttaaaaacat cataccgcac atcaaactta    660

aaataacctt ttgtgcatat caaacttaaa ataacttttc tcaacaaatt aaagcgacat    720

aaaattgata atttttgttt ttttttaaa tatatattca agaaaatcga caaatccaaa    780

tgacaagttg ttcacctgta tattaaaaaa aacaataatg aaaatttgaa aggagagatg    840

agaaaaaaaa aatcaatcca tcaatccaac ttgaattttt gggtcgacag catatcccta    900

attataatag gaagcaccct actttttttta caaaagtatc gaaattatta gtcgaaaatc    960

ttaattagag tccaaattgg atgcagcaag gatagtttta aatccaatta atagcatgcc   1020

taatgctatt acaaatatat tttggattat acataaatag aaaaaaaaaa gtgaacttcc   1080

agactcaaat agattttact ctattgttat aaaaactata cattaaaatt agatgtagag   1140

aatgagagct caaaaccaag aaaagtaaat gataaaaggg aaacaggagg tgaaaagaaa   1200

aggtgatacc gcggatttga tgtggctctc ggtttttgcc tcccaagcaa tccccattgc   1260

ccatctcctc tacaccaacc cacttttctc cctttctttc tttctttctt tctaaaactt   1320
```

```
ttgttttcca attttgacct ctcttcttgg gcccacttac taacaaatca aaaccaattt   1380

tcattttttt ttcttttctc tattcccttc cacaaataag aaaaaacttt atataaatca   1440

atacaagaat gacatttatt ataatagtat atactataag gtgggaggga tggcaattgc   1500

caattgtata agtaactatt aatagacagt aaaactttga aatagaaggt atttagatgt   1560

ctgagggtaa acttataaca ttttatgaaa tctaaaaact aaaattaaaa ttattgggac   1620

aatataaact ttagacataa gaagaaaaca tatttttgtt aataatttaa caaagaacac   1680

aacaagaatg gtagagtgtt gattaagagt gagcataata gacaaaaaaa aatatagtca   1740

atcagccaaa atagacggtg gttggtcgga gatgaagaga gtttcaatct aatcagttgg   1800

taaaaaattc aaacatcgtc acattcttta aaacttttaa aggtttaaat ctgctaagat   1860

ttatcgaaca atgacctatt tgtactactt tatgattgac atcaatttaa atatttaccg   1920

gtgaatttag taacgattag ggcgagagcg gttttaaaaa caggagtgga gtagtggaca   1980

aggagggggc ggaccaaccg                                               2000


<210> SEQ ID NO 110
<211> LENGTH: 2000
<212> TYPE: DNA
<213> ORGANISM: Cucumis melo

<400> SEQUENCE: 110

ataatactat aaaacaaata aattttaatt aagttgtttt tactttcata ttatactaac     60

aagaacagtt tgttaagttt tatatgtatt tataaaagat atatgagtta ttggttaatc    120

tataatatca atgtcgaatc tctaacaaat attttagtgt ctagacctta tgtaaaaatc    180

agaagtgacg ctcaatattt ggaaacagga atcattggga tacgtggaaa tcaatctttc    240

tgacattgtt acaaacaaaa gaataaacga aaagtatcac cttatagact caaagaatgg    300

aaggattcag attgagttgc aatggaggac ttcatcctga agtacctata tatttttctt    360

cttggttagt ttttcagtct tctcttctat ggatcaagtg gggaatacag caagagacaa    420

gaaagacatt ttcctataca aattcatttt attattcttt cattgtctct ataaataaag    480

aggcatttaa atccttttcc taatttaggt ttggtatcaa tattttgttt gtaacagagt    540

aatagaacca aaatatttca ttatgttact tgaaatgttg atttttttgt gcccattctc    600

ttctgagtcg acaagtgaga gtagatatga aagtagctta catttatatt ttaagagttt    660

ggaatctctt accttaaata ttttctaaaa gaatatcgtt gtgggaatat gatttttcta    720

ttttataaat ttgacactat cgatcaattt aaacacgacg tataatttta gttttatttt    780

tagaaaaata agctttttag tttaagtttt tttttacgta attactattg aatccctaaa    840

gttttaaaat gctatagctt tactcttata ctttgagttt agtttgtata tatggtcgat    900

aaattttaag attatgtacc gtaattctaa gttaaaacat tgctcacctc ttgtcctcaa    960

agttaatgta aatgaaatta taatactcat acataataga actttttttt attcttaatt   1020

atgcaaaaag aatagtgaag gttaatttag ttataatcag ttctagaaaa ttaacacaaa   1080

cattctaaaa gtagtttgaa attgagataa aatgaaagtc aaattcaaaa caacgaaata   1140

aagttataaa tatgaaactt tgaaaaatat agataaaatt agaactacgc atgaaaactc   1200

taagacaaat agacaattct cgagatagaa gtttgaaatc gaaatctggg gaaggaaaaa   1260

tctttacatt tccattttat tcctatatct actaataagt tttgtattaa aaaagaacat   1320

caaatagagt aaataactgc acactaaaca acactcaccc aaccacccca tatctcaatg   1380

agaaatctta atgtgaacta caaagctagg gacagaaaaa tgattcatta gattccagaa   1440
```

```
caataataat tatgattaca ttttggattc attagattcc aaaataataa taattatgat   1500
tacatttggt gtttgaccta tttatttatt tattttatat aaatattttg tcgaagagat   1560
agaaaaaagg atgcatttaa attaaaaaag aaaaattata ttgataaaga agaagatggc   1620
gggctgacaa gagaagaccg ggaggctgat gtggcaatgg gaattccaat tttccaatca   1680
aaaactaaaa acaaaaaaga aaaaaaaaaa gcaaaataat tttggttcac tgaaaatttt   1740
catataaata catgtggcgg ttgatggccc aaaggatgag ctttgaaggt cgcattatca   1800
aaagtttggg gaagcagatt tttgctaact tcgaggtact ctcctctcct ctcctctcct   1860
cactttcctt tctctctata ctaactataa tttccattcc tcctccatca ataatttctt   1920
catcctcttc cttagctaat ctctctcttc tctaccagtc aaacgccctc ccttttggtg   1980
ctctctagcc tcctcctccc                                                2000
```

<210> SEQ ID NO 111
<211> LENGTH: 2000
<212> TYPE: DNA
<213> ORGANISM: Cucumis melo

<400> SEQUENCE: 111

```
ttctctctct cttttaatct acaacgtatc caattatatg gagaaagttg aggttgttgg     60
atttaattca ttttttcaca ttttttaggg ttaaaatcta aaaacacatt tcgattttgc    120
gactgttcaa ggcgtatatg tttctttaaa tattatagtt gaaattacga tcaaattctt    180
acgctggtta agaaagagaa aatcgtagga gagaaattgt gagcatataa gtgaaaataa    240
cctcctagag ttttttggat ttttgagcga aacaaaagta aggttgtaac gatttatgtc    300
taaaatgaac aatgtcatat cattgtggga atatgtgtga atgataaatt atcacaactt    360
ccaacaatga gtatcacaat acatatcatt gatgggtttt gagaaaatga gggttgactt    420
ggacatgaca acttgataga cttataactg tgtggtgtac ttataagaaa tcggaagttg    480
gtttaaaagg agaatcattt gcgtcgacaa gatgattatt attgcaaaag atgcaaccaa    540
ggtatgtcga tacataggct agataaaaag aagatcaagt aatgatataa ctatgtctct    600
gttgatatgt ttttaagtga aataaaaaac aaaactatta atcctatacc taaaatgaac    660
catatcgtac tatattagaa aagaataatg tacctcttga tagaaactta tagtaaaagt    720
gattaataaa atatcactag agagatacgt aaatacttcg ttatcataat ttattttact    780
tataaatgaa ctataacaaa aagtatttat atccacaaaa tcaacgttaa gaatattagg    840
gcgtcgaaga agacgccaaa ctattttaat ataggttacg tttggtatct catctacata    900
acaatctttt gctttcaaat acactcaata aagtaaatgg aatgattttt tgttttctaa    960
ttttgtcatt aaaaacagtg ttttacattg tacttgaatt tgtgacatat aatgatatat   1020
ttctttttac aatacccaaa atcaacagta aaaaaacaaa tacttacttc ttttcattca   1080
aatttttcat atgcttttga ccgttattag cctttagtag tttatcgtaa atagattgtg   1140
atatttttat caagaagttt tattttttaa aataaatttc ctttttcata accacaaaaa   1200
gcacccttgc aaaatcaata tttcattttg gaccgggttg acattaggtg ctttaaggat   1260
cggcccaatc tagattcaat aatctcagta aggcccactt gtaaaccaca aaaaggcatg   1320
gcccaccgag cccactatgc caatagttgg gcctttcttt cgcaaatgca cgcagctaat   1380
taaggcttca ttacttaata atcagtaatt aattttgctc caaaacgggt caaagagcga   1440
cccgacccgc gaatatgtat ctgggccgtt gattatttta gtagtaatct caaccgttca   1500
```

gtcggtcctt ttatatgtct gtcctccctc gtaatcaatt cttagggttt tctagggttt 1560
ttagttcttc tctacgcttg gttggaagtg cccttcctct cattcttcct gctttactac 1620
aggttttcaa tcttcaacaa tttaaatctc aacatttaat ttgttttgca cattgattca 1680
agtgtgtttt ttttctttcg tttgggcttt tgttgattga aattactcaa gaaattgcag 1740
ccacaaggat agtctaaaaa tgcatttgat ttagtgtagg tgctgctctc tttttgtga 1800 ttgttcttag cttacttgga gctgtatgtt aatgctagag ttcattgagt atcaatgctc 1860
aattacagat agttttgttt tgtaatttcc acatatattt tcgtatttgt gaaattaagc 1920
tcgtttgttt tcattgtttg ttggcaattt atgttttatg ttatgccaac gattcatgat 1980
ttgtagcttg actcgaaagg 2000

<210> SEQ ID NO 112
<211> LENGTH: 1027
<212> TYPE: DNA
<213> ORGANISM: Cucumis melo

<400> SEQUENCE: 112 gggggggtt gtcttcctca aactctgtta tcgaaattag gtttacattt agtatctggt 60
tgacgttttg attgtattcc tgggcctgaa atatgataaa taaatatgac cattgaagtt 120
ggtgtttatt ctgggtttct atcattaaga gggtgtgaac ttacgaggga accaagaaag 180
ggatggaaat aggaatattt agaatagtag gaagctcaaa tgaattattt cgttcgataa 240
ggcggagtga atataaataa tatgcaagga gatgcggaga atattaccca ccttatgaga 300
gagagccaca aatcagaaaa cagtaacaaa tataacaaat caaacaacac catttgcaag 360
cgaattcaaa cgtttttcgg gtatgttgtt ccattaccac attcaaacat gaattgaaac 420
ctgagctctt gggcacttta attttatttt caacacatta cgtttaaatt gccgagtggt 480
caatatcatg tattgcttag tactaggtgg atacaaacct tacatataag gtcaaagtat 540
tgtgggcatg atataaatgc tctagcatat tggtctcata gagtttttta tacttttaca 600
tatccattaa tgagataagt taatgtttca acattaaatt tttagttaat atgaattcta 660
gatgcatttg ttatacaaat ggtctgatgt atttgaggtt ctgaatgtca aataggattg 720
tagtttattc acgttgaata ttgtaaagag ttaggacgtt tttttaagat tagatgatgg 780
gtgccatatg ctaccccata cgccaacaat tataatgaaa attatatttt gtcatttggt 840
atttaacaat tttttttaaa aaataagcta ataacgcata gaattcctga gatttaaaca 900
actttctgta atttcttttc tatgtactaa ttgttataga acctgtgatg tgcttgtcca 960
tcatgcagat tacaacgact ttgaacataa cttcaaaatt gttgataatg gtagccgagt 1020
ttttgcc 1027

<210> SEQ ID NO 113
<211> LENGTH: 2000
<212> TYPE: DNA
<213> ORGANISM: Cucumis melo

<400> SEQUENCE: 113
agccaaagtt taatatgatt caatcttgca caaatgcagg ttacccaaat ggttaaggtt 60
aagacaggca acaccactct agcagttggt gatggtgcaa acgatgttgg aatgatccaa 120
gaagcggata tcgggatcgg tattagtggt gtagaaggga tgcaggtaaa tttaaaacag 180
atcccagctg gagtgataaa atatagcttt cattcatctc aattttgttt tatacttctt 240
atctttctga atttcaggcg gtcatgtcaa gtgatattgc aatcgcacag ttccgatact 300
tggagcggct gctccttgtg catggacatt ggtgttacag aaggatctct tccatggtac 360
attatgatct ataaatatta ctttatatta gcttcttagt gagaatcatc cagattaatg 420
tgcaactata cagtctcaac atcattttca gcttgaaaat ctttgaaata tgtcgaactc 480
atcgcatttt atatatggca gatatgctat ttcttctaca agaacattgt ttttgggttc 540
actctattct tctttgagat gtatgcatca ttctccggcc aaactgtata caacgactgg 600
ttcctttctt tgtataacgt ctttttttact tctctccctg tgattgcttt gggagtgttt 660
gaccaagacg tctcatcccg gtactgtctt aaggtaagtt caactttcct ttatttcatt 720
ggtgcaatct tttgccttcc ttaagtacaa tatcaaatgg ctcattgccc tcaacatttt 780
tggattttca gttctcactt ttataccaag aaggtgtcca aaatgtgtta tttagttggg 840
ttcgaatttt cggatgggtg ttcaatgggc tactcagttc tgtcatcata ttcttctttt 900
gtgttggggc aatggaccat caagctttcc gcaacagcgg agaggtcgtc gggctggaaa 960
ttcttggtgc caccatgtac acttgtgttg tttgggttgt aaactgccaa atggcattgt 1020
ccatcagtta cttcacctat attcaacatc tcttcatctg gggcagcatc attctttggt 1080
atttattcct catggcatat ggagctataa acccagccat atccaccaca gcatttcagg 1140
tattcattga ggcctgcgcc ccggcaccat cattttggat cctcacacta ttggctcttg 1200
gagcttccct tcttccatac ttcgtctttt catcgatcca aatgcgattc ttcccaatgt 1260
atcatcaaat gattcaatgg ataaaagctg acggacaatc gaacgatcca gaatactgtc 1320
aggtagtgag acagaggtca ttacgtcaca caaccgtcgg ttacacagct cggttcgaag 1380
catcaaagca ttttgaagaa ttctcagaaa tcaagagtca ctaggtttga tgattagatc 1440
gtagaaagat tcaaaacatt ttttctacgt aaagtttctt ctcagtgtat atatatatat 1500
acatttatat atttatacaa catgtgtaca taagattctt gtgtagtttt gatctccttg 1560
tagcttaagt gaccattccc aattcaaatg gtcaaaaatt ttcttccttt catgaaattt 1620
ttaggaaata agccaattgt agtattcaat cgtatatttc aaatagtcat tgagaagttc 1680
taactctact atagttctca attataagta tgatggtttt gtcttattca tcttgtagta 1740
gaaacaaaag aataaattta cgaaggatga agcattgtta ttttaattat aatttgggaa 1800
atttggagcc acgaaatgaa atccaatttt gtgccaagta gatgtgcaac aatgggcaaa 1860
gaatcacttt ttctttttca taattttccc ttccaacact caccactaat tcatcacctc 1920
aatcctcttc ttcttcttct tcttcttctt cttcttcttc actcgccttt gggttgaggt 1980
tggctctgtt acagtcatcc 2000

<210> SEQ ID NO 114
<211> LENGTH: 2000
<212> TYPE: DNA
<213> ORGANISM: Cucumis melo

<400> SEQUENCE: 114
aaaagagtca tagtgaaaaa agctgagatc ataatagttt caccctaaac acaacttata 60
ataacacata ctatcataat atacacacca aacacagact ctatagtctt cactctaaac 120
gcagattaca atagtctgca ccccaaacgt agactattat aatcttctga ctattataat 180
actcttttca cttatcgccc caaacgtccc ctaagagaac aaagataggt tataaaagag 240
agatgagggt ttatattatg caacaagtat aaggttctag aacgatgtag tcttcaaagt 300
aacgaaagca ataggctaca cgagaaaaat atttttaaaa tatagtgctt tccctaaact 360

-continued agatttcaat gacaaattat tataaaaaat agaatcatta atccaacatg gcttgcatgt 420
cacaccttgg ccaaaactga agacggatgt catactcgac ttcaatatat ttttttaatt 480
aattttcatg tgacaacaca taaatattta aaatttagat tgggttggat tttttttcaa 540
gtgggtccca aaatactctt caaacccaaa ccaacccaac ttgtttaccc atctaataat 600
aacccaccag gttcaagaag acgaaccgaa ccgaaccgat ccggtctaac tttgtttcat 660
acttaagtcg aacttagcgg tacttttggt tcggttctcg gtttccccaa acagagccac 720
tcaaaattag atttagggtt ccgttcgcaa ttttcagcgc atttttattt gaatcggtcg 780
tttgttgaac acgttctctc tcagctggtt tagggttcat cgttctctct tctcgcgcta 840
tatctttctc tctctcaggt tcgtttcttt ctcttaggcc attttatcag aaagatcctc 900
ttcgtttctc cgattttctt tccgtgttcg ccctcggttt ctcagcagac gtaggaagtt 960
tggtttccgt ttagtgaatc tgtttggggt attacgaatg atattttgta ctgggctttc 1020
cgcatagtct ttttctttct aggaatatat gcatctgaga atttatttgt ttggcttttc 1080
tttataaagt atgaggacat atacatctcg attgctaatc cttgattata atcttttttt 1140
ttctatgttg tttgaatctg tttttttttt tttaatttct aggtttttttg aatctaaaaa 1200 tgtatttctt ggatgaattg catactgttg aattagaagt ttattgatta gattgttgat 1260
atttgcccta agttccatgg ataggtttgc gtctttcacc ttttcgtttg ctttttcttt 1320
tggctgacga catcttacat agcctctgct ctaaaaggtg ccatgatttt ttttcctggc 1380
tttatctgag tttgcgcaat ttagatttga agtgatgatt tgtctaaata taaatatcta 1440
tcggccatac tattttttgt tattttgagt ttttcaagga tgactgctag agaatgaaaa 1500
atcttgaaaa cattgtgttt tgaagttcaa ggatcttgta gttttgttct tttctagact 1560
atctcatttg atatagccct ttaaatttaa tcaaaatttg ttaatattca aatcctcgga 1620
cattttaatt atttatctaa atagttgttt aggcattact caggttgccc actattttaa 1680
gcttagaagc ctactctggt tgacctaaag tttgcatgct atttgcctta tttcgcacga 1740
ctctaaactg ttatagacat cttttttcag ccttcaggta aatgaacaca aaaaggagtg 1800
aaagtctgac ttctgtgtga tggtctttta atcaattata gggattaaga tggttttttt 1860
attcattgta taaatattaa attagaatga tgacaaccaa taatattaaa actgacaatg 1920
gaaggttcct tatattattt ggagtgtaca ttacaacagc ctgattcttg gcttggcagg 1980
ttcctgatca ccttgtaaac 2000

<210> SEQ ID NO 115
<211> LENGTH: 2000
<212> TYPE: DNA
<213> ORGANISM: Cucumis melo

<400> SEQUENCE: 115
aatgtaaata gtttataaac ttaagataaa attggtaatt gtttaataca aatacaaatt 60
gttaaatgaa atgacacacc ttgagcaatt ttcttttcta atcttctctt atagattaat 120
tttatttaat catgaaggtt agaatttctt tagcattatt tatttattta tttattagaa 180
aaagatagtt tgtgtatatt ttatatcata aagtttcaga agaaaccata aaattaatgg 240
agaataataa aaggtgggga tctctaacat ttttgccata aacaaatcac taagttaaga 300
atatgacact aaacttcttc taatttaata ttatatacaa agattttaaa attataaagt 360
aagagccttg aattgtagct aatttaagaa tatgctctaa gtttttttaaa atcacttttg 420 ccctacggtt attatttatt tttttgttga aatatgttta atccaaatca atttcaatcg 480
aacatagtca aggatatgac tgcggattcg tatattagtt gattttgaaa cgattaaatg 540
tttgaaatat tgtagtttag gaacaattac aattataaca atcagattca aaattttagt 600
atatacagta acatttaaaa gaataataaa tatatcaaaa tctatcgaca atagacttct 660
cttcatagat aaattatcag ggtctgactt ctctcataga taaattatca gggtctatta 720
gcaatagact aaatccttga tggtttatca ttggtagacc aaaagagttt attagtgtga 780
tagactttac tacataattt gcaatttgtt taaaatgttg ttatacattt ggttgctatc 840
cttaacatta caatccataa catttgtcgt gtctttaact tgaattgatt gttatctgtg 900
ataaaaagag atgatcactt tttgtcatga gatttgaaca attgatgtta aaagtggtaa 960
ttaatgtacc attcactaac caatgtcaat atttattttg tttaataaaa agaaaaagga 1020
gattgtgaca ttagttttat actcttttct aaacataggt ttggtttgtg ttagatttgg 1080
cctacactta gctcaaatcc actctttata aaattccctt acttattaca agttatattt 1140
tcactccaat cataatcttt taaaggataa tatttgtatt agaagatacg acacatgtag 1200
aagataattc ttttttaacc aaaacaacat acaatttcga ggatatgaca aattaccttt 1260
tctattttta actatttgat cttcaagtcc catctaaaca tcaaatgaaa gttgattagg 1320
ttaaagaatt ggacaattag agaaggaatg gagaatcaaa cctctaactt ttaaggaatt 1380
aggtcattca cattttcatt gagctaagct cacattaaca agatcaatat tacttgtatg 1440
tagttaattc agatgtgaat ccttgaggtt tcaaaagtga cactttagtt cgaggtttaa 1500
aaaatattta tatatataca catgttacaa cccaaattta aggtatatat ataaatatat 1560
ataatttaat tatcttgaat tataattacc ttaaattact taaagtaaag attggtttat 1620
ttatgattaa gttatgatga atgttaagta atttgaaaat ttgaagttta gaggattgtt 1680
aattcacttc attgtgggcc tcattaattg gcccattaaa tctccatatg ggcctgtcta 1740
gggcttcatt tccccaagct tccaactgta atggcggcca cagttctctc ctccatctcc 1800
tctcttctta cctacttatt atgttaatat ctacgttttc cagattcatt ttctttttat 1860
ttgtattatt ctaaatctcc agaactgctt agctgctctg gtttttgggg attttagggg 1920
gctcgatctg gtgggtttac ggttaaattt tgcagctttt cgaggtcctt ttcggcttcc 1980
attttgtcgg aagttacaaa 2000

<210> SEQ ID NO 116
<211> LENGTH: 2000
<212> TYPE: DNA
<213> ORGANISM: Cucumis melo

<400> SEQUENCE: 116
acacttgtaa tgttgagcag ggtaacttat ggtaaatttg acatgagctg gcgcacaaag 60
gcctagcatg ctcggagctg tttttccatg gagtcaatgc ttgatcgcat tattggctat 120
attctaaatg aaactaaaat tattgatggg ttccatctgt ttggatacca actttataca 180
caggtgtttt tctatttatg agtgtaaagt ttgatttgct tcatcatcgt atattcaacg 240
tagagtttct tagttaatcc aatccatatg cctcaactat catgctcttt tccctgtaat 300
tgaatgtttt ttttggtgtc cacatggtca tggaggtttt gttctgcact agcttcacga 360
tgctactaaa catgatgatg aagcttgagt ttatttattt cttagtactt tgtgatgaaa 420
aaaaagtaga agaaaacggt agaaaattgg aatggatacg gtacaatgga tgggttgtgc 480
taagtcacgt ctcgtggata caactacaat tagttatttt gttttgtaga tttcatatta 540

-continued

```
gcatttcctt ctgaatagtt gaaatcacca tagaatgtgt actgatgttt tgtgatttta    600
gtgcttcggt ataatttgaa cgctttacaa gtaaaaattt cctcaggtaa acgagtcttc    660
cgaagtactt gttcataaaa tgttcttgtg tgggagagtt gattggagag gatcatggtc    720
aaattcttct tggtgtgttt tatataaggt tttaatgatt ctttgaaatt gtaatgtttc    780
cttagttttt ttaagtgata ctggtgggtt ttccttggaa taaatattaa gggctgaaac    840
ttaggaatta tatggatttg agggaggttt gtggattctc aaatcaaatc aaaccaaaac    900
cagataattt taaattctag aattttgaag ttactatttg tgtttagaaa taaaaagaaa    960
gaatatcgct tctttgtcct tccaatattc tttagaacca aaagagaacc aaaattatat   1020
ataaaagagt cgataaaatc aaatatatat ctataatata gtttattatt atttttcatt   1080
tgctatcaat aagaattttg aaatgtaata tttgctccaa attatattaa aaacagctgt   1140
tgaaatttca acaaaatgag aatttgtact ctggattttg ttattagttt tttttcaat    1200
atcttaaact atttcttaaa tattctcatt gcgagtcctt ccatttacat agaactaaaa   1260
atggattgag tttggttaga gaataatccc aatcttactc atatttttag gttgattaga   1320
ttggtaattt gattagcggt taagttattg ggttgtattg tttcataaat tcgatagatt   1380
acatcgatgg caatgtagtg tggaacataa aaaataatga aataccagcg gaacacaatg   1440
gagactgaaa aggatagacg atcgaagatg atgaaatgag aagctgacaa caatgagggg   1500
cgtgagttga gaagccgaga caagagggag agagtgagtc ggaaagagat gtggggcgtt   1560
acaagttgtg ttgaacaaag tgaggtcaaa tttaaattta ctatttgcta aattaataat   1620
aaaataaaat ataaatataa acatataaat atatatatga ttgggttggg ttgatacaaa   1680
atttctaacc ctaactcgat aaagcaaaat gcaacccaaa ttttaaatta accagatcgg   1740
gttattctta tcctaacctt aggacagtga ttacttaatc tgtacgcagg ggcaattttg   1800
acctttgata aactctccca ttttgttttc ttttttcggc aattttccct ccctctctag   1860
tctcttctgt tctcagttca gctctctagg gttttgtcga acagccattt ctaagtgtac   1920
atctcctctc aatttccctc gctttattcc atttttcac gtactatcgg cggatccttt    1980
gagctccaac tctctcatcc                                               2000
```

```
<210> SEQ ID NO 117
<211> LENGTH: 1025
<212> TYPE: DNA
<213> ORGANISM: Cucumis melo

<400> SEQUENCE: 117
```

```
tttttcttac ttcattatcg aacaataatt tgatttccaa gcgacccttt caaattcaaa     60
caaacccatt tctcctctca gccagagcaa gtgattgaac tgctgcgctg cgcgtgacct    120
gttatcttct ccgtttttct taccgccgcc cgcccctcac ggcggagtag tttcaccgcc    180
gacccatttc gccggccgcc ggcggtgttt cgattcctct tgttttgtcc cttttcgtct    240
taccagtttt ctctctgtct acattgtgtg ctcgttaaca gccagctgta tagccactgc    300
ttttttattt gactcttgaa acagagagat aggggagatt ctgtatagtc ccactgtttc    360
tgctcaactt tttcggttta atgtctgttt ctatattcga ttcttcgttt tatgttcgtg    420
attcgatatt gcttttgctt ggaatcgttt agaggcaagt gattgtctct gcttttgcta    480
tgtagttact ctgttttttt tccctttctc tctctctctc tctccccccc tctttctcaa    540
aagggggttg gtttttttat cgtcggagga tgttgggttg atcttttgat agggtctgtt    600
gactaattta gctggtgttc ttggtctgct gaatccgaac ttctcttagt tttagagttt    660
```

```
tcgatgttgt tggtttacac tgattcttct tcgtttgttt gggattattt ttgacaggac    720

tatagtgttt aactgctagc tgccatggaa catgcagaat ctgcggtgag tttttagaat    780

aaacttgttc ggttggtgag aaaagcatgg gaaagaggag ggggaggttt ttctttatgt    840

caaatatttt ctcaaactca ggttttagaa taaaaaagcc tttgtttctt aaccaaatag    900

tttatttgat aatcagctgt tttgttttag ctccctcatc tcattttcgg aaatcttagt    960

tatcagttta atcaactctg tgttctatga tgctcatttg tacttaggca aaggttataa   1020

agaac                                                               1025
```

<210> SEQ ID NO 118
<211> LENGTH: 2000
<212> TYPE: DNA
<213> ORGANISM: Cucumis melo

<400> SEQUENCE: 118

```
tgcattttat cagagatgaa attgaaaaag gaagaataaa cacgtactgt aaaatcaaaa     60

cataagaaac ccagctgact tagcttgtta attaaccaaa caaagtttga gcattgtcta    120

aattaaagtt gttcaacttg actgttgtag ggttattaat ttttcttgaa aagaaaacgc    180

agcatataat attaaaggag tattttgtct cgagggggaa gattattggt taaaagtata    240

tatggtgtga cataattaaa tactttgtaa ctaaaaaata aaacataatg ggaagttatc    300

tctaccaatt tttttgttaa agggctgaat atataacctc caacattact tagttactga    360

tatatcagtt tctctagccg tcaacagtac tacatagttg ctgatcataa atagaagaaa    420

caagttagaa attttgtgaa gagaaaggcg agattatgtg atttttgctt tgtataattt    480

tgaaaaccct tgatataagg aagttccttg ttgctgcatg ccttcttaga gatcagcagt    540

tactgtatgt ctatatataa ttctctctct caatattttt ttctgttctt gagcttgatt    600

gtttactgct tcagaaatct tctttacaac tactactgta tttggaagtt ttagttccat    660

atatatttct atttttttaa tgatttcaaa tcttgttgtt tcaaacagta ctctcctaat    720

tacaaataca ataaaattat atctagcatt acaattttac aaagtccttt tcttgtgaaa    780

aataaattac gtgagacttt gtaaatggta ttttgaatgt attaaggtac tatatgacac    840

ttagaattgc tttgctttag ctctaaccat gggttcaaat gtaaagttaa aaataaaaca    900

atcaactatt taaggtttta cttaaaaatg taattatttg tcaaaataag cataataatt    960

gagtagtaat ttacatatat tgcctccaca tttgagatca aaactagaga tgttcatttt   1020

cttagatata ttattaagct aagaatgaga gaatgggtga ggggaaaagt gaacggaggc   1080

aggaagacca aatcacccat tcctgaaaat ggaaggatta aaattgcaat tttccttgca   1140

atttaatacc aacatgattt tgtatatata tatttgaaga ggggttttaa aaaaatataa   1200

caaactgtta aaatatttac actatataca acaatcgtta agataaaaaa actcataggt   1260

ccacaatgaa aaatataaca aatgtcatag tcaacacgcg attaatcagc cacactcacg   1320

ttcgagtaat cttcttctga atgattgtgt attacagtca aaatacacaa tcgtagagtt   1380

cttttctaat gatgttgaaa aatacttcaa atttagggtt tagggtttag ggtttaatga   1440

tcgtgttaac cgtgaaaaat aatcgtgtta atcaatggaa aacgatcgtg ttgattatga   1500

taagtgatcg tgtagtccaa tgtaaacgat cgtgtttgac tatgttaaat gatcactatg   1560

gtaagtgatc gtttaaatca tataaacacg acgatcatgt agttcttttt aaaagatgga   1620

aaaagaattc aaatgcaaac gttcgtgtta acaatgacaa atcattgttt agatcatgtc   1680
```

aaaattaata tttaaacgat ctattgatat tcttaaatag gaggaagatg aagtagttct 1740
aaagaatact gtcgaaaaca ataaagatag aatatgatat ttaaattaaa aaataaatga 1800
tatcggaaga gaagatgaat aaatcagaga aacagatata aaaggggaag tgactgatcc 1860
tccaaatcta aaagataaaa atattttaca tgactctgta aactttggtt tcttttgcta 1920
ggcagtaaat atttgagggt tttggtattg tatttgtggc ggaatggagt aagtgggcct 1980
ggcattgggc cgtatacgta 2000

<210> SEQ ID NO 119
<211> LENGTH: 2000
<212> TYPE: DNA
<213> ORGANISM: Cucumis melo

<400> SEQUENCE: 119
tcattccaga aaaggtaatc tttgattttg agaagttaat ttgaatttta ttttaaggga 60
attcaggcag caagattaat catctggctt cctggaaaaa ggtcaagttt tctcaatcag 120 aagggggggct aggtttgggc agtttaaaaa ataaaaaaaa taaggccctc tttctttact 180
aaataaatgg tgttggaggt ttttgaaaga agactccaca ttgtggggta agttatcaaa 240
agtatccatg gcttcaaaaa aatttaattg gcagactcta aacaaactag aaaatagcct 300
tagaagttcg tggatcatgg gaaagttgag ttggcaactt tcaaaacaga gaacgaaagg 360
agagtaactt tctggacaga ttcgtggatt agtgatctcc ctcttaaata tccatttcca 420
aatatattca gattagctca acaacccaat gattcaatta ctgcgcactg ggattatgtc 480
actaattctt ggtcattagt attttgaaga ttgctaaaag atgaagaaat tcaagatttc 540
caaaggcttt taacactcaa atcctagaaa gtaatagact tggatgatag aagagtttgg 600
tcattaaaaa cctcaggcca tttttcagtt aagtcccttt cgaagcacct ctctccttct 660
tcacctttgg aaaaagatta ctttaaagca ccttggaaaa ccaggagtcc aagaagaata 720
aatgttctgg tttggattat agcagtgggt tctctaaact gttatgagac tatataaagg 780
aagcttccta atatgtgttt actaccttta gtgtgctcca tttgcttgaa aaacagtgag 840
ctcctaatac acttattcat tttttgtccc ttctcatcta cttgttggtt tagcatattt 900
tctatgctca aacaacttgg gtctttgatg gttcattaaa caccaacgtt gttcctaatt 960
ttttaggggg tccttattta tatatatata tataaaaaaa acttttctaa tttgggttaa 1020
tttgataaaa gcactcctag ctgagatttg gtttgaatgt aaccaatgca tcttccatga 1080
taaaagagag agagagagat tgggttgaca ttgtagacaa ttctaaaaga aacgtggtag 1140
cttggtgttc ttcaaatgca gaattcaaat gcaggatatc tacttattgg actaccttca 1200
tatgaagaga ttcaatgcag tttcccccga ctactagttt agaatttgtg tttttgtagt 1260
tttaatgggc tgtaatatgt atttctacct ttaagttttt acttttcagt cttgcttctg 1320
tctaccatag gtagtattgt tattttgggt atttactttt gtcttttcat gaccttagtc 1380
ttgttcttgt attttggata taatgagggt gctatcgggg tatcaaccta gttgagatgt 1440
tcgagtgcac ctactgatcc ccttatttgt aggcttctct attattctca atgtataact 1500
ctcttgtact ttgagtttat caataataaa gaagcttgtc tcattctaaa aaaacaaaaa 1560
ggaaaaggaa gataattgct cctaatcgtt gaaattacta ctaattactc ttaattactc 1620
caaatgatcg tataacatac atttataatt tttaactttc ttttcctttt taaataccaa 1680
cattaaattt taaatacatc cattaatttg aaattagttt tcaaattcca aatcgaaaga 1740
tttaaagtcc tttgaatcca aagggagaat gagcccatcc aagcaagttt ttgtgtcgta 1800
gttgcatatt ttaagtcgtt tcatattagc ctcgagtttg gcttaatgac ttggtggtgt 1860
ctagtgcagg cttgtggcga ctggcgagcg tggttctaaa gataaggttt gcattcgctc 1920
cttctccctc cctttcacta cttcatatcc atttcctttc tcgatttctc gtcttccctt 1980
ctgaattccc cattccagcc 2000

<210> SEQ ID NO 120
<211> LENGTH: 2000
<212> TYPE: DNA
<213> ORGANISM: Cucumis melo

<400> SEQUENCE: 120
atttatttgt ttagagataa gacgcacatg agaatatgag atggattcca ctccactcac 60
actccaattt ctacctatcc tattactgtt tactattatc attccacccc tcgacccctc 120
attcttcttc tcaccttact tttttatgat ttactactac ttcattttgg atcacaatct 180
gatcaatgct gggtgggctg ccctcggcct gtcaccaggc ccagcccact tccaaattaa 240
acctcttggc ccaccgccca ttgtccccat cccattccat ttaatattcc caaccttccc 300
tttttctttc ccaatgcgat gcttctccaa tatacctttc ctgccctcca tgtttccttt 360
ttactgcttt cttatattta taacacacct tctacagtct tttggctggg aatgctgcgt 420
atgtgaatga gattcaagat ttcgttgatg ttatttgagt ctctatattc ataagttttg 480
ttcttagttt tctctagacc aactgcaaga gttagcgttc catatgctca taagtttcag 540
atttctgctg tgtggtttga agacagtcat cgatccatgg gtgaattcgg ctttttatta 600
ttattattat tattatttat tgttgtctta cttttctatt tgaatcttcc tatcttttta 660
ctcattgttg gactctaata attcttgcta aacacaatct ccatttttat tggacatttt 720
aaatcccatc tcaactcata attttagtta ccttccacca tcaccatatc caaatccgaa 780
ataaactcaa ataaaatcct tcacgtgcat gtgctctcca tatatttttt ctacatggta 840
aaaataaaat gaaaacaatc taaatttaat aaaataacat atatggcaga cttttattga 900
tgtagagact gggtgttgta caagaacagt gcagccaaga aaaaaaaaat acttccaatg 960
aatcgtacat tttaaggatt atgaaactaa ctagttccaa ccatttttttc acgaccacgt 1020 gcttgttaaa cacgcaagta gaatcaaaat gtgggcttct tcgctttata taactgtgaa 1080
tcattctcca aaaagggaag gggatctcat tccctaattc aataaagaaa aagaaaaatg 1140
ctagcgaact tcatccatct cattcctttt acctatttca tgagatgccc attgtatata 1200
agtatttttt tttttttat ttcattttac ttagtttact cctcacctct aaaaaaaatt 1260
aggagagttt gctaaatcca ttctcaaact tagctttatt tttttaattt tatttaacct 1320
cgtcgtggat gttaacctca aatgtcagtt ctttttattc tatttattga tgttataatt 1380
tactttagga ttccaatttt ataaaaataa gaatacaaat aaagataaag agtgtgaaag 1440
ccagaaagaa aaaaaggaaa tcgtaatatg ggtaaaattg gtacaaattg ggtcccgtta 1500
aatattaact caaaaaatgc gagaaaatgg tagaaaagga aatagggggt aagagcaaag 1560
tagtggaagg agagcattga acatattctc tagtttttgc acttggatct aaacacgagg 1620
aattataggt ttattcattt actaattaca taaataggat tggattttaa aatttgaccg 1680
agtgattatg catatttgat agagttagaa aatagtggtg gggcaggtac aagttacaag 1740
taatgtataa gagatatgat gagcatatta ggaaactata gatttaaatt cgtccgtaaa 1800
taaataatta gaaatataat attcgagtgg aagggtatta gggttaggcg aaaccaattg 1860
cagttgcacc tataaaaccc cttttacgcc tccacccgct tcaacagcgg tctcggcgtc 1920
tacaactaca cactacacac tacacactac acactacaca gttgcagacc agaagcataa 1980
cgtaacgccg gtccacaaaa 2000

<210> SEQ ID NO 121
<211> LENGTH: 2000
<212> TYPE: DNA
<213> ORGANISM: Cucumis melo

<400> SEQUENCE: 121
tgaagagccg gaaaagcatg gcaaggtcaa ggcatttcag caagaatacg aggatgaatt 60
ctgggtttgt aagtccggtt cttcttcgga gttgtggttc gaatttcaaa cggccatgag 120
gagccctaca gcttaggaag cttcaggtct gagactctga ctccgacaga aattgctgat 180
ttttgtgtgt gttttgaata accattgtat gagtatgatt ggttgtatag gtttgaaatg 240
agggaaagtg atccatctcc ttgttgtctt tgcaggaaag gctcatattc gaccaagaac 300
gctttgtcat tgctttcgat aatcatagaa tccacaatgg tttggcatat tagcaaacaa 360
atcttcttta ggcattgcag acagaaaatt ggagagtaag ttattataat taaggattct 420
aaatgagtaa gaataataag atcaggcaaa gattggaaga actaaagcgt ttagtatttt 480
gtgtggtaca gaagaattgt aattagatac gtagtctaga gaagcagatg gtgagatttg 540
tgaaagacaa atgttagtgg agagtgaaga gtgtttctca acaaccgaca tagaaggatt 600
ctcagaaaat gagaaagatt tttattgcgc aaaatagctc ccatatcatc atatgccgtt 660
gccattccct ctggggttgc atgtaatgag taatggaaag ctgtagacag gctaacttca 720
ccctttgtct tgggtatagg gtgcattttt ggtcactcca ttttaagttt tctaataata 780
aaaggatgaa gaaaagatat tgaaaaacag ctcaggtttt aaagttgtca cacttgagaa 840
taatgcattt aacagttaga attttgcatc aacgtctttc aaatagaaaa gtaaaggaga 900
gtctagtttg agctggatag ctaaactggt ttaatcatat cttctatcaa gtggttagag 960
ttttagacct cccaacttta tatgtcgttg ccctaacaat gttgatggat gtttagtcct 1020
aagctctaac attgtccccg tatcatattt cataatagaa tgtactgagt aatggaaaac 1080
tagagaggta ggaagttgga cgaactttga atctatattg atttactat agtctttctt 1140 ccaagtctta atgagagctt tagctaaagt ttttcaaaaa ctcaaaagaa gtttttgttt 1200
tccaattctt cgatccatag attgtcaaga tggctataat atccttgaag ttaatagcct 1260
tcaaagtttc atagctttta tcctatgatc tttagaaatt caagagttat attctttaga 1320
actacagaac tttgatcttc gattcttcac ctcttccaga acctttatag tagagtttct 1380
tgaccttaca tgggcttggg attgggcctg gctacttatg ggcttagaga ttgaccttgg 1440
gtttaagcac attcgtttta cttggcccaa ttttcttaaa cttctgcaaa atcctaatta 1500
actaacacct caacaaaagt ccagtattaa atggggcata taaacaaaag ttaaacaaaa 1560
ttgtcgtaca gaatcctaat ttgctaacct cagcaaattt tatgccattc gtccttgtgt 1620
atctaattag tgttaatttg aggaaatata ataatataga cgtaggacgg atattggtat 1680
ttggtgcaac atcctccgaa ccaattcctg gaaagtaatt ggggcaacaa gataatgtta 1740
tcgtcagttt caagtgcaaa acttgccacg tggaacagcg gcaacatgat atctcaaata 1800
tggacctctc acccggtcaa gcttccacca ccaccaccac ctccgtattc taaaataaag 1860
tcaggaacaa gaacagacac accttaacaa aaccaatatt cttcatctct atctctctct 1920
catttcagca tagaagagag ctgagtaaaa ggaaaaaact tcaatcaaat ttgacagaga 1980
agagcccaag agaaaaccaa 2000

<210> SEQ ID NO 122
<211> LENGTH: 2000
<212> TYPE: DNA
<213> ORGANISM: Cucumis melo

<400> SEQUENCE: 122
agatgaacca gaaagatgga aaatctactt ggggttcagc agtgagtttg gaaaagagag 60
aactatttga agaaagagca gaaaccatct tgctaatact taaacaccgc ttccctggaa 120
ttccacaatc ttcactagac atcagcaaaa ttcagttcaa ccgggtaaaa gaacgctcct 180
tccttgtcta taatctcatc taaaattatc aacaatccaa acacaattta tacaaactaa 240
aatgaaagct tctcaacttt aggctacaaa aacagatgct tattataatt ctgcccaaca 300
atatcttctc ctaaataaga tgatatatgt tttttgccca tataatcaaa taggaaataa 360
caatcctgtg cccatttctt tggagtgtga gatcataaaa cactgtctaa aacaacatgt 420
ccaaacatat cgtaaatacc tagtttcata gtgtgatgaa ccaccacaaa caaacttact 480
ctttggtgaa ctgcaggacg tggggcacgc cgttttagag agctactcca gaatactgga 540
aagcttagcc ttcacagtga tgtcacgaat tgaagacgta ctccacgccg ataggttaac 600
tcagaaccca tcacaaatag caacaaggag gaaaccgacg agcgaacccc caatggagaa 660
atcagaagag ttgaacaaca acggcccaga aacgccagct tcaatgacgc tgttggattt 720
catggggtgg ggacaggatc aaaacgagtt ggagatgaag aaggaatggt ttgggaattc 780
agatgattta aacgcggatt cagatctgaa acaagggaat aagccaggga atatagtgac 840
gaacaagagg gtttcatacc tggagaattt gagcgctgtg agaagtccaa cggcgcgcca 900
ttgaagaaga agaatagata gagagatgat ttggaggcaa aattccatga tttcagttat 960
atacattcct tttgtgtaaa taggaagaag aagaaggaga atgagatcaa ccccattttt 1020
ttctctcttc ttttttaat ttggattttg gaatcacaac tctttgtgtt tgtgtaaaac 1080
caaaattgtt ctatgtatca tttgtatcaa ttaatgtagt cattttagat tcatacattc 1140
aaaaatatca actccatttt ccaactacta tcttcctcca tctcacctct aatcataatt 1200
caaagcggat acaaattcat gttagaatga aagattcgag tatagcctat tccattgatc 1260
aaatgcatgt atctatacta ttgacacttt tcaactcaag tcatgcttga acaattgttt 1320
tttataaatg ttaattacaa gagtgtacac aaatcgagtt gggaaaaaat atgaaccaac 1380
ccaaaccaaa aactttgagt tggaccgaat ttgaataaat aattcaattt tcattatttt 1440
tatatagttt ttcaaccaaa ttttttatct tttttttctc aaatttcaag tttacaataa 1500
tgtccattca aaagtttaaa ttttcatatt tcgaacattg aagttggaag gtccaaacga 1560
aagaactaaa tgattatgac acatgtctag ggtttatata tattgttgag ttgagtaatc 1620
caagtttttg aaacaccact agttatttat gttaaataat taactgagta ctcgactttc 1680
ttagttcgag aatatttttt agaaaaaaga agagaggatg tgtttagaaa taatagcaag 1740
ttagggtgtt ggtgagtgag aaatattttg ggatcttctt gtaatagtta ttaagaagat 1800
ttttcaaaga atttgagagt taaagaaata ataataataa ataagtaaac atttaatagt 1860
aaacgacatg tcgttttata cagcatcgta tttacttacc atgtgctcat tcacacacga 1920
ttcctcctcc tcctcctccc gttcatctct tcttatcttc gtcttcttca tttcggataa 1980
cacaaaaatc cctaaaaaaa 2000

<210> SEQ ID NO 123
<211> LENGTH: 2000
<212> TYPE: DNA
<213> ORGANISM: Cucumis melo

<400> SEQUENCE: 123
tcattttcgt ttggttaaag aatatatcat cgtttctttt ataaaatgtt tttgtagaat 60
taatcttcga gtacttctca taaaaacatt ttttttaatt acatagagtc agtaataatt 120
agaactatct caaaccaaag tactataaca tttcaaacca taacactgta ttttttagaa 180
aagttattgt aaaggataga attacaaaaa tattatagca tatgaaacat tattgttata 240
ttttataaat attccatata caatataatt gattctagat gtctctaaaa atagggaagc 300
atatgtgtta ataactaaat ttaaaaatta aaaaattact cgattactgt ttatttattt 360
atgtgttgag gctatacata ctatatttta gtaattattt taaaattaaa aacaaaatca 420
catggctaat agaaacgata gatatctagt agtaaaattt tgttatattt ataataagtt 480
gtcttatttt acttaatgta actacaaata tctcactgtt attttccttt ttttttcagc 540
ttattggttt atatgtttag aaaatttggt aaaatatttg tgtagctgcg gttatcatgt 600
atcaacttaa ctatgtaatc tatgaaaaaa tagtcattct ttaaaaaaaa aatgaaaagt 660
taaaaaagaa aaaaaggata aatttataac aatattcttt aattgaattt tatcatttga 720
ttcaaagata ttcttatact tttaaaagct gcaatgttat ttatgaaatt gttttaaaat 780
tacatttata atgaaaaaat ctttaaaaat gtagaaaaat caaggcttag aattgtattg 840
tcatttccat caaggagagg atgtaatttt ttctttatca ctttatttga atcctcaaat 900
tttcgataag tatatatttt gacatttgag aatatttttg tttactttaa atttaaagtt 960
atttttaaaa caaatgaaac aaaatattca taacgtggat caaatcacca taatttagaa 1020
agcgttcttt tgaaacatga ccccaaaact ttagaagata aattacaatt tgaactattt 1080
tgaaaatggt agcaaggaga caggtaaaaa aagaccacat aaatcacttt aggctttaaa 1140
gaaacaatgt taattggaga aagattcatt ggcatataat tttgaaatat gattgtattt 1200
tatatttcaa atcatattcc atgaatttat ctatctttgc ttgtagtcta aatcatgcaa 1260
actttgaaaa taacaatgtt attgtatcaa aatttaaaag tttaaaacat ataattgatt 1320
aaataaagaa aaatatttag aaatgttgta tgccaatagg tattatgtaa taaattataa 1380
atgatataat attaaaaaca ataattcata ccattttttta aacataaaaa catgcttagt 1440
agattagtta taaacagttt caagtaatat ttaaaagaga gtcataagta gttttataat 1500
ttataaaata caatatcaaa cgtacttaaa actaattgct tttaacttca aatctaaatt 1560
aagaataaga aaagggagag tgggaaagag caaaatgaga gaaaatgtcg aaaatacgcc 1620
caacggttcg gaccggtcca tttttgtccc gcgcaatggt aaaaatagat taggttacga 1680
caatcaccat gatgatgagg atgatgatga tcatagcaat tcaagaagca tagggcccca 1740
cttttggccc tcttattttc tcttctctta cttactttaa agaatctaac tgtcctccat 1800
taccccgccg atcaatgctc tatttttctc tctctttttt cttttcttta ttaaacaata 1860
ataacaaaaa ccatcaaatt ttcaaaattt tgaattatat tcccttaaca caaaacactc 1920
tcctcttttc ctttctctta taaatacaag tggagctcca cacacttgtc attttgtacc 1980
cttcttcccc aacctcccaa 2000

<210> SEQ ID NO 124
<211> LENGTH: 2000

<212> TYPE: DNA
<213> ORGANISM: Cucumis melo

<400> SEQUENCE: 124
gggcttccat tggcctcctt cccgtcgccg tagtgagaga aaaaagaaag aaaggggaga 60
ggcagaagaa tttgagagat ggatcgagga gaggttttgg aatgaatggg aaatttgaag 120
gaagaggttt aaacataaaa gtgaggcacg tgcgagaatg caaatattta cggggctaaa 180
aatgggagag ccaacggatt caccccagta aaaaggtaaa ttcaaacacg tttatgcctt 240
tttacctttt tctttctttt tttaacacct atagatgtaa gatatttcat attcttaact 300
ttctctttct cttttctttt ttgttttact atttcccttt cgttggctaa taataaaaat 360
tgatggatac agtatatttg gtatgtcatc ataaatttag agaaggtatt aagattttgt 420
gacataaaaa cccaatttct tttaatgaga ttcttagaaa ttttattgaa gagaattata 480
aactttacgt aaattaggta aagtctttcc ctccttctcg atagaagttg ataataaaca 540
tagcatacct agataaaagt ttgggaacat ttttgttgtt tggagggttg aaaaaaatta 600
agaaatttca atttggttag gatttgatgt cttgattttt tgaaatataa actttcaatt 660
ccaaatggtc ggacttggaa cctaacaaat cgtgttttca attttacctt gatattttag 720
atgtgtgaga ctccattaag tattctcttc gctctcttct tactatttct ctgttttgct 780
atcgaacgat attttttta aaagatttat tttttaattg gtggaatgtt tgtatgagag 840
tatataagtt aaggtaaaca aataataatt ggttatttag caatcttcct agtcaataag 900
caaaacagac ctaacatgca tcaaagaaac aaaatcaaaa ccttaaaata tcatggttgg 960
gcgttgattt tttttttctt ttaatgtttg aaaatgtggg ctttgggtgc cgcagtcgta 1020
tggttgtagg gatttctttt aagaaaatta ttttatattg tattcgtttt gatctgaaga 1080
tatcaattat acaataattg gaatataagg agtaatttaa ctttgttcgt gattgttttc 1140
tactttattc gatgtgtatt ttggaattaa atatgatttc aaatgatttt gtttatttct 1200
ttttattgat tttgttttga ttttactttg tatcaatttt gaatatcaat gtagtgatgt 1260
gcttgtatta aatgtattgg ttgataaatt tactatgcaa atttttttc aaaatttatg 1320
caattcattg tagtattatt aactatatca acacatcagt aaagtgaatc attatcaagt 1380
atatcaatta agttacaaag tgtatatatc aataatgtat caagtttatc agtagcactt 1440
taagcatata aagtgtattt aatcaattaa ctgtaccagt gaatcttact agatgtattt 1500
gcagtacatc cgacgtatca aacatatcat gtgtatcata tgtttaaatt tgttgagtat 1560
attagtgaaa cataacaagt ttattagtag tgcatcaagt atatcaaatt tatcagttaa 1620
acatttaagt ctactaagaa aaaatgagtg caataaaaat tatttttcgg atatataaaa 1680
aaatattgag tgtatcgaag agttccatgg tgcatcaaat atataaagat aaaaaaaatat 1740
caagaaatat taaatgtata tccatatatc aagaaacaaa cctaacatgt atttcgtgat 1800
ccaacaaccg gactggaaga caaatttcgg cccgggactt tcatagtcca aataaaggcc 1860
cattaaactt aacctgggcc caaattaatt tgtaaatttt aagtataaaa agaagagaaa 1920
ccctagggtt tccttcattc accaggcctt cctatcccct tcccttcccc ccctccccat 1980
tcccattttt gccggccgcc 2000

<210> SEQ ID NO 125
<211> LENGTH: 2000
<212> TYPE: DNA
<213> ORGANISM: Cucumis melo

<400> SEQUENCE: 125

```
ggacttatgg ggaatgggtt caagtgatgg taactagcta cttcagattt aatatcctaa      60
attgccttgg caacccaatt caaatgtatt aggattagat aggtgttttg tgaggatagt     120
taataaggtg cttgcaagtt ggtgtcgaca ttcccaaatg tgaagggaaa aaaaccccaa     180
tctttggtct caactggact ttggttcatt gcagttgaaa ataaattatt ttagttcaaa     240
ccaataaaac acatttttta aaatctttgg atatttgttt cttaaagttc ctgaaacagc     300
ccaccaagtc catagcaatt aggaaggcat aagttagagc tagtatgctt ggcatggttg     360
ggggtgggtt accttgttat gtaaattcat agaaatattc atatcttgtg ctaaaagtca     420
aatggaaaga gggtgattgc tgtgatgctg tctaatacaa agtgctagaa gccatatgga     480
gaaagggtat ttctacagtg tctaataagt taattacata ataaatttct aggttatgag     540
aatccaatcc gcatgaattt aaggactgca cacttgctcc atttgcaaca tgtgtaccac     600
tttagaatca tatttcacct gagttcatta ttcaactaga ttaatgtatc tcttttggtg     660
ttacatgttt ttaagaacat aattatttta gtttactgtc ggagagaagc aagtactggt     720
tatgcatggt tctagtgagc ctaatagagt aaggctatgg tttgggcatt tggaagtttt     780
agtggattag aattttgaag gcaaagctaa ggatcataca cgcccttctt ccctttttgac     840
cagttggaga tctatcatgt aactctattg tcttgggctt cggccttatt ttataaattt     900
catatatcaa tgaaatttat ttcctataaa aaaaagaaaa aagaaaaaaa gctaaggatt     960
ttaatatcat tgttagtttc tttaattttt ttctttggga agtgtgcatg tagagctcct    1020
ttgaaagaga aaaagcaaag aactcttgaa tgtaaaatct ctatgtttga gttttatagt    1080
agcgtaccac attcacttca tggtgatgta gttatagttt tcctatggaa tatggctatt    1140
aatttttgcg aggctcttat tttatagttc ttttggggtg ttctttcctg taccccctcc    1200
cctttttgtg agaaggggag gtttctgtgg ctagctgggt tggtttagat ttgtggacct    1260
tttttgtgag aggaaccata gaaccttttg atgaggacct cgagcactat ttgatcattt    1320
ataagtttcc ataggctttt gtaattacct ttttggtctt attttaattg gagtcccctt    1380
cctccccttt tgttggcttt tttgttgtat ggttgggcat tctttcgtta gggaagtttg    1440
ataattcaca taataaacat acaataaaca accatcaata caatcaacaa gcaggattag    1500
tgtaatactg taaatgtctt ttattttctt tactcctttt ttcttttgag gtctatgata    1560
attgatatcc aacagtgtat tggccaaaat gatttatcat ggtcagtacc ttaggggttt    1620
gacttccaat ccaggattta aggtttgaga ccagatattc tgtgcctcaa ggccctcaac    1680
aaccttctca tggctttttc ctgtatacat attattatat aaagttataa ccaataaaag    1740
ggacaggtca aatcctctta atatatgcga aaatcaacct aatgtctact gtataccttc    1800
tcaatcgcca ccttcctcct gctgtcatcc aaggtagggc cttattgtat cagctagctc    1860
cctttactta tttatttatt ttttgaagtg cgcagtttgt ttgtttacct tgttatagga    1920
aattcaatct attctcattt tattggtgca ttcgtctcag aaattcttgt acggtttcag    1980
gttatcatct acccttgtag                                                2000
```

<210> SEQ ID NO 126
<211> LENGTH: 1397
<212> TYPE: DNA
<213> ORGANISM: Cucumis melo

<400> SEQUENCE: 126

```
tatatatatt aacttttaaa attttgaaaa cgtcatagat aaattatata caaaataaaa      60
```

```
agtttgatta tttacgaaag ttaaaaagtt tatccgaaag ttgactcaac gataaaaaca    120
ctaaatatca cttttagaga tgatgatatt atacataaac atacgaactt acgcgtcaaa    180
cttttatact aacacaagat caaaacaact ttgttgagta gtgagaattt tatctgctga    240
tatggttgaa acttgggaag caagcagagg aagttccatt cattaccaaa atccattttg    300
tattcatcaa aatatgaagt ttagcgactt gataaagtca agtcaagtgg tcctatcgat    360
ttgttaatgt caatgtttgg ttttgaattt gatacctatt agacaatgat atataatttt    420
aagtatggtt tacactgtga tgctttatat atttttaaat gtaaaatatt agaacttgta    480
atttcaataa attttaaaaa tgattttgtg ttatttcctt ttttaaattg aaatatcaat    540
gtatcaatat tgcgtcatag agtattgcaa cacaacctta tgttaaattg tttattgctt    600
attgctctaa ttcaactcct tcatcaaatg tgcacagaat ttaaacaaga aaaagagtag    660
gtgctttttt actaaaatat actaaaagct ttttatacca aatcttatga caaaatcatt    720
ccaacaaaat gactatttaa atataagatc gaatccctaa tttaaaaaaa aaaaatcaaa    780
gatgttaatt tctattatta aactcacttt agcgtagcta acaaaaaaag gaaaaatgag    840
aggctacaaa gcttgagccc tctgcctccc tttattgcat tgtttgaaat tagatcaata    900
ctttgtattt ttttcaaaat gaaaaatcgt acatagaatt aattctatgg acaaaaaatc    960
agagaaggaa ataatctaga ataaaattcg atttttaacc caaaaaaaaa aaaaaaactc   1020
gattctgatt tttgtaagca atcacccaaa ttaccataaa taaatggtat tcaattactc   1080
aattatggat attttagaaa tgataaattt ttattcataa actcttttct ttctctttca   1140
aaaagaaaaa aattagcata aacttcaatg acatttattt attcttcttc gtttggagtc   1200
aaaagtttaa attgagcatc agtccagccc aaaagcccac gaagaagccc aagaatcttc   1260
agctttttcg ttcaaacgtc ccttttttggt ttataaaatt aaagaaaata aaaactaaat   1320
ttatttgtta tttaacaaaa catttttggt taagacattc tctttgatta tttttcttcc   1380
attcttcgtc gtcaatc                                                  1397
```

```
<210> SEQ ID NO 127
<211> LENGTH: 2000
<212> TYPE: DNA
<213> ORGANISM: Cucumis melo
<220> FEATURE:
<221> NAME/KEY: misc_feature
<222> LOCATION: (1)..(2000)
<223> OTHER INFORMATION: n=g, a, c or t.
<220> FEATURE:
<221> NAME/KEY: unsure
<222> LOCATION: (1)..(2000)
<223> OTHER INFORMATION: unsure at all n locations

<400> SEQUENCE: 127
```

```
tttatattta tgaaaatgaa gtctctaaac aatttttcta ctcccaaatt tgttgatttt     60
tctgcctatt ctttatcggt gctttaaaaa atgaaaccaa atttcaaaac taaaaaaacc    120
aagcttttaa aaaaatgtta ggttattttt gaaattcaac taaatgttga actcttttac    180
ttattaaata ggcaaattat tgaaataaat ttagagcaag taagcttaat ttttaaaact    240
aatatactta ccaaatcgag gactaaaata ttcaaatact ctttaaaatt aagattaaca    300
ttaatcactt tgttatgttt aaaaagttgc agtgtcactt gaaccttttt aaattaatat    360
aatgaaaatg aatccaactc aatatatata atatctatat tattaatctc gatgtcagat    420
gtttgatacg cacatatctc aaaaattata cctcaactaa catcggtgca cgatgtatta    480
```

```
tttcgtgagg ataaaaatcg tttttagtat aaattgatgg aaagattatt tgaattactg    540

aaaaatgcac cggtacatta tttgaaactt ccccttcatt taaagaggct aatattagaa    600

aaagacacgc tgaggctatt tttacaatta atgtgggctg ttgacttggc ccagcccaaa    660

acataaaccc taaagtagca caaacaaacg cctctttctt cttgaaaccg catattaagc    720

gttttatcac ttctcaccac ctctcattcc tcctcttccg cacgttgttt cgctcctcaa    780

cgggagtgcc ttccctttgc tctccctcca ggttcttctt ccttctcatc tcatttccaa    840

gtaatttcat tccgtttctt ttctcttaat cgtatcttgt tcagactctt tcgcgttttt    900

ttttagttgc gccttaccag atctgtgttt tcactcgttt ctattcgata catgcttcca    960

agatccattt cttaatcgca tgtattcggt tgattggatg attgtctttt tgtaagtttt   1020

gattactttt ttggaatgga tcggttgaac caacggggtt taagtcgatg gaagtaggtt   1080

atgttaaaga tttgcttctt ttttttatg aagatgtgtg tgttcttttt ctttgctaga   1140

tgatgttatt atttgattgt tttaacagtc gtgttttgtt tttctgcagt ttatagtcct   1200

cggtcttttg aagacttgtc aagatggtta gtacacctct tgtcatcgtg attttgattg   1260

agtgatgtgt taagtgcttc tttaggttac agctaacgcg atttttata ttcaattgtg   1320

cctgtgcagg tgaagtttac agcagaagag ctccgtcgga ttatggacta taagcataac   1380

attcgtaata tgtctgttat tgctcacgtc gatcatggta agctacttag tttaagttta   1440

tttatgccga gcgtctattt aagaagatta acatcttagc tttcatttat tgtttatttg   1500

gtaagcatcg tttctttttc tccgaggaac tgtacatgtc agttcacatg acaataaaac   1560

gatcttcctt ggacattagt ttttgaagtt caattagacg ccaaattttg ttggttaaaa   1620

gatgcttgtg gagcatatgg acctaatgga atcagtactt tttgatggat ggacttgtct   1680

tttgttcttt tattttcaaa agaaattgca tgtgcaatta catcatcttt gatcgaaaga   1740

ttgggtaatt gggtaattgg ggtaaagaca tgttgtaaaa actaatgtta attatcaatt   1800

accattatat accttattta gtgcttattt atatcctttt tccccatttc agggaagtcc   1860

actctcacag attctcttgt ggctgctgcc ggtatcattg cacaagaagt tgcnnngatg   1920

tacgaatgac agatactcgt caagatgagg cagagcgtgg tatcaccatt aaatctactg   1980

gaatctccct ctactatgag                                               2000


<210> SEQ ID NO 128
<211> LENGTH: 1657
<212> TYPE: DNA
<213> ORGANISM: Cucumis melo

<400> SEQUENCE: 128

ggcaaaatgg agagaaaaaa gtttctccct attgccacat ttatatatag tatatagata     60

tatactatag acatgatgga gaatcataag ataaggtaag gctgaggaag attttgacga    120

tatagaatgg aaaattttga agatataaaa tggaagattt tgaaaatata gaataagatc    180

atcaaatgat agcaaaaaaa tccaaatgag tcagatgaaa cactacgcca aattttcatc    240

actccaaaat tgttgcaaag gagattgatt aatagggtat tatacacaat catatttttc    300

gtagcatgat aattggttaa taattagaca taatggcaat caattagtta actaatacaa    360

cattttaggt agcaatatta aaattggaga tccggaaaaa aactaaaaac tcagaaaaat    420

cttgggcaaa atgagcacgg tttatcaaat ttttaggctt ttttggtaca attttgtcta    480

ggatgaaacg agatccataa ttttctttga gaagataaaa aaaattaaga tttggtgtaa    540

gatttgggaa gatttgaata attttttaa aagaaaaaat aagatttgga aaatggtaga    600
```

ataacggtct aatgtctccc aagatgcacc gggaaagcaa aaaacaacca aaacaataaa 660
taaattggaa aattttaata ttttaggaaa atctcgatgt caatttcgtc taagattgga 720
tcgagaaaaa cagttttacg agtttttaaa aaatgtgtta tatttaaaaa taaaatcaaa 780
attgtgctac ttttgtcaat ttcccaagat aaaaatgtat gcttccacgt aaaaagtaac 840
attactaccc ttctttcatt taatctctat atttggaaat gtcgcactag ttcttggtag 900
ctaatatttg gatactaatt atcttatatg acaaaatatt taatgtactt ttttttaca 960 acaaatattg aatgaactta aataatcttt tcactgcaat gaaaaaagat aaattagagc 1020
atcccaaaaa gatgaaaagt tcgaaagtct gctaactaca ttgaaaaaca aagcatttaa 1080
ttcttcaaac ttgatagttc aattaaattt ctaccaacta actcaagtaa atctattatt 1140
agtgtttgag tgaggctatg aactctaaga ctaagcctat aagtttggtt aaatttaatt 1200
ataccagccc ttttgtaagt aatttgattt gaaaggtaag acgtaatacc gattacccaa 1260
cccaaaatta ctgtgaatga gttaaaaaat aaaattagtt gaattttaaa taaaaagcat 1320
accaataaga cgatgacaca tgtacaaaat cttagaagga gaagcttcat ttgaggacaa 1380
aaaagagtgt gtggagtgag aagaaagaat agtcacgaat attgctgact gtgcaacaaa 1440
tgtacatttg gcaccaatca aaacctataa aaccttatcc aaaaatcaat aatctcatcc 1500
cttcttcgct gttcttcccc aatccaaacc ccaaccattc tcctccacac acacacacac 1560
tcacatacac aaatccttcc aacattattc tatacccact tcccaattct cattgcattt 1620
cacaatcatt gttctaactc acttacaacc tccatca 1657

<210> SEQ ID NO 129
<211> LENGTH: 2000
<212> TYPE: DNA
<213> ORGANISM: Cucumis melo

<400> SEQUENCE: 129
atgaacgaag gagaatatcg gataatgaag aggagatcca tgaatcacag agaatgaatg 60
aaggagaccc acgtgaatta aatagaacga aggagaatga agagaaagga tgaatacttc 120
ttttctttaa ttttaaccta atcgggtgaa tcaaactcaa atcgaaactg gtttagttcg 180
attatgtttg gtaccattgt cttttaaacc gatcaaacct gaaccaaacg aatcggtacg 240
gttttttgca cccctaattt atatcatgtg aaaggtttta agttaagggt cagctagtgt 300
cgtttagagg gaatgatatt ggttgacttc atgtcgtctc ttggatcaag agtaggagat 360
tcgggagggg tgtgacgaaa tcaaccccga gattgtccta cagatggcat gtaaaatgca 420
tcatatctcg ggactccttc tacaaactcg agaaaaatgt ctcttgagat tcttcttcta 480
cacagcccca aattgatgaa atgactgaga ttctttgaaa gacaccacat gcattaactg 540
aaactaatgt tgtacatcta aaaaactaca tcacgccacc aactaaaaag ttttccattt 600
gcctgatttc aaactaaaaa caaaagactt aaacgataaa ctaaaaacta aaccacaaac 660
aatgaaatcg ttaaaagtgc accttgagag atttaagaga gtaaatgagt tcacatagtt 720
ttttgaagga aaaatcacta aaacaagttg gattgtagga gcgaaattgt tcactcctta 780
accgaaatta gcaaaatgtt tggagtttag cgtttttaga gaatatgtaa cgttatgaat 840
aataagggta ttttggtaat ttgatatatc cctttatttt caaattttta ataaaaaaca 900
cacatcttgg tgacacactc gactgaaaag gaccaagata tttccttgaa agattttttt 960
ttttaaattg ggaaagaatc ttggggtcga tctcgatcga gattgatcga gaaaaataga 1020
attacgagtt ttctaaaact gtgcttttga aatatcacac caaaaaagcg ttatttctca 1080
aaatttccca agtttatatg tgggggttat tgcgagttag cttttgatgg gtttgctttt 1140
gggtgtttgt atataggttt gaaatgtacc tttaatgtcg atttttgaag aaaggtacct 1200
ttattgttta aaattgacat tgtaccttca tatttgattt cagtttaaaa ttgatattaa 1260
ttatccgcat tttaaaaacc aacatcaaac atccatgttc atttcttttc aaatttaagc 1320
ttgaggatga cttcgtgaaa ctttttgagc aaacacgttt atcggttgtt caaagtaaat 1380
caccttcaca aatttaagct tgaggacgac tttgtgaaat ttcggcaagc aaaaatcaga 1440
caaatctctt caatcttttt tgagcaaaca cactttatct ctgctgaaat gagcacaagg 1500
tttagggttt tgagaatatc tagcatttag gctttcaatg gtattttggt catttgagaa 1560
taccatttat tttgaaattt taaaacaaaa acctaccatc ttggtgacga tcatttaggc 1620
cgagatgtat tgaaaaatta tgttaaaatg agtttttcaa atttgattag aacctcgtgt 1680
tgaggtcgac cgaaattgac cgagaaaaat aaatttacga atttttttc aaaatgtgct 1740 acttttaaaa tataaaacta aatgggttac ttctcaaaag ctaaccgaaa ctattagtta 1800
tattgcggaa atatcaattt cgcccaattt tagtcatcca gagcctgact catcgaattt 1860
aggagattct agacgttgca ttcaggagat ttttatccgt tgtcgccgac tctctttact 1920
gatctacatt gtacttcatt gctgaactca acgagtcaac tcaatcgttt ctagatttgg 1980
aagaatctgc ttcagcgacg 2000

<210> SEQ ID NO 130
<211> LENGTH: 2000
<212> TYPE: DNA
<213> ORGANISM: Cucumis melo
<220> FEATURE:
<221> NAME/KEY: misc_feature
<222> LOCATION: (1)..(2000)
<223> OTHER INFORMATION: n=g, a, t or c.
<220> FEATURE:
<221> NAME/KEY: unsure
<222> LOCATION: (1)..(2000)
<223> OTHER INFORMATION: unsure at all n locations

<400> SEQUENCE: 130
aaaaggcgaa aaaaaagtta gcttcccgag aaggagaaga cgaggaagag tttgacttcc 60
cggggagata aagtttgtgt ctcgagggaa tctctaatct ggagttgacc gtcgacttat 120
gtgtcgagcc tggatttagt tgcatggtgc gacaaagcga taaggcggca tatgtaaagt 180
agtaattcaa aactagcggt taaagaaata atcagccaaa aaatttagta caaatacggg 240
tggaggccct aagtgaagtg ctgctattca gaggttttgg caaaagagtg caaagagttg 300
agttgtgcag agaaagtact aggtgaggag aggcgtttgg aaaagaaaag gatcaaacat 360
ttgcatgagt gatattctta aactaaacac tcttgtgtga gtgacttgcc taagctaaac 420
actcttgcat gagtaacttt cttaaactaa acgttttgta atgttttctt aatggattct 480
tttcgagtct gagttatgct taacacgttt tgtttctctc gtgttattgt tgttgttgtt 540
tgaaaagaga aaactattgt tttctatgtg ctgattgtga tgaatgtgtg cgaaccatta 600
gccttaatcc tatcaagtga atagtgatta tgtggtgtgt gcacataatg taaatgacat 660
tgtgtggatg gccagtgcaa caagaaatga atcagaaagc ttcccaaata ctgtgaatgg 720
agtgaacatc acactagctc aatggcaaga tattggcgat agtgaatcac aataggcttg 780
acaaggggaa ggattcatgt tcttggttga aaggaataag agaggctaat gtgagatttc 840
tgtgatttgc aaaatgaggc gttggaagac acgtttgaga aatgaaaacg aattagtgct 900

```
tgacttgtat tcctaaaaaa gttgtccaat atcttcaatc actaaatatt tgatgtgcct    960
aagttttcct tccttagttg ttgaggcgtt gaggccgagt aaggaaagat aagataatta   1020
tgacgttgaa aagctggtca agttatccat ctttggatgg tttaaagtta ttacatgtag   1080
ggagggttgc attccaattt tgtgtgtgag atgagtctta ttttcgagat gggttgctag   1140
gcgatcaagg agaagtataa gaaatgagtt cttatactct tgaacaactt gacacgaaga   1200
ataacatcct agtggatgaa ggaaggtgat ggaacttaaa gtttaggttt tattttnnnn   1260
nnnnnnnnnn nnnnnaaatg taattgtaaa gtattagatc aagtaataaa acagagttgt   1320
gttttctatt tttgctgtgt tgggttgtgt atctttattg tgcttatggc ctagttgcta   1380
aagagttaag gttattacct aaatgtttta cggtgtgttg agttgtaaag atctcctgag   1440
ttaaagttgg aattttgtat tggagattgt tttgagaagt ttagcttact aattgtttaa   1500
ctcattaggt gtctaagcga cacgcctcct tttggtcgca tgaagtggct agcagggtgg   1560
ggcggaccgg ggtggggtgt gataataaac ctaaaaaatc acccagataa gcctaaatta   1620
tacgttgaag ttaaacttac aatttgatta gaagaagaag gaatatctga tttggacatg   1680
aattaattac aaatacggcg ccaatcatac aaagcacatg taagatcaac gcattctaca   1740
ctcaatctca gccgttgatt gctttcaatc cttcaaaaag aaaaaaagaa gggcagttcg   1800
ggcagagtca tacctacccg ttgactataa aagcaactac aaatcgaaaa cctccatttc   1860
tccgttacca ttacagagaa aatcaaagaa atttggcgtt gagagattgg gagagaggtt   1920
tctctttcta gggttgcttc ttcttcttca tcctccattg ttgcaaattt cacttccttc   1980
tcctcttgtt ctcatctccc                                               2000
```

<210> SEQ ID NO 131
<211> LENGTH: 2000
<212> TYPE: DNA
<213> ORGANISM: Cucumis melo

<400> SEQUENCE: 131

```
atagagtaac caatatgccc ttttcagcag ccaaagtttt ctatgggcag acttaatcaa     60
ttaaggttcc tattgaggcc ccactcttag tgaaaagcct agacccttct ttccaacatg    120
tctcaattgg tcacctccat caaaagcttc tatcatttaa tctaaaagca tactcttttt    180
tcctttttaa atttcatttt gatggtctat atttgaaaat aataatcact acaacgacga    240
cacgttgttt tcaaactatt attttgtatg aattaataat ttttttaata gtatagttgt    300
tttacttatg gaatctatac gtttaatcga ttcggtcaca tctatttact ttgatgtttt    360
tgttatttta tttagacgtg gttgtaaaga gtttaaagca atggagaaga aattgatgct    420
ttccaaagca atacaaattt atatatacct tcaaatgaga ctaacattag acaatacata    480
aactataata aacattttga aagtacatag atcaaaatga accaaagtcg aaaaagtaca    540
attatcaaat tagtttttaa accttggata aacttcagca ttcaaacttt gtatttcttt    600
tttttttcga tcgatatata tagtgataga agattttttt tttctgttta ttatttttga    660
cgatacgttg agtagaagaa tcgaacatca aacctttaaa tcaataatat atattttacg    720
actcaatatc tagccatcaa tattttaaaa tagcaattat tattcactaa attatgttag    780
agattggatg tcatacaaca attgttaaag attatttgtc tagtttgttc aattaatcaa    840
gagagcatta agcattaaag tcaattattg tgataagatg cttttgcact atgtaactaa    900
aaatagttgg atacaccatt taaggcccta catgcaaacc atgataggcc cacaaaaaaa    960
```

```
aatctctttt tggaaacaat ggtcaaataa tttctttcaa ataataataa taattacaac   1020

aaataaatac ataaaccaaa ttactaaact aatgtatcaa gttctagaga aaacaaaatt   1080

atgccctttc aagttgcaac atcccctact ataatttttc ttcaaatttt ccatttaata   1140

taatccaatt ctaaacatgg aaaagaaatg taacaatatt tacattattt caatctttcc   1200

tatattcatc gactaatttt aataagacgt gaaatcaaca tttttctaaa ctcgttgatg   1260

tcataaaaaa taaacttaaa ttatgtacaa gatcgtctat taaattatgt ataacacgtg   1320

tggtgtatga gtaatagaaa ctttaaactc ttgatcaagg acatgtacct ataaataaat   1380

agatttcttt aagtcttgac tattaaccaa cttgtattca gtaaggttaa agtgatctat   1440

tatcatacta aatacacaag tttatttcga gtatgaatgc aaagaatcaa agatatatgg   1500

tttaaacaaa atctattata ccaataaaaa aggttaacca tatgcaataa aaactaaaaa   1560

gtctattgct caaatctctt tcgagaccat attaaaaatg ttagtttaat tgacgtatgt   1620

atttattgga tttatctaat aacattttaa gagattgttg caaatatagc tattagattc   1680

aaaataatta agtatatagc aaagtctgtc aaattctatc gatgatagga ctatgttaaa   1740

attgttgttc gatcgttggt aaactataaa aatctacgac aataaactac tattcaaaaa   1800

ttttttacta cccaaatttt aaatccatct catggatcga gtcaagccca cttctaaatt   1860

gggccacgaa tattgattgt gaagctcaat aatcccatac gtatggctga aaacgcatta   1920

cgaacgaacg cccttcaact atccaaatcc gaacccaccc aaattccggt taggcttctt   1980

ctccgagatc gacgaccgcg                                                2000
```

<210> SEQ ID NO 132
<211> LENGTH: 2000
<212> TYPE: DNA
<213> ORGANISM: Cucumis melo

<400> SEQUENCE: 132

```
tgcagctgca caaaagattc caaatgatat aacataatag tttatgaaaa tttaatgcat     60

ttaatttccc cttccacaga agacactata tttttcaact acccaacaat accaataatt    120

atcattatta ttatacctct aattagtaat tagtcacaac ataaacagct attctcatta    180

atacatataa tcaacaactt cataaattct taaatttgta tgtgtacttg atgggtgtag    240

atttaagaag tccaagagtt tgacaccctt tgttaaaatg atatacaaat tcctgcaaat    300

taaatttacc attggtatga ttgttgttgg agtggtcaca acactaattt actaattagc    360

ttcgtattta acatagttgg ccatgcgagg aggtagcttt tgaacttcca ataacctggc    420

ttggaaggac gtcgataaac agaataacaa ctatgctaaa ttttgaataa tatactttat    480

atatattata taaagacgac aaagttgagg agcatccgtc ccctacattt gttggtgctc    540

atatcatcct attgcatatg ccttttacca atgaaaccct atctccttaa ttatttctac    600

tccacactca taattatcat tcatttattt tcatgcatga ctttctttta ccaaatttag    660

tttccaatta aactccatta actaccaaca atcaactcca ataacgtaac tcacattcat    720

tctaaccaat tgtttggatt gactcgagaa aaaaaaatgt tttttctaac tcatttttac    780

ttatacattt aaaaattctt ttggaagtga tcgtcaaaca ttttgatatt tttttccttt    840

taaaatgact tattttttaa aaaacttaaa tattcaaaaa ggttttccaa atgaatgtaa    900

ttaattactc aacatagatc tccattaatc attattatat gtaacaatag taattcaaag    960

taaaaaaaaa attatgtgga gtgcaaagat gaaaattttg acctatttta catgatttga   1020

actatatgtt tatgcgtacc tatgatttaa ctcttatata cacatatttt tgtctcaatt   1080
```

taatttaatt ttacgatttt cttgaataat tttattctct aaccactttt gaaaaacatt 1140
ttttaaactt tagaaaagaa tatctttacc aaacttaatt caatatatga aaatagctaa 1200
ataaaattta aaaaacagat aaccaccctt tgataactgt agctgatatt attaattaat 1260
tgtcatattt atatttgcaa tatgaaaaag gagatgtcat gagttttttt ttttttaatc 1320
aatctaatgc aattttctta aatttaatta atgtgaaggt gagagagaga ggcaatttca 1380
aattttaggt aagtattatg aataaggtta cttaacatta ttttaattta attttacatt 1440
atgttttatt tgaatttttt taaagactct catttttcca ttttggaact tttggaaaag 1500
aaaattttac ttcaatctct tatgcaagca agttaaaact acatttgtct tttcatggga 1560
tttttaagga gatgtgtggg gaaatacaat aagccttttt ttatttgcaa tttgctaaat 1620
gtgtattctt ccaattggct aattattaaa gtgaaattta gattgaaaaa agagataaaa 1680
ttgaattgaa gttgtataga tgggttagga atatgaaaat tgtttgagat atagtgagta 1740
ttggttttat ccaatgccat gtcatagggg tggaatccaa atgaaccaat gagaatcact 1800
caaaagaaaa cagatataat gcactatcca aacctaaaac taaaagccac acattgctca 1860
tccattcact cccattctca aaaccacaca aaaataaata tcaaatcaat ctctttccct 1920
tttccatata taccactttc ccctctcttc gcctctttga ttattaccca ccaaatattc 1980
ccatatatct tacaacaacc 2000

<210> SEQ ID NO 133
<211> LENGTH: 2000
<212> TYPE: DNA
<213> ORGANISM: Cucumis melo
<220> FEATURE:
<221> NAME/KEY: misc_feature
<222> LOCATION: (1)..(2000)
<223> OTHER INFORMATION: n=g, a, t or c.
<220> FEATURE:
<221> NAME/KEY: unsure
<222> LOCATION: (1)..(2000)
<223> OTHER INFORMATION: unsure at all n locations

<400> SEQUENCE: 133
aagcttgttt gaccctattt ttaatgtctt aacacaggat tatgaacaaa agaagaaact 60
agtgaatcac agaggaactc acgcaaagac taggtgagaa gatcatatca aaatgagaga 120
ataagttcgc tagaagataa aagtggtagt tgaagttgat gtgacttgac caagaggcag 180
cttctggtgt tgatatattc agaagactag atttcctgcc taaatctacc tatataaaga 240
actccatctc cattaagaaa atgaggcctg aatggaccac ccaagtggtc gactgtgtga 300
agagccaaat gtttgtgaac tgcccatgag tgcctgaaag gcccgatcct agagagtggt 360
gggaaggagc agcctttcca ccatctgtaa agtctttctt catcttctcc agttagttta 420
agagtgaaag tttgaggttg agtgaagaag attccattcc tatctttttc taactggtaa 480
tgtcatttct attctttcca tttttgtata tttctttgta atgtatttnn ncatattgta 540
cagtggccta agacctatat tctttaatac atttcatgtt tatatctttt caatctatca 600
cgtttgttat tattcatctg tccttgtgct attggtagct taagatttat gataagttct 660
tgataagaag gttagcttat atttcttatg tgtgttagtt gtgagctatt ttcatcacct 720
ggctagtgta tattgcaaac tacctgagag ggtaagtagc aaagatatgg cttaggcgca 780
caaggaggag tttggagaca aaatccacat tggcaagata acttccatca tttgtgtctc 840
aaaaggagaa caagtgtggg tattaagcat tgagatgttg tgacccttaa acgagaagct 900

-continued

```
atataagtct tagtgaaggt cgtttggatc tcgagaggtg agcaagtgtg gtgtttaaag    960
acaccgagag gtgctcgtct taatcataag ctcgttaact aagttatatt gcattaggga   1020
tattttattg cttaatttct tggtaatgca cgaacttttt ttcacccatt cttttatgcc   1080
agctagttca caattccatc tcgcatccat tttaatcccc ctttacagat tctccggtgt   1140
agataagtag atatagttta aacttacatg ctttcacact atatatttta ttcttttata   1200
ctacctaaat gcctagtgaa gcctagaact aagctttgat atcgattccc tgcattcgac   1260
tctaaatcgc ccatataaac ctattgtttc gcttacactt gggcaagcaa taggaaaact   1320
tgtactcaac gaggacttat gagttacatg atgacgagat acatagagag catctaatat   1380
gcattgacca tgatcattga ctcttcatgt agatttaaat acctttcagc ttaattagat   1440
agaagatata taataaagcc attccattag tttaaaagaa ttaagttaga ggtagttgaa   1500
atgctttata agtgggggtt aattctattt tagctgtaat gctgagctga tctcaagcca   1560
aggttgcctt gagatatccc cgagtttaaa aacagaagct aaaatggaaa ctaaaaacta   1620
agacatataa actttttagt tacttttagg gaaatatctt agctataaat taaagaatat   1680
gaccaacatg gaagttcctc catcactttt ccaccaactc attttattgg gggttagtca   1740
ttttaaggcc aattagttta aattaaagtt caatctcagt gatgcactag gccgagagag   1800
accgagataa atcattcaaa tatttttta aatttgggaa gaatcttgag gtcgagattg   1860
atcctgagaa aaacaaaatt acgagttttt taaaactgtg aaatataaaa caaaaaagtg   1920
ctagttttgt caattcccat ttatcttgct cattgttgat acaagatcat taaaagttta   1980
tggataaatg ttggttgaga                                               2000
```

<210> SEQ ID NO 134
<211> LENGTH: 1696
<212> TYPE: DNA
<213> ORGANISM: Cucumis melo

<400> SEQUENCE: 134

```
tatatatata tataaaaaga ggaatacaat taagacatcc cattgttaat aaggggtgga     60
ataaattggg aaattaccat tcgagaaatc attgacgaga gcaaatatgt caaagtagaa    120
aattagtcat ctcaaaagaa tgtaatcgtt acaaaaatta aaagtacgta aatttaatca    180
tcgttacaaa aattaaaaga atataaatta caccgttaca caataatacc aacaatccat    240
ttataatatg ttgtttttat ttcaactttg aataaaattt gaactctttg ataaaatttg    300
tttaaaataa atttaaaacc atttcaaaag ctatttttat attatccaaa tacatatatt    360
cttttctttt tccaaaatga cttgtttcta aattcgaaca tccaaaaatt aaaacataac    420
atttttagta tattaagaat tataaattaa gagataaaat attcaatact attataataa    480
aatcggtgtt ttcagtaatt gtatttgtac aagtaaataa aattaatagt aaaattttta    540
atatataaac aagttttaaa agaaacttaa agatataaaa aataaattga aataaaattc    600
aaacccatca acaaataaag aaaataaaga tggttttatt gaaatgaatg aactaaaatt    660
tgaaggaggc aaaagtaagt acaccaaaaa tagaatacta aaatggtaga ggacaataat    720
tgcatatgtt tggtagattt ttcattaact atcataccaa ttaacaataa tgaaataaac    780
tttctcgttg atattgatta caatcgtaat agggcaaccc actgtttaac ttgtcaaagt    840
tttcttaact ttattatttt tgactttatt tgtttgtttt attgattaga ttgatagatt    900
atatatttta atcatattat ttatagtaca acaactacga ggtaagtgat tgaagcttta    960
gtctctaaga acaaaggttc gacctaattt tttagtctgt ttttatttga catattttgt   1020
```

```
ccattgatag aattactatc acttaagtta aatgtattat tattgcaaac cactaattct   1080
acgtaaaatc tctaagtagc aagtgttatg tcaataaaat agcaattttt tttttaccaa   1140
ttacacacat catggtgata attattatca tgcacgggta aatttttaat tataaaattt   1200
caactttcaa aattatacca atactaaatt tattacaaaa gttattttag gtaaattata   1260
aaaacttgat aacaattaca agtacattct aaaactttca ataataaaga ttgaatcatc   1320
caattcatcc aaatgttaaa tttataatcc gatttcaaga agaaaattaa aaactcaatt   1380
tttatgaaaa tgtaactaca accacaacca tattaaacaa aaactcacaa tttgtccata   1440
ttttttaagt taaaaatata ggtttaggat tcaaatattt ataaaataaa ataaaatgaa   1500
actatttgaa aacatagttt aaaaaagaag aagaagaagt gttaaataaa gtcccatttt   1560
ttaaaaaaat atcaagaccg atattaatat tatatatata tagaaatgta cacaaagtta   1620
aaaaaaagta tcctataaat atctaagttt ctccccgtct agccttcgcc aaccttatct   1680
caaaaactcg gaagcc                                                   1696
```

<210> SEQ ID NO 135
<211> LENGTH: 2000
<212> TYPE: DNA
<213> ORGANISM: Cucumis melo

<400> SEQUENCE: 135

```
tttacatatt tatgaacatt ttcctatttt tgtaaatatc ttgattcaag atttttgttc     60
gatatattta aaaataaact tattttaaat tcatacttct ttctccttct atatgattat    120
ataagtattg tagttactat agattaaact cataacctcc tagttagata ttgagattat    180
tactttcttt tattatcggg ccagtacaga aacgctttta tgacgattac attcgtcatt    240
cgtcacttat ttgtgcatta aagttggcat tgtaatgttt gtttttacat gattctctat    300
tccatagatt tcctttatcc ttttccttgc atttgagtgg ccctttccta agatgtattc    360
ttcggacttt caaataaata aagattagaa gcatttttct cttcaatatt gacttcatcc    420
ttaatcctta agccttaagc ggaggctaaa aaggctttat ttgcctcgaa tcccaactaa    480
ttctccctct catgcccatt tcaatctctt gcctaattgt taattaatgg gtcaaatttc    540
gtattgaatt tcaattttgg atcaatccta cgattatctc aattaggggt caaaattaat    600
ggttgatgta ggagcaagtg gaagacacaa ttttggtgta gcaattggag cttcatcatc    660
aacaacatga gatttaatcc cgtggttgca gttaaatggt gtagaagaag tagtcaacac    720
aacccaaggt gaagaagagg gagacaagag aagtggttga ggttgtggct ctatttgcct    780
atggcagcct tcacctcttc tctctcgctc cctctccgtt tcaatccctt atccccttcc    840
tctccccgcc attttcttct tctcttcttc ttccctccac caatttcacc tcccgattct    900
ctgccctaac catctcttcc tcctccttgc actccgcctc cgacaatttc gatcatgcca    960
aaagctcccc tttttcatct aaggtctgat tcatttctgt tgtttgttta actcaatttg   1020
tcttagttat attcaatcgg gattttgctt gcttgtggaa ttaattttcg tttattaagt   1080
ggaagatatg ggtatgcttg gtgacactgt atttactgtt aaatttcaaa caatcctacc   1140
aaattttggt ttaaattgag tatttttagt tccttcttgg taaattggat ttgcgaatga   1200
ttaacttaac tatgttggca cttcgttgta agaccgttaa ctatttagct tccttacggg   1260
taatgatgtt tagaaggggg gtgcttggtc cactaagtgg agttaagtct atggtaaaca   1320
tgttggcatt agtaagtttt tggtaaacat gttggcatta gtaagttttt ggtaaacacg   1380
```

-continued

```
ttggcattag taagtttttg gtaaacatgt tggcattagt aagtttttgt ttgtgatgta   1440

gagttgtaag attgagttct ttaataattt gagttgtaag attgaattct tcgataactg   1500

tgaaaagtat attaagaaag taagatagag ttacttgata aatttgaata gtggagatag   1560

gggcaagatt gagttccttg ataaaagtat aataaagtaa atgtgcaact cttgcctata   1620

tacagcttag caggaactct tacttttgtg tgtcatgtat tcttattggt tcgttcttat   1680

tgcatttagt agatagtgga tcccagtgaa ctttttaat cgctagaatg gcgccttaaa   1740

aagttagttg gagcttctac ttgttggttg gtatggtgcg gttgcaagta tttttccttt   1800

ctatgattat gtttttagat ctaaatttta aagcactcga tgaatgctga tgcttgatat   1860

gttttctgtg ttaaattctt ttgttgatga atattatttc catttttcag aaatcagttc   1920

tttcatcttt gatacaagag atagagccgt tagatgtaag cttaattcaa aaagatgttc   1980

cacctactac tgtggatgct                                                2000
```

<210> SEQ ID NO 136
<211> LENGTH: 2000
<212> TYPE: DNA
<213> ORGANISM: Cucumis melo

<400> SEQUENCE: 136

```
ttcttgatta gcttggtgtg ctgttgtata tcatatttgg tgcgagcata acttaccctt     60

ggctaccttg catctaccct aagtggttta gtcagattgt atgatttgag gtatttcgtt    120

tctttgttgc tctaagtggc tttgagcttc tactgaggga acctaggacg tctcttcttt    180

ttgggatctt ttttctcgag tagttggatg cctagttggt ttttttgttc ctttactcaa    240

gtcctttgtt tgtcatttga tcgtgtcaaa gtccaaatgc tttctattgc aattcagtat    300

cttaaaaaac tgttctttgt tgatttatgt aaatgacata ctgtatgtat aaaaggacag    360

aatgctacca tttcttgaag tttctggcac ttaccctgat aatcgttacg gtaattatta    420

tgtgcagatt gacggcaata acgcagctag cacatcatgg tatgatattt gtacctcttg    480

ggtacacatt tgggagtaag atgatggaaa tgaatgaggt gaaaggtggc tctccttatg    540

gtgctggaac ctttgcagcc gatggaactc gacacccgac tgagttggag cttgaacagg    600

ctttttacca aggtaagtat gttgctgagt taaccaagaa actcaaaaac taatgccatg    660

tttgaaatgt tgttgggtat ttgaaaacgt gttattacac tagcacactt ttactgtact    720

tccttccaac atctattatt cagcttctca catcatggct atataaataa aggttaatgg    780

aagttactaa aaatgatgta aatctatcac attgttaata ctcctgtaat tatattgatt    840

gatgaacaat tcgatcacca tcttttgtta tttaaaatta aacttgtaat atgtattcga    900

acgtttttag ctttattgca tgcttattat ttcactgttt taaaactatc tttagacttc    960

aaatcaaatt ctgaaaaaca aaattaagtt ttcacataca ttatgtcatg aatataaaat   1020

tttagatatt ttagttcatt ttactatatt taaaaatgtt ttattattat taattttgta   1080

aaacaaccat gatcgtttat taattgaatt gtcacaatta agccattatt ttttttttta   1140

ctttcctttt tcccatcaat ttctttattt tctaaaaatt attggcctcc cagactcttt   1200

gttatttgca aataatgagt ctaatcataa tagaatttca ttgataaaac caatcatagc   1260

gagtcttaaa accaatcata gcgagtcgta attataaata ttattgaatt gctcttggtc   1320

cagtttagct agaattatga atttgatcaa attttctgtt atcattaccg tataacaata   1380

aatgataaaa ttcaaaaaaa aaaaagaaag aaaattgata tgttaacgac aatggtaatg   1440

ataaccataa ttgtaatggt aaccgtaact acaatacata atttttgaat ccaatgagat   1500
```

gaatcactta cttagttgat ttgcgtacca aattatagaa caccaatcat ttttgtaatt 1560
aggattgatt tactagcgtt agattagaga aaagcttggc ttatttctaa ttcctcctcc 1620
ctcttccact cattttgtcc ttaactaaaa catagtgata gttccctttt tcttttagag 1680
aaaagaaaag aaaagaaaag aaaaagagtg ttaattggta atacataata acatatcaca 1740
tacataaata aatcatgccg agttcgcctt agaaacgacg ccgtttaaag taagtcaaca 1800
agtcaacact gacagctaat ttccgcaata aatacgtaaa aatgaaaaga aaattaaaaa 1860
acgatataat ataaatagaa gcaagaggct cccatcacaa gatcccattc gcaaccacat 1920
tccggccttg aggcttcaaa aaatcgaagg aaaacactct ctgtatctct cccctctacc 1980
caccgattcc gtcgcggccg 2000

<210> SEQ ID NO 137
<211> LENGTH: 1575
<212> TYPE: DNA
<213> ORGANISM: Cucumis melo

<400> SEQUENCE: 137
atatatatat atataattta actaaataaa caaatgaaag aaaaaagtga gttcccattc 60
ggaaaatgca gatggatcca tttcttcaaa tattaaaaaa taaaaaataa aataaaataa 120
cttaaatatg caaatagaaa gaattttaat ttctggatta tccatatggg acaattttta 180
aaactcattt attttatttt ttttatttat ttgattttga tatatctatg gggaaatttt 240
tcgtaataat tttcgaaaaa atattgcaat atatcatttg atcagatcgg tattattaaa 300
tctctatcac atttggtctt aaattatcca aagattcctt taagataatt tagataacca 360
tctacagatc actactataa tcaacaaaag gaacaactta aattatttaa acaaattcat 420
taatattaga ctttgtgctt cattagaaaa tgatcttatc acaaccacaa ccatagtggt 480
ggtttaaaat tttattttaa actcttatta gtattatttt aattcatact taatcaaact 540
aattacttta aaaaacatat atatataaat aagttaaatc attccccctt atctaaataa 600
cataaaaaaa aattgtttac tctacaagaa gtttgtatat atatatgctc ggtactattt 660
agcatcttta taataaaatt tctaaatcaa ttttttatat ctctttatta aatgtatagt 720
catcaaaaaa tttaacgaga taatgtgtca aagatttatt ttattaacgt tcataaatat 780
caaattatac ttagcttata attgaaaaca tgttcgataa atataagtaa ataaaatttt 840
atttttttta aatattacaa aataaactaa ataagttata aatatgacaa taaacattat 900
atattttatt atatttataa atacttaata atttagtcgt ttaaaataat tttcttaatt 960
ttcaaaacat gtttcatatg ttaataataa ataaatggaa aaccttccaa aagaagaaaa 1020
aaagatatct taaaatttaa aaattgagat tttgaggatc aataattaat aaaagaagga 1080
ttaataaggg tgaaattaaa tcccaaaaag aaaattgaaa atgaagaaaa gaaaagtgaa 1140
gaaataattg aacgtgggaa gtggattcga tgtctccaga gaacaagcga aaggagacga 1200
aatccacata atttgcacgt tacgtgtccc tatcaaccgt agacacgtgt caacatctca 1260
acaccctacg ccgaattgct tcgctggatc tggacggtca tcggataaca gcggcaacca 1320
attaatattt ccccttatat ttcacagcct ggccatgtcc accaatcacg ttcaactatt 1380
aattcatttt tcatttcctt tttctttttt tttttaattc ccctcaatta ttaccgacaa 1440
cctgttgtag ccggttaacc ctaccctcca acgttccatt ataaggccta gaaaatggac 1500
gtgaaaatgg agtactacaa actacaatta attttaaaga attttaattt taaagttctc 1560
taattactat tagcc 1575

<210> SEQ ID NO 138
<211> LENGTH: 2000
<212> TYPE: DNA
<213> ORGANISM: Cucumis melo
<220> FEATURE:
<221> NAME/KEY: misc_feature
<222> LOCATION: (1)..(2000)
<223> OTHER INFORMATION: n=g, a, t or c.
<220> FEATURE:
<221> NAME/KEY: unsure
<222> LOCATION: (1)..(2000)
<223> OTHER INFORMATION: unsure at all n locations

<400> SEQUENCE: 138
ccgtcgggaa cctctgctct gacataatta atattcatgt atttcctgat acccatgcaa 60
gtcgtcggga aatatgttac caattttcga cgccagacga gaatcgttag gaacaagtgt 120
caccatgccc aacttcttgt atggggcatc aggataagtt aaatttcttt tttagttgtg 180
aactattccc gacgccataa acctagatgt cggaaatgtc ttcttgtttt tcgacggctt 240
cgtgaatctt cgaaaaaacg taagattaaa ataatgtttt cgacgagttc cgacctgtgc 300
aaaacgacat cgggaatagg tatttattcc aacgttctag cttctgacat ctagaaccct 360
tcaatttctt gtagtgccag tgcaaagatt gacactctta aacgatggga cttgtcaaat 420
agatgttgcg cagatatcca taggttatct aaggttttgt tttgttacct aagttatcat 480
caaacttctt catgaattct cttagctatt tctaagtacc taagttctcc tctatccact 540
aggattgtct ctcttaaagt caagggtggc tgttggtagg atgtagactt tgtcggcatt 600
ggtctaccaa tttaatctct tatatcccta aagacctaga ctccatggtc tccacctatt 660
tccataaatg tacccataac atcattaaat gaaattatta ctcaagtaca aaaaaattgt 720
ttaattttat tgataaaaac catatgtgaa aaaatagatg acatttttaa aagcttgtaa 780
acagtgtgtg aaataagtat cctaagtgaa ggctattaat ttaacttaaa cacaataatt 840
attattgttt taatgatgaa aataattaac ttatataacc aattttcatc aacacataca 900
taccttttgt ataaacattt atttgaacac aaatgagaga caaatagaca tttttatttg 960
gtaattttct cagcattatt aattatcatt ttcagatatc ttaattgaaa tttctgaata 1020
atttttattt tttcggattt tcacattata atattttgaa ttagttagtt gaaaaccaaa 1080
gccagcatca gtgaaaactc attaatacat gtaaaatact aaaattgttt ttttaaactt 1140
ctcaaagaaa aaaagtctta atttttattt tcttaacttg acataaaaat cattggtgtt 1200
gtttttaata aagtaaatgt taaagtagac tcagttaaaa acgaaaaaaa aagttaaagt 1260
ggactcaaca cttggagtaa acattttttt taaaaaaaat taatcctaaa attatgatta 1320
taatttttat ttggcttaaa tatttcaaaa tgtgttacac atggtttagt ttcaatttag 1380
ttgttacaaa atttattatt gtatttgaat ttttgataga ctaattaaaa tttgaaaatc 1440
aatttattta tacagttgtt tttcttttaa tgatgtaaat agaggtctaa tgattttaac 1500
ttgtaagggt taatttttct tatgatctaa tgtaattcaa tgagcattaa ttttagaaga 1560
aaatgtgtac ttattttgtg taaaaataaa ttataataac aattttttca ttttggtata 1620
acgtatgatt aagttccatg aaaaaacaaa ataaaaaaga ataaaatatt tttccattta 1680
aagaaaaaca ataataaaaa tggagggatt caataggaat ttcggagggc ccacttccca 1740
attccaactc cccactcact cactcactca cnnnnnnnnn nnnnnnnnnn nnnnnnnnnn 1800
nnnnnnnnnn nntttttttt attattatat tagaaattaa taattattgt ttatttcgct 1860
gtcaaataaa aataaaattg tggggcaggt gcagctcacg tgcctcctca cattgacacc 1920
acatttaaac actttcattt tcaaaggctg ctgctttata ttcttcacaa aaacttcctc 1980
ttccctttct cacactacta 2000

<210> SEQ ID NO 139
<211> LENGTH: 1006
<212> TYPE: DNA
<213> ORGANISM: Cucumis melo

<400> SEQUENCE: 139
ataataataa taaatacata aaataaaaaa ataataatag taatgaaaat caatagaata 60
attttaaaat cgggaaggaa gtcgtgtaca atccttgcac gttggagagt caaatggcct 120
aagtggtgat gtggaagtcg tgtaccgggt acacgatttt cctacaagtc aataataata 180
atatggttat tttttttcta gtttagggtt catgacaaaa gattgttcag tcgactggat 240
gtagacaaat ctaaaaaata aattaaaatc taatatgaaa actagtttta atttccaaat 300
tattaagggt tgaattcgac caataaataa taataatacg gttattttga aatttaggaa 360
attgaataaa gttgttaaaa tcttcaagca aattgttaag ccccgagata ttaagaagag 420
gtaataatag aggattctat atttataaca tgttaaaatt aattgcaaac tcataaatgc 480
atcacacaga ttaacaacat aggagggact tccgataaaa gtgcaaatat tgaaataatt 540
acagttcgcg aacatgagta ttttaatatt tttataaaata gtatgcacgt gtatttttgc 600
caaaagaaaa aaagaataga ttttgccatt tttcaaagtg actctcggtt atatctttta 660
tggcgattgt attttatagc gtatgttgtt tgtagttaac ccatttctca ttggcaaatt 720
caatcgtggg ccacaacgtt tgggcatagc ttcaatttgg attaactcaa ttatgtctga 780
atgggttgga ctagttcgga ctcttcggct gggccagaat cagattcggg ccgcaatctg 840
ttcatttcac acctatatcc aaacaccccc aaaatcgata cccatcaaac cctaactctc 900
aataaccccc atatataaat tccttcttta gggtttttca tcctcataca ctctcaaacc 960
tccggtcatt ctcattttcc ctgccgcttc ttcaataacc ctaatc 1006

<210> SEQ ID NO 140
<211> LENGTH: 2000
<212> TYPE: DNA
<213> ORGANISM: Cucumis melo

<400> SEQUENCE: 140
aaggagtaga ctctcaagtc cactattcta acttcttacc cgaaagagcc aaaacttttc 60
attcaaattc aactagaaag ttattattga tctatcaatt tgattttaat ctacaggcgt 120
gcgttgcaat ttgggaaggg attgagtttg taactggagt acgggcaacc tcattgaatt 180
ctcttcgatc aacgtgggga tgaagttctt tcaccagttg gagtctggaa aaacttttgc 240
tagactaacc tattgctact gccttttggt gaaatctttg tgctctaata ttaaaaagac 300
tccaactttg aatcgttaat tataaactag tgttatttgc ttgtaaatct tacttatagt 360
ttgaaatgag tgcttggcga aagtgttgtt caaatcggta cgtgtaagtt taaagattct 420
tatttcagct ttgaatcaga tcagagtctt ttaaacttaa tcaaccgaca ccaccacacc 480
ccactcttgt tcttctccac gtgggagttc ccaaattggt tgatttgtta tctctttgaa 540
tcatctcaaa tcaagaaatt tcagaacagg tttggggaaa tttgataaac tacactctct 600
tgctcgaact ttgcaaggtt tttactgttt gttatatgat tcaatattcc catttcttct 660

-continued

```
aattggatga actgttgaaa attggaaatg ctcagctgcc aagttttttt ccgaaatagg    720
tataaattca aagattcaat cagtgtgggt ttacccaaaa aaccaatggg gtaagtccat    780
tttggactca tgtggagggc acatgtttag gcaaagcctt atctctttgc cagtgggctc    840
acaatcaata cggacaagac aagaaatgct tcctaacacc gtcattgtca gcgaccatgt    900
gagctttcag caaattggat ccttcaagta actcacgtga aagatattta gtgattgact    960
taattactct ccccttcctg tttatctaaa ttaggcgaat agatccaaag tgggtatttt   1020
tggagatcat ttatctgttt cctgttcttg tttatcgttt ataattattg attgtttttc   1080
tggctcaagt aaaacgagga ctttgacatt tcaatacccc cttttttgtt ttctggtagg   1140
tagcgctaag tgggtttctg atatcgtact gaaaaagtta tagttttgct agaacactcg   1200
atagatttta gcttttgtat tgattttttt gttgatattt cctggtttca gtgaatgaat   1260
gatattcttt tatgacggtt gttgtgaaga ctcataagtt tgtctcagat cttcagttat   1320
actcttgaag cttcttcgtt catacttcaa cagttcttgt acattttacc ccctctgttc   1380
ctctttccat cggcttgtga atctgtgatt gtaaattgtg ctgatgattg tttttaagct   1440
gttgagatgg cgttggggtt gtgtcctaat ttgagactgg tcaacttgat catttggggt   1500
agtgatggcc ttcttttcta tatcattctg tgaagagtac tttctaaccg attttgttaa   1560
aaacacatgt cggattgctt gcttgttttg tggtgtttct gatttgtgat atgatttgat   1620
taatctctga tcgagttgtt atgaatttga ttgacagcaa ttgggggacc atggaatcat   1680
tgtggttcct ctcatagatt ttgatttctg aggtgttgag aaggctttaa cctttttgtc   1740
actgaaatgg atggtggaag ctctgaatcc ccagatatgg gttgtaacaa gaccatagta   1800
tggtttcgta ggacctcagg attgaggaca accctgcttt agctgctgct gctaggaatg   1860
gttttgtata tcctgtgtac atatggtgtc ctaaagaaga gggacaattc tatcctggtc   1920
gggtatcgag gtggtggttg aagcaatccc ttgcccattt gaaacagtct cttaaatcac   1980
ttggtgctga cctagtgctg                                                2000
```

<210> SEQ ID NO 141
<211> LENGTH: 1556
<212> TYPE: DNA
<213> ORGANISM: Cucumis melo

<400> SEQUENCE: 141

```
ttttagtcat tatacttcaa catctcgttg gttttaggtt tttggaaagc aaacctacaa     60
aacacactct ttcattcatt ggttttaagt tttgttgaca actttttagg agtgctttga    120
ctaagatttc aaagtcttgt acttaaaatg atgcatacta tcgtaaaatt agtataagag    180
actagatttt taaaaaagaa gaagatcggt ggaagtatgt tctaatttct aagtttttca    240
acacttacaa atttattgaa aaacagctgt cggtacatgc acacatacta tttatggatc    300
tacaattcca agcatagaag agtttagtat atatccaaat tcttattttt aaggggaaaa    360
aatgaacgaa agaatgcatt gtattctcgc ttttgtcgtg ataacgtatg attttcaagc    420
tctttcgtcg aaaaacatca acaaacaaac aagctaagtg taatctaaat aatcttcaac    480
atccttggaa atttattgaa aaataaagat ggctagcaat gcatactttt tatggatcta    540
tatcccattt caaccgtaga agattcaaag tattcgaatt cttaaaaaaa caaaacaaac    600
tgccttgtta agataaaatg gaattagaat gaaattttca aaattgaagt ggggccttgt    660
aaaagaataa actttgtttg aaaattaatt tccatcgttg gttggtagat gtgtccttaa    720
ttgaaaaagt ggaagaaatg aaggatgaat atgaaagttc tgaaaagaat atggacggaa    780
```

```
ttggaaaaaa caaaaaacct aatttcataa attaaccaga atctaaacat tgggggatga    840
agggagcgga ggccattcat gtaattggcc gtacagattc atggtttaac aaaagccaca    900
acgactccca ttcttccacc acagaaattt cctctcctcc taaattcact tatctctttc    960
tatataattg cttcgttccc caactttcta tcttcgtgca gccccattca atccccccatt   1020
ttacccactt cgtcttctcc tttctccttc gtcttccagt tccgttttcc ccatctgggt   1080
tctcctgatt tctctttaaa atcaactacc catgttcgac tttgaggaac tggtgcgttg   1140
gaattgagct ttcgaaggag atttattgtt tttatcacaa cccatctgct cgaggtaagg   1200
ggtaaaaccc gggttcgtca ggctgtagac atcacggcta tacacgtagt ttcccggtcg   1260
ttctttcatg tccgggctgt acgacggaag ggttgtataa ctccgacaaa cccttcgccg   1320
cacggcggac gtggtgcttt gccttccgaa ggtggtagtc cttctgatct tctttttctc   1380
gccggcggtg gattctcttg cttcttctct tcttcgtatt agctttgcaa cgagtccgtt   1440
tgtgttttag ctctaccggt ttaggatttg acatcagcaa gtttctgttt tgcgtttctt   1500
tgttttgggt ggggagattt tggtgttggg tttggtttga attagaagca gacgat         1556
```

<210> SEQ ID NO 142
<211> LENGTH: 2000
<212> TYPE: DNA
<213> ORGANISM: Cucumis melo

<400> SEQUENCE: 142

```
gagtacctaa tctaaactaa ttaactcgct caccctctta tttactgccc catactaatg     60
atcctaatag attgtttggt tggttgata aattctcttt aaaattatca agttttccaa    120
tttttgccac ctaagttgtt ttcttacaaa aaataaaaaa taaaaaaagg caatgttatt    180
tctcgtatgc attaattgat tgattttctc aactaaccct tcaatttgac tttatatgta    240
ataatagtgt aaaatatata cgcacatacc tacatatgac caacaataaa aacgataaca    300
ttaaattcag acagaaataa aaattacgat tatgatttta ataaatataa atgcacataa    360
ataaaattta cagttcatag aaaaatccga tgtaatgaag tttaaatcgt tagttatttt    420
atttcgtaaa ataccaattt atgatttgca tgacaaattt ttaaaatata acttatgaaa    480
ttaaaagttg gttttgagaa aacattcaag actttattac aaccaaacaa aaattttatt    540
gagttttgtt tcattaaaaa aattattaaa ttacaaatat ttggacttac gtaatttgtt    600
ttctttcttt ttagggtaga aaaatatgat agattaaaag gattcgaaat caaactttat    660
atcaatttcc ttttaaataa ttatttcttt ccaaatttag tttttatatg atagcctaag    720
tctccatcat aagaaacaac gttaattata ataaaaaatg gatgtagatt caccaatatt    780
ttccaactat attattactt tcacgtttac attaaaatta aatccacaca ataatataat    840
agttttcttt gtttgattca aagtttctct tggttaaaat taaatttcga aatgataata    900
aataaactcg tgattaataa actttaattt aaatttcaaa cttaggtgtc taataaattc    960
ctatattttg tatcacaact tttcaattat gtgcaataaa ttttctaatg atttattatt   1020
ttttttaaga atgtaaagtt gattatattc atattaaaca taagattgaa aagagagagt   1080
tgattatata ccgagtagcc gacagtcatt ggaagcatta acccattatc atctccggcg   1140
agcaaaagca aggatctaca aacaaacatg acaattaata tgaaactcat caatccacgt   1200
atccaaacat tccatatgtt agacatggaa gagcaataat tacaaagctc tctcatcgtc   1260
tccgatcact ccatttatcg tacaaatccg tctttcttca ccttaatcat tttccccgaa   1320
```

attcatccca ctgtttcgca acaaaatcca agtttggaaa gatgagtttg tttttagtga 1380
tcaaggaaag gacaaagaat gtagcattgg caatgacggg caaacaagag aggtgtggct 1440
aaacttatac atgcttttgt ttggtgaaag gttaaagcga agaacgccaa agacagagga 1500
aaccgtataa aatatgagta aatgtcaatg ctaatgaatg ggcagaggtg aagcggtcgt 1560
ctatggctgg agaagggcag atgtgaaaca atatgaggta gacgaaggtg gagacaaaac 1620
aatttagtaa agtcaaaaca attcatccat atcctaatcc aattatattt ctttaaaaag 1680
tttaagtatc aaaattggac tgcttgatca tctatcaagt tatttttgaa ctttatttta 1740
aaaagtttaa gattattaat aaaaatgtaa tgtttaaagt ggttagtgct ttggaagcca 1800
ttacgtccta tggattatgt ggtgtgttgg gctactctct atttggacat gttttgacgt 1860
accgtgcgaa gtcctgactc tatttgtaaa acgtcacccg gcaaaaaccc aacttaaaaa 1920
acagaacttt atttcattta atttgcgggg tttatccgga aagaattgtg agagctctct 1980
tgtgtttggt ttgcttatct 2000

<210> SEQ ID NO 143
<211> LENGTH: 2000
<212> TYPE: DNA
<213> ORGANISM: Cucumis melo

<400> SEQUENCE: 143
gtaatgcaat attagcaatt attttggagc aatacaaaca actaggtttg gatcaaatat 60
cacgaaatac aggagcaata acattaacaa caaataaatg cacgaagttt ttttttttga 120
acaaacactt aactctctcc aaaccaaaac gagctaagtt agacctaaaa aaacaaagta 180
tcggaataca atatagctta aacaaaaatc atgtttagat tattggttag gttcatctaa 240
actagtggtt agccattttt caaaagaaaa atatgatttg tccttgctaa ttttccaaat 300
ctatatttta aaagtatcac tctcgtcata attttccata gctcaattaa tactaatctc 360
acggtagctt ttaattgttc ttgacaagta atggattaac ttaaaacatt tatataactt 420
tgtaggtatt attttataga aaaattagtt tatacgtgaa aacttcttaa atatctaact 480
acaatcaaat acctagatta cataatgtat ttttcataat atttatacat tatatttgaa 540
aaaggactct catttctttt attggtatct acgcagaaat taagattttc gagttgcgac 600
atctcaatca acgaaccagc taagaagacc ggcaaattcc aaacgtatcc ttcgggaagc 660
actgagtgtt tccacgtcaa taacaaaata ttgacccaat aaatttcagc cacgtagaaa 720
caaagcaatg aaagccgtcg gattctccac atcggctacc gtatgccgtt aagatcatca 780
agtagacttc taattcccat gtcttccgtg ggggccagaa atggaaaatt gaaatcgctt 840
tatccacgtc aagctaacaa aaaacaacca ataataattc gccacgtttt ctcattagaa 900
aagtgcaccg ttggatcatc cacgttggca acatagatcg atccgatgga cttatataaa 960
tttgggtagc tcgtcgagaa atcagatcag tgatcgaagc tactggaagt ttttgctaag 1020
aaccatgagg aagtggacga tcgcttctgc tcttctcctt ctttgcattc tctctctcgt 1080
tcccgatgaa ggtgtgattt cgtttcttcc ttcagcagtt tgatttattt gttggaatgt 1140
aaactgaatg cattgcatta tcttaatcac gagggctgat gctttaattt ttgggggttc 1200
gaggagaaat ttggatgaga ttcgagcttc gtttgaactg cgaaggtttg atggtgatat 1260
ttctattgtg tttgaatttt caggtcctag atttcatgcc aaggccgacg gtgatgccga 1320
cgaggttgta gatccaccaa aggttgagga aaaaatcggc gccgttccac atggtctttc 1380
cactgattct gatgttgtta agaggttcgt gaatgtctaa tctcgttgat acacgcttca 1440
agtatagatt tgtccacttc gggaaaaaaa attatcgaac cttcttttga atgttgattc 1500
agagagtcgg agtcaatctc gaagagatct cttcgcagta gcggggagaa atttgagttc 1560
caagctgagg tgtctcggct catggatatt atcatcaatt ccttatatag taacaaagac 1620
attttcctaa gagaattgat ctccaacgct tctgatgtaa gttcactctg cctcttctca 1680
cttcattaga tctagtaatc tcattgttag atttgtgtta gttaataatg gcgtctctgc 1740
atttcaggcg ttggataaga ttaggttcct ttccctaacc gacaaagaga tattgggtga 1800
gggagacaac tcgaagctgg agattcaagt gagttcgacc ttcatactga catattgttt 1860
tcttattacc tcgctgaaaa aagctgctcg ttctggttga tgaaccttgc atacttttat 1920
tgttgtccat aaatcaaata tcgcagatta agttggacaa agcaaacaaa atcctttcaa 1980
ttcgcgacag aggtattggt 2000

<210> SEQ ID NO 144
<211> LENGTH: 1337
<212> TYPE: DNA
<213> ORGANISM: Cucumis melo

<400> SEQUENCE: 144
ttttttttaa ttttcttttt gcagattgtg gggctgatcg tccacgatat gattccactt 60
tggctacgag gggtgtcggg caccttgtcc gtaagggcac tggtgggaga tcgtctgtta 120
ggtaacctag ccctagcttt ttcgtgtttg gattcttcta tttaattgtt ggcttgatgt 180
tgtagatgta atgctgggtt tgagtgcttt gaaatgttga gggaaattta agaaatttaa 240
tgggatgaag atgaacagtg gtacttcaag cctcaaattg aattaaaatt attttaaaca 300
tcctaaattg gtatgactaa gtattgctaa acatgatagt catataaaag cgcaaaagaa 360
aagaaaaatc acccctctac taggattggt ttattctatg gatttttgcc ttcagtgttc 420
ttgaagtcac aataataaaa gtagtaatag ttgcagtcac aactcaaacc tttatatgtt 480
ttttaagatt gtggtaaata ttgttttgat cattagacaa gacatagaga ttttaagtct 540
ctgggccttt tcacgaagcc ataagcctct tatggttcag caaaggcata ctcaaggcta 600
gaagttaaaa aagccttgcc ttgagatgta attctgaata cctttttaaa acatttggta 660
cttcaaattt ataagtttat tagtggaaaa tataatcttt cagtctcttt tttagctgaa 720
atacttatac cttttttccc cattgtcatt gatttcttaa ttcatatgca gaggaaagga 780
ctaattagat atactttgtt ttattgagta atctaaaaga tgtggcacta cccactatga 840
acattttgac gtcattccag cttttatggg atattgaagc aggcaatttt aatctgagct 900
ggtttctctg tcgctgtcag ataatccttg tttgtgctta tgtgttctct ttcaagcatg 960
cacattagga ttctcaggca gatcagatca ttgatattta attcaatttg tggatttagt 1020
ttgtagtgaa tacactaaat tctgtctctg gtttctctga tcttactgtt ttattacaaa 1080
attgttttgc agtgggattg ttgctactgt cttcggagct actggattcc ttggccgata 1140
tgttgtacag caactaggta ataggtgaac ataaatggta ctagcattcg actttctttt 1200
tgcttagata tgtaatttat tacgtttctc tataccttct actactagtg ggttttggca 1260
gctttggctc tattcttgat ttttatatca attttatgct aagcatgatt ttggaaatga 1320
attgtgtttc agctaaa 1337

<210> SEQ ID NO 145
<211> LENGTH: 2000
<212> TYPE: DNA

<213> ORGANISM: Cucumis melo

<400> SEQUENCE: 145

```
atatgtgacg attaattacc taaaaattaa ttatttacat agggttagtc aagttgtccc     60
gtgagactag ttgaggtgag cataagttga tccgaaagct cacaaaaata taaaatacgt    120
caatctccat gctttcataa aaataacaat ttgattctca tgactactca ttcacttatc    180
gtaaactctt ttaaagaata ttaagagcgt attagtgtag tgggctagtt tgttacaaaa    240
gttggcgaca aatagatgaa attagagtta tctcgagatt cgacgagggt taaaaagagc    300
atttgcttta ccctgtattt tcatcgtagt tcatatttat ttatattcaa attctatcaa    360
gttaaggcca cgtatattcc aagaaaacat aatccattaa tggtaatatg aaaaatgagt    420
tttaatttga tcatgttgtc ggcattatgt aatcacaaag atatctaaag ctcaatgtta    480
aatctaatta atggaggccg ataatccaat tatatttgaa aattaagtgg aacctacggt    540
gagatatttg tactatcaca attacaatta ctcttacttg ttcggaaaag aaattttgta    600
aacatgtcaa aattatcgtt actattccaa atattgtcac tgacctgaac attgtcaaaa    660
agaaataaat aaataaaata atattagata atgtaaaata aaccacctaa actttaatct    720
attatggtcg caaatgcttt gataacacat aaaccgattg atccgtcaat gaaattttac    780
cataatcttt attatggatc gataaatatg acttaatttt cttttaaaaa agtgtttttt    840
aatttaaaaa aaaaaaagga aaggaaaggg ggaggggcaa aggttctaga gtgttccaaa    900
taggacaatg gaggagggtc tccaatggag ggaggagcca aatccaacgg ccaacaattg    960
ctggaagctt caggagccta catgattctt gggttcgttt ttctctcctc ttcctatcca   1020
tccttttgaa atttgctata aagaaaccta cttctcttct ccttacaaaa aatccatttt   1080
acactctctg taatacccc agttttgcct cactcgcagc gctcatttct caccctctta   1140
tccaaatcaa tccttctccc tctaaaccct aaaacccctt tgcacctccg ccgttttctt   1200
gtaagattcc ccctctcttt tcattctgtt ggactttctt atccttttac tttactgggt   1260
catgcttaca tttctatttg ggttttgttt ttgcttgccg attcagtctt ctgtattgtg   1320
ttttgagctt tctgactgtt ttggctttct gggtttcaat tgttggtgta gacttatcga   1380
ttgattcgtt tgttttgtgt cctttcattt ctgggtttg atttctttaa cattttcttc   1440
atgggttttg gattttgggt cttcttcttg tgtgcatctc tgtagcttgc tgattcattt   1500
gtatctcgtg tttatctatt tgtttgagtt cctgacatgt gggtttttgt tgttgtctga   1560
gaattatgtg tcaaatgtca attgtcaatt cctatgttct tgaatttgtt tatgtcattt   1620
cctttctggg ttttctctgt tcaatcttgc tacatgggtt ttgggttttc ttacccttgt   1680
tgtgtgtagt tttagctgat ttttgtttat gcttactgat tcggttctgt attctcgatg   1740
atttgcttac ctggtttttt atgtcgtttg agaattgtgt gtcaattcct ttgttgttga   1800
ttttgtttgt catttctggt ttgacattcc atccaatcct ctctgctcta agtctacttg   1860
gttttcaatt catgaatttc catcagacgc attgtcggcc ccctgctcta tttgtttaca   1920
attctggttg tgaagttgtt tcagtttgaa ctaattgatg gtctggtgat tacgttctgt   1980
atcagtttgg aagagggtaa                                               2000
```

<210> SEQ ID NO 146
<211> LENGTH: 1212
<212> TYPE: DNA
<213> ORGANISM: Cucumis melo

<400> SEQUENCE: 146

```
atatatatat atataatgga ataggctatt tgatttagat gaaagctatt acgtcctggg     60
gtttacatca taatctctat tataatgtta atcgagaaac tttataaagg ttaactcatt    120
atctctcttg tcttcagttt attattgttg tttttatatc ggtggaattc cacctttcac    180
caactctcaa gctgtggtgt gaatctatgg gattaatcta gggcgaataa gggagctgag    240
tattttctat ttgtggaatt aaatctatag tacacaaaac atttgctcaa ctactaagga    300
tatgaaaacc cttggctctg ccaacatggc ttatagaaag tatctgaaaa cgttcaccac    360
tttgcaattt caacaataag tgtaaattct tttcctattg ttgttattta gtcgatttga    420
tcgttgtaca atatttgctg taacatgttt gatttttggc cattttagtg ttcacaagaa    480
gatattgttt gttataagaa tctacctgat ccttttcaat tgttattcaa tatattgcct    540
actccgttga cagcaggtcc atgcagagga acaagttcta aagttcaaac tcgatgctga    600
tattcttcag gtactacttt tctgttttca caagtttgtt gtttcaatag ttctaagaca    660
gtgacactca tccctttatc tccgtaaccc aattcattaa cgatgacttt tgatcggttt    720
gaagaaaaaa tttataacac tttctcatct cgttcccttt ggattttcag tttttaaaat    780
tgcatctata tgtattcttt tgttatcaaa ttttacttga taatgacttt taaattgtac    840
taactcattt agatgtgaat attaataatt ttaaacttca tttctgacgt ctaatactaa    900
taaaataata ataacaatta tccttcttaa ttaaatatgg tttacctacc ggtctattgt    960
tctgaactgg atatattcaa tttgttttat ctgaataatc ttttgaggtt gagttatcaa   1020
gagcctgttt aacttaccta aagcatttct aacctgaact atgccccata tgaatacttc   1080
atttcttta ttctattgta aaacattgtt gttattataa tttgaaacgc ctgtaatagt   1140
ttttacgatg tcttgcagga gtctatcgtt cggcatgtaa acgaacaccc acaggctggc   1200
tggaaagcta cc                                                       1212
```

```
<210> SEQ ID NO 147
<211> LENGTH: 2000
<212> TYPE: DNA
<213> ORGANISM: Cucumis melo
<220> FEATURE:
<221> NAME/KEY: misc_feature
<222> LOCATION: (1)..(2000)
<223> OTHER INFORMATION: n=g, a, t or c.
<220> FEATURE:
<221> NAME/KEY: unsure
<222> LOCATION: (1)..(2000)
<223> OTHER INFORMATION: unsure at all n locations

<400> SEQUENCE: 147
```

```
acatagtatt aataaattag ggaatgactt agttatttaa tttaagcggt agtaaatatt     60
attaactttt gttcgttgtg ttattttact ttcaaaacgt tcatcttgat ctttatcctt    120
tctaatattt atttatttta gttaatatca aaaaactaaa tttaatttat acgttaagtt    180
acaacttcat ttatttcaat ctaaaacttt tagaattaca ctttattcac taaaaaatta    240
ctcgtaaatg caaccattcc aaaaaggttt caatattata taaaatatca taatttttcg    300
aacattctta aaataaatta aacaaaatag tagttttcat atacataaaa ttcgaataaa    360
tcctcataca aaaattttaa atttgaatca tcacattgtt ttattttaga taatcaatca    420
aataatttag gaaaagagaa gaaagaaaag taaaaggaag ttgaaggtat tttatttagt    480
gatagaatta taaaataggg tattttagaa ataaaaacac aaatatataa aaatacagaa    540
attgatgcat ttaatggaac actatttgac aatcaataag aaagaaaaaa aagaannnnn    600
```

-continued

```
nnnaaaaaaa gaaaaaagag aaaaggtttg gtattgggtt tgtgggattt tattaataaa    660
tgaaataaaa aaaaaagaaa gaaaaattta attgattaat ttggtgggag aatattacaa    720
tgaaacccca ctttgtgaac aaatacattg catttgggtt gtaatcaagt gtacatgcat    780
ctacccaaac ctttcttgaa ctcaccataa atccttcttt tagaccgctt cgacttccca    840
atttttcttc acttttttc cccttctct ctcttcctcc gtttcccccc ccctttttt    900
tccctatctc atagggtttc catccacctt cttcttcttc cgttctctca tgcattgtca    960
ttcacaatct cattctgaat tcctcttgat cttcttcatc ttcatttcct ccttattttt   1020
tgctctcttt cgagggtttt tcggttcatt tccgtccaga ttccaccacc tcccgtggtt   1080
ttttcaccca tactcatgtc gaagctcttc gccttttccg gtaagtttat ggatttttac   1140
tgattttttt tttttgtttg ttttgccttt ctttggattt gacttagatt gggtagctgg   1200
tagggttaag cgtcgtgttt tgtatgggtg tttggattgt tatttggatc gtagggaaag   1260
atttggaatt attggtttta gtttttgggg gtttcttgat tcgccaggtg gcggatcatg   1320
gcttggtatg aattgtgagg gaatatggat ttgggtttct ttctattagg attgttttat   1380
tgtgttgatt gattggctat tttattgtct tgaacagtcc atgccagatg taagtttctt   1440
gaaaagagat atcgtagttt gaagatgggt ttacctttta agtgatgtgt atgtgttgtt   1500
gatctgtcgt tcccgtacag atttagattt gaggtttaga ataagagagc acatcaatag   1560
taaatattaa agggtcaaat atagttttgc agagattgct tcttgttttt ctctgttgat   1620
aaattttcga tcttttgatc tagaagttga ggggtatttt ggtctgagga tttatttgtg   1680
atgttggatg atgtatctaa cttgtagttc ttgttgttga aatttcaggt agtgaagatt   1740
tttgcactgg agggtcaata tacccaaatc ccaaggactc cagtttattc ttgtcccttc   1800
ctcaccacgt tgatgtctat tttcctcctc gaaagaggtc tcgcatcact gctccatttg   1860
tgtttggtgg agaagaagtt gaatcaaaag caaatgtttc tatcgagatt cttccggatg   1920
agtgcctgtt tgagattttc agacggttgt ctggtggcaa agaaaggagt gcctgcgcaa   1980
ccgtttctaa acgatggcta                                                2000
```

<210> SEQ ID NO 148
<211> LENGTH: 1254
<212> TYPE: DNA
<213> ORGANISM: Cucumis melo
<220> FEATURE:
<221> NAME/KEY: misc_feature
<222> LOCATION: (1)..(1254)
<223> OTHER INFORMATION: n=g, a, t or c.
<220> FEATURE:
<221> NAME/KEY: unsure
<222> LOCATION: (1)..(1254)
<223> OTHER INFORMATION: unsure at all n locations

<400> SEQUENCE: 148

```
tcataaatat atatataaaa aaacaaatat tataacctac cttttgcaaa tgataaaatt     60
gtaaagtctc gtgccgataa tgtgttataa aataaaagaa caaagaaact aaataagaac    120
aatgcaacaa nnnnnnnnnn nnnaatagag aagagaggaa gaaggggaaa caattaaaaa    180
ctcaattgta gtgtgactta cacaaatgca acacatatat ctatttatag gacatatcat    240
ggtatatgtt atattatgaa attcaatgaa atgaatgtta caataaagaa ttgaatgaga    300
gttgtatgaa aattgtaacc ttcataaatt atggatatct actcttataa tatatcatta    360
tatttataat gtatactata tgtttgtatt ttaataagaa aattatccca ttggatttgc    420
gatcttagat ctaacctact aaacaaatat tccaacgaag aggaacgaga tgagaacgcc    480
```

```
gttctaacct acgcaatatc aatcgtttct tcgctgctac tttacgcctc aagttcctac    540

ccttcaagtt tcatcttcaa cgatcaaccc aacgattaac ccactgcacc accttatctc    600

ttgttggtgt catctaatcc atcttcttcc tgcatcttct gcaaatgctc tcaggttctt    660

tcctctctct tgtgcacaaa ctgatcaccc atgttgttcg ccggaaaatg attcagattc    720

ttcgtatctt gcctgcattg tctttgacta taatatgatt gaaattcact tgttgattgg    780

ttttcaattg ttaattaccg ttggttttgc tgtttagtga tagtatatta tgaggttttt    840

gttcgttttc gggtttttgg atgtgatttc atcctataga atgaagagta tgcaacgtat    900

gctgtcacct tgcgggggaa atggtacacg tggacccgaa atggagctag gttttgatac    960

gtgcagtttg agttttggtt ttgggaggat ttggcattcg ttatatgaat tttgtaatta   1020

actatgccgt ttgattgtta tttataacgg tgcattgctt tttgaggttt agaatttgga   1080

cttaacgcct ctttctattc atggttattg gttttatttc ttcctttttg ttgactgaga   1140

ttggtcgtag aactcgttgc ctgtctatgt tttaatgttg gcctgatttt gaatttctaa   1200

tccatgacta agtatttctt tattgtcttg atatagttga ttgaatcatc aatc         1254
```

```
<210> SEQ ID NO 149
<211> LENGTH: 2000
<212> TYPE: DNA
<213> ORGANISM: Cucumis melo

<400> SEQUENCE: 149

cattttaaat tgacctttca tgaaaaatcg tatgtttttg gtgtgatttt gagtataata     60

aaaatgattt taaccatttg aaaatcactt taaattacac ctaatgggtg actgaggttt    120

tagctttcgt ctttgtttag ctctaaattt gcatggcaag ttttccattc caatgattga    180

tgtggcttgt aatagttgaa atatatatat atatatatga ggtatcaaaa tccccagcct    240

tgtgttaggt tgaatatgga gggagtgggg agttattttt cctgctctta ccccgttcct    300

aattcccacc ttgtttacta tgtgttattg ttattgccat atttactatg tacataatat    360

ttcgattaga aattttattg tttaaccatt agacaatttt atatgtctaa accataggtt    420

tgaacaaacc atttagatta tatatatgtt gacaattaga ttgatagggc aattattttg    480

tttatcctaa aaatggtaaa taatgttctt aaacttggtt ctttgtgaaa taccttcaac    540

tttcaaagtt tttaataata ttcttacgct tataaaaaga aaaaaaggat aagttgaaaa    600

aagaatactt ctatgataag ttttagatgg aaactattta ctttttcatt taaaaaatac    660

ttttcaaatt tatgaagttc caaaagtatg acttaaagaa atagttatac ccttattgat    720

aatatacgac aaaaacaacg caatatttcg ttacaaaaat aaatctagct gcattactat    780

cttactttaa agatactctt atcgtctatc taaactacct tactctagaa ttaataatta    840

agttcctttt actttataaa tataacttat tcctactatt agtatatatt tatattggta    900

tctaatagct aattttgaat tttgttccaa aaaaaaaata tcgctgagtt ttgttttgaa    960

gtcttttttt ttttttaaat atatattttc gattaaagct agatgttgca gttgatatgt   1020

agatttaaaa gaaatgtgtg agatcgttta taactatata gaagattaag catttattac   1080

ttcaaaatat atcgttaaaa ttattcacat aaccaatttt tactcatcaa atattatgtc   1140

agagaaaaga aaaacgaaaa agaaaaccta cttcaacgga caaagaagtc cttagttcaa   1200

atcttcaaac ctttatttgt attaaaaaat ggcatataaa ttttttcaat ttttacgcat   1260

tacctgttgc gtgaaaaaca ttgatttaat agaaaagaac tgtcctttca gttttgtttt   1320
```

-continued

```
tttaaaacca atttcgaaat tcaagaatag aaacaaaact ttaagtctag aggatcacta   1380

aaatctatca taaggctaga aatacatctt gtaatctgca gtaggcattt gccgggatga   1440

caattttctg gtgcttggat taagaaaaaa gaaaaaaaga aaaaagaaaa aaaaatggtg   1500

aggacttaga ggccataatg agtttggcat tgggcccaca gtaggatgag taaattataa   1560

ttgggagaaa atgagcatag ggtgtggagg ggaaaaggag aaggctaaaa cactatcaca   1620

aatcacacag tagaagatac acagaagaag taaccacagc cattcattga gtgagaggct   1680

atccataatc tcatcctctt acccttctca tcattcattc aaagccattc aactcaacat   1740

cccactctta gttaaccaac aaaatatata tacatccttc tcaatttccc ttctctctac   1800

tgctttaatc ttttgcttct tcttcttctt cttcttcttc ttctgctttc tcaataccct   1860

caaccatggc tacggctact ctatcagtag ccaaaccatc tattcaggtt cctccattac   1920

taaacaccat cctctttccc ttccactctt ctttaatttt ttgtatctga taaacattac   1980

tgcattttct tgcatagcag                                                2000
```

<210> SEQ ID NO 150
<211> LENGTH: 1680
<212> TYPE: DNA
<213> ORGANISM: Cucumis melo

<400> SEQUENCE: 150

```
tttttatgaa gggagttgtt attttccttt gggatttgga gggatatgat atatatcctt     60

tttttgcaat ttgatgacag aattctgctt ttagagactt ttcaaactgt ttcgtaatga    120

atttgatggg ttgggggtgg cttagttcaa tactttgtgg gttgaaaatt ttgatttgca    180

ataaatgaaa gccaaaaatg tggggaagct ttcagttcaa gtaagttaag ggaaaactgc    240

agaatatctg gcttgaaata agagatgtct tcgaaggtta atagttttac attgactttt    300

ttaaaaaaaa gattatatta taagtacaaa tatgggtgga tgtgaactta tattattcaa    360

agagactaat ataagttttg ggcgcttaat attttatatt ttcatttagc agtcaaagat    420

gtataagaaa actttggtaa tgcattttat actagtttat ttatgtagga tgtaggatct    480

atcgaataat acaacatatt tttaaatgat gtgtacaatt gtgaaaaaaa aaggaacata    540

cagtattgta gaaactaaaa tattttctaa gatatatcga gatgtaaaaa aaatgaatgg    600

atgtcaattc cagcataact taattgttga actaaaaaca aaaagaagaa ataaaggggg    660

caatggtttg atcctcatgc cccacatgaa agtcaaagtt atgtaaaggt tccgtgtagg    720

atatccttcc tcctaataag gggagatagg attttatgag ggtgccaaca gctcagaatt    780

ccaaattccc aaaataccct cttgcttgaa aatttcaaac tcttctgttt ttgccttgtg    840

taccattcac tattccgatg cgtacagttc attaaccaca caagttctcc ttttgcaggc    900

aggtttagct aaacttattg gacttgctgg agagaccaat gttcaggtaa gatcttattt    960

gttataatga actcacaaac taatttagat tagccaaaga attctgtttc tgaagaaaga   1020

gaggatgaaa atcatctcat accaaatttc tttcttttt tggaattatg tcttcacatt   1080

tattcatttt ccttgtcaac agggtgaaga gcaaaagaaa ctggatgtgc tctcaaatga   1140

agtctttatc aaagctttgg tcagcagtgg cagaactgta agctgctatc taatcataca   1200

aatgacacga caaaaatatc tggtgactta ctctaatagt tgacaaattg gtggcagtgt   1260

attcttgttt ctgaagaaga tgaagagcca acatatgtcg agccatctcg gcgtggaagg   1320

tttgttttcc attcttgatg atttttgtct aatgcttaca attatcatca gtatcaactc   1380

ctcttacttt gttttaattt taatgttatt tcttcttatt ttccaatgac aaaggtattc   1440
```

tgtggtgttc gatccactgg atggttcctc caacattgat tgtggtgttt ccattggaac 1500
ggtaacatcc ctatgctacc ttctgaatga gatttcaaat atttttggta taatttcttt 1560
ccaataagct gagtgtatga ttgtttgaat atctactttt tcatgtagat ttttggaatt 1620
tatcacttga acgacagcca cgaacctaac ctagaagacg tcttgcaacc tggaaagaat 1680

<210> SEQ ID NO 151
<211> LENGTH: 1524
<212> TYPE: DNA
<213> ORGANISM: Cucumis melo

<400> SEQUENCE: 151
tatatatata tatataggta atgagtaaag aaatgaaaaa gaatgagttg aagaatcaca 60
cccttaccat tctatttgaa actcgtgagt cttgtagact tttacatgtc ttctccttca 120
cttaatatca ttctggattt tgattatatg tatctttatt tctaaacagc ttggacagat 180
ttattattgt tagaatacct tgaatatgtt ttctggtgct tagaacgatc atacatgggt 240
ttttctaggg ttagaggagt gcgctataca taaactttct agttctagag gcattgctgt 300
aatcttaagt ttaacagttt ctctttaata acaaaaactg ctcttcccct acggtttaag 360
ttttctcctt atcttaacag ttataattat gaaaaatgat ggaaccaaaa caaagttctg 420
ttaaaatttg actaattgat tgaatgaact tttgtttcca agattcttaa tttgtaaagt 480
aataatgttc ttacaaatca ttattttgat gtctgagtta taacccttaa gcttggtggt 540
tcatattcca ttcaggtgaa gaagattgtg agtgaaagct gttcccaaga ggttttagaa 600
gtggcgttaa actccatctc atccctaatt accatcctct cctccatgtc atcgtctacc 660
aaactccatt cttcactttg atggtataag aaagtgaatt agatttggga ttgagcttca 720
aaacatgtat gatgatgtga atatttactc gtgtaaataa tataacatgt tgtattcttg 780
cttgtttctc tttgctcatc ttcgttttgt taagagcaaa gaaaagctta cgagcatgaa 840
catgtgcaaa tttatgaagg tcaatgggct tcgtaatttt ttttccccat tgatttaacg 900
atttatggaa gatggatata gtaaatttag gttaagctgt acaaaaccag agaattttca 960
ttatagtaaa tactttacaa ttttcaatta gctacaataa acaccgtttc aaaatctccc 1020
tcatttgcta ccatatttac tattcgatat ttatcatttt ttttattcct gttgtaatgt 1080
ctactatttt tcttttaaac tattacacca caaacacata ctattataat tcaaattaaa 1140
ataatcacta gtataactca actataataa ctcagatgat ttcattccat gaaagtggta 1200
attataaata tttaatatct tatatgataa ggataactat ctatttggtg aaaccaaatc 1260
acaatgatgc agtggtaagt gctttggact ttgaatctct tttttatagt atttcattct 1320
tttttcaacg aagcagcatc atgggccttg aatggaggcc agctagaacg agcccattac 1380
atttgacaga gcatctcttc ggcccatgag cccaaacact attcatcttg ttaaaccacg 1440
aacaaatcga gactgccgag agtgtaagag aattgagtaa ttttttttcga gacacaggga 1500 gtttagagag taagtcggag aaca 1524

<210> SEQ ID NO 152
<211> LENGTH: 1851
<212> TYPE: DNA
<213> ORGANISM: Cucumis melo

<400> SEQUENCE: 152
ttgggtcgtt acaatatcac tgtttaaact taagtttatt tttatttatt tttttatttt 60

```
ttaatctttt tcccttcttc ctttcatctt ccattcattt atacaaaaat aaataatgag    120
aaaattactt ttcacttttg agtttaatta tttttaagtt ctaaaatcta cattttaatc    180
tttaaattta aaaaaaaaag gatttacaag attcttgagt aatttattat tattattatt    240
ttgaacgtaa atataacctt ttacaaaatc taaatgagtg tttgggacaa tgagttgatt    300
attataagta ttgaattata ataatttttt gtggggtata gactatttta atttgaagaa    360
taataggtac gtgtttgaaa tataaattat gttagttggg aaagaaaata gtaaatatcg    420
tagaaaaaaa taaaataaat gaacaataag aatataaaat atggtaataa attgggactt    480
tgaaataatg gtaataatta attaattaat tgaaagctac aaaacaatgt tcacttcatt    540
gctatagttc taaacagact aacaatctca atcaatgacc taatgggtca ggccattata    600
ttgggctcaa atagattttg gcaaaacgaa tcgaaagccc aatggggcct atattatgta    660
gggccgaaat gaatttcaac gaaaggaacc caaagcccaa taggcccaaa ttgagactta    720
caaaggcgca tgttagcatg aagagagaat tgaaagctta aacagcgcca tcacaaaaca    780
tttgcatttt cgtgttgaaa tcgcatttgg gccgtaaacc aatgaaacac aaaacaaaca    840
aatcctggaa tagcctcaac ggttctggaa gaagaagaat cttctggaac ctccaatccc    900
acaataaaaa tcaaacccta aactcttaca ttcagctctt tgcttacctt atcccaacaa    960
accttcacca acgctctacc ggaactaaaa cccctccgac ctcccacttc cgacttacga   1020
cctctgttgc ctgaacatgg cgtctgccaa tgctctttct tccgcttcta ttctatgttc   1080
ttctcacaag gtacttcact tataaccccc tcatttcttc cttgtatttt tcacaattcc   1140
tctttggaaa tgatgatatc tagattgtag tagttgggat tgtatgttag gtagagattt   1200
tgtggagtta gctgagagcg gctgagaata ctaatatatc gtttccagta gcttacgttg   1260
cgtttttcta atgttgcaga gcttgagaaa ggtgaatcaa acgcagaaca acagagtaaa   1320
ttacagacag gctggtagta gatttgttgt gagagccact gcaaaggaga tagcattcga   1380
ccagagttct agaactgcac ttcagtctgg gattgataag cttgctaatg cagttggttt   1440
gactcttgga cctaggggta actttctgtt tatatttatt tatgaattgg ttagtattgg   1500
atgttgttct aatattgaaa tccctacagg atatattcat cacatttata gattcgtgtt   1560
atggttatgt tgagaaattt gggttcttca cataattctc aatcttgttg tgatattttg   1620
tatttgaagg gaggaatgtg gtgttggatg agtttggtag tcccaaagtg gttaatgatg   1680
gtgtgacaat tgctcgggca attgagttac ctgatcccat ggaaaatgct ggtgcagctt   1740
taattagaga ggttggtttt ttatactttg ttatgaagca aaattttctc atctatcgat   1800
tattgaagtc ttattagttc ttacattgcg ttgacaagta ttctatatgt c            1851
```

<210> SEQ ID NO 153
<211> LENGTH: 2000
<212> TYPE: DNA
<213> ORGANISM: Cucumis melo

<400> SEQUENCE: 153

```
actaattaat agtaatttgt atgggatata tgtatatgtg tgtataacag gaactacaga     60
gatagagatt cactttctag aaataaagtt gactgccatt ggagtttatt tggagccttc    120
agttgtggag catttgcaac aatggaaggg aaaagctgct aaggacttag tggaagatga    180
tgacttcttt caggctattg tttctggtat ctccctagtt atcctatttt taactatact    240
atctcatcac attcctaaat gtgaattact tgacgatctg ttcaaacata tatatttcat    300
tgtttgatcg taatgtttca tatttatgat gtttcatata ctacctcgtc acacgtgcaa    360
```

aggatttaga tccgttcaaa catatttcat tattggatcg taatgtttca tatctatgat 420
gtttcttata ctatcgcatc acacatgaga tccattcaaa catatctcat tgttagaaag 480
attatacatt atttcaattc aaatagctct aaccaatgac aaaattagat tcgtcccgtt 540
tagcttattc tatatatata gatagataga tagatagata gtatggatat gcttgtgata 600
agtgtttttt tcttcttttt tttttctttt tttgtttttt ttcttttttt gtcactttct 660
aaattatcta tctcacagtt agctagttgg cggggtgatg acttttggtg tgtcagtcta 720
gtgagaagtt tgggggttat ttttattttc gaaagcttcc taattgaatg acttgtaaag 780
gttaatgttt atgtttttgt acatgttttt catgaactat tggttttaca agagttacaa 840
ttctatttat ttgtgtaaga aagatcatat cacattttta cccctggtgt gttcgtttta 900
tgttcttgat ttgctttttg tttttcaata atttacgggg aaagagagaa taaaattttc 960
tttctccgat ctccgcattc aatttttttt tttttgaaag gtgcattcaa tttttttgtg 1020
cttattaaat attcacttac atcttttgtt ttgtttattt ttttattttc atctttctta 1080
tatgaaaata aaatattttt tagtacaaca atagaacctc ttgttaccat tgaaatgaat 1140
tacaggaaat taaaactttt actttttatt tgagagaatt aaaagagtag tttttaaata 1200
taacaaaacg actttcgcaa tagatccaga tgatcattta ttaacaattt tctaattaaa 1260
attgttacta aattttaaca attattaaaa aatattaatt gaaaaacacg tgtatatata 1320
taggaacatt ttcaattata gccaaaagtt ataattattt actctataaa attctttaga 1380
gtctatttaa cctttttgtt aaattttgtt aatagtttta ctttgccatt cataaaaatt 1440
tctcatatta tatacagtga gaattttata agtctcaaaa gtcaaagatt tgattaaaaa 1500
aaaaagaaat gaaagcatat ctaaatatat tatttatact ttgaaaatta cttccgaagc 1560
aaaatgtaaa accgttataa gtgaacttag aatccaaaaa catatattaa attaagttta 1620
aattatataa caacaccttt ggattttgtc attttctaaa ataccttttta tcatttcaat 1680 aattgtaaaa tgagtcctaa attttcacaa atgtttcaaa aatatttgga ggagacaatt 1740
ccttgagaat ttcaaagata tattaaagag gacgtattga cccaaatctt ttgttctatg 1800
tcactatgat caccctttta tatcacaatt tatttccatc tacaattcta aagaatttat 1860
aatttaaaag tagtttcaaa atgtttctaa attttcgagg gtaatatttt aacttttgga 1920
agtacggaaa gttaatcaaa tctttgtctc aaaatctcaa ctaataactg gaattgggaa 1980
agctaaagtc tagaccttaa 2000

<210> SEQ ID NO 154
<211> LENGTH: 1288
<212> TYPE: DNA
<213> ORGANISM: Cucumis melo
<220> FEATURE:
<221> NAME/KEY: misc_feature
<222> LOCATION: (1)..(1288)
<223> OTHER INFORMATION: n=g, a, t or c.
<220> FEATURE:
<221> NAME/KEY: unsure
<222> LOCATION: (1)..(1288)
<223> OTHER INFORMATION: unsure at all n locations

<400> SEQUENCE: 154
cgagaagtac ccggcgttgg tcaccggatt tttcttcttc atgtggtggg tttaattgtt 60
ggtcacgtgt tttgcacggc gaaggccggg tggtaattat tacgttgcgg caagtttgag 120
cttggttgtg tgaaattacc gtgttgtcct ttctgttttg taggtacttt ttgaacgtga 180

```
ttttcaatat cctcaataag aagatatata attacttccc ctatccatag tatgtatttc    240

caatttacat tttcatccct gtatttttct tcttcttctt cttnnnnttt tttttttaat    300

attgttatta atatttgttt acgttccagt tttgtgtcgg tgatccattt agttgttggg    360

gttgtgtact gtttgataag ctgggcagtg ggtcttccta agcgagcagt aagtcaactc    420

tttctatagc ccaatatgcc aattttgtct ttttctttca ttaaaattgt tatttttaac    480

tttttcatac ccaatttagt ttttttagtc tgtttattag tcttgttttc ttcaaattta    540

gtagtattgg tagtctaatt ggtagggctg ttttgaaagt aattacctaa tataatgagt    600

atttagattg agacagtact atagtctaaa cgatgtcatt gcagttttga ttgaaatttt    660

ttctccttta tttatttcga aaatgacaat ataacttctg taatctttgt aaccatgttt    720

atttgaagct acgttgtaaa ggggaaaaag aaaaggaaag tgtaaaatgg tcaaataaat    780

tatattttta agtgaataga ttatataatg tgcggtaaaa tatagcactc acaagtaaat    840

gcaacttagt aatctaaaga ttgaactatc aattcatgaa tttttttata attagcatgg    900

ttttctatag tttttgggag tctgtttttc aatgaaaata ttgccagtat ggtaatcttg    960

tatgacaatg tattttctaa agtatggata taattaaatt ttctttaatt tatcggctta   1020

aacttttcgt tgtactaaaa atctaggata ggacgtttaa tatttgaacc tttgtaatgc   1080

catttaatca ccgattaata tagatctaac tattgaaact tcttcaaaag ttttaatcca   1140

acggatggct aagagtgtta aaatattgat acaattaaat ttatcgtagc ttaagctttg   1200

acagtgtcaa aagctaattc agttattttc tctgcccttg gtataagggt aactctgttc   1260

tctctatttc acacaagtga ttgctaac                                       1288
```

<210> SEQ ID NO 155
<211> LENGTH: 2000
<212> TYPE: DNA
<213> ORGANISM: Cucumis melo

<400> SEQUENCE: 155

```
ttatgtttta ttaactccat agttttacta accccatttc acgggaaagt acaataaaac     60

atttgtgtta aaaaggagtt gtttgtatag atcgaataaa cattttgtac taattccaat    120

catattacca aatgttttaa gagcatgcgt tcttgtgtgc ttgaataggg gtgatcatca    180

attgagtggc gtcagattta aatttaaagt ggcaccaatc atcgacttgt tggtttagat    240

cgatcggtag ttgttgtttg tgggacaatc atagttatca tttttctcct tctatatgaa    300

taatagtcaa ctagatagaa ttgacatttc ttagtattaa aaaaacgacc actgacctgt    360

ctatatcact aaactgcttg acctaagtga gtttggttgg acttgattgc ttcgttgtgg    420

tctaattcac ttaaccctac ttgaaagtaa aggtagaata taacatgatt ctttccaaat    480

tggcaagttg tgacttgatt tatgcatgca cgaagattct tccactctcc acctaactag    540

tactcgatca cattggaaaa tggatctgtc ccgtgaagga tcgcaatatt acatgccttc    600

ctactttttt cttttcttcc accaaagaaa aagaaaacgg gacacacaat aactatacat    660

tatcaataat aattaaacga atcatcccac caaatgtaaa ccatgaatat tgaaatcatc    720

atgttttaag aatcatttta ataattatgt tatttcattg ttttatatag aacacaccgt    780

tcatgaaatc aaacaaagag agagaaatta taattttgta acaaattacc aacattcttt    840

ttctttctat ttttcataaa tgagcatatg tttgtgtata tatacatact gttatttgat    900

ctccacattg ttgaacaaaa aagttggtgt tcttgaaaat agctatcacc gaaaatacgt    960

catatactgg gttgttatgt accaaggccc agaagaaagc ccaaaatcac cggcccatga   1020
```

-continued gcagtgaaca aataattggg ctaaaagccc aatatacgtg atgatgggcc aacccagaga 1080
agtttatagt tatgttatta tagaattcca gatcagggag tatcgaaaca aaagcctcca 1140
ttgtcctcgt tctcttctcc ttgtgctctc tctctctctc tcttgctctt ttctctttct 1200
ctttctctcc gacgacaggt tcctgaagct cgaccagcca agggcattga tctaggtgag 1260
tccgctttca cttttccact ttcctctgcc gtttttcttg tcatttccaa ttctccattc 1320
tttgttctgg atttcacttc tttacttcgt cgttgattag aagataatag tgagatcgaa 1380
ttctatgtct cgcatacctt cagtttcaag gaacaagaca atgattcaac cgcgccgtcc 1440
acgttatgga tagagggttt tgattctcac ctttatagct gcataacacc gttcttaggg 1500
ttcggacctt tgaatctgcg atatttctca cactgttttg gacgttttta ccgttttcct 1560
atggttcttt agccttacct tatcttgcct tcagatcttc gattgcggat ctgattcgtt 1620
catttctact tgttactttt tcttggaagt cgaggattat aaatcaacaa caaagcattc 1680
aaaatctcta gtgcaattag tgttttccat ctagttattg gagatcgttt gtagctttga 1740
ttttgtccac tttcttattt tgaacgtctg gaagacgttt tatacatgtt ctttgggtaa 1800
agttgcgttt gggcactgtt cttcacctct gggttttcgt tcttatgcta tgtttcatga 1860
tttcttttga tatctttgtt attgtttccc catcatcgag tatctgattc ttattcggaa 1920
gccgtcttct tgaagctgcg aaccggtttt ctttttctcc ctcatcaagt ctttaatttt 1980
acaggaaagc gctgaataag 2000

<210> SEQ ID NO 156
<211> LENGTH: 2011
<212> TYPE: DNA
<213> ORGANISM: Cucumis melo

<400> SEQUENCE: 156
ttgttagagg agttagcttt tcagggagtc ggttacaact tacaagacag acaaccatac 60
tgtacaatca atcactactg cctcaaagtc gaaaccattt aataccagtt gagcctcatt 120
gtgactgcat aattttgacc cctaccacga ggtaatttca gttcaaatca attgtatctc 180
tcttctggat atcagtcaag aatctcatgt tctcaagtta tagtacattg ataattactg 240
tgcattttta ttaatttatg agttaaaatc ctgctgatta attcaactaa aggaataaaa 300
tagttattgg catttggatg agaatagaat gtgaatccca tcattcatcg ctagattgga 360
ccgtaattat aagtgagagg gagaaacttc tgttgctatt ccctttttat ttcttaattc 420
atttataaat tgtttttagg ccttttatat atatatattt ctaccatttt tacatttaaa 480
attcttttaa ctttattatg tatggactca aactaacaag ctttatttga taaaattgtt 540
caaactatta tattagtttt atatttgtaa accataaaac aaatccataa aattccacct 600
gcatcactca ctcatgttgt tgaatggtac gaaataaaca atacatgtga aagatgaaaa 660
taagaattgt tctcttatta aatctaaaat ctagattttc tttttagtac atttaacact 720
tcaatgaaag gtctaaaaca ttattgaatg acgtcacgaa ctattacaaa agattattcc 780
gatttatctc aaaaggggtc tatttcacta attttggtgt cccacatctg taaagagaat 840
tttcgtgata tgtgtagata tttaaatata attgaattcg atgaaagcaa agcaagaatc 900
gatatccgta gttattttga tatagatcgg tgataaataa aagacaatat gcataaagtt 960
tgtgggtaca gagtcggcta gttgcaatga ggggtatggc cccaagactt ttccccaacc 1020
ccaacggtca attaatcacc ccaatggggc atcgaatctt ccccaccatt ttccttttct 1080

```
tcgccgactc ttctacccat ctcttttgcc gactctttct cacaggtttg attaaatccc   1140

attcatattc agatacacta tttcaaaata ctcgcaaatt aatttgtttt tttaaatatt   1200

ggtataataa taaaattaat tataaattgt gacctaaaaa gtactttgtg gaagagggga   1260

tatagtctgt ctaatatatt attgattaaa tatataatag aaccataaat gcaaaccact   1320

agaattgtta ataaaaatca acgctctttt aagtctttcc atagaaagaa aggcaaagac   1380

gcgcaacgtc tagaattttc tttataacgg aagctaactc tgttataacg gccgtccaca   1440

taatatggta gatttaaaat gacgtcagca tgtcgcttct aaatttgggt ccaaaggggg   1500

gattcattta tagggaaggg aaacggcaaa tgcaagcata gtgagtaaat acgtggcggc   1560

aaagtaatgg ataattctgc ctctgccgtg acgacattgc ccttccattt cactataaat   1620

acacctcctc tatccctcga tttcttcgca attgaatttc tcttctcatc tctgtcgtag   1680

caaaccaaat cgatttcttc aaaggtattt cttcctttcc tttttttttt tttttttttt   1740

tttttaaatc atgttgttca aactttgaga gatgaaatga ttaggggctt tcaaagtggt   1800

tttcgtttga tatgtttctt agatcgatag ggtttagaat cgagcatcct tgtaggtatc   1860

ctgaggtttg gtggttggat ctgcttaatt tttatgtggt tgcatggaaa attgggattt   1920

ttttttcta attacgtgat tctggaaata ttgatctgtg gttcagatgg aattgaatct   1980

gatctttctg ttttgttctg tataggtggg c                                  2011
```

<210> SEQ ID NO 157
<211> LENGTH: 1698
<212> TYPE: DNA
<213> ORGANISM: Cucumis melo

<400> SEQUENCE: 157

```
ttgttagagg agttagcttt tcagggagtc ggttacaact tacaagacag acaaccatac     60

tgtacaatca atcactactg cctcaaagtc gaaaccattt aataccagtt gagcctcatt    120

gtgactgcat aattttgacc cctaccacga ggtaatttca gttcaaatca attgtatctc    180

tcttctggat atcagtcaag aatctcatgt tctcaagtta tagtacattg ataattactg    240

tgcattttta ttaatttatg agttaaaatc ctgctgatta attcaactaa aggaataaaa    300

tagttattgg catttggatg agaatagaat gtgaatccca tcattcatcg ctagattgga    360

ccgtaattat aagtgagagg gagaaacttc tgttgctatt cccttttat ttcttaattc     420

atttataaat tgtttttagg ccttttatat atatatattt ctaccatttt tacatttaaa    480

attcttttaa ctttattatg tatggactca aactaacaag ctttatttga taaaattgtt    540

caaactatta tattagtttt atatttgtaa accataaaac aaatccataa aattccacct    600

gcatcactca ctcatgttgt tgaatggtac gaaataaaca atacatgtga aagatgaaaa    660

taagaattgt tctcttatta aatctaaaat ctagattttc tttttagtac atttaacact    720

tcaatgaaag gtctaaaaca ttattgaatg acgtcacgaa ctattacaaa agattattcc    780

gatttatctc aaaaggggtc tatttcacta attttggtgt cccacatctg taaagagaat    840

tttcgtgata tgtgtagata tttaaatata attgaattcg atgaaagcaa agcaagaatc    900

gatatccgta gttattttga tatagatcgg tgataaataa aagacaatat gcataaagtt    960

tgtgggtaca gagtcggcta gttgcaatga ggggtatggc cccaagactt ttccccaacc   1020

ccaacggtca attaatcacc ccaatggggc atcgaatctt ccccaccatt ttccttttct   1080

tcgccgactc ttctacccat ctcttttgcc gactctttct cacaggtttg attaaatccc   1140

attcatattc agatacacta tttcaaaata ctcgcaaatt aatttgtttt tttaaatatt   1200
```

ggtataataa taaaattaat tataaattgt gacctaaaaa gtactttgtg gaagagggga 1260
tatagtctgt ctaatatatt attgattaaa tatataatag aaccataaat gcaaaccact 1320
agaattgtta ataaaaatca acgctctttt aagtctttcc atagaaagaa aggcaaagac 1380
gcgcaacgtc tagaattttc tttataacgg aagctaactc tgttataacg gccgtccaca 1440
taatatggta gatttaaaat gacgtcagca tgtcgcttct aaatttgggt ccaaaggggg 1500
gattcattta tagggaaggg aaacggcaaa tgcaagcata gtgagtaaat acgtggcggc 1560
aaagtaatgg ataattctgc ctctgccgtg acgacattgc ccttccattt cactataaat 1620
acacctcctc tatccctcga tttcttcgca attgaatttc tcttctcatc tctgtcgtag 1680
caaaccaaat cgatttct 1698

<210> SEQ ID NO 158
<211> LENGTH: 313
<212> TYPE: DNA
<213> ORGANISM: Cucumis melo

<400> SEQUENCE: 158
tcaaaggtat ttcttccttt ccttttttt tttttttttt ttttttaaa tcatgttgtt 60 caaactttga gagatgaaat gattaggggc tttcaaagtg gttttcgttt gatatgtttc 120
ttagatcgat agggtttaga atcgagcatc cttgtaggta tcctgaggtt tggtggttgg 180
atctgcttaa tttttatgtg gttgcatgga aaattgggat ttttttttc taattacgtg 240 attctggaaa tattgatctg tggttcagat ggaattgaat ctgatctttc tgttttgttc 300
tgtataggtg ggc 313

<210> SEQ ID NO 159
<211> LENGTH: 2010
<212> TYPE: DNA
<213> ORGANISM: Cucumis melo

<400> SEQUENCE: 159
tagaaaaaaa ttgaagatct tcttaatgct aataataaaa gcatatataa aaaggcttca 60
tattacacaa gcatcttaaa accaaaccga acttgatttg aaattatccc actaattctg 120
tagatttcac caaagtcctt aacctttata ctaacatctg catttgactc tttcatttga 180
cctccaacat attctttctc attttccttc cattcaccac aaaaaccaac aaatacaaaa 240
aaccacaaat acatagaaaa ttaataaaaa aatcaaaatt tcgagatgaa atcattataa 300
actcatccga taactttgag atttgaaacc ttacactata taaagaaact catccgataa 360
ctttgaattc gcatcgaaat tacgtaagtg aagacgaaaa tgtaaatgat tagatgcgaa 420
taacaaaaaa aacataattt ctaaacgtaa aacactatat tcaccttatt atacttgatt 480
attttggaaa agtatgaaat ttgagtgtgg gagaggagcc aaagaattgg aaacttgtta 540
ttaggagtcg ttatgaaaca ttttcaacaa gccaatattc tttcacatac tataatgata 600
tacatagaaa taatacaata atatttttga aattgaggca tttttgtcgt aatttatcta 660
aaaatgtcag ggtagattca tcatgtatac aaatctctcg ctatcaaaac tatataaaaa 720
tcttgtgaat gatttcaatc gaaatggacc gagaaaaaac atcgtaacca cctctaaaat 780
cgataaattt gtttcaattt caaatcccta aaactaaagg tgctactttg tacaatttcc 840
cctgattagg gtgctaaagt taaaccctaa ataaaggtgt gtacgtttcc ggaagtttct 900
agaatcccca gcgaagttct ccaaatcgtg gcttgcagac caaggacccc cattaaaatt 960

-continued

```
cgtttcttcc tctaaacctc ctcccttaat tttggcattt tggtattttg gctcctataa   1020

attcaccccc tccttatccc taatcctttg tcttccaaat tttccttcaa agcctgcttt   1080

tcccatttcg tcgtgctttt tcttcatcta aaggtatatt tcagttctag ttttctttct   1140

ctgttgatct cttggatttg agggacgttt gaagttggct ttgtttaatt ctttgttatt   1200

caatctcttt ttttgttaga gttgttgttt aatcgtttcc cttgttgttt ttctcccttc   1260

tagttcgatt ttagaacgct ttttgtgggt tgattttaat ttctccgttt tcttacatct   1320

ttcacaaaga aacgattgaa atcgtgtttg ttttttttcc cacggcatac gttattagat   1380

cttgtagata atgatctcaa tctattgttt agtttttgca aataagaagt tggtttttta   1440

tctccaactt ttatatattc gattcgatga gatgttctac accgttagga tggaaccaag   1500

aagtgaggta agggtgtttg attgaaaaat tgaactgaga agttaaagtt ccttcctaac   1560

tttttaatgg attgtataat tcgttcaatt ccttgtcgtt ccatttttat ttctgtttcg   1620

tttttcgtgt tgctgcgtat cgcttccctt gttgttttcc tcccctattg attttgcgtt   1680

tcttggagtt tctctgtttt ctctcttcat ttttctacaa aaatcaattc tatttttatt   1740

cgttttcaat tcccgagctc cttggaatgt tatccttttc tcctgtgtaa ataagaaccc   1800

gtattcaatc ccagttcata gtttggcttt cccaaataag agcaaaaaga ttgtactgag   1860

aagttgaaga tttcaaaatt ttgtacatga tttcttctaa tttatcaatt tgattggact   1920

ttttgtatat agatttggtt cttgagctat ttatgttatg acgttttcat attgaggcca   1980

tgcgttgaat tggtttctta acaggtgggc                                    2010
```

<210> SEQ ID NO 160
<211> LENGTH: 1107
<212> TYPE: DNA
<213> ORGANISM: Cucumis melo

<400> SEQUENCE: 160

```
tagaaaaaaa ttgaagatct tcttaatgct aataataaaa gcatatataa aaaggcttca     60

tattacacaa gcatcttaaa accaaaccga acttgatttg aaattatccc actaattctg    120

tagatttcac caaagtcctt aacctttata ctaacatctg catttgactc tttcatttga    180

cctccaacat attctttctc attttccttc cattcaccac aaaaaccaac aaatacaaaa    240

aaccacaaat acatagaaaa ttaataaaaa aatcaaaatt tcgagatgaa atcattataa    300

actcatccga taactttgag atttgaaacc ttacactata taaagaaact catccgataa    360

ctttgaattc gcatcgaaat tacgtaagtg aagacgaaaa tgtaaatgat tagatgcgaa    420

taacaaaaaa aacataattt ctaaacgtaa aacactatat tcaccttatt atacttgatt    480

attttggaaa agtatgaaat ttgagtgtgg gagaggagcc aaagaattgg aaacttgtta    540

ttaggagtcg ttatgaaaca ttttcaacaa gccaatattc tttcacatac tataatgata    600

tacatagaaa taatacaata atatttttga aattgaggca tttttgtcgt aatttatcta    660

aaaatgtcag ggtagattca tcatgtatac aaatctctcg ctatcaaaac tatataaaaa    720

tcttgtgaat gatttcaatc gaaatggacc gagaaaaaac atcgtaacca cctctaaaat    780

cgataaattt gtttcaattt caaatcccta aaactaaagg tgctactttg tacaatttcc    840

cctgattagg gtgctaaagt taaaccctaa ataaaggtgt gtacgtttcc ggaagtttct    900

agaatcccca gcgaagttct ccaaatcgtg gcttgcagac caaggacccc cattaaaatt    960

cgtttcttcc tctaaacctc ctcccttaat tttggcattt tggtattttg gctcctataa   1020

attcaccccc tccttatccc taatcctttg tcttccaaat tttccttcaa agcctgcttt   1080
```

tcccatttcg tcgtgctttt tcttcat 1107

<210> SEQ ID NO 161
<211> LENGTH: 903
<212> TYPE: DNA
<213> ORGANISM: Cucumis melo

<400> SEQUENCE: 161
ctaaaggtat atttcagttc tagttttctt tctctgttga tctcttggat ttgagggacg 60
tttgaagttg gctttgttta attctttgtt attcaatctc tttttttgtt agagttgttg 120
tttaatcgtt tcccttgttg tttttctccc ttctagttcg attttagaac gctttttgtg 180
ggttgatttt aatttctccg ttttcttaca tctttcacaa agaaacgatt gaaatcgtgt 240
ttgttttttt tcccacggca tacgttatta gatcttgtag ataatgatct caatctattg 300
tttagttttt gcaaataaga agttggtttt ttatctccaa cttttatata ttcgattcga 360
tgagatgttc tacaccgtta ggatggaacc aagaagtgag gtaagggtgt ttgattgaaa 420
aattgaactg agaagttaaa gttccttcct aactttttaa tggattgtat aattcgttca 480
attccttgtc gttccatttt tatttctgtt tcgtttttcg tgttgctgcg tatcgcttcc 540
cttgttgttt tcctccccta ttgattttgc gtttcttgga gtttctctgt tttctctctt 600
catttttcta caaaaatcaa ttctattttt attcgttttc aattcccgag ctccttggaa 660
tgttatcctt ttctcctgtg taaataagaa cccgtattca atcccagttc atagtttggc 720
tttcccaaat aagagcaaaa agattgtact gagaagttga agatttcaaa attttgtaca 780
tgatttcttc taatttatca atttgattgg actttttgta tatagatttg gttcttgagc 840
tatttatgtt atgacgtttt catattgagg ccatgcgttg aattggtttc ttaacaggtg 900
ggc 903

<210> SEQ ID NO 162
<211> LENGTH: 1235
<212> TYPE: DNA
<213> ORGANISM: Cucumis melo

<400> SEQUENCE: 162
aaattttaat aattaaaatg aacaattttt caagagtaat agagtttgag agatgtcaga 60
gaagtttgag gaagaagata acaagtggga gaagagaata agtttgttgt gtgaaagaga 120
aggggaaatt tcattcaagg gtatattgaa ctttttactc aaattttgta agtctatttt 180
ttccgatcaa tcctaaaatc acacacaccc ttaaaaaatg gattatattt ggcaattttc 240
catgataaac tcatttttaa tttagagtta ttttttcaac gagatattaa cagttttagt 300
tcatatacta attgtaagaa tagtttcttt taagttgaat agaatttttg aaacttttaa 360
tagttcaaaa ggtatttttg aaacaaaata agaatgtttt tgaacttttt ataaaaagaa 420
ttgagatttt tttgaaattt ttgataaaga gaaaagaaaa gaagaaagaa aaaagaaaaa 480
caagtttgta gaactccgtg ggaaaatcgt cgagggccct gtgaaggaat tttgaaatta 540
taatgagggt attttcgtca acaagggaat ttagacatcg tatataagca tcctcaaacc 600
ctataattaa gcccttcaat ccaattgcca ttctccatct ctcgccgcaa gggtttaaga 660
gcagcttctc tcctcaggtt ggggtttccc cctatcttct tcattcttcc tcttctcgat 720
ttctttcttc tatttgctcg atagtctctt atttcttgag cttttgctgt ttttctcctg 780
tacatcctaa catgaattat aacttggttt tgattttgtc ttttacttct gtattaaaca 840

-continued

```
acttttctta cccttttatt cttctcttct tcttcgtgtc cctgcccttt tgtttttatg    900

ctaattttat gtttctgttt atcaatctat cgaggcgtga cctgtcgttc ttccaatagc    960

gtagatctgc acttaatcta ttctagctga ttggattggt cgtttttcgt tttttttaatt  1020

tattttctct gttctagttc cgataaattt ttttatatat aattaacaag ttctccagcc   1080

aaaagggtta atattgcgtt ggatatttta atttttacgt tatttagatg tgtgaatcta   1140

ataaaattag ggttattcat aaatttcagt aatgatattt tggttatctg ttcttgctgt   1200

tcctgtttcg cagttctttt acctaatatt caagc                              1235
```

<210> SEQ ID NO 163
<211> LENGTH: 617
<212> TYPE: DNA
<213> ORGANISM: Cucumis melo

<400> SEQUENCE: 163

```
aaattttaat aattaaaatg aacaattttt caagagtaat agagtttgag agatgtcaga     60

gaagtttgag gaagaagata acaagtggga gaagagaata agtttgttgt gtgaaagaga    120

aggggaaatt tcattcaagg gtatattgaa ctttttactc aaattttgta agtctatttt    180

ttccgatcaa tcctaaaatc acacacaccc ttaaaaaatg gattatattt ggcaattttc    240

catgataaac tcatttttaa tttagagtta tttttcaac gagatattaa cagttttagt    300

tcatatacta attgtaagaa tagtttcttt taagttgaat agaatttttg aaacttttaa    360

tagttcaaaa ggtatttttg aaacaaaata agaatgtttt tgaacttttt ataaaaagaa    420

ttgagatttt tttgaaattt ttgataaaga gaaaagaaaa gaagaaagaa aaaagaaaaa    480

caagtttgta gaactccgtg ggaaaatcgt cgagggccct gtgaaggaat tttgaaatta    540

taatgagggt attttcgtca acaagggaat ttagacatcg tatataagca tcctcaaacc    600

ctataattaa gcccttc                                                   617
```

<210> SEQ ID NO 164
<211> LENGTH: 54
<212> TYPE: DNA
<213> ORGANISM: Cucumis melo

<400> SEQUENCE: 164

```
aatccaattg ccattctcca tctctcgccg caagggttta agagcagctt ctct           54
```

<210> SEQ ID NO 165
<211> LENGTH: 545
<212> TYPE: DNA
<213> ORGANISM: Cucumis melo

<400> SEQUENCE: 165

```
cctcaggttg ggtttcccc ctatcttctt cattcttcct cttctcgatt tctttcttct     60

atttgctcga tagtctctta tttcttgagc ttttgctgtt tttctcctgt acatcctaac    120

atgaattata acttggtttt gattttgtct tttacttctg tattaaacaa cttttcttac    180

ccttttattc ttctcttctt cttcgtgtcc ctgccctttt gtttttatgc taattttatg    240

tttctgttta tcaatctatc gaggcgtgac ctgtcgttct tccaatagcg tagatctgca    300

cttaatctat tctagctgat tggattggtc gtttttcgtt tttttaattt attttctctg    360

ttctagttcc gataaatttt tttatatata attaacaagt tctccagcca aaagggttaa    420

tattgcgttg gatattttaa tttttacgtt atttagatgt gtgaatctaa taaaattagg    480

gttattcata aatttcagta atgatatttt ggttatctgt tcttgctgtt cctgtttcgc    540
```

agttc 545

<210> SEQ ID NO 166
<211> LENGTH: 19
<212> TYPE: DNA
<213> ORGANISM: Cucumis melo

<400> SEQUENCE: 166
ttttacctaa tattcaagc 19

<210> SEQ ID NO 167
<211> LENGTH: 2003
<212> TYPE: DNA
<213> ORGANISM: Cucumis melo

<400> SEQUENCE: 167
cagtgtgctg gaattcgccc ttatccaagg agattaatgt cgagagatta ttatcgaggt 60
ttgaatttat tttgtccaat catatgattc caagagctga ccatcaattc aacagaacat 120
gaaccggaac ctcataccta ttgtaatggt tcacagcatc ctaatacaga acatgaaccg 180
aaacctctta cccattgtaa tggttcacag catctttata cgtattatag gtagtaccat 240
tgaagatgca tttaaatgct gtccatgctc tgttctctaa aaagttggac ttggacttgg 300
acgtcagctg aaagtatgaa atgcactgta gccaacgaag ctatgttttc aggcttcaac 360
atggttttag gaaagtggag gctctttggt tgaagggttg aatgaatgct tttctaattc 420
cagcatgatc ttcaaatttc gacacaaaaa gcttaagtat tttgttccgt tattctttta 480
atccttgtat tgttatatat tcttttctct gaactgaatg tacgatgatt gcaggggtcg 540
agagcaagtc cgatataatg aaacacgtaa ggacgtgatt gaatgaaaaa ctatgagcag 600
agatacaaag tctaacttac gggatgaacg atgagaggtt tgaccaagag ctgtgacgcc 660
tgtatatttc aacaaaagtt gatgactaac atcacatgtc agagtaatca aagaaatgca 720
gccgcacata tatatatcta tatatatatc gagttttttt tttttttttt tttttttttt 780
tttttttatc taatatattt taatctattt tcctctgccc tcctcccccct cctcttcccc 840 cacccttctt ctgcacatag tagccaagga ttgatcggtt tcttttgatt cgggggggaaa 900 atgttgtaca atttttgctt ccatagaagc ttgaaagttt tgcagattat gttgtaaaat 960 taccccttgtg tactcacact agttcttctc gtggaaactt atattacaat ggttgagttt 1020
taaggggcat attcacactg gtaactacca ttttctaatt tatgaatgcc gagtttctct 1080
ccatgaaaga cctttcaaat gccctttcct ccgcggtgcg tttgttgttg taaatgtgca 1140
gtgtcgttgg atacacgatt gtgtgaaagg gaaaagggaa tacgattaac tcttaaattc 1200
aacccctatc tccatcagta tcaatcacat ttcagcaact agctcttgaa taacattgag 1260
attcttgttt aatccacgta ctactactac tattactact atttgacagt tgatatctca 1320
aataacatcc atatttatca aattggtatt ttaaggactt ttaatttctt cgtacatatt 1380
tcattataat ttaactactc tgaccatcat tgaaaatttc acaaagaaga cattttaaat 1440
tgaattgagt tgaattaagt tgatataatg gttgaacgtt ggatttaatt tataatttag 1500
tggtgtatgg gtccattgta ataattctta aaaaaaatat catattctga attctaaaga 1560
accatctaag accaaaacta aggggtcacc aatgagtatg gtaaagtcaa caaagtttgt 1620
ctacttttct tatccttatc atcaagagtg caatatgata tcaaagataa attgtacgtg 1680
ggcgtcatcc attgggtaag accaagaagc aaaatatcat agagaagttg ttttagtagc 1740

```
cataggaagg aaggaagcaa aataataata tagatttgaa attgtggatg ataaactgcc   1800

aaatgggaat tcaaaataaa ctaaataaat aaaataaaaa gagaaatctt gggagtttcc   1860

attttagcca atgaggaaac agatagagat ctcatcaaga taaggaccct attctcttct   1920

tcatctataa aacaaaaaca aatcaaaccc tcatttcact cattcaaaac aaaaagtact   1980

ccaaagtcaa actaacaaat acg                                           2003


<210> SEQ ID NO 168
<211> LENGTH: 2004
<212> TYPE: DNA
<213> ORGANISM: Cucumis melo

<400> SEQUENCE: 168

tggatcgacc atgacattca aaaaccttta agatatggat cttataaaat aaatgtaaag     60

ggtaaacaat tcttccttgc ttaacccaag ctatatattt tatgcactaa tttaggtatt    120

agagtatatt cagctgaaca ccacctacca atgctagtac tttaatcagt caattctaac    180

ttcgataata tatctcaacc aaattagtga aaaagagtcg taaatgaaaa actatgtacc    240

aagatattct atttgttttt tttatgttta aatatctcaa agataatacc taaaacgttt    300

tctcctcgta caaagattcc tcatttactt tttattgtcg taaactctaa tacaataaac    360

taaaacaagt acaaatacac tagctttaga aatctacttt ttattgaaac caaaaccaat    420

aattcaacat ttcattttca ccgacaaacc tttgtaaaca attgaagtaa tttttgttgg    480

tactatgaat agtaacatca agtcttcaag tgcatcatat caaccaagac atgttcttaa    540

aagcgacact aaaagattta aaaccaaaag catttatgaa atccgaactt aatcaaatcc    600

taaatatttt tcacttaaaa aaaaaaaaat aggaagaaaa attgacataa atgggatatt    660

ttcgttttca aactggcaag ccagcatgca ccacgttgtt gacgtgtcct tccacgtcgg    720

aaaaaaaaat attaccacag taaaaagaga ataaaatgaa agtcgttgac tctcccttag    780

tcggaggaag cgcgtgaagc tgaagccgga ttagaaatcg gcaataaccc cgacacgtca    840

tcgaaatgct agtatcaaat attgtccgtt ggatcttcct tcaccaactc tatttgaacg    900

gccacgatct tccaggtcca acggttcgga agaatctttt cgaaattcca tggctagtcc    960

ctacactcct ccctattggc tccctagggc atcccgaccg gttattccgg ttgccgggaa   1020

ggtggctgga cgctataaat acccgctttg ttcatctcgt agtccttgta ccgttgagct   1080

tcgccttcta atagagctct ggttcggttg gcgtattagc tcgaattctt tctctcttcc   1140

agatctacgc tgccgatttc atcaggtttg cgagctctgt tccaccattt ttcttttcct   1200

gaagctttga gcatgcttgt gattcttcat ttcctcattt ctttgatggt ttatgaaaga   1260

atttagggga attttctctt tttgtattct agtggtactg gtagatttgt ttgaagtttg   1320

tttctcttct tctgagaagt gaattcttcc agatctgaca gttgcttttg atttttttctt   1380

tgggaattag tgaatgatac ttcgatactg tttttttgctc tctgagattc tggatctcgg   1440

gccttggggt tttctattgt cttttggtag ctatgtttcg tttgtcagct tgtatttgtc   1500

attgttgaat ggttcgatcc ggtttgtaaa taaaataaat tttgtaggcg cacttgtttt   1560

ccacggtttt cgtgttacgg tttcatgatt ccctagatct ctggttagaa ctaagttttt   1620

tgtcggtaat tggatttggt aagggactgt tactgtggtt gaattgtaga tccagtcatc   1680

ttctacatga gtgtagggtt ccttagggca gatcttgtgt tttataattt taattttgtt   1740

gtttccctga ttttgaacct gtttggttgt tcagattcgt cgagtcattt ccattcatta   1800

aaagtttcta taattttatt tgaatcttct gaatctgtgc ttgtattacc cagatttcta   1860
```

taaacctatc ttgatttcaa gtgtgctatg tggtaactgt tgatattttc aagcttaagc 1920
aatactgatg tgactaaaac ttaactaatg aactgaatgt tttttgtaca cgaactaata 1980
tggtgttttg ttatgtttca gagg 2004

<210> SEQ ID NO 169
<211> LENGTH: 1067
<212> TYPE: DNA
<213> ORGANISM: Cucumis melo

<400> SEQUENCE: 169
tggatcgacc atgacattca aaaaccttta agatatggat cttataaaat aaatgtaaag 60
ggtaaacaat tcttccttgc ttaacccaag ctatatattt tatgcactaa tttaggtatt 120
agagtatatt cagctgaaca ccacctacca atgctagtac tttaatcagt caattctaac 180
ttcgataata tatctcaacc aaattagtga aaaagagtcg taaatgaaaa actatgtacc 240
aagatattct atttgttttt tttatgttta aatatctcaa agataatacc taaaacgttt 300
tctcctcgta caaagattcc tcatttactt tttattgtcg taaactctaa tacaataaac 360
taaaacaagt acaaatacac tagctttaga aatctacttt ttattgaaac caaaaccaat 420
aattcaacat ttcattttca ccgacaaacc tttgtaaaca attgaagtaa tttttgttgg 480
tactatgaat agtaacatca agtcttcaag tgcatcatat caaccaagac atgttcttaa 540
aagcgacact aaaagattta aaaccaaaag catttatgaa atccgaactt aatcaaatcc 600
taaatatttt tcacttaaaa aaaaaaaaat aggaagaaaa attgacataa atgggatatt 660
ttcgttttca aactggcaag ccagcatgca ccacgttgtt gacgtgtcct tccacgtcgg 720
aaaaaaaaat attaccacag taaaaagaga ataaaatgaa agtcgttgac tctcccttag 780
tcggaggaag cgcgtgaagc tgaagccgga ttagaaatcg gcaataaccc cgacacgtca 840
tcgaaatgct agtatcaaat attgtccgtt ggatcttcct tcaccaactc tatttgaacg 900
gccacgatct tccaggtcca acggttcgga agaatctttt cgaaattcca tggctagtcc 960
ctacactcct ccctattggc tccctagggc atcccgaccg gttattccgg ttgccgggaa 1020
ggtggctgga cgctataaat acccgctttg ttcatctcgt agtcctt 1067

<210> SEQ ID NO 170
<211> LENGTH: 92
<212> TYPE: DNA
<213> ORGANISM: Cucumis melo

<400> SEQUENCE: 170
gtaccgttga gcttcgcctt ctaatagagc tctggttcgg ttggcgtatt agctcgaatt 60
ctttctctct tccagatcta cgctgccgat tt 92

<210> SEQ ID NO 171
<211> LENGTH: 845
<212> TYPE: DNA
<213> ORGANISM: Cucumis melo

<400> SEQUENCE: 171
catcaggttt gcgagctctg ttccaccatt tttcttttcc tgaagctttg agcatgcttg 60
tgattcttca tttcctcatt tctttgatgg tttatgaaag aatttagggg aattttctct 120
ttttgtattc tagtggtact ggtagatttg tttgaagttt gtttctcttc ttctgagaag 180
tgaattcttc cagatctgac agttgctttt gattttttct ttgggaatta gtgaatgata 240

```
cttcgatact gttttttgct ctctgagatt ctggatctcg ggccttgggg ttttctattg    300

tcttttggta gctatgtttc gtttgtcagc ttgtatttgt cattgttgaa tggttcgatc    360

cggtttgtaa ataaaataaa ttttgtaggc gcacttgttt tccacggttt tcgtgttacg    420

gtttcatgat tccctagatc tctggttaga actaagtttt ttgtcggtaa ttggatttgg    480

taagggactg ttactgtggt tgaattgtag atccagtcat cttctacatg agtgtagggt    540

tccttagggc agatcttgtg ttttataatt ttaattttgt tgtttccctg attttgaacc    600

tgtttggttg ttcagattcg tcgagtcatt tccattcatt aaaagtttct ataattttat    660

ttgaatcttc tgaatctgtg cttgtattac ccagatttct ataaacctat cttgatttca    720

agtgtgctat gtggtaactg ttgatatttt caagcttaag caatactgat gtgactaaaa    780

cttaactaat gaactgaatg ttttttgtac acgaactaat atggtgtttt gttatgtttc    840

agagg                                                                845
```

```
<210> SEQ ID NO 172
<211> LENGTH: 2018
<212> TYPE: DNA
<213> ORGANISM: Cucumis melo

<400> SEQUENCE: 172

actattggag acgacgaagg aaaactctaa tgtgagctta gaattgaaga tggtgaacaa     60

ttgggagtct tttttaaaaa tctttcgtcg gtatattgaa atttcctttt acactcaaat    120

aacccccctt ttcacgcgtt caacgtcttc aaaccttcct ttttcaatta ttttttcgtt    180

tacattaatg acatttaggt aataagataa attagtggat tcttttgtga aaaatgttag    240

cccatttaag acttttatga aatatattag aaaaaaatca tatagcaatt tatattattc    300

tagttaaaag cccataatag aaactaaccc aacctaaagt aacgtaaaca ttcaataaga    360

gagacaaatt ttaaaataat ttctaattaa aaaaaaaatt gtcaagaccg tccgggtcgg    420

atccaaaata taacccgaac cggccggttt agcatctata taaatacacc tttagggttt    480

ttattctctc aagacttcac cgcatttcca cttctctgag gccacggtca gccattggag    540

cagctcaata atcctttgac tccctactac ggtaagtcga ccttactgct ttcggcttct    600

agtttttca atcctgtcat tagtcctttg gagttcttct gtacatttat gacgttttcg    660

gctcgtgttt tgtttcgcct gtatgtagtg ggtttttcga gttttgtttt tacttttttt    720

tatacttgca ggaattagtt gaaatctatg tacttcatgc cttggataat actcttgatc    780

tgttgtgtta ttcaaaaatg aattgtttta agatggtatt tgagaatggt catgtgagtt    840

ttgcctactt ggttattaaa atgaattgtt ttaggatggt atttgagaat ggtcttctgg    900

gtatttggtt ggaacctttg tgctctgcta tgaattaggg tgttctcccc gttttttttt    960

ttttttttct tttggttatt aatatatctt ttatgactac ttattcatat atgatatctt   1020

ttactcgtaa attttgactc atttgaaagt tttatcctta gtcctttctc attcagggtg   1080

taaaggtatg ttgttagggt taaaatagcc tatgcaggaa agttctgtat ttgttctaat   1140

tattgcattt gtgtgcattt gtatctagtt tatttcttgc tgagagtatg cttcattttt   1200

tagtacacat cacttgtgcc actttattat agttgcacat ttttgtttat ggagaggatg   1260

aatagcattt agggatgtca attttttatt gagaaaaccc tctctcctac ttaagcttgg   1320

ggaatttttg ttctaaatgt ggtaaacata atacttcttc ttattttaat ttgaatggaa   1380

ggggaagacg aatactaata ttttcaacga accttcacaa cttttttttc ttatttagga   1440

agccatgttt ttcaaaattg tactgtgtga tccacatatt tatcgattat tagtgaatcg   1500
```

```
aataataatt agagttttat tggtataatt ttgaagttca gacttattac atttgtggaa   1560

agtttggtta caattttcaa ttttattgga atcctaagaa ctttgtgtta acatatattg   1620

agttttcttc tctttttttt tactcattaa gttctctatt aggaatgttt ggttcaatgt   1680

cacatagtcg atagctaaga ccagtgaccc acaaagctat gattgaacga aaaacaagcc   1740

tttcacatct tggtaggaat ttgttatttc tcaatagatt tacagagctg tttcatgtga   1800

tcacaatttt tttctatttt tctgaagttc tctattagga atgggctatc tggttagttg   1860

cttttgagag aacatgtgga ttggtgttgc tcggtttcct tgcctttgta attttgtcct   1920

tggaaaaagc aaaatgatta ggtatcctga tatgcataac atgtttaagc caactagttc   1980

tcactttttt agtgcaaata attgatcttc aggaatcg                            2018
```

<210> SEQ ID NO 173
<211> LENGTH: 565
<212> TYPE: DNA
<213> ORGANISM: Cucumis melo

<400> SEQUENCE: 173

```
actattggag acgacgaagg aaaactctaa tgtgagctta gaattgaaga tggtgaacaa     60

ttgggagtct tttttaaaaa tctttcgtcg gtatattgaa atttcctttt acactcaaat    120

aacccccctt ttcacgcgtt caacgtcttc aaaccttcct ttttcaatta ttttttcgtt    180

tacattaatg acatttaggt aataagataa attagtggat tcttttgtga aaaatgttag    240

cccatttaag acttttatga aatatattag aaaaaaatca tatagcaatt tatattattc    300

tagttaaaag cccataatag aaactaaccc aacctaaagt aacgtaaaca ttcaataaga    360

gagacaaatt ttaaaataat ttctaattaa aaaaaaaatt gtcaagaccg tccgggtcgg    420

atccaaaata taacccgaac cggccggttt agcatctata taaatacacc tttagggttt    480

ttattctctc aagacttcac cgcatttcca cttctctgag gccacggtca gccattggag    540

cagctcaata atcctttgac tccct                                          565
```

<210> SEQ ID NO 174
<211> LENGTH: 1453
<212> TYPE: DNA
<213> ORGANISM: Cucumis melo

<400> SEQUENCE: 174

```
actacggtaa gtcgacctta ctgctttcgg cttctagttt tttcaatcct gtcattagtc     60

ctttggagtt cttctgtaca tttatgacgt tttcggctcg tgttttgttt cgcctgtatg    120

tagtgggttt ttcgagtttt gtttttactt ttttttatac ttgcaggaat tagttgaaat    180

ctatgtactt catgccttgg ataatactct tgatctgttg tgttattcaa aaatgaattg    240

ttttaagatg gtatttgaga atggtcatgt gagttttgcc tacttggtta ttaaaatgaa    300

ttgttttagg atggtatttg agaatggtct tctgggtatt tggttggaac ctttgtgctc    360

tgctatgaat tagggtgttc tccccgtttt tttttttttt tttcttttgg ttattaatat    420

atcttttatg actacttatt catatatgat atcttttact cgtaaatttt gactcatttg    480

aaagttttat ccttagtcct ttctcattca gggtgtaaag gtatgttgtt agggttaaaa    540

tagcctatgc aggaaagttc tgtatttgtt ctaattattg catttgtgtg catttgtatc    600

tagtttattt cttgctgaga gtatgcttca ttttttagta cacatcactt gtgccacttt    660

attatagttg cacatttttg tttatggaga ggatgaatag catttaggga tgtcaatttt    720
```

-continued

```
ttattgagaa aaccctctct cctacttaag cttggggaat ttttgttcta aatgtggtaa     780
acataatact tcttcttatt ttaatttgaa tggaagggga agacgaatac taatattttc     840
aacgaacctt cacaactttt ttttcttatt taggaagcca tgtttttcaa aattgtactg     900
tgtgatccac atatttatcg attattagtg aatcgaataa taattagagt tttattggta     960
taattttgaa gttcagactt attacatttg tggaaagttt ggttacaatt ttcaatttta    1020
ttggaatcct aagaactttg tgttaacata tattgagttt tcttctcttt ttttttactc    1080
attaagttct ctattaggaa tgtttggttc aatgtcacat agtcgatagc taagaccagt    1140
gacccacaaa gctatgattg aacgaaaaac aagcctttca catcttggta ggaatttgtt    1200
atttctcaat agatttacag agctgtttca tgtgatcaca attttttttct atttttctga    1260
agttctctat taggaatggg ctatctggtt agttgctttt gagagaacat gtggattggt    1320
gttgctcggt ttccttgcct ttgtaatttt gtccttggaa aaagcaaaat gattaggtat    1380
cctgatatgc ataacatgtt taagccaact agttctcact tttttagtgc aaataattga    1440
tcttcaggaa tcg                                                       1453
```

<210> SEQ ID NO 175
<211> LENGTH: 1999
<212> TYPE: DNA
<213> ORGANISM: Cucumis melo

<400> SEQUENCE: 175

```
ggtctcagac ccataggaat agatcattta ttgccttatg aattagttta tgagtacata      60
ataattgtca accgtataca aatcaacatg aaagaatata atgttgtaca tagtcattcc     120
aagtttacta atattatatt ttaggagtgt tctacaccga acctgtcaca tgtacactgg     180
gtatgctacc cctgaattca atatcataaa gcaactttaa ttgtcaagca ttctcttgac     240
catttgtgac ccatttgctc ctactttttc aatcaataac tatcacaaaa agctagatac     300
cacatgtgat aaactcactg aaatcaggta tatggttacc tgtgcttggt cagcactcaa     360
tcagattcga aggcctagtc tttgtatttc cccccctctg cacactacaa atagtcctcc     420
acgtaaagac ccataacaaa acgcaaacca agtacagaaa atctagccga aatccagacc     480
actcaaacat aacaaatctt ctggtaagtt tgaataaaat ataaaactaa cctatttaat     540
caaataatac aataaaatgg aagcaactaa cataacatat ctaaatatga tcacgtagta     600
ggaaaaaaaa aaacattcca aaactattaa caatcattct taatggtatg ggtcaatccc     660
cattatttag gactataaca agaattcctc atacctaatg ccacatccta tgtccaaccc     720
tcgagattac ctcgtgagta atcaatctta ttcatcctta tttcaaatta tgtgaaattt     780
ctcatcaggt tgatcatatt gactttcaat acaacttatg attaatcttt cccttgatat     840
aatttcgtat gaaaaggaag ttgacattat gtgattttct cataaggtaa accaagtaaa     900
cttgacatga cgtcttaaca agtcttggtt tctaagtgta atttactgca gaaaaaatcc     960
taaattctat gacttttcct atgagattga ccaaatcaac tttacgagaa atcttgggaa    1020
gccataccta caaagtcttc ccccaagaaa ttacaatttc tagtaaagat tgttgaaatt    1080
taccctccaa tttttccgtg aaaatttgac aaacttgtaa gaatatcaaa tttgggttgg    1140
atattgacat tccaaaataa gtagttttaa aaaggattta tccaacaata atagaagaaa    1200
aaagatagga aataacatac ccacgtaaat ggaatgtaaa tatttatata ttaggtgtct    1260
tgaacgaccg tcaaacgaaa ataaattgtt catccgaagt tgaaactctt taagtgtaca    1320
tttatctttt cgtaagaata aaatgtaaaa ttaacgtgtg aaaggttggg ttaaataagt    1380
```

-continued

```
tatgtagaga taatattgaa gatgatagaa taatcacgat cgatgaatta gtatagtccc   1440

agagcggatt taaacctctc tcactttcat gctttctata tatatcaaaa taatttcaag   1500

tagttggttt agtcgtaaaa aagtcaacca atctctttta gataaacctt gagttattaa   1560

aaaattagat caaagataat cgttgaaatt gaaattttaa gagtataatt ataacaaatt   1620

ggaaagttct aaagtagttt ttgcaatatt ctccatcaaa atagagtaga aaaatatttt   1680

agtaattttc ttatcttaat tttagttttg taatagttat taggatggtc ctaagttctc   1740

aatccgcttt tagtccataa aaagaaagaa gagagagaaa aaaagtcccc gatccgcgac   1800

acataccaat ccaaccaatt atgcacaatc catgtgatat cgaacggtca caagaataaa   1860

tgctttctac acacggatca ccatccaacg gctttccttc catctcatcc tctatataat   1920

ctaccaactc tgtcatcttc gacacacttc aattatctca gcttttattt catcggattt   1980

tccatcaaac aaggcaaca                                                 1999
```

<210> SEQ ID NO 176
<211> LENGTH: 2004
<212> TYPE: DNA
<213> ORGANISM: Cucumis melo

<400> SEQUENCE: 176

```
tatagtttgt aacaatctac tctatgttct ttcaattttg atacatttga atcttaaact     60

ttattgagtt acacaatata gtccttgtat ttttaaaatt tataatgact ctatttatat    120

taatattata gaaatttttg ttaaggttta ataaaaattt ttctgtataa ataaatcgaa    180

cacgaagtct atatttagac tgcaatatag taaaacctga catctaagtt tggtgaattt    240

tgttttgctt taaaaactaa actattacaa ttttaaaaat attttaattt agttaatgca    300

cattaacttt acggagtaaa tttttacaag attgaatata catagattaa atagttataa    360

aaccaaagat tagagtaaaa aacatttaaa tagaaagaac taagattttt ttaaaacgaa    420

aatgatacta gatacatata tatgtatcta tattataatt actcatttta acatatagtt    480

ttgaaagaac aaagattagt tgcatgtgtt gattgttttt aagaaggaaa taatttttga    540

atggaaaatt ttcaaaagtt ttaaatttga caataaactc atatttaaag tgtactacaa    600

attttaactt ttggttaaac tccttgttta gttcaatcat gtaataaatt ctcattccaa    660

gaatcgtttt agaaaatttt attgtgcatt taataaaata tagaacatat atggcatata    720

aaaattgatt actttttttct ttttttggga cgaaaaacac attagatata atcttttttg    780

aaagtttatg aactttaaaa atgggttatt ttatacggtg gtcaacttta ttttattgaa    840

attattgagt ttataaagat tgttatatca ttttcttctt ctctttcact agaatacaat    900

caaacctatc aaactctcta tgacttattt agaattcttt ttgttatatt tttgaaatta    960

ataaatgaaa agcttagagt ctaaattata acaattaaaa ttgaaaattt tgcaataatt   1020

ttatttttag caaaatgacg tttggttttt ggggattggg aatggatcga tactatcccg   1080

attccggaca aagaaaccga cccgagattc gaatttttttc cattcccaaa cagagcactt   1140

aaaatttaag caacgttata acggcgtcac cgaactaaac ggaaaaatat gaagaaaatt   1200

agaaaaagaa aaacggaaca gtcaaacgtt acttcacgtc aatggcaata ttcatttttt   1260

tttttgttta aataattgaa tttaattaat ttggtttata aaaatagagt cctcatatat   1320

cgcgaatgcg catttgatcg tgaaggacag cttctccctt gtgttcaaga gagagagatc   1380

tatcattctt atttggggcc gatctctcta ttctcctctc ttctattccg taagtttttc   1440
```

-continued

```
tcattcattc tcctctctca tttctctccg agatctgttt acaatccttt tgattttcat   1500

ttttcctgct tcgatctgtg ctcctggtga ttccctttc ctgttttatc ttttgttgat   1560

cttggaattg attgttcttt tgtgggtttt cattgatttg tattttctga tctgggtttc   1620

tgttttctcg ccttgatgtt ttgtatttgg atctgatctg acgacccttt tttttttttt   1680

tttttatttg aattgctttt ccaatgttta tacctggatt tttattgatg catgggttta   1740

accgattggt tggatgcgtt ttctttgtgc tggatctagg tgtccttgtt tttaatttga   1800

attgtgggta aaaatggcat tattgtaatg tgtttggagt ttgattttga atcttggcta   1860

gttgattttt gaattacaaa gatcggatcc tcttcttttt tgggttgtct taagattttt   1920

ggctggttta agtatttgat gtcgttgtat tttaaggggt aactgatgcc ggcttgttgt   1980

gtttgtattc agtttacttg aaaa                                          2004
```

<210> SEQ ID NO 177
<211> LENGTH: 2005
<212> TYPE: DNA
<213> ORGANISM: Cucumis melo

<400> SEQUENCE: 177

```
aattagcaaa ttgtatgtaa caacgtcatg aagaggcatt tcatcgaaca atttaatagc     60

agagtcaaga tggcccagtt ttataagttt attgatttct cgattcttaa ggtaaatgag    120

atcgcgagca tggaaatgca gacccaaacg agaatatggg tgtggtaaat ggaccggtga    180

tgttgtggct acaaattcgg attttacagc agtaatagtt ctgacgaagg aagcgaattt    240

agtgaccttt cgcatcacag tttaagctta tcagagacct gaacaagggc tctagctcta    300

caacttagaa aggtttgata tggtccgtga tcgggaggga ccgaataaca ggcgcttaaa    360

ttgttgttca taaagaagag gattgtcgtt gatgtatttt aaccaagaga tgattagtta    420

tccacatcca cagagagaac agaagacggc tttctaaatc tacaccgata aaaataaccc    480

taccactttg tttctttaga aaagggtcac attctttaaa aacattagcg tcgaggatta    540

atagggtata ttgactaatg ctctgtttgg atttcgagaa ataccaattt acaattgatt    600

tcaaattaat tatgttttgt tgttgcacga aagataaaaa gaatttaaaa ttcaaaagga    660

tctcaaatct tatttttaac ttaaaaactt ttatgaccca aacggtttat gtatgattta    720

aaagtagaat acctctgtga attcttaatt tttttttctt tccaattacc acataaatat    780

gaaattttaa atacatttat tttaaatttt atatccgaaa caaaataata atttaaaact    840

atttctcata tatgaagtgt gattcgatct aaattataaa ataataaaaa tttacatcta    900

gttttgatta tttttttttc gttagatact aaattgttaa gaaaataaca tttttaatcc    960

aaagttttga agaatatatg acttttaaaa tggtatttat ctttttagtg tctgattttt   1020

aaaaaatgga tttcaaaagt tcatcaaata gcattgtatt tttattttaa ataattttga   1080

catttaaaat tagagtaatg gtttataaaa gacacttgat ctctaaaact attttcttag   1140

atataaatac gtatgattat ttttaaaaat caatcaaaat aggtaaattg taaaaaaaaa   1200

aaaaaaatca taaaacatga tagtagttgt aattatgctc tcaaactttc ggttatgaaa   1260

aataaacatt ttaactttta gacgtgtcaa agttgagtca agttggacct tcaaagttat   1320

gtagttatat aaattgtaat atatgtataa gcttgtggat tcaattttat catttatggg   1380

tccaatctct acaattatcg taagtctatg ggtcaattgt aacacatgtg gagtttaaga   1440

gctcaatttt ggacgtggat gtgttttgca accaactcca caccttaaaa aggtgttttt   1500

ttttaattta tcaaaaaaca agaatttaga atctttaagt ttatctttaa aaatcaacgg   1560
```

acattttgaa aaccaattga aactactgtt ataaacctaa caactaaaag tatatttttt 1620
aagaccgaaa gcataaatcc ataaaaaaaa aatccagaac tgaaaatgta acttttatag 1680
ttgaaaattt agctaaatta tacatattaa aattcaagga ccatataaaa ttaaagtacc 1740
tgattaaata ataacgaatt aatgtttggt atttttaacc tacattagaa aaaaaaaaca 1800
aaagaaaaac ggcatactat ttgtcaagcg tccgatggga agaaaatcca acggtgagtg 1860
ttagtattga aatacgcagt tctcgtgaat gagcctggct tagatttggg aacaagagcc 1920
aacccctttc gaccgagaag ccgtcgtctt caccatattc gcctcaacca ttcgatagcc 1980
acgtttgaag aagaatagga ttgcc 2005

<210> SEQ ID NO 178
<211> LENGTH: 1978
<212> TYPE: DNA
<213> ORGANISM: Cucumis melo

<400> SEQUENCE: 178
aattctaaca actccggaac aaataattta gcatggattg aaatataaat cttcttgact 60
tgcaaaaaaa tcattgtaat ggtcttatgt tggttatagt tagggtatcg aaacgccata 120
caggaatatg ggattaaagt taacttttgt tcatcaattt cagcttatga acttctaaaa 180
tatcaatttt acctttgaac ttatatgtta ttaccccttt cgattgtggt atgttaatta 240
atatctgaat ctcagtcctt atgaaacttt tttatactgt cacaaacata tgaagtttta 300
ttgtaagttc ttagaaatca tctaaaaaga gtagtttgtt ggactattta ttttattttt 360
tcttattaag ttgttttcac gccatttcag taaaataact atagtgaata gagaatcaaa 420
cttctaatct taagttaagg tagtagggta tatgctaatt caataagata atccgtgatg 480
cttgacatct gacttaattg ttataagttt taaatttttt attgtaatat ttaaaatact 540
agtttttggt ttctaataaa gaaataattg aacaattaca aatatttata caaaattaaa 600
ctagaatata tgatcatttt ccttcgtgtt agaaaaaggg aaatatatgt gtgtatttat 660
acatattaga tattgtttta ctatattcca ttttcctcac gggaaatgga ggattgagtg 720
ggagataaac attgtcccca agagaattgg gaatggaaat gcaaatgaca tggccctcca 780
caaaattgtt cgcctaaaaa tgggctttct cacttctcac tccgcaagaa aaatatcgtt 840
tcccttcgaa ttcgggcaag atctcaaaac cacatgtttt tctttcttta tttttcaagc 900
ctacattatt tataaaaata taacttaagc agagaattat gtaaattcaa gtccattttt 960
cgcttcactt agctaaatca ttaacaaatc tgtaattttg ttcataaatt agctcaccaa 1020
ttatgtttta gcccactaag gcccattaga catttttatt agaaaaacat gaaccgttgg 1080
atcaagatgt gtgttttctt ttctttttct ttttattttt tttgggtttt ggtggatcaa 1140
ttcgtagctt tagcaaccta ttattatatg gagggaaagg gcgtattaat ctgttagcgc 1200
cgtccgggag tttagctttc ttccccgagc ctcggtctta tcccctaact ccaaaaccct 1260
agcccaaagg taatccactc cttccccctc cgctcttcat ctttttctat tcatcatctt 1320
taatctgttc tccctttggg ttcttagatt cttcttttgt tggattcttt taatctttac 1380
tcatggttgg ccttgtaagt ttagacgacg tttttataca ttggttaatc ctgcttctct 1440
atctattcgc acgctagggt tttcctattg ttttctattc tgctctactt ctgcaaggtt 1500
gtgttcttct tcgttcaggt cccttttttt aaccgaaatt aaattaatgc aaattcgttt 1560
gtgcttctaa ttaggaagcc ttttggaaca tctcgacatt ttgattgctg catttcattt 1620

-continued

```
cgggtatatt tctatgattg aaggatgtgg gtctgttcac tgcatggtca ttacttatgc   1680

agctatgctt atcgagtcca ttatgtttgt gcaatctgtt tccggattca taattttta    1740

gtaattgatc agtagatgaa aaaagatatt gtaatattcc ttgagtgttg caccagtctt   1800

ggtgggtatc tgctcctgct ctttgcttgt ggattttact tttattatat ctgtattatt   1860

cgaaatgttc tgttcttgtt ataacttata cccgaagatg tgttcctccc cgcgtctagc   1920

gttgtgggtt acttatgatg gacatggttt tgattctgtt tggtttgtgc agggtacc     1978
```

<210> SEQ ID NO 179
<211> LENGTH: 1263
<212> TYPE: DNA
<213> ORGANISM: Cucumis melo

<400> SEQUENCE: 179

```
aattctaaca actccggaac aaataattta gcatggattg aaatataaat cttcttgact     60

tgcaaaaaaa tcattgtaat ggtcttatgt tggttatagt tagggtatcg aaacgccata    120

caggaatatg ggattaaagt taacttttgt tcatcaattt cagcttatga acttctaaaa    180

tatcaatttt acctttgaac ttatatgtta ttacccctttt cgattgtggt atgttaatta   240

atatctgaat ctcagtcctt atgaaacttt tttatactgt cacaaacata tgaagtttta    300

ttgtaagttc ttagaaatca tctaaaaaga gtagtttgtt ggactattta ttttattttt    360

tcttattaag ttgttttcac gccatttcag taaaataact atagtgaata gagaatcaaa    420

cttctaatct taagttaagg tagtagggta tatgctaatt caataagata atccgtgatg    480

cttgacatct gacttaattg ttataagttt taaatttttt attgtaatat ttaaaatact    540

agtttttggt ttctaataaa gaaataattg aacaattaca aatatttata caaaattaaa    600

ctagaatata tgatcatttt ccttcgtgtt agaaaaaggg aaatatatgt gtgtatttat    660

acatattaga tattgtttta ctatattcca ttttcctcac gggaaatgga ggattgagtg    720

ggagataaac attgtcccca agagaattgg gaatggaaat gcaaatgaca tggccctcca    780

caaaattgtt cgcctaaaaa tgggctttct cacttctcac tccgcaagaa aaatatcgtt    840

tcccttcgaa ttcgggcaag atctcaaaac cacatgtttt tctttcttta tttttcaagc    900

ctacattatt tataaaaata taacttaagc agagaattat gtaaattcaa gtccattttt    960

cgcttcactt agctaaatca ttaacaaatc tgtaattttg ttcataaatt agctcaccaa   1020

ttatgtttta gcccactaag gcccattaga catttttatt agaaaaacat gaaccgttgg   1080

atcaagatgt gtgttttctt ttctttttct ttttattttt tttgggtttt ggtggatcaa   1140

ttcgtagctt tagcaaccta ttattatatg gagggaaagg gcgtattaat ctgttagcgc   1200

cgtccgggag tttagctttc ttccccgagc ctcggtctta tcccctaact ccaaaaccct   1260

agc                                                                 1263
```

<210> SEQ ID NO 180
<211> LENGTH: 715
<212> TYPE: DNA
<213> ORGANISM: Cucumis melo

<400> SEQUENCE: 180

```
ccaaaggtaa tccactcctt ccccctccgc tcttcatctt tttctattca tcatctttaa     60

tctgttctcc cttttggttc ttagattctt cttttgttgg attcttttaa tctttactca    120

tggttggcct tgtaagttta gacgacgttt ttatacattg gttaatcctg cttctctatc    180

tattcgcacg ctagggtttt cctattgttt tctattctgc tctacttctg caaggttgtg    240
```

ttcttcttcg ttcaggtccc tttttttaac cgaaattaaa ttaatgcaaa ttcgtttgtg 300
cttctaatta ggaagccttt tggaacatct cgacattttg attgctgcat ttcatttcgg 360
gtatatttct atgattgaag gatgtgggtc tgttcactgc atggtcatta cttatgcagc 420
tatgcttatc gagtccatta tgtttgtgca atctgtttcc ggattcataa ttttttagta 480
attgatcagt agatgaaaaa agatattgta atattccttg agtgttgcac cagtcttggt 540
gggtatctgc tcctgctctt tgcttgtgga ttttactttt attatatctg tattattcga 600
aatgttctgt tcttgttata acttataccc gaagatgtgt tcctccccgc gtctagcgtt 660
gtgggttact tatgatggac atggttttga ttctgtttgg tttgtgcagg gtacc 715

<210> SEQ ID NO 181
<211> LENGTH: 2000
<212> TYPE: DNA
<213> ORGANISM: Cucumis melo

<400> SEQUENCE: 181
aaataatttg tggattttat catattatgt accttagact ttgtaaggtt tataacacaa 60
gatgtggaga aatcccatga tgaacattgg acgttattat atcctttgaa actaaaaaca 120
aaggaaaaaa gacaaatggc tgagtataag aaaaagagaa gaaacaacca aaaagctaaa 180
atgtcatgct ctcatatgta acatatttga attgggattg atttcaagat gtattttaaa 240
ataatttaac acacgataaa ataattctaa caaactcaaa attactctta aacatttact 300
tgatatcttc gacataatga cttttgtttt aatacaactc aaaacataat taaggttggt 360
tttaaatgac aacaaacgaa aaactcgatt ctaatttcaa tactagtctt tgaaagccct 420
aaggagcgtg gttttgaatt gtatagcaag gtttcgaaaa ttttaatcat caaacaatag 480
gtatatttac ctgttcctca agtacagtta attcatagct acttgtcgtg cttcctacga 540
caacattgta agacttgcca cacactaatt gaagccgttg ttgaaggtag ttttccatgt 600
atagcttgaa tcgacggatg accaaagagg ttgaagaagg tttgaaaaat aggggaaggg 660
atatacaaag tttgagagtg agagagggag agaaatagaa atagaagaga ctgaaaaatg 720
taaaagaaag gatgaaaaaa tgtggggtaa acgcaaattg gatttttata gtagtatttt 780
gaaaatgcta tagaaaggct atgtatagta gtgcttccaa agttctatat gaatgagaca 840
aatcaaaata tatttttttt gattaattaa ccccaaaaag actcataaaa aaatcttata 900
aatcccacta agatattgca tgttatatgt agtaaaattt atcgttcaaa taaaccttaa 960
acataattca aacgaagaaa gtaaaaattt gaatttctta tcttacatca ttcaaccaaa 1020
caatttccat ataagagatt aaacttctaa ctttaagaga gagatatcca gcatatgcaa 1080
cctaaaccaa cagtgacttt gctatatatt tgcacaaaat gtgggggaca aagttgtaat 1140
ttcggaatat caatgattaa agaaaaggta aaatttaaaa ttcggaagct tgacgtggca 1200
acacggaatg gtgatgatat ttccaactcc tcgcgacttt tagaagttgg cctcaccaac 1260
cgcatatccg cccctttgcc acgtgtcaga ctacaacaac ttccaacaat ttcctttaag 1320
aacaccaaat tatatcaata aatatttaac ttaaattaag aatatatttg ttacaatttt 1380
cctactgagt tagatagata gacagacttg tcaattaact aataagtcca aagtcaattt 1440
actcaacata gatacaattc taatttgagt gtgaaataca tattcaaatc aaaattatta 1500
ttaagaggaa aaactgattt gctttctcaa tttaaaatat aatattttga aaaagaaaca 1560
cacatgtatt atggttttca atatatttac tttcttagtc acctaatctc aaactaattt 1620

```
ttgaagaaat taaatatata tattatcatt tttattttct tggttatgat attggtatag   1680
aatcaacaaa actacaagtg tcctctcctc tgctatcgat ggggattaga ctctaaactt   1740
gtttagcgat tagtaattat atattagaaa aagtttatgt taatgtggac ccgacaatct   1800
caccaatagg ctcttcactt caccaacccc cgacccattc cctctaataa ttcgacacgg   1860
ctcatccccg gttcgaaccg ggccgacgtc ttcctattta acacacctcc atttcctctt   1920
ccctccgcaa cacaaacaga gacctcaccg gaaaatcaag ttaaagcaaa accaaagaga   1980
agcttcatca ctctccggaa                                                2000
```

<210> SEQ ID NO 182
<211> LENGTH: 2000
<212> TYPE: DNA
<213> ORGANISM: Cucumis melo

<400> SEQUENCE: 182

```
gcatcttatg gatgtagtca caacatattt atatggattt tctgataatg atatttatat     60
gaaagtccca aaaggattta agatacctaa aacatataaa tcaaattccc ataaactatg    120
ttcaataaag ttacagagat cattgtatgg attgaaaaaa tcatgacgaa tgtgatacaa    180
tcgcctgagt gaatatttgt taaaaaaata atatcaatat aattcaatat gtccatgcgt    240
ttttataaag aaatcaccgt caggatttgc tattataact gtatatgttg atgatttaaa    300
tataattgaa attttgaaga gttttcaaag gcaatagaat attaagaaag aatttgagat    360
gaaagatctc agaaaaataa aattttgtct tgattttcaa atcgagcatc tagtaaaagg    420
gatatttgtt catcaattaa cttatacaga gaaaatttta aaaagatttt atatagataa    480
aacacattca ttgaacattc taatgcaagt tcattcatta aatgtgaaga aagatatttt    540
tcgacgtcga gatgataatg aagaactcct tagtccagaa gtaccatacc ttaatacaat    600
tggtgcactt attttgtcaa taatcaagac cagatattgc attttctata aatttattag    660
ctagattcag ttctccaaca aaacaacatt ggaatgaagt taaacatata cttcgttatt    720
ttcgaggaac aattaatata agattatttt attcaaataa atcaaatttt aacctagtta    780
gttttgcata ttcttgattt ttatctgatc cacataaatc tagatctcaa acaggttatc    840
tattcacatg tggaggaact gctatatctt aacgatcagt gaaacaaatt accataacag    900
tcaactcttc aaaccgtgct gaaattctta caattcttga ggcattcatg aggctagcgg    960
agaatgaata tggttaaggt cgatgactca acacattcga aaattatgtg gtttgtcttc   1020
tagtaaactc cttccaacaa cattatacga agacaacaca acttgtatag ctcaaataaa   1080
atgaggttat attaaaagtg atagaacaaa acacatctca ccgaagtttt tctatactca   1140
tgatcttgaa gaaaatggtg acatcacagt acaaaaaatt tgttcaaaag ataatttggt   1200
agatttattt acaaaattat tacctactgc aacctttgaa aaattggtgc acaacattgg   1260
aacgcgacga cttagatatc tcaagtaatg ttacatctta cttgccaagt taactataca   1320
tagtgacatt tggtggagtt gtaagaaaca ctaatattgg agaaaaatcg aaagaaattg   1380
gaaaatatgg agaattgaat ttttttaga tttttcttat tttctaattt taggtttccg    1440
tattctgatt atgcctcatt ttcacaacat taataacttt aataagatga tttcttgggt   1500
taagggaaaa aaatcatttt tttagagttg cacgtacaaa aatattatca taacatatcg   1560
attataataa accaattcac cgtcaaccta acctaggtag agtttgagtt aaatgttaaa   1620
agaatatcca cccctcaaca ttgtaatccc aactaataaa tcagcaacct aaagtttttt   1680
ttaaaaaact aaaaagaaga gcaatatatt ttttttacta ttattttttt aaagagtgga   1740
```

tttatttatt aaattaaaaa atgaaaagaa gaaaatttgt tagtttgggt aatccgaaaa 1800
cccgattatt tgggcccgag aaaccgacgt tttgtttatt gttcctcacg gcaataagta 1860
atggcgtgaa tcgaccgcgt gcgcttcaag ctatctagac atttttatat cctccgatta 1920
gaaaccctaa ttcagattct ccgtattacc caccctggaa catctttgaa acgcgaaaag 1980
gtgacccgaa gaaacttgaa 2000

<210> SEQ ID NO 183
<211> LENGTH: 1989
<212> TYPE: DNA
<213> ORGANISM: Cucumis melo

<400> SEQUENCE: 183
attacttgaa cttaatccac atttatgtct ttatataaag ttcgaatact cataatatag 60
ccaagaaacc ttgtttattg gattttgagt tttatcataa gcaaatctct tatccaataa 120
caaattatta aacaacactt caacaataac tttattcaac aatatattag tttaacattc 180
acaaatcacg agtattagaa cataaaacgc aacaaagaat ggactaaggt actatattct 240
aacttaggtt gtttaggatt tccatatgtc aatgcttttg tgatttttga actagatttt 300
cttgttagat taattcaatt ctatttttaa atggcttaat atcttatttt cggatgcttg 360
gggattgcta gactaccgct ttgttgaagc aataagttaa atttgtttgt tacaggtatt 420
gatcaatcta acatagaatt gaatttgtat gaatatttag ttagacgctt gaaaactaat 480
tattctacca atgagccgta gatcttaatg caattgttat taatttgaac tttgtatgct 540
tctcatcgat taaatttata tcaagtagtt aattaggaca aatctattgg ctttttcatt 600
taattttgtt aagtaaaagc aacttagaat tttgaaaatg atgaacccat gatccaatac 660
attgaaagag aattttgttt aactcaaact aggattcttc tcacattgat ttcgtataat 720
ttaacttttt caatttatat caatcccccc agggtgaaaa aaatttgttt gaagaattca 780
tgtgctttct aaatctgatc tagacttgcc actaaaatta acttttgata tgtaatttgg 840
ttaaatattt gattcggatt tcgacgacaa acaattgatc aatgtggtat taaattctga 900
tctccatgta agaaatttac acattttcat aagttcaatg ttgacacaaa gagagtaaga 960
gcattttaaa aaaaaagata cttttaatct tttctaaaaa aacaccaaaa tgccattatg 1020
taaatgtaac ctaaataata aacatttaaa cttagaattc atgcaattag gctttgtatg 1080
ggacattgaa ttgattatta aaatcagtag ttatagaccg tgagttataa tggtttgtat 1140
tagaagcata aattatttta attttgatcg taatagcatg tatttgagat ataaattaat 1200
ttagtttggg tggcaaatag taaacagtaa agcaaaatat aaaaaaatga atttaaaata 1260
gtaagatttg taacaaatga ttaatactat aacaaacgtg gttttaaaat aacgttgatc 1320
gtagctaatt gaacattatt tattgtaaaa ttgagtgttt ttaatatttg gagcctcaaa 1380
cttcgggtgg atcaccacaa tataatcata ttcaaattta aaattttatt tttattataa 1440
atattgttaa tagatgctca ttatgggcca tctgtcactc cctccgtgca tatcctacct 1500
gaaacatcat atatcttaaa caatgtccat tgccatgtgt cactattttt acatcccatc 1560
cacttgacaa atatgttgaa gatgcctact tttttaggga tcatgtaatc tatctcatgc 1620
ttgtcaaatt gttcgataat agtgttacaa aaaatttagt aattattatt attatatttc 1680
ttcgatattt atgcttcata tgccattgtg ctctccattt ttaccatact taaaaaaatt 1740
tcttattata aatttttttca aaaaaaaatt tactatatag tcatcatctt tattaaaatt 1800
aaaattgaga acctgatatt tttgatatta ataatttaaa atttgaatta atccacttta 1860
aaattattaa taatttattc gaatttgggc cttaaggaag agatacggaa acaaacccta 1920
gatcccatct atatataaat cgccacaaaa ccctaccttt ctctcagttt ctcgttttag 1980
ccggcaaaa 1989

<210> SEQ ID NO 184
<211> LENGTH: 1463
<212> TYPE: DNA
<213> ORGANISM: Cucumis melo

<400> SEQUENCE: 184
ttttcttctt gatttgaaat tcttcctcct tcctgttgca aacaaaccca gatgaataat 60
cagacaaaaa aagcagcaaa tttgaagata tgcatatacg aagaagaaga agaaaaagag 120
agggaaggat aaggtaggag atagcttgag attacagcgt agaaaccgat cgaaccggag 180
atcaacggcg cgaattaggt caagaagaag tgagggtttt tatgaagaag aagtgagggt 240
ttttatgtgc cgatgaaaaa ccctacttct gtgttggtga tctaacgttg tttgatcggt 300
tcggtttttt tgagaatcga gtaccctcat tattattatt attattgtta ttattataag 360
tttgttgtaa gaattaataa attatttcaa aaattacaat ttttatttat atatagttta 420
aaaaatttta taattttttt aaataaattt cgaaatataa ggttggattt cttaaaaata 480
tatgaaaaaa gagatgaagt ttataaatta aaaatgaaat aaaaatagta agtttgtact 540
cttattctta tttacaattt aattttccat taaaatttta aattaaatag aaatataatt 600
aaaatcttaa attagataga aatataatta aaattttcag aatgtaaatt taaattagct 660
tagtgtatat ttaaaatata taagattgaa ataattgatt ttgtttatct aaatatttta 720
tattattatt tattgaataa atataattat atatggtaaa ttgttttgga taataagaaa 780
gtaaagatgg tatttatata tataattaac caaaatttaa gtttgttaaa aagaaaagtt 840
ttcaaaaata ttttttacg agtaattagg aaaaacccac attttacatc gaagtcatag 900
actgggtcta tgtcttcatt gccttgtcgt gtacccgatc cacgataacg cattatgaac 960
cgagtagatg acttaacttt ttgtaatagc ttttcttcta ccatattttt gacatttttt 1020
taaaagtaac attatttata aaaaaaaaat cgtagtttga tctcacatga aactattatt 1080
acatcattaa ctaatatatc tatatttaat gtagttttct tgacatgatt ttaatgctaa 1140
ttgaaatagt tacaattttt gtgtcccatt ttgtttagat caatatgact tcacgtatta 1200
tgacatatgg ggccatctta ccagaaattg gtgccaatga gaaaatgaat gtaccttaac 1260
caatggagca acccatgtga gccattgatg aacccaactt tcttggtttc ccatcttcta 1320
ttcatatgtc acaatacctt ctcttttctc attctatata tagactctaa acaaacaact 1380
aatctccaac ttcaaatctt tcacatattc tcattcaagc attgaagttt accacttcca 1440
aaaagattca atccaattta gcc 1463

<210> SEQ ID NO 185
<211> LENGTH: 2006
<212> TYPE: DNA
<213> ORGANISM: Cucumis melo

<400> SEQUENCE: 185
cagcgatctt cgtagaaact aattcaatgc tagctcatta tttgactttt ctcaggcaag 60
gctccgcgag gaagagaaaa ggtccaattt caggaaccaa gggcatggac aggttccggt 120
cagaagaagc tttttacgta aaccctttgc cagattgttt atgtcaagga gaattaccaa 180

-continued atggaagtac gacttccatt ttcagatagt tcagtagaac atcaaagata aaatgctctt 240
agagagctca atgtatatgc aggcgaccac tcaacgtgtc accagctttg tacatccaat 300
aagccagcta cgatggaacg acggagtgtt tataacctga gttttggtag ttggcggagg 360
cggtgatggt ggtatagaag gaaggtcgag ggatggcaaa ccctttacgc caagtagtgg 420
aagggagtag ttggagatga acacattttg agaagtttcc aagatcactc catttggggg 480
agaggggatg ttggttattt agcacaattg ttttcatgtt ttagtaattt tatccaataa 540
tgagcgaggc attgaagcaa ttaaatttat ttttaatgat tttttcaccc ttccataggc 600
tttttctttt ttcttttcct tttagtttgc aaactttagc tccttttatc ggctgtcgaa 660
ctcatttttg aagttattga atgaaacaca gtttgggctg tgtcagatgg gtggtgaaat 720
tttatacatt ataattacta cataaaatga aatcatattg taatttttcta tctatgccac 780 aattttttttt tattgcatca tgaggattaa attgtacgag tccaaatttg tacagtcatg 840
tttttaaagc tttcgagcat tgttactaat gcatggaaag gatcgattat caagtatcct 900
cccaacttca tgaaagttat tatttgtctt ctaaatttgt tttagaaaat gtttaattaa 960
ttatttgaga agaaagttta actaaatcct attggtttcc tctaaggttg tcatacttat 1020
ccaataacaa ttacgtttaa aatcaaaatt attctaatgg tataagacta atgttttaaa 1080
agcataaaat tgatgaggaa ggattggaag taatactatt tattttgaag gtaaacattc 1140
ttgaatgtct gtcctaaaat cactaatgtt ttcttagttt gagactttga gtcgttgaac 1200
ctctccatct ttataaaata taatacgagt ccttcacaat aacttaaaat atatactaaa 1260
tcctaattaa tgaaaaataa ataaataaaa ggtacaaaat cattaaagcc taaaaatcta 1320
ttactccttt aaaacttttc aagggtccct acaaccaatg agaaactacc acgtcatttt 1380
cacaatccgt tcagtgttta gaaaagtcaa atcgcaccgt ccatttatcc actcgtacca 1440
agtacggtag gaatctatct accgtccgat taagcacaaa gaagcacagt aaatgtcaat 1500
cgtgtccatc cgccgccata ccgcacatcc ttcgtccgac cggaaggccc tatataaagt 1560
cctttggttt tccgaatttc tacttcattc gcttttgaaa gatttcccaa tctcttcgtc 1620
ggccaaaatt ctctctcgct tctcaaccct tcttcggctt tttcatccag gtttgtttct 1680
cttctctttt ttcttccttt gttgttcttg gaatatgttt aatttcattt gtttttccat 1740
tcaatttcat gctagatttt acgattaggt tgattttctg ttcgtagatt gtaattgatg 1800
gttagggtta gctttttctc ccattccttc tggaatctgt ttcttgacct tcgaacttcg 1860
ttgataaatc tttagaaaca tttacataac caaacaataa ttgaacaact cgtgttgtta 1920
tgcctatata atagcggtta ggaaactgga aacgccctta taattgaaat cgccttagaa 1980
atttgttttg attcatacag ggtacc 2006

<210> SEQ ID NO 186
<211> LENGTH: 1664
<212> TYPE: DNA
<213> ORGANISM: Cucumis melo

<400> SEQUENCE: 186
cagcgatctt cgtagaaact aattcaatgc tagctcatta tttgactttt ctcaggcaag 60
gctccgcgag gaagagaaaa ggtccaattt caggaaccaa gggcatggac aggttccggt 120
cagaagaagc tttttacgta aaccctttgc cagattgttt atgtcaagga gaattaccaa 180
atggaagtac gacttccatt ttcagatagt tcagtagaac atcaaagata aaatgctctt 240

```
agagagctca atgtatatgc aggcgaccac tcaacgtgtc accagctttg tacatccaat    300
aagccagcta cgatggaacg acggagtgtt tataacctga gttttggtag ttggcggagg    360
cggtgatggt ggtatagaag gaaggtcgag ggatggcaaa ccctttacgc caagtagtgg    420
aagggagtag ttggagatga acacattttg agaagtttcc aagatcactc catttggggg    480
agaggggatg ttggttattt agcacaattg ttttcatgtt ttagtaattt tatccaataa    540
tgagcgaggc attgaagcaa ttaaatttat ttttaatgat tttttcaccc ttccataggc    600
tttttctttt ttcttttcct tttagtttgc aaactttagc tccttttatc ggctgtcgaa    660
ctcattttttg aagttattga atgaaacaca gtttgggctg tgtcagatgg gtggtgaaat    720
tttatacatt ataattacta cataaaatga aatcatattg taattttcta tctatgccac    780
aattttttttt tattgcatca tgaggattaa attgtacgag tccaaatttg tacagtcatg    840
tttttaaagc tttcgagcat tgttactaat gcatggaaag gatcgattat caagtatcct    900
cccaacttca tgaaagttat tatttgtctt ctaaatttgt tttagaaaat gtttaattaa    960
ttatttgaga agaaagttta actaaatcct attggtttcc tctaaggttg tcatacttat   1020
ccaataacaa ttacgtttaa aatcaaaatt attctaatgg tataagacta atgttttaaa   1080
agcataaaat tgatgaggaa ggattggaag taatactatt tattttgaag gtaaacattc   1140
ttgaatgtct gtcctaaaat cactaatgtt ttcttagttt gagactttga gtcgttgaac   1200
ctctccatct ttataaaata taatacgagt ccttcacaat aacttaaaat atatactaaa   1260
tcctaattaa tgaaaaataa ataaataaaa ggtacaaaat cattaaagcc taaaaatcta   1320
ttactccttt aaaacttttc aagggtccct acaaccaatg agaaactacc acgtcatttt   1380
cacaatccgt tcagtgttta gaaaagtcaa atcgcaccgt ccatttatcc actcgtacca   1440
agtacggtag gaatctatct accgtccgat taagcacaaa gaagcacagt aaatgtcaat   1500
cgtgtccatc cgccgccata ccgcacatcc ttcgtccgac cggaaggccc tatataaagt   1560
cctttggttt tccgaatttc tacttcattc gcttttgaaa gatttcccaa tctcttcgtc   1620
ggccaaaatt ctctctcgct tctcaaccct tcttcggctt tttc                    1664
```

<210> SEQ ID NO 187
<211> LENGTH: 342
<212> TYPE: DNA
<213> ORGANISM: Cucumis melo

<400> SEQUENCE: 187

```
atccaggttt gtttctcttc tctttttttct tcctttgttg ttcttggaat atgtttaatt     60
tcatttgttt ttccattcaa tttcatgcta gattttacga ttaggttgat tttctgttcg    120
tagattgtaa ttgatggtta gggttagctt tttctcccat tccttctgga atctgtttct    180
tgaccttcga acttcgttga taaatcttta gaaacattta cataaccaaa caataattga    240
acaactcgtg ttgttatgcc tatataatag cggttaggaa actggaaacg cccttataat    300
tgaaatcgcc ttagaaattt gttttgattc atacagggta cc                       342
```

<210> SEQ ID NO 188
<211> LENGTH: 2003
<212> TYPE: DNA
<213> ORGANISM: Cucumis melo

<400> SEQUENCE: 188

```
aactagacta gcgagtgcac aaccaaatta caaaatcctt aacagagaca accatctatc     60
tcctttaaag caacaataac atcaaccgaa ttagaatcca caatcagtaa agacgatgcc    120
```

```
gacaccaatg accaaaaccg atcaaatata gcttattacg gaccattact tcaacagtta    180
catcaacaaa aaaaaaaaaa ttaaacattg ctaataaaat ctgaaaatga ggaaaaagag    240
attaaaagtt ttgaagatag aaagaataaa tctgaaatgt tctaatttga tatataagaa    300
atatgaggta atatgacgaa agcattttga tagttttcac caactccctt tgtgaaagga    360
tacatccaac caattttaca atttctgttc aaattttgtc cacctaccct tctcttctgc    420
cccccaaggc tgctttcttt cttttattat ttgctaaatt accaaaaact attttcgaat    480
taaaccatct atttcaatta tatacgtcat tcgaatttta acttaattaa cattagtata    540
tgtttcggat caaggatagt ggtataaatc atcctaattt caatttgtat ttagaaaagt    600
tcaattatac ttaaaacttc taaaaatttt atattttaaa tttggatata aattaaattt    660
aagatttatg gaaggtaaat aattagagca aaacaaactt caaactatat ggaaaataga    720
aaaggaatat tttagccaaa caaaaacact tattatttta ttttgttttt ttgttttttt    780
tttaatttaa caattttttt ttttattggt tgaatgtgtt tctccactgg tgagtctcca    840
actttgacct gcaaagggtc tatatagcga gtttcacgag cacctaacca atatctgtgt    900
aataattccc atttttcttt catacccact tcatttgatc atctttttca caaccccgga    960
tctctaattc ttgggaattt gcctctttct cgatccattt ccaccgtaat tgaaaaatat   1020
tcaggtttga tttcttctgg gttttcattc aactgtctaa cttcattatg ccctttatgt   1080
gtttgttgaa agccccccac ccaccatcgt tcaatgcggt ttctttacct tttgttcggt   1140
ttcaacgatg atttagaagt tatagatgga tgctaattgt ttcgttgttg gtttgatcca   1200
ctgatctgcc tttgattggc ataaaaggag attctagatc ttgttttgat gttgtgattt   1260
atggatatta ttgttatagt cgtggaagtt tttcttgtcg ttctgcggta tatggttgtt   1320
ttattttttg agtggtaaat tgagcagatt gtgaactttt gggttttatg gtgaaagcat   1380
gaattagtaa atgtagagct gctgaaacaa aatggaggtt tgctagacct ctttgtgaat   1440
tcttaatggt cagcctccat cttaagaggc taagtccaaa aatttaaggc agtcttttgt   1500
tattgttaca aaggacaaga aataacagag gagttatttt aattgaatca agttggaaag   1560
aagtactact tcatgcttct ttcaaaagca ggtcaaagtg ctttaaagtc ttcttattta   1620
tttatttttt cctgaatcaa tttaaactaa tgatagaaag aagtgttttt taatgggtta   1680
ttataagtaa catcaatttt taaccattcc aaaagttaca tcaaattcat catagtgtga   1740
gtttacgaat tttggaagtt gtaattttaa gttaatactt cttttaagga aatgtacact   1800
ttgcatgttg tgttcataag gggtatttct ttgacaaacg cagcaaccac cccttaatga   1860
aaactacacc acggtggttg gttttttctt gttatttttt tacttggaat ttacaataag   1920
ttgttatatt cggatatatg gcaaagcaga tatctgtttt tatccgaaac ctcataaatc   1980
ttgaatgtgc agcaggtaaa aac                                           2003
```

```
<210> SEQ ID NO 189
<211> LENGTH: 1024
<212> TYPE: DNA
<213> ORGANISM: Cucumis melo

<400> SEQUENCE: 189

tcattgatga agaaggaaac tttaagccaa ttcgacaact tatccattca acaactttcc     60
accttcagac attcagattc aactataata taacataaat tgatagtcaa gtctttttttg   120
agacaaccat aaatcatctt agcttcgaga actgtcactt ccttaaattg gtgaatatat    180
```

-continued

```
cacattccat ccattcaaaa ctttgtttcg aactttactg tagttatgaa tcaataaatt    240
gggagagata ttgttaaaaa gagagagcat atttgtttct attatttact ctctcctaag    300
agagggttaa ttagtctata aatgatctat tcttctcgtc cattgaaatt ttgttatcct    360
aaatttatga atacttctac ccaaaataaa gactttttt tttttgaaa agtgtcaaaa    420
aaacataaag aaattgacaa aacattcatt tttagtggat tttttacgga cgtaaatagt    480
ttgtttttgt ttcttttaat aatacaattt tttttactt taaaaaaatat ttttgttata    540
aaaccaccgt atttttattc aattttaata aataaataaa tgaaagaata taaaaaaagag    600
gaaggaaaaa gaagccaacg aaccaacggt tgccacgtat caaaggtcta aagtgcgcaa    660
aacgaggcct tcggaaacca aaatgcgtgg cttcaattgg agcaagtaaa catggaaacc    720
acgtccattg taacgcttcc tgatctcttc tttacaaccg ttggattcga gtactttttc    780
tcaacgatta acgactgagt ggacctccac ttgcttctgt tccacgcgcg tgggattgac    840
gtgtggtcca cgcaactctt ctcgatagga tcattcgaga acatccttta cttaaaccgc    900
ctctctctgc ctcaatttct cgtcacttcc ttctccttct ttacccttc cactgcggct    960
gattcttctt cgccttttat tctctcgtac gccgccatat tcttcacttc tttttccggc   1020
gaca                                                               1024
```

<210> SEQ ID NO 190
<211> LENGTH: 2001
<212> TYPE: DNA
<213> ORGANISM: Cucumis melo

<400> SEQUENCE: 190

```
attcgtcttc gcattatcag taaatttatc attttaagag tttgttcttt tttaaaaaaa     60
attaatcatt tcgataaagt tggagaattc aaaaatttct ccaaataatt tataaaaact    120
ttcggttata tatcgaaaaa attaacatgg tattaaaacg atcataactc aattaacata    180
aacactccct ctcaacttta ataccaaatt tctttattaa cgcaaaattt aaaatttgtt    240
tttaaaattt tcacataaca taatagaaat acttttcttt atggcaaaaa tacaataatc    300
aaaattgatt gatggtgaca ggacaccaca caatattttt aaattttgaa tatacgaact    360
atataataag atatttatga gattcccatc ctaaagattc ctagagattt ccttgtgtac    420
aatattacac aagtatcttg gaagtccaaa gtcctgagaa aaaagctatg tataaagtaa    480
tagtgtttgt cgtaggaaat ttacttcatt cgtgtcatta gctttttatt gaaaaaaaaa    540
attaggtata tcttagtgaa tctcacttaa tcgttgtcga tagttattct tttaatatca    600
ttatatacta aaatataaca atattgaaaa gctaaaactg tatataaaaa aaatgttacc    660
tctaaacttt tatcgtttat ttaaaagata aatatattct ttcaaaactt acaatcaaca    720
tcctacgact atcattatag gtacaaatct tttcatgttt acacaaaaat tagattttta    780
aatggtgtaa tgatgatata taacgaaatt ttgaatgatt actatttgag gttaccattg    840
taattggtcg tgttgtttga aatttaattt tattagaaaa tttgtcaaaa gtagcaaaaa    900
tgaataaact atttaaactt taggataaaa tcaagtgtta tgagtttttg tctagtttat    960
atatttttat ttttattgaa aaccctttc ctatcttttc attacttcaa aatagtttta   1020
aaatgtctat taaggctaaa gttagtataa ataaaatttc ggaaattttt tttcgaaaaa   1080
aattgataaa ttatttatat tttatattaa agtcaaaatt tattacgcgt agatgtttat   1140
caaattttct ttctttttgt tgataatttt ccaaaatttg gataattttt taaaatagta   1200
aaattattat aaaaatgaaa acaaactatt tataccttaa gcaagaaata ctaaaaaggc   1260
```

```
aaaaattcat ttacttcatg aagcgtaaaa attaaatatt ttaccacttt ttgttatttt   1320
ttaccatctc tatcaattat ttgtaaaaag aaaactacaa aattagatgt tttttctttt   1380
ttaaggttta atcaatatta aaatttctta aattggcaga caagttggtg ttggtaatta   1440
cgaataaatc ccgaattgac taaaaataaa ttcttctcca agtaaaatag acacgtggat   1500
gaagaaataa gtgaatcaaa ggcatccaca gttcaataaa tggaaaaaac tactttctgc   1560
tgactcattc ataagttttc ataaaatttc ataagaaagg ccaaagggct tatgaaagtg   1620
aatgtcatag cagtaaatga agcacagcgc cattgaaaga caactcaaat tgcatgcaaa   1680
cccacataat tattcaacaa acccacatca aatttcccat aaagatcaat tctttagggg   1740
gttcaattac ccaaaagtga ggtagttgaa aaccattaaa caacaagaaa tcaacaattt   1800
tgtaatttgt ttgtacagaa gtaagagata aaatcatcgt taaccattcc tttatttcgt   1860
aatacaaccc atcaaccatc tctctctctc tctctctctc tctctcggcc tttatctttc   1920
tcttcctcaa ttatttaagt actacccaag tgagctaaaa gcaagttcag tggacagtgt   1980
tgtaagaacc actacagaaa a                                             2001
```

```
<210> SEQ ID NO 191
<211> LENGTH: 4175
<212> TYPE: DNA
<213> ORGANISM: Cucumis melo

<400> SEQUENCE: 191
```

```
tagtttggtt cataggttat agtttccaaa tttgttaggc tatcattaat caaacacaat     60
acttctcttg taggatggct gccccctata gtactttttt aacttaggag aaggatataa    120
taattatatt ccttttagaa aatataataa taattgtgta gtgctttgat ataccttaaa    180
ttagctactc acgtttttag gaggaagctt ccgttgcttt tcatggtgtt atgatctttt    240
ttattttata aaggactgaa ctttaaaatt tctctttcat ctattttgga ttggattcca    300
tctattttat acgggaagtg aactctaaga tttctcttca cctattgtga atcggactcc    360
gtcatgtagg tcaagactac gacagataag aatagacttc cacgaaagaa agtggtcaat    420
cgagatggct atatttggct ctttcagctc aatttcttct tttttccttg catgttcttc    480
cgttggtaca tttcttgcac ttttttttgtt ctcacatgac taatgtattc caagtttatc    540
attggcattg tgcctctttt aggcttgtaa actctcgatc caaaattatc taggacatat    600
gtttcctagt gaagaaatac tagtatattc cttatgtcaa tatgtcaaaa ttttcaattt    660
cttaaccttt gagtaaatca atattatatt tttatggagg ttatttataa ttggaaaaaa    720
gttacaccca tctcaaccct aattaacacc aaatgaaatt gtaccatgcg gcacaatatt    780
tttttgtgag tttttttgcaa agagaaacaa agtagcagac aaagaacaaa cattcccccca    840
aaaacagcag agaataccta agagagaatg ctctctcgta aaaaataata cccaagaatc    900
ttcccaaaaa gagggagtaa aagagtccaa aacaaacgaa ccgaagattg acaagaaggg    960
cactctcgcc ctccactgcg ccgctaaatt gtaagaagca tattttcttg agttaacata   1020
ggaataggtg taactcaaga gaaatgtaat tcgtagaatt gaactttgta tattaattta   1080
tatggtgttg tagatacaat ctttagtatt tactcatttg gtgctttctc tcaaatacaa   1140
tttaaattta gaacttttttg atcttcgatt ttcaggaagt tggagttgca aatcaattcg   1200
agtttcaatc tctggaattt aataaaagtt tgatcttcca agttttcaat ctttcagaag   1260
acgatgatct tgatatggat aaaaaattgc acatcatgag agctttttga agtttaaatc   1320
```

-continued

```
ttcaattctc tagagcttaa attcttcctt aaaccaaaga tcaccaaatg aatgacaaat   1380
gtctctattt atcgaaaaat ttcatagact tttagatggg cttaggcaca ttacttgttg   1440
ggcttggact tgggcttatt tgcttggcgg gctcatgctc gagcccatta tttctttggc   1500
ctatttttca tgaggggctt gaacttggtt gtatacgaaa aaacttgact acctaaatct   1560
aatcaaatta taatcatcac aattttgacg tgttacgatt taattggcca aaaattcttg   1620
ttcaacactt gtctctaatc attttcctat ataatttaac taaaatattt aactttaagt   1680
aacttaaaag atatagttta attcgaatca aaatacaaat acaatttcgt ctatctattc   1740
ccatcataaa tgttgattga gattcatatt ataaacttct ttcaggaaaa gaaagaggaa   1800
aattcaccta aaccacgttt tcctattttg gtaagaatcc ccaaaccata aatcattcca   1860
aaattatttt ttttagatta gaaaagaaaa aagaaaaaaa gaaattcaca tggcgtaaaa   1920
tttcagcccc gtgagatatt ttcgaacccc cagatacaat ctacaccgtg aaaacaaaat   1980
cggacggtgg ttgctataat gtccgtttag aggcaatggc agggatgaaa ttgccaacgc   2040
aagataagga acgaataaga gaaggacacg taagtacaag tttaggatgg gcgggcccac   2100
agccacaagt gccgttcgtg cttatataca agtcgctcat attcctagaa gtgtctccaa   2160
ataaaggaaa gaaaagttca ctcatagaga gaaagagaaa aataaagctt cgttgccggc   2220
gatctgaagg cggcggccat ttctctcggg agagagaaag agagagattg atagagcgga   2280
gagttcgagg ctctctcaaa cttcggtcct cttcttctct ttcaggtatc gttcttctct   2340
atcccttcgt attctgtttc ctcttttctc tttcttcgcc atcatgctct ttctcttgtt   2400
ttgtactcac tcaatgtgat tgactttatg ttgtttttct gttttatttt tccattaatg   2460
ctcgttgtaa tgtgtagatc tatgataaga tttgaattat tgctcattaa tgtgttgcat   2520
gcttttgatt tcattttaaa aacagagatt actttctcta tattgattaa atcgttggat   2580
tttaggttct tacagagttt gtaaacagtg atgttaagga ttgctgagat ttatgactga   2640
tgagagttag tgtttgtctt ttagcttgtc gttttcctct ttgaaatcac atggattcga   2700
tctggatatc tgggtttggc tcgtctgaaa tggctacact atagcatatt tgagtttgtg   2760
atgttgaaga tttgttaatt tcttggaaaa tcgggagttc gttttgtttt tcctcttttt   2820
acaggtttta ttgattggtt tattgatcgg cgatatctcg ttttcaactt ccgaaatgct   2880
atttttcata agaagaaatt gtggatgtct ttttctactc gattagagat ccttgaaact   2940
atgccaaaaa aaattggttc tttcaccaaa ttgttttttg tcgtttgtga tattaatgca   3000
ttttcttatt cttaattaag ttcaagtatt cttttattat tttttaatga tggttgttgt   3060
aatggttttt tcccttttac taaaagcttt ttccatgtga ttcaaaggtg tacttggggt   3120
ttcccggtct ttgttcccaa gtcaattagg atgggcgcca attcgatttt agcttctgta   3180
tcattggtgt atattctgtt ctggggagga aaaaaaaaaa gaaaaaaatc ttccgtccta   3240
cagtgtgctg agtaacaatt tgaccagcct tttctgccga aaactttttg aaattatttt   3300
ttaattgtga tttggtgaac ttaaattgtt ttaataaata aggtggattg aatcttaaca   3360
gaaacatcaa ataaaatcga gttttaaaaa aaaaacatat ttttagtgaa tgtttatttt   3420
atttaaaaga tctccatcag tcctgatgtt tcctagaaaa cttatacatc ataggtcttg   3480
attaacaaat ttggaggaag tcaataggtt attcttttttt tctttttcca ttctagtttg   3540
aaacaatttt cttttctttt ttaacttaga aaataatggg tagctagaaa tatggaaatc   3600
aatgtatttt gggcttctcc ttgaaactgg agcagcggtc aatttctctt tcgtttgtat   3660
agatgtgata gaaatagaat gtttccttcg cttacggcat cagagagttg gaattggtct   3720
```

ttctcaacct caatatcaat taaatcaagt ttcgtcataa acaggttttt tttttcttcg 3780
tttcaaatgt ttggtagggt caaataattt gtaaaatacc tagccgtcca atatgataca 3840
aactggagga tttcacttgc tcttttaaat tacaaaaaat attttatcat tgatgttgcc 3900
tgtctgtgtt tatcttttct ctttccgcct caagtaggcg tctaattgtc ttggcaagtt 3960
ggttttttgt acttccgccc cttgtccttt ggcccttttg attaagtttt tcatttaatt 4020
ttctggtcgg cgtacgttga attattaggt ttgcatttaa tgtggtacct ggtgctttga 4080
ctcttatttg ataaggtatt ttgaagtcta aaacgttaaa ccctttgttt gatgtttatt 4140
tttttatcgt tccaggacaa tatcctttgg aaaaa 4175

<210> SEQ ID NO 192
<211> LENGTH: 1999
<212> TYPE: DNA
<213> ORGANISM: Cucumis melo

<400> SEQUENCE: 192
aaaagagtca tagtgaaaaa agctgagatc ataatagttt caccctaaac acaacttata 60
ataacacata ctatcataat atacacacca aacacagact ctatagtctt cactctaaac 120
gcagattaca atagtctgca ccccaaacgt agactattat aatcttctga ctattataat 180
actcttttca cttatcgccc caaacgtccc ctaagagaac aaagataggt tataaaagag 240
agatgagggt ttatattatg caacaagtat aaggttctag aacgatgtag tcttcaaagt 300
aacgaaagca ataggctaca cgagaaaaat atttttaaaa tatagtgctt tccctaaact 360
agatttcaat gacaaattat tataaaaaat agaatcatta atccaacatg gcttgcatgt 420
cacaccttgg ccaaaactga agacggatgt catactcgac ttcaatatat ttttttaatt 480
aattttcatg tgacaacaca taaatattta aaatttagat tgggttggat tttttttcaa 540
gtgggtccca aaatactctt caaacccaaa ccaacccaac ttgtttaccc atctaataat 600
aacccaccag gttcaagaag acgaaccgaa ccgaaccgat ccggtctaac tttgtttcat 660
acttaagtcg aacttagcgg tacttttggt tcggttctcg gtttccccaa acagagccac 720
tcaaaattag atttagggtt ccgttcgcaa ttttcagcgc atttttattt gaatcggtcg 780
tttgttgaac acgttctctc tcagctggtt tagggttcat cgttctctct tctcgcgcta 840
tatctttctc tctctcaggt tcgtttcttt ctcttaggcc attttatcag aagatcctct 900
tcgttctccg attttctttc cgtgttcgcc ctcggtttct cagcagacgt aggaagtttg 960
gtttccgttt agtgaatctg tttggggtat tacgaatgat attttgtact gggctttccg 1020
catagtcttt ttctttctag gaatatatgc atctgagaat ttatttgttt ggcttttctt 1080
tataaagtat gaggacatat acatctcgat tgctaatcct tgattataat cttttttttt 1140
tctatgttgt ttgaatctgt tttttttttt ttaatttcaa taggtttttt gaatctaaaa 1200
atgtatttct tggatgaatt gcatactgtt gaattagaag tttattgatt agattgttga 1260
tatttgccct aagttccatg gataggtttg cgtctttcac cttttcgttt gctttttctt 1320
ttggctgacg acatcttaca tagcctctgc tctaaaaggt gccatgattt tttttcctgg 1380
ctttatctga gtttgcgcaa tttagatttg aagtgatgat ttgtctaaat ataaatatct 1440
atcggccata ctattttttg ttattttgag tttttcagga tgactgctag agaatgaaaa 1500
atcttgaaac attgtgtttt gaagttcaag gatcttgtag ttttgttctt ttctagacta 1560
tctcatttga tatagccctt taaatttaat caaaatttgt taatattcaa atcctcggac 1620
attttaatta tttatctaaa tagttgttta ggcattactc aggttgccca ctattttaag 1680
cttagaagcc tactctggtt gacctaaagt ttgcatgcta tttgccttat ttcgcacgac 1740
tctaaactgt tatagacatc ttttttcagc cttcaggtaa atgaacacaa aaaggagtga 1800
aagtctgact tctgtgtgat ggtcttttaa tcaattatag ggattaagat ggttttttta 1860
ttcattgtat aaatattaaa ttagaatgat gacaaccaat aatattaaaa ctgacaatgg 1920
aaggttcctt atattatttg gagtgtacat tacaacagcc tgattcttgg cttggcaggt 1980
tcctgatcac cttgtaaac 1999

<210> SEQ ID NO 193
<211> LENGTH: 2000
<212> TYPE: DNA
<213> ORGANISM: Cucumis melo

<400> SEQUENCE: 193
atttatttgt ttagagataa gacgcacatg agaatatgag atggattcca ctccactcac 60
actccaattt ctacctatcc tattactgtt tactattatc attccacccc tcgacccctc 120
attcttcttc tcaccttact tttttatgat ttactactac ttcattttgg atcacaatct 180
gatcaatgct gggtgggctg ccctcggcct gtcaccaggc ccagcccact tccaaattaa 240
acctcttggc ccaccgccca ttgtccccat cccattccat ttaatattcc caaccttccc 300
tttttctttc ccaatgcgat gcttctccaa tatacctttc ctgccctcca tgtttccttt 360
ttactgcttt cttatattta taacacacct tctacagtct tttggctggg aatgctgcgt 420
atgtgaatga gattcaagat ttcgttgatg ttatttgagt ctctatattc ataagttttg 480
ttcttagttt tctctagacc aactgcaaga gttagcgttc catatgctca taagtttcag 540
atttctgctg tgtggtttga agacagtcat cgatccatgg gtgaattcgg ctttttatta 600
ttattattat tattatttat tgttgtctta cttttctatt tgaatcttcc tatctttttt 660
actcattgtt ggactctaat aattcttgct aaacacaatc tccattttta ttggacattt 720
taaatcccat ctcaactcat aattttagtt accttccacc atcaccatat ccaaatccga 780
aataaactca aataaaatcc ttcacgtgca tgtgctctcc atatattttt tctacatggt 840
aaaaataaaa tgaaaacaat ctaaatttaa taaaataaca tatatggcag acttttattg 900
atgtagagac tgggtgttgt acaagaacag tgcagccaag aaaaaaaaaa tacttccaat 960
gaatcgtaca ttttaaggat tatgaaacta actagttcca accatttttt cacgaccacg 1020
tgcttgttaa acacgcaagt agaatcaaaa tgtgggcttc ttcgctttat ataactgtga 1080
atcattctcc aaaaagggaa ggggatctca ttccctaatt caataaagaa aaagaaaaat 1140
gctagcgaac ttcatccatc tcattccttt tacctatttc atgagatgcc cattgtatat 1200
aagtattttt ttttttattt cattttactt agtttactcc tcacctctaa aaaaaattag 1260
gagagtttgc taaatccatt ctcaaactta gctttatttt ttttaatttt atttaacctc 1320
gtcgtggatg ttaacctcaa atgtcagttc tttttattct atttattgat gttataattt 1380
actttaggat tccaatttta taaaaataag aatacaaata aagataaaga gtgtgaaagc 1440
cagaaagaaa aaaaaggaaa tcgtaatatg ggtaaaattg gtacaaattg ggtcccgtta 1500
aatattaact caaaaaatgc gagaaaatgg tagaaaagga aataggggt aagagcaaag 1560 tagtggaagg agagcattga acatattctc tagtttttgc acttggatct aaacacgagg 1620
aattataggt ttattcattt actaattaca taaataggat tggattttaa aatttgaccg 1680
agtgattatg catatttgat agagttagaa aatagtggtg gggcaggtac aagttacaag 1740
taatgtataa gagatatgat gagcatatta ggaaactata gatttaaatt cgtccgtaaa 1800
taaataatta gaaatataat attcgagtgg aagggtatta gggttaggcg aaaccaattg 1860
cagttgcacc tataaaaccc cttttacgcc tccacccgct tcaacagcgg tctcggcgtc 1920
tacaactaca cactacacac tacacactac acactacaca gttgcagacc agaagcataa 1980
cgtaacgccg gtccacaaaa 2000

<210> SEQ ID NO 194
<211> LENGTH: 2000
<212> TYPE: DNA
<213> ORGANISM: Cucumis melo

<400> SEQUENCE: 194
tgaagagccg gaaaagcatg gcaaggtcaa ggcatttcag caagaatacg aggatgaatt 60
ctgggtttgt aagtccggtt cttcttcgga gttgtggttc gaatttcaaa cggccatgag 120
gagccctaca gcttaggaag cttcaggtct gagactctga ctccgacaga aattgctgat 180
ttttgtgtgt gttttgaata accattgtat gagtatgatt ggttgtatag gtttgaaatg 240
agggaaagtg atccatctcc ttgttgtctt tgcaggaaag gctcatattc gaccaagaac 300
gctttgtcat tgctttcgat aatcatagaa tccacaatgg tttggcatat tagcaaacaa 360
atcttcttta ggcattgcag acagaaaatt ggagagtaag ttattataat taaggattct 420
aaatgagtaa gaataataag atcaggcaaa gattggaaga actaaagcgt ttagtatttt 480
gtgtggtaca gaagaattgt aattagatac gtagtctaga gaagcagatg gtgagatttg 540
tgaaagacaa atgttagtgg agagtgaaga gtgtttctca acaaccgaca tagaaggatt 600
ctcagaaaat gagaaagatt tttattgcgc aaaatagctc ccatatcatc atatgccgtt 660
gccattccct ctggggttgc atgtaatgag taatggaaag ctgtagacag gctaacttca 720
ccctttgtct tgggtatagg gtgcattttt ggtcactcca ttttaagttt tctaataata 780
aaaggatgaa gaaaagatat tgaaaaacag ctcaggtttt aaagttgtca cacttgagaa 840
taatgcattt aacagttaga attttgcatc aacgtctttc aaatagaaaa gtaaaggaga 900
gtctagtttg agctggatag ctaaactggt ttaatcatat cttctatcaa gtggttagag 960
ttttagacct cccaacttta tatgtcgttg ccctaacaat gttgatggat gtttagtcct 1020
aagctctaac attgtccccg tatcatattt cataatagaa tgtactgagt aatggaaaac 1080
tagagaggta ggaagttgga cgaactttga atctatattg attttactat agtctttctt 1140
ccaagtctta atgagagctt tagctaaagt ttttcaaaaa ctcaaaagaa gtttttgttt 1200
tccaattctt cgatccatag attgtcaaga tggctataat atccttgaag ttaatagcct 1260
tcaaagtttc atagctttta tcctatgatc tttagaaatt caagagttat attctttaga 1320
actacagaac tttgatcttc gattcttcac ctcttccaga acctttatag tagagtttct 1380
tgaccttaca tgggcttggg attgggcctg gctacttatg ggcttagaga ttgaccttgg 1440
gtttaagcac attcgtttta cttggcccaa ttttcttaaa cttctgcaaa atcctaatta 1500
actaacacct caacaaaagt ccagtattaa atggggcata taaacaaaag ttaaacaaaa 1560
ttgtcgtaca gaatcctaat ttgctaacct cagcaaattt tatgccattc gtccttgtgt 1620
atctaattag tgttaatttg aggaaatata ataatataga cgtaggacgg atattggtat 1680
ttggtgcaac atcctccgaa ccaattcctg gaaagtaatt ggggcaacaa gataatgtta 1740
tcgtcagttt caagtgcaaa acttgccacg tggaacagcg gcaacatgat atctcaaata 1800

```
tggacctctc acccggtcaa gcttccacca ccaccaccac ctccgtattc taaaataaag   1860

tcaggaacaa gaacagacac accttaacaa aaccaatatt cttcatctct atctctctct   1920

catttcagca tagaagagag ctgagtaaaa ggaaaaaact tcaatcaaat ttgacagaga   1980

agagcccaag agaaaaccaa                                                2000


<210> SEQ ID NO 195
<211> LENGTH: 1400
<212> TYPE: DNA
<213> ORGANISM: Cucumis melo

<400> SEQUENCE: 195

tatatatatt aacttttaaa attttgaaaa cgtcatagat aaattatata caaaataaaa     60

agtttgatta tttacgaaag ttaaaaagtt tatccgaaag ttgactcaac gataaaaaca    120

ctaaatatca cttttagaga tgatgatatt atacataaac atacgaactt acgcgtcaaa    180

cttttatact aacacaagat caaaacaact ttgttgagta gtgagaattt tatctgctga    240

tatggttgaa acttgggaag caagcagagg aagttccatt cattaccaaa atccattttg    300

tattcatcaa aatatgaagt ttagcgactt gataaagtca agtcaagtgg tcctatcgat    360

ttgttaatgt caatgtttgg ttttgaattt gatacctatt agacaatgat atataatttt    420

aagtatggtt tacactgtga tgctttatat atttttaaat gtaaaatatt agaacttgta    480

atttcaataa attttaaaaa tgattttgtg ttatttcctt ttttaaattg aaatatcaat    540

gtatcaatat tgcgtcatag agtattgcaa cacaacctta tgttaaattg tttattgctt    600

attgctctaa ttcaactcct tcatcaaatg tgcacagaat ttaaacaaga aaaagagtag    660

gtgctttttt actaaaatat actaaaagct ttttatacca aatcttatga caaaatcatt    720

ccaacaaaat gactatttaa atataagatc gaatccctaa tttaaaaaaa aaaaaaaatc    780

aaagatgtta atttctatta ttaaactcac tttagcgtag ctaacaaaaa aaggaaaatg    840

agaggctaca aagcttgagc cctctgcctc cctttattgc attgtttgaa attagatcaa    900

tactttgtat ttttttcaaa atgaaaaatc gtacatagaa ttaattctat ggacaaaaaa    960

tcagagaagg aaataatcta gaataaaatt cgatttttaa cccaaaaaaa aaaaaaaaaa   1020

ctcgattctg atttttgtaa gcaatcaccc aaattaccat aaataaatgg tattcaatta   1080

ctcaattatg gatattttag aaatgataaa tttttattca taaactcttt tctttctctt   1140

tcaaaaagaa aaaaattagc ataaacttca atgacattta tttattcttc ttcgtttgga   1200

gtcaaaagtt taaattgagc atcagtccag cccaaaagcc cacgaagaag cccaagaatc   1260

ttcagctttt tcgttcaaac gtcccttttt ggtttataaa attaaagaaa ataaaaacta   1320

aatttatttg ttatttaaca aaacattttt ggttaagaca ttctctttga ttatttttct   1380

tccattcttc gtcgtcaatc                                                1400


<210> SEQ ID NO 196
<211> LENGTH: 2019
<212> TYPE: DNA
<213> ORGANISM: Cucumis melo

<400> SEQUENCE: 196

tttatattta tgaaaatgaa gtctctaaac aatttttcta ctcccaaatt tgttgatttt     60

tctgcctatt ctttatcggt gctttaaaaa atgaaaccaa atttcaaaac taaaaaaacc    120

aagcttttaa aaaaatgtta ggttattttt gaaattcaac taaatgttga actcttttac    180

ttattaaata ggcaaattat tgaaataaat ttagagcaag taagcttaat ttttaaaact    240
```

```
aatatactta ccaaatcgag gactaaaata ttcaaatact ctttaaaatt aagattaaca    300
ttaatcactt tgttatgttt aaaaagttgc agtgtcactt gaaccttttt aaattaatat    360
aatgaaaatg aatccaactc aatatatata atatctatat tattaatctc gatgtcagat    420
gtttgatacg cacatatctc aaaaattata cctcaactaa catcggtgca cgatgtatta    480
tttcgtgagg ataaaaatcg tttttagtat aaattgatgg aaagattatt tgaattactg    540
aaaaatgcac cggtacatta tttgaaactt ccccttcatt taaagaggct aatattagaa    600
aaagacacgc tgaggctatt tttacaatta atgtgggctg ttgacttggc ccagcccaaa    660
acataaaccc taaagtagca caaacaaacg cctctttctt cttgaaaccg catattaagc    720
gttttatcac ttctcaccac ctctcattcc tcctcttccg cacgttgttt cgctcctcaa    780
cgggagtgcc ttccctttgc tctccctcca ggttcttctt ccttctcatc tcatttccaa    840
gtaatttcat tccgtttctt ttctcttaat cgtatcttgt tcagactctt tcgcgttttt    900
ttttagttgc gccttaccag atctgtgttt tcactcgttt ctattcgata catgcttcca    960
agatccattt cttaatcgca tgtattcggt tgattggatg attgtctttt tgtaagtttt   1020
gattactttt ttggaatgga tcggttgaac caacggggtt taagtcgatg gaagtaggtt   1080
atgttaaaga tttgcttctt ttttatgaag atgtgtgtgt tctttttttct ttgctagatg   1140
atgttattat ttgattgttt taacagtcgt gttttgtttt tctgcagttt atagtcctcg   1200
gtcttttgaa gacttgtcaa gatggttagt acacctcttg tcatcgtgat tttgattgag   1260
tgatgtgtta agtgcttctt taggttacag ctaacgcgat tttttatatt caattgtgcc   1320
tgtgcaggtg aagtttacag cagaagagct ccgtcggatt atggactata agcataacat   1380
tcgtaatatg tctgttattg ctcacgtcga tcatggtaag ctacttagtt taagtttatt   1440
tatgccgagc gtctatttaa gaagattaac atcttagctt tcatttattg tttatttggt   1500
aagcatcgtt tctttttctc cgaggaactg tacatgtcag ttcacatgac aataaaacga   1560
tcttccttgg acattagttt ttgaagttca attagacgcc aaattttgtt ggttaaaaga   1620
tgcttgtgga gcatatggac ctaatggaat cagtactttt tgatggatgg acttgtcttt   1680
tgttctttta ttttcaaaag aaattgcatg tgcaattaca tcatctttga tcgaaagatt   1740
gggtaattgg gtaattgggg taaagacatg ttgtaaaaac taatgttaat tatcaattac   1800
cattatatac cttatttagt gcttatttat atccttttttc cccatttcag ggaagtccac   1860
tctcacagat tctcttgtgg ctgctgccgg tatcattgca caagaagttg ctggtgatgt   1920
acgaatgaca gatactcgtc aagatgaggc agagcgtggt atcaccatta aatctactgg   1980
aatctccctc tactatgagc agaagagctc cgtcggatt                          2019
```

<210> SEQ ID NO 197
<211> LENGTH: 1999
<212> TYPE: DNA
<213> ORGANISM: Cucumis melo

<400> SEQUENCE: 197

```
aaaaggcgaa aaaaaagtta gcttcccgag aaggagaaga cgaggaagag tttgacttcc     60
cggggagata aagtttgtgt ctcgagggaa tctctaatct ggagttgacc gtcgacttat    120
gtgtcgagcc tggatttagt tgcatggtgc gacaaagcga taaggcggca tatgtaaagt    180
agtaattcaa aactagcggt taaagaaata atcagccaaa aaatttagta caaatacggg    240
tggaggccct aagtgaagtg ctgctattca gaggttttgg caaaagagtg caaagagttg    300
```

```
agttgtgcag agaaagtact aggtgaggag aggcgtttgg aaaagaaaag gatcaaacat    360

ttgcatgagt gatattctta aactaaacac tcttgtgtga gtgacttgcc taagctaaac    420

actcttgcat gagtaacttt cttaaactaa acgttttgta atgttttctt aatggattct    480

tttcgagtct gagttatgct taacacgttt tgtttctctc gtgttattgt tgttgttgtt    540

tgaaaagaga aaactattgt tttctatgtg ctgattgtga tgaatgtgtg cgaaccatta    600

gccttaatcc tatcaagtga atagtgatta tgtggtgtgt gcacataatg taaatgacat    660

tgtgtggatg gccagtgcaa caagaaatga atcagaaagc ttcccaaata ctgtgaatgg    720

agtgaacatc acactagctc aatggcaaga tattggcgat agtgaatcac aataggcttg    780

acaaggggaa ggattcatgt tcttggttga aaggaataag agaggctaat gtgagatttc    840

tgtgatttgc aaaatgaggc gttggaagac acgtttgaga aatgaaaacg aattagtgct    900

tgacttgtat tcctaaaaaa gttgtccaat atcttcaatc actaaatatt tgatgtgcct    960

aagttttcct tccttagttg ttgaggcgtt gaggccgagt aaggaaagat aagataatta   1020

tgacgttgaa aagctggtca agttatccat ctttggatgg tttaaagtta ttacatgtag   1080

ggagggttgc attccaattt tgtgtgtgag atgagtctta ttttcgagat gggttgctag   1140

gcgatcaagg agaagtataa gaaatgagtt cttatactct tgaacaactt gacacgaaga   1200

ataacatcct agtggatgaa ggaaggtgat ggaacttaaa gtttaggttt tatttttggc   1260

cttgtgataa aaaaaatgta attgtaaagt attagatcaa gtaataaaaa cagagttgtg   1320

ttttctattt ttgctgtgtt gggttgtgta tctttattgt gcttatggcc tagttgctaa   1380

agagttaagg ttattaccta aatgttttac ggtgtgttga gttgtaaaga tctcctgagt   1440

taaagttgga attttgtatt ggagattgtt ttgagaagtt tagcttacta attgtttaac   1500

tcattaggtg tctaagcgac acgcctcctt ttggtcgcat gaagtggcta gcagggtggg   1560

gcggaccggg gtggggtgtg ataataaacc taaaaaatca cccagataag cctaaattat   1620

acgttgaagt taaacttaca atttgattag aagaagaagg aatatctgat ttggacatga   1680

attaattaca aatacggcgc caatcataca aagcacatgt aagatcaacg cattctacac   1740

tcaatctcag ccgttgattg ctttcaatcc ttcaaaaaga aaaaaagaag ggcagttcgg   1800

gcagagtcat acctacccgt tgactataaa agcaactaca aatcgaaaac ctccatttct   1860

ccgttaccat tacagagaaa atcaaagaaa tttggcgttg agagattggg agagaggttt   1920

ctctttctag ggttgcttct tcttcttcat cctccattgt tgcaaatttc acttccttct   1980

cctcttgttc tcatctccc                                                1999
```

<210> SEQ ID NO 198
<211> LENGTH: 1578
<212> TYPE: DNA
<213> ORGANISM: Cucumis melo

<400> SEQUENCE: 198

```
atatatatat atataattta actaaataaa caaatgaaag aaaaaagtga gttcccattc     60

ggaaaatgca gatggatcca tttcttcaaa tattaaaaaa taaaaaaata aaataaaata    120

acttaaatat gcaaatagaa agaattttaa tttctggatt atccatatgg gacaattttt    180

aaaactcatt tattttattt tttttattta tttgattttg atatatctat ggggaaattt    240

ttcgtaataa ttttcgaaaa aatattgcaa tatatcattt gatcagatcg gtattattaa    300

atctctatca catttggtct taaattatcc aaagattcct ttaagataat ttagataacc    360

atctacagat cactactata atcaacaaaa ggaacaactt aaattattta aacaaattca    420
```

-continued ttaatattag actttgtgct tcattagaaa atgatcttat cacaaccaca accatagtgg 480
tggtttaaaa ttttatttta aactcttatt agtattattt taattcatac ttaatcaaac 540
taattacttt aaaaaacata tatatataaa taagttaaat cattccccct tatatctaaa 600
taacataaaa aaaaattgtt tactctacaa gaagtttgta tatatatatg ctcggtacta 660
tttagcatct ttataataaa atttctaaat caatttttta tatctcttta ttaaatgtat 720
agtcatcaaa aaatttaacg agataatgtg tcaaagattt attttattaa cgttcataaa 780
tatcaaatta tacttagctt ataattgaaa acatgttcga taaatataag taaataaaat 840
tttatttttt ttaaatatta caaaataaac taaataagtt ataaatatga caataaacat 900
tatatatttt attatattta taaatactta ataatttagt cgtttaaaat aattttctta 960
attttcaaaa catgtttcat atgttaataa taaataaatg gaaaaccttc caaaagaaga 1020
aaaaaagata tcttaaaatt taaaaattga gattttgagg atcaataatt aataaaagaa 1080
ggattaataa gggtgaaatt aaatcccaaa aagaaaattg aaaatgaaga aaagaaaagt 1140
gaagaaataa ttgaacgtgg gaagtggatt cgatgtctcc agagaacaag cgaaaggaga 1200
cgaaatccac ataatttgca cgttacgtgt ccctatcaac cgtagacacg tgtcaacatc 1260
tcaacaccct acgccgaatt gcttcgctgg atctggacgg tcatcggata acagcggcaa 1320
ccaattaata tttcccctta tatttcacag cctggccatg tccaccaatc acgttcaact 1380
attaattcat ttttcatttc ctttttcttt tttttttaa ttcccctcaa ttattaccga 1440
caacctgttg tagccggtta accctaccct ccaacgttcc attataaggc ctagaaaatg 1500
gacgtgaaaa tggagtacta caaactacaa ttaattttaa agaattttaa ttttaaagtt 1560
ctctaattac tattagcc 1578

<210> SEQ ID NO 199
<211> LENGTH: 1023
<212> TYPE: DNA
<213> ORGANISM: Cucumis melo

<400> SEQUENCE: 199
ataataataa taaatacata atagtaataa taataaaaaa aataaaaaaa taataatagt 60
aatgaaaatc aatagaataa ttttaaaatc gggaaggaag tcgtgtacaa tccttgcacg 120
ttggagagtc aaatggccta agtggtgatg tggaagtcgt gtaccgggta cacgattttc 180
ctacaagtca ataataataa tatggttatt tttctagttt agggttcatg acaaaagatt 240
gttcagtcga ctggatgtag acaaatctaa aaaataaatt aaaatctaat atgaaaacta 300
gttttaattt ccaaattatt aagggttgaa ttcgaccaat aaataataat aatacggtta 360
ttttgaaatt taggaaattg aataaagttg ttaaaatctt caagcaaatt gttaagcccc 420
gagatattaa gaagaggtaa taatagagga ttctatattt ataacatgtt aaaattaatt 480
gcaaactcat aaatgcatca cacagattaa caacatagga gggacttccg ataaaagtgc 540
aaatattgaa ataattacag ttcgcgaaca tgagtatttt aatattttat aaaatagtat 600
gcacgtgtat ttttgccaaa agaaaaaaag aatagatttt gccatttttc aaagtgactc 660
tcggttatat cttttatggc gattgtattt tatagcgtat gttgtttgta gttaacccat 720
ttctcattgg caaattcaat cgtgggccac aacgtttggg catagcttca atttggatta 780
actcaattat gtctgaatgg gttggactag ttcggactct tcggctgggc cagaatcaga 840
ttcgggccgc aatctgttca tttcacacct atatccaaac acccccaaaa tcgataccca 900
tcaaacccta actctcaata acccccatat ataaattcct tctttagggt tttttcatcc 960
tcatacactc tcaaacctcc ggtcattctc attttccctg ccgcttcttc aataacccta 1020
atc 1023

<210> SEQ ID NO 200
<211> LENGTH: 1654
<212> TYPE: DNA
<213> ORGANISM: Arabidopsis thaliana

<400> SEQUENCE: 200
tgatgattct tgttgttgta gttcttttta aaagtcccac ctgagcctct atagactctg 60
attctctttt aagttactat tttcaccgct ctctaataag gctcgtgatt ttttgggagc 120
catactgtat actcgccggc cctctcacga tgttgttcaa ttcacagact aaatttgatt 180
tatctatttc gccaaaacat aacttcatta aaaaatgttc tccaaataac taaacgaatt 240
aaataaaaga aacctttcat gtaaagttaa aggtatgaga ctttaagggc agttgctgaa 300
cattcgtaac acatgggaga acaatagaga aagttgaaaa gaaacgtagc atatagaaaa 360
attatctttg taaccaagtt gatttagaaa aatatcacta tttgtgaaaa atactagatc 420
agtttattat tacttttttt tttttgtata ttcacaaata tcatattcat atagaagaaa 480
ataaacaaag ttgtaaaaat ctggcattta aaataaaatt gaacacttca atttatttcc 540
tttcataata ataattttgg cataagatat ttgcaaattg atctggttcg gtatggtcga 600
caaaataatt ttccacgcta cccttccagc cgtccattca ctatttgccc tcaacgttac 660
caaataacgg tccagattcc tagggcaaga tctaacggtt agcaagtaaa gtcgtaccat 720
cagaaagaat aacaattctt tcacaaagta aacataacca acggttaaca agttcttagg 780
gttaaatcag taagatccaa cggatattaa attgcaaggc ccaaatagtt tttttgcagc 840
agataataac tcgtccccac tggcgagtga cgaccgagac tctgtgaccc tatttttcga 900
gacgataaaa gggcaaacaa tcgctctttt caaagctcgc ctcttcacca cagagaaaac 960
ttcgtctctc ttctctgctt cgccctctca tttcctgtga gataaaggcg gagtctctct 1020
ccagttattt tgctcatcca tcgattctta ggtatgactc gtttctctca gatctgtgat 1080
tctttataat ctcgtcgttc ttcaaatcat tgttatattc gtttcttcga tctgtgtttt 1140
ttagatctgt aaggtaaatg agacgtttcg atctgtagat ctgattgtta tattgataga 1200
ttatgttatc tgctttgctt aaagtccgat cggaatgttt tgtgctcatt gtcgaatatc 1260
tgatgtatcg gtttcataga tctgcttctt tttgtgcgtt tcgttgatct gataatcttc 1320
tagtgatcaa aatcgtttgg atctgttgac tttagtttaa aatgtatccg atctgatgtc 1380
gaggcttcat tattggaagt tgttattgtt gtaatcctga tttaagttgc tgttcttaaa 1440
tttatatgat ctttgcgtta taatatgaca tggtagatct tggttcatgg ttcactgttt 1500
tccaataaac ttggtttgtt tggttggata gcgttctgtg atacgaccat gtcttgtgtt 1560
ggataagaat tctctgaatt tccttggctg gtttgtagta tgttattcac gtctggtttc 1620
tcatcaatga ttatgtgatt ttgcagagtt cacc 1654

<210> SEQ ID NO 201
<211> LENGTH: 712
<212> TYPE: DNA
<213> ORGANISM: Artificial sequence
<220> FEATURE:
<221> NAME/KEY: misc_feature
<222> LOCATION: (1)..(712)
<223> OTHER INFORMATION: Chimeric transcriptional regulatory expression element.

<400> SEQUENCE: 201
ggtccgatgt gagacttttc aacaaagggt aatatccgga aacctcctcg gattccattg 60
cccagctatc tgtcacttta ttgtgaagat agtggaaaag gaaggtggct cctacaaatg 120
ccatcattgc gataaaggaa aggccatcgt tgaagatgcc tctgccgaca gtggtcccaa 180
agatggaccc ccacccacga ggagcatcgt ggaaaaagaa gacgttccaa ccacgtcttc 240
aaagcaagtg gattgatgtg atggtccgat tgagactttt caacaaaggg taatatccgg 300
aaacctcctc ggattccatt gcccagctat ctgtcacttt attgtgaaga tagtggaaaa 360
ggaaggtggc tcctacaaat gccatcattg cgataaagga aaggccatcg ttgaagatgc 420
ctctgccgac agtggtccca aagatggacc cccacccacg aggagcatcg tggaaaaaga 480
agacgttcca accacgtctt caaagcaagt ggattgatgt gatatctcca ctgacgtaag 540
ggatgacgca caatcccact atccttcgca agacccttcc tctatataag gaagttcatt 600
tcatttggag aggacactct agacagaaaa atttgctaca ttgtttcaca aacttcaaat 660
attattcatt tatttgtcag ctttcaaact ctttgtttct tgtttgttga tt 712

<210> SEQ ID NO 202
<211> LENGTH: 938
<212> TYPE: DNA
<213> ORGANISM: Arabidopsis thaliana

<400> SEQUENCE: 202
caaaagccga gccgataaat cctaagccga gcctaacttt agccgtaacc atcagtcacg 60
gctcccgggc taattcattt gaaccgaatc ataatcaacg gtttagatca aactcaaaac 120
aatctaacgg caacatagac gcgtcggtga gctaaaaaga gtgtgaaagc caggtcacca 180
tagcattgtc tctcccagat tttttatttg ggaaataata gaagaaatag aaaaaaataa 240
aagagtgaga aaaatcgtag agctatatat tcgcacatgt actcgtttcg ctttccttag 300
tgttagctgc tgccgctgtt gtttctcctc catttctcta tctttctctc tcgctgcttc 360
tcgaatcttc tgtatcatct tcttcttctt caaggtgagt ctctagatcc gttcgcttga 420
ttttgctgct cgttagtcgt tattgttgat tctctatgcc gatttcgcta gatctgttta 480
gcatgcgttg tggttttatg agaaaatctt tgttttgggg gttgcttgtt atgtgattcg 540
atccgtgctt gttggatcga tctgagctaa ttcttaaggt ttatgtgtta gatctatgga 600
gtttgaggat tcttctcgct tctgtcgatc tctcgctgtt atttttgttt ttttcagtga 660
agtgaagttg tttagttcga aatgacttcg tgtatgctcg attgatctgg ttttaatctt 720
cgatctgtta ggtgttgatg tttacaagtg aattctagtg ttttctcgtt gagatctgtg 780
aagtttgaac ctagttttct caataatcaa catatgaagc gatgtttgag tttcaataaa 840
cgctgctaat cttcgaaact aagttgtgat ctgattcatg tttacttcat gagcttatcc 900
aattcatttc ggtttcattt tacttttttt ttagtgaa 938

<210> SEQ ID NO 203
<211> LENGTH: 633
<212> TYPE: DNA
<213> ORGANISM: Pisum sativum

<400> SEQUENCE: 203
agctttcgtt cgtatcatcg gtttcgacaa cgttcgtcaa gttcaatgca tcagtttcat 60
tgcgcacaca ccagaatcct actgagtttg agtattatgg cattgggaaa actgtttttc 120
ttgtaccatt tgttgtgctt gtaatttact gtgtttttta ttcggttttc gctatcgaac 180
tgtgaaatgg aaatggatgg agaagagtta atgaatgata tggtcctttt gttcattctc 240
aaattaatat tatttgtttt ttctcttatt tgttgtgtgt tgaatttgaa attataagag 300
atatgcaaac attttgtttt gagtaaaaat gtgtcaaatc gtggcctcta atgaccgaag 360
ttaatatgag gagtaaaaca cttgtagttg taccattatg cttattcact aggcaacaaa 420
tatattttca gacctagaaa agctgcaaat gttactgaat acaagtatgt cctcttgtgt 480
tttagacatt tatgaacttt cctttatgta attttccaga atccttgtca gattctaatc 540
attgctttat aattatagtt atactcatgg atttgtagtt gagtatgaaa atatttttta 600
atgcatttta tgacttgcca attgattgac aac 633

<210> SEQ ID NO 204
<211> LENGTH: 315
<212> TYPE: DNA
<213> ORGANISM: Gossypium barbadense

<400> SEQUENCE: 204
tgatcacctg tcgtacagta tttctacatt tgatgtgtga tttgtgaaga acatcaaaca 60
aaacaagcac tggctttaat atgatgataa gtattatggt aattaattaa ttggcaaaaa 120
caacaatgaa gctaaaattt tatttattga gccttgcggt taatttcttg tgatgatctt 180 ttttttttatt ttctaattat atatagtttc ctttgctttg aaatgctaaa ggtttgagag 240
agttatgctc tttttttctt cctctttctt ttttaacttt atcatacaaa ttttgaataa 300
aaatgtgagt acatt 315

<210> SEQ ID NO 205
<211> LENGTH: 315
<212> TYPE: DNA
<213> ORGANISM: Gossypium barbadense

<400> SEQUENCE: 205
accatatgac actggtgcat gtgccatcat catgcagtaa tttcatggta tatcttaatt 60
atatggttaa taaaaaaaag atggtgagtg aataatgtgc gtgcattcct ccatgcacca 120
atggtgaatc tctttgcata catagagatt ctgaatgatt atagtttatg ttgtagtgaa 180
attaattttg aatgttgttt ttaaatttta atgtcacttg gcttgattta tgttttaacg 240
aagcttatgt tatgtatttt actttaatga tattgcatgt attgttaatt taacattgct 300
tgatcagtat actct 315

<210> SEQ ID NO 206
<211> LENGTH: 2001
<212> TYPE: DNA
<213> ORGANISM: Artificial sequence
<220> FEATURE:
<221> NAME/KEY: misc_feature
<222> LOCATION: (1)..(2001)
<223> OTHER INFORMATION: Codon redesigned coding sequence.

<400> SEQUENCE: 206
atggtccgtc ctgtagaaac cccaacccgt gaaatcaaaa aactcgacgg cctgtgggca 60
ttcagtctgg atcgcgaaaa ctgtggaatt gatcagcgtt ggtgggaaag cgcgttacaa 120
gaaagccggg caattgctgt gccaggcagt tttaacgatc agttcgccga tgcagatatt 180
cgtaattatg cgggcaacgt ctggtatcag cgcgaagtct ttataccgaa aggttgggca 240

```
ggccagcgta tcgtgctgcg tttcgatgcg gtcactcatt acggcaaagt gtgggtcaat    300

aatcaggaag tgatggagca tcagggcggc tatacgccat ttgaagccga tgtcacgccg    360

tatgttattg ccgggaaaag tgtacgtaag tttctgcttc tacctttgat atatatataa    420

taattatcat taattagtag taatataata tttcaaatat ttttttcaaa ataaaagaat    480

gtagtatata gcaattgctt ttctgtagtt tataagtgtg tatattttaa tttataactt    540

ttctaatata tgaccaaaat ttgttgatgt gcaggtatca ccgtttgtgt gaacaacgaa    600

ctgaactggc agactatccc gccgggaatg gtgattaccg acgaaaacgg caagaaaaag    660

cagtcttact tccatgattt ctttaactat gccggaatcc atcgcagcgt aatgctctac    720

accacgccga acacctgggt ggacgatatc accgtggtga cgcatgtcgc gcaagactgt    780

aaccacgcgt ctgttgactg gcaggtggtg gccaatggtg atgtcagcgt tgaactgcgt    840

gatgcggatc aacaggtggt tgcaactgga caaggcacta gcgggacttt gcaagtggtg    900

aatccgcacc tctggcaacc gggtgaaggt tatctctatg aactgtgcgt cacagccaaa    960

agccagacag agtgtgatat ctacccgctt cgcgtcggca tccggtcagt ggcagtgaag   1020

ggcgaacagt tcctgattaa ccacaaaccg ttctacttta ctggctttgg tcgtcatgaa   1080

gatgcggact tgcgtggcaa aggattcgat aacgtgctga tggtgcacga ccacgcatta   1140

atggactgga ttggggccaa ctcctaccgt acctcgcatt acccttacgc tgaagagatg   1200

ctcgactggg cagatgaaca tggcatcgtg gtgattgatg aaactgctgc tgtcggcttt   1260

aacctctctt taggcattgg tttcgaagcg ggcaacaagc cgaaagaact gtacagcgaa   1320

gaggcagtca acggggaaac tcagcaagcg cacttacagg cgattaaaga gctgatagcg   1380

cgtgacaaaa accacccaag cgtggtgatg tggagtattg ccaacgaacc ggatacccgt   1440

ccgcaaggtg cacgggaata tttcgcgcca ctggcggaag caacgcgtaa actcgacccg   1500

acgcgtccga tcacctgcgt caatgtaatg ttctgcgacg ctcacaccga taccatcagc   1560

gatctctttg atgtgctgtg cctgaaccgt tattacggat ggtatgtcca aagcggcgat   1620

ttggaaacgg cagagaaggt actggaaaaa gaacttctgg cctggcagga gaaactgcat   1680

cagccgatta tcatcaccga atacggcgtg gatacgttag ccgggctgca ctcaatgtac   1740

accgacatgt ggagtgaaga gtatcagtgt gcatggctgg atatgtatca ccgcgtcttt   1800

gatcgcgtca gcgccgtcgt cggtgaacag gtatggaatt tcgccgattt tgcgacctcg   1860

caaggcatat tgcgcgttgg cggtaacaag aaagggatct tcactcgcga ccgcaaaccg   1920

aagtcggcgg cttttctgct gcaaaaacgc tggactggca tgaacttcgg tgaaaaaccg   1980

cagcagggag gcaaacaatg a                                             2001
```

<210> SEQ ID NO 207
<211> LENGTH: 1653
<212> TYPE: DNA
<213> ORGANISM: Artificial sequence
<220> FEATURE:
<221> NAME/KEY: misc_feature
<222> LOCATION: (1)..(1653)
<223> OTHER INFORMATION: Codon redesinged coding sequence.

<400> SEQUENCE: 207

```
atggaagacg ccaaaaacat aaagaaaggc ccggcgccat tctatcctct agaggatgga     60

accgctggag agcaactgca taaggctatg aagagatacg ccctggttcc tggaacaatt    120

gcttttacag atgcacatat cgaggtgaac atcacgtacg cggaatactt cgaaatgtcc    180

gttcggttgg cagaagctat gaaacgatat gggctgaata caaatcacag aatcgtcgta    240
```

```
tgcagtgaaa actctcttca attctttatg ccggtgttgg gcgcgttatt tatcggagtt    300

gcagttgcgc ccgcgaacga catttataat gaacgtgaat tgctcaacag tatgaacatt    360

tcgcagccta ccgtagtgtt tgtttccaaa aaggggttgc aaaaaatttt gaacgtgcaa    420

aaaaaattac caataatcca gaaaattatt atcatggatt ctaaaacgga ttaccaggga    480

tttcagtcga tgtacacgtt cgtcacatct catctacctc ccggttttaa tgaatacgat    540

tttgtaccag agtcctttga tcgtgacaaa acaattgcac tgataatgaa ttcctctgga    600

tctactgggt tacctaaggg tgtggccctt ccgcatagaa ctgcctgcgt cagattctcg    660

catgccagag atcctatttt tggcaatcaa atcattccgg atactgcgat tttaagtgtt    720

gttccattcc atcacggttt tggaatgttt actacactcg gatatttgat atgtggattt    780

cgagtcgtct taatgtatag atttgaagaa gagctgtttt tacgatccct tcaggattac    840

aaaattcaaa gtgcgttgct agtaccaacc ctattttcat tcttcgccaa aagcactctg    900

attgacaaat acgatttatc taatttacac gaaattgctt ctgggggcgc acctctttcg    960

aaagaagtcg gggaagcggt tgcaaaacgc ttccatcttc cagggatacg acaaggatat   1020

gggctcactg agactacatc agctattctg attacacccg agggggatga taaaccgggc   1080

gcggtcggta aagttgttcc attttttgaa gcgaaggttg tggatctgga taccgggaaa   1140

acgctgggcg ttaatcagag aggcgaatta tgtgtcagag gacctatgat tatgtccggt   1200

tatgtaaaca atccggaagc gaccaacgcc ttgattgaca aggatggatg gctacattct   1260

ggagacatag cttactggga cgaagacgaa cacttcttca tagttgaccg cttgaagtct   1320

ttaattaaat acaaaggata tcaggtggcc cccgctgaat tggaatcgat attgttacaa   1380

caccccaaca tcttcgacgc gggcgtggca ggtcttcccg acgatgacgc cggtgaactt   1440

cccgccgccg ttgttgtttt ggagcacgga aagacgatga cggaaaaaga gatcgtggat   1500

tacgtcgcca gtcaagtaac aaccgcgaaa aagttgcgcg gaggagttgt gtttgtggac   1560

gaagtaccga aaggtcttac cggaaaactc gacgcaagaa aaatcagaga gatcctcata   1620

aaggccaaga agggcggaaa gtccaaattg taa                                1653
```

<210> SEQ ID NO 208
<211> LENGTH: 936
<212> TYPE: DNA
<213> ORGANISM: Artificial sequence
<220> FEATURE:
<221> NAME/KEY: misc_feature
<222> LOCATION: (1)..(936)
<223> OTHER INFORMATION: Codon redesigned coding sequence.

<400> SEQUENCE: 208

```
atggcttcca aggtgtacga ccccgagcaa cgcaaacgca tgatcactgg gcctcagtgg     60

tgggctcgct gcaagcaaat gaacgtgctg gactccttca tcaactacta tgattccgag    120

aagcacgccg agaacgccgt gatttttctg catggtaacg ctgcctccag ctacctgtgg    180

aggcacgtcg tgcctcacat cgagcccgtg gctagatgca tcatccctga tctgatcgga    240

atgggtaagt ccggcaagag cgggaatggc tcatatcgcc tcctggatca ctacaagtac    300

ctcaccgctt ggttcgagct gctgaacctt ccaaagaaaa tcatctttgt gggccacgac    360

tggggggctt gtctggcctt tcactactcc tacgagcacc aagacaagat caaggccatc    420

gtccatgctg agagtgtcgt ggacgtgatc gagtcctggg acgagtggcc tgacatcgag    480

gaggatatcg ccctgatcaa gagcgaagag ggcgagaaaa tggtgcttga gaataacttc    540
```

```
ttcgtcgaga ccatgctccc aagcaagatc atgcggaaac tggagcctga ggagttcgct    600

gcctacctgg agccattcaa ggagaagggc gaggttagac ggcctaccct ctcctggcct    660

cgcgagatcc ctctcgttaa gggaggcaag cccgacgtcg tccagattgt ccgcaactac    720

aacgcctacc ttcgggccag cgacgatctg cctaagatgt tcatcgagtc cgaccctggg    780

ttcttttcca acgctattgt cgagggagct aagaagttcc ctaacaccga gttcgtgaag    840

gtgaagggcc tccacttcag ccaggaggac gctccagatg aaatgggtaa gtacatcaag    900

agcttcgtgg agcgcgtgct gaagaacgag cagtaa                              936
```

<210> SEQ ID NO 209
<211> LENGTH: 253
<212> TYPE: DNA
<213> ORGANISM: Agrobacterium tumefaciens

<400> SEQUENCE: 209

```
gatcgttcaa acatttggca ataaagtttc ttaagattga atcctgttgc cggtcttgcg     60

atgattatca tataatttct gttgaattac gttaagcatg taataattaa catgtaatgc    120

atgacgttat ttatgagatg ggtttttatg attagagtcc cgcaattata catttaatac    180

gcgatagaaa acaaaatata gcgcgcaaac taggataaat tatcgcgcgc ggtgtcatct    240

atgttactag atc                                                       253
```

<210> SEQ ID NO 210
<211> LENGTH: 622
<212> TYPE: DNA
<213> ORGANISM: Cauliflower mosaic virus

<400> SEQUENCE: 210

```
ggtccgattg agacttttca acaaagggta atatccggaa acctcctcgg attccattgc     60

ccagctatct gtcactttat tgtgaagata gtggaaaagg aaggtggctc ctacaaatgc    120

catcattgcg ataaaggaaa ggccatcgtt gaagatgcct ctgccgacag tggtcccaaa    180

gatggacccc cacccacgag gagcatcgtg gaaaaagaag acgttccaac cacgtcttca    240

aagcaagtgg attgatgtga tggtccgatt gagacttttc aacaaagggt aatatccgga    300

aacctcctcg gattccattg cccagctatc tgtcacttta ttgtgaagat agtggaaaag    360

gaaggtggct cctacaaatg ccatcattgc gataaaggaa aggccatcgt tgaagatgcc    420

tctgccgaca gtggtcccaa agatggaccc ccacccacga ggagcatcgt ggaaaaagaa    480

gacgttccaa ccacgtcttc aaagcaagtg gattgatgtg atatctccac tgacgtaagg    540

gatgacgcac aatcccacta tctagacgca agacccttcc tctatataag gaagttcatt    600

tcatttggag aggacacgct ga                                             622
```

<210> SEQ ID NO 211
<211> LENGTH: 1446
<212> TYPE: DNA
<213> ORGANISM: Cucumis melo

<400> SEQUENCE: 211

```
tcccttcagc cacttaacac ttaaaaatct taggaaactc catgggctcc tctttctcca     60

atgaaatttt gacatctgtg ttgttgatag ctcctatatc ctttgagaat ttgatataca    120

cctgtcattt gctgatttgt ggataactgt tagccttttg atattgatac gttccttttt    180

ttatgaattt ttgtaaatcc attcaatttt aatgctgtcg taaatgaaaa gccctttcat    240

taatgttgtt tatatacata ttttaaaatt aattcaataa caagtttagt tctgttagct    300
```

```
tctaggtttg tatctatttt atctattaaa ggtatgtttg ggcttcaggt tggaatggag    360
tagaattgaa tgggttgggg agtaaatttt ccattcaaca agttcaattt caaaatggct    420
aataagtttt gaactcaatt ttattttcaa taaattcctt aattttttgt tccttgtttg    480
taaactattg acttattcga tatattttaa aattgaggta ttttaaaaaa ataatacaat    540
attaaaatta tttataaaat ataacaaaat ttatgtatag tttatttgaa aattttacta    600
tagtttcatt tttatattat tcctaaccat ttccatttaa aattatttca attatttctt    660
ttattaatat aattgaaatt tcatggattt attagacaca tgatttgaaa ttttatgggt    720
ttattaagta ttttctaaca caaaatcgct tccgcatcgt tttcaattca ttcagtaata    780
gaagtaattt tttaaaagaa ccaaatttgc caaattttga gttccataag gactctgaaa    840
actcattatg tctattactc ttcactaatt gtagagactt aaattcaaga taagagacac    900
taattgatga taattgccca aaaaataaaa ataaaaatgt ttcttcccca tcctcaacct    960
ccatgaattc acagagccca aagattaatt attgggcccc aattcctact catatatacc   1020
ttacagtccc tcaaagaaat cttaggaagt aatcaatttc tgtttattca agatgtagcc   1080
tcccaaaaga aaaatacatc acatcaaatt caaacaaaaa tatctacagc tagcaaaacc   1140
tcaaaccgtt aaaatttcaa gccacataaa tgaaattttc atctgaaaaa aggacaatct   1200
atctagacgt tagatttcag ccctaatatg aatctgaagc atttggtgga cgagaaagag   1260
ccatgtagga atgcatcaaa caaaggaaaa atctttgaac tccaatggga ttgaagatac   1320
agataccaat ggataagaat ctgttctctt tgcccactat ttaaactcac caaacccacc   1380
agtatcttcc tcaccacaaa atacattcca ccgttgatca caagccttat tccaccacct   1440
ccaaca                                                              1446
```

<210> SEQ ID NO 212
<211> LENGTH: 2018
<212> TYPE: DNA
<213> ORGANISM: Cucumis melo

<400> SEQUENCE: 212

```
actattggag acgacgaagg aaaactctaa tgtgagctta gaattgaaga tggtgaacaa     60
ttgggagtct tttttaaaaa tctttcgtcg gtatattgaa atttcctttt acactcaaat    120
aacccccctt ttcacgcgtt caacgtcttc aaaccttcct ttttcaatta ttttttcgtt    180
tacattaatg acatttaggt aataagataa attagtggat tcttttgtga aaaatgttag    240
cccatttaag acttttatga aatatattag aaaaaaatca tatagcaatt tatattattc    300
tagttaaaag cccataatag aaactaaccc aacctaaagt aacgtaaaca ttcaataaga    360
gagacaaatt ttaaaataat ttctaattaa aaaaaaaatt gtcaagaccg tccgggtcgg    420
atccaaaata taacccgaac cggccggttt agcatctata taaatacacc tttagggttt    480
ttattctctc aagacttcac cgcatttcca cttctctgag gccacggtca gccattggag    540
cagctcaata atcctttgac tccctactac ggtaagtcga ccttactgct ttcggcttct    600
agttttttca atcctgtcat tagtcctttg gagttcttct gtacatttat gacgttttcg    660
gctcgtgttt tgtttcgcct gtatgtagtg ggtttttcga gttttgtttt tacttttttt    720
tatacttgca ggaattagtt gaaatctatg tacttcatgc cttggataat actcttgatc    780
tgttgtgtta ttcaaaatga attgttttaa gatggtattt gagaatggtc atgtgagttt    840
tgcctacttg gttattaaaa tgaattgttt taggatggta tttgagaatg gtcttctggg    900
```

-continued

```
tatttggttg gaacctttgt gctctgctat gaattagggt gttctccccg ttttttttt    960
tttttttctt ttggttatta atatatcttt tatgactact tattcatata tgatatcttt   1020
tactcgtaaa ttttgactca tttgaaagtt ttatccttag tcctttctca ttcagggtgt   1080
aaaggtatgt tgttagggtt aaaatagcct atgcaggaaa gttctgtatt tgttctaatt   1140
attgcatttg tgtgcatttg tatctagttt atttcttgct gagagtatgc ttcatttttt   1200
agtacacatc acttgtgcca ctttattata gttgcacatt tttgtttatg gagaggatga   1260
atagcattta gggatgtcaa tttttattg agaaaaccct ctctcctact taagcttggg    1320
gaatttttgt tctaaatgtg gtaaacataa tacttcttct tattttaatt tgaatggaag   1380
gggaagacga atactaatat tttcaacgaa ccttcacaac tttttttttc ttatttagga   1440
agccatgttt ttcaaaattg tactgtgtga tccacatatt tatcgattat tagtgaatcg   1500
aataataatt agagttttat tggtataatt ttgaagttca gacttattac atttgtggaa   1560
agtttggtta caattttcaa ttttattgga atcctaagaa ctttgtgtta acatatattg   1620
agttttcttc tctttttttt tactcattaa gttctctatt aggaatgttt ggttcaatgt   1680
cacatagtcg atagctaaga ccagtgaccc acaaagctat gattgaacga aaaacaagcc   1740
tttcacatct tggtaggaat ttgttatttc tcaatagatt tacagagctg tttcatgtga   1800
tcacaatttt tttctatttt tctgaagttc tctattagga atgggctatc tggttagttg   1860
cttttgagag aacatgtgga ttggtgttgc tcggtttcct tgcctttgta attttgtcct   1920
tggaaaaagc aaaatgatta ggtatcctga tatgcataac atgtttaagc caactagttc   1980
tcactttttt agtgcaaata attgatcttc aggaatcg                           2018
```

PLANT REGULATORY ELEMENTS AND USES THEREOF

REFERENCE TO RELATED APPLICATIONS

This application is a divisional of U.S. application Ser. No. 16/549,573, filed Aug. 23, 2019 (pending), which application is a divisional of U.S. application Ser. No. 15/802,843, filed Nov. 3, 2017 (pending), which application is a divisional of U.S. application Ser. No. 14/117,342, filed Oct. 23, 2014, (now U.S. Pat. No. 9,845,477), which application is a 371 National Stage application of International Application No. PCT/US2012/037561 filed May 11, 2012 which application claims the benefit of priority to U.S. Provisional Application No. 61/485,876 filed May 13, 2011, which are herein incorporated by reference in their entireties.

INCORPORATION OF SEQUENCE LISTING

The sequence listing that is contained in the file named "MONS304WO.txt", which is 463 kilobytes (as measured in Microsoft Windows®) and was created on May 9, 2012, is filed herewith by electronic submission and is incorporated by reference herein.

FIELD OF THE INVENTION

The invention relates to the field of plant molecular biology and plant genetic engineering, and DNA molecules useful for modulating gene expression in plants.

BACKGROUND

Regulatory elements are genetic elements that regulate gene activity by modulating the transcription of an operably linked transcribable polynucleotide molecule. Such elements include promoters, leaders, introns, and 3' untranslated regions and are useful in the field of plant molecular biology and plant genetic engineering.

SUMMARY OF THE INVENTION

The present invention provides novel gene regulatory elements such as promoters, leaders and introns derived from *Cucumis melo*, a plant species commonly referred to as muskmelon, for use in plants. The present invention also provides DNA constructs, transgenic plant cells, plants, and seeds comprising the regulatory elements. The sequences may be provided operably linked to a transcribable polynucleotide molecule which may be heterologous with respect to a regulatory sequence provided herein. The present invention also provides methods of making and using the regulatory elements, the DNA constructs comprising the regulatory elements, and the transgenic plant cells, plants, and seeds comprising the regulatory elements operably linked to a transcribable polynucleotide molecule.

Thus, in one aspect, the present invention provides a DNA molecule, such as a transcriptional regulatory expression element group, or promoter, or leader, or intron, comprising a polynucleotide sequence selected from the group consisting of: a) a sequence with at least 85 percent sequence identity to any of SEQ ID NOs: 1-199, 211 and 212; b) a sequence comprising any of SEQ ID NOs: 1-199, 211 and 212; and c) a fragment of any of SEQ ID NOs: 1-199, 211 and 212 exhibiting gene-regulatory activity, wherein said DNA molecule is operably linked to a heterologous transcribable polynucleotide molecule. In specific embodiments, a transcriptional regulatory expression element group, or promoter, or leader, or intron is at least 90 percent, at least 95 percent, at least 98 percent, or at least 99 percent identical to any of SEQ ID NOs: 1-199, 211 and 212. In particular embodiments, the heterologous transcribable polynucleotide molecule comprises a gene of agronomic interest, a gene capable of providing herbicide resistance in plants, or a gene capable of providing plant pest resistance in plants.

The invention also provides a transgenic plant cell containing a DNA molecule such as a transcriptional regulatory expression element group, or promoter, or leader, or intron, comprising a polynucleotide sequence selected from the group consisting of: a) a sequence with at least 85 percent sequence identity to any of SEQ ID NOs: 1-199, 211 and 212; b) a sequence comprising any of SEQ ID NOs: 1-199, 211 and 212; and c) a fragment of any of SEQ ID NOs: 1-199, 211 and 212 exhibiting gene-regulatory activity, wherein said DNA molecule is operably linked to a heterologous transcribable polynucleotide molecule. Further, the transcriptional regulatory expression element group, or promoter, or leader, or intron regulates the expression of a gene. The transgenic plant cell can be a monocotyledonous or dicotyledonous plant cell.

Further provided by the invention is a transgenic plant, or part of the transgenic plant containing a DNA molecule such as a transcriptional regulatory expression element group, or promoter, or leader, or intron, comprising a polynucleotide sequence selected from the group consisting of: a) a sequence with at least 85 percent sequence identity to any of SEQ ID NOs: 1-199, 211 and 212; b) a sequence comprising any of SEQ ID NOs: 1-199, 211 and 212; and c) a fragment of any of SEQ ID NOs: 1-199, 211 and 212 exhibiting gene-regulatory activity, wherein said DNA molecule is operably linked to a heterologous transcribable polynucleotide molecule. In specific embodiments, the transgenic plant may be a progeny plant of any generation that contains the transcriptional regulatory expression element group, or promoter, or leader, or intron.

Still further provided is a transgenic seed containing a DNA molecule such as a transcriptional regulatory expression element group, or promoter, or leader, or intron, comprising a polynucleotide sequence selected from the group consisting of: a) a sequence with at least 85 percent sequence identity to any of SEQ ID NOs: 1-199, 211 and 212; b) a sequence comprising any of SEQ ID NOs: 1-199, 211 and 212; and c) a fragment of any of SEQ ID NOs: 1-199, 211 and 212 exhibiting gene-regulatory activity, wherein said DNA molecule is operably linked to a heterologous transcribable polynucleotide molecule.

In yet another aspect, the invention provides a method of producing a commodity product from the transgenic plant, transgenic plant part or transgenic seed which contains a DNA molecule such as a transcriptional regulatory expression element group, or promoter, or leader, or intron, comprising a polynucleotide sequence selected from the group consisting of: a) a sequence with at least 85 percent sequence identity to any of SEQ ID NOs: 1-199, 211 and 212; b) a sequence comprising any of SEQ ID NOs: 1-199, 211 and 212; and c) a fragment of any of SEQ ID NOs: 1-199, 211 and 212 exhibiting gene-regulatory activity, wherein said DNA molecule is operably linked to a heterologous transcribable polynucleotide molecule. In one embodiment, the commodity product is protein concentrate, protein isolate, grain, starch, seeds, meal, flour, biomass, or seed oil.

In another aspect, the invention provides a commodity product comprising a DNA molecule such as a transcriptional regulatory expression element group, or promoter, or leader, or intron, comprising a polynucleotide sequence selected from the group consisting of: a) a sequence with at least 85 percent sequence identity to any of SEQ ID NOs: 1-199, 211 and 212; b) a sequence comprising any of SEQ ID NOs: 1-199, 211 and 212; and c) a fragment of any of SEQ ID NOs: 1-199, 211 and 212 exhibiting gene-regulatory activity, wherein said DNA molecule is operably linked to a heterologous transcribable polynucleotide molecule.

In still yet another aspect, the invention provides a method of expressing a transcribable polynucleotide molecule in a transgenic plant using a DNA molecule such as a transcriptional regulatory expression element group, or promoter, or leader, or intron which has a DNA sequence which is at least 85 percent identical to that of any of SEQ ID NOs: 1-199, 211 and 212, or contains any of SEQ ID NOs: 1-199, 211 and 212, or consists of a fragment of any of SEQ ID NOs: 1-199, 211 and 212; and cultivating the transgenic plant.

BRIEF DESCRIPTION OF THE SEQUENCES

SEQ ID NOs: 1, 5, 7, 9, 11, 13, 14, 15, 16, 17, 18, 19, 20, 21, 22, 23, 24, 25, 26, 27, 28, 29, 30, 31, 32, 33, 34, 35, 36, 37, 38, 39, 40, 41, 42, 43, 44, 45, 46, 47, 48, 49, 50, 51, 52, 53, 54, 55, 56, 57, 58, 59, 60, 61, 62, 63, 64, 65, 66, 67, 68, 69, 70, 71, 72, 73, 74, 75, 76, 77, 78, 79, 80, 81, 82, 83, 84, 85, 86, 87, 88, 89, 90, 91, 92, 93, 94, 95, 96, 97, 98, 99, 100, 101, 102, 103, 104, 105, 106, 107, 108, 109, 110, 111, 112, 113, 114, 115, 116, 117, 118, 119, 120, 121, 122, 123, 124, 125, 126, 127, 128, 129, 130, 131, 132, 133, 134, 135, 136, 137, 138, 139, 140, 141, 142, 143, 144, 145, 146, 147, 148, 149, 150, 151, 152, 153, 154, 155, 156, 159, 162, 167, 168, 172, 175, 176, 177, 178, 181, 182, 183, 184, 185, 188, 189, 190, 191, 192, 193, 194, 195, 196, 197, 198, 199, 211 and 212 are *Cucumis* transcriptional regulatory expression element groups or EXP sequences which are comprised of either a promoter element, operably linked to a leader element; or a promoter element, operably linked to a leader element and an intron element, or a promoter element, operably linked to a leader element, operably linked to an intron element, operably linked to a leader element.

SEQ ID NOs: 2, 6, 8, 10, 12, 163 and 169 are promoter elements.

SEQ ID NOs: 3, 164, 166 and 170 are leader sequences.

SEQ ID NOs: 4, 165 and 171 are intron sequences.

SEQ ID NOs: 157, 160, 173, 179 and 186 are sequences wherein a promoter is operably linked to a leader element.

SEQ ID NOs: 158, 161, 174, 180 and 187 are sequences wherein an intron is operably linked to a leader element.

BRIEF DESCRIPTION OF THE DRAWINGS

FIGS. 1*a*-1*f* depict alignment of promoter variant segments corresponding to promoter elements isolated from the *Cucumis melo*. In particular, FIGS. 1*a*-1*f* show alignment of the 2068 bp promoter sequence P-CUCme.Ubq1-1:1:15 (SEQ ID NO: 2), found in the transcriptional regulatory expression element group EXP-CUCme.Ubq1:1:1 (SEQ ID NO: 1), vs. promoter sequences derived via 5' deletions of the promoter, P-CUCme.Ubq1-1:1:15. Deletion, for instance of the 5' end of P-CUCme.Ubq1-1:1:15, produced the promoters, P-CUCme.Ubq1-1:1:16 (SEQ ID NO: 6) a 1459 bp promoter which is found within EXP-CUCme.Ubq1:1:2 (SEQ ID NO: 5); P-CUCme.Ubq1-1:1:17 (SEQ ID NO: 8), a 964 bp sequence comprised within EXP-CUCme.Ubq1:1:3 (SEQ ID NO: 7); P-CUCme.Ubq1-1:1:18 (SEQ ID NO: 10), a 479 bp sequence comprised within EXP-CUCme.Ubq1:1:4 (SEQ ID NO: 9); and P-CUCme.Ubq1-1:1:19 (SEQ ID NO: 12), a 173 bp sequence comprised within EXP-CUCme.Ubq1:1:5 (SEQ ID NO: 11).

DETAILED DESCRIPTION OF THE INVENTION

The invention disclosed herein provides polynucleotide molecules obtained from *Cucumis melo* having beneficial gene regulatory activity. The design, construction, and use of these polynucleotide molecules are described. The nucleotide sequences of these polynucleotide molecules are provided among SEQ ID NOs: 1-199, 211 and 212. These polynucleotide molecules are, for instance, capable of affecting the expression of an operably linked transcribable polynucleotide molecule in plant tissues, and therefore selectively regulating gene expression, or activity of an encoded gene product, in transgenic plants. The present invention also provides methods of modifying, producing, and using the same. The invention also provides compositions, transformed host cells, transgenic plants, and seeds containing the promoters and/or other disclosed nucleotide sequences, and methods for preparing and using the same.

The following definitions and methods are provided to better define the present invention and to guide those of ordinary skill in the art in the practice of the present invention. Unless otherwise noted, terms are to be understood according to conventional usage by those of ordinary skill in the relevant art.

DNA Molecules

As used herein, the term “DNA” or “DNA molecule” refers to a double-stranded DNA molecule of genomic or synthetic origin, i.e. a polymer of deoxyribonucleotide bases or a polynucleotide molecule, read from the 5' (upstream) end to the 3' (downstream) end. As used herein, the term “DNA sequence” refers to the nucleotide sequence of a DNA molecule.

As used herein, the term “isolated DNA molecule” refers to a DNA molecule at least partially separated from other molecules normally associated with it in its native or natural state. In one embodiment, the term “isolated” refers to a DNA molecule that is at least partially separated from some of the nucleic acids which normally flank the DNA molecule in its native or natural state. Thus, DNA molecules fused to regulatory or coding sequences with which they are not normally associated, for example as the result of recombinant techniques, are considered isolated herein. Such molecules are considered isolated when integrated into the chromosome of a host cell or present in a nucleic acid solution with other DNA molecules, in that they are not in their native state.

Any number of methods are known in the to isolate and manipulate a DNA molecule, or fragment thereof, disclosed in the present invention. For example, PCR (polymerase chain reaction) technology can be used to amplify a particular starting DNA molecule and/or to produce variants of the original molecule. DNA molecules, or fragment thereof, can also be obtained by other techniques such as by directly synthesizing the fragment by chemical means, as is commonly practiced by using an automated oligonucleotide synthesizer.

As used herein, the term “sequence identity” refers to the extent to which two optimally aligned polynucleotide sequences or two optimally aligned polypeptide sequences are identical. An optimal sequence alignment is created by manually aligning two sequences, e.g. a reference sequence and another sequence, to maximize the number of nucleotide matches in the sequence alignment with appropriate internal nucleotide insertions, deletions, or gaps. As used herein, the term "reference sequence" refers to a sequence provided as the polynucleotide sequences of SEQ ID NOs: 1-199, 211 and 212.

As used herein, the term "percent sequence identity" or "percent identity" or "% identity" is the identity fraction times 100. The "identity fraction" for a sequence optimally aligned with a reference sequence is the number of nucleotide matches in the optimal alignment, divided by the total number of nucleotides in the reference sequence, e.g. the total number of nucleotides in the full length of the entire reference sequence. Thus, one embodiment of the invention is a DNA molecule comprising a sequence that when optimally aligned to a reference sequence, provided herein as SEQ ID NOs: 1-199, 211 and 212, has at least about 85 percent identity at least about 90 percent identity at least about 95 percent identity, at least about 96 percent identity, at least about 97 percent identity, at least about 98 percent identity, or at least about 99 percent identity to the reference sequence. In particular embodiments such sequences may be defined as having gene-regulatory activity or encoding a peptide that functions to localize an operably linked polypeptide within a cell.

Regulatory Elements

A regulatory element is a DNA molecule having gene regulatory activity, i.e. one that has the ability to affect the transcription and/or translation of an operably linked transcribable polynucleotide molecule. The term "gene regulatory activity" thus refers to the ability to affect the expression pattern of an operably linked transcribable polynucleotide molecule by affecting the transcription and/or translation of that operably linked transcribable polynucleotide molecule. As used herein, a transcriptional regulatory expression element group (EXP) may be comprised of expression elements, such as enhancers, promoters, leaders and introns, operably linked. Thus a transcriptional regulatory expression element group may be comprised, for instance, of a promoter operably linked 5' to a leader sequence, which is in turn operably linked 5' to an intron sequence. The intron sequence may be comprised of a sequence beginning at the point of the first intron/exon splice junction of the native sequence and further may be comprised of a small leader fragment comprising the second intron/exon splice junction so as to provide for proper intron/exon processing to facilitate transcription and proper processing of the resulting transcript. Leaders and introns may positively affect transcription of an operably linked transcribable polynucleotide molecule as well as translation of the resulting transcribed RNA. The pre-processed RNA molecule comprises leaders and introns, which may affect the post-transcriptional processing of the transcribed RNA and/or the export of the transcribed RNA molecule from the cell nucleus into the cytoplasm. Following post-transcriptional processing of the transcribed RNA molecule, the leader sequence may be retained as part of the final messenger RNA and may positively affect the translation of the messenger RNA molecule.

Regulatory elements such as promoters, leaders, introns, and transcription termination regions are DNA molecules that have gene regulatory activity and play an integral part in the overall expression of genes in living cells. The term "regulatory element" refers to a DNA molecule having gene regulatory activity, i.e. one that has the ability to affect the transcription and/or translation of an operably linked transcribable polynucleotide molecule. Isolated regulatory elements, such as promoters and leaders that function in plants are therefore useful for modifying plant phenotypes through the methods of genetic engineering.

Regulatory elements may be characterized by their expression pattern effects (qualitatively and/or quantitatively), e.g. positive or negative effects and/or constitutive or other effects such as by their temporal, spatial, developmental, tissue, environmental, physiological, pathological, cell cycle, and/or chemically responsive expression pattern, and any combination thereof, as well as by quantitative or qualitative indications. A promoter is useful as a regulatory element for modulating the expression of an operably linked transcribable polynucleotide molecule.

As used herein, a "gene expression pattern" is any pattern of transcription of an operably linked DNA molecule into a transcribed RNA molecule. The transcribed RNA molecule may be translated to produce a protein molecule or may provide an antisense or other regulatory RNA molecule, such as a dsRNA, a tRNA, an rRNA, a miRNA, and the like.

As used herein, the term "protein expression" is any pattern of translation of a transcribed RNA molecule into a protein molecule. Protein expression may be characterized by its temporal, spatial, developmental, or morphological qualities as well as by quantitative or qualitative indications.

As used herein, the term "promoter" refers generally to a DNA molecule that is involved in recognition and binding of RNA polymerase II and other proteins (trans-acting transcription factors) to initiate transcription. A promoter may be initially isolated from the 5' untranslated region (5' UTR) of a genomic copy of a gene. Alternately, promoters may be synthetically produced or manipulated DNA molecules. Promoters may also be chimeric, that is a promoter produced through the fusion of two or more heterologous DNA molecules. Promoters useful in practicing the present invention include any of SEQ ID NOs: 2, 6, 8, 10, 12, 163 and 169, or the promoter elements comprised within any of SEQ ID NOs: 13 through 199, 211 and 212, or fragments or variants thereof. In specific embodiments of the invention, such molecules and any variants or derivatives thereof as described herein, are further defined as comprising promoter activity, i.e., are capable of acting as a promoter in a host cell, such as in a transgenic plant. In still further specific embodiments, a fragment may be defined as exhibiting promoter activity possessed by the starting promoter molecule from which it is derived, or a fragment may comprise a "minimal promoter" which provides a basal level of transcription and is comprised of a TATA box or equivalent sequence for recognition and binding of the RNA polymerase II complex for initiation of transcription.

In one embodiment, fragments of a promoter molecule are provided. Promoter fragments provide promoter activity, as described above, and may be useful alone or in combination with other promoters and promoter fragments, such as in constructing chimeric promoters. In specific embodiments, fragments of a promoter are provided comprising at least about 50, 95, 150, 250, 500, 750, or at least about 1000 contiguous nucleotides, or longer, of a polynucleotide molecule having promoter activity disclosed herein.

Compositions derived from any of the promoters presented as SEQ ID NOs: 2, 6, 8, 10, 12, 163 and 169, or the promoter elements comprised within SEQ ID NOs: 13 through 199, 211 and 212, such as internal or 5' deletions, for example, can be produced to improve or alter expression, including by removing elements that have either positive or negative effects on expression; duplicating elements that have positive or negative effects on expression; and/or duplicating or removing elements that have tissue or cell specific effects on expression. Compositions derived from any of the promoters presented as SEQ ID NOs: 2, 6, 8, 10, 12, 163 and 169, or the promoter elements comprised within SEQ ID NOs: 13 through 199, 211 and 212 comprised of 3' deletions in which the TATA box element or equivalent sequence thereof and downstream sequence is removed can be used, for example, to make enhancer elements. Further deletions can be made to remove any elements that have positive or negative; tissue specific; cell specific; or timing specific (such as, but not limited to, circadian rhythms) effects on expression. Any of the promoters presented as SEQ ID NOs: 2, 6, 8, 10, 12, 163 and 169, or the promoter elements comprised within SEQ ID NOs: 13 through 199, 211 and 212, and fragments or enhancers derived there from can be used to make chimeric transcriptional regulatory element compositions comprised of any of the promoters presented as SEQ ID NOs: 2, 6, 8, 10, 12, 163 and 169, or the promoter elements comprised within SEQ ID NOs: 13 through 199, 211 and 212, and the fragments or enhancers derived therefrom operably linked to other enhancers and promoters. The efficacy of the modifications, duplications or deletions described herein on the desired expression aspects of a particular transgene may be tested empirically in stable and transient plant assays, such as those described in the working examples herein, so as to validate the results, which may vary depending upon the changes made and the goal of the change in the starting molecule.

As used herein, the term "leader" refers to a DNA molecule isolated from the untranslated 5' region (5' UTR) of a genomic copy of a gene and defined generally as a nucleotide segment between the transcription start site (TSS) and the protein coding sequence start site. Alternately, leaders may be synthetically produced or manipulated DNA elements. A leader can be used as a 5' regulatory element for modulating expression of an operably linked transcribable polynucleotide molecule. Leader molecules may be used with a heterologous promoter or with their native promoter. Promoter molecules of the present invention may thus be operably linked to their native leader or may be operably linked to a heterologous leader. Leaders useful in practicing the present invention include SEQ ID NOs: 3, 164, 166 and 170, or the leader element comprised within SEQ ID NOs: 13 through 199, 211 and 212, or fragments or variants thereof. In specific embodiments, such sequences may be provided defined as being capable of acting as a leader in a host cell, including, for example, a transgenic plant cell. In one embodiment such sequences are decoded as comprising leader activity.

The leader sequences (5' UTR) presented as SEQ ID NOs: 3, 164, 166 and 170, or the leader element comprised within any of SEQ ID NOs: 13 through 199, 211 and 212 may be comprised of regulatory elements or may adopt secondary structures that can have an effect on transcription or translation of a transgene. The leader sequences presented as SEQ ID NOs: 3, 164, 166 and 170, or the leader element comprised within SEQ ID NOs: 13 through 199, 211 and 212 can be used in accordance with the invention to make chimeric regulatory elements that affect transcription or translation of a transgene. In addition, the leader sequences presented as SEQ ID NOs: 3, 164, 166 and 170, or the leader element comprised within any of SEQ ID NOs: 13 through 199, 211 and 212 can be used to make chimeric leader sequences that affect transcription or translation of a transgene.

The introduction of a foreign gene into a new plant host does not always result in a high expression of the incoming gene. Furthermore, if dealing with complex traits, it is sometimes necessary to modulate several genes with spatially or temporarily different expression pattern. Introns can principally provide such modulation. However, multiple use of the same intron in one transgenic plant has shown to exhibit disadvantages. In those cases it is necessary to have a collection of basic control elements for the construction of appropriate recombinant DNA elements. As the available collection of introns known in the art with expression enhancing properties is limited, alternatives are needed.

Compositions derived from any of the introns presented as SEQ ID NOs: 4, 165 and 171 or the intron element comprised within SEQ ID NOs: 13 through 199, 211 and 212 can be comprised of internal deletions or duplications of cis regulatory elements; and/or alterations of the 5' and 3' sequences comprising the intron/exon splice junctions can be used to improve expression or specificity of expression when operably linked to a promoter+leader or chimeric promoter+leader and coding sequence. Alterations of the 5' and 3' regions comprising the intron/exon splice junction can also be made to reduce the potential for introduction of false start and stop codons being produced in the resulting transcript after processing and splicing of the messenger RNA. The introns can be tested empirically as described in the working examples to determine the intron's effect on expression of a transgene.

In accordance with the invention a promoter or promoter fragment may be analyzed for the presence of known promoter elements, i.e. DNA sequence characteristics, such as a TATA-box and other known transcription factor binding site motifs. Identification of such known promoter elements may be used by one of skill in the art to design variants having a similar expression pattern to the original promoter.

As used herein, the term "enhancer" or "enhancer element" refers to a cis-acting transcriptional regulatory element, a.k.a. cis-element, which confers an aspect of the overall expression pattern, but is usually insufficient alone to drive transcription, of an operably linked polynucleotide sequence. Unlike promoters, enhancer elements do not usually include a transcription start site (TSS) or TATA box or equivalent sequence. A promoter may naturally comprise one or more enhancer elements that affect the transcription of an operably linked polynucleotide sequence. An isolated enhancer element may also be fused to a promoter to produce a chimeric promoter.cis-element, which confers an aspect of the overall modulation of gene expression. A promoter or promoter fragment may comprise one or more enhancer elements that effect the transcription of operably linked genes. Many promoter enhancer elements are believed to bind DNA-binding proteins and/or affect DNA topology, producing local conformations that selectively allow or restrict access of RNA polymerase to the DNA template or that facilitate selective opening of the double helix at the site of transcriptional initiation. An enhancer element may function to bind transcription factors that regulate transcription. Some enhancer elements bind more than one transcription factor, and transcription factors may interact with different affinities with more than one enhancer domain. Enhancer elements can be identified by a number of techniques, including deletion analysis, i.e. deleting one or more nucleotides from the 5' end or internal to a promoter; DNA binding protein analysis using DNase I footprinting, methylation interference, electrophoresis mobility-shift assays, in vivo genomic footprinting by ligation-mediated PCR, and other conventional assays; or by DNA sequence similarity analysis using known cis-element motifs or enhancer elements as a target sequence or target motif with conventional DNA sequence comparison methods, such as BLAST. The fine structure of an enhancer domain can be further studied by mutagenesis (or substitution) of one or more nucleotides or by other conventional methods. Enhancer elements can be obtained by chemical synthesis or by isolation from regulatory elements that include such elements, and they can be synthesized with additional flanking nucleotides that contain useful restriction enzyme sites to facilitate subsequence manipulation. Thus, the design, construction, and use of enhancer elements according to the methods disclosed herein for modulating the expression of operably linked transcribable polynucleotide molecules are encompassed by the present invention.

In plants, the inclusion of some introns in gene constructs leads to increased mRNA and protein accumulation relative to constructs lacking the intron. This effect has been termed "intron mediated enhancement" (IME) of gene expression (Mascarenhas et al., (1990) *Plant Mol. Biol.* 15:913-920). Introns known to stimulate expression in plants have been identified in maize genes (e.g. tubA1, Adh1, Sh1, Ubi1 (Jeon et al. (2000) *Plant Physiol.* 123:1005-1014; Callis et al. (1987) *Genes Dev.* 1:1183-1200; Vasil et al. (1989) *Plant Physiol.* 91:1575-1579; Christiansen et al. (1992) *Plant Mol. Biol.* 18:675-689) and in rice genes (e.g. salt, tpi: McElroy et al., *Plant Cell* 2:163-171 (1990); Xu et al., *Plant Physiol.* 106:459-467 (1994)). Similarly, introns from dicotyledonous plant genes like those from *Petunia* (e.g. rbcS), potato (e.g. st-ls1) and from *Arabidopsis thaliana* (e.g. ubq3 and pat1) have been found to elevate gene expression rates (Dean et al. (1989) *Plant Cell* 1:201-208; Leon et al. (1991) *Plant Physiol.* 95:968-972; Norris et al. (1993) *Plant Mol Biol* 21:895-906; Rose and Last (1997) *Plant J.* 11:455-464). It has been shown that deletions or mutations within the splice sites of an intron reduce gene expression, indicating that splicing might be needed for IME (Mascarenhas et al. (1990) *Plant Mol Biol.* 15:913-920; Clancy and Hannah (2002) *Plant Physiol.* 130:918-929). However, that splicing per se is not required for a certain IME in dicotyledonous plants has been shown by point mutations within the splice sites of the pat1 gene from *A. thaliana* (Rose and Beliakoff (2000) *Plant Physiol.* 122:535-542).

Enhancement of gene expression by introns is not a general phenomenon because some intron insertions into recombinant expression cassettes fail to enhance expression (e.g. introns from dicot genes (rbcS gene from pea, phaseolin gene from bean and the stls-1 gene from *Solanum tuberosum*) and introns from maize genes (adh1 gene the ninth intron, hsp81 gene the first intron)) (Chee et al. (1986) *Gene* 41:47-57; Kuhlemeier et al. (1988) *Mol Gen Genet* 212:405-411; Mascarenhas et al. (1990) *Plant Mol. Biol.* 15:913-920; Sinibaldi and Mettler (1992) In W E Cohn, K Moldave, eds, *Progress in Nucleic Acid Research and Molecular Biology*, Vol 42. Academic Press, New York, pp 229-257; Vancanneyt et al. 1990 *Mol. Gen. Genet.* 220:245-250). Therefore, not each intron can be employed in order to manipulate the gene expression level of non-endogenous genes or endogenous genes in transgenic plants. What characteristics or specific sequence features must be present in an intron sequence in order to enhance the expression rate of a given gene is not known in the prior art and therefore from the prior art it is not possible to predict whether a given plant intron, when used heterologously, will cause IME.

As used herein, the term "chimeric" refers to a single DNA molecule produced by fusing a first DNA molecule to a second DNA molecule, where neither first nor second DNA molecule would normally be found in that configuration, i.e. fused to the other. The chimeric DNA molecule is thus a new DNA molecule not otherwise normally found in nature. As used herein, the term "chimeric promoter" refers to a promoter produced through such manipulation of DNA molecules. A chimeric promoter may combine two or more DNA fragments; an example would be the fusion of a promoter to an enhancer element. Thus, the design, construction, and use of chimeric promoters according to the methods disclosed herein for modulating the expression of operably linked transcribable polynucleotide molecules are encompassed by the present invention.

As used herein, the term "variant" refers to a second DNA molecule that is in composition similar, but not identical to, a first DNA molecule and yet the second DNA molecule still maintains the general functionality, i.e. same or similar expression pattern, of the first DNA molecule. A variant may be a shorter or truncated version of the first DNA molecule and/or an altered version of the sequence of the first DNA molecule, such as one with different restriction enzyme sites and/or internal deletions, substitutions, and/or insertions. A "variant" can also encompass a regulatory element having a nucleotide sequence comprising a substitution, deletion and/or insertion of one or more nucleotides of a reference sequence, wherein the derivative regulatory element has more or less or equivalent transcriptional or translational activity than the corresponding parent regulatory molecule. The regulatory element "variants" may also encompass variants arising from mutations that naturally occur in bacterial and plant cell transformation. In the present invention, a polynucleotide sequence provided as SEQ ID NOs: 1-199, 211 and 212 may be used to create variants similar in composition, but not identical to, the polynucleotide sequence of the original regulatory element, while still maintaining the general functionality of, i.e. same or similar expression pattern, the original regulatory element. Production of such variants of the present invention is well within the ordinary skill of the art in light of the disclosure and is encompassed within the scope of the present invention. "Variants" of chimeric regulatory element comprise the same constituent elements as a reference chimeric regulatory element sequence but the constituent elements comprising the chimeric regulatory element may be operatively linked by various methods known in the art such as, restriction enzyme digestion and ligation, ligation independent cloning, modular assembly of PCR products during amplification, or direct chemical synthesis of the chimeric regulatory element as well as other methods known in the art. The resulting "variant" chimeric regulatory element is comprised of the same, or variants of the same, constituent elements as the reference sequence but differ in the sequence or sequences that are used to operably link the constituent elements. In the present invention, the polynucleotide sequences provided as SEQ ID NOs: 1-199, 211 and 212 each provide a reference sequence wherein the constituent elements of the reference sequence may be joined by methods known in the art and may consist of substitutions, deletions and/or insertions of one or more nucleotides or mutations that naturally occur in bacterial and plant cell transformation.

Constructs

As used herein, the term "construct" means any recombinant polynucleotide molecule such as a plasmid, cosmid, virus, autonomously replicating polynucleotide molecule, phage, or linear or circular single-stranded or double-stranded DNA or RNA polynucleotide molecule, derived from any source, capable of genomic integration or autonomous replication, comprising a polynucleotide molecule where one or more polynucleotide molecule has been linked in a functionally operative manner, i.e. operably linked. As used herein, the term "vector" means any recombinant polynucleotide construct that may be used for the purpose of transformation, i.e. the introduction of heterologous DNA into a host cell. The term includes an expression cassette isolated from any of the aforementioned molecules.

As used herein, the term "operably linked" refers to a first molecule joined to a second molecule, wherein the molecules are so arranged that the first molecule affects the function of the second molecule. The two molecules may or may not be part of a single contiguous molecule and may or may not be adjacent. For example, a promoter is operably linked to a transcribable polynucleotide molecule if the promoter modulates transcription of the transcribable polynucleotide molecule of interest in a cell. A leader, for example, is operably linked to coding sequence when it is capable of serving as a leader for the polypeptide encoded by the coding sequence.

The constructs of the present invention may be provided, in one embodiment, as double Ti plasmid border DNA constructs that have the right border (RB or AGRtu.RB) and left border (LB or AGRtu.LB) regions of the Ti plasmid isolated from *Agrobacterium tumefaciens* comprising a T-DNA, that along with transfer molecules provided by the *A. tumefaciens* cells, permit the integration of the T-DNA into the genome of a plant cell (see, for example, U.S. Pat. No. 6,603,061). The constructs may also contain the plasmid backbone DNA segments that provide replication function and antibiotic selection in bacterial cells, for example, an *Escherichia coli* origin of replication such as ori322, a broad host range origin of replication such as oriV or oriRi, and a coding region for a selectable marker such as Spec/Strp that encodes for Tn7 aminoglycoside adenyltransferase (aadA) conferring resistance to spectinomycin or streptomycin, or a gentamicin (Gm, Gent) selectable marker gene. For plant transformation, the host bacterial strain is often *A. tumefaciens* ABI, C58, or LBA4404; however, other strains known in the art of plant transformation can function in the present invention.

Methods are available for assembling and introducing constructs into a cell in such a manner that the transcribable polynucleotide molecule is transcribed into a functional mRNA molecule that is translated and expressed as a protein product. For the practice of the present invention, conventional compositions and methods for preparing and using constructs and host cells can be found in, for example, *Molecular Cloning: A Laboratory Manual, 3rd* edition Volumes 1, 2, and 3 (2000) J. F. Sambrook, D. W. Russell, and N. Irwin, Cold Spring Harbor Laboratory Press. Methods for making recombinant vectors particularly suited to plant transformation include, without limitation, those described in U.S. Pat. Nos. 4,971,908; 4,940,835; 4,769,061; and 4,757,011 in their entirety. These types of vectors have also been reviewed in the scientific literature (see, for example, Rodriguez, et al., *Vectors: A Survey of Molecular Cloning Vectors and Their Uses*, Butterworths, Boston, (1988) and Glick, et al., *Methods in Plant Molecular Biology and Biotechnology*, CRC Press, Boca Raton, Fla. (1993)). Typical vectors useful for expression of nucleic acids in higher plants are well known in the art and include vectors derived from the tumor-inducing (Ti) plasmid of *Agrobacterium tumefaciens* (Rogers, et al., *Methods in Enzymology* 153: 253-277 (1987)). Other recombinant vectors useful for plant transformation, including the pCaMVCN transfer control vector, have also been described in the scientific literature (see, for example, Fromm, et al., *Proc. Natl. Acad. Sci. USA* 82: 5824-5828 (1985)).

Various regulatory elements may be included in a construct including any of those provided herein. Any such regulatory elements may be provided in combination with other regulatory elements. Such combinations can be designed or modified to produce desirable regulatory features. In one embodiment, constructs of the present invention comprise at least one regulatory element operably linked to a transcribable polynucleotide molecule operably linked to a 3' transcription termination molecule.

Constructs of the present invention may include any promoter or leader provided herein or known in the art. For example, a promoter of the present invention may be operably linked to a heterologous non-translated 5' leader such as one derived from a heat shock protein gene (see, for example, U.S. Pat. Nos. 5,659,122 and 5,362,865). Alternatively, a leader of the present invention may be operably linked to a heterologous promoter such as the Cauliflower Mosaic Virus 35S transcript promoter (see, U.S. Pat. No. 5,352,605). The expression properties imparted by such operable linkages of heterologous elements is not necessarily additive of the elucidated properties of each promoter and leader, but rather is determined through empirical analysis of expression driven by the operably linked heterologous promoter and leader.

As used herein, the term "intron" refers to a DNA molecule that may be isolated or identified from the genomic copy of a gene and may be defined generally as a region spliced out during mRNA processing prior to translation. Alternately, an intron may be a synthetically produced or manipulated DNA element. An intron may contain enhancer elements that effect the transcription of operably linked genes. An intron may be used as a regulatory element for modulating expression of an operably linked transcribable polynucleotide molecule. A DNA construct may comprise an intron, and the intron may or may not be heterologous with respect to the transcribable polynucleotide molecule sequence. Examples of introns in the art include the rice actin intron (U.S. Pat. No. 5,641,876) and the corn HSP70 intron (U.S. Pat. No. 5,859,347). Introns useful in practicing the present invention include SEQ ID NOs: 4, 165 and 171 or the intron element comprised within any of SEQ ID NOs: 13 through 199, 211 and 212.

As used herein, the term "3' transcription termination molecule" or "3' UTR" refers to a DNA molecule that is used during transcription to produce the 3' untranslated region (3' UTR) of an mRNA molecule. The 3' untranslated region of an mRNA molecule may be generated by specific cleavage and 3' polyadenylation, a.k.a. polyA tail. A 3' UTR may be operably linked to and located downstream of a transcribable polynucleotide molecule and may include polynucleotides that provide a polyadenylation signal and other regulatory signals capable of affecting transcription, mRNA processing, or gene expression. PolyA tails are thought to function in mRNA stability and in initiation of translation. Examples of 3' transcription termination molecules are the nopaline synthase 3' region (see, Fraley, et al., *Proc. Natl. Acad. Sci. USA,* 80: 4803-4807 (1983)); wheat hsp17 3' region; pea rubisco small subunit 3' region; cotton E6 3' region (U.S. Pat. No. 6,096,950); 3' regions disclosed in WO0011200A2; and the coixin 3' UTR (U.S. Pat. No. 6,635,806).

3' UTRs typically find beneficial use for the recombinant expression of specific genes. In animal systems, a machinery of 3' UTRs has been well defined (e.g. Zhao et al., *Microbiol Mol Biol Rev* 63:405-445 (1999); Proudfoot, *Nature* 322: 562-565 (1986); Kim et al., *Biotechnology Progress* 19:1620-1622 (2003); Yonaha and Proudfoot, *EMBO J.* 19:3770-3777 (2000); Cramer et al., *FEBS Letters* 498:179-182 (2001); Kuerstem and Goodwin, *Nature Reviews Genetics* 4:626-637 (2003)). Effective termination of RNA transcription is required to prevent unwanted transcription of trait-unrelated (downstream) sequences, which may interfere with trait performance. Arrangement of multiple gene expression cassettes in local proximity to one another (e.g. within one T-DNA) may cause suppression of gene expression of one or more genes in said construct in comparison to independent insertions (Padidam and Cao, *BioTechniques* 31:328-334 (2001). This may interfere with achieving adequate levels of expression, for instance in cases were strong gene expression from all cassettes is desired.

In plants, clearly defined polyadenylation signal sequences are not known. Hasegawa et al., *Plant J.* 33:1063-1072, (2003)) were not able to identify conserved polyadenylation signal sequences in both in vitro and in vivo systems in *Nicotiana sylvestris* and to determine the actual length of the primary (non-polyadenylated) transcript. A weak 3' UTR has the potential to generate read-through, which may affect the expression of the genes located in the neighboring expression cassettes (Padidam and Cao, *BioTechniques* 31:328-334 (2001)). Appropriate control of transcription termination can prevent read-through into sequences (e.g. other expression cassettes) localized downstream and can further allow efficient recycling of RNA polymerase, to improve gene expression. Efficient termination of transcription (release of RNA Polymerase II from the DNA) is pre-requisite for re-initiation of transcription and thereby directly affects the overall transcript level. Subsequent to transcription termination, the mature mRNA is released from the site of synthesis and template to the cytoplasm. Eukaryotic mRNAs are accumulated as poly(A) forms in vivo, so that it is difficult to detect transcriptional termination sites by conventional methods. However, prediction of functional and efficient 3' UTRs by bioinformatics methods is difficult in that there are no conserved sequences which would allow easy prediction of an effective 3' UTR.

From a practical standpoint, it is typically beneficial that a 3' UTR used in a transgene cassette possesses the following characteristics. The 3' UTR should be able to efficiently and effectively terminate transcription of the transgene and prevent read-through of the transcript into any neighboring DNA sequence which can be comprised of another transgene cassette as in the case of multiple cassettes residing in one T-DNA, or the neighboring chromosomal DNA into which the T-DNA has inserted. The 3' UTR should not cause a reduction in the transcriptional activity imparted by the promoter, leader and introns that are used to drive expression of the transgene. In plant biotechnology, the 3' UTR is often used for priming of amplification reactions of reverse transcribed RNA extracted from the transformed plant and used to (1) assess the transcriptional activity or expression of the transgene cassette once integrated into the plant chromosome; (2) assess the copy number of insertions within the plant DNA; and (3) assess zygosity of the resulting seed after breeding. The 3' UTR is also used in amplification reactions of DNA extracted from the transformed plant to characterize the intactness of the inserted cassette.

3' UTRs useful in providing expression of a transgene in plants may be identified based upon the expression of expressed sequence tags (ESTs) in cDNA libraries made from messenger RNA isolated from seed, flower and other tissues derived from Foxtail millet (*Setaria italica* (L.) Beauv). Libraries of cDNA are made from tissues isolated from selected plant species using flower tissue, seed, leaf and root. The resulting cDNAs are sequenced using various sequencing methods. The resulting ESTs are assembled into clusters using bioinformatics software such as clc_ref_assemble_complete version 2.01.37139 (CLC bio USA, Cambridge, Mass. 02142). Transcript abundance of each cluster is determined by counting the number of cDNA reads for each cluster. The identified 3' UTRs may be comprised of sequence derived from cDNA sequence as well as sequence derived from genomic DNA. The cDNA sequence is used to design primers, which are then used with GenomeWalker™ (Clontech Laboratories, Inc, Mountain View, Calif.) libraries constructed following the manufacturer's protocol to clone the 3' region of the corresponding genomic DNA sequence to provide a longer termination sequence. Analysis of relative transcript abundance either by direct counts or normalized counts of observed sequence reads for each tissue library can be used to infer properties about patters of expression. For example, some 3' UTRs may be found in transcripts seen in higher abundance in root tissue as opposed to leaf. This is suggestive that the transcript is highly expressed in root and that the properties of root expression may be attributable to the transcriptional regulation of the promoter, the lead, the introns or the 3' UTR. Empirical testing of 3' UTRs identified by the properties of expression within specific organs, tissues or cell types can result in the identification of 3' UTRs that enhance expression in those specific organs, tissues or cell types.

Constructs and vectors may also include a transit peptide coding sequence that expresses a linked peptide that is useful for targeting of a protein product, particularly to a chloroplast, leucoplast, or other plastid organelle; mitochondria; peroxisome; vacuole; or an extracellular location. For descriptions of the use of chloroplast transit peptides, see U.S. Pat. Nos. 5,188,642 and 5,728,925. Many chloroplast-localized proteins are expressed from nuclear genes as precursors and are targeted to the chloroplast by a chloroplast transit peptide (CTP). Examples of such isolated chloroplast proteins include, but are not limited to, those associated with the small subunit (SSU) of ribulose-1,5,-bisphosphate carboxylase, ferredoxin, ferredoxin oxidoreductase, the light-harvesting complex protein I and protein II, thioredoxin F, enolpyruvyl shikimate phosphate synthase (EPSPS), and transit peptides described in U.S. Pat. No. 7,193,133. It has been demonstrated in vivo and in vitro that non-chloroplast proteins may be targeted to the chloroplast by use of protein fusions with a heterologous CTP and that the CTP is sufficient to target a protein to the chloroplast. Incorporation of a suitable chloroplast transit peptide such as the *Arabidopsis thaliana* EPSPS CTP (CTP2) (See, Klee et al., *Mol. Gen. Genet.* 210:437-442 (1987)) or the *Petunia hybrida* EPSPS CTP (CTP4) (See, della-Cioppa et al., *Proc. Natl. Acad. Sci. USA* 83:6873-6877 (1986)) has been show to target heterologous EPSPS protein sequences to chloroplasts in transgenic plants (See, U.S. Pat. Nos. 5,627,061; 5,633,435; and 5,312,910 and EP 0218571; EP 189707; EP 508909; and EP 924299).

Transcribable Polynucleotide Molecules

As used herein, the term "transcribable polynucleotide molecule" refers to any DNA molecule capable of being transcribed into a RNA molecule, including, but not limited to, those having protein coding sequences and those producing RNA molecules having sequences useful for gene suppression. A "transgene" refers to a transcribable polynucleotide molecule heterologous to a host cell at least with respect to its location in the genome and/or a transcribable polynucleotide molecule artificially incorporated into a host cell's genome in the current or any prior generation of the cell.

A promoter of the present invention may be operably linked to a transcribable polynucleotide molecule that is heterologous with respect to the promoter molecule. As used herein, the term "heterologous" refers to the combination of two or more polynucleotide molecules when such a combination is not normally found in nature. For example, the two molecules may be derived from different species and/or the two molecules may be derived from different genes, e.g. different genes from the same species or the same genes from different species. A promoter is thus heterologous with respect to an operably linked transcribable polynucleotide molecule if such a combination is not normally found in nature, i.e. that transcribable polynucleotide molecule is not naturally occurring operably linked in combination with that promoter molecule.

The transcribable polynucleotide molecule may generally be any DNA molecule for which expression of a RNA transcript is desired. Such expression of an RNA transcript may result in translation of the resulting mRNA molecule and thus protein expression. Alternatively, for example, a transcribable polynucleotide molecule may be designed to ultimately cause decreased expression of a specific gene or protein. In one embodiment, this may be accomplished by using a transcribable polynucleotide molecule that is oriented in the antisense direction. Briefly, as the antisense transcribable polynucleotide molecule is transcribed, the RNA product hybridizes to and sequesters a complimentary RNA molecule inside the cell. This duplex RNA molecule cannot be translated into a protein by the cell's translational machinery and is degraded in the cell. Any gene may be negatively regulated in this manner.

Thus, one embodiment of the invention is a regulatory element of the present invention, such as those provided as SEQ ID NOs: 1-199, 211 and 212, operably linked to a transcribable polynucleotide molecule so as to modulate transcription of the transcribable polynucleotide molecule at a desired level or in a desired pattern when the construct is integrated in the genome of a plant cell. In one embodiment, the transcribable polynucleotide molecule comprises a protein-coding region of a gene, and the promoter affects the transcription of an RNA molecule that is translated and expressed as a protein product. In another embodiment, the transcribable polynucleotide molecule comprises an antisense region of a gene, and the promoter affects the transcription of an antisense RNA molecule, double stranded RNA or other similar inhibitory RNA molecule in order to inhibit expression of a specific RNA molecule of interest in a target host cell.

Genes of Agronomic Interest

Transcribable polynucleotide molecules may be genes of agronomic interest. As used herein, the term "gene of agronomic interest" refers to a transcribable polynucleotide molecule that when expressed in a particular plant tissue, cell, or cell type confers a desirable characteristic, such as associated with plant morphology, physiology, growth, development, yield, product, nutritional profile, disease or pest resistance, and/or environmental or chemical tolerance. Genes of agronomic interest include, but are not limited to, those encoding a yield protein, a stress resistance protein, a developmental control protein, a tissue differentiation protein, a meristem protein, an environmentally responsive protein, a senescence protein, a hormone responsive protein, an abscission protein, a source protein, a sink protein, a flower control protein, a seed protein, an herbicide resistance protein, a disease resistance protein, a fatty acid biosynthetic enzyme, a tocopherol biosynthetic enzyme, an amino acid biosynthetic enzyme, a pesticidal protein, or any other agent such as an antisense or RNAi molecule targeting a particular gene for suppression. The product of a gene of agronomic interest may act within the plant in order to cause an effect upon the plant physiology or metabolism or may be act as a pesticidal agent in the diet of a pest that feeds on the plant.

In one embodiment of the invention, a promoter of the present invention is incorporated into a construct such that the promoter is operably linked to a transcribable polynucleotide molecule that is a gene of agronomic interest. The expression of the gene of agronomic interest is desirable in order to confer an agronomically beneficial trait. A beneficial agronomic trait may be, for example, but is not limited to, herbicide tolerance, insect control, modified yield, fungal disease resistance, virus resistance, nematode resistance, bacterial disease resistance, plant growth and development, starch production, modified oils production, high oil production, modified fatty acid content, high protein production, fruit ripening, enhanced animal and human nutrition, biopolymers, environmental stress resistance, pharmaceutical peptides and secretable peptides, improved processing traits, improved digestibility, enzyme production, flavor, nitrogen fixation, hybrid seed production, fiber production, and biofuel production. Examples of genes of agronomic interest include those for herbicide resistance (U.S. Pat. Nos. 6,803,501; 6,448,476; 6,248,876; 6,225,114; 6,107,549; 5,866,775; 5,804,425; 5,633,435; and 5,463,175), increased yield (U.S. Pat. Nos. USRE38,446; 6,716,474; 6,663,906; 6,476,295; 6,441,277; 6,423,828; 6,399,330; 6,372,211; 6,235,971; 6,222,098; and 5,716,837), insect control (U.S. Pat. Nos. 6,809,078; 6,713,063; 6,686,452; 6,657,046; 6,645,497; 6,642,030; 6,639,054; 6,620,988; 6,593,293; 6,555,655; 6,538,109; 6,537,756; 6,521,442; 6,501,009; 6,468,523; 6,326,351; 6,313,378; 6,284,949; 6,281,016; 6,248,536; 6,242,241; 6,221,649; 6,177,615; 6,156,573; 6,153,814; 6,110,464; 6,093,695; 6,063,756; 6,063,597; 6,023,013; 5,959,091; 5,942,664; 5,942,658, 5,880,275; 5,763,245; and 5,763,241), fungal disease resistance (U.S. Pat. Nos. 6,653,280; 6,573,361; 6,506,962; 6,316,407; 6,215,048; 5,516,671; 5,773,696; 6,121,436; 6,316,407; and 6,506,962), virus resistance (U.S. Pat. Nos. 6,617,496; 6,608,241; 6,015,940; 6,013,864; 5,850,023; and 5,304, 730), nematode resistance (U.S. Pat. No. 6,228,992), bacterial disease resistance (U.S. Pat. No. 5,516,671), plant growth and development (U.S. Pat. Nos. 6,723,897 and 6,518,488), starch production (U.S. Pat. Nos. 6,538,181; 6,538,179; 6,538,178; 5,750,876; 6,476,295), modified oils production (U.S. Pat. Nos. 6,444,876; 6,426,447; and 6,380, 462), high oil production (U.S. Pat. Nos. 6,495,739; 5,608, 149; 6,483,008; and 6,476,295), modified fatty acid content (U.S. Pat. Nos. 6,828,475; 6,822,141; 6,770,465; 6,706,950; 6,660,849; 6,596,538; 6,589,767; 6,537,750; 6,489,461; and 6,459,018), high protein production (U.S. Pat. No. 6,380, 466), fruit ripening (U.S. Pat. No. 5,512,466), enhanced animal and human nutrition (U.S. Pat. Nos. 6,723,837; 6,653,530; 6,5412,59; 5,985,605; and 6,171,640), biopolymers (U.S. Pat. Nos. USRE37,543; 6,228,623; and U.S. Pat. Nos. 5,958,745, and 6,946,588), environmental stress resistance (U.S. Pat. No. 6,072,103), pharmaceutical peptides and secretable peptides (U.S. Pat. Nos. 6,812,379; 6,774, 283; 6,140,075; and 6,080,560), improved processing traits (U.S. Pat. No. 6,476,295), improved digestibility (U.S. Pat. No. 6,531,648) low raffinose (U.S. Pat. No. 6,166,292), industrial enzyme production (U.S. Pat. No. 5,543,576), improved flavor (U.S. Pat. No. 6,011,199), nitrogen fixation (U.S. Pat. No. 5,229,114), hybrid seed production (U.S. Pat. No. 5,689,041), fiber production (U.S. Pat. Nos. 6,576,818; 6,271,443; 5,981,834; and 5,869,720) and biofuel production (U.S. Pat. No. 5,998,700).

Alternatively, a gene of agronomic interest can affect the above mentioned plant characteristic or phenotype by encoding a RNA molecule that causes the targeted modulation of gene expression of an endogenous gene, for example via antisense (see e.g. U.S. Pat. No. 5,107,065); inhibitory RNA ("RNAi", including modulation of gene expression via miRNA-, siRNA-, trans-acting siRNA-, and phased sRNA-mediated mechanisms, e.g. as described in published applications US 2006/0200878 and US 2008/0066206, and in U.S. patent application Ser. No. 11/974,469); or cosuppression-mediated mechanisms. The RNA could also be a catalytic RNA molecule (e.g. a ribozyme or a riboswitch; see e.g. US 2006/0200878) engineered to cleave a desired endogenous mRNA product. Thus, any transcribable polynucleotide molecule that encodes a transcribed RNA molecule that affects an agronomically important phenotype or morphology change of interest may be useful for the practice of the present invention. Methods are known in the art for constructing and introducing constructs into a cell in such a manner that the transcribable polynucleotide molecule is transcribed into a molecule that is capable of causing gene suppression. For example, posttranscriptional gene suppression using a construct with an anti-sense oriented transcribable polynucleotide molecule to regulate gene expression in plant cells is disclosed in U.S. Pat. Nos. 5,107,065 and 5,759,829, and posttranscriptional gene suppression using a construct with a sense-oriented transcribable polynucleotide molecule to regulate gene expression in plants is disclosed in U.S. Pat. Nos. 5,283,184 and 5,231,020. Expression of a transcribable polynucleotide in a plant cell can also be used to suppress plant pests feeding on the plant cell, for example, compositions isolated from coleopteran pests (U.S. Patent Publication No. US20070124836) and compositions isolated from nematode pests (U.S. Patent Publication No. US20070250947). Plant pests include, but are not limited to arthropod pests, nematode pests, and fungal or microbial pests. Exemplary transcribable polynucleotide molecules for incorporation into constructs of the present invention include, for example, DNA molecules or genes from a species other than the target species or genes that originate with or are present in the same species, but are incorporated into recipient cells by genetic engineering methods rather than classical reproduction or breeding techniques. The type of polynucleotide molecule can include, but is not limited to, a polynucleotide molecule that is already present in the plant cell, a polynucleotide molecule from another plant, a polynucleotide molecule from a different organism, or a polynucleotide molecule generated externally, such as a polynucleotide molecule containing an antisense message of a gene, or a polynucleotide molecule encoding an artificial, synthetic, or otherwise modified version of a transgene.

Selectable Markers

As used herein the term "marker" refers to any transcribable polynucleotide molecule whose expression, or lack thereof, can be screened for or scored in some way. Marker genes for use in the practice of the present invention include, but are not limited to transcribable polynucleotide molecules encoding ß-glucuronidase (GUS described in U.S. Pat. No. 5,599,670), green fluorescent protein and variants thereof (GFP described in U.S. Pat. Nos. 5,491,084 and 6,146,826), proteins that confer antibiotic resistance, or proteins that confer herbicide tolerance. Useful antibiotic resistance markers include those encoding proteins conferring resistance to kanamycin (nptII), hygromycin B (aph IV), streptomycin or spectinomycin (aad, spec/strep) and gentamycin (aac3 and aacC4). Herbicides for which transgenic plant tolerance has been demonstrated and the method of the present invention can be applied, include, but are not limited to: amino-methyl-phosphonic acid, glyphosate, glufosinate, sulfonylureas, imidazolinones, bromoxynil, delapon, dicamba, cyclohezanedione, protoporphyrinogen oxidase inhibitors, and isoxasflutole herbicides. Transcribable polynucleotide molecules encoding proteins involved in herbicide tolerance include, but are not limited to, a transcribable polynucleotide molecule encoding 5-enolpyruvylshikimate-3-phosphate synthase (EPSPS for glyphosate tolerance described in U.S. Pat. Nos. 5,627,061; 5,633,435; 6,040,497; and 5,094,945); a transcribable polynucleotide molecule encoding a glyphosate oxidoreductase and a glyphosate-N-acetyl transferase (GOX described in U.S. Pat. No. 5,463,175; GAT described in U.S. Patent publication No. 20030083480, and dicamba monooxygenase U.S. Patent publication No. 20030135879); a transcribable polynucleotide molecule encoding bromoxynil nitrilase (Bxn for Bromoxynil tolerance described in U.S. Pat. No. 4,810,648); a transcribable polynucleotide molecule encoding phytoene desaturase (crtI) described in Misawa, et al., *Plant Journal* 4:833-840 (1993) and Misawa, et al., *Plant Journal* 6:481-489 (1994) for norflurazon tolerance; a transcribable polynucleotide molecule encoding acetohydroxyacid synthase (AHAS, aka ALS) described in Sathasiivan, et al., *Nucl. Acids Res.* 18:2188-2193 (1990) for tolerance to sulfonylurea herbicides; and the bar gene described in DeBlock, et al., *EMBO Journal* 6:2513-2519 (1987) for glufosinate and bialaphos tolerance. The promoter molecules of the present invention can express linked transcribable polynucleotide molecules that encode for phosphinothricin acetyltransferase, glyphosate resistant EPSPS, aminoglycoside phosphotransferase, hydroxyphenyl pyruvate dehydrogenase, hygromycin phosphotransferase, neomycin phosphotransferase, dalapon dehalogenase, bromoxynil resistant nitrilase, anthranilate synthase, aryloxyalkanoate dioxygenases, acetyl CoA carboxylase, glyphosate oxidoreductase, and glyphosate-N-acetyl transferase.

Included within the term "selectable markers" are also genes which encode a secretable marker whose secretion can be detected as a means of identifying or selecting for transformed cells. Examples include markers that encode a secretable antigen that can be identified by antibody interaction, or even secretable enzymes which can be detected catalytically. Selectable secreted marker proteins fall into a number of classes, including small, diffusible proteins which are detectable, (e.g. by ELISA), small active enzymes which are detectable in extracellular solution (e.g, alpha-amylase, beta-lactamase, phosphinothricin transferase), or proteins which are inserted or trapped in the cell wall (such as proteins which include a leader sequence such as that found in the expression unit of extension or tobacco pathogenesis related proteins also known as tobacco PR-S). Other possible selectable marker genes will be apparent to those of skill in the art and are encompassed by the present invention.

Cell Transformation

The invention is also directed to a method of producing transformed cells and plants which comprise a promoter operably linked to a transcribable polynucleotide molecule.

The term "transformation" refers to the introduction of nucleic acid into a recipient host. As used herein, the term "host" refers to bacteria, fungi, or plant, including any cells, tissue, organs, or progeny of the bacteria, fungi, or plant. Plant tissues and cells of particular interest include protoplasts, calli, roots, tubers, seeds, stems, leaves, seedlings, embryos, and pollen.

As used herein, the term "transformed" refers to a cell, tissue, organ, or organism into which a foreign polynucleotide molecule, such as a construct, has been introduced. The introduced polynucleotide molecule may be integrated into the genomic DNA of the recipient cell, tissue, organ, or organism such that the introduced polynucleotide molecule is inherited by subsequent progeny. A "transgenic" or "transformed" cell or organism also includes progeny of the cell or organism and progeny produced from a breeding program employing such a transgenic organism as a parent in a cross and exhibiting an altered phenotype resulting from the presence of a foreign polynucleotide molecule. The term "transgenic" refers to a bacteria, fungi, or plant containing one or more heterologous polynucleic acid molecules.

There are many methods for introducing polynucleic acid molecules into plant cells. The method generally comprises the steps of selecting a suitable host cell, transforming the host cell with a recombinant vector, and obtaining the transformed host cell. Suitable methods include bacterial infection (e.g. *Agrobacterium*), binary bacterial artificial chromosome vectors, direct delivery of DNA (e.g. via PEG-mediated transformation, desiccation/inhibition-mediated DNA uptake, electroporation, agitation with silicon carbide fibers, and acceleration of DNA coated particles, etc. (reviewed in Potrykus, et al., *Ann. Rev. Plant Physiol. Plant Mol. Biol.* 42: 205 (1991)).

Any transformation methods may be utilized to transform a host cell with one or more promoters and/or constructs of the present invention. Host cells may be any cell or organism such as a plant cell, algae cell, algae, fungal cell, fungi, bacterial cell, or insect cell. Preferred hosts and transformed cells include cells from: plants, *Aspergillus*, yeasts, insects, bacteria and algae.

Regenerated transgenic plants can be self-pollinated to provide homozygous transgenic plants. Alternatively, pollen obtained from the regenerated transgenic plants may be crossed with non-transgenic plants, preferably inbred lines of agronomically important species. Descriptions of breeding methods that are commonly used for different traits and crops can be found in one of several reference books, see, for example, Allard, *Principles of Plant Breeding,* John Wiley & Sons, NY, U. of CA, Davis, Calif., 50-98 (1960); Simmonds, *Principles of crop improvement*, Longman, Inc., NY, 369-399 (1979); Sneep and Hendriksen, Plant breeding perspectives, Wageningen (ed), Center for Agricultural Publishing and Documentation (1979); Fehr, *Soybeans: Improvement, Production and Uses,* 2nd Edition, Monograph, 16:249 (1987); Fehr, *Principles of variety development, Theory and Technique*, (Vol. 1) and *Crop Species Soybean* (Vol 2), Iowa State Univ., Macmillan Pub. Co., NY, 360-376 (1987). Conversely, pollen from non-transgenic plants may be used to pollinate the regenerated transgenic plants.

The transformed plants may be analyzed for the presence of the genes of interest and the expression level and/or profile conferred by the regulatory elements of the present invention. Those of skill in the art are aware of the numerous methods available for the analysis of transformed plants. For example, methods for plant analysis include, but are not limited to Southern blots or northern blots, PCR-based approaches, biochemical analyses, phenotypic screening methods, field evaluations, and immunodiagnostic assays. The expression of a transcribable polynucleotide molecule can be measured using TaqMan® (Applied Biosystems, Foster City, Calif.) reagents and methods as described by the manufacturer and PCR cycle times determined using the TaqMan® Testing Matrix. Alternatively, the Invader® (Third Wave Technologies, Madison, Wis.) reagents and methods as described by the manufacturer can be used transgene expression.

The seeds of the plants of this invention can be harvested from fertile transgenic plants and be used to grow progeny generations of transformed plants of this invention including hybrid plant lines comprising the construct of this invention and expressing a gene of agronomic interest.

The present invention also provides for parts of the plants of the present invention. Plant parts, without limitation, include leaves, stems, roots, tubers, seeds, endosperm, ovule, and pollen. The invention also includes and provides transformed plant cells which comprise a nucleic acid molecule of the present invention.

The transgenic plant may pass along the transgenic polynucleotide molecule to its progeny. Progeny includes any regenerable plant part or seed comprising the transgene derived from an ancestor plant. The transgenic plant is preferably homozygous for the transformed polynucleotide molecule and transmits that sequence to all offspring as a result of sexual reproduction. Progeny may be grown from seeds produced by the transgenic plant. These additional plants may then be self-pollinated to generate a true breeding line of plants. The progeny from these plants are evaluated, among other things, for gene expression. The gene expression may be detected by several common methods such as western blotting, northern blotting, immunoprecipitation, and ELISA.

Having now generally described the invention, the same will be more readily understood through reference to the following examples which are provided by way of illustration, and are not intended to be limiting of the present invention, unless specified. It should be appreciated by those of skill in the art that the techniques disclosed in the following examples represent techniques discovered by the inventors to function well in the practice of the invention. However, those of skill in the art should, in light of the present disclosure, appreciate that many changes can be made in the specific embodiments that are disclosed and still obtain a like or similar result without departing from the spirit and scope of the invention, therefore all matter set forth or shown in the accompanying drawings is to be interpreted as illustrative and not in a limiting sense.

EXAMPLES

Example 1: Identification and Cloning of Regulatory Elements

Novel transcriptional regulatory elements, or transcriptional regulatory expression element group (EXP) sequences were identified and isolated from genomic DNA of the dicot species *Cucumis melo* WSH-39-1070AN.

Transcriptional regulatory elements were selected based upon proprietary and public microarray data derived from transcriptional profiling experiments conducted in soybean (*Glycine max*) and *Arabidopsis* as well as homology based searches using known dicot sequences as query against proprietary *Cucumis melo* sequences.

Using the identified sequences, a bioinformatic analysis was conducted to identify regulatory elements within the amplified DNA, followed by identification of the transcriptional start site (TSS) and any bi-directionality, introns, or upstream coding sequence present in the sequence. Using the results of this analysis, regulatory elements were defined within the DNA sequences and primers designed to amplify the regulatory elements. The corresponding DNA molecule for each regulatory element was amplified using standard polymerase chain reaction conditions with primers containing unique restriction enzyme sites and genomic DNA isolated from *Cucumis melo*. The resulting DNA fragments were ligated into base plant expression vectors using standard restriction enzyme digestion of compatible restriction sites and DNA ligation methods.

Analysis of the regulatory element TSS and intron/exon splice junctions can be performed using transformed plant protoplasts. Briefly, the protoplasts are transformed with the plant expression vectors comprising the cloned DNA fragments operably linked to a heterologous transcribable polynucleotide molecule and the 5' RACE System for Rapid Amplification of cDNA Ends, Version 2.0 (Invitrogen, Carlsbad, Calif. 92008) is used to confirm the regulatory element TSS and intron/exon splice junctions by analyzing the sequence of the mRNA transcripts produced thereby.

Sequences encoding ubiquitin 1 transcriptional regulatory expression element groups (EXP) were analyzed as described above and each transcriptional regulatory expression element groups ("EXP's") was also broken down into the corresponding promoters, leaders and introns comprising each transcriptional regulatory expression element group. Sequences of the identified ubiquitin 1 transcriptional regulatory expression element groups ("EXP's") are provided herein as SEQ ID NOs: 1, 5, 7, 9 and 11 and is listed in Table 1 below. The corresponding ubiquitin 1 promoters are provided herein as SEQ ID NOs: 2, 6, 8, 10 and 12. The ubiquitin 1 leader and intron are herein provided as SEQ ID NOs: 3 and 4, respectively.

Sequences encoding other *Cucumis* transcriptional regulatory expression element groups or EXP sequences which are comprised of either a promoter element, operably linked to a leader element; or a promoter element, operably linked to a leader element and an intron element, or a promoter element, operably linked to a leader element, operably linked to an intron element, operably linked to a leader element are provided as SEQ ID NOs: 13, 14, 15, 16, 17, 18, 19, 20, 21, 22, 23, 24, 25, 26, 27, 28, 29, 30, 31, 32, 33, 34, 35, 36, 37, 38, 39, 40, 41, 42, 43, 44, 45, 46, 47, 48, 49, 50, 51, 52, 53, 54, 55, 56, 57, 58, 59, 60, 61, 62, 63, 64, 65, 66, 67, 68, 69, 70, 71, 72, 73, 74, 75, 76, 77, 78, 79, 80, 81, 82, 83, 84, 85, 86, 87, 88, 89, 90, 91, 92, 93, 94, 95, 96, 97, 98, 99, 100, 101, 102, 103, 104, 105, 106, 107, 108, 109, 110, 111, 112, 113, 114, 115, 116, 117, 118, 119, 120, 121, 122, 123, 124, 125, 126, 127, 128, 129, 130, 131, 132, 133, 134, 135, 136, 137, 138, 139, 140, 141, 142, 143, 144, 145, 146, 147, 148, 149, 150, 151, 152, 153, 154, 155, 156, 159, 162, 167, 168, 172, 175, 176, 177, 178, 181, 182, 183, 184, 185, 188, 189, 190, 191, 192, 193, 194, 195, 196, 197, 198, 199, 211 and 212 and are also listed in Table 1 below. Additional promoter elements are provided as SEQ ID NOs: 163 and 169. Additional leader elements are provided as SEQ ID NOs: 164, 166 and 170. Additional intron elements are provided as SEQ ID NOs: 165 and 171. Elements wherein a promoter is operably linked to a leader element are provided as SEQ ID NOs: 157, 160, 173, 179 and 186. Elements wherein an intron is operably linked to a leader element are provided as SEQ ID NOs: 158, 161, 174, 180 and 187. With respect to the subset of sequences provided as SEQ ID NOs: 13 through 199, 211 and 212, these sequences were selected and cloned based upon the results of experiments such as transcript profiling or expression driven by promoters from homologous genes of a different species suggesting desirable patterns of expression such as constitutive expression, root expression, above ground expression or seed expression. The actual activity imparted by the *Cucumis* sequences is determined empirically and is not necessarily the same as that of a regulatory element derived from a homologous gene from a species other than *Cucumis melo* when used in a transformed plant host cell and whole transgenic plant.

TABLE 1

Transcriptional regulatory expression element groups, promoters, leaders and introns isolated from *Cucumis melo*.

| Annotation | SEQ ID NO: | Description | Composition Type | Size (bp) | Composition | Coordinates of Elements within EXP |
|---|---|---|---|---|---|---|
| EXP-CUCme.Ubq1:1:1 | 1 | Ubiquitin 1 | EXP | 2611 | Promoter; Leader; Intron | 1-2068; 2069-2150; 2151-2608 |
| P-CUCme.Ubq1-1:1:15 | 2 | Ubiquitin 1 | P | 2068 | Promoter | |
| L-CUCme.Ubq1-1:1:1 | 3 | Ubiquitin 1 | L | 82 | Leader | |
| I-CUCme.Ubq1-1:1:1 | 4 | Ubiquitin 1 | I | 461 | Intron | |
| EXP-CUCme.Ubq1:1:2 | 5 | Ubiquitin 1 | EXP | 2002 | Promoter; Leader; Intron | 1-1459; 1460-1541; 1542-1999 |
| P-CUCme.Ubq1-1:1:16 | 6 | Ubiquitin 1 | P | 1459 | Promoter | |
| EXP-CUCme.Ubq1:1:3 | 7 | Ubiquitin 1 | EXP | 1507 | Promoter; Leader; Intron | 1-964; 965-1046; 1047-1504 |
| P-CUCme.Ubq1-1:1:17 | 8 | Ubiquitin 1 | P | 964 | Promoter | |
| EXP-CUCme.Ubq1:1:4 | 9 | Ubiquitin 1 | EXP | 1022 | Promoter; Leader; Intron | 1-479; 480-561; 562-1019 |
| P-CUCme.Ubq1-1:1:18 | 10 | Ubiquitin 1 | P | 479 | Promoter | |
| EXP-CUCme.Ubq1:1:5 | 11 | Ubiquitin 1 | EXP | 716 | Promoter; Leader; Intron | 1-173; 174-255; 256-713 |
| P-CUCme.Ubq1-1:1:19 | 12 | Ubiquitin 1 | P | 173 | Promoter | |
| P-CUCme.1-1:1:1 | 13 | Phosphatase 2A | EXP | 2000 | Promoter; Leader; Intron; Leader | Reverse compliment; see SEQ ID NO: 155 |
| P-CUCme.2-1:1:1 | 14 | Actin 1 | EXP | 2000 | Promoter; Leader; Intron; Leader | 1-964; 965-1028; 1029-1991; 1992-2003 |
| P-CUCme.3-1:1:3 | 15 | Actin 2 | EXP | 1990 | Promoter; Leader; Intron; Leader | 1-1243; 1244-1319; 1320-1982; 1983-1990 |
| P-CUCme.4-1:1:2 | 16 | Ubiquitin 2 | EXP | 2005 | Promoter; Leader; Intron; Leader | 1-1646; 1647-1704; 1705-2005; 2006-2008 |
| P-CUCme.5-1:1:2 | 17 | Ubiquitin 3 | EXP | 2004 | Promoter; Leader; Intron | 1-748; 749-819; 820-2004 |

TABLE 1-continued

Transcriptional regulatory expression element groups, promoters, leaders and introns isolated from *Cucumis melo*.

| Annotation | SEQ ID NO: | Description | Composition Type | Size (bp) | Composition | Coordinates of Elements within EXP |
|---|---|---|---|---|---|---|
| P-CUCme.6-1:1:1 | 18 | Tubulin beta chain | EXP | 1935 | Promoter; Leader; Intron; Leader | 1-1436; 1437-1482; 1483-1919; 1920-1935 |
| P-CUCme.8-1:1:2 | 19 | Tubulin beta chain | EXP | 1606 | Promoter; Leader | 1-1527; 1528-1606 |
| P-CUCme.9-1:1:2 | 20 | Tubulin beta chain | EXP | 1487 | Promoter; Leader | 1-1384; 1385-1487 |
| P-CUCme.10-1:1:1 | 21 | Tubulin beta chain | EXP | 1448 | Promoter; Leader | 1-1363; 1364-1448 |
| P-CUCme.11-1:1:2 | 22 | Elongation Factor 1 alpha | EXP | 1235 | Promoter; Leader; Intron; Leader | 1-617; 618-677; 678-1213; 1214-1235 |
| P-CUCme.15-1:1:2 | 23 | Elongation Factor 1 alpha | EXP | 2003 | Promoter; Leader; Intron; Leader | 1-1330; 1331-1435; 1430-1975; 1976-2002 |
| P-CUCme.16a-1:1:2 | 24 | Ubiquitin 7 | EXP | 2015 | Promoter; Leader | |
| P-CUCme.16b-1:1: 1 | 25 | Ubiquitin 6 | EXP | 2006 | Promoter; Leader | |
| P-CUCme.17-1:1:2 | 26 | ubiquitin-40S ribosomal protein S27a | EXP | 2017 | Promoter; Leader | 1-1969; 1970-2017 |
| P-CUCme.18-1:1:2 | 27 | ubiquitin-40S ribosomal protein S27a | EXP | 1353 | Promoter; Leader | 1-1308; 1309-1353 |
| P-CUCme.19-1:1:2 | 28 | Chloropyll a/b binding protein | EXP | 2005 | Promoter; Leader | 1-1960; 1961-2005 |
| P-CUCme.20-1:1:2 | 29 | Chloropyll a/b binding protein | EXP | 1445 | Promoter; Leader | 1-1390; 1391-1445 |
| P-CUCme.21-1:1:1 | 30 | Chloropyll a/b binding protein | EXP | 1282 | Promoter; Leader | 1-1233; 1234-1282 |
| P-CUCme.22-1:1:3 | 31 | Elongation Factor 4 alpha | EXP | 2002 | | |
| P-CUCme.24-1:1:2 | 32 | S-Adenosylmethionine Synthetase | EXP | 2003 | Promoter; Leader; Intron; Leader | 1-1067; 1068-1165; 1166-2001; 2002-2003 |
| P-CUCme.26-1:1:2 | 33 | Stress responsive protein | EXP | 1372 | Promoter; Leader; Intron; Leader | 1-577; 578-654; 655-1366; 1367-1372 |
| P-CUCme.28-1:1:2 | 34 | Ribosomal protein S5a | EXP | 1122 | | |
| P-CUCme.29-1:1:2 | 35 | Ribosomal protein S5a | EXP | 2017 | Promoter; Leader; Intron; Leader | 1-490; 491-571; 572-2012; 2013-2017 |
| CumMe_WSM_SF143981. G5150 | 36 | LHCB6 (LIGHT HARVESTING COMPLEX PSII SUBUNIT 6) | EXP | 2000 | | |
| CumMe_WSM_SF144839. G5080 | 37 | EIF2 GAMMA translation initiation factor | EXP | 1760 | | |
| CumMe_WSM_SF146040. G5050 | 38 | EIF2 translation initiation factor | EXP | 1767 | | |
| CumMe_WSM_SF16408. G5350 | 39 | elongation factor Tu | EXP | 2000 | | |
| CumMe_WSM_SF16429. G5670 | 40 | unknown protein | EXP | 2000 | | |
| CumMe_WSM_SF16444. G5140 | 41 | histone H4 | EXP | 2000 | Promoter; Leader | 1-1947; 1948-2000 |
| CumMe_WSM_SF16530. G6000 | 42 | HMGB2 (HIGH MOBILITY GROUP B 2) transcription factor | EXP | 2000 | | |
| CumMe_WSM_SF16553. G5090 | 43 | PBG1; threonine-type endopeptidase | EXP | 1115 | | |
| CumMe_WSM_SF16563. G5560 | 44 | ATARFB1A (ADP-ribosylation factor B1A) | EXP | 2000 | Promoter; Leader; Intron; Leader | 1-1329; 1330-1427; 1428-1988; 1989-2000 |
| CumMe_WSM_SF16675. G5720 | 45 | chromatin protein family | EXP | 2000 | | |
| CumMe_WSM_SF16920. G5650 | 46 | CSD1 (COPPER/ZINC SUPEROXIDE DISMUTASE 1) | EXP | 2000 | | |
| CumMe_WSM_SF16953. G5180 | 47 | SCE1 (SUMO CONJUGATION ENZYME 1) ; SUMO ligase | EXP | 2000 | | |
| CumMe_WSM_SF17051. G5470 | 48 | 60S ribosomal protein L9 (RPL90D) | EXP | 2000 | | |
| CumMe_WSM_SF17111. G5790 | 49 | ubiquinol-cytochrome C reductase complex ubiquinone-binding protein | EXP | 2000 | Promoter; Leader | 1-1895; 1896-2000 |
| CumMe_WSM_SF17142. G5920 | 50 | peptidyl-prolyl cis-trans isomerase, chloroplast | EXP | 2000 | | |
| CumMe_WSM_SF17190. G6200 | 51 | PRK (PHOSPHORIBULOKINASE) | EXP | 2000 | | |
| CumMe_WSM_SF17250. G5910 | 52 | LHCB5 (LIGHT HARVESTING COMPLEX OF PHOTOSYSTEM II 5) | EXP | 2000 | | |

TABLE 1-continued

Transcriptional regulatory expression element groups, promoters, leaders and introns isolated from *Cucumis melo*.

| Annotation | SEQ ID NO: | Description | Composition Type | Size (bp) | Composition | Coordinates of Elements within EXP |
|---|---|---|---|---|---|---|
| CumMe_WSM_SF17252. G7330 | 53 | nascent polypeptide-associated complex (NAC) domain-containing protein | EXP | 2000 | Promoter; Leader; Intron | 1-1195; 1196-1297; 1298-2000 |
| CumMe_WSM_SF17253. G5150 | 54 | RPS9 (RIBOSOMAL PROTEIN S9) | EXP | 1547 | | |
| CumMe_WSM_SF17322. G5110 | 55 | 60S ribosomal protein L22 (RPL22A) | EXP | 2000 | | |
| CumMe_WSM_SF17349. G5770 | 56 | PGRL1B (PGR5-Like B) | EXP | 2000 | | |
| CumMe_WSM_SF17357. G5630 | 57 | 40S ribosomal protein S10 (RPS10B) | EXP | 2000 | | |
| CumMe_WSM_SF17494. G5140 | 58 | MEE34 (maternal effect embryo arrest 34) | EXP | 1591 | | |
| CumMe_WSM_SF17524. G6410 | 59 | SUS2 (ABNORMAL SUSPENSOR 2) | EXP | 2000 | | |
| CumMe_WSM_SF17672. G5610 | 60 | PSAK (photosystem I subunit K) | EXP | 2000 | | |
| CumMe_WSM_SF17773. G6620 | 61 | aconitase C-terminal domain-containing protein | EXP | 2000 | | |
| CumMe_WSM_SF17866. G6050 | 62 | ATPDIL5-1 (PDI-like 5-1) | EXP | 2000 | | |
| CumMe_WSM_SF18004. G6600 | 63 | hydroxyproline-rich glycoprotein family protein | EXP | 2000 | | |
| CumMe_WSM_SF18045. G6670 | 64 | | EXP | 2000 | | |
| CumMe_WSM_SF18053. G5410 | 65 | endomembrane protein 70 | EXP | 2000 | | |
| CumMe_WSM_SF18287. G5380 | 66 | CP12-1 | EXP | 2000 | | |
| CumMe_WSM_SF18488. G5340 | 67 | caffeoyl-CoA 3-O-methyltransferase | EXP | 2000 | Promoter; Leader | 1-1923; 1924-2000 |
| CumMe_WSM_SF18504. G5090 | 68 | vacuolar ATP synthase subunit H family protein | EXP | 2000 | | |
| CumMe_WSM_SF18530. G5750 | 69 | GUN5 (GENOMES UNCOUPLED 5); magnesium chelatase | EXP | 2000 | | |
| CumMe_WSM_SF18536. G6480 | 70 | MBF1A (MULTIPROTEIN BRIDGING FACTOR 1A) transcription coactivator | EXP | 2000 | | |
| CumMe_WSM_SF18575. G6410 | 71 | unknown protein | EXP | 2000 | | |
| CumMe_WSM_SF18634. G5190 | 72 | 60S ribosomal protein L23 (RPL23A) | EXP | 2000 | Promoter; Leader | 1-1971; 1972-2000 |
| CumMe_WSM_SF18645. G5380 | 73 | GS2 (GLUTAMINE SYNTHETASE 2) | EXP | 2000 | | |
| CumMe_WSM_SF18716. G5860 | 74 | 40S ribosomal protein S12 (RPS12A); reverse compliment: Auxin-induced protein x10A-like | EXP | 2000 | Promoter; Leader | Reverse compliment; see SEQ ID NO: 184 |
| CumMe_WSM_SF18801. G5040 | 75 | | EXP | 2000 | | |
| CumMe_WSM_SF18806. G6220 | 76 | unknown protein | EXP | 2000 | | |
| CumMe_WSM_SF18850. G5630 | 77 | PAC1: threonine-type endopeptidase | EXP | 2000 | | |
| CumMe_WSM_SF18863. G7550 | 78 | ATP synthase gamma chain, mitochondrial (ATPC) | EXP | 2000 | | |
| CumMe_WSM_SF18986. G6110 | 79 | GER1 (GERMIN-LIKE PROTEIN 1); oxalate oxidase | EXP | 2000 | | |
| CumMe_WSM_SF19064. G5690 | 80 | histone H3.2 | EXP | 2000 | Promoter; Leader; Intron | 1-1581; 1582-1670; 1671-2000 |
| CumMe_WSM_SF19323. G5120 | 81 | chloroplast outer envelope GTP-binding protein, putative | EXP | 2000 | | |
| CumMe_WSM_SF19452. G5090 | 82 | glucan phosphorylase, putative | EXP | 1072 | | |
| CumMe_WSM_SF19631. G5170 | 83 | RuBisCO activase, putative | EXP | 1730 | | |
| CumMe_WSM_SF19647. G5760 | 84 | 6-phosphogluconate dehydrogenase family protein | EXP | 2000 | Promoter; Leader; Intron; Leader | 1-936; 937-1021; 1022-1992; 1993-2000 |

TABLE 1-continued

Transcriptional regulatory expression element groups, promoters, leaders and introns isolated from *Cucumis melo*.

| Annotation | SEQ ID NO: | Description | Composition Type | Size (bp) | Composition | Coordinates of Elements within EXP |
|---|---|---|---|---|---|---|
| CumMe_WSM_SF19839.G5090 | 85 | ATPDX1.1 (pyridoxine biosynthesis 1.1) | EXP | 1020 | Promoter; Leader | 1-928; 929-1020 |
| CumMe_WSM_SF19850.G5130 | 86 | HMGB2 (HIGH MOBILITY GROUP B 2) transcription factor | EXP | 2000 | | |
| CumMe_WSM_SF19902.G5260 | 87 | universal stress protein (USP) family protein / early nodulin ENOD18 family protein | EXP | 2000 | | |
| CumMe_WSM_SF19992.G6100 | 88 | unknown protein | EXP | 2000 | | |
| CumMe_WSM_SF20132.G5560 | 89 | peroxidase 21 | EXP | 2000 | Promoter; Leader | 1-1962; 1963-2000 |
| CumMe_WSM_SF20147.G7910 | 90 | CSD1 (COPPER/ZINC SUPEROXIDE DISMUTASE 1) | EXP | 2000 | | |
| CumMe_WSM_SF20355.G5130 | 91 | ATP synthase family | EXP | 2000 | | |
| CumMe_WSM_SF20359.G5870 | 92 | NADH-ubiquinone oxidoreductase 20 kDa subunit, mitochondrial | EXP | 2000 | | |
| CumMe_WSM_SF20368.G5700 | 93 | PGR5 (proton gradient regulation 5) | EXP | 2000 | | |
| CumMe_WSM_SF20409.G5240 | 94 | elongation factor 1B alpha-subunit 1 (eEF1Balpha1) | EXP | 2000 | | |
| CumMe_WSM_SF20431.G6340 | 95 | DHS2 (3-deoxy-d-arabino-heptulosonate 7-phosphate synthase) | EXP | 2000 | | |
| CumMe_WSM_SF20505.G5440 | 96 | THIC (ThiaminC); ADP-ribose pyrophosphohydrolase | EXP | 1373 | | |
| CumMe_WSM_SF20509.G5920 | 97 | Y14; RNA binding/protein binding | EXP | 2000 | | |
| CumMe_WSM_SF206458.G5970 | 98 | FAD2 (FATTY ACID DESATURASE 2) | EXP | 2000 | Promoter | 1-2000 |
| CumMe_WSM_SF206534.G5200 | 99 | unknown protein | EXP | 2000 | | |
| CumMe_WSM_SF20997.G6990 | 100 | ALD1 (AGD2-LIKE DEFENSE RESPONSE PROTEIN1) | EXP | 2000 | | |
| CumMe_WSM_SF21035.G5090 | 101 | sodium/calcium exchanger family protein | EXP | 1078 | | |
| CumMe_WSM_SF21117.G5370 | 102 | 30S ribosomal protein, putative | EXP | 2000 | | |
| CumMe_WSM_SF21141.G5630 | 103 | 40S ribosomal protein S24 (RPS24A) | EXP | 2000 | | |
| CumMe_WSM_SF21198.G5180 | 104 | | EXP | 1974 | | |
| CumMe_WSM_SF21366.G5980 | 105 | GRF12 (GENERAL REGULATORY FACTOR 12) | EXP | 2000 | | |
| CumMe_WSM_SF21828.G5150 | 106 | cpHsc70-1 (chloroplast heat shock protein 70-1) | EXP | 1643 | | |
| CumMe_WSM_SF21886.G5080 | 107 | NPQ4 (NONPHOTOCHEMICAL QUENCHING) | EXP | 2000 | | |
| CumMe_WSM_SF22008.G5670 | 108 | NAP 1;2 (NUCLEOSOME ASSEMBLY PROTEIN 1;2) | EXP | 2000 | | |
| CumMe_WSM_SF22070.G5280 | 109 | fructose-bisphosphate aldolase, putative | EXP | 2000 | | |
| CumMe_WSM_SF22097.G5540 | 110 | APX3 (ASCORBATE PEROXIDASE 3) | EXP | 2000 | | |
| CumMe_WSM_SF22254.G5760 | 111 | 40S ribosomal protein S7 (RPS7B) | EXP | 2000 | | |
| CumMe_WSM_SF22275.G5780 | 112 | ribosomal protein L17 family protein | EXP | 1027 | | |
| CumMe_WSM_SF22355.G5310 | 113 | | EXP | 2000 | | |
| CumMe_WSM_SF22531.G5120 | 114 | eukaryotic translation initiation factor 1A , putative | EXP | 2000 | Promoter; Leader; Intron; Leader | 1-759; 760-858; 859-1979; 1980-2000 |

TABLE 1-continued

Transcriptional regulatory expression element groups, promoters, leaders and introns isolated from *Cucumis melo*.

| Annotation | SEQ ID NO: | Description | Composition Type | Size (bp) | Composition | Coordinates of Elements within EXP |
|---|---|---|---|---|---|---|
| CumMe_WSM_SF22870.G5370 | 115 | ATSARA1A (*ARABIDOPSIS THALIANA* SECRETION-ASSOCIATED RAS SUPER FAMILY 1) | EXP | 2000 | | |
| CumMe_WSM_SF22934.G5290 | 116 | T-complex protein 1 epsilon subunit, putative | EXP | 2000 | | |
| CumMe_WSM_SF23181.G5100 | 117 | CEV1 (CONSTITUTIVE EXPRESSION OF VSP 1) | EXP | 1025 | | |
| CumMe_WSM_SF23186.G6160 | 118 | ubiquinol-cytochrome C reductase complex 14 kDa protein, putative | EXP | 2000 | | |
| CumMe_WSM_SF23397.G5210 | 119 | RPL27 (RIBOSOMAL PROTEIN LARGE SUBUNIT 27) | EXP | 2000 | | |
| CumMe_WSM_SF23760.G5200 | 120 | NDPK1; ATP binding/nucleoside diphosphate kinase | EXP | 2000 | Promoter; Leader | 1-1901; 1902-2000 |
| CumMe_WSM_SF23906.G6180 | 121 | PSBX (photosystem II subunit X) | EXP | 2000 | | |
| CumMe_WSM_SF24040.G5450 | 122 | RPS17 (RIBOSOMAL PROTEIN S17) | EXP | 2000 | | |
| CumMe_WSM_SF24045.G5400 | 123 | EXL3 (EXORDIUM LIKE 3) | EXP | 2000 | | |
| CumMe_WSM_SF24117.G5600 | 124 | 60S ribosomal protein L26 (RPL26A) | EXP | 2000 | | |
| CumMe_WSM_SF25084.G5580 | 125 | | EXP | 2000 | | |
| CumMe_WSM_SF25141.G5160 | 126 | isocitrate dehydrogenase, putative | EXP | 1397 | Promoter; Leader | 1-1322; 1323-1397 |
| CumMe_WSM_SF25355.G5000 | 127 | LOS1; copper ion binding translation elongation factor | EXP | 2000 | Promoter; Leader; Intron; Leader; CDS | 1-734; 735-811; 812-1340; 1341-1360; 1361-2000 |
| CumMe_WSM_SF25370.G5000 | 128 | PSBP-1 (PHOTOSYSTEM II SUBUNIT P-1) | EXP | 1657 | | |
| CumMe_WSM_SF25455.G5370 | 129 | GLY3 (GLYOXALASE II 3) | EXP | 2000 | | |
| CumMe_WSM_SF25936.G5450 | 130 | mitochondrial substrate carrier family protein | EXP | 2000 | Promoter; Leader | 1-1878; 1879-2000 |
| CumMe_WSM_SF27080.G5510 | 131 | LIP1 (LIPOIC ACID SYNTHASE 1) | EXP | 2000 | | |
| CumMe_WSM_SF27222.G5150 | 132 | DRT112; copper ion binding/electron carrier | EXP | 2000 | | |
| CumMe_WSM_SF27957.G5450 | 133 | SMAP1 (SMALL ACIDIC PROTEIN 1) | EXP | 2000 | | |
| CumMe_WSM_SF28729.G5340 | 134 | RNA-binding protein cp29, putative | EXP | 1696 | | |
| CumMe_WSM_SF28805.G6200 | 135 | unknown protein | EXP | 2000 | | |
| CumMe_WSM_SF31264.G5380 | 136 | ATPH1 (*ARABIDOPSIS THALIANA* PLECKSTRIN HOMOLOGUE 1) | EXP | 2000 | | |
| CumMe_WSM_SF35856.G5150 | 137 | TIP4; 1 (tonoplast intrinsic protein 4; 1) | EXP | 1575 | | |
| CumMe_WSM_SF40859.G5250 | 138 | SMT2 (STEROL METHYL-TRANSFERASE 2) | EXP | 2000 | | |
| CumMe_WSM_SF41124.G5080 | 139 | 40S ribosomal protein S2 (RPS2C) | EXP | 1006 | Promoter; Leader | 1-883; 884-1006 |
| CumMe_WSM_SF41128.G5410 | 140 | CRY2 (CRYPTOCHROME 2) | EXP | 2000 | | |
| CumMe_WSM_SF41254.G5160 | 141 | GDP-D-glucose phosphorylase | EXP | 1556 | | |
| CumMe_WSM_SF41588.G5470 | 142 | PRPL11 (PLASTID RIBOSOMAL PROTEIN L11) | EXP | 2000 | | |
| CumMe_WSM_SF41644.G6400 | 143 | SHD (SHEPHERD) | EXP | 2000 | | |
| CumMe_WSM_SF41983.G5000 | 144 | catalytic/coenzyme binding | EXP | 1337 | | |
| CumMe_WSM_SF42075.G5100 | 145 | CPN60B (CHAPERONIN 60 BETA) | EXP | 2000 | | |
| CumMe_WSM_SF42141.G5110 | 146 | cathepsin B-like cysteine protease, putative | EXP | 1212 | | |

TABLE 1-continued

Transcriptional regulatory expression element groups, promoters, leaders and introns isolated from *Cucumis melo*.

| Annotation | SEQ ID NO: | Description | Composition Type | Size (bp) | Composition | Coordinates of Elements within EXP |
|---|---|---|---|---|---|---|
| CumMe_WSM_SF44933. G5290 | 147 | EBF1 (EIN3-BINDING F BOX PROTEIN 1) ubiquitin-protein ligase | EXP | 2000 | | |
| CumMe_WSM_SF44977. G5000 | 148 | PAP26 (PURPLE ACID PHOSPHATASE 26) | EXP | 1254 | | |
| CumMe_WSM_SF45441. G5510 | 149 | GAPA-2 (GLYCERALDEHYDE 3-PHOSPHATE DEHYDROGENASE A SUBUNIT 2) | EXP | 2000 | | |
| CumMe_WSM_SF45882. G5120 | 150 | fructose-1,6-bisphosphatase, putative | EXP | 1680 | | |
| CumMe_WSM_SF47806. G5070 | 151 | ATP synthase epsilon chain, mitochondrial | EXP | 1524 | | |
| CumMe_WSM_SF53106. G5190 | 152 | CPN60A (CHAPERONIN-60ALPHA) | EXP | 1851 | | |
| CumMe_WSM_SF65588. G5230 | 153 | vacuolar calcium-binding protein-related | EXP | 2000 | | |
| CumMe_WSM_SF9060. G5120 | 154 | APE2 (ACCLIMATION OF PHOTOSYNTHESIS TO ENVIRONMENT 2) | EXP | 1288 | | |
| P-CUCme.1-1:1:1rc | 155 | Phosphatase 2A | EXP | 2000 | Promoter; Leader; Intron; Leader | 1-1135; 1136-1249; 1250-1990; 1991-2000 |
| EXP-CUCme.4:1:1 | 156 | Ubiquitin 2 | EXP | 2011 | Promoter; Leader; Intron; Leader | 1-1646; 1647-1704; 1705-2005; 2006-2008 |
| P-CUCme.4-1:1:4 | 157 | Ubiquitin 2 | P; L | 1698 | Promoter; Leader | |
| I-CUCme.4-1:1:1 | 158 | Ubiquitin 2 | I; L | 313 | Intron; Leader | |
| EXP-CUCme.5:1:1 | 159 | Ubiquitin 3 | EXP | 2010 | Promoter; Leader; Intron; Leader | 1-748; 749-819; 820-2004; 2005-2007 |
| P-CUCme.5-1:1:3 | 160 | Ubiquitin 3 | P; L | 1107 | Promoter; Leader | |
| I-CUCme.5-1:1:1 | 161 | Ubiquitin 3 | I; L | 903 | Intron; Leader | |
| EXP-CUCme.eEF1a:1:1 | 162 | Elongation Factor 1 alpha | EXP | 1235 | Promoter; Leader; Intron; Leader | 1-617; 618-677; 678-1213; 1214-1235 |
| P-CUCme.eEF1a-1:1:1 | 163 | Elongation Factor 1 alpha | P | 617 | Promoter | |
| L-CUCme.eEF1a-1:1:1 | 164 | Elongation Factor 1 alpha | L | 54 | Leader | |
| I-CUCme.eEF1a-1:1:1 | 165 | Elongation Factor 1 alpha | I | 545 | Intron | |
| L-CUCme.eEF1a-1:1:2 | 166 | Elongation Factor 1 alpha | L | 19 | Leader | |
| P-CUCme.19-1:1:3 | 167 | Chloropyll a/b binding protein | EXP | 2003 | Promoter; Leader | 1-1958; 1959-2003 |
| EXP-CUCme.SAMS2:1:1 | 168 | S-Adenosylmethionine Synthetase | EXP | 2004 | Promoter; Leader; Intron | 1-1067; 1068-1165; 1166-2003 |
| P-CUCme.SAMS2-1:1:1 | 169 | S-Adenosylmethionine Synthetase | P | 1067 | Promoter | |
| L-CUCme.SAMS2-1:1:1 | 170 | S-Adenosylmethionine Synthetase | L | 92 | Leader | |
| I-CUCme.SAMS2-1:1:1 | 171 | S-Adenosylmethionine Synthetase | I | 845 | Intron | |
| EXP-CUCme.29:1:1 | 172 | Ribosomal protein S5a | EXP | 2018 | Promoter; Leader; Intron; Leader | 1-490; 491-571; 572-2012; 2013-2018 |
| P-CUCme.29-1:1:4 | 173 | Ribosomal protein S5a | P; L | 565 | Promoter; Leader | |
| I-CUCme,29-1:1:1 | 174 | Ribosomal protein S5a | I; L | 1453 | Intron; Leader | |
| P-CUCme. CumMe_WSM_SF16444. G5140-1:1:1 | 175 | histone H4 | EXP | 1999 | Promoter; Leader; Intron | 1-1946; 947-1999 |
| P-CUCme. CumMe_WSM_SF16563. G5560-1:1:1 | 176 | ATARFB1A (ADP-ribosylation factor B1A) | EXP | 2004 | Promoter; Leader; Intron; Leader | 1-1331; 1332-1429; 1430-1992; 1993-2004 |
| P-CUCme. CumMe_WSM_SF17111. G5790-1:1:1 | 177 | ubiquinol-cytochrome C reductase complex ubiquinone-binding protein | EXP | 2005 | Promoter; Leader | 1-1901; 1902-2005 |
| EXP-CumMe. WSM_SF17252. G7330:1:1 | 178 | nascent polypeptide-associated complex (NAC) domain-containing protein | EXP | 1978 | Promoter; Leader; Intron; Leader | 1-1167; 1168-1269; 1270-1972; 1973-1975 |
| P-CUCme.WSM_SF17252. G7330-1:1:1 | 179 | nascent polypeptide-associated complex (NAC) domain-containing protein | P; L | 1263 | Promoter; Leader | |
| I-CUCme.WSM_SF17252. G7330-1:1:1 | 180 | nascent polypeptide-associated complex (NAC) domain-containing protein | I; L | 715 | Intron; Leader | |
| P-CUCme. | 181 | caffeoyl-CoA 3-O- | EXP | 2000 | Promoter; Leader | 1-923; 1924-2000 |

TABLE 1-continued

| Annotation | SEQ ID NO: | Description | Composition Type | Size (bp) | Composition | Coordinates of Elements within EXP |
|---|---|---|---|---|---|---|
| Transcriptional regulatory expression element groups, promoters, leaders and introns isolated from *Cucumis melo*. | | | | | | |
| CumMe_WSM_SF18488. G5340- 1:1:1 | | methyltransferase | | | | |
| P-CUCme. CumMe_WSM_SF18536. G6480-1:1:1 | 182 | MBF1A (MULTIPROTEIN BRIDGING FACTOR 1A) transcription coactivator | EXP | 2000 | Promoter; Leader; Intron | |
| P-CUCme. CumMe_WSM_SF18634. G5190-1:1:1 | 183 | 60S ribosomal protein L23 (RPL23A) | EXP | 1989 | Promoter; Leader | 1-1960; 1961-1989 |
| P-CUCme. CumMe_WSM_SF18716. G5860-1:1:1 | 184 | Auxin-induced protein X10A-like | EXP | 1463 | Promoter; Leader | 1-1392; 1393-1463 |
| EXP-CUCme.WSM_SF19064. G5690:1:1 | 185 | histone H3.2 | EXP | 2006 | Promoter; Leader; Intron; Leader | 1-1581; 1582-1670; 1671-2000; 2001-2003 |
| P-CUCme.WSM_SF19064. G5690-1:1:1 | 186 | histone H3.2 | P; L | 1664 | Promoter; Leader | |
| I-CUCme.WSM_SF19064. G5690-1:1:1 | 187 | histone H3.2 | I; L | 342 | Intron; Leader | |
| P-CUCme. CumMe_WSM_SF19647. G5760- 1:1:1 | 188 | 6-phosphogluconate dehydrogenase family protein | EXP | 2003 | Promoter; Leader; Intron; Leader | 1-939; 940-1024; 1025-1995; 1996-2003 |
| P-CUCme. CumMe_WSM_SF19839. G5090-1:1:1 | 189 | ATPDX1.1 (pyridoxine biosynthesis 1.1) | EXP | 1024 | Promoter; Leader | 1-904; 905-1024 |
| P-CUCme. CumMe_WSM_SF20132. G5560-1:1:1 | 190 | peroxidase 21 | EXP | 2001 | Promoter; Leader | 1-1962; 1963-2001 |
| P-CUCme. CumMe_WSM_SF206458. G5970-1:1:1 | 191 | FAD2 (FATTY ACID DESATURASE 2) | EXP | 4175 | Promoter; Leader; Intron; Leader | 1-2171; 2172-2325; 2326-4155; 4156-4175 |
| P-CUCme. CumMe_WSM_SF22531. G5120-1:1:1 | 192 | eukaryotic translation initiation factor 1A, putative | EXP | 1999 | Promoter; Leader; Intron; Leader | 1-759; 760-858; 859-1978; 1979-1999 |
| P-CUCme. CumMe_WSM_SF23760. G5200-1:1:1 | 193 | NDPK1; ATP binding/ nucleoside diphosphate kinase | EXP | 2000 | Promoter; Leader | 1-1901; 1902-2000 |
| P-CUCme. CumMe_WSM_SF23906. G6180-1:1:1 | 194 | PSBX (photosystem II subunit X) | EXP | 2000 | Promoter; Leader | |
| P-CUCme. CumMe_WSM_SF25141. G5160-1:1:2 | 195 | isocitrate dehydrogenase, putative | EXP | 1400 | Promoter; Leader | 1-1325; 1326-1400 |
| P-CUCme. CumMe_WSM_SF25355. G5000-1:1:1 | 196 | LOS1; copper ion binding translation elongation factor | EXP | 2019 | Promoter; Leader; Intron; Leader; CDS | 1-734; 735-811; 812-1340; 1341-1360; 1361-2019 |
| P-CUCme. CumMe_WSM_SF25936. G5450-1:1:1 | 197 | mitochondrial substrate carrier family protein | EXP | 1999 | Promoter; Leader | 1-1877; 1878-1999 |
| P-CUCme. CumMe_WSM_SF35856. G5150-1:1:1 | 198 | TIP4; 1 (tonoplast intrinsic protein 4; 1) | EXP | 1578 | | |
| P-CUCme. CumMe_WSM_SF41124. G5080-1:1:1 | 199 | 40S ribosomal protein S2 (RPS2C) | EXP | 1023 | Promoter; Leader | 1-945; 946-1023 |
| P-CUCme.20-1:3 | 211 | Chloropyll a/b binding protein | EXP | 1446 | Promoter; Leader | 1-1390; 1391-1446 |
| EXP-CUCme.29:1:2 | 212 | Ribosomal protein S5a | EXP | 2018 | Promoter; Leader; Intron; Leader | 1-490; 491-571; 572-2011; 2013-2018 |

As shown in Table 1, for example, the transcriptional regulatory expression element group (EXP) designated EXP-CUCme.Ubq1:1:1 (SEQ ID NO: 1), with components isolated from *C. melo*, comprises a 2068 base pair sized (bp) promoter element, P-CUCme.Ubq1-1:1:15 (SEQ ID NO: 2), operably linked 5' to a leader element, L-CUCme.Ubq1-1:1:1 (SEQ ID NO: 3), operably linked 5' to an intron element, I-CUCme.Ubq1-1:1:1 (SEQ ID NO: 4). The transcriptional regulatory expression element group (EXP) designated EXP-CUCme.Ubq1:1:2 (SEQ ID NO: 5), with components isolated from *C. melo*, comprises a 1459 bp promoter element, P-CUCme.Ubq1-1:1:16 (SEQ ID NO: 6), operably linked 5' to a leader element, L-CUCme.Ubq1-1:1:1 (SEQ ID NO: 3), operably linked 5' to an intron element, I-CUCme.Ubq1-1:1:1 (SEQ ID NO: 4). The transcriptional regulatory expression element group (EXP) designated EXP-CUCme.Ubq1:1:3 (SEQ ID NO: 7), with components isolated from *C. melo*, comprises a 964 bp promoter element, P-CUCme.Ubq1-1:1:17 (SEQ ID NO: 8), operably linked 5' to a leader element, L-CUCme.Ubq1-1:1:1 (SEQ ID NO: 3), operably linked 5' to an intron element, I-CUCme.Ubq1-1:1:1 (SEQ ID NO: 4). The transcriptional regulatory expression element group (EXP) designated EXP-CUCme.Ubq1:1:4 (SEQ ID NO: 9), with components isolated from *C. melo*, comprises a 479 bp promoter element, P-CUCme.Ubq1-1:1:18 (SEQ ID NO: 10), operably linked 5' to a leader element, L-CUCme.Ubq1-1:1:1 (SEQ ID NO: 3), operably linked 5' to an intron element, I-CUCme.Ubq1-1:1:1 (SEQ ID NO: 4). The transcriptional regulatory expression element group (EXP) designated EXP-CUCme.Ubq1:1:5 (SEQ ID NO: 11), with components isolated from *C. melo*, comprises a 173 bp promoter element, P-CUCme.Ubq1-1:1:19 (SEQ ID NO: 12), operably linked 5' to a leader element, L-CUCme.Ubq1-1:1:1 (SEQ ID NO: 3), operably linked 5' to an intron element, I-CUCme.Ubq1-1:1:1 (SEQ ID NO: 4).

An alignment of the ubiquitin 1 promoter sequences is provided in FIGS. 1*a*-1*f*. The promoter elements, P-CUCme.Ubq1-1:1:16 (SEQ ID NO: 6), P-CUCme.Ubq1-1:1:17 (SEQ ID NO: 8), P-CUCme.Ubq1-1:1:18 (SEQ ID NO: 10) and P-CUCme.Ubq1-1:1:19 (SEQ ID NO: 12) were built by introducing varying lengths of deletions from the 5' end of the promoter, P-CUCme.Ubq1-1:1:15 (SEQ ID NO: 2).

Example 2: Analysis of Regulatory Elements Driving GUS in Soy Cotyledon Protoplasts Soybean cotyledon protoplasts were transformed with plant expression vectors containing a test transcriptional regulatory expression element group driving expression of the ß-glucuronidase (GUS) transgene and compared to GUS expression in leaf protoplasts in which expression of GUS is driven by known constitutive promoters.

Expression of a transgene driven by EXP-CUCme.Ubq1:1:1 (SEQ ID NO: 1), EXP-CUCme.Ubq1:1:2 (SEQ ID NO: 5), EXP-CUCme.Ubq1:1:3 (SEQ ID NO: 7), EXP-CUCme.Ubq1:1:4 (SEQ ID NO: 9) and EXP-CUCme.Ubq1:1:5 (SEQ ID NO: 11) was compared with expression from known constitutive promoters. Each plant expression vector was comprised of a right border region from *Agrobacterium tumefaciens*, a first transgene cassette comprised of an EXP sequence or known constitutive promoter operably linked 5' to a coding sequence for ß-glucuronidase (GUS, SEQ ID NO: 206) containing a processable intron derived from the potato light-inducible tissue-specific ST-LS1 gene (Genbank Accession: X04753), operably linked 5' to a 3' termination region from the *Gossypium barbadense* E6 gene (T-Gb.E6-3b:1:1, SEQ ID NO: 204), the *Pisum sativum* RbcS2-E9 gene (T-Ps.RbcS2-E9-1:1:6, SEQ ID NO: 203), or the *Gossypium barbadense* FbLate-2 gene (T-Gb.FbL2-1:1:1, SEQ ID NO: 205); a second transgene selection cassette used for selection of transformed plant cells that either confers resistance to the herbicide glyphosate (driven by the *Arabidopsis* Actin 7 promoter) or the antibiotic, kanamycin and a left border region from *A. tumefaciens*. A promoterless control plant expression vector (pMON124912) served as a negative control for expression. The foregoing test and constitutive expression element groups were cloned into plant expression vectors as shown in Table 2 below.

TABLE 2

Plant expression vectors and corresponding expression element group and 3' UTR.

| Expression Vector | Regulatory Element | SEQ ID NO: | 3' UTR |
|---|---|---|---|
| pMON80585 | EXP-At.Atntt1:1:2 | 200 | T-Ps.RbcS2-E9-1:1:6 |
| pMON109584 | EXP-CaMV.35S-enh + Ph.DnaK:1:3 | 201 | T-Gb.E6-3b:1:1 |
| pMON118756 | EXP-At.Act7:1:11 | 202 | T-Gb.E6-3b:1:1 |
| pMON124912 | No promoter | | T-Gb.FbL2-1:1:1 |
| pMON138776 | EXP-CUCme.Ubq1:1:1 | 1 | T-Gb.FbL2-1:1:1 |
| pMON138777 | EXP-CUCme.Ubq1:1:2 | 5 | T-Gb.FbL2-1:1:1 |
| pMON138778 | EXP-CUCme.Ubq1:1:3 | 7 | T-Gb.FbL2-1:1:1 |
| pMON138779 | EXP-CUCme.Ubq1:1:4 | 9 | T-Gb.FbL2-1:1:1 |
| pMON138780 | EXP-CUCme.Ubq1:1:5 | 11 | T-Gb.FbL2-1:1:1 |

Two plasmids, for use in co-transformation and normalization of data, were also constructed. One transformation control plasmid was comprised of a constitutive promoter, driving the expression of the firefly (*Photinus pyralis*) luciferase coding sequence (FLuc, SEQ ID NO: 207), operably linked 5' to a 3' termination region from the *Agrobacterium tumefaciens* nopaline synthase gene (T-AGRtu.nos-1:1:13, SEQ ID NO: 209). The other transformation control plasmid was comprised of a constitutive promoter, driving the expression of the sea pansy (*Renilla reniformis*) luciferase coding sequence (RLuc, SEQ ID NO: 208), operably linked 5' to a 3' termination region from the *Agrobacterium tumefaciens* nopaline synthase gene.

The plant expression vectors, pMON80585, pMON109584, pMON118756, pMON124912, pMON138776, pMON138777, pMON138778, pMON138779 and pMON138780 were used to transform soybean cotyledon protoplast cells using PEG transformation methods. Protoplast cells were transformed with equimolar amounts of each of the two transformation control plasmids and a test plant expression vector. GUS and luciferase activity was assayed. Measurements of both GUS and luciferase were conducted by placing aliquots of a lysed preparation of cells transformed as above into two different small-well trays. One tray was used for GUS measurements, and a second tray was used to perform a dual luciferase assay using the dual luciferase reporter assay system (Promega Corp., Madison, Wis.; see for example, Promega Notes Magazine, No: 57, 1996, p. 02). Sample measurements were made using 3 or 4 replicates per transformation. The average GUS and luciferase values are presented in Table 3 below.

TABLE 3

Average GUS and luciferase expression values and GUS/luciferase ratios.

| Construct | Regulatory Element | SEQ ID NO: | Average GUS | Average FLuc | Average RLuc | GUS/FLuc | GUS/RLuc |
|---|---|---|---|---|---|---|---|
| pMON80585 | EXP-At.Atntt1:1:2 | 200 | 55173 | 6498 | 30503 | 8.49 | 1.81 |
| pMON109584 | EXP-CaMV.35S-enh + Ph.DnaK:1:3 | 200 | 24940 | 5050.75 | 35495 | 4.94 | 0.70 |
| pMON118756 | EXP-At.Act7:1:11 | 201 | 9871 | 6880 | 40850 | 1.43 | 0.24 |
| pMON124912 | No promoter | | 2000 | 11670 | 73187 | 0.17 | 0.03 |
| pMON138776 | EXP-CUCme.Ubq1:1:1 | 1 | 26972 | 6467.25 | 37200 | 4.17 | 0.73 |
| pMON138777 | EXP-CUCme.Ubq1:1:2 | 5 | 41307 | 5902.5 | 24396 | 7.00 | 1.69 |
| pMON138778 | EXP-CUCme.Ubq1:1:3 | 7 | 90140 | 10710.5 | 60983 | 8.42 | 1.48 |
| pMON138779 | EXP-CUCme.Ubq1:1:4 | 9 | 35526 | 5590 | 28001 | 6.36 | 1.27 |
| pMON138780 | EXP-CUCme.Ubq1:1:5 | 11 | 23298 | 4483.25 | 19075 | 5.20 | 1.22 |

To compare the relative activity of each promoter in soybean cotyledon protoplasts, GUS values were expressed as a ratio of GUS to luciferase activity and normalized with respect to the expression levels observed for the constitutive expression element groups, EXP-At.Act7:1:11 and EXP-CaMV.35S-enh+Ph.DnaK:1:3. Table 4 below shows the GUS to firefly luciferase (FLuc) ratios normalized with respect to EXP-At.Act7:1:11 and EXP-CaMV.35S-enh+Ph.DnaK:1:3. Table 5 below shows the GUS to renilla luciferase (RLuc) ratios normalized with respect to EXP-At.Act7:1:11 and EXP-CaMV.35S-enh+Ph.DnaK:1:3.

TABLE 4

GUS to firefly luciferase (FLuc) ratios normalized with respect to EXP-At.Act7:1:11 and EXP-CaMV.35S-enh + Ph.DnaK:1:3.

| Construct | Regulatory Element | SEQ ID NO: | GUS/FLuc normalized with respect to EXP-At.Act7:1:11 | GUS/FLuc normalized with respect to EXP-CaMV.35S-enh + Ph.DnaK:1:3 |
|---|---|---|---|---|
| pMON80585 | EXP-At.Atntt1:1:2 | 200 | 5.92 | 1.72 |
| pMON109584 | EXP-CaMV.35S-enh + Ph.DnaK:1:3 | 201 | 3.44 | 1.00 |
| pMON118756 | EXP-At.Act7:1:11 | 202 | 1.00 | 0.29 |
| pMON124912 | No promoter | | 0.12 | 0.03 |
| pMON138776 | EXP-CUCme.Ubq1:1:1 | 1 | 2.91 | 0.84 |
| pMON138777 | EXP-CUCme.Ubq1:1:2 | 5 | 4.88 | 1.42 |
| pMON138778 | EXP-CUCme.Ubq1:1:3 | 7 | 5.87 | 1.70 |
| pMON138779 | EXP-CUCme.Ubq1:1:4 | 9 | 4.43 | 1.29 |
| pMON138780 | EXP-CUCme.Ubq1:1:5 | 11 | 3.62 | 1.05 |

TABLE 5

GUS to *renilla* luciferase (RLuc) ratios normalized with respect to EXP-At.Act7:1:11 and EXP-CaMV.35S-enh + Ph.DnaK:1:3.

| Construct | Regulatory Element | SEQ ID NO: | GUS/RLuc normalized with respect to EXP-At.Act7:1:11 | GUS/RLuc normalized with respect to EXP-CaMV.35S-enh + Ph.DnaK:1:3 |
|---|---|---|---|---|
| pMON80585 | EXP-At.Atntt1:1:2 | 200 | 7.49 | 2.57 |
| pMON109584 | EXP-CaMV.35S-enh + Ph.DnaK:1:3 | 201 | 2.91 | 1.00 |
| pMON118756 | EXP-At.Act7:1:11 | 202 | 1.00 | 0.34 |
| pMON124912 | No promoter | | 0.11 | 0.04 |
| pMON138776 | EXP-CUCme.Ubq1:1:1 | 1 | 3.00 | 1.03 |
| pMON138777 | EXP-CUCme.Ubq1:1:2 | 5 | 7.01 | 2.41 |
| pMON138778 | EXP-CUCme.Ubq1:1:3 | 7 | 6.12 | 2.10 |

TABLE 5-continued

GUS to *renilla* luciferase (RLuc) ratios normalized with respect to EXP-At.Act7:1:11 and EXP-CaMV.35S-enh + Ph.DnaK:1:3.

| Construct | Regulatory Element | SEQ ID NO: | GUS/RLuc normalized with respect to EXP-At.Act7:1:11 | GUS/RLuc normalized with respect to EXP-CaMV.35S-enh + Ph.DnaK:1:3 |
|---|---|---|---|---|
| pMON138779 | EXP-CUCme.Ubq1:1:4 | 9 | 5.25 | 1.81 |
| pMON138780 | EXP-CUCme.Ubq1:1:5 | 11 | 5.05 | 1.74 |

As can be seen in Tables 4 and 5 above, each of the expression element groups EXP-CUCme.Ubq1:1:1 (SEQ ID NO: 1), EXP-CUCme.Ubq1:1:2 (SEQ ID NO: 5), EXP-CUCme.Ubq1:1:3 (SEQ ID NO: 7), EXP-CUCme.Ubq1:1:4 (SEQ ID NO: 9) and EXP-CUCme.Ubq1:1:5 (SEQ ID NO: 11) demonstrated the ability of driving transgene expression in soybean cotyledon protoplasts. Expression levels were greater than that of EXP-At.Act7:1:11 and was 2.9 to 5.8 (FLuc) or 3 to 7 (RLuc) fold higher than EXP-At.Act7:1:11 in this assay. Expression was equivalent or higher than expression observed for EXP-CaMV.35S-enh+Ph.DnaK:1:3. Expression levels were 0.8 to 1.7 (FLuc) or 1 to 2.4 (RLuc) fold higher than expression observed for EXP-CaMV.35S-enh+Ph.DnaK:1:3.

Example 3: Analysis of Regulatory Elements Driving GUS in Bombarded Soybean Leaves and Roots Soybean leaves and roots were transformed with plant expression vectors containing a test transcriptional regulatory expression element group driving expression of the ß-glucuronidase (GUS) transgene and compared to GUS expression in roots and leaves in which expression of GUS is driven by known constitutive promoters.

Expression of a transgene driven by EXP-CUCme.Ubq1:1:1 (SEQ ID NO: 1), EXP-CUCme.Ubq1:1:2 (SEQ ID NO: 5), EXP-CUCme.Ubq1:1:3 (SEQ ID NO: 7), EXP-CUCme.Ubq1:1:4 (SEQ ID NO: 9) and EXP-CUCme.Ubq1:1:5 (SEQ ID NO: 11) was compared with expression from known constitutive promoters in particle bombarded soybean leaves and roots. The plant expression vectors used for transformation of leaves and roots was the same as those presented in Table 2 of Example 2 above.

The plant expression vectors, pMON80585, pMON109584, pMON118756, pMON124912, pMON138776, pMON138777, pMON138778, pMON138779 and pMON138780 were used to transform soybean leaves and roots using particle bombardment transformation methods.

Briefly, A3244 soybean seeds were surface sterilized and allowed to germinate in trays with a photoperiod of 16 hours light and 8 hours of darkness. After approximately 13 days, leaf and root tissue was harvested under sterile conditions from the seedlings and used for bombardment. The tissue samples were randomly placed on a petri dish containing plant culture medium. Ten micrograms of plasmid DNA was used to coat 0.6 micron gold particles (Catalog #165-2262 Bio-Rad, Hercules, Calif.) for bombardment. Macro-carriers were loaded with the DNA-coated gold particles (Catalog #165-2335 Bio-Rad, Hercules Calif.). A PDS 1000/He biolistic gun was used for transformation (Catalog #165-2257 Bio-Rad, Hercules Calif.). The bombarded root and leaf tissues were allowed to incubate in the dark for 24 hours at 26 degrees Celsius. Following this overnight incubation, the tissues were stained in solution for GUS expression overnight at 37 degrees Celsius. After staining overnight, the tissues were soaked in 70% ethanol overnight to remove chlorophyll and reveal the GUS staining. The tissues were then photographed and a rating scale of "0", "+" to "++++++" reflecting the level of GUS expression is assigned to each construct (0—no expression, + to ++++++—low to high, respectively).

Expression of the GUS transgene demonstrated in each tissue is used to infer the relative potential level and specificity of each element's capacity to drive transgene expression in stably transformed corn plants. Average GUS expression ratings are provided in Table 6 below.

TABLE 6

GUS expression ratings for particle bombarded leaf and root.

| Construct | Regulatory Element | SEQ ID NO: | Leaf Expression Rating | Root Expression Rating |
|---|---|---|---|---|
| pMON80585 | EXP-At.Atntt1:1:2 | 200 | ++++ | ++ |
| pMON109584 | EXP-CaMV.35S-enh + Ph.DnaK:1:3 | 201 | +++++ | +++ |
| pMON118756 | EXP-At.Act7:1:11 | 202 | ++++ | ++ |
| pMON124912 | No promoter | | 0 | 0 |
| pMON138776 | EXP-CUCme.Ubq1:1:1 | 1 | ++++ | +++ |
| pMON138777 | EXP-CUCme.Ubq1:1:2 | 5 | +++ | ++ |
| pMON138778 | EXP-CUCme.Ubq1:1:3 | 7 | +++ | ++ |
| pMON138779 | EXP-CUCme.Ubq1:1:4 | 9 | +++ | ++ |
| pMON138780 | EXP-CUCme.Ubq1:1:5 | 11 | ++ | + |

As can be seen in Table 6 above, each of the expression element groups EXP-CUCme.Ubq1:1:1 (SEQ ID NO: 1), EXP-CUCme.Ubq1:1:2 (SEQ ID NO: 5), EXP-CUCme.Ubq1:1:3 (SEQ ID NO: 7), EXP-CUCme.Ubq1:1:4 (SEQ ID NO: 9) and EXP-CUCme.Ubq1:1:5 (SEQ ID NO: 11) demonstrated the ability of driving transgene expression in particle bombarded transformed leaf and root tissues.

Example 4: Analysis of Regulatory Elements Driving GUS in Soy Cotyledon Protoplasts Soybean cotyledon protoplasts were transformed with plant expression vectors containing a test transcriptional regulatory expression element group driving expression of the ß-glucuronidase (GUS) transgene and compared to GUS expression in leaf protoplasts in which expression of GUS is driven by known constitutive promoters.

Expression of a transgene driven by P-CUCme.1-1:1:1rc (SEQ ID NO: 155), P-CUCme.2-1:1:1 (SEQ ID NO: 14), P-CUCme.3-1:1:3 (SEQ ID NO: 15), EXP-CUCme.4:1:1 (SEQ ID NO: 156), EXP-CUCme.5:1:1 (SEQ ID NO: 159), P-CUCme.6-1:1:1 (SEQ ID NO: 18), P-CUCme.8-1:1:2 (SEQ ID NO: 19), P-CUCme.9-1:1:2 (SEQ ID NO: 20), P-CUCme.10-1:1:1 (SEQ ID NO: 21), EXP-CUCme.eEF1a: 1:1 (SEQ ID NO: 162), P-CUCme.15-1:1:2 (SEQ ID NO: 23), P-CUCme.16a-1:1:2 (SEQ ID NO: 24), P-CUCme.17-1:1:2 (SEQ ID NO: 26), P-CUCme.18-1:1:2 (SEQ ID NO: 27), P-CUCme.19-1:1:3 (SEQ ID NO: 167), P-CUCme.20-1:3 (SEQ ID NO: 211), P-CUCme.21-1:1:1 (SEQ ID NO: 30), P-CUCme.22-1:1:3 (SEQ ID NO: 31), EXP-CUCme.SAMS2:1:1 (SEQ ID NO: 168), P-CUCme.26-1:1:2 (SEQ ID NO: 33), P-CUCme.28-1:1:2 (SEQ ID NO: 34) and EXP-CUCme.29:1:2 (SEQ ID NO: 212) was compared with expression from known constitutive expression element groups. Each plant expression vector was comprised of a right border region from *Agrobacterium tumefaciens*, a first transgene cassette comprised of a test promoter or known constitutive promoter operably linked 5' to a coding sequence for ß-glucuronidase (GUS, SEQ ID NO: 206) containing a processable intron derived from the potato light-inducible tissue-specific ST-LS1 gene (Genbank Accession: X04753), operably linked 5' to a 3' termination region from the *Gossypium barbadense* E6 gene (T-Gb.E6-3b:1:1, SEQ ID NO: 204), the *Pisum sativum* RbcS2-E9 gene (T-Ps.RbcS2-E9-1:1:6, SEQ ID NO: 203), or the *Gossypium barbadense* FbLate-2 gene (T-Gb.FbL2-1:1:1, SEQ ID NO: 205); a second transgene selection cassette used for selection of transformed plant cells that either confers resistance to the herbicide glyphosate (driven by the *Arabidopsis* Actin 7 promoter) or the antibiotic, kanamycin and a left border region from *A. tumefaciens*. A promoterless control plant expression vector (pMON124912) served as a negative control for expression. The foregoing test and constitutive expression element groups were cloned into plant expression vectors as shown in Table 7 below.

TABLE 7

Plant expression vectors and corresponding expression element group and 3' UTR.

| Construct | Regulatory Element | SEQ ID NO: | 3' UTR |
|---|---|---|---|
| pMON80585 | EXP-At.Atntt1:1:2 | 200 | T-Ps.RbcS2-E9-1:1:6 |
| pMON109584 | EXP-CaMV.35S-enh + Ph.DnaK:1:3 | 201 | T-Gb.E6-3b:1:1 |
| pMON118756 | EXP-At.Act7:1:11 | 202 | T-Gb.E6-3b:1:1 |
| pMON124912 | Promoterless | | T-Gb.FbL2-1:1:1 |
| pMON140818 | P-CUCme.1-1:1:1rc | 155 | T-Gb.FbL2-1:1:1 |
| pMON140819 | P-CUCme.2-1:1:1 | 14 | T-Gb.FbL2-1:1:1 |
| pMON140820 | P-CUCme.3-1:1:3 | 15 | T-Gb.FbL2-1:1:1 |
| pMON140821 | EXP-CUCme.4:1:1 | 156 | T-Gb.FbL2-1:1:1 |
| pMON140822 | EXP-CUCme.5:1:1 | 159 | T-Gb.FbL2-1:1:1 |
| pMON140823 | P-CUCme.6-1:1:1 | 18 | T-Gb.FbL2-1:1:1 |
| pMON140824 | P-CUCme.8-1:1:2 | 19 | T-Gb.FbL2-1:1:1 |
| pMON140825 | P-CUCme.9-1:1:2 | 20 | T-Gb.FbL2-1:1:1 |

TABLE 7-continued

Plant expression vectors and corresponding expression element group and 3' UTR.

| Construct | Regulatory Element | SEQ ID NO: | 3' UTR |
|---|---|---|---|
| pMON140826 | P-CUCme.10-1:1:1 | 21 | T-Gb.FbL2-1:1:1 |
| pMON140827 | EXP-CUCme.eEF1a:1:1 | 162 | T-Gb.FbL2-1:1:1 |
| pMON140828 | P-CUCme.15-1:1:2 | 23 | T-Gb.FbL2-1:1:1 |
| pMON140829 | P-CUCme.16a-1:1:2 | 24 | T-Gb.FbL2-1:1:1 |
| pMON140830 | P-CUCme.17-1:1:2 | 26 | T-Gb.FbL2-1:1:1 |
| pMON140831 | P-CUCme.18-1:1:2 | 27 | T-Gb.FbL2-1:1:1 |
| pMON140832 | P-CUCme.19-1:1:3 | 167 | T-Gb.FbL2-1:1:1 |
| pMON140833 | P-CUCme.20-1:3 | 211 | T-Gb.FbL2-1:1:1 |
| pMON140834 | P-CUCme.21-1:1:1 | 30 | T-Gb.FbL2-1:1:1 |
| pMON140835 | P-CUCme.22-1:1:3 | 31 | T-Gb.FbL2-1:1:1 |
| pMON140836 | EXP-CUCme.SAMS2:1:1 | 168 | T-Gb.FbL2-1:1:1 |
| pMON140837 | P-CUCme.26-1:1:2 | 33 | T-Gb.FbL2-1:1:1 |
| pMON140838 | P-CUCme.28-1:1:2 | 34 | T-Gb.FbL2-1:1:1 |
| pMON140839 | EXP-CUCme.29:1:2 | 212 | T-Gb.FbL2-1:1:1 |

Two plasmids, for use in co-transformation and normalization of data, were also constructed. One transformation control plasmid was comprised of a constitutive promoter, driving the expression of the firefly (*Photinus pyralis*) luciferase coding sequence (FLuc, SEQ ID NO: 207), operably linked 5' to a 3' termination region from the *Agrobacterium tumefaciens* nopaline synthase gene (T-AGRtu.nos-1:1:13, SEQ ID NO: 209). The other transformation control plasmid was comprised of a constitutive promoter, driving the expression of the sea pansy (*Renilla reniformis*) luciferase coding sequence (RLuc, SEQ ID NO: 208), operably linked 5' to a 3' termination region from the *Agrobacterium tumefaciens* nopaline synthase gene.

The plant expression vectors, pMON80585, pMON109584, pMON118756, pMON124912, pMON140818, pMON140819, pMON140820, pMON140821, pMON140822, pMON140823, pMON140824, pMON140825, pMON140826, pMON140827, pMON140828, pMON140829, pMON140830, pMON140831, pMON140832, pMON140833, pMON140834, pMON140835, pMON140836, pMON140837, pMON140838 and pMON140839 were used to transform soybean cotyledon protoplast cells using PEG transformation methods. Protoplast cells were transformed with equimolar amounts of each of the two transformation control plasmids and a test plant expression vector. GUS and luciferase activity was assayed. Measurements of both GUS and luciferase were conducted by placing aliquots of a lysed preparation of cells transformed as above into two different small-well trays. One tray was used for GUS measurements, and a second tray was used to perform a dual luciferase assay using the dual luciferase reporter assay system (Promega Corp., Madison, Wis.; see for example, Promega Notes Magazine, No: 57, 1996, p. 02). Sample measurements were made using 3 or 4 replicates per transformation. The average GUS and luciferase values are presented in Table 8 below.

TABLE 8

Average GUS and luciferase expression values and GUS/luciferase ratios.

| Construct | Regulatory Element | SEQ ID NO: | Average GUS | Average FLuc | Average RLuc | GUS/ FLuc | GUS/ RLuc |
|---|---|---|---|---|---|---|---|
| pMON80585 | EXP-At.Atntt1:1:2 | 200 | 586 | 5220.7 | 8323 | 0.1100 | 0.0700 |
| pMON109584 | EXP-CaMV.35S-enh +Ph.DnaK:1:3 | 201 | 5768 | 4275 | 15098 | 1.3500 | 0.3800 |
| pMON118756 | EXP-At.Act7:1:11 | 202 | 773 | 7722 | 10545 | 0.1000 | 0.0700 |
| pMON124912 | Promoterless | | 48 | 9746.5 | 13905 | 0.0000 | 0.0000 |
| pMON140818 | P-CUCme.1-1:1:1rc | 155 | 194 | 4772 | 6363 | 0.0400 | 0.0300 |
| pMON140819 | P-CUCme.2-1:1:1 | 14 | 171 | 6855 | 10123 | 0.0200 | 0.0200 |
| pMON140820 | P-CUCme.3-1:1:3 | 15 | 37 | 7089.3 | 9593 | 0.0100 | 0.0000 |
| pMON140821 | EXP-CUCme.4:1:1 | 156 | 4211 | 7626.8 | 13935 | 0.5500 | 0.3000 |
| pMON140822 | EXP-CUCme.5:1:1 | 159 | 626 | 15609.3 | 21140 | 0.0400 | 0.0300 |
| pMON140823 | P-CUCme.6-1:1:1 | 18 | 331 | 15178.5 | 22818 | 0.0200 | 0.0100 |
| pMON140824 | P-CUCme.8-1:1:2 | 19 | 238 | 17514.5 | 28429 | 0.0100 | 0.0100 |
| pMON140825 | P-CUCme.9-1:1:2 | 20 | 510 | 13208 | 19567 | 0.0400 | 0.0300 |
| pMON140826 | P-CUCme.10-1:1:1 | 21 | 352 | 14805.3 | 22200 | 0.0200 | 0.0200 |
| pMON140827 | EXP-CUCme.eEF1a:1:1 | 162 | 724 | 9326.8 | 14476 | 0.0800 | 0.0500 |
| pMON140828 | P-CUCme.15-1:1:2 | 23 | 304 | 11798 | 17486 | 0.0300 | 0.0200 |
| pMON140829 | P-CUCme.16a-1:1:2 | 24 | 88 | 5429 | 9596 | 0.0200 | 0.0100 |
| pMON140830 | P-CUCme.17-1:1:2 | 26 | 180 | 10477.8 | 15291 | 0.0200 | 0.0100 |
| pMON140831 | P-CUCme.18-1:1:2 | 27 | 111 | 5059.3 | 6778 | 0.0200 | 0.0200 |
| pMON140832 | P-CUCme.19-1:1:3 | 167 | 121 | 3765 | 6032 | 0.0300 | 0.0200 |
| pMON140833 | P-CUCme.20-1:3 | 211 | 155 | 10458.8 | 14748 | 0.0100 | 0.0100 |
| pMON140834 | P-CUCme.21-1:1:1 | 30 | 582 | 7760 | 11440 | 0.0800 | 0.0500 |
| pMON140835 | P-CUCme.22-1:1:3 | 31 | 400 | 11393.8 | 18654 | 0.0400 | 0.0200 |
| pMON140836 | EXP-CUCme.SAMS2:1:1 | 168 | 568 | 9466.3 | 13962 | 0.0600 | 0.0400 |
| pMON140837 | P-CUCme.26-1:1:2 | 33 | 87 | 6683 | 8494 | 0.0100 | 0.0100 |
| pMON140838 | P-CUCme.28-1:1:2 | 34 | 171 | 19104.8 | 29619 | 0.0100 | 0.0100 |
| pMON140839 | EXP-CUCme.29:1:2 | 212 | 90 | 11247.3 | 15919 | 0.0100 | 0.0057 |

To compare the relative activity of each promoter in soybean cotyledon protoplasts, GUS values were expressed as a ratio of GUS to luciferase activity and normalized with respect to the expression levels observed for the constitutive expression element groups, EXP-At.Act7:1:11 and EXP-CaMV.35S-enh+Ph.DnaK:1:3. Table 9 below shows the GUS to firefly luciferase (FLuc) ratios normalized with respect to EXP-At.Act7:1:11 and EXP-CaMV.35S-enh+Ph.DnaK:1:3. Table 10 below shows the GUS to *renilla* luciferase (RLuc) ratios normalized with respect to EXP-At.Act7:1:11 and EXP-CaMV.35S-enh+Ph.DnaK:1:3.

TABLE 9

GUS to firefly luciferase (FLuc) ratios normalized with respect to EXP-At.Act7:1:11 and EXP-CaMV.35S-enh + Ph.DnaK:1:3.

| Construct | Regulatory Element | SEQ ID NO: | GUS/FLuc normalized with respect to EXP-At.Act7:1:11 | GUS/FLuc normalized with respect to EXP-CaMV.35S-enh + Ph.DnaK:1:3 |
|---|---|---|---|---|
| pMON80585 | EXP-At.Atntt1:1:2 | 200 | 1.12 | 0.08 |
| pMON109584 | EXP-CaMV.35S-enh + Ph.DnaK:1:3 | 201 | 13.48 | 1.00 |
| pMON118756 | EXP-At.Act7:1:11 | 202 | 1.00 | 0.07 |
| pMON124912 | Promoterless | | 0.05 | 0.00 |
| pMON140818 | P-CUCme.1-1:1:1rc | 155 | 0.41 | 0.03 |
| pMON140819 | P-CUCme.2-1:1:1 | 14 | 0.25 | 0.02 |
| pMON140820 | P-CUCme.3-1:1:3 | 15 | 0.05 | 0.00 |
| pMON140821 | EXP-CUCme.4:1:1 | 156 | 5.52 | 0.41 |
| pMON140822 | EXP-CUCme.5:1:1 | 159 | 0.40 | 0.03 |
| pMON140823 | P-CUCme.6-1:1:1 | 18 | 0.22 | 0.02 |
| pMON140824 | P-CUCme.8-1:1:2 | 19 | 0.14 | 0.01 |
| pMON140825 | P-CUCme.9-1:1:2 | 20 | 0.39 | 0.03 |
| pMON140826 | P-CUCme.10-1:1:1 | 21 | 0.24 | 0.02 |
| pMON140827 | EXP-CUCme.eEF1a:1:1 | 162 | 0.78 | 0.06 |
| pMON140828 | P-CUCme.15-1:1:2 | 23 | 0.26 | 0.02 |
| pMON140829 | P-CUCme.16a-1:1:2 | 24 | 0.16 | 0.01 |
| pMON140830 | P-CUCme.17-1:1:2 | 26 | 0.17 | 0.01 |
| pMON140831 | P-CUCme.18-1:1:2 | 27 | 0.22 | 0.02 |
| pMON140832 | P-CUCme.19-1:1:3 | 167 | 0.32 | 0.02 |
| pMON140833 | P-CUCme.20-1:3 | 211 | 0.15 | 0.01 |

TABLE 9-continued

GUS to firefly luciferase (FLuc) ratios normalized with respect to EXP-At.Act7:1:11 and EXP-CaMV.35S-enh + Ph.DnaK:1:3.

| Construct | Regulatory Element | SEQ ID NO: | GUS/FLuc normalized with respect to EXP-At.Act7:1:11 | GUS/FLuc normalized with respect to EXP-CaMV.35S-enh + Ph.DnaK:1:3 |
|---|---|---|---|---|
| pMON140834 | P-CUCme.21-1:1:1 | 30 | 0.75 | 0.06 |
| pMON140835 | P-CUCme.22-1:1:3 | 31 | 0.35 | 0.03 |
| pMON140836 | EXP-CUCme.SAMS2:1:1 | 168 | 0.60 | 0.04 |
| pMON140837 | P-CUCme.26-1:1:2 | 33 | 0.13 | 0.01 |
| pMON140838 | P-CUCme.28-1:1:2 | 34 | 0.09 | 0.01 |
| pMON140839 | EXP-CUCme.29:1:2 | 212 | 0.08 | 0.01 |

TABLE 10

GUS to *renilla* luciferase (RLuc) ratios normalized with respect to EXP-At.Act7:1:11 and EXP-CaMV.35S-enh + Ph.DnaK:1:3.

| Construct | Regulatory Element | SEQ ID NO: | GUS/RLuc normalized with respect to EXP-At.Act7:1:11 | GUS/RLuc normalized with respect to EXP-CaMV.35S-enh + Ph.DnaK:1:3 |
|---|---|---|---|---|
| pMON80585 | EXP-At.Atntt1:1:2 | 200 | 0.96 | 0.18 |
| pMON109584 | EXP-CaMV.35S-enh + Ph.DnaK:1:3 | 201 | 5.21 | 1.00 |
| pMON118756 | EXP-At.Act7:1:11 | 202 | 1.00 | 0.19 |
| pMON124912 | Promoterless | | 0.05 | 0.01 |
| pMON140818 | P-CUCme.1-1:1:1rc | 155 | 0.42 | 0.08 |
| pMON140819 | P-CUCme.2-1:1:1 | 14 | 0.23 | 0.04 |
| pMON140820 | P-CUCme.3-1:1:3 | 15 | 0.05 | 0.01 |
| pMON140821 | EXP-CUCme.4:1:1 | 156 | 4.12 | 0.79 |
| pMON140822 | EXP-CUCme.5:1:1 | 159 | 0.40 | 0.08 |
| pMON140823 | P-CUCme.6-1:1:1 | 18 | 0.20 | 0.04 |
| pMON140824 | P-CUCme.8-1:1:2 | 19 | 0.11 | 0.02 |
| pMON140825 | P-CUCme.9-1:1:2 | 20 | 0.36 | 0.07 |
| pMON140826 | P-CUCme.10-1:1:1 | 21 | 0.22 | 0.04 |
| pMON140827 | EXP-CUCme.eEF1a:1:1 | 162 | 0.68 | 0.13 |
| pMON140828 | P-CUCme.15-1:1:2 | 23 | 0.24 | 0.05 |
| pMON140829 | P-CUCme.16a-1:1:2 | 24 | 0.13 | 0.02 |
| pMON140830 | P-CUCme.17-1:1:2 | 26 | 0.16 | 0.03 |
| pMON140831 | P-CUCme.18-1:1:2 | 27 | 0.22 | 0.04 |
| pMON140832 | P-CUCme.19-1:1:3 | 167 | 0.27 | 0.05 |
| pMON140833 | P-CUCme.20-1:3 | 211 | 0.14 | 0.03 |
| pMON140834 | P-CUCme.21-1:1:1 | 30 | 0.69 | 0.13 |
| pMON140835 | P-CUCme.22-1:1:3 | 31 | 0.29 | 0.06 |
| pMON140836 | EXP-CUCme.SAMS2:1:1 | 168 | 0.55 | 0.11 |
| pMON140837 | P-CUCme.26-1:1:2 | 33 | 0.14 | 0.03 |
| pMON140838 | P-CUCme.28-1:1:2 | 34 | 0.08 | 0.02 |
| pMON140839 | EXP-CUCme.29:1:2 | 212 | 0.08 | 0.01 |

As can be seen in Tables 9 and 10, most of the expression element groups tested, demonstrated the ability to drive transgene expression in soybean cotyledon protoplast cells. One expression element group, EXP-CUCme.4:1:1 (SEQ ID NO: 156) demonstrated levels of transgene expression higher than that of EXP-At.Act7:1:11 in this assay.

Example 5: Analysis of Regulatory Elements Driving GUS in Bombarded Soybean Leaves and Roots Soybean leaves and roots were transformed with plant expression vectors containing a test transcriptional regulatory expression element group driving expression of the ß-glucuronidase (GUS) transgene and compared to GUS expression in roots and leaves in which expression of GUS is driven by known constitutive promoters.

Expression of a transgene driven by P-CUCme.1-1:1:1rc (SEQ ID NO: 155), P-CUCme.2-1:1:1 (SEQ ID NO: 14), P-CUCme.3-1:1:3 (SEQ ID NO: 15), EXP-CUCme.4:1:1 (SEQ ID NO: 156), EXP-CUCme.5:1:1 (SEQ ID NO: 159), P-CUCme.6-1:1:1 (SEQ ID NO: 18), P-CUCme.8-1:1:2 (SEQ ID NO: 19), P-CUCme.9-1:1:2 (SEQ ID NO: 20), P-CUCme.10-1:1:1 (SEQ ID NO: 21), EXP-CUCme.eEF1a:1:1 (SEQ ID NO: 162), P-CUCme.15-1:1:2 (SEQ ID NO: 23), P-CUCme.16a-1:1:2 (SEQ ID NO: 24), P-CUCme.17-1:1:2 (SEQ ID NO: 26), P-CUCme.18-1:1:2 (SEQ ID NO: 27), P-CUCme.19-1:1:3 (SEQ ID NO: 167), P-CUCme.20-

1:3 (SEQ ID NO: 211), P-CUCme.21-1:1:1 (SEQ ID NO: 30), P-CUCme.22-1:1:3 (SEQ ID NO: 31), EXP-CUCme.SAMS2:1:1 (SEQ ID NO: 168), P-CUCme.26-1:1:2 (SEQ ID NO: 33), P-CUCme.28-1:1:2 (SEQ ID NO: 34) and EXP-CUCme.29:1:2 (SEQ ID NO: 212) was compared with expression from known constitutive expression element groups in particle bombarded soybean leaves and roots. The plant expression vectors used for transformation of leaves and roots was the same as those presented in Table 7 of Example 4 above.

The plant expression vectors, pMON80585, pMON109584, pMON118756, pMON124912, pMON140818, pMON140819, pMON140820, pMON140821, pMON140822, pMON140823, pMON140824, pMON140825, pMON140826, pMON140827, pMON140828, pMON140829, pMON140830, pMON140831, pMON140832, pMON140833, pMON140834, pMON140835, pMON140836, pMON140837, pMON140838 and pMON140839 were used to transform soybean leaves and roots using particle bombardment transformation methods.

Briefly, A3244 soybean seeds were surface sterilized and allowed to germinate in trays with a photoperiod of 16 hours light and 8 hours of darkness. After approximately 13 days, leaf and root tissue was harvested under sterile conditions from the seedlings and used for bombardment. The tissue samples were randomly placed on a petri dish containing plant culture medium. Ten micrograms of plasmid DNA was used to coat 0.6 micron gold particles (Catalog #165-2262 Bio-Rad, Hercules, Calif.) for bombardment. Macro-carriers were loaded with the DNA-coated gold particles (Catalog #165-2335 Bio-Rad, Hercules Calif.). A PDS 1000/He biolistic gun was used for transformation (Catalog #165-2257 Bio-Rad, Hercules Calif.). The bombarded root and leaf tissues were allowed to incubate in the dark for 24 hours at 26 degrees Celsius. Following this overnight incubation, the tissues were stained in solution for GUS expression overnight at 37 degrees Celsius. After staining overnight, the tissues were soaked in 70% ethanol overnight to remove chlorophyll and reveal the GUS staining. The tissues were then photographed and a rating scale of "0", "+" to "++++++" reflecting the level of GUS expression is assigned to each construct (0—no expression, + to ++++++—low to high, respectively).

Expression of the GUS transgene demonstrated in each tissue is used to infer the relative potential level and specificity of each element's capacity to drive transgene expression in stably transformed corn plants. Average GUS expression ratings are provided in Table 11 below.

TABLE 11

GUS expression ratings for particle bombarded leaf and root.

| Construct | Regulatory Element | SEQ ID NO: | Leaf Expression | Root Expression |
|---|---|---|---|---|
| pMON80585 | EXP-At.Atntt1:1:2 | 200 | +++ | +++ |
| pMON109584 | EXP-CaMV.35S-enh + Ph.DnaK:1:3 | 201 | +++++ | ++ |
| pMON118756 | EXP-At.Act7:1:11 | 202 | ++++ | +++ |
| pMON124912 | Promoterless | | 0 | 0 |
| pMON140818 | P-CUCme.1-1:1:1rc | 155 | +++ | + |
| pMON140819 | P-CUCme.2-1:1:1 | 14 | ++ | + |
| pMON140820 | P-CUCme.3-1:1:3 | 15 | 0 | 0 |
| pMON140821 | EXP-CUCme.4:1:1 | 156 | ++++++ | +++ |
| pMON140822 | EXP-CUCme.5:1:1 | 159 | ++ | + |
| pMON140823 | P-CUCme.6-1:1:1 | 18 | ++ | + |
| pMON140824 | P-CUCme.8-1:1:2 | 19 | + | + |
| pMON140825 | P-CUCme.9-1:1:2 | 20 | ++ | + |
| pMON140826 | P-CUCme.10-1:1:1 | 21 | +++ | +++ |
| pMON140827 | EXP-CUCme.eEF1a:1:1 | 162 | ++++ | +++ |
| pMON140828 | P-CUCme.15-1:1:2 | 23 | + | + |
| pMON140829 | P-CUCme.16a-1:1:2 | 24 | + | − |
| pMON140830 | P-CUCme.17-1:1:2 | 26 | ++++ | + |
| pMON140831 | P-CUCme.18-1:1:2 | 27 | +++ | + |
| pMON140832 | P-CUCme.19-1:1:3 | 167 | + | + |
| pMON140833 | P-CUCme.20-1:3 | 211 | + | + |
| pMON140834 | P-CUCme.21-1:1:1 | 30 | + | + |
| pMON140835 | P-CUCme.22-1:1:3 | 31 | ++++ | + |
| pMON140836 | EXP-CUCme.SAMS2:1:1 | 168 | +++++ | +++ |
| pMON140837 | P-CUCme.26-1:1:2 | 33 | + | + |
| pMON140838 | P-CUCme.28-1:1:2 | 34 | + | + |
| pMON140839 | EXP-CUCme.29:1:2 | 212 | + | + |

As can be seen in Table 11 above, all but one of the expression element groups demonstrated the ability to drive transgene expression in particle bombarded soybean leaf and root tissue. Two expression element groups, P-CUCme.28-1:1:2 (SEQ ID NO: 34) and EXP-CUCme.4:1:1 (SEQ ID NO: 156) demonstrated similar or higher levels of expression relative to expression driven by EXP-CaMV.35S-enh+Ph.DnaK:1:3 in this assay.

Example 6: Analysis of Regulatory Elements Driving GUS in Soy Cotyledon Protoplast Using Transgene Cassette Amplicons Soybean cotyledon protoplasts were transformed with transgene cassette amplicons containing a transcriptional regulatory expression element group driving expression of the ß-glucuronidase (GUS) transgene and compared to GUS expression in leaf protoplasts in which expression of GUS is driven by known constitutive promoters. The transgene cassette amplicons were comprised of an EXP sequence, operably linked to a GUS coding sequence (GUS, SEQ ID NO: 206), operably linked to a 3' UTR (T-Gb.FbL2-1:1:1, SEQ ID NO: 205). Average GUS expression was compared to the control EXP elements, P-CaMV.35S-enh-1:1:102/L-CaMV.35S-1:1:2 (SEQ ID NO: 210) and EXP-At.Atntt1:1:2 (SEQ ID NO: 200).

A plasmid, for use in co-transformation and normalization of data was also used in a similar manner as that described above in Example 2. The transformation control plasmid was comprised of a constitutive promoter, driving the expression of the firefly (*Photinus pyralis*) luciferase coding sequence (FLuc, SEQ ID NO: 205), operably linked 5' to a 3' termination region from the *Agrobacterium tumefaciens* nopaline synthase gene (T-AGRtu.nos-1:1:13, SEQ ID NO: 209).

Table 12 below shows the mean GUS expression values conferred by each transgene amplicon. Table 13 below shows the GUS to firefly luciferase (FLuc) ratios normalized with respect to EXP-At.Atntt1:1:2 and P-CaMV.35S-enh-1:1:102/L-CaMV.35S-1:1:2

TABLE 12

| Average GUS and luciferase expression values and GUS/luciferase ratios. | | | | | |
|---|---|---|---|---|---|
| Amplicon ID | Regulatory Element | SEQ ID NO: | Mean GUS | Mean Fluc | GUS/Fluc |
| No DNA | | | 0.00 | 0.00 | 0.00 |
| pMON124912 | No promoter | | 54.67 | 34905.00 | 0.00 |
| pMON33449 | P-CaMV.35S-enh-1:1:102/L-CaMV.35S-1:1:2 | 210 | 107064.67 | 21757.67 | 4.92 |
| pMON80585 | EXP-At.Atntt1:1:2 | 200 | 4962.33 | 40778.67 | 0.12 |
| 56969 | CumMe_WSM_SF16429.G5670 | 40 | 283.67 | 53452.00 | 0.01 |
| 56877 | P-CUCme.CumMe_WSM_SF16444.G5140-1:1:1 | 175 | 5297.67 | 46576.67 | 0.11 |
| 56749 | P-CUCme.CumMe_WSM_SF16563.G5560-1:1:1 | 176 | 280.67 | 41958.33 | 0.01 |
| 56918 | CumMe_WSM_SF17051.G5470 | 48 | 1088.00 | 36321.00 | 0.03 |
| 56849 | P-CUCme.CumMe_WSM_SF17111.G5790-1:1:1 | 177 | 196.00 | 48128.00 | 0.00 |
| 56754 | P-CUCme.WSM_SF17252.G7330-1:1:1 | 179 | 175.67 | 45427.00 | 0.00 |
| 56892 | CumMe_WSM_SF17349.G5770 | 56 | 34.00 | 38016.00 | 0.00 |
| 56477 | CumMe_WSM_SF17866.G6050 | 62 | 862.00 | 52203.33 | 0.02 |
| 56842 | P-CUCme.CumMe_WSM_SF18488.G5340-1:1:1 | 181 | 2892.67 | 49144.33 | 0.06 |
| 56852 | P-CUCme.CumMe_WSM_SF18536.G6480-1:1:1 | 182 | 3462.67 | 46549.33 | 0.07 |
| 56497 | CumMe_WSM_SF18575.G6410 | 71 | 92.67 | 47628.33 | 0.00 |
| 56847 | P-CUCme.CumMe_WSM_SF18634.G5190-1:1:1 | 183 | 122.33 | 36815.33 | 0.00 |
| 56746 | P-CUCme.CumMe_WSM_SF18716.G5860-1:1:1 | 184 | 14.33 | 62483.33 | 0.00 |
| 56883 | CumMe_WSM_SF18986.G6110 | 79 | 863.33 | 54379.33 | 0.02 |
| 56734 | EXP-CUCme.WSM_SF19064.G5690:1:1 | 185 | 142.00 | 46962.67 | 0.00 |
| 56912 | P-CUCme.CumMe_WSM_SF19647.G5760-1:1:1 | 188 | 7659.00 | 46935.67 | 0.16 |
| 56482 | P-CUCme.CumMe_WSM_SF19839.G5090-1:1:1 | 189 | 3279.00 | 37070.67 | 0.09 |
| 56963 | CumMe_WSM_SF19902.G5260 | 87 | 1629.00 | 55649.00 | 0.03 |
| 56747 | P-CUCme.CumMe_WSM_SF20132.G5560-1:1:1 | 190 | 340.33 | 40577.00 | 0.01 |
| 56479 | CumMe_WSM_SF20359.G5870 | 92 | 192.00 | 61341.67 | 0.00 |
| 56744 | CumMe_WSM_SF206458.G5970 | 98 | 154.67 | 33139.33 | 0.00 |
| 56948 | CumMe_WSM_SF206534.G5200 | 99 | 62.00 | 52118.00 | 0.00 |
| 56896 | CumMe_WSM_SF22008.G5670 | 108 | 1585.00 | 53540.00 | 0.03 |
| 56919 | CumMe_WSM_SF22275.G5780 | 112 | 8.33 | 48546.33 | 0.00 |
| 56967 | CumMe_WSM_SF22355.G5310 | 113 | 74.33 | 36202.67 | 0.00 |
| 56837 | P-CUCme.CumMe_WSM_SF22531.G5120-1:1:1 | 192 | 1526.67 | 52799.33 | 0.03 |
| 56940 | CumMe_WSM_SF22870.G5370 | 115 | 14.67 | 53663.33 | 0.00 |
| 56495 | P-CUCme.CumMe_WSM_SF23760.G5200-1:1:1 | 193 | 196.33 | 49870.67 | 0.00 |
| 56868 | P-CUCme.CumMe_WSM_SF23906.G6180-1:1:1 | 194 | 1584.33 | 42532.33 | 0.04 |
| 56998 | CumMe_WSM_SF24045.G5400 | 123 | 80.67 | 47553.00 | 0.00 |
| 56976 | P-CUCme.CumMe_WSM_SF25141.G5160-1:1:2 | 195 | 4506.00 | 57213.00 | 0.08 |
| 56742 | P-CUCme.CumMe_WSM_SF25355.G5000-1:1:1 | 196 | 4.00 | 41114.33 | 0.00 |
| 56915 | P-CUCme.CumMe_WSM_SF25936.G5450-1:1:1 | 197 | 965.33 | 34494.67 | 0.03 |
| 56854 | CumMe_WSM_SF28729.G5340 | 134 | 208.33 | 53956.00 | 0.00 |
| 56936 | CumMe_WSM_SF31264.G5380 | 136 | 292.67 | 42320.67 | 0.01 |
| 56863 | P-CUCme.CumMe_WSM_SF35856.G5150-1:1:1 | 198 | 125.00 | 48705.33 | 0.00 |
| 56751 | P-CUCme.CumMe_WSM_SF41124.G5080-1:1:1 | 199 | 31.33 | 53595.00 | 0.00 |
| 56921 | CumMe_WSM_SF41254.G5160 | 141 | 11.67 | 52643.67 | 0.00 |
| 56884 | CumMe_WSM_SF42141.G5110 | 146 | 48.33 | 40556.67 | 0.00 |

TABLE 13

| GUS to firefly luciferase (FLuc) ratios normalized with respect to EXP-At.Atntt1:1:2 and P-CaMV.35S-enh-1:1:102/L-CaMV.35S-1:1:2. | | | | |
|---|---|---|---|---|
| Amplicon ID | Regulatory Element | SEQ ID NO: | GUS/Fluc normalized with respect to EXP-At.Atntt1:1:2 | GUS/Fluc normalized with respect to P-CaMV.35S-enh-1:1:102/L-CaMV.35S-1:1:2 |
| No DNA | | | 0.00 | 0.00 |
| pMON124912 | No promoter | | 0.01 | 0.00 |
| pMON33449 | P-CaMV.35S-enh-1:1:102/L-CaMV.35S-1:1:2 | 210 | 40.44 | 1.00 |
| pMON80585 | EXP-At.Atntt1:1:2 | 200 | 1.00 | 0.02 |
| 56969 | CumMe_WSM_SF16429.G5670 | 40 | 0.04 | 0.00 |
| 56877 | P-CUCme.CumMe_WSM_SF16444.G51140-1:1:1 | 175 | 0.93 | 0.02 |
| 56749 | P-CUCme.CumMe_WSM_SF16563.G5560-1:1:1 | 176 | 0.05 | 0.00 |
| 56918 | CumMe_WSM_SF17051.G5470 | 48 | 0.25 | 0.01 |
| 56849 | P-CUCme.CumMe_WSM_SF17111.G5790-1:1:1 | 177 | 0.03 | 0.00 |
| 56754 | P-CUCme.WSM_SF17252.G7330-1:1:1 | 179 | 0.03 | 0.00 |
| 56892 | CumMe_WSM_SF17349.G5770 | 56 | 0.01 | 0.00 |
| 56477 | CumMe_WSM_SF17866.G6050 | 62 | 0.14 | 0.00 |
| 56842 | P-CUCme.CumMe_WSM_SF18488.G5340-1:1:1 | 181 | 0.48 | 0.01 |
| 56852 | P-CUCme.CumMe_WSM_SF18536.G6480-1:1:1 | 182 | 0.61 | 0.02 |
| 56497 | CumMe_WSM_SF18575.G6410 | 71 | 0.02 | 0.00 |
| 56847 | P-CUCme.CumMe_WSM_SF18634.G5190-1:1:1 | 183 | 0.03 | 0.00 |
| 56746 | P-CUCme.CumMe_WSM_SF18716.G5860-1:1:1 | 184 | 0.00 | 0.00 |

TABLE 13-continued

GUS to firefly luciferase (FLuc) ratios normalized with respect
to EXP-At.Atntt1:1:2 and P-CaMV.35S-enh-1:1:102/L-CaMV.35S-1:1:2.

| Amplicon ID | Regulatory Element | SEQ ID NO: | GUS/Fluc normalized with respect to EXP-At.Atntt1:1:2 | GUS/Fluc normalized with respect to P-CaMV.35S-enh-1:1:102/L-CaMV.35S-1:1:2 |
|---|---|---|---|---|
| 56883 | CumMe_WSM_SF18986.G6110 | 79 | 0.13 | 0.00 |
| 56734 | EXP-CUCme.WSM_SF19064.G5690:1:1 | 185 | 0.02 | 0.00 |
| 56912 | P-CUCme.CumMe_WSM_SF19647.G5760-1:1:1 | 188 | 1.34 | 0.03 |
| 56482 | P-CUCme.CumMe_WSM_SF19839.G5090-1:1:1 | 189 | 0.73 | 0.02 |
| 56963 | CumMe_WSM_SF19902.G5260 | 87 | 0.24 | 0.01 |
| 56747 | P-CUCme.CumMe_WSM_SF20132.G5560-1:1:1 | 190 | 0.07 | 0.00 |
| 56479 | CumMe_WSM_SF20359.G5870 | 92 | 0.03 | 0.00 |
| 56744 | CumMe_WSM_SF206458.G5970 | 98 | 0.04 | 0.00 |
| 56948 | CumMe_WSM_SF206534.G5200 | 99 | 0.01 | 0.00 |
| 56896 | CumMe_WSM_SF22008.G5670 | 108 | 0.24 | 0.01 |
| 56919 | CumMe_WSM_SF22275.G5780 | 112 | 0.00 | 0.00 |
| 56967 | CumMe_WSM_SF22355.G5310 | 113 | 0.02 | 0.00 |
| 56837 | P-CUCme.CumMe_WSM_SF22531.G5120-1:1:1 | 192 | 0.24 | 0.01 |
| 56940 | CumMe_WSM_SF22870.G5370 | 115 | 0.00 | 0.00 |
| 56495 | P-CUCme.CumMe_WSM_SF23760.G5200-1:1:1 | 193 | 0.03 | 0.00 |
| 56868 | P-CUCme.CumMe_WSM_SF23906.G6180-1:1:1 | 194 | 0.31 | 0.01 |
| 56998 | CumMe_WSM_SF24045.G5400 | 123 | 0.01 | 0.00 |
| 56976 | P-CUCme.CumMe_WSM_SF25141.G5160-1:1:2 | 195 | 0.65 | 0.02 |
| 56742 | P-CUCme.CumMe_WSM_SF25355.G5000-1:1:1 | 196 | 0.00 | 0.00 |
| 56915 | P-CUCme.CumMe_WSM_SF25936.G5450-1:1:1 | 197 | 0.23 | 0.01 |
| 56854 | CumMe_WSM_SF28729.G5340 | 134 | 0.03 | 0.00 |
| 56936 | CumMe_WSM_SF31264.G5380 | 136 | 0.06 | 0.00 |
| 56863 | P-CUCme.CumMe_WSM_SF35856.G5150-1:1:1 | 198 | 0.02 | 0.00 |
| 56751 | P-CUCme.CumMe_WSM_SF41124.G5080-1:1:1 | 199 | 0.00 | 0.00 |
| 56921 | CumMe_WSM_SF41254.G5160 | 141 | 0.00 | 0.00 |
| 56884 | CumMe_WSM_SF42141.G5110 | 146 | 0.01 | 0.00 |

As can be seen in Table 12 above, not all EXP sequences demonstrated the ability to drive transgene expression when compared to the promoterless control. However, the EXP sequences, CumMe_WSM_SF16429.G5670 (SEQ ID NO: 40), P-CUCme.CumMe_WSM_SF16444.G5140-1:1:1 (SEQ ID NO: 175), P-CUCme.CumMe_WSM_SF16563.G5560-1:1:1 (SEQ ID NO: 176), CumMe_WSM_SF17051.G5470 (SEQ ID NO: 48), P-CUCme.CumMe_WSM_SF17111.65790-1:1:1 (SEQ ID NO: 177), P-CUCme.WSM_SF17252.G7330-1:1:1 (SEQ ID NO: 179), CumMe_WSM_SF17866.G6050 (SEQ ID NO: 62), P-CUCme.CumMe_WSM_SF18488.G5340-1:1:1 (SEQ ID NO: 181), P-CUCme.CumMe_WSM_SF18536.G6480-1:1:1 (SEQ ID NO: 182), CumMe_WSM_SF18575.G6410 (SEQ ID NO: 71), P-CUCme.CumMe_WSM_SF18634.G5190-1:1:1 (SEQ ID NO: 183), CumMe_WSM_SF18986.G6110 (SEQ ID NO: 79), EXP-CUCme.WSM_SF19064.G5690:1:1 (SEQ ID NO: 185), P-CUCme.CumMe_WSM_SF19647.G5760-1:1:1 (SEQ ID NO: 188), P-CUCme.CumMe_WSM_SF19839.G5090-1:1:1 (SEQ ID NO: 189), CumMe_WSM_SF19902.G5260 (SEQ ID NO: 87), P-CUCme.CumMe_WSM_SF20132.G5560-1:1:1 (SEQ ID NO: 190), CumMe_WSM_SF20359.G5870 (SEQ ID NO: 92), CumMe_WSM_SF206458.G5970 (SEQ ID NO: 98), CumMe_WSM_SF206534.G5200 (SEQ ID NO: 99), CumMe_WSM_SF22008.G5670 (SEQ ID NO: 108), CumMe_WSM_SF22355.G5310 (SEQ ID NO: 113), P-CUCme.CumMe_WSM_SF22531.G5120-1:1:1 (SEQ ID NO: 192), EXP-CUCme.WSM_SF19064.G5690:1:1 (SEQ ID NO: 193), P-CUCme.CumMe_WSM_SF23906.G6180-1:1:1 (SEQ ID NO: 194), CumMe_WSM_SF24045.G5400 (SEQ ID NO: 123), P-CUCme.CumMe_WSM_SF25141.G5160-1:1:2 (SEQ ID NO: 195), P-CUCme.CumMe_WSM_SF25936.G5450-1:1:1 (SEQ ID NO: 197), CumMe_WSM_SF28729.G5340 (SEQ ID NO: 134), CumMe_WSM_SF31264.G5380 (SEQ ID NO: 136) and P-CUCme.CumMe_WSM_SF35856.G5150-1:1:1 (SEQ ID NO: 198) demonstrated the ability to drive transgene expression in soybean cotyledon protoplasts at a level similar or greater than EXP-At.Atntt1:1:2. As shown in Table 13 above, the EXP sequence P-CUCme.CumMe_WSM_SF19647.G5760-1:1:1 (SEQ ID NO: 188) demonstrated the ability to drive transgene expression in this assay at a level greater than EXP-At.Atntt1:1:2.

Example 7: Analysis of Regulatory Elements Driving GUS in Cotton Leaf Protoplasts Cotton leaf protoplasts were transformed with plant expression vectors containing a test transcriptional regulatory expression element group driving expression of the ß-glucuronidase (GUS) transgene and compared to GUS expression in leaf protoplasts in which expression of GUS is driven by known constitutive promoters.

Expression of a transgene driven by P-CUCme.1-1:1:1rc (SEQ ID NO: 155), P-CUCme.2-1:1:1 (SEQ ID NO: 14), P-CUCme.3-1:1:3 (SEQ ID NO: 15), EXP-CUCme.4:1:1 (SEQ ID NO: 156), P-CUCme.6-1:1:1 (SEQ ID NO: 18), P-CUCme.8-1:1:2 (SEQ ID NO: 19), P-CUCme.9-1:1:2 (SEQ ID NO: 20), P-CUCme.10-1:1:1 (SEQ ID NO: 21), EXP-CUCme.eEF1a:1:1 (SEQ ID NO: 162), P-CUCme.15-1:1:2 (SEQ ID NO: 23), P-CUCme.16a-1:1:2 (SEQ ID NO: 24), P-CUCme.17-1:1:2 (SEQ ID NO: 26), P-CUCme.18-1:1:2 (SEQ ID NO: 27), P-CUCme.19-1:1:3 (SEQ ID NO: 167), P-CUCme.20-1:3 (SEQ ID NO: 211), P-CUCme.21-

1:1:1 (SEQ ID NO: 30), P-CUCme.22-1:1:3 (SEQ ID NO: 31), EXP-CUCme.SAMS2:1:1 (SEQ ID NO: 168), P-CUCme.26-1:1:2 (SEQ ID NO: 33), P-CUCme.28-1:1:2 (SEQ ID NO: 34) and EXP-CUCme.29:1:2 (SEQ ID NO: 212) was compared with expression from known constitutive expression element groups. Each plant expression vector was comprised of a right border region from *Agrobacterium tumefaciens*, a first transgene cassette comprised of a test promoter or known constitutive promoter operably linked 5' to a coding sequence for ß-glucuronidase (GUS, SEQ ID NO: 206) containing a processable intron derived from the potato light-inducible tissue-specific ST-LS1 gene (Genbank Accession: X04753), operably linked 5' to a 3' termination region from the *Gossypium barbadense* E6 gene (T-Gb.E6-3b:1:1, SEQ ID NO: 204), the *Pisum sativum* RbcS2-E9 gene (T-Ps.RbcS2-E9-1:1:6, SEQ ID NO: 203), or the *Gossypium barbadense* FbLate-2 gene (T-Gb.FbL2-1:1:1, SEQ ID NO: 205); a second transgene selection cassette used for selection of transformed plant cells that either confers resistance to the herbicide glyphosate (driven by the *Arabidopsis* Actin 7 promoter) or the antibiotic, kanamycin and a left border region from *A. tumefaciens*. A promoterless control plant expression vector (pMON124912) served as a negative control for expression. The foregoing test and constitutive expression element groups were cloned into plant expression vectors as shown in Table 14 below.

TABLE 14

Plant expression vectors and corresponding expression element group and 3' UTR.

| Construct | Regulatory Element | SEQ ID NO: | 3' UTR |
|---|---|---|---|
| pMON109584 | EXP-CaMV.35S-enh + Ph.DnaK:1:3 | 201 | T-Gb.E6-3b:1:1 |
| pMON118756 | EXP-At.Act7:1:11 | 202 | T-Gb.E6-3b:1:1 |
| pMON124912 | Promoterless | | T-Gb.FbL2-1:1:1 |
| pMON140818 | P-CUCme.1-1:1:1rc | 155 | T-Gb.FbL2-1:1:1 |
| pMON140819 | P-CUCme.2-1:1:1 | 14 | T-Gb.FbL2-1:1:1 |
| pMON140820 | P-CUCme.3-1:1:3 | 15 | T-Gb.FbL2-1:1:1 |
| pMON140821 | EXP-CUCme.4:1:1 | 156 | T-Gb.FbL2-1:1:1 |
| pMON140823 | P-CUCme.6-1:1:1 | 18 | T-Gb.FbL2-1:1:1 |
| pMON140824 | P-CUCme.8-1:1:2 | 19 | T-Gb.FbL2-1:1:1 |
| pMON140825 | P-CUCme.9-1:1:2 | 20 | T-Gb.FbL2-1:1:1 |
| pMON140826 | P-CUCme.10-1:1:1 | 21 | T-Gb.FbL2-1:1:1 |
| pMON140827 | EXP-CUCme.eEF1a:1:1 | 162 | T-Gb.FbL2-1:1:1 |
| pMON140828 | P-CUCme.15-1:1:2 | 23 | T-Gb.FbL2-1:1:1 |
| pMON140829 | P-CUCme.16a-1:1:2 | 24 | T-Gb.FbL2-1:1:1 |
| pMON140830 | P-CUCme.17-1:1:2 | 26 | T-Gb.FbL2-1:1:1 |
| pMON140831 | P-CUCme.18-1:1:2 | 27 | T-Gb.FbL2-1:1:1 |
| pMON140832 | P-CUCme.19-1:1:3 | 167 | T-Gb.FbL2-1:1:1 |

TABLE 14-continued

Plant expression vectors and corresponding expression element group and 3' UTR.

| Construct | Regulatory Element | SEQ ID NO: | 3' UTR |
|---|---|---|---|
| pMON140833 | P-CUCme.20-1:3 | 211 | T-Gb.FbL2-1:1:1 |
| pMON140834 | P-CUCme.21-1:1:1 | 30 | T-Gb.FbL2-1:1:1 |
| pMON140835 | P-CUCme.22-1:1:3 | 31 | T-Gb.FbL2-1:1:1 |
| pMON140836 | EXP-CUCme.SAMS2:1:1 | 168 | T-Gb.FbL2-1:1:1 |
| pMON140837 | P-CUCme.26-1:1:2 | 33 | T-Gb.FbL2-1:1:1 |
| pMON140838 | P-CUCme.28-1:1:2 | 34 | T-Gb.FbL2-1:1:1 |
| pMON140839 | EXP-CUCme.29:1:2 | 212 | T-Gb.FbL2-1:1:1 |

Two plasmids, for use in co-transformation and normalization of data, were also constructed. One transformation control plasmid was comprised of a constitutive promoter, driving the expression of the firefly (*Photinus pyralis*) luciferase coding sequence (FLuc, SEQ ID NO: 205), operably linked 5' to a 3' termination region from the *Agrobacterium tumefaciens* nopaline synthase gene (T-AGRtu.nos-1:1:13, SEQ ID NO: 209). The other transformation control plasmid was comprised of a constitutive promoter, driving the expression of the sea pansy (*Renilla reniformis*) luciferase coding sequence (RLuc, SEQ ID NO: 206), operably linked 5' to a 3' termination region from the *Agrobacterium tumefaciens* nopaline synthase gene.

The plant expression vectors, pMON80585, pMON109584, pMON118756, pMON124912, pMON140818, pMON140819, pMON140820, pMON140821, pMON140823, pMON140824, pMON140825, pMON140826, pMON140827, pMON140828, pMON140829, pMON140830, pMON140831, pMON140832, pMON140833, pMON140834, pMON140835, pMON140836, pMON140837, pMON140838 and pMON140839 were used to transform cotton leaf protoplast cells using PEG transformation methods. Protoplast cells were transformed with equimolar amounts of each of the two transformation control plasmids and a test plant expression vector. GUS and luciferase activity was assayed. Measurements of both GUS and luciferase were conducted by placing aliquots of a lysed preparation of cells transformed as above into two different small-well trays. One tray was used for GUS measurements, and a second tray was used to perform a dual luciferase assay using the dual luciferase reporter assay system (Promega Corp., Madison, Wis.; see for example, Promega Notes Magazine, No: 57, 1996, p. 02). Sample measurements were made using 4 replicates per transformation. The average GUS and luciferase values are presented in Table 15 below.

TABLE 15

Average GUS and luciferase expression values and GUS/luciferase ratios.

| Construct | Regulatory Element | SEQ ID NO: | Average GUS | Average FLuc | Average RLuc | GUS/ FLuc | GUS/ RLuc |
|---|---|---|---|---|---|---|---|
| pMON109584 | EXP-CaMV.35S-enh + Ph.DnaK:1:3 | 201 | 5322.8 | 14842.8 | 27990.5 | 0.3586 | 0.1902 |
| pMON118756 | EXP-At.Act7:1:11 | 202 | 1006.3 | 19746.8 | 25582.3 | 0.0510 | 0.0393 |
| pMON124912 | Promoterless | | 21 | 19248.5 | 25012 | 0.0011 | 0.0008 |
| pMON140818 | P-CUCme.1-1:1:1rc | 155 | 170.3 | 17796.8 | 22026.3 | 0.0096 | 0.0077 |
| pMON140819 | P-CUCme.2-1:1:1 | 14 | 34.8 | 16326.3 | 21407.5 | 0.0021 | 0.0016 |
| pMON140820 | P-CUCme.3-1:1:3 | 15 | 51.5 | 17356.8 | 21523.8 | 0.0030 | 0.0024 |
| pMON140821 | EXP-CUCme.4:1:1 | 156 | 3497.8 | 18745.3 | 26065.3 | 0.1866 | 0.1342 |

TABLE 15-continued

Average GUS and luciferase expression values and GUS/luciferase ratios.

| Construct | Regulatory Element | SEQ ID NO: | Average GUS | Average FLuc | Average RLuc | GUS/ FLuc | GUS/ RLuc |
|---|---|---|---|---|---|---|---|
| pMON140823 | P-CUCme.6-1:1:1 | 18 | 40.8 | 19533.8 | 26361.5 | 0.0021 | 0.0015 |
| pMON140824 | P-CUCme.8-1:1:2 | 19 | 22 | 19701 | 26278 | 0.0011 | 0.0008 |
| pMON140825 | P-CUCme.9-1:1:2 | 20 | 372.5 | 21972.3 | 28755 | 0.0170 | 0.0130 |
| pMON140826 | P-CUCme.10-1:1:1 | 21 | 198 | 21362.8 | 28902 | 0.0093 | 0.0069 |
| pMON140827 | EXP-CUCme.eEF1a:1:1 | 162 | 725 | 21589 | 27635.3 | 0.0336 | 0.0262 |
| pMON140828 | P-CUCme.15-1:1:2 | 23 | 55.3 | 17706 | 28846 | 0.0031 | 0.0019 |
| pMON140829 | P-CUCme.16a-1:1:2 | 24 | 14 | 23289.5 | 30190 | 0.0006 | 0.0005 |
| pMON140830 | P-CUCme.17-1:1:2 | 26 | 155.5 | 23178.3 | 31602.8 | 0.0067 | 0.0049 |
| pMON140831 | P-CUCme.18-1:1:2 | 27 | 86.8 | 19085.8 | 22396.5 | 0.0045 | 0.0039 |
| pMON140832 | P-CUCme.19-1:1:3 | 167 | 130 | 21520.3 | 27270.5 | 0.0060 | 0.0048 |
| pMON140833 | P-CUCme.20-1:3 | 211 | 88.5 | 22223.8 | 30786 | 0.0040 | 0.0029 |
| pMON140834 | P-CUCme.21-1:1:1 | 30 | 98.5 | 18579 | 20506.3 | 0.0053 | 0.0048 |
| pMON140835 | P-CUCme.22-1:1:3 | 31 | 363 | 21780.3 | 28816.3 | 0.0167 | 0.0126 |
| pMON140836 | EXP-CUCme.SAMS2:1:1 | 168 | 515 | 17906 | 23031 | 0.0288 | 0.0224 |
| pMON140837 | P-CUCme.26-1:1:2 | 33 | 125 | 15529.3 | 15169.3 | 0.0080 | 0.0082 |
| pMON140838 | P-CUCme.28-1:1:2 | 34 | 115.8 | 17013.5 | 22236.5 | 0.0068 | 0.0052 |
| pMON140839 | EXP-CUCme.29:1:2 | 212 | 15.5 | 16370.3 | 20409 | 0.0009 | 0.0008 |

To compare the relative activity of each promoter in cotton leaf protoplasts, GUS values were expressed as a ratio of GUS to luciferase activity and normalized with respect to the expression levels observed for the constitutive expression element groups, EXP-At.Act7:1:11 and EXP-CaMV.35S-enh+Ph.DnaK:1:3. Table 16 below shows the GUS to firefly luciferase (FLuc) ratios normalized with respect to EXP-At.Act7:1:11 and EXP-CaMV.35S-enh+Ph.DnaK:1:3. Table 17 below shows the GUS to *Renilla* luciferase (RLuc) ratios normalized with respect to EXP-At.Act7:1:11 and EXP-CaMV.35S-enh+Ph.DnaK:1:3.

TABLE 16

GUS to firefly luciferase (FLuc) ratios normalized with respect to EXP-At.Act7:1:11 and EXP-CaMV.35S-enh + Ph.DnaK:1:3.

| Construct | Regulatory Element | SEQ ID NO: | GUS/FLuc normalized with respect to EXP-At.Act7:1:11 | GUS/FLuc normalized with respect to EXP-CaMV.35S-enh + Ph.DnaK:1:3 |
|---|---|---|---|---|
| pMON109584 | EXP-CaMV.35S-enh + Ph.DnaK:1:3 | 201 | 7.037 | 1.000 |
| pMON118756 | EXP-At.Act7:1:11 | 202 | 1.000 | 0.142 |
| pMON124912 | Promoterless | | 0.021 | 0.003 |
| pMON140818 | P-CUCme.1-1:1:1rc | 155 | 0.188 | 0.027 |
| pMON140819 | P-CUCme.2-1:1:1 | 14 | 0.042 | 0.006 |
| pMON140820 | P-CUCme.3-1:1:3 | 15 | 0.058 | 0.008 |
| pMON140821 | EXP-CUCme.4:1:1 | 156 | 3.662 | 0.520 |
| pMON140823 | P-CUCme.6-1:1:1 | 18 | 0.041 | 0.006 |
| pMON140824 | P-CUCme.8-1:1:2 | 19 | 0.022 | 0.003 |
| pMON140825 | P-CUCme.9-1:1:2 | 20 | 0.333 | 0.047 |
| pMON140826 | P-CUCme.10-1:1:1 | 21 | 0.182 | 0.026 |
| pMON140827 | EXP-CUCme.eEF1a:1:1 | 162 | 0.659 | 0.094 |
| pMON140828 | P-CUCme.15-1:1:2 | 23 | 0.061 | 0.009 |
| pMON140829 | P-CUCme.16a-1:1:2 | 24 | 0.012 | 0.002 |
| pMON140830 | P-CUCme.17-1:1:2 | 26 | 0.132 | 0.019 |
| pMON140831 | P-CUCme.18-1:1:2 | 27 | 0.089 | 0.013 |
| pMON140832 | P-CUCme.19-1:1:3 | 167 | 0.119 | 0.017 |
| pMON140833 | P-CUCme.20-1:3 | 211 | 0.078 | 0.011 |
| pMON140834 | P-CUCme.21-1:1:1 | 30 | 0.104 | 0.015 |
| pMON140835 | P-CUCme.22-1:1:3 | 31 | 0.327 | 0.046 |
| pMON140836 | EXP-CUCme.SAMS2:1:1 | 168 | 0.564 | 0.080 |
| pMON140837 | P-CUCme.26-1:1:2 | 33 | 0.158 | 0.022 |
| pMON140838 | P-CUCme.28-1:1:2 | 34 | 0.134 | 0.019 |
| pMON140839 | EXP-CUCme.29:1:2 | 212 | 0.019 | 0.003 |

TABLE 17

| GUS to *renilla* luciferase (RLuc) ratios normalized with respect to EXP-At.Act7:1:11 and EXP-CaMV.35S-enh + Ph.DnaK:1:3. | | | | |
|---|---|---|---|---|
| Construct | Regulatory Element | SEQ ID NO: | GUS/RLuc normalized with respect to EXP-At.Act7:1:11 | GUS/RLuc normalized with respect to EXP-CaMV.35S-enh + Ph.DnaK:1:3 |
| pMON109584 | EXP-CaMV.35S-enh + Ph.DnaK:1:3 | 201 | 4.83 | 1.00 |
| pMON118756 | EXP-At.Act7:1:11 | 202 | 1.00 | 0.21 |
| pMON124912 | Promoterless | | 0.02 | 0.00 |
| pMON140818 | P-CUCme.1-1:1:1rc | 155 | 0.20 | 0.04 |
| pMON140819 | P-CUCme.2-1:1:1 | 14 | 0.04 | 0.01 |
| pMON140820 | P-CUCme.3-1:1:3 | 15 | 0.06 | 0.01 |
| pMON140821 | EXP-CUCme.4:1:1 | 156 | 3.41 | 0.71 |
| pMON140823 | P-CUCme.6-1:1:1 | 18 | 0.04 | 0.01 |
| pMON140824 | P-CUCme.8-1:1:2 | 19 | 0.02 | 0.00 |
| pMON140825 | P-CUCme.9-1:1:2 | 20 | 0.33 | 0.07 |
| pMON140826 | P-CUCme.10-1:1:1 | 21 | 0.17 | 0.04 |
| pMON140827 | EXP-CUCme.eEF1a:1:1 | 162 | 0.67 | 0.14 |
| pMON140828 | P-CUCme.15-1:1:2 | 23 | 0.05 | 0.01 |
| pMON140829 | P-CUCme.16a-1:1:2 | 24 | 0.01 | 0.00 |
| pMON140830 | P-CUCme.17-1:1:2 | 26 | 0.13 | 0.03 |
| pMON140831 | P-CUCme.18-1:1:2 | 27 | 0.10 | 0.02 |
| pMON140832 | P-CUCme.19-1:1:3 | 167 | 0.12 | 0.03 |
| pMON140833 | P-CUCme.20-1:3 | 211 | 0.07 | 0.02 |
| pMON140834 | P-CUCme.21-1:1:1 | 30 | 0.12 | 0.03 |
| pMON140835 | P-CUCme.22-1:1:3 | 31 | 0.32 | 0.07 |
| pMON140836 | EXP-CUCme.SAMS2:1:1 | 168 | 0.57 | 0.12 |
| pMON140837 | P-CUCme.26-1:1:2 | 33 | 0.21 | 0.04 |
| pMON140838 | P-CUCme.28-1:1:2 | 34 | 0.13 | 0.03 |
| pMON140839 | EXP-CUCme.29:1:2 | 212 | 0.02 | 0.00 |

As can be seen in Tables 16 and 17, most of the expression element groups tested, demonstrated the ability to drive transgene expression in cotton leaf protoplast cells. One expression element group, EXP-CUCme.4:1:1 (SEQ ID NO: 156) demonstrated levels of transgene expression higher than that of EXP-At.Act7:1:11 in this assay.

Example 8: Analysis of Regulatory Elements Driving GUS in Cotton Leaf Protoplasts Using Transgene Cassette Amplicons Cotton leaf protoplasts were transformed with transgene cassette amplicons containing a transcriptional regulatory expression element group driving expression of the ß-glucuronidase (GUS) transgene and compared to GUS expression in leaf protoplasts in which expression of GUS is driven by known constitutive promoters. The transgene cassette amplicons were comprised of an EXP sequence, operably linked to a GUS coding sequence (GUS, SEQ ID NO: 206), operably linked to a 3' UTR (T-Gb.FbL2-1:1:1, SEQ ID NO: 205). Average GUS expression was compared to the control EXP elements, P-CaMV.35S-enh-1:1:102/L-CaMV.35S-1:1:2 (SEQ ID NO: 210) and EXP-At.Atntt1:1:2 (SEQ ID NO: 200).

A plasmid, for use in co-transformation and normalization of data was also used in a similar manner as that described above in Example 2. The transformation control plasmid was comprised of a constitutive promoter, driving the expression of the firefly (*Photinus pyralis*) luciferase coding sequence (FLuc, SEQ ID NO: 205), operably linked 5' to a 3' termination region from the *Agrobacterium tumefaciens* nopaline synthase gene (T-AGRtu.nos-1:1:13, SEQ ID NO: 209).

Table 18 below shows the mean GUS expression values conferred by each transgene amplicon. Table 19 below shows the GUS to firefly luciferase (FLuc) ratios normalized with respect to EXP-At.Atntt1:1:2 and P-CaMV.35S-enh-1:1:102/L-CaMV.35S-1:1:2.

TABLE 18

| Average GUS and luciferase expression values and GUS/luciferase ratios. | | | | | |
|---|---|---|---|---|---|
| Amplicon ID | Regulatory Element | SEQ ID NO: | Mean GUS | Mean Fluc | GUS/Fluc |
| Empty Vector | No DNA | | 32.8 | 14087.5 | 0.002 |
| pMON124912 | No promoter | | 12 | 20486.3 | 0.001 |
| pMON80585 | EXP-At.Atntt1:1:2 | 200 | 55.5 | 18811 | 0.003 |
| pMON33449 | P-CaMV.35S-enh-1:1:102/L-CaMV.35S-1:1:2 | 210 | 12472.5 | 19126.3 | 0.652 |
| 56741 | CumMe_WSM_SF143981.G5150 | 36 | 5.8 | 17449.5 | 0.000 |
| 56492 | CumMe_WSM_SF144839.G5080 | 37 | 27.5 | 16674 | 0.002 |
| 56877 | P-CUCme.CumMe_WSM_SF16444.G5140-1:1:1 | 175 | 96.3 | 17237.8 | 0.006 |

TABLE 18-continued

Average GUS and luciferase expression values and GUS/luciferase ratios.

| Amplicon ID | Regulatory Element | SEQ ID NO: | Mean GUS | Mean Fluc | GUS/Fluc |
|---|---|---|---|---|---|
| 56485 | CumMe_WSM_SF16530.G6000 | 42 | 27.3 | 17858.5 | 0.002 |
| 56844 | CumMe_WSM_SF16953.G5180 | 47 | 22.3 | 19398.5 | 0.001 |
| 56500 | CumMe_WSM_SF17250.G5910 | 52 | 12.3 | 23980.3 | 0.001 |
| 56754 | P-CUCme.WSM_SF17252.G7330-1:1:1 | 179 | 16 | 13848.8 | 0.001 |
| 56740 | CumMe_WSM_SF17672.G5610 | 60 | 12 | 16646.8 | 0.001 |
| 56870 | CumMe_WSM_SF18287.G5380 | 66 | 39.3 | 13930.5 | 0.003 |
| 56478 | CumMe_WSM_SF18504.G5090 | 68 | 11.8 | 15830.5 | 0.001 |
| 56481 | CumMe_WSM_SF18530.G5750 | 69 | 6.5 | 15211.3 | 0.000 |
| 56498 | CumMe_WSM_SF18645.G5380 | 73 | 36 | 14569.8 | 0.002 |
| 56746 | P-CUCme.CumMe_WSM_SF18716.G5860-1:1:1 | 184 | 11 | 18054.5 | 0.001 |
| 56490 | CumMe_WSM_SF18801.G5040 | 75 | 21.5 | 14147.3 | 0.002 |
| 56488 | CumMe_WSM_SF19323.G5120 | 81 | 15.3 | 11985.3 | 0.001 |
| 56499 | CumMe_WSM_SF19631.G5170 | 83 | 12.5 | 20140.5 | 0.001 |
| 56482 | P-CUCme.CumMe_WSM_SF19839.G5090-1:1:1 | 189 | 75 | 18690.5 | 0.004 |
| 56489 | CumMe_WSM_SF19850.G5130 | 86 | 38.3 | 19756.5 | 0.002 |
| 56476 | CumMe_WSM_SF20355.G5130 | 91 | 10.5 | 27901.8 | 0.000 |
| 56895 | CumMe_WSM_SF20431.G6340 | 95 | 34.8 | 16283.8 | 0.002 |
| 56744 | CumMe_WSM_SF206458.G5970 | 98 | 11 | 19659 | 0.001 |
| 56480 | CumMe_WSM_SF21366.G5980 | 105 | 10.8 | 17367 | 0.001 |
| 56930 | CumMe_WSM_SF22070.G5280 | 109 | 25.3 | 14210.5 | 0.002 |
| 56484 | CumMe_WSM_SF23181.G5100 | 117 | 20.3 | 13506 | 0.002 |
| 56495 | P-CUCme.CumMe_WSM_SF23760.G5200-1:1:1 | 193 | 7.8 | 15138.5 | 0.001 |
| 56971 | CumMe_WSM_SF25084.G5580 | 125 | 16 | 16135.3 | 0.001 |
| 56742 | P-CUCme.CumMe_WSM_SF25355.G5000-1:1:1 | 196 | 18 | 13782.8 | 0.001 |
| 56494 | CumMe_WSM_SF25455.G5370 | 129 | 10.5 | 16089.8 | 0.001 |
| 56751 | P-CUCme.CumMe_WSM_SF41124.G5080-1:1:1 | 199 | 24.3 | 17884.3 | 0.001 |
| 56483 | CumMe_WSM_SF41644.G6400 | 143 | 14.5 | 13130.5 | 0.001 |
| 56904 | CumMe_WSM_SF44933.G5290 | 147 | 33 | 13369 | 0.002 |
| 56743 | CumMe_WSM_SF9060.G5120 | 154 | 11.3 | 15230.8 | 0.001 |

TABLE 19

GUS to firefly luciferase (FLuc) ratios normalized with respect to EXP-At.Atntt1:1:2 and P-CaMV.35S-enh-1:1:102/L-CaMV.35S-1:1:2.

| Amplicon ID | Regulatory Element | SEQ ID NO: | GUS/Fluc normalized with respect to EXP-At.Atntt1:1:2 | GUS/Fluc normalized with respect to P-CaMV.35S-enh-1:1:102/L-CaMV.35S-1:1:2 |
|---|---|---|---|---|
| Empty Vector | No DNA | | | |
| pMON124912 | No promoter | | | |
| pMON80585 | EXP-At.Atntt1:1:2 | 200 | 1.000 | 0.005 |
| pMON33449 | P-CaMV.35S-enh-1:1:102/L-CaMV.35S-1:1:2 | 210 | 221.025 | 1.000 |
| 56741 | CumMe_WSM_SF143981.G5150 | 36 | 0.113 | 0.001 |
| 56492 | CumMe_WSM_SF144839.G5080 | 37 | 0.559 | 0.003 |
| 56877 | P-CUCme.CumMe_WSM_SF16444.G5140-1:1:1 | 175 | 1.893 | 0.009 |
| 56485 | CumMe_WSM_SF16530.G6000 | 42 | 0.518 | 0.002 |
| 56844 | CumMe_WSM_SF16953.G5180 | 47 | 0.390 | 0.002 |
| 56500 | CumMe_WSM_SF17250.G5910 | 52 | 0.174 | 0.001 |
| 56754 | P-CUCme.WSM_SF17252.G7330-1:1:1 | 179 | 0.392 | 0.002 |
| 56740 | CumMe_WSM_SF17672.G5610 | 60 | 0.244 | 0.001 |
| 56870 | CumMe_WSM_SF18287.G5380 | 66 | 0.956 | 0.004 |

TABLE 19-continued

GUS to firefly luciferase (FLuc) ratios normalized with respect to EXP-At.Atntt1:1:2 and P-CaMV.35S-enh-1:1:102/L-CaMV.35S-1:1:2.

| Amplicon ID | Regulatory Element | SEQ ID NO: | GUS/Fluc normalized with respect to EXP-At.Atntt1:1:2 | GUS/Fluc normalized with respect to P-CaMV.35S-enh-1:1:102/L-CaMV.35S-1:1:2 |
|---|---|---|---|---|
| 56478 | CumMe_WSM_SF18504.G5090 | 68 | 0.253 | 0.001 |
| 56481 | CumMe_WSM_SF18530.G5750 | 69 | 0.145 | 0.001 |
| 56498 | CumMe_WSM_SF18645.G5380 | 73 | 0.837 | 0.004 |
| 56746 | P-CUCme.CumMe_WSM_SF18716.G5860-1:1:1 | 184 | 0.207 | 0.001 |
| 56490 | CumMe_WSM_SF18801.G5040 | 75 | 0.515 | 0.002 |
| 56488 | CumMe_WSM_SF19323.G5120 | 81 | 0.433 | 0.002 |
| 56499 | CumMe_WSM_SF19631.G5170 | 83 | 0.210 | 0.001 |
| 56482 | P-CUCme.CumMe_WSM_SF19839.G5090-1:1:1 | 189 | 1.360 | 0.006 |
| 56489 | CumMe_WSM_SF19850.G5130 | 86 | 0.657 | 0.003 |
| 56476 | CumMe_WSM_SF20355.G5130 | 91 | 0.128 | 0.001 |
| 56895 | CumMe_WSM_SF20431.G6340 | 95 | 0.724 | 0.003 |
| 56744 | CumMe_WSM_SF206458.G5970 | 98 | 0.190 | 0.001 |
| 56480 | CumMe_WSM_SF21366.G5980 | 105 | 0.211 | 0.001 |
| 56930 | CumMe_WSM_SF22070.G5280 | 109 | 0.603 | 0.003 |
| 56484 | CumMe_WSM_SF23181.G5100 | 117 | 0.509 | 0.002 |
| 56495 | P-CUCme.CumMe_WSM_SF23760.G5200-1:1:1 | 193 | 0.175 | 0.001 |
| 56971 | CumMe_WSM_SF25084.G5580 | 125 | 0.336 | 0.002 |
| 56742 | P-CUCme.CumMe_WSM_SF25355.G5000-1:1:1 | 196 | 0.443 | 0.002 |
| 56494 | CumMe_WSM_SF25455.G5370 | 129 | 0.221 | 0.001 |
| 56751 | P-CUCme.CumMe_WSM_SF41124.G5080-1:1:1 | 199 | 0.461 | 0.002 |
| 56483 | CumMe_WSM_SF41644.G6400 | 143 | 0.374 | 0.002 |
| 56904 | CumMe_WSM_SF44933.G5290 | 147 | 0.837 | 0.004 |
| 56743 | CumMe_WSM_SF9060.G5120 | 154 | 0.251 | 0.001 |

As can be seen in Table 18 above, not all EXP sequences demonstrated the ability to drive transgene expression when compared to the promoterless control. However, the EXP sequences, P-CUCme.CumMe_WSM_SF16444.G5140-1:1:1 (SEQ ID NO: 175) and P-CUCme.CumMe_WSM_SF19839.G5090-1:1:1 (SEQ ID NO: 189) demonstrated the ability to drive transgene expression in soybean cotyledon protoplasts at a level similar or greater than EXP-At.Atntt1:1:2. As shown in Table 19 above, the EXP sequence, P-CUCme.CumMe_WSM_SF19839.G5090-1:1:1 (SEQ ID NO: 189) demonstrated the ability to drive transgene expression in this assay at a level greater than EXP-At.Atntt1:1:2.

Example 9: Analysis of Regulatory Elements Driving GUS in Stably Transformed Soybean Soybean plants were transformed with plant expression vectors containing an EXP sequence driving expression of the ß-glucuronidase (GUS) transgene.

Expression of the GUS transgene driven by EXP-CUCme.Ubq1:1:1 (SEQ ID NO: 1), EXP-CUCme.Ubq1:1:3 (SEQ ID NO: 7), P-CUCme.1-1:1:1rc (SEQ ID NO: 155), P-CUCme.2-1:1:1 (SEQ ID NO: 14), P-CUCme.3-1:1:3 (SEQ ID NO: 15), EXP-CUCme.4:1:1 (SEQ ID NO: 156), EXP-CUCme.5:1:1 (SEQ ID NO: 159), P-CUCme.6-1:1:1 (SEQ ID NO: 18), P-CUCme.8-1:1:2 (SEQ ID NO: 19), P-CUCme.9-1:1:2 (SEQ ID NO: 20), P-CUCme.10-1:1:1 (SEQ ID NO: 21), EXP-CUCme.eEF1a:1:1 (SEQ ID NO: 162), P-CUCme.15-1:1:2 (SEQ ID NO: 23), P-CUCme.17-1:1:2 (SEQ ID NO: 26), P-CUCme.18-1:1:2 (SEQ ID NO: 27), P-CUCme.19-1:1:3 (SEQ ID NO: 167), P-CUCme.20-1:3 (SEQ ID NO: 211), P-CUCme.21-1:1:1 (SEQ ID NO: 30), EXP-CUCme.SAMS2:1:1 (SEQ ID NO: 168), P-CUCme.26-1:1:2 (SEQ ID NO: 33), EXP-CUCme.29:1:2 (SEQ ID NO: 212), P-CUCme.CumMe_WSM_SF25355.G5000-1:1:1 (SEQ ID NO: 196), P-CUCme.CumMe_WSM_SF17111.G5790-1:1:1 (SEQ ID NO: 177), P-CUCme.CumMe_WSM_SF22531.G5120-1:1:1 (SEQ ID NO: 192), P-CUCme.CumMe_WSM_SF18488.G5340-1:1:1 (SEQ ID NO: 181), P-CUCme.CumMe_WSM_SF23760.G5200-1:1:1 (SEQ ID NO: 193), EXP-CUCme.WSM_SF19064.G5690:1:1 (SEQ ID NO: 185), P-CUCme.WSM_SF17252.G7330-1:1:1 (SEQ ID NO: 179), P-CUCme.CumMe_WSM_SF18634.G5190-1:1:1 (SEQ ID NO: 183), P-CUCme.CumMe_WSM_SF19647.G5760-1:1:1 (SEQ ID NO: 188), P-CUCme.CumMe_WSM_SF25936.G5450-1:1:1 (SEQ ID NO: 197), P-CUCme.CumMe_WSM_SF19839.G5090-1:1:1 (SEQ ID NO: 189), CumMe_WSM_SF206458.G5970 (SEQ ID NO: 98) and P-CUCme.CumMe_WSM_SF18716.G5860-1:1:1 (SEQ ID NO: 184) assayed both qualitatively through inspection of stained tissue sections and quantitatively. Each plant expression vector was comprised of a right border region from *Agrobacterium tumefaciens*, a first transgene cassette comprised of an EXP sequence operably linked 5' to a coding sequence for ß-glucuronidase (GUS, SEQ ID NO: 206) containing a processable intron derived from the potato light-inducible tissue-specific ST-LS1 gene (Genbank Accession: X04753), operably linked 5' to a 3' termination region from the *Gossypium barbadense* FbLate-2 gene (T-Gb.FbL2-1:1:1, SEQ ID NO: 205); a second transgene selection cassette used for selection of transformed plant cells that conferred resistance to the herbicide glyphosate (driven by the *Arabidopsis* Actin 7 promoter) and a left border region from *A. tumefaciens.*

The foregoing EXP sequences were cloned into plant expression constructs as shown in Tables 20 through 23 below and used to transform soybean plants using an *Agrobacterium* mediated transformation method. Expression of GUS was assayed qualitatively using histological sections of selected tissues and quantitatively.

Histochemical GUS analysis was used for qualitative expression analysis of transformed plants. Whole tissue sections were incubated with GUS staining solution X-Gluc (5-bromo-4-chloro-3-indolyl-b-glucuronide) (1 milligram/milliliter) for an appropriate length of time, rinsed, and visually inspected for blue coloration. GUS activity was qualitatively determined by direct visual inspection or inspection under a microscope using selected plant organs and tissues. The $R_0$ generation plants were inspected for expression in Vn5 Root, R1 Root, Vn5 Sink Leaf, Vn5 Source Leaf, R1 Source Leaf, R1 Petiole, Yellow Pod Embryo, Yellow Pod Cotyledon, R3 Immature Seed, R3 Pod, R5 Cotyledon and R1 Flower.

For quantitative analysis, total protein was extracted from selected tissues of transformed corn plants. One microgram of total protein was used with the fluorogenic substrate 4-methylumbelliferyl-β-D-glucuronide (MUG) in a total reaction volume of 50 microliters. The reaction product, 4-methylumbelliferone (4-MU), is maximally fluorescent at high pH, where the hydroxyl group is ionized. Addition of a basic solution of sodium carbonate simultaneously stops the assay and adjusts the pH for quantifying the fluorescent product. Fluorescence was measured with excitation at 365 nm, emission at 445 nm using a Fluoromax-3 (Horiba; Kyoto, Japan) with Micromax Reader, with slit width set at excitation 2 nm and emission 3 nm.

Tables 20 and 21 below show the mean quantitative expression levels measured in the $R_0$ generation plant tissues. Those tissued not assayed are shown as blank cells in both tables.

TABLE 20

Mean GUS expression in Vn5 Root, R1 Root, Vn5 Sink Leaf, Vn5 Source Leaf, R1 Source Leaf and R1 Petiole of $R_0$ generation transformed soybean plants

| Construct | Regulatory Element | SEQ ID NO: | Vn5_ Root | R1_Root | Vn5_Sink_ Leaf | Vn5_Source Leaf | R1_Source_ Leaf | R1_Petiole |
|---|---|---|---|---|---|---|---|---|
| pMON138776 | EXP-CUCme.Ubq1:1:1 | 1 | 4 | | | | 4 | 4 |
| pMON138778 | EXP-CUCme.Ubq1:1:3 | 7 | 16 | | 1 | 2 | 13 | 23 |
| pMON140818 | P-CUCme.1-1:1:1rc | 155 | 48.21 | | 22.35 | 20.24 | 33.01 | 78.17 |
| pMON140819 | P-CUCme.2-1:1:1 | 14 | | | | | | |
| pMON140820 | P-CUCme.3-1:1:3 | 15 | | | | | | |
| pMON140821 | EXP-CUCme.4:1:1 | 156 | 96.82 | | 28.32 | 39.17 | 322.98 | 280.03 |
| pMON140822 | EXP-CUCme.5:1:1 | 159 | 28.88 | | | | 41.11 | |
| pMON140823 | P-CUCme.6-1:1:1 | 18 | 23.94 | | | | 32.14 | 30.22 |
| pMON140824 | P-CUCme.8-1:1:2 | 19 | | | | | | |
| pMON140825 | P-CUCme.9-1:1:2 | 20 | 22.06 | | | | 21.22 | 23.08 |
| pMON140826 | P-CUCme.10-1:1:1 | 21 | | | | | | |
| pMON140827 | EXP-CUCme.eEF1a:1:1 | 162 | 189.24 | 153.52 | 59.6 | 37.44 | 103.01 | 130.6 |
| pMON140828 | P-CUCme.15-1:1:2 | 23 | 30.53 | | | | | |
| pMON140830 | P-CUCme.17-1:1:2 | 26 | 51.62 | | 30.07 | 31.08 | 30.49 | 60.14 |
| pMON140831 | P-CUCme.18-1:1:2 | 27 | 57.38 | | | | | 30.03 |
| pMON140832 | P-CUCme.19-1:1:3 | 167 | 23.07 | | 50.21 | 59.73 | 65.58 | 137.42 |
| pMON140833 | P-CUCme.20-1:3 | 211 | 23.15 | | 61.6 | 118.76 | 502.55 | 119.46 |
| pMON140834 | P-CUCme.21-1:1:1 | 30 | 25.49 | | | | | |
| pMON140836 | EXP-CUCme.SAMS2:1:1 | 168 | 230.89 | 184.88 | 65.44 | 53.36 | 118.82 | 351.49 |
| pMON140837 | P-CUCme.26-1:1:2 | 33 | 56.21 | | 26.81 | 45.07 | 51.61 | 47.42 |
| pMON140839 | EXP-CUCme.29:1:2 | 212 | 82.17 | | 45.2 | 28.27 | 64.96 | 109.9 |
| pMON144926 | P-CUCme.CumMe_WSM_SF25355.G5000-1:1:1 | 196 | 28.53 | | | | | |
| pMON144927 | P-CUCme.CumMe_WSM_SF17111.G5790-1:1:1 | 177 | 23.62 | | | | | |
| pMON144928 | P-CUCme.CumMe_WSM_SF22531.G5120-1:1:1 | 192 | 75.62 | | 23 | 20.46 | 21.78 | 39.77 |
| pMON144931 | P-CUCme.CumMe_WSM_SF18488.G5340-1:1:1 | 181 | 43.2 | | | | | 52.55 |
| pMON144933 | P-CUCme.CumMe_WSM_SF23760.G5200-1:1:1 | 193 | 25.61 | | 20.45 | 0 | 0 | 28.69 |
| pMON146941 | EXP-CUCme.WSM_SF1906.G5690:1:1 | 185 | 33.5 | | 0 | 0 | 24.27 | 47.82 |

TABLE 20-continued

Mean GUS expression in Vn5 Root, R1 Root, Vn5 Sink Leaf, Vn5 Source Leaf, R1 Source Leaf and R1 Petiole of $R_0$ generation transformed soybean plants

| Construct | Regulatory Element | SEQ ID NO: | Vn5_ Root | R1_Root | Vn5_Sink_ Leaf | Vn5_Source Leaf | R1_Source_ Leaf | R1_Petiole |
|---|---|---|---|---|---|---|---|---|
| pMON144932 | P-CUCme.WSM_SF17252.G7330-1:1:1 | 179 | 32.54 | | 23.76 | 21.5 | 0 | 22.21 |
| pMON146940 | P-CUCme.CumMe_WSM_SF18634.G5190-1:1:1 | 183 | 0 | | 0 | 0 | 0 | 0 |
| pMON147340 | P-CUCme.CumMe_WSM_SF19647.G5760-1:1:1 | 188 | 28.9 | | 0 | 0 | 29.77 | 25.82 |
| pMON147342 | P-CUCme.CumMe_WSM_SF25936.G5450-1:1:1 | 197 | 50.15 | | 24.26 | 0 | 29.38 | 29.91 |
| pMON147343 | P-CUCme.CumMe_WSM_SF19839.G5090-1:1:1 | 189 | 36.05 | | 25.7 | 27.54 | 22.85 | 37.15 |
| pMON144929 | CumMe_WSM_SF206458.G5970 | 98 | | | | | | |
| pMON147304 | P-CUCme.CumMe_WSM_S18716.G5860-1:1:1 | 184 | 35.01 | | 21.17 | 21.23 | 22 | 44.57 |

TABLE 21

Mean GUS expression in Yellow Pod Embryo, Yellow Pod Cotyledon, R3 Immature Seed, R3 Pod, R5 Cotyledon and R1 Flower of $R_0$ generation transformed soybean plants

| Construct | Regulatory Element | SEQ ID NO: | Yellow_Pod_ Embryo | Yellow_Pod_ Cotyledon | R3_ Immature_ Seed | R3_Pod | R5_ Cotyledon | R1_ Flower |
|---|---|---|---|---|---|---|---|---|
| pMON138776 | EXP-CUCme.Ubq1:1:1 | 1 | 12 | 9 | 13 | 11 | 10 | 7 |
| pMON138778 | EXP-CUCme.Ubq1:1:3 | 7 | 3 | 1 | 13 | 9 | 13 | 27 |
| pMON140818 | P-CUCme.1-1:1:1rc | 155 | 100.79 | 117.5 | 38.31 | 84.72 | 132.27 | 66.8 |
| pMON140819 | P-CUCme.2-1:1:1 | 14 | | | | | 20.35 | 36.18 |
| pMON140820 | P-CUCme.3-1:1:3 | 15 | | | | | | |
| pMON140821 | EXP-CUCme.4:1:1 | 156 | 86.68 | 225.53 | 105.62 | 342.07 | 119.08 | 184.92 |
| pMON140822 | EXP-CUCme.5:1:1 | 159 | 21.48 | 32.27 | 21.47 | 21.66 | | 36.88 |
| pMON140823 | P-CUCme.6-1:1:1 | 18 | 38.75 | | 23.03 | | 25.32 | 58.7 |
| pMON140824 | P-CUCme.8-1:1:2 | 19 | | | | | 90.33 | 25.77 |
| pMON140825 | P-CUCme.9-1:1:2 | 20 | 132.04 | | | 20.56 | 34.78 | |
| pMON140826 | P-CUCme.10-1:1:1 | 21 | | | | | 22.34 | |
| pMON140827 | EXP-CUCme.eEF1a:1:1 | 162 | 200.28 | 291.26 | 58.21 | 131.17 | 114.29 | 130.38 |
| pMON140828 | P-CUCme.15-1:1:2 | 23 | | | 142.24 | 26.2 | | |
| pMON140830 | P-CUCme.17-1:1:2 | 26 | 343.34 | 302.94 | 65.55 | 80.94 | 137.02 | 62.7 |
| pMON140831 | P-CUCme.18-1:1:2 | 27 | 103.17 | 135.97 | 30 | 34.62 | 88.14 | 23.73 |
| pMON140832 | P-CUCme.19-1:1:3 | 167 | 30.96 | 64.46 | | 316.66 | | 53.46 |
| pMON140833 | P-CUCme.20-1:3 | 211 | 174.62 | 524.88 | | 222.04 | 59.43 | 124.68 |
| pMON140834 | P-CUCme.21-1:1:1 | 30 | | | 28.15 | 20.52 | 23.89 | |
| pMON140836 | EXP-CUCme.SAMS2:1:1 | 168 | 110.23 | 159.43 | 61.99 | 248.96 | 49.17 | 224.24 |
| pMON140837 | P-CUCme.26-1:1:2 | 33 | 56.73 | 50.06 | 70 | 143.05 | 25.06 | 49.92 |
| pMON140839 | EXP-CUCme.29:1:2 | 212 | 251.76 | 237.2 | 49.16 | 89.28 | 114.92 | 57.84 |
| pMON144926 | P-CUCme.CumMe_WSM_S25355.G5000-1:1:1 | 196 | | | 21.41 | | 22.23 | |
| pMON144927 | P-CUCme.CumMe_WSM_SF17111.G5790-1:1:1 | 177 | 58.84 | 28.94 | | | 20.97 | |

TABLE 21-continued

Mean GUS expression in Yellow Pod Embryo, Yellow Pod Cotyledon, R3 Immature Seed, R3 Pod, R5 Cotyledon and R1 Flower of $R_0$ generation transformed soybean plants

| Construct | Regulatory Element | SEQ ID NO: | Yellow_Pod_ Embryo | Yellow_Pod_ Cotyledon | R3_ Immature_ Seed | R3_Pod | R5_ Cotyledon | R1_ Flower |
|---|---|---|---|---|---|---|---|---|
| pMON144928 | P-CUCme.CumMe_WSM_SF22531.G5120-1:1:1 | 192 | 135.62 | 152.48 | 30.45 | 51.71 | 129.72 | 42.2 |
| pMON144931 | P-CUCme.CumMe_WSM_SF18488.G5340-1:1:1 | 181 | 866.94 | | 23.26 | 21.49 | | |
| pMON144933 | P-CUCme.CumMe_WSM_SF23760.G5200-1:1:1 | 193 | | | 29.03 | 34.9 | 69.63 | 24.42 |
| pMON146941 | EXP-CUCme.WSM_SF19064.G5690:1:1 | 185 | | | 36.69 | 83.08 | 89.81 | 33.99 |
| pMON144932 | P-CUCme.WSM_SF17252.G7330-1:1:1 | 179 | | | 34.29 | 39.89 | 113.83 | 0 |
| pMON146940 | P-CUCme.CumMe_WSM_SF18634.G5190-1:1:1 | 183 | | | 30.25 | 0 | 0 | 0 |
| pMON147340 | P-CUCme.CumMe_WSM_SF19647.G5760-1:1:1 | 188 | | | 25.73 | 28.28 | 24.04 | 23.35 |
| pMON147342 | P-CUCme.CumMe_WSM_SF25936.G5450-1:1:1 | 197 | | | 104.02 | 80.27 | 31.06 | 26.8 |
| pMON147343 | P-CUCme.CumMe_WSM_SF19839.G5090-1:1:1 | 189 | | | | | | 29.09 |
| pMON144929 | CumMe_WSM_SF206458.G5970 | 98 | | | 24.42 | 25.33 | | |
| pMON147304 | P-CUCme.CumMe_WSM_SF18716.G5860-1:1:1 | 184 | | | | 283.49 | | 61.43 |

As can be seen in Tables 20 and 21, the EXP sequences, EXP-CUCme.Ubq1:1:1 (SEQ ID NO: 1), EXP-CUCme.Ubg1:1:3 (SEQ ID NO: 7), P-CUCme.1-1:1:1rc (SEQ ID NO: 155), P-CUCme.2-1:1:1 (SEQ ID NO: 14), EXP-CUCme.4:1:1 (SEQ ID NO: 156), EXP-CUCme.5:1:1 (SEQ ID NO: 159), P-CUCme.6-1:1:1 (SEQ ID NO: 18), P-CUCme.8-1:1:2 (SEQ ID NO: 19), P-CUCme.9-1:1:2 (SEQ ID NO: 20), P-CUCme.10-1:1:1 (SEQ ID NO: 21), EXP-CUCme.eEF1a:1:1 (SEQ ID NO: 162), P-CUCme.15-1:1:2 (SEQ ID NO: 23), P-CUCme.17-1:1:2 (SEQ ID NO: 26), P-CUCme.18-1:1:2 (SEQ ID NO: 27), P-CUCme.19-1:1:3 (SEQ ID NO: 167), P-CUCme.20-1:3 (SEQ ID NO: 211), P-CUCme.21-1:1:1 (SEQ ID NO: 30), EXP-CUCme.SAMS2:1:1 (SEQ ID NO: 168), P-CUCme.26-1:1:2 (SEQ ID NO: 33), EXP-CUCme.29:1:2 (SEQ ID NO: 212), P-CUCme.CumMe_WSM_SF25355.G5000-1:1:1 (SEQ ID NO: 196), P-CUCme.CumMe_WSM_SF17111.G5790-1:1:1 (SEQ ID NO: 177), P-CUCme.CumMe_WSM_SF22531.G5120-1:1:1 (SEQ ID NO: 192), P-CUCme.CumMe_WSM_SF18488.G5340-1:1:1 (SEQ ID NO: 181), P-CUCme.CumMe_WSM_SF23760.G5200-1:1:1 (SEQ ID NO: 193), EXP-CUCme.WSM_SF19064.G5690:1:1 (SEQ ID NO: 185), P-CUCme.WSM_SF17252.G7330-1:1:1 (SEQ ID NO: 179), P-CUCme.CumMe_WSM_SF18634.G5190-1:1:1 (SEQ ID NO: 183), P-CUCme.CumMe_WSM_SF19647.G5760-1:1:1 (SEQ ID NO: 188), P-CUCme.CumMe_WSM_SF25936.G5450-1:1:1 (SEQ ID NO: 197), P-CUCme.CumMe_WSM_SF19839.G5090-1:1:1 (SEQ ID NO: 189), CumMe_WSM_SF206458.G5970 (SEQ ID NO: 98) and P-CUCme.CumMe_WSM_SF18716.G5860-1:1:1 (SEQ ID NO: 184) demonstrated quantitatively the capacity to drive transgene expression in some or all tissues assayed, depending upon the EXP sequence used to drive expression.

Histological analysis of selected tissue sections provided further evidence of expression for many of the EXP sequences. EXP-CUCme.Ubq1:1:1 (SEQ ID NO: 1) and EXP-CUCme.Ubq1:1:3 (SEQ ID NO: 7) demonstrated a constitutive expression pattern with staining observed in all tissues, even though quantitative analysis showed fairly low levels of expression. This type of expression pattern can be most adventitious to driving expression of transgenes that require a low level of constitutive expression. Expression driven by P-CUCme.1-1:1:1rc (SEQ ID NO: 155) demonstrated expression in sink and source leaf vascular bundles and xylem and in the root cortex, phloem, xylem, endodermis, stele and tip. Expression driven by EXP-CUCme.4:1:1 (SEQ ID NO: 156) was observed in all tissues with the highest expression observed in the reproductive phase of the plant. Expression driven by P-CUCme.10-1:1:1 (SEQ ID NO: 21) was observed only in V5 Sink Leaf and R1 Flower anthers. Expression driven by EXP-CUCme.eEF1a:1:1 (SEQ ID NO: 162) demonstrated a constitutive expression pattern with highest expression being observed in yellow pod embryo and cotyledon. The yellow pod embryo activity was 5 fold higher in the R1 generation than in the R0 generation (see Table 23 below). Expression driven by P-CUCme.15-1:1:2 (SEQ ID NO: 23), P-CUCme.17-1:1:2 (SEQ ID NO: 26) and P-CUCme.18-1:1:2 (SEQ ID NO: 27) demonstrated a constitutive level of expression histologically. Expression driven by P-CUCme.19-1:1:3 (SEQ ID NO: 167) demonstrated a constitutive pattern of expression histologically with the exception of the V5 root and R1 petiole. R3 pod showed the highest expression.

Expression driven by P-CUCme.20-1:3 (SEQ ID NO: 211) demonstrated a constitutive expression pattern histologically with the exception of expression in V5 root. Expression was highest in the R8 stage cotyledon. Expression driven by EXP-CUCme.SAMS2:1:1 (SEQ ID NO: 168) demonstrated a constitutive pattern of expression with expression observed histologically in all tissues. GUS expression was observed to increase in the R1 generation (see Tables 22 and 23 below). The R1 stage flowers and petioles demonstrated the highest levels of expression in soybean. Expression driven by P-CUCme.CumMe_WSM_SF22531.G5120-1:1:1 (SEQ ID NO: 192) demonstrated a constitutive pattern of expression histologically with highest expression in the R8 stage cotyledon and embryo. Expression driven by P-CUCme.CumMe_WSM_SF18488.G5340-1:1:1 (SEQ ID NO: 181) demonstrated a constitutive level of expression while quantitatively high expression was observed in the yellow pod embryo.

$R_0$ generation plants transformed with the plasmid constructs comprising EXP-CUCme.eEF1a:1:1 (SEQ ID NO: 162) and EXP-CUCme.SAMS2:1:1 (SEQ ID NO: 168) were allowed to set seed and the $R_1$ generation plants analyzed for GUS expression. The $R_1$ generation plants were analyzed for expression in Vn5 Root, Vn5 Sink Leaf, Vn5 Source Leaf, R1 Source Leaf, R1 Petiole Yellow Pod Embryo, Yellow Pod Cotyledon, R3 Immature Seed, R3 Pod, R5 Cotyledon and R1 Flower. Tables 22 and 23 show the mean GUS expression measured in each tissue of the $R_1$ generation transformed plants.

TABLE 22

Mean GUS expression in Vn5 Root, Vn5 Sink Leaf, Vn5 Source Leaf, R1 Source Leaf, R1 Petiole of $R_1$ generation transformed soybean plants

| Construct | Regulatory Element | SEQ ID NO: | Vn5_ Root | Vn5_ Sink_Leaf | Vn5_ Source Leaf | R1_ Source_Leaf | R1_Petiole |
|---|---|---|---|---|---|---|---|
| pMON140827 | EXP-CUCme.eEF1a:1:1 | 162 | 145.84 | 50.24 | 43.73 | 107.98 | 357.67 |
| pMON140836 | EXP-CUCme.SAMS2:1:1 | 168 | 260.41 | 65.52 | 51.12 | 129.86 | 623.42 |

TABLE 23

Mean GUS expression in Yellow Pod Embryo, Yellow Pod Cotyledon, R3 Immature Seed, R3 Pod, R5 Cotyledon, R1 Flower of $R_1$ generation transformed soybean plants

| Construct | Regulatory Element | SEQ ID NO: | Yellow_ Pod_ Embryo | Yellow_ Pod_ Cotyledon | R3_ Immature Seed | R3_Pod | R5_ Cotyledon | R1_ Flower |
|---|---|---|---|---|---|---|---|---|
| pMON140827 | EXP-CUCme.eEF1a:1:1 | 162 | 1098.51 | 764.83 | 288.77 | 214.6 | 459.62 | 394.77 |
| pMON140836 | EXP-CUCme.SAMS2:1:1 | 168 | 219.04 | 291.58 | 241.48 | 382.73 | 397.91 | 653.23 |

As can be seen in Tables 22 and 23 above expression driven in $R_1$ generation by EXP-CUCme.eEF1a:1:1 (SEQ ID NO: 162) and EXP-CUCme.SAMS2:1:1 (SEQ ID NO: 168) shows a constitutive level of expression with increase in expression observed in many tissues at $R_1$ generation relative to $R_0$ generation.

Having illustrated and described the principles of the present invention, it should be apparent to persons skilled in the art that the invention can be modified in arrangement and detail without departing from such principles. All modifications that are within the spirit and scope of the claims are intended to be included within the scope of the present invention. All publications and published patent documents cited herein are hereby incorporated by reference to the same extent as if each individual publication or patent application is specifically and individually indicated to be incorporated by reference.

What is claimed is:

1. A DNA molecule exhibiting a gene regulatory functional activity comprising a polynucleotide sequence selected from the group consisting of:

a) a sequence with at least 95 percent sequence identity to SEQ ID NO: 22;

b) a sequence comprising SEQ ID NO: 22; and c) a fragment comprising at least 250 contiguous nucleotides of SEQ ID NO: 22 exhibiting promoter activity;

wherein said DNA molecule is operably linked to a heterologous transcribable polynucleotide molecule.

2. The DNA molecule of claim 1, wherein said polynucleotide sequence has at least 97 percent sequence identity to the polynucleotide sequence as set forth in SEQ ID NO: 22.

3. The DNA molecule of claim 1, wherein said polynucleotide sequence has at least 99 percent sequence identity to the polynucleotide sequence as set forth in SEQ ID NO: 22.

4. The DNA molecule of claim 1, wherein the heterologous transcribable polynucleotide molecule comprises a gene of agronomic interest.

5. The DNA molecule of claim 4, wherein the gene of agronomic interest confers herbicide tolerance in plants.

6. The DNA molecule of claim 4, wherein the gene of agronomic interest confers pest resistance in plants.

7. A transgenic plant cell comprising the DNA molecule of claim 1.

8. The transgenic plant cell of claim 7, wherein said transgenic plant cell is a monocotyledonous plant cell.

9. The transgenic plant cell of claim 7, wherein said transgenic plant cell is a dicotyledonous plant cell.

10. A transgenic plant, or part thereof, comprising the DNA molecule of claim 1.

11. A progeny plant of the transgenic plant of claim 10, or part thereof, wherein the progeny plant or part thereof comprises said DNA molecule exhibiting a gene regulatory functional activity.

12. A transgenic seed comprising the DNA molecule of claim 1.

13. A method of producing a commodity product comprising:

a) obtaining a transgenic plant or part thereof comprising the DNA molecule of claim 1; and b) producing the commodity product therefrom.

14. The method of claim 13, wherein the commodity product is protein concentrate, protein isolate, grain, starch, seeds, meal, flour, biomass, or seed oil.

15. A commodity product comprising the DNA molecule of claim 1.

16. A method of expressing a transcribable polynucleotide molecule comprising:

a) obtaining a transgenic plant comprising the DNA molecule of claim 1; and b) cultivating said transgenic plant, wherein the transcribable polynucleotide is expressed.

17. The DNA molecule of claim 1, wherein said polynucleotide sequence comprises a sequence with at least 95 percent sequence identity to SEQ ID NO: 22.

18. The DNA molecule of claim 1, wherein said polynucleotide sequence comprises SEQ ID NO:22.

19. The DNA molecule of claim 1, wherein said polynucleotide sequence comprises a fragment comprising at least 250 contiguous nucleotides of SEQ ID NO: 22 exhibiting promoter activity.

* * * * *